US011753675B2

(12) United States Patent
Ramachandran Iyer

(10) Patent No.: US 11,753,675 B2
(45) Date of Patent: Sep. 12, 2023

(54) GENERATING CAPTURE PROBES FOR SPATIAL ANALYSIS

(71) Applicant: 10x Genomics, Inc., Pleasanton, CA (US)

(72) Inventor: Eswar Prasad Ramachandran Iyer, Oakland, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/974,226

(22) Filed: Oct. 26, 2022

(65) Prior Publication Data

US 2023/0129552 A1 Apr. 27, 2023

Related U.S. Application Data

(63) Continuation of application No. 17/212,681, filed on Mar. 25, 2021, now Pat. No. 11,649,485, which is a continuation of application No. PCT/US2019/065013, filed on Dec. 6, 2019.

(60) Provisional application No. 62/941,581, filed on Nov. 27, 2019, provisional application No. 62/939,488, filed on Nov. 22, 2019, provisional application No. 62/935,043, filed on Nov. 13, 2019, provisional application No. 62/934,883, filed on Nov. 13, 2019, provisional application No. 62/931,587, filed on Nov. 6, 2019, provisional application No. 62/931,779, filed on Nov. 6, 2019, provisional application No. 62/860,993, filed on Jun. 13, 2019, provisional application No. 62/842,463, filed on May 2, 2019, provisional application No. 62/839,264, filed on Apr. 26, 2019, provisional application No. 62/839,575, filed on Apr. 26, 2019, provisional application No. 62/839,212, filed on Apr. 26, 2019, provisional application No. 62/839,346, filed on Apr. 26, 2019, provisional application No. 62/839,320, filed on Apr. 26, 2019, provisional application No. 62/839,223, filed on Apr. 26, 2019, provisional application No. 62/822,722, filed on Mar. 22, 2019, provisional application No. 62/822,680, filed on Mar. 22, 2019, provisional application No. 62/822,606, filed on Mar. 22, 2019, provisional application No. 62/822,605, filed on Mar. 22, 2019, provisional application No. 62/822,554, filed on Mar. 22, 2019, provisional application No. 62/822,566, filed on Mar. 22, 2019, provisional application No. 62/822,627, filed on Mar. 22, 2019, provisional application No. 62/822,592, filed on Mar. 22, 2019, provisional application No. 62/822,565, filed on Mar. 22, 2019, provisional application No. 62/822,610, filed on Mar. 22, 2019, provisional application No. 62/819,470, filed on Mar. 15, 2019, provisional application No. 62/819,449, filed on Mar. 15, 2019, provisional application No. 62/819,478, filed on Mar. 15, 2019, provisional application No. 62/819,456, filed on Mar. 15, 2019, provisional application No. 62/819,495, filed on Mar. 15, 2019, provisional application No. 62/812,219, filed on Feb. 28, 2019, provisional application No. 62/811,495, filed on Feb. 27, 2019, provisional application No. 62/788,885, filed on Jan. 6, 2019, provisional application No. 62/788,897, filed on Jan. 6, 2019, provisional application No. 62/788,871, filed on Jan. 6, 2019, provisional application No. 62/788,906, filed on Jan. 6, 2019.

(51) Int. Cl.
*C12Q 1/6837* (2018.01)

(52) U.S. Cl.
CPC .................. *C12Q 1/6837* (2013.01)

(58) Field of Classification Search
CPC .............. C12Q 1/6837; C07H 21/02
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,472,881 A | 12/1995 | Beebe et al. |
| 5,494,810 A | 2/1996 | Barany et al. |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Kwon et al., Polyelectrolyte Gels-Fundamentals and Applications, 2006, Polymer Journal, 38, pp. 1211-1219 . (Year: 2006).*

(Continued)

*Primary Examiner* — Narayan K Bhat
(74) *Attorney, Agent, or Firm* — Fish & Richardson P.C.

(57) ABSTRACT

The present disclosure relates to compositions and methods for generating capture probes on a substrate for identifying the location of analytes in a biological sample.

29 Claims, 57 Drawing Sheets
Specification includes a Sequence Listing.

(56) References Cited

U.S. PATENT DOCUMENTS

| | | |
|---|---|---|
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,610,287 A | 3/1997 | Nikiforov et al. |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,807,522 A | 9/1998 | Brown et al. |
| 5,830,711 A | 11/1998 | Barany et al. |
| 5,837,832 A | 11/1998 | Chee et al. |
| 5,837,860 A | 11/1998 | Anderson et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,919,626 A | 7/1999 | Shi et al. |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,306,597 B1 | 10/2001 | Macevicz |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,391,937 B1 | 5/2002 | Beuhler et al. |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 6,969,488 B2 | 11/2005 | Bridgham |
| 7,001,792 B2 | 2/2006 | Sauer et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,259,258 B2 | 8/2007 | Kozlov et al. |
| 7,264,929 B2 | 9/2007 | Rothberg |
| 7,282,328 B2 | 10/2007 | Kong et al. |
| 7,297,518 B2 | 11/2007 | Quake |
| 7,315,019 B2 | 1/2008 | Turner |
| 7,329,492 B2 | 2/2008 | Hardin |
| 7,358,047 B2 | 4/2008 | Hafner et al. |
| 7,361,488 B2 | 4/2008 | Fan et al. |
| 7,375,234 B2 | 5/2008 | Sharpless et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,427,678 B2 | 9/2008 | Pieken et al. |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,700,286 B2 | 4/2010 | Stroun et al. |
| 7,709,198 B2 | 5/2010 | Luo et al. |
| 7,754,429 B2 | 7/2010 | Rigatti |
| 7,776,547 B2 | 8/2010 | Roth |
| 7,776,567 B2 | 8/2010 | Mao |
| 7,785,869 B2 | 8/2010 | Belgrader et al. |
| 7,803,943 B2 | 9/2010 | Mao |
| 7,844,940 B2 | 11/2010 | Shin et al. |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,960,120 B2 | 6/2011 | Rigatti |
| 7,985,565 B2 | 7/2011 | Mayer et al. |
| 8,003,354 B2 | 8/2011 | Shen et al. |
| 8,030,477 B2 | 10/2011 | Cerrina et al. |
| 8,076,063 B2 | 12/2011 | Fan |
| 8,092,784 B2 | 1/2012 | Mao |
| 8,148,068 B2 | 4/2012 | Brenner |
| 8,148,518 B2 | 4/2012 | Buchanan |
| 8,198,028 B2 | 6/2012 | Rigatti et al. |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |

(56) References Cited

U.S. PATENT DOCUMENTS

| | | |
|---|---|---|
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,486,625 B2 | 7/2013 | Gunderson |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| RE44,596 E | 11/2013 | Stroun et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,778,849 B2 | 7/2014 | Bowen |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,895,249 B2 | 11/2014 | Shen |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,889,422 B2 | 2/2018 | Smith et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,138,509 B2 | 11/2018 | Church et al. |
| 10,144,966 B2 | 12/2018 | Cantor |
| 10,179,932 B2 | 1/2019 | Church et al. |
| 10,208,982 B2 | 2/2019 | Bannish et al. |
| 10,227,639 B2 | 3/2019 | Levner et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |

(56) References Cited

U.S. PATENT DOCUMENTS

| | | |
|---|---|---|
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0137031 A1 | 9/2002 | Wolber |
| 2002/0164611 A1 | 11/2002 | Bamdad |
| 2002/0168645 A1 | 11/2002 | Taylor |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0073086 A1 | 4/2003 | Guire et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0175844 A1 | 9/2003 | Nadler et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0224326 A1 | 11/2004 | Kim et al. |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0116161 A1 | 6/2005 | Hafeman et al. |
| 2005/0130173 A1 | 6/2005 | Leamon et al. |
| 2005/0130188 A1 | 6/2005 | Walt |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0244850 A1 | 11/2005 | Huang |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0199207 A1 | 9/2006 | Matysiak |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0275799 A1 | 12/2006 | Banerjee et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0231823 A1 | 10/2007 | McKernan |
| 2007/0254305 A1 | 11/2007 | Paik et al. |
| 2007/0264656 A1 | 11/2007 | Kawamura |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0032301 A1 | 2/2008 | Rank et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0280773 A1 | 11/2008 | Fedurco et al. |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0062148 A1 | 3/2009 | Goldberg |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0009871 A1 | 1/2010 | Reed et al. |
| 2010/0035249 A1 | 2/2010 | Hayashizaki et al. |
| 2010/0055733 A1 | 3/2010 | Lutolf et al. |
| 2010/0069263 A1 | 3/2010 | Shendure et al. |
| 2010/0105052 A1 | 4/2010 | Drmanac et al. |
| 2010/0105112 A1 | 4/2010 | Heltze et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0137143 A1 | 6/2010 | Rothberg et al. |
| 2010/0145037 A1 | 6/2010 | Brive et al. |
| 2010/0151464 A1 | 6/2010 | Stuelpnagel et al. |
| 2010/0159446 A1 | 6/2010 | Haff et al. |

(56) References Cited

U.S. PATENT DOCUMENTS

| | | |
|---|---|---|
| 2010/0173384 A1 | 7/2010 | Johnsson et al. |
| 2010/0184614 A1 | 7/2010 | Ye et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2010/0282617 A1 | 11/2010 | Rothberg et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0059865 A1 | 3/2011 | Smith et al. |
| 2011/0111409 A1 | 5/2011 | Sinicropi et al. |
| 2011/0152111 A1 | 6/2011 | Fan et al. |
| 2011/0244448 A1 | 10/2011 | Shirai et al. |
| 2011/0245101 A1 | 10/2011 | Chee et al. |
| 2011/0245111 A1 | 10/2011 | Chee |
| 2011/0275077 A1 | 11/2011 | James |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0129248 A1 | 5/2012 | Chee et al. |
| 2012/0135871 A1 | 5/2012 | van Eijk et al. |
| 2012/0156728 A1 | 6/2012 | Li et al. |
| 2012/0157322 A1 | 6/2012 | Myllykangas |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0270305 A1 | 10/2012 | Reed et al. |
| 2012/0270748 A1 | 10/2012 | Chee et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0065768 A1 | 3/2013 | Zheng et al. |
| 2013/0065788 A1 | 3/2013 | Glezer et al. |
| 2013/0079232 A1 | 3/2013 | Kain et al. |
| 2013/0096033 A1 | 4/2013 | Routenberg |
| 2013/0109595 A1 | 5/2013 | Routenberg |
| 2013/0244884 A1 | 9/2013 | Jacobson et al. |
| 2013/0260372 A1 | 10/2013 | Buermann et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0079923 A1 | 3/2014 | George et al. |
| 2014/0121118 A1 | 5/2014 | Warner |
| 2014/0155295 A1 | 6/2014 | Hindson et al. |
| 2014/0243224 A1 | 8/2014 | Barnard et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378345 A1 | 12/2014 | Hindson et al. |
| 2014/0378350 A1 | 12/2014 | Hindson et al. |
| 2015/0005447 A1 | 1/2015 | Berti et al. |
| 2015/0087027 A1 | 3/2015 | Makarov et al. |
| 2015/0148239 A1 | 5/2015 | Jon |
| 2015/0219618 A1 | 8/2015 | Krishnan et al. |
| 2015/0246336 A1 | 9/2015 | Somoza et al. |
| 2015/0292988 A1 | 10/2015 | Bharadwaj et al. |
| 2015/0344942 A1 | 12/2015 | Frisen et al. |
| 2015/0376609 A1 | 12/2015 | Hindson et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |
| 2017/0283860 A1 | 4/2017 | Kool et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0253918 A1 | 9/2017 | Kohman |
| 2017/0275669 A1 | 9/2017 | Weissleder et al. |
| 2017/0335297 A1 | 11/2017 | Ha et al. |
| 2017/0335410 A1 | 11/2017 | Driscoll et al. |
| 2017/0343545 A1 | 11/2017 | Hadrup et al. |
| 2017/0349940 A1 | 12/2017 | Morin et al. |
| 2018/0052081 A1 | 2/2018 | Kohman |
| 2018/0057873 A1 | 3/2018 | Zhou et al. |
| 2018/0094316 A1 | 4/2018 | Oliphant et al. |
| 2018/0105808 A1 | 4/2018 | Mikkelsen et al. |
| 2018/0112261 A1 | 4/2018 | Van Driel et al. |
| 2018/0127817 A1 | 5/2018 | Borchert et al. |
| 2018/0156784 A1 | 6/2018 | Usmani et al. |
| 2018/0163265 A1 | 6/2018 | Zhang et al. |
| 2018/0179591 A1 | 6/2018 | van Eijk |
| 2018/0180601 A1 | 6/2018 | Pedersen et al. |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0017106 A1 | 1/2019 | Frisen et al. |
| 2019/0024153 A1 | 1/2019 | Frisen et al. |
| 2019/0024154 A1 | 1/2019 | Frisen et al. |
| 2019/0032121 A1 | 1/2019 | Daugharthy et al. |
| 2019/0055594 A1 | 2/2019 | Samusik et al. |
| 2019/0064173 A1 | 2/2019 | Bharadwaj et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |

(56) References Cited

U.S. PATENT DOCUMENTS

| | | |
|---|---|---|
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |

(56) References Cited

U.S. PATENT DOCUMENTS

| | | |
|---|---|---|
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| EP | 3425053 | 8/2020 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1999/044062 | 9/1999 |
| WO | WO 1999/044063 | 9/1999 |
| WO | WO 1999/063385 | 12/1999 |
| WO | WO 1999/067641 | 12/1999 |
| WO | WO 2000/017390 | 3/2000 |
| WO | WO 2000/063437 | 10/2000 |
| WO | WO 2001/006012 | 1/2001 |
| WO | WO 2001/007915 | 2/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/113804 | 12/2005 |
| WO | WO 2006/020515 | 2/2006 |
| WO | WO 2006/064199 | 6/2006 |
| WO | WO 2006/124771 | 11/2006 |
| WO | WO 2007/010251 | 1/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/022332 | 2/2008 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/014879 | 2/2011 |
| WO | WO 2011/062933 | 5/2011 |
| WO | WO 2011/068088 | 6/2011 |
| WO | WO 2011/071943 | 6/2011 |
| WO | WO 2011/094669 | 8/2011 |
| WO | WO 2011/127099 | 10/2011 |
| WO | WO 2012/049316 | 4/2012 |
| WO | WO 2012/071428 | 5/2012 |
| WO | WO 2012/129242 | 9/2012 |
| WO | WO 2012/139110 | 10/2012 |
| WO | WO 2012/140224 | 10/2012 |
| WO | WO 2012/148477 | 11/2012 |
| WO | WO 2012/159089 | 11/2012 |
| WO | WO 2012/168003 | 12/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/085725 | 6/2014 |
| WO | WO 2014/130576 | 8/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210225 | 12/2014 |
| WO | WO 2014/210233 | 12/2014 |
| WO | WO 2015/031691 | 3/2015 |
| WO | WO 2015/069374 | 5/2015 |
| WO | WO 2015/085275 | 6/2015 |
| WO | WO 2015/161173 | 10/2015 |
| WO | WO 2016/007839 | 1/2016 |
| WO | WO 2016/057552 | 4/2016 |
| WO | WO 2016/077763 | 5/2016 |
| WO | WO 2016/126882 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/027367 | 2/2017 |
| WO | WO 2017/027368 | 2/2017 |
| WO | WO 2017/075293 | 5/2017 |
| WO | WO 2017/096158 | 7/2017 |
| WO | WO 2017/143155 | 8/2017 |
| WO | WO 2017/144338 | 8/2017 |
| WO | WO 2017/147483 | 8/2017 |
| WO | WO 2017/156336 | 9/2017 |
| WO | WO 2017/184984 | 10/2017 |
| WO | WO 2017/192633 | 11/2017 |
| WO | WO 2017/222453 | 12/2017 |
| WO | WO 2018/022809 | 2/2018 |
| WO | WO 2018/023068 | 2/2018 |
| WO | WO 2018/026873 | 2/2018 |
| WO | WO 2018/045181 | 3/2018 |
| WO | WO 2018/045186 | 3/2018 |
| WO | WO 2018/057999 | 3/2018 |
| WO | WO 2018/064640 | 4/2018 |
| WO | WO 2018/075693 | 4/2018 |
| WO | WO 2018/085599 | 5/2018 |
| WO | WO 2018/091676 | 5/2018 |

(56) References Cited

FOREIGN PATENT DOCUMENTS

| | | |
|---|---|---|
| WO | WO 2018/107054 | 6/2018 |
| WO | WO 2018/136397 | 7/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/075091 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/098810 | 5/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/086880 | 5/2023 |

OTHER PUBLICATIONS

U.S. Appl. No. 13/080,616, filed Oct. 6, 2011, Chee.
U.S. Appl. No. 16/353,937, filed Mar. 14, 2019, Frisen et al.
U.S. Appl. No. 17/707,189, filed Mar. 29, 2022, Chell et al.
U.S. Appl. No. 60/416,118, filed Oct. 3, 2002, Fan et al.
U.S. Appl. No. 61/267,363, filed Dec. 7, 2009, Fan et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrNOcH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.

(56) References Cited

OTHER PUBLICATIONS

Abaan et al., "The exomes of the NCI-60 panel: a genomic resource for cancer biology and systems pharmacology," Cancer Res., Jul. 2013, 73(14):4372-82.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Agbavwe et al., "Efficiency, error and yield in light-directed maskless synthesis of DNA microarrays," Journal of Nanobiotechnology, Dec. 2011, 9:57, 17 pages.
Ahmed et al., "Hydrogel: Preparation, characterization, and applications: A review," J Adv Res., Mar. 2015, 6(2):105-21.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Algayer et al., "Novel pH Selective, Highly Lytic Peptides Based on a Chimeric Influenza Hemagglutinin Peptide/Cell Penetrating Peptide Motif," Molecules, May 2019, 24(11):2079, 23 pages.
Allawi et al., "Thermodynamics and NMR of Internal G·T Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Deciphering the Antibodyome—Peptide Arrays for Serum Antibody Biomarker Diagnostics," Current Proteomics, 6(1):1-12, 2009.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asano et al., "Expansion Microscopy: Protocols for Imaging Proteins and RNA in Cells and Tissues," Curr Protoc Cell Biol., Sep. 2018, 80(1):e56, 41 pages.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.

Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Bechara et al., "Cell-penetrating peptides: 20 years later, where do we stand?," FEBS Lett., Jun. 2013, 587(12):1693-702.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Beier et al., "Versatile derivatisation of solid support media for covalent bonding on DNA-microchips," Nucleic Acids Res., May 1999, 27(9):1970-7.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolognesi et al., "Multiplex Staining by Sequential Immunostaining and Antibody Removal on Routine Tissue Sections," J. Histochem. Cytochem., Aug. 2017, 65(8):431-444.
Bolotin et al., "MiXCR: software for comprehensive adaptive immunity profiling," Nat Methods., May 2015, 12(5):380-1.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.

(56) References Cited

OTHER PUBLICATIONS

Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Carter et al., "Stabilization of an optical microscope to 0.1 nm in three dimensions," Applied Optics, 2007, 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chatterjee et al., "Protein Microarray On-Demand: A Novel Protein Microarray System," PLos One, 2008, 3(9):e3265, 5 pages.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cheung et al., "Chitosan: An Update on Potential Biomedical and Pharmaceutical Applications," Mar Drugs, Aug. 2015, 13(8):5156-86.
Chiang et al., "NFkappaB translocation in human microvessel endothelial cells using a four-compartment subcellular protein redistribution assay," J Biochem Biophys Methods, Nov. 2000, 46(1-2):53-68.
Choi et al., "Recent advances in photo-crosslinkable hydrogels for biomedical applications," Biotechniques, Jan. 2019, 66(1):40-53.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Cockroft et al., "A single-molecule nanopore device detects DNA polymerase activity with single-nucleotide resolution," J Am Chem Soc., Jan. 2008, 130(3):818-20.
Codeluppi et al., "Spatial organization of the somatosensory cortex revealed by osmFISH," Nature Methods, Nov. 2018, 15:932-935.
Condina et al., "A sensitive magnetic bead method for the detection and identification of tyrosine phosphorylation in proteins by MALDI-TOF/TOF MS," Proteomics, 2009, 9:3047-3057.
Constantine et al., "Use of genechip high-density oligonucleotide arrays for gene expression monitoring," Life Science News, Amersham Life Science, 1998, pp. 11-14.
Cook et al., "The effects of secondary structure and O2 on the formation of direct strand breaks upon UV irradiation of 5-bromodeoxyuridine-containing oligonucleotides," Chem Biol., Jul. 1999, 6(7):451-9.
Corces et al., "An improved ATAC-seq protocol reduces background and enables interrogation of frozen tissues," Nat. Methods, 2017, 14(10):959-962.
Cox et al., "Tissue subcellular fractionation and protein extraction for use in mass-spectrometry-based proteomics," Nat Protoc., 2006, 1(4):1872-8.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Doddridge et al., "UV-induced strand break damage in single stranded bromodeoxyuridine-containing DNA oligonucleotides," Chem Commun., 1998, p. 1997-1998.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "Accurate sequencing by hybridization for DNA diagnostics and individual genomics," Nature Biotechnology, 16:54-58, 1998.
Drmanac et al., "CoolMPS™: Advanced massively parallel sequencing using antibodies specific to each natural nucleobase," BioRxiv, 2020, 19 pages.

(56) References Cited

OTHER PUBLICATIONS

Druley et al., "Quantification of rare allelic variants from pooled genomic DNA," Nat. Methods, 2009, 6(4):263-65.
Dtp.cancer.gov, [online], "A Catalog of in Vitro Cell Lines, Transplantable Animal and Human Tumors and Yeast," The Division of Cancer Treatment and Diagnosis (DCTD), National Cancer Institute, May 5, 2020, retrieved on Jun. 7, 2021, retrieved from URL<https://dtp.cancer.gov/organization/btb/docs/DCTDTumor-RepositoryCatalog.pdf>, 77 pages.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi-C," Trends in Biochemical Sciences, Jun. 2018, 43(6):469-478.
Eberwine, "Amplification of mRNA populations using aRNA generated from immobilized oligo(dT)-T7 primed cDNA," BioTechniques, 1996, 20(4):584-91.
Echeverria et al., "Functional Stimuli-Responsive Gels: Hydrogels and Microgels," Gels., Jun. 2018, 4(2):54, 37 pages.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.
Evers et al., "The effect of formaldehyde fixation on RNA: optimization of formaldehyde adduct removal," J Mol Diagn., May 2011, 13(3):282-8.
Fahy et al., "Design and synthesis of polyacrylamide-based oligonucleotide supports for use in nucleic acid diagnostics," Nucleic Acids Res., Apr. 1993, 21(8):1819-26.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Faruqi et al., "High-throughput genotyping of single nucleotide polymorphisms with rolling circle amplification," BMC Genomics, Aug. 2001, 2:4, 10 pages.
Ferreira et al., "Photocrosslinkable Polymers for Biomedical Applications," Biomedical Engineering- Frontiers and Challenges, Prof. Reza, 2011, 22 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forcucci et al., "All-plastic miniature fluorescence microscope for point-of-care readout of bead-based bioassays.," J. Biomed Opt., 2015, 20(10):105010, 15 pages.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gans et al., "Inkjet Printing of Polymers: State of the Art and Future Developments," Advanced Materials, Feb. 2004, 16(3):203-213.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gould et al., "Selective lysis of breast carcinomas by simultaneous stimulation of sodium channels and blockade of sodium pumps," Oncotarget, Feb. 2018, 9(21):15606-15615.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.

(56) References Cited

OTHER PUBLICATIONS

Gudjonsson et al., "Myoepithelial cells: their origin and function in breast morphogenesis and neoplasia," J Mammary Gland Biol Neoplasia, Jul. 2005, 10(3):261-72.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells, " Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Han et al., "Isolation of intact bacteria from blood by selective cell lysis in a microfluidic porous silica monolith," Microsyst Nanoeng., Jun. 2019, 5:30, 11 pages.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hein et al., "Click Chemistry, A Powerful Tool for Pharmaceutical Sciences," Pharm Res, 2008, 25(10): 2216-2230.
Hejatko et al., "In situ hybridization technique for mRNA detection in whole mount *Arabidopsis* samples," Nature Protocols, 2006, 1(4):1939-1946.
Hernandez et al., "Solution-phase and solid-phase sequential, selective modification of side chains in KDYWEC and KDYWE as models for usage in single-molecule protein sequencing," New J Chem., Jan. 2017, 41(2):462-469.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Hipp et al., "A novel BCMA/CD3 bispecific T-cell engager for the treatment of multiple myeloma induces selective lysis in vitro and in vivo," Leukemia, Oct. 2017, 31(10):2278, 31 pages.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Holmstrøm et al., "A highly sensitive and fast nonradioactive method for detection of polymerase chain reaction products," Anal Biochem, Mar. 1993, 209(2):278-83.

Hölz et al., "High-Efficiency Reverse (5'→3') Synthesis of Complex DNA Microarrays," Scientific Reports, Oct. 2018, 8(1):15099, 12 pages.
Hoyer et al., "Electrostatic spraying: a novel technique for preparation of polymer coatings on electrodes," Anal Chem, Nov. 1996, 68(21):3840-4.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jennane et al., "Photolithography of self-assembled monolayers: optimization of protecting groups by an electroanalytical method," Can. J Chem., Dec. 1996, 74(12):2509-2517.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Joos et al., "Covalent attachment of hybridizable oligonucleotides to glass supports," Anal Biochem., Apr. 1997, 247(1):96-101.
Jucá et al., "Effect of dimethyl sulfoxide on reverse transcriptase activity," Braz. J. Med. Biol. Res., Mar. 1995, 28(3):285-90.
Juliano, "The delivery of therapeutic oligonucleotides," Nucleic Acids Res., Aug. 2016, 44(14):6518-6548.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLOS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kashyap et al., "Selective local lysis and sampling of live cells for nucleic acid analysis using a microfluidic probe," Sci Rep., Jul. 2016, 6:29579, 10 pages.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1):173-86.

(56) References Cited

OTHER PUBLICATIONS

Kleckner et al., "Tn10 and IS10 transposition and chromosome rearrangements: mechanism and regulation in vivo and in vitro," Curr Top Microbiol Immunol., 1996, 204:49-82.
Koch et al., "Photochemical immobilization of anthraquinone conjugated oligonucleotides and PCR amplicons on solid surfaces," Bioconjugate Chem., Jul. 2000, 11(4):474-483.
Kolb et al., "Click Chemistry: Diverse Chemical Function from a Few Good Reactions," Angew. Chem. Int. Ed., Jun. 2001, 40(11):2004-2021.
Kolbert et al., "Ribosomal DNA sequencing as a tool for identification of bacterial pathogens," Curr Opin Microbiol, Jun. 1999, 2(3):299-305.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA, 2008, 105:1176-1181.
Kozlov et al., "A highly scalable peptide-based assay system for proteomics," Plos One, 2012, 7(6):e37441, 10 pages.
Kozlov et al., "A method for rapid protease substrate evaluation and optimization," Comb Chem High Throughput Screen, 2006, 9(6):481-87.
Kretschy et al., "Next-Generation o-Nitrobenzyl Photolabile Groups for Light-Directed Chemistry and Microarray Synthesis," Angewandte Chemie International Edition, Jul. 2015, 54(29):8555-8559.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Lamture et al., "Direct detection of nucleic acid hybridization on the surface of a charge coupled device," Nucleic Acid Res., Jun. 1994, 22(11):2121-5.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Larman et al., "Sensitive, multiplex and direct quantification of RNA sequences using a modified RASL assay," Nucleic Acids Research, 2014, 42(14):9146-9157.
Lee et al., "Assembly of metallic nanoparticle arrays on glass via nanoimprinting and thin-film dewetting," Beilstein J Nanotechnol., May 2017, 8:1049-1055.
Lee et al., "Fluorescent in situ sequencing (FISSEQ) of RNA for gene expression profiling in intact cells and tissues," Nature Protocols, 2015, 10(3):442-458.

Lee et al., "Highly multiplexed subcellular RNA sequencing in situ", Science, 2014, 343(6177):1360-1363.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Levene et al., "Zero-Mode Waveguides for Single-Molecule Analysis at High Concentrations," Science, 2003, 299:682-686.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "DNA molecules and configurations in a solid-state nanopore microscope," Nat Mater., Sep. 2003, 2(9):611-5.
Li et al., "Long non-coding RNA linc00645 promotes TGF-β-induced epithelial-mesenchymal transition by regulating miR-205-3p-ZEB1 axis in glioma," Cell Death Dis, Sep. 2019, 10(10):717, 17 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lietard et al., "High-Density RNA Microarrays Synthesized In Situ by Photolithography," Angew. Chem. Int. Ed. Engl., Nov. 2018, 57(46):15257-15261.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "An integrated and sensitive detection platform for biosensing application based on Fe@Au magnetic nanoparticles as bead array carries," Biosens Bioelectron, Dec. 2010, 26(4):1442-8.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Liu et al., "Surface and interface control on photochemically initiated immobilization," J Am Chem Soc., Nov. 2006, 128(43):14067-72.
Lizardi et al., "Mutation detection and single-molecule counting using isothermal rolling-circle amplification," Nat. Genet., 1998, 19(3):225-232.
Long et al., "Printing nanomaterials in shrinking gels," Science, Dec. 2018, 362(6420):1244-1245.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lu et al., "A microfluidic electroporation device for cell lysis," Lab Chip., Jan. 2005, 5(1):23-29.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.

(56) References Cited

OTHER PUBLICATIONS

Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLOS One, Apr. 2010, 5(4):e10029, 7 pages.
Lundquist et al., "Parallel confocal detection of single molecules in real time," Opt. Lett., 2008, 33:1026-1028.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality Dna, Rna and protein analysis," Nucleic Acids Res., Jun. 2007, 35(12):e85, 10 pages.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Macosko et al., "Highly Parallel Genome-wide Expression Profiling of Individual Cells Using Nanoliter Droplets," Cell, 2015, 161:1202-1214.
Martinez-Rivas et al., "Methods of Micropatterning and Manipulation of Cells for Biomedical Applications," Micromachines (Basel), Nov. 2017, 8(12):347, 20 pages.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Mcgee, "Structure and Analysis of Affymetrix Arrays," UTSW Microarray Analysis Course, Oct. 28, 2005, 68 pages.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Mitra et al., "In situ localized amplification and contact replication of many individual DNA molecules," Nucleic Acids Res., Dec. 1999, 27(24):e34, 6 pages.
Mitsuhashi et al., "Gene manipulation on plastic plates," Nature 357: 519-520, 1992.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3 A," Gene, 1982, 20(3):317-322.
Moffitt et al., "RNA Imaging with Multiplexed Error-Robust Fluorescence In Situ Hybridization (MERFISH)," Methods Enzymol., 2016, 572:1-49.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLOS One, Aug. 2012, 7(8):e42882, 8 pages.
Moshrefzadeh et al., "Nonuniform photobleaching of dyed polymers for optical waveguides," Applied Physics Letters, 1993, 62:16-18.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec. 1, 2001, 29(23):e118, 9 pages.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nguyen et al., "Two-photon polymerization for biological applications," Materials Today, Jul. 2017, 20(6):314-322.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.

(56) References Cited

OTHER PUBLICATIONS

Oleinikov et al., "Self-assembling protein arrays using electronic semiconductor microchips and in vitro translation," J Proteome Res, May-Jun. 2003, 2(3): 313-319.
Olivier, "The Invader assay for SNP genotyping," Mutat. Res., Jun. 2005, 573(1-2):103-110.
Oran et al., "3D nanofabrication by volumetric deposition and controlled shrinkage of patterned scaffolds," Science, Dec. 2018, 362(6420):1281-1285.
Oren et al., "Selective lysis of bacteria but not mammalian cells by diastereomers of melittin: structure-function study," Biochemistry, Feb. 1997, 36(7):1826-35.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/EP2016/057355, dated Oct. 10, 2017, 7 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Preliminary Report on Patentability in International Appln. No. PCT/US2019/065013, dated Jun. 8, 2021, 15 pages.
PCT International Search Report and Written Opinion in International Appln. No. PCT/US2019/065013 dated Mar. 3, 2020, 20 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
PCT Invitation to Pay Additional Fees in International Appln. No. PCT/US2019/065013, dated Mar. 19, 2020, 17 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins, " PLOS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Rajeswari et al., "Multiple pathogen biomarker detection using an encoded bead array in droplet PCR," J. Microbial Methods, Aug. 2017, 139:22-28.
Ramachandran et al., "Next-generation high-density self-assembling functional protein arrays," Nature Methods, Jun. 2008, 5(6):535-538.
Ranki et al., "Sandwich hybridization as a convenient method for the detection of nucleic acids in crude samples," Gene, 1983, 21(1-2):77-85.
Raouane et al., "Lipid conjugated oligonucleotides: a useful strategy for delivery," Bioconjug Chem., Jun. 2012, 23(6):1091-104.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Rideau et al., "Liposomes and polymersomes: a comparative review towards cell mimicking," Chem Soc Rev., Nov. 2018, 47(23):8572-8610.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Ronaghi et al., "A sequencing method based on real-time pyrophosphate, " Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rouillard et al., "OligoArray 2.0: design of oligonucleotide probes for DNA microarrays using a thermodynamic approach," Nuc. Acid Research, Jun. 2003, 31(12): 3057-3062.
Roy et al., "Assessing long-distance RNA sequence connectivity via RNA-templated DNA-DNA ligation," eLife, 2015, 4:e03700, 21 pages.
Rubina et al., "Hydrogel-based protein microchips: manufacturing, properties, and applications," Biotechniques, May 2003, 34(5):1008-14.

(56) References Cited

OTHER PUBLICATIONS

Running et al., "A procedure for productive coupling of synthetic oligonucleotides to polystyrene microtiter wells for hybridization capture," Biotechniques, Mar. 1990, 8(3):276-279.
Sack et al., "Express photolithographic DNA microarray synthesis with optimized chemistry and high-efficiency photolabile groups," Journal of Nanobiotechnology, Mar. 2016, 14:14, 13 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schlapak et al., "Glass surfaces grafted with high-density poly (ethylene glycol) as substrates for DNA oligonucleotide microarrays," Langinuir, Jan. 2006, 22: 277-285.
Schouten et al., "Relative quantification of 40 nucleic acid sequences by multiplex ligation-dependent probe amplification," Nucleic Acids Res., Jun. 2002, 30(12):e57, 13 pages.
Schwartz et al., "Capturing native long-range contiguity by in situ library construction and optical sequencing," PNAS, Nov. 13, 2012, 109(46):18749-18754.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Seurynck-Servoss et al., "Evaluation of Surface Chemistries for Antibody Microarrays," Anal Biochem., 371(1):105-115, 2007.
Shalon et al., "A DNA microarray system for analyzing complex DNA samples using two-color fluorescent probe hybridization," Genome Res., Jul. 1996, 6(7):639-45.
Sharma, "Self-Assembly of Colloidal Particles," Resonance, 2018, 23:263-275.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Shirai et al., "Photocrosslinkable polymers with degradable properties," Polymer Journal, Sep. 2014, 46:859-865.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Söderberg et al., "Characterizing proteins and their interactions in cells and tissues using the in situ proximity ligation assay," Methods, Jul. 2008, 45(3):227-32.
Soni and Meller, "Progress toward ultrafast DNA sequencing using solid-state nanopores," Clin Chem., 2007, 53:1996-2001.
Sountoulidis et al., "SCRINSHOT, a spatial method for single-cell resolution mapping of cell states in tissue sections," PLOS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stevens Jr. et al., "Enhancement of phosphoprotein analysis using a fluorescent affinity tag and mass spectrometry," Rapid Commun Mass Spectrom, 2005, 19(15):2157-62.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein—protein interactions," J. Mass Spectrom., Jun. 2008, 43(6):699-715.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," Plos One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12): 1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Van Ness et al., "A versatile solid support system for oligodeoxynucleotide probe-based hybridization assays", Nucleic Acids Res., 19:3345-3350, 1991.
Vandenbroucke et al., "Quantification of splice variants using real-time PCR," Nucleic Acids Research, 2001, 29(13):e68, 7 pages.

(56) References Cited

OTHER PUBLICATIONS

Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization, " Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vlassakis et al., "Effect of Polymer Hydration State on In-Gel Immunoassays," Anal Chem., Nov. 2015, 87(21):11030-8.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging plasma membranes without cellular internalization: multisite membrane anchoring reagents based on glycol chitosan derivatives," J Master Chem B., Aug. 2015, 3(30):6165-6173.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang et al., "Three-dimensional intact-tissue sequencing of single-cell transcriptional states," Science, Jul. 2018, 361(6400):eaat5691, 22 pages.
Wang, "RNA amplification for successful gene profiling analysis," J Transl Med., Jul. 2005, 3:28, 11 pages.
Wassie et al., "Expansion microscopy: principles and uses in biological research," Nat Methods, Jan. 2019, 16(1):33-41.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Willner, "Stimuli-Controlled Hydrogels and Their Applications," Acc Chem Res., Apr. 2017, 50(4):657-658.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1): 10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yamauchi et al., "Subcellular western blotting of single cells," Microsyst Nanoeng., 2017, 3:16079, 9 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Ye et al., "Triggered self-assembly of magnetic nanoparticles," Sci Rep., Mar. 2016, 6:23145, 9 pages.
Yeakley et al., "A trichostatin A expression signature identified by TempO-Seq targeted whole transcriptome profiling," PLOS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Long Non-Coding RNA and Breast Cancer," Technol Cancer Res Treat., Jan. 2019, 18:1-10.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhang et al., "Single-base mutational analysis of cancer and genetic diseases using membrane bound modified oligonucleotides," Nucleic Acids Res., Jul. 1991, 19(14):3929-33.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.

(56) References Cited

OTHER PUBLICATIONS

Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Angenendt et al., "Cell-free Protein expression and functional assay in a nanowell chip format," Analytical Chemistry, 2004, 76(7):1844-49.
Angenendt et al., "Generation of High Density Protein Microarrays by Cell-free in Situ Expression of Unpurified PCR Products," Molecular and Cellular Proteomics, (2006) Ch. 5.9, pp. 1658-1666.
Bibikova et al., "Quantitative gene expression profiling in formalin-fixed paraffin-embedded tissues using universal bead arrays," The American Journal of Pathology, Nov. 1, 2004, 165(5):1799-1807.
Burgess, "Spatial transcriptomics coming of age," Nat Rev Genet., Jun. 2019, 20(6):317, 1 page.
Burns et al., "Well-less, gel-permeation formats for ultra-HTS," DDT, 2001, 6(12):S40-S47.
Chen et al., "Gray-scale photolithography using microfluidic photomasks," PNAS, Feb. 2003, 100(4):1499-1504.
Choi et al., "Multiplexed detection of mRNA using porosity-tuned hydrogel microparticles," Analytical chemistry, Sep. 28, 2012, 84(21):9370-9378.
Extended European Search Report in European Appln. No. 19835341.1, dated May 10, 2023, 6 pages.
Fan et al., "A versatile assay for high-throughput gene expression profiling on universal array matrices," Genome Research, May 1, 2004, 14(5):878-885.
Fan et al., "Highly parallel SNP genotyping," Cold Spring Symp. Quant. Biol., 68: 69-78, 2003.
Gao et al., "High density peptide microarrays. In situ synthesis and applications," Molecular Diversity, 8, 177-187, 2004.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Kozlov et al., "A High-Complexity Multiplexed Solution-Phase Assay for Profiling Protease Activity on Microarrays," Comb. Chem. And High Throughput, 11: 24-35, 2008.
Kumar et al., "Template-directed oligonucleotide strand ligation, covalent intramolecular DNA circularization and catenation using click chemistry," J Am Chem Soc., May 2007, 129(21):6859-64.
Lindstrom et al., "Miniaturization of biological assays—Overview on microwell devices for single-cell analyses," Biochimica et Biophysica Acta, 2011, 1810:308-316.
Nawy, "Spatial transcriptomics", Nature Methods, vol. 15, No. 1, 2018.
Ozsolak et al., "Digital transcriptome profiling from attomole-level RNA samples," Genome Res., Apr. 2010, 20(4):519-25.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Takei et al., "Integrated Spatial Genomics Reveals Global Architecture Of Single Nuclei," Nature, Jan. 27, 2021, 590(7845):344-350, 53 pages.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.

\* cited by examiner

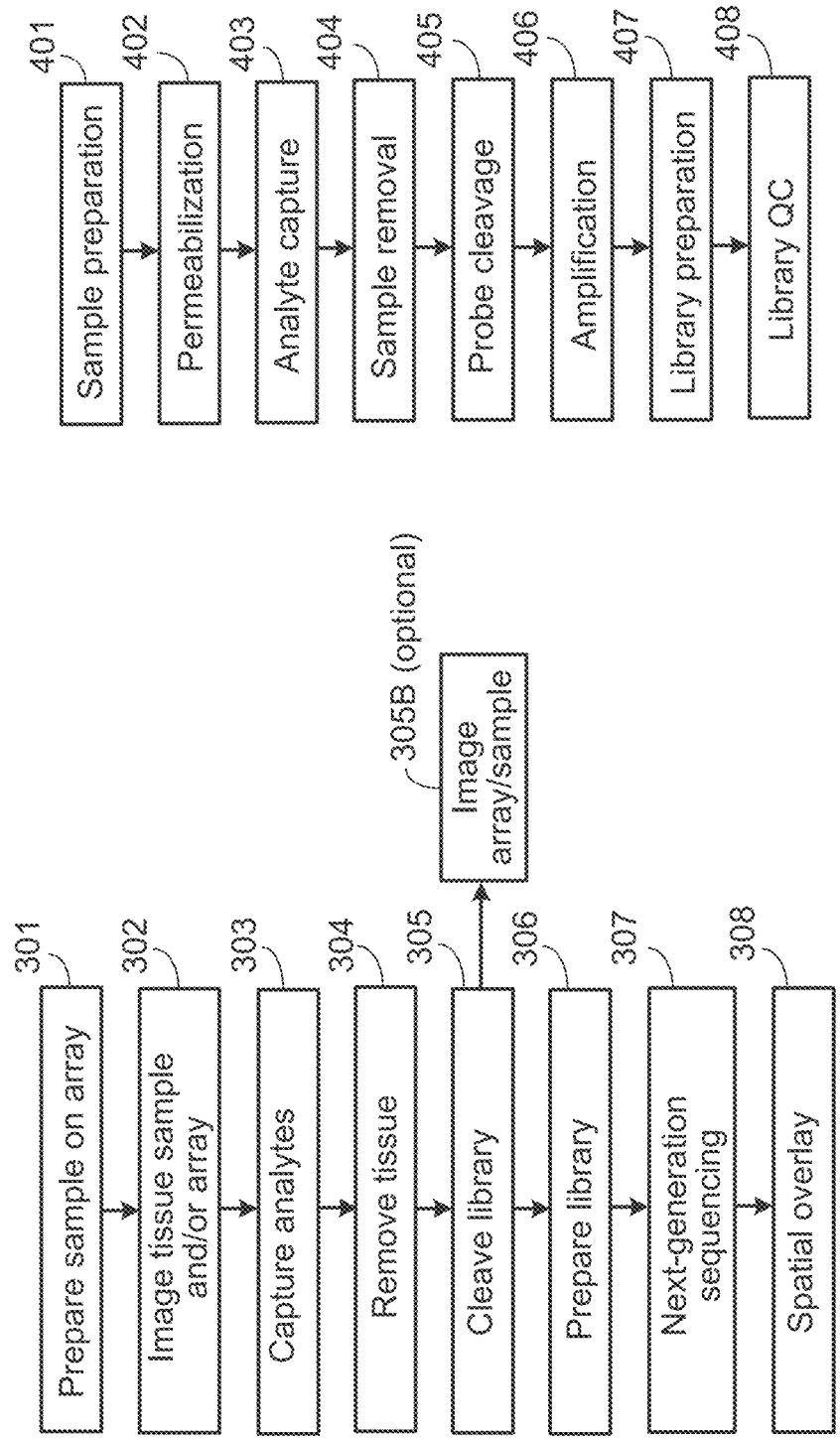

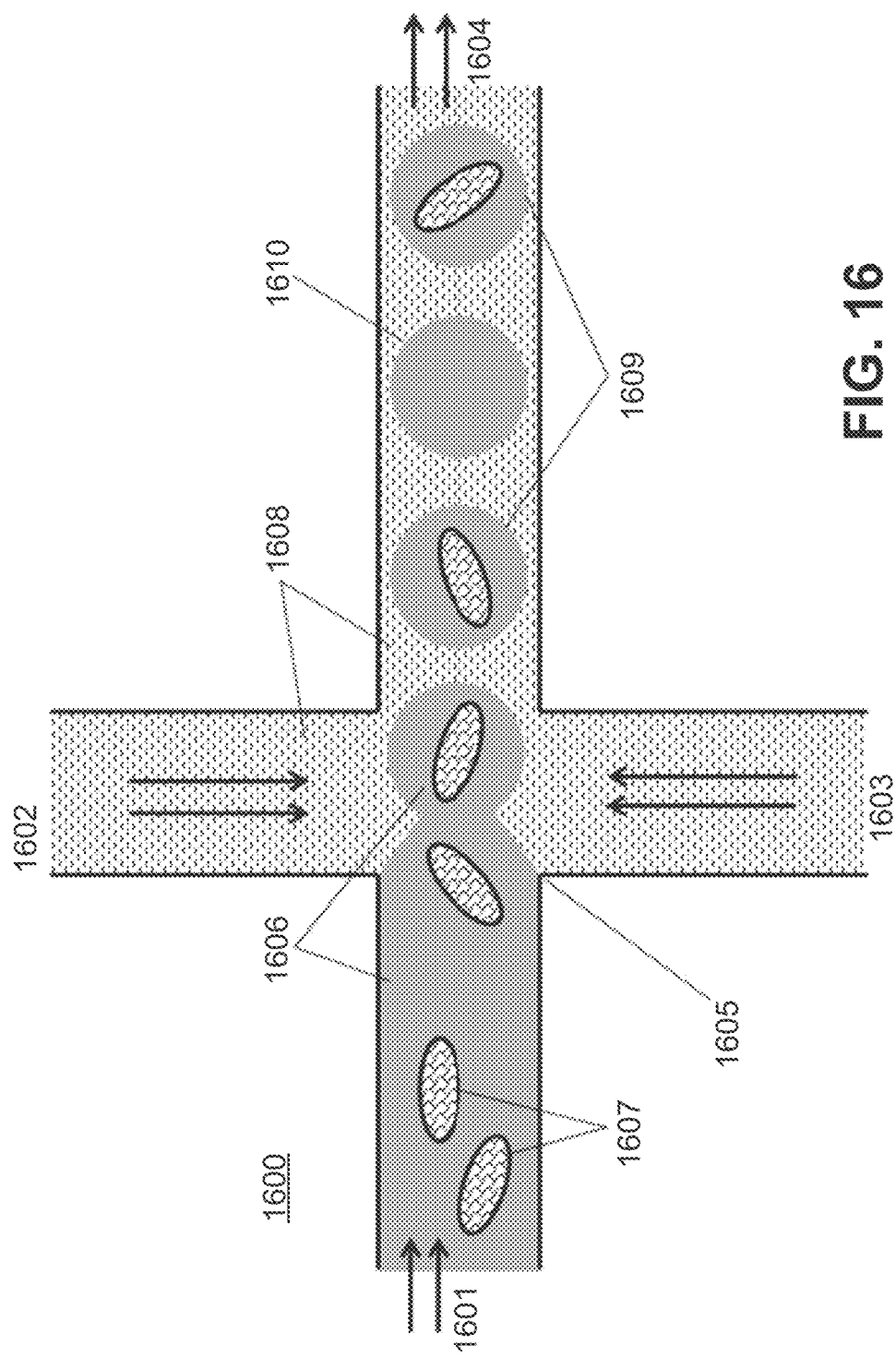

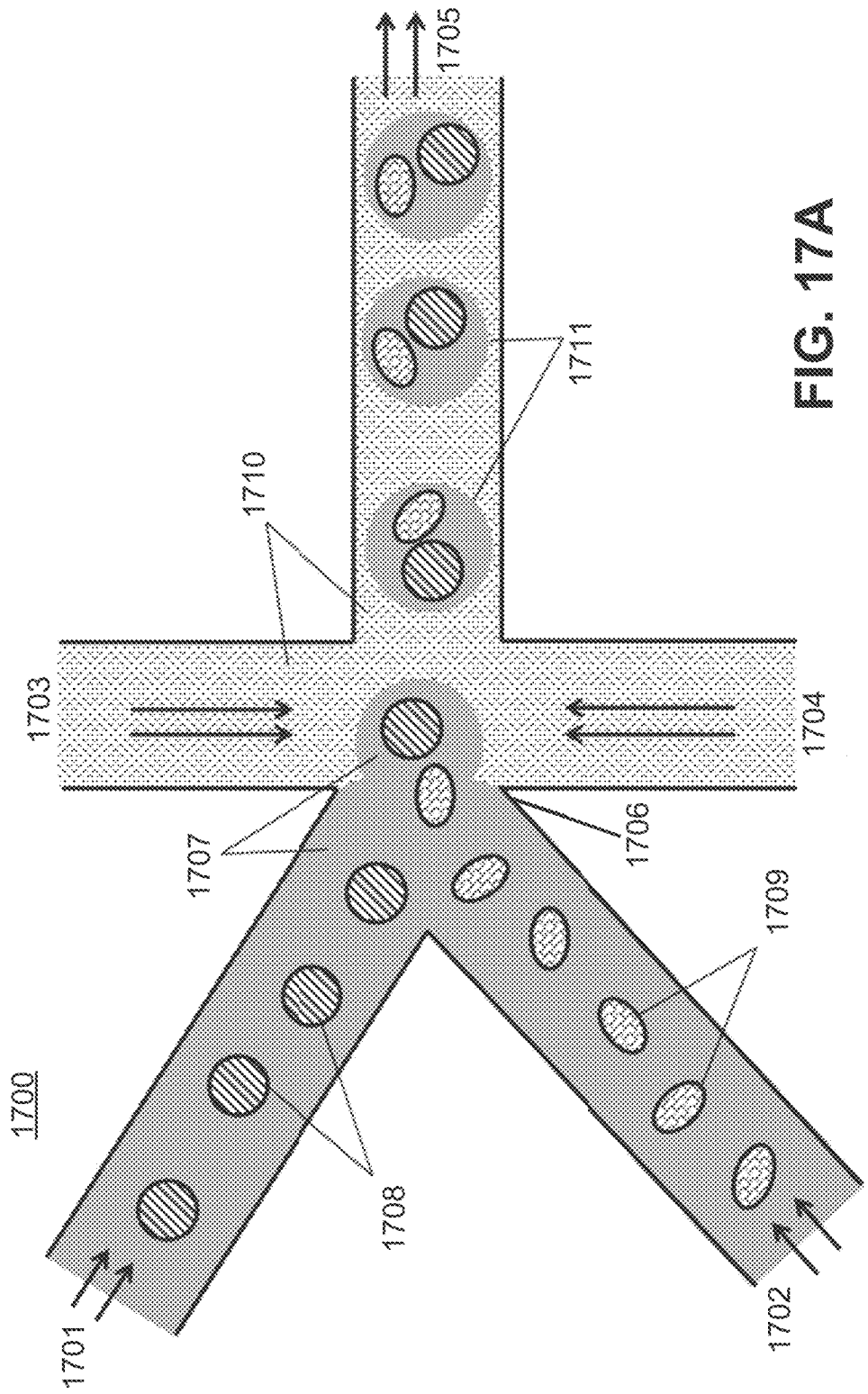

— Inasive carcinoma
— Fibrous tissue
— Ductal Cancer In Situ (DCIS)

▦ Cluster 1
▦ Cluster 2
▦ Cluster 3
▦ Cluster 4
▦ Cluster 5
▦ Cluster 6
▦ Cluster 7
▦ Cluster 8
▦ Cluster 9

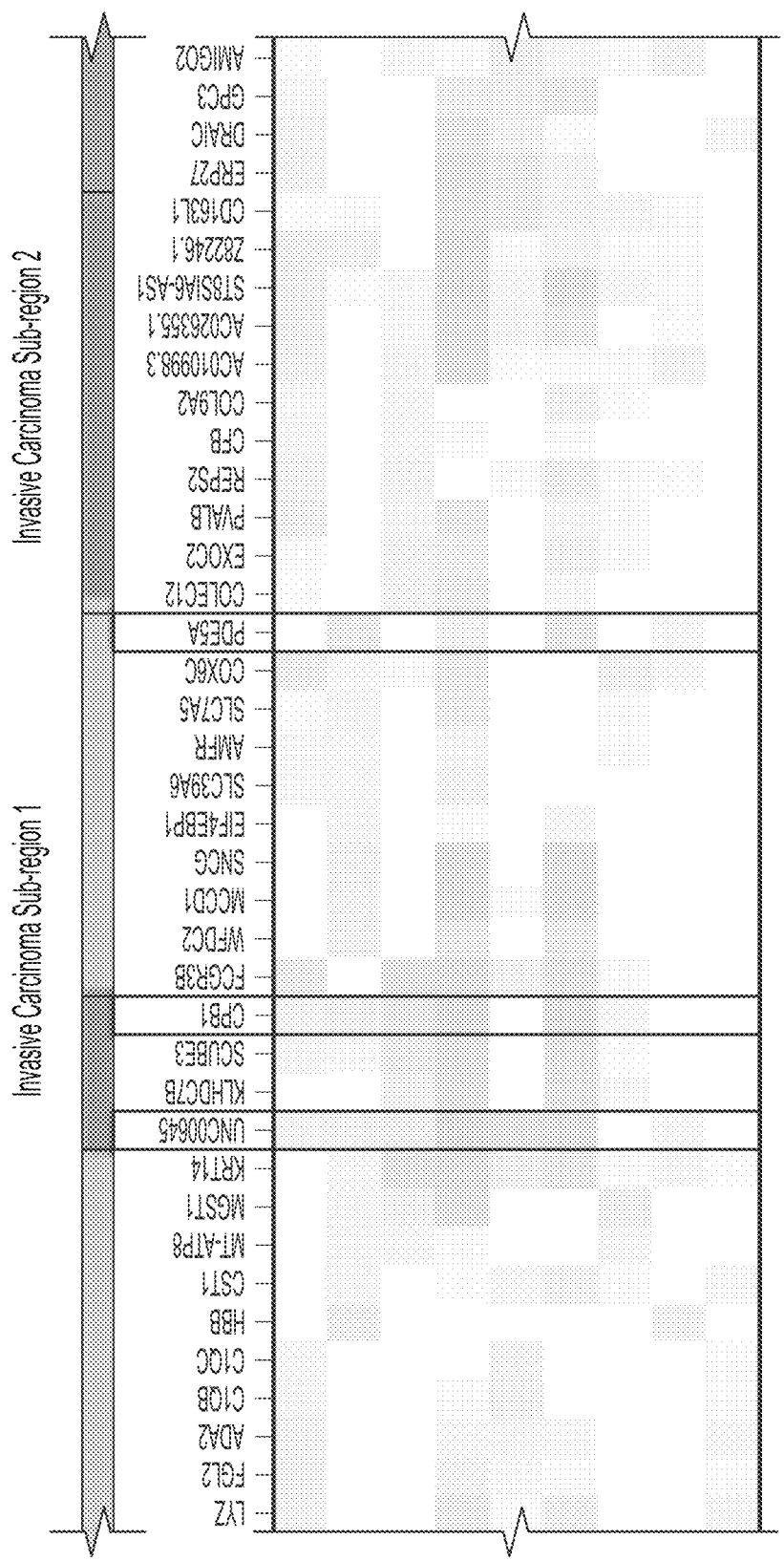
FIG. 23D(Cont. 1)

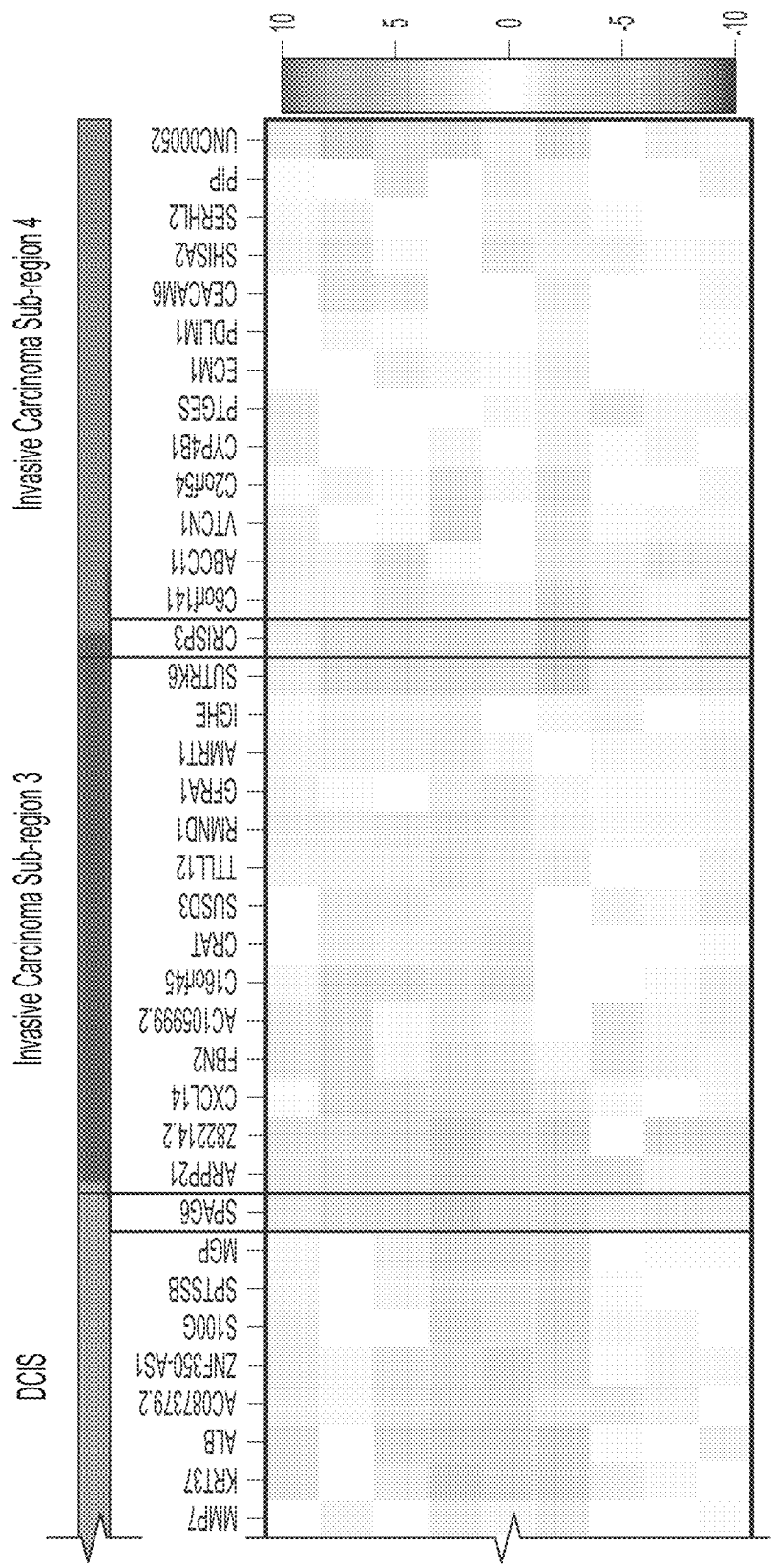
FIG. 23D(Cont. 2)

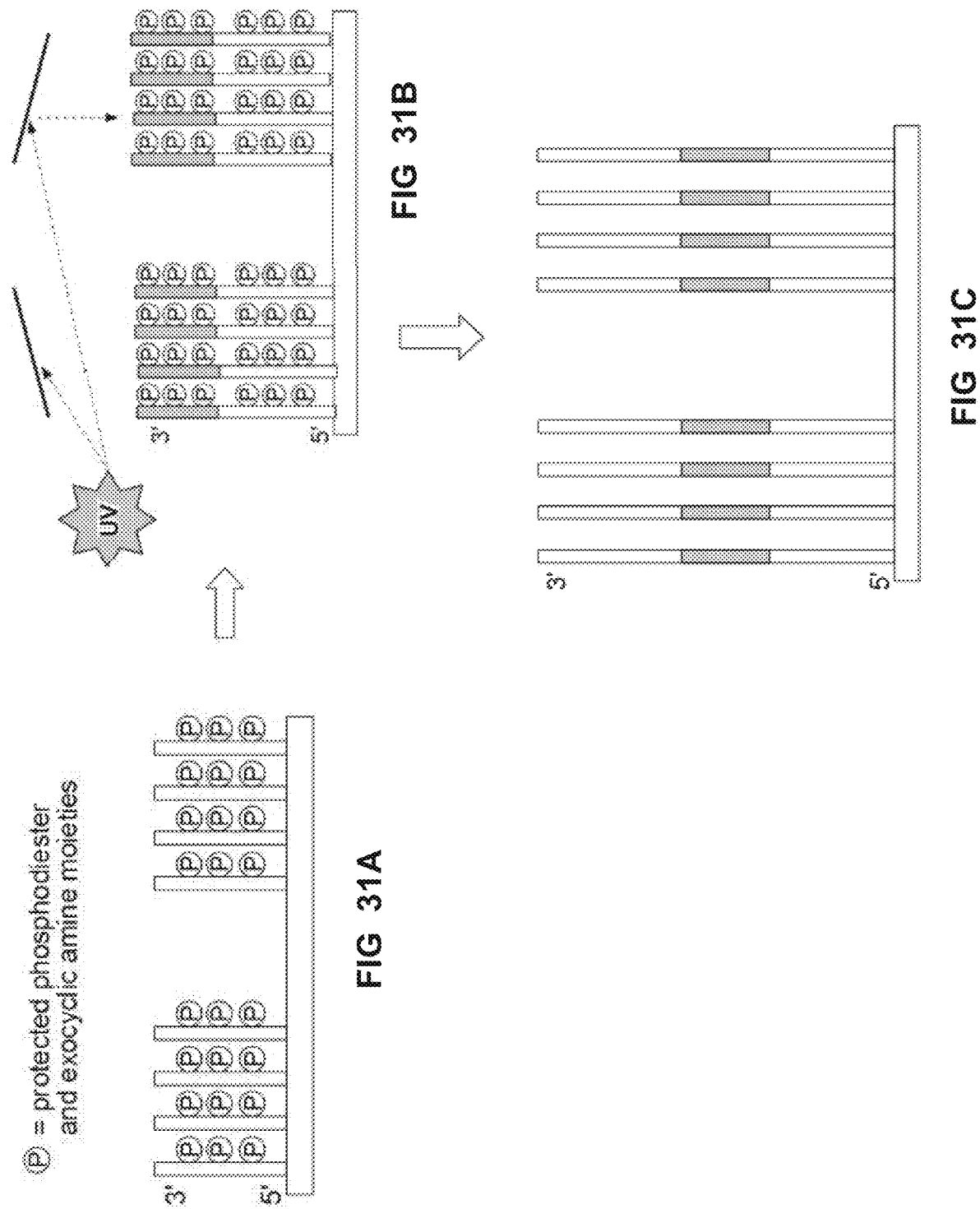

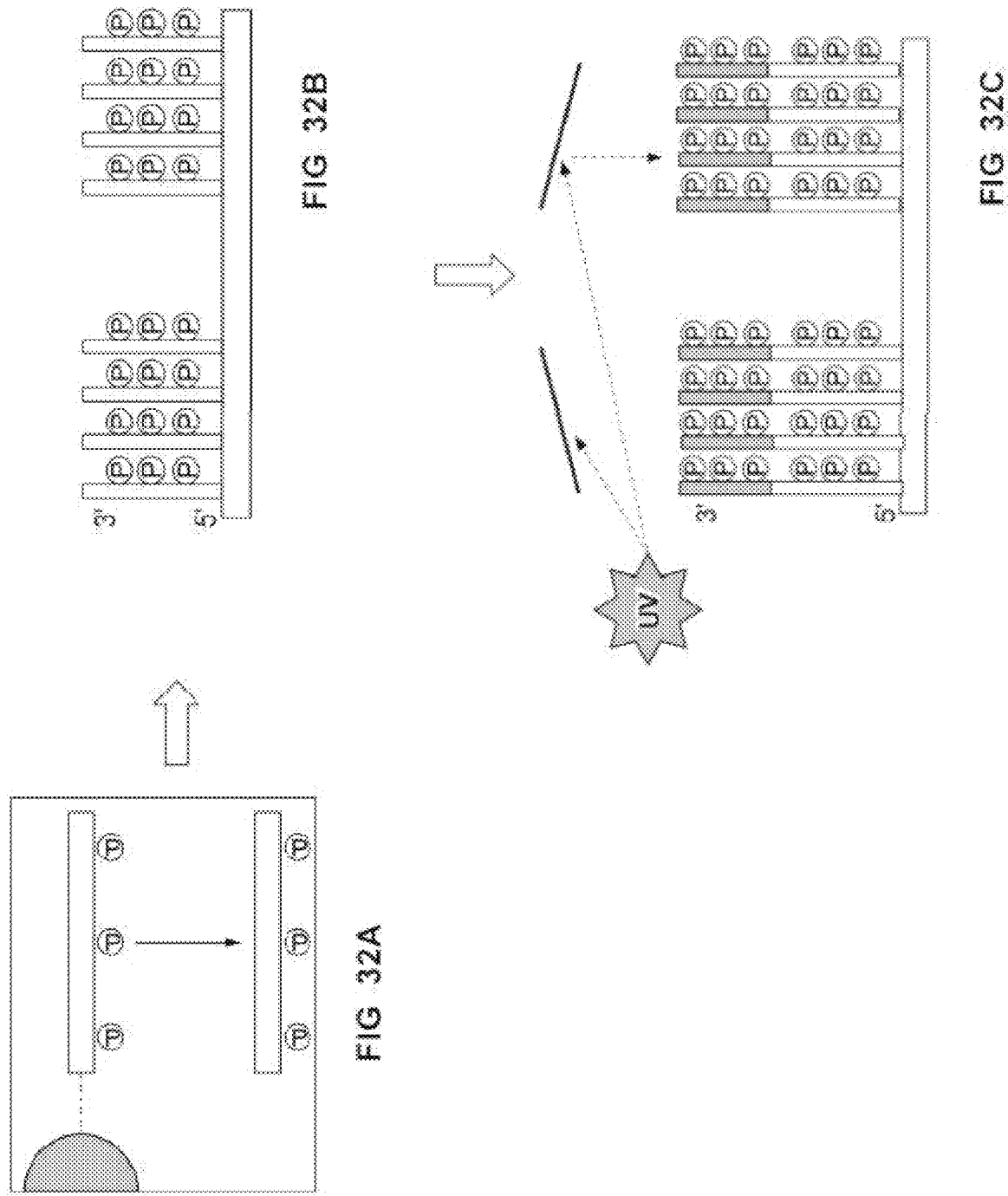

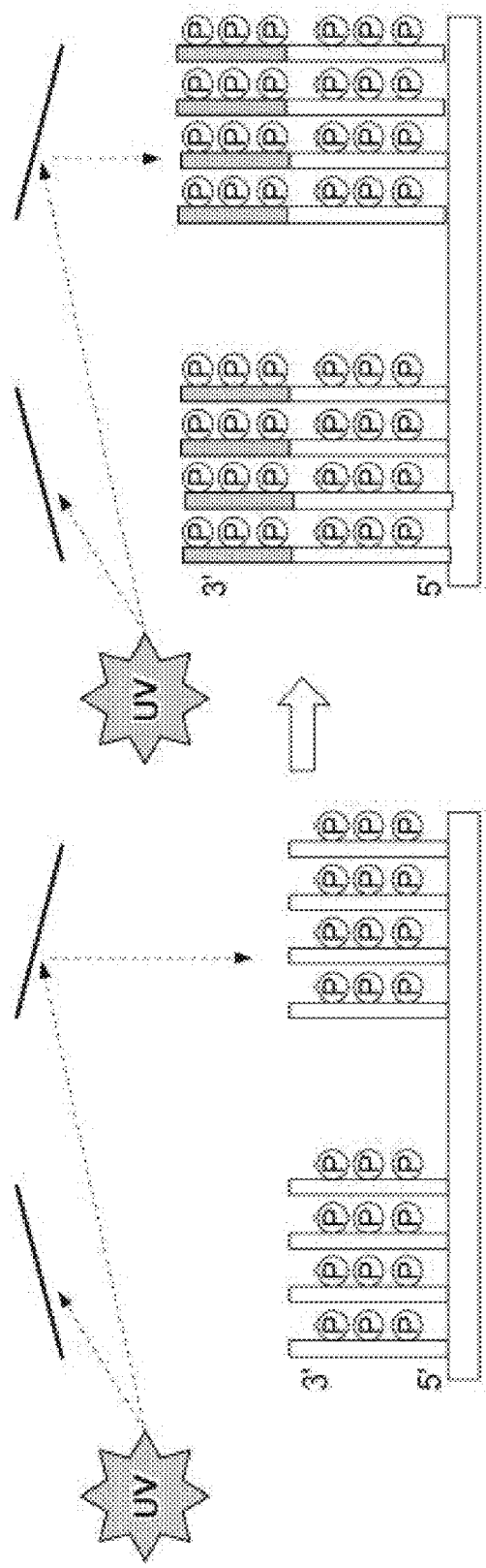

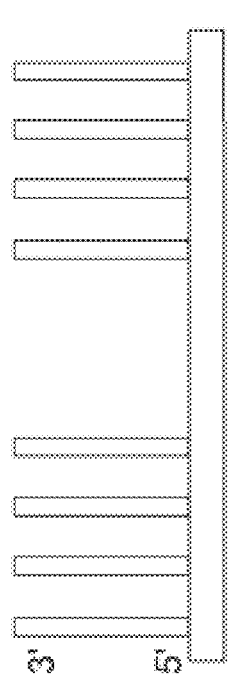
FIG 35A
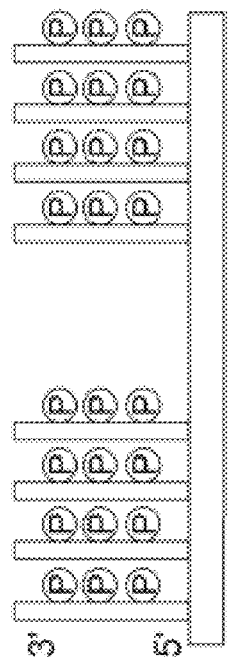
FIG 35B
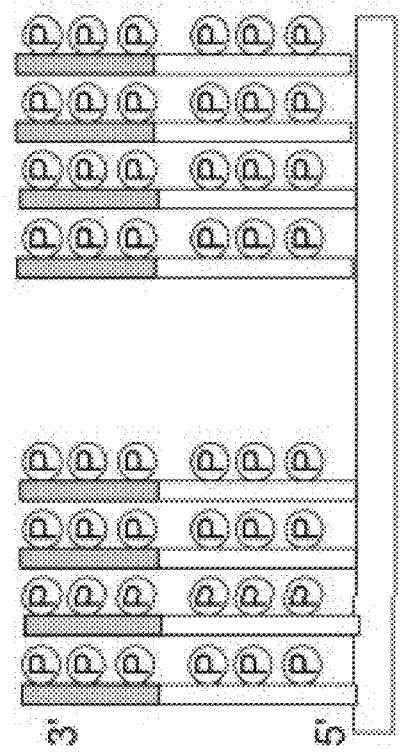
FIG 35C
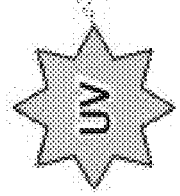

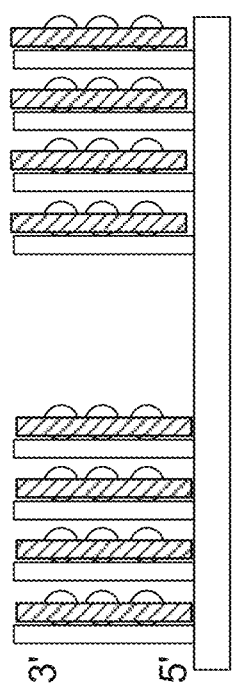
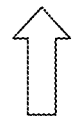
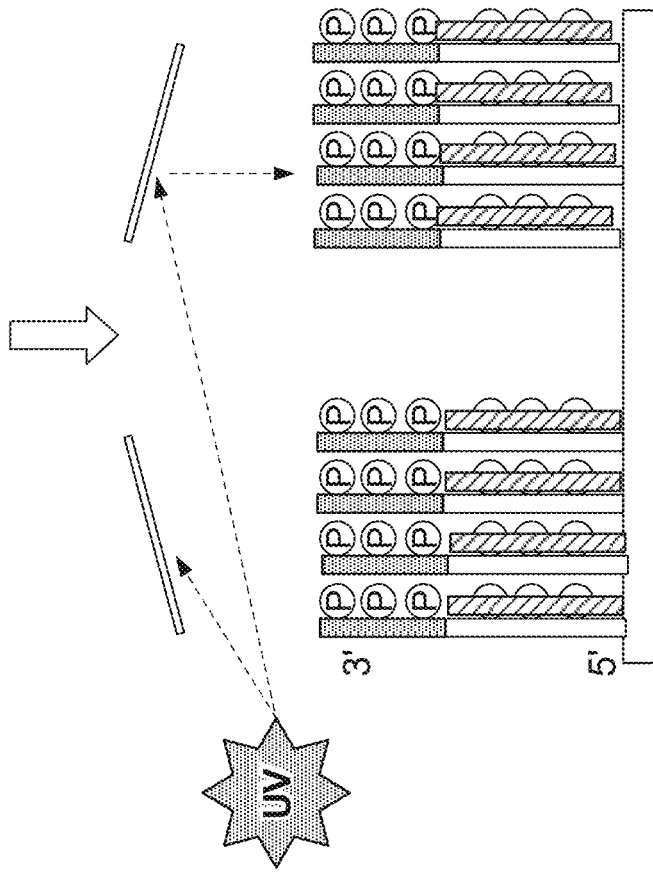

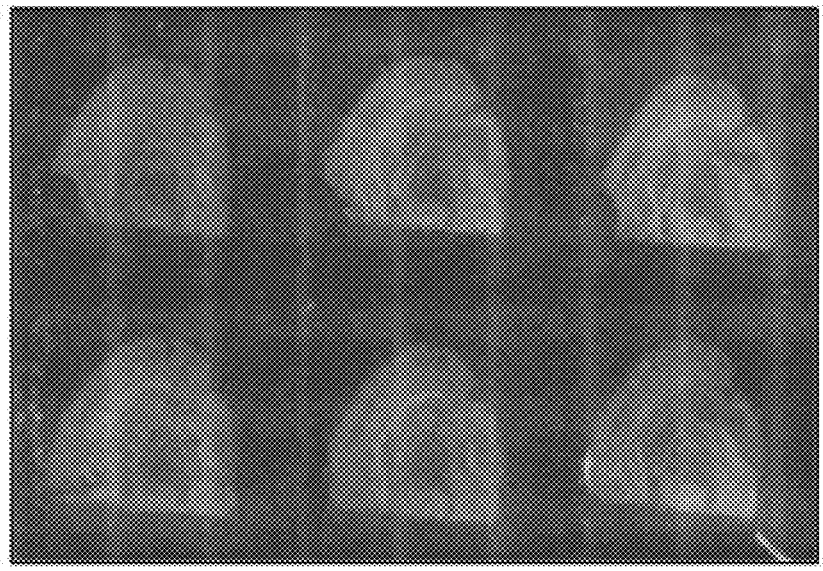
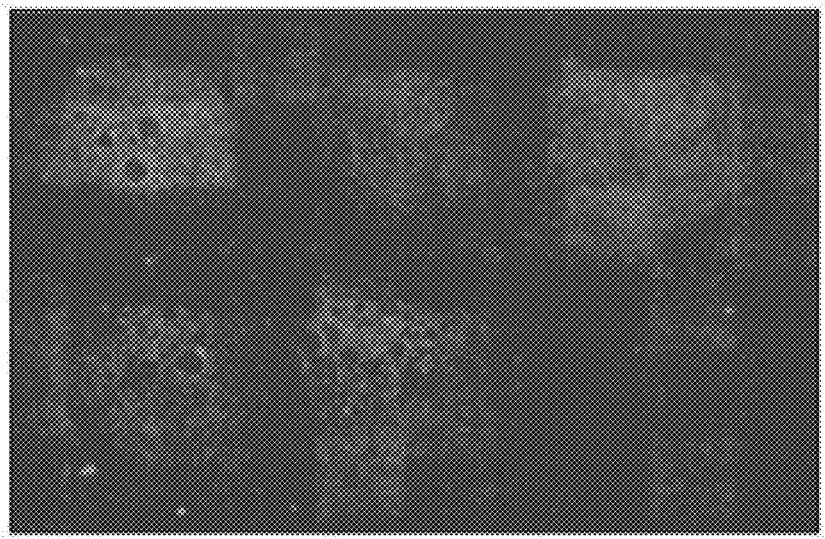
FIG 43

SEQUENCE LISTING

```
Sequence total quantity: 12
SEQ ID NO: 1          moltype = AA   length = 16
FEATURE               Location/Qualifiers
REGION                1..16
                      note = Synthetic Trademark of PURAMATRIX polypeptide
                       sequence
source                1..16
                      mol_type = protein
                      organism = synthetic construct
SEQUENCE: 1
RADARADARA DARADA                                                       16

SEQ ID NO: 2          moltype = AA   length = 16
FEATURE               Location/Qualifiers
REGION                1..16
                      note = Synthetic EAK16 polypeptide sequence
source                1..16
                      mol_type = protein
                      organism = synthetic construct
SEQUENCE: 2
AEAEAKAKAE AEAKAK                                                       16

SEQ ID NO: 3          moltype = AA   length = 12
FEATURE               Location/Qualifiers
REGION                1..12
                      note = Synthetic KLD12 polypeptide sequence
source                1..12
                      mol_type = protein
                      organism = synthetic construct
SEQUENCE: 3
KLDLKLDLKL DL                                                           12

SEQ ID NO: 4          moltype = DNA   length = 18
FEATURE               Location/Qualifiers
misc_feature          1..18
                      note = 18s cDNA Probe 1
source                1..18
                      mol_type = other DNA
                      organism = synthetic construct
SEQUENCE: 4
gaggaattcc cagtaagt                                                     18

SEQ ID NO: 5          moltype = DNA   length = 18
FEATURE               Location/Qualifiers
misc_feature          1..18
                      note = 18S cDNA Probe 2
source                1..18
                      mol_type = other DNA
                      organism = synthetic construct
SEQUENCE: 5
gagattgagc aataacag                                                     18
```

```
SEQ ID NO: 6              moltype = DNA  length = 18
FEATURE                   Location/Qualifiers
misc_feature              1..18
                          note = 18s cDNA Probe 3
source                    1..18
                          mol_type = other DNA
                          organism = synthetic construct
SEQUENCE: 6
gtagttccga ccataaac                                                   18

SEQ ID NO: 7              moltype = DNA  length = 18
FEATURE                   Location/Qualifiers
misc_feature              1..18
                          note = 18s cDNA Probe 4
source                    1..18
                          mol_type = other DNA
                          organism = synthetic construct
SEQUENCE: 7
ggtgactcta gataacct                                                   18

SEQ ID NO: 8              moltype = RNA  length = 35
FEATURE                   Location/Qualifiers
misc_feature              1..35
                          note = Analyte poly(A) tail from biological sample
misc_feature              12..35
                          note = n is a, c, g, or u
source                    1..35
                          mol_type = other RNA
                          organism = unidentified
SEQUENCE: 8
aaaaaaaaaa annnnnnnnn nnnnnnnnnn nnnn                                 35

SEQ ID NO: 9              moltype = DNA  length = 68
FEATURE                   Location/Qualifiers
misc_feature              1..68
                          note = Capture Probe
misc_feature              49..60
                          note = n is a, c, g, t or u
source                    1..68
                          mol_type = other DNA
                          organism = synthetic construct
SEQUENCE: 9
tttttttttt ttctacacga ctcttccgat ctacgtacgt acgtacgtnn nnnnnnnnnn     60
gcggcccg                                                              68

SEQ ID NO: 10             moltype = DNA  length = 18
FEATURE                   Location/Qualifiers
misc_feature              1..18
                          note = Splint Oligonucleotide
source                    1..18
                          mol_type = other DNA
                          organism = synthetic construct
SEQUENCE: 10
aaaaaaaaaa cgggccgc                                                   18

SEQ ID NO: 11             moltype = DNA  length = 27
FEATURE                   Location/Qualifiers
misc_feature              1..27
                          note = Capture domain poly(T) sequence
source                    1..27
                          mol_type = other DNA
                          organism = synthetic construct
SEQUENCE: 11
tttttttttt tttttttttt ttttttt                                         27

SEQ ID NO: 12             moltype = DNA  length = 62
FEATURE                   Location/Qualifiers
misc_feature              1..62
                          note = Capture probe 2
misc_feature              44..55
                          note = n is a, c, g, or t
source                    1..62
                          mol_type = other DNA
                          organism = synthetic construct
SEQUENCE: 12
tttttctaca cgacgctctt ccgatctacg tacgtacgta cgtnnnnnnn nnnnncgcta     60
cg                                                                    62
```

GENERATING CAPTURE PROBES FOR SPATIAL ANALYSIS

CROSS-REFERENCE TO RELATED APPLICATIONS

This application is a continuation application of U.S. patent application Ser. No. 17/212,681, filed Mar. 25, 2021, which is a continuation application of International Application PCT/US2019/065013, with an international filing date of Dec. 6, 2019, which claims priority to U.S. Provisional Patent Application No. 62/788,871, filed Jan. 6, 2019, U.S. Provisional Patent Application No. 62/788,885, filed Jan. 6, 2019, U.S. Provisional Patent Application No. 62/788,897, filed Jan. 6, 2019, U.S. Provisional Patent Application No. 62/788,906, filed Jan. 6, 2019, U.S. Provisional Patent Application No. 62/811,495, filed Feb. 27, 2019, U.S. Provisional Patent Application No. 62/812,219, filed Feb. 28, 2019, U.S. Provisional Patent Application No. 62/819,449, filed Mar. 15, 2019, U.S. Provisional Patent Application No. 62/819,456, filed Mar. 15, 2019, U.S. Provisional Patent Application No. 62/819,470, filed Mar. 15, 2019, U.S. Provisional Patent Application No. 62/819,478, filed Mar. 15, 2019, U.S. Provisional Patent Application No. 62/819,495, filed Mar. 15, 2019, U.S. Provisional Patent Application No. 62/822,554, filed Mar. 22, 2019, U.S. Provisional Patent Application No. 62/822,565, filed Mar. 22, 2019, U.S. Provisional Patent Application No. 62/822,566, filed Mar. 22, 2019, U.S. Provisional Patent Application No. 62/822,592, filed Mar. 22, 2019, U.S. Provisional Patent Application No. 62/822,605, filed Mar. 22, 2019, U.S. Provisional Patent Application No. 62/822,606, filed Mar. 22, 2019, U.S. Provisional Patent Application No. 62/822,610, filed Mar. 22, 2019, U.S. Provisional Patent Application No. 62/822,627, filed Mar. 22, 2019, U.S. Provisional Patent Application No. 62/822,680, filed Mar. 22, 2019, U.S. Provisional Patent Application No. 62/822,722, filed Mar. 22, 2019, U.S. Provisional Patent Application No. 62/839,212, filed Apr. 26, 2019, U.S. Provisional Patent Application No. 62/839,223, filed Apr. 26, 2019, U.S. Provisional Patent Application No. 62/839,264, filed Apr. 26, 2019, U.S. Provisional Patent Application No. 62/839,320, filed Apr. 26, 2019, U.S. Provisional Patent Application No. 62/839,346, filed Apr. 26, 2019, U.S. Provisional Patent Application No. 62/839,575, filed Apr. 26, 2019, U.S. Provisional Patent Application No. 62/842,463, filed May 2, 2019, U.S. Provisional Patent Application No. 62/860,993, filed Jun. 13, 2019, U.S. Provisional Patent Application No. 62/931,779, filed Nov. 6, 2019, U.S. Provisional Patent Application No. 62/931,587, filed Nov. 6, 2019, U.S. Provisional Patent Application No. 62/934,883, filed Nov. 13, 2019, U.S. Provisional Patent Application No. 62/935,043, filed Nov. 13, 2019, U.S. Provisional Patent Application No. 62/939,488, filed Nov. 22, 2019, and U.S. Provisional Patent Application No. 62/941,581, filed Nov. 27, 2019. The contents of each of these applications are incorporated herein by reference in their entireties.

SEQUENCE LISTING

This application contains a Sequence Listing that has been submitted electronically as an XML file named "47706-0007003.XML." The XML file, created on Oct. 26, 2022, is 17,448 bytes in size. The material in the XML file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the contact of an intact tissue or a portion of a tissue, or provide a lot of analyte data for single cells, but fail to provide information regarding the position of the single cell in a parent biological sample (e.g., tissue sample).

Arrays that capture spatial information of analytes within a biological sample can be prepared in various ways. Arrays can be designed with pluralities of capture probes. Capture probes can be designed to capture a substantial population of analytes (e.g., mRNA) or to capture specific (e.g., gene specific) analytes. The methods described herein provide for ways of preparing arrays with capture probes and capturing analytes.

SUMMARY

Provided herein are methods of generating a spatial array including: (a) providing an array including a plurality of oligonucleotides, where the 3' end of an oligonucleotide of the plurality of oligonucleotides is attached to a substrate, (b) providing a plurality of primers, where a primer of the plurality of primers is substantially complementary to a portion of the oligonucleotide, (c) extending the primer using the oligonucleotide as a template, thereby generating a first oligonucleotide with a free 3' end, (d) extending the first oligonucleotide to produce a 3' overhang, (e) providing a splint oligonucleotide that hybridizes to the 3' end of the first oligonucleotide, and (f) ligating a second oligonucleotide to the 3' end of the first oligonucleotide, where the second oligonucleotide includes a sequence that is substantially complementary to a portion of the splint oligonucleotide, and where the second oligonucleotide includes a capture domain, thereby generating a spatial array.

In some embodiments of methods of generating a spatial array, the oligonucleotide of the plurality of oligonucleotides includes a spatial barcode. In some embodiments, the oligonucleotide of the plurality of oligonucleotides includes a first constant sequence. In some embodiments of methods of generating a spatial array, the oligonucleotide of the plurality of oligonucleotides further includes a second constant sequence. In some embodiments of methods of generating a spatial array, the oligonucleotide of the plurality of oligonucleotides has a length of between 20 and 60 nucleotides.

In some embodiments of methods of generating a spatial array, the second oligonucleotide further includes a constant sequence, and where the constant sequence is substantially complementary to a portion of the splint oligonucleotide. In some embodiments of methods of generating a spatial array, the second oligonucleotide further includes a unique molecular identifier. In some embodiments of methods of generating a spatial array, the second oligonucleotide further includes a spatial barcode.

In some embodiments of methods of generating a spatial array, the capture domain includes a poly-T sequence. In some embodiments of methods of generating a spatial array, the capture domain includes a gene-specific sequence.

In some embodiments of methods of generating a spatial array, the 3' end overhang of step (d) is produced by an enzyme. In some embodiments of methods of generating a spatial array, the enzyme is a template-independent polymerase. In some embodiments of methods of generating a spatial array, the template-independent polymerase is terminal deoxynucleotidyl transferase (TdT) or poly(A) polymerase.

In another aspect, provided herein are methods for determining the location of an analyte in a biological sample including (a) contacting the biological sample with a spatial array produced by any of the variety of methods herein (b) permeabilizing the biological sample to allow the analyte in the biological sample to specifically bind with a capture domain on the spatial array, and (c) identifying the analyte specifically bound to the capture domain, thereby determining the spatial location of the analyte in the biological sample.

In some embodiments of methods for determining the location of an analyte in a biological sample, a second analyte in the biological sample interacts with a second capture domain on the spatial array, and step (c) includes identifying the second analyte specifically bound to the second capture domain, thereby determining the spatial location of the analyte in the second biological sample.

In another aspect, provided herein are methods for preparing a spatial array, including (a) contacting an array including one or more pluralities of first oligonucleotides with a hydrogel including one or more pluralities of second oligonucleotides, where a first oligonucleotide of the one or more pluralities of first oligonucleotides includes a capture domain, a second oligonucleotide of the one or more pluralities of second oligonucleotides includes a capture domain, or both, (b) attaching the first oligonucleotide to the second oligonucleotide to generate a capture probe including a capture domain, (c) reducing the size of the hydrogel including the capture probe by removing water to form a shrunken hydrogel including the capture probe, thereby generating the spatial array.

In some embodiments of methods for preparing a spatial array, the one or more pluralities of second oligonucleotides are immobilized in the hydrogel. In some embodiments of methods for preparing a spatial array, the immobilized second oligonucleotides are partitioned such that a first population of the immobilized second oligonucleotides is partitioned away from another population of immobilized second oligonucleotides.

In some embodiments of methods for preparing a spatial array, the immobilized second oligonucleotides are partitioned into a plurality of second oligonucleotide partitions such that different populations of the immobilized second oligonucleotides are partitioned away from each other. In some embodiments of methods for preparing a spatial array, a first immobilized second oligonucleotide of a partitioned population of immobilized second oligonucleotides is different from a second immobilized second oligonucleotide of another partitioned population of immobilized second oligonucleotides. In some embodiments of methods for preparing a spatial array, the first immobilized second oligonucleotide, the second immobilized second oligonucleotide, or both include a spatial barcode.

In some embodiments of methods for preparing a spatial array, the first immobilized second oligonucleotide of a partitioned population of immobilized second oligonucleotides includes a spatial barcode that is different from a spatial barcode of the second immobilized second oligonucleotide of another partitioned population of immobilized second oligonucleotides.

In some embodiments of methods for preparing a spatial array, one or more second oligonucleotide partitions include a population of immobilized capture probes including a spatial barcode different from a spatial barcode of the population of immobilized capture probes of another second oligonucleotide partition.

In some embodiments of methods for preparing a spatial array, the one or more pluralities of first oligonucleotides are partitioned. In some embodiments of methods for preparing a spatial array, the one or more pluralities of first oligonucleotides are partitioned into a first oligonucleotide partitions. In some embodiments of methods for preparing a spatial array, one or more first oligonucleotide partitions include a population of first oligonucleotides that is different from first oligonucleotides in another first oligonucleotide partition. In some embodiments of methods for preparing a spatial array, a first oligonucleotide of a population of first oligonucleotides in one or more first oligonucleotide partitions includes a spatial barcode. In some embodiments of methods for preparing a spatial array, the first oligonucleotide of a population of first oligonucleotides in one or more first oligonucleotide partitions includes a spatial barcode that is different from the spatial barcode of a first oligonucleotide of a population of first oligonucleotides in another first oligonucleotide partition. In some embodiments of methods for preparing a spatial array, a spatial barcode of the first oligonucleotide of a population of first oligonucleotides in one or more first oligonucleotide partitions is different from a spatial barcode of a second oligonucleotide of a population of second oligonucleotides in one or more second oligonucleotide partitions. In some embodiments of methods for preparing a spatial array, a first oligonucleotide partition includes a first population of first oligonucleotides including a spatial barcode that is different from a spatial barcode of a second population of first oligonucleotides in another first oligonucleotide partition.

In some embodiments of methods for preparing a spatial array, the reduction in the size of the hydrogel in step (c) is isometric. In some embodiments of methods for preparing a spatial array, the removal of water in step (c) includes a dehydrating solvent. In some embodiments of methods for preparing a spatial array, the solvent includes at least one of an alcohol, a ketone, an aldehyde, acetonitrile, or a combination thereof. In some embodiments of methods for preparing a spatial array, the solvent includes at least one of glycerol, ethanol, acetonitrile, acetone, 2-propanol, and a combination thereof. In some embodiments, the removal of water in step (c) includes the use of a salt. In some embodiments of methods for preparing a spatial array, the salt includes an inorganic salt. In some embodiments of methods for preparing a spatial array, the removal of water in step (c) includes an acid. In some embodiments of methods for preparing a spatial array, the removal of water in step (c) includes a dehydrating process.

In some embodiments of methods for preparing a spatial array, the shrunken hydrogel is about 2 to about 10 fold smaller in a linear dimension than the size of the hydrogel prior to step (c) pre-shrunk hydrogel. In some embodiments of methods for preparing a spatial array, the shrunken hydrogel is at least 2-fold smaller in a linear dimension than the pre-shrunk hydrogel. In some embodiments of methods for preparing a spatial array, the shrunken hydrogel is at least 4-fold smaller in a linear dimension than the pre-shrunk hydrogel. In some embodiments of methods for preparing a spatial array, the shrunken hydrogel is at least 8-fold smaller in a linear dimension than the pre-shrunk hydrogel.

In some embodiments of methods for preparing a spatial array, attaching includes a polymerase chain reaction. In some embodiments of methods for preparing a spatial array, the hydrogel includes a DNA polymerase, a plurality of primers, and a plurality of nucleotides. In some embodiments of methods for preparing a spatial array, members of a plurality of first oligonucleotides are cross-linked to the hydrogel. In some embodiments of methods for preparing a spatial array, the capture probe is amplified. In some embodiments of methods for preparing a spatial array, the capture probe is amplified prior to the reduction of the size of the hydrogel.

In some embodiments of methods for preparing a spatial array, the hydrogel is prepared from hydrogel subunits including at least one of: acrylamide, bis-acrylamide, a poly(ethylene glycol), a polyaliphatic polyurethane, a polyether polyurethane, a polyester polyurethane, a polyethylene copolymer, a polyamide, a polyvinyl alcohol, polypropylene glycol, polytetramethylene oxide, polyvinyl pyrrolidone, polyacrylamide, poly(hydroxyethyl acrylate), poly(hydroxyethyl methacrylate), collagen, hyaluronic acid, chitosan, dextran, agarose, gelatin, alginate, a protein polymer, methylcellulose, and a combination thereof.

In some embodiments of methods for preparing a spatial array, the first oligonucleotide of the one or more pluralities of first oligonucleotides includes a spatial barcode. In some embodiments of methods for preparing a spatial array, the first oligonucleotide of the one or more pluralities of first oligonucleotides includes a unique molecular identifier. In some embodiments of methods for preparing a spatial array, the first oligonucleotide of the one or more pluralities of first oligonucleotides includes a spatial barcode and a capture domain.

In another aspect, provided herein are methods for determining the location of an analyte in a biological sample, including (a) providing a spatial array of any of the variety of methods described herein, (b) contacting a biological sample with a spatial array of any one of the spatial arrays described herein under conditions that allow the analyte to specifically bind to a capture probe of the spatial array, and (c) determining the identity of the analyte specifically bound to the capture probe, thereby determining the location of the analyte in the biological sample.

In some embodiments of methods for determining the location of an analyte in a biological sample, the biological sample is a tissue sample. In some embodiments of methods for determining the location of an analyte in a biological sample, the tissue sample is a fresh-frozen tissue sample. In some embodiments of methods for determining the location of an analyte in a biological sample, the tissue sample includes a tumor cell. In some embodiments of methods for determining the location of an analyte in a biological sample, the tissue sample includes a tissue section.

In some embodiments, methods for determining the location of an analyte in a biological sample further includes migrating the analyte in the biological sample to the capture probe. In some embodiments of methods for determining the location of an analyte in a biological sample, migrating includes passive migration. In some embodiments of methods for determining the location of an analyte in a biological sample, migrating includes active migration.

In some embodiments of methods for determining the location of an analyte in a biological sample, the analyte includes at least one of RNA, DNA, protein, lipid, peptide, metabolite, small molecule, and a analyte capture agent.

In another aspect, provided herein are methods of generating an array including (a) providing a substrate including a plurality of features immobilized on the substrate, where a feature of the plurality of features includes a first oligonucleotide, and where the first oligonucleotide includes a first spatial barcode, (b) delivering a second oligonucleotide to the first oligonucleotide, where the second oligonucleotide includes a second spatial barcode and a capture domain, and (c) attaching the first oligonucleotide and the second oligonucleotide, thereby generating a capture probe including the first spatial barcode, the second spatial barcode, and the capture domain.

In some embodiments of methods of generating an array, the first oligonucleotide is associated with one of a number of different first spatial barcodes. In some embodiments of methods of generating an array, the second oligonucleotide is associated with one of a number of different second spatial barcodes.

In some embodiments of methods of generating an array, step (c) includes ligating the first oligonucleotide and the second oligonucleotide. In some embodiments of methods of generating an array, the ligating includes the use of a ligase. In some embodiments of methods of generating an array, the first oligonucleotide and the second oligonucleotide are attached to one another by a chemical coupling reaction.

In some embodiments of methods of generating an array, the first oligonucleotide includes a 3' end that is masked by a protective group. In some embodiments of methods of generating an array, the protective group is removed prior to delivering the second oligonucleotide to the first oligonucleotide. In some embodiments of methods of generating an array, the protective group is a photocleavable protective group. In some embodiments of methods of generating an array, the photocleavable protective group is removed by exposing the first oligonucleotide to light. In some embodiments of methods of generating an array, the photocleavable protective group coupled to the first oligonucleotide is protected by applying a photomask.

In some embodiments of methods of generating an array, a first feature is separated from other features of the plurality by one or more physical barriers, where the one or more physical barriers form one or more chambers, and where the first oligonucleotide is delivered to a chamber of the one or more chambers.

In some embodiments of methods of generating an array, the one or more physical barriers include a hydrophobic surface. In some embodiments of methods of generating an array, the one or more physical barriers include one or more chamber walls having a tapered end in contact with the substrate. In some embodiments of methods of generating an array, the first oligonucleotide includes a unique molecular identifier.

In another aspect, provided herein are methods of generating an array including (a) providing a substrate including two or more partitions, where a first partition of the two or more partitions includes a feature immobilized on the substrate, where the feature includes a first oligonucleotide, and where the first oligonucleotide includes a first spatial barcode, (b) delivering a second oligonucleotide to the first partition, where the second oligonucleotide includes a second spatial barcode and a capture domain, and (c) attaching the first oligonucleotide and the second oligonucleotide in the first partition, thereby generating a capture probe including the first spatial barcode, the second spatial barcode, and the capture domain in the first partition.

In some embodiments, methods of generating an array further include (d) delivering a third oligonucleotide to a second partition of the two or more partitions, where the third oligonucleotide includes a third spatial barcode and a second capture domain, where the second partition includes a second feature, where the second feature includes a fourth oligonucleotide including the first spatial barcode, and (e) attaching the third oligonucleotide and the fourth oligonucleotide, thereby generating a second capture probe including the first spatial barcode, the third spatial barcode, and the second capture domain in the second partition.

In some embodiments of methods of generating an array, the two or more partitions are separated by one or more physical barriers. In some embodiments of methods of generating an array, the one or more physical barriers are printed on the substrate. In some embodiments of methods of generating an array, the one or more physical barriers form one or more chambers including one or more chamber walls. In some embodiments of methods of generating an array, the one or more chamber walls include a hydrophobic surface. In some embodiments, the one or more chamber walls include a tapered end in contact with the substrate. In some embodiments of methods of generating an array, the second oligonucleotide is delivered using a microfluidic device.

In another aspect, provided herein are methods for enriching a population of capture probes including (a) providing a plurality of capture probes where: (i) members of the plurality of capture probes include a plurality of different spatial barcodes, and (ii) a target capture probe of the population of capture probes to be enriched includes a target spatial barcode, and (b) enriching a population of target capture probes including the target spatial barcode from the plurality of capture probes.

In another aspect, provided herein are methods for determining the location of an analyte in a biological sample including (a) providing a substrate including a plurality of capture probes, where a subset of the plurality of capture probes is attached at a location on the substrate, and where two or more capture probes of the subset of capture probes includes a first common spatial barcode, (b) contacting the biological sample with the substrate such that a capture probe of the subset of capture probes specifically binds to the analyte from the biological sample, where the analyte that is specifically bound to the capture probe includes the first common spatial barcode or a complement thereof, (c) identifying a region of interest within the biological sample, where the region of interest includes the analyte specifically bound to the capture probe, and (d) enriching the analyte specifically bound to the capture probe to determine the location of the analyte in the biological sample.

In some embodiments of methods for determining the location of an analyte in a biological sample, the substrate further includes a second subset of capture probes attached at a second location on the substrate, where two or more capture probes of the second subset of capture probes include a second common spatial barcode that is different from the first common spatial barcode.

In some embodiments of methods for determining the location of an analyte in a biological sample, the substrate further includes a third subset of capture probes attached at a third position on the substrate, where two or more capture probes of the third subset of capture probes includes a third common spatial barcode that is different from the first common spatial barcode and the second common spatial barcode. In some embodiments of methods for determining the location of an analyte in a biological sample, the capture probe includes a capture domain.

In some embodiments of methods for determining the location of an analyte in a biological sample, the analyte includes at least one of RNA, DNA, and a analyte capture agent. In some embodiments of methods for determining the location of an analyte in a biological sample, the analyte capture agent includes an antigen binding molecule. In some embodiments of methods for determining the location of an analyte in a biological sample, the analyte capture agent includes a region configured to couple or specifically bind to the capture domain of the capture probe.

In some embodiments of methods for determining the location of an analyte in a biological sample, the region of interest is identified by performing shallow sequencing of at least a subset of a plurality of analytes specifically bound to capture probes, and identifying the first common spatial barcode associated with the region of interest. In some embodiments of methods for determining the location of an analyte in a biological sample, the region of interest is identified by at least one of immunostaining, immunohistochemistry, microscopy, visual inspection, and combinations thereof.

In some embodiments of methods for determining the location of an analyte in a biological sample, step (d) includes performing a nucleic acid extension reaction using (i) the analyte specifically bound to the capture probe and (ii) a primer including a sequence specific for the first common spatial barcode or a complement thereof to generate an enriched plurality of the analyte specifically bound to the capture probe(s) including the first common barcode or a complement thereof.

In some embodiments of methods for determining the location of an analyte in a biological sample, the analyte is amplified by performing a polymerase chain reaction (PCR).

In some embodiments, methods for determining the location of an analyte in a biological sample further include enriching a population of capture probes present in a subregion of interest (a) where the subregion of interest is located within the region of interest, where the subregion of interest includes a sub-plurality of capture probes, and where: (i) two or more capture probes of the sub-plurality of capture probes include a first common sub-spatial barcode, and (ii) the first common sub-spatial barcode sequence is associated with the subregion of interest, and (b) enriching a population of capture probe including the first common sub-spatial barcode.

In some embodiments, methods for determining the location of an analyte in a biological sample further include enriching a population of capture probes present in a sub-subregion of interest (a) where the sub-subregion of interest is located within the subregion of interest, where the sub-subregion of interest includes a sub-sub-plurality of capture probes, and where: (i) two or more capture probes of the sub-sub plurality of capture probes include a first common sub-sub spatial barcode, and (ii) the first common sub-sub spatial barcode is associated with the sub-sub region of interest, and (b) enriching the population of capture probes including the first sub-sub spatial barcode.

In some embodiments of methods for determining the location of an analyte in a biological sample, the first common spatial barcode is associated with a single cell of the biological sample.

In some embodiments of methods for determining the location of an analyte in a biological sample, the analyte includes an mRNA. In some embodiments of methods for determining the location of an analyte in a biological sample, the analyte includes a protein. In some embodiments of methods for determining the location of an analyte in a biological sample, the analyte includes an antibody. In some embodiments of methods for determining the location of an analyte in a biological sample, the analyte includes DNA. In some embodiments of methods for determining the location of an analyte in a biological sample, the DNA encodes a T-cell receptor. In some embodiments of methods for determining the location of an analyte in a biological sample, the DNA includes one or more regions of chromatin in the biological sample.

In another aspect, provided herein are methods for generating a spatial array including (a) providing a substrate including a plurality of first oligonucleotides, where a first oligonucleotide of the plurality of first oligonucleotides is attached to a region of the substrate through its 3'-end or its 5'-end, (b) attaching a second oligonucleotide to an unattached end of the first oligonucleotide, where the second oligonucleotide includes a spatial barcode.

In some embodiments, methods for generating a spatial array further include after (b): (c) attaching a third oligonucleotide segment to an unattached end of the second oligonucleotide.

In some embodiments of methods for generating a spatial array, the first oligonucleotide is attached to the substrate through its 5'-end and the second oligonucleotide is generated using spatially-directed in situ synthesis on the 3'-end of the first oligonucleotide. In some embodiments of methods for generating a spatial array, the first oligonucleotide is attached to the substrate through its 3'-end and the second oligonucleotide is generated using spatially-directed in situ synthesis on the 5'-end of the first oligonucleotide.

In some embodiments of methods for generating a spatial array, phosphodiester and exocyclic amine moieties of the first oligonucleotide are protected.

In some embodiments of methods for generating a spatial array, the second oligonucleotide has a length selected from 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

In some embodiments of methods for generating a spatial array, the in situ synthesis is light-directed synthesis.

In some embodiments of methods for generating a spatial array, the region of the substrate is less than about 2500 $\mu m^2$, less than about 1600 $\mu m^2$, less than about 400 $\mu m^2$, less than about 100 $\mu m^2$, less than about 50 $\mu m^2$, less than about 25 $\mu m^2$, less than about 15 $\mu m^2$, less than about 10 $\mu m^2$, or less than about 5 $\mu m^2$.

In some embodiments of methods for generating a spatial array, two or more second oligonucleotides are attached to two or more first oligonucleotides, where a member of the two or more second oligonucleotides differs from another member of the two or more second oligonucleotides.

In some embodiments of methods for generating a spatial array, the first oligonucleotide includes a protected phosphodiester and exocyclic amine moieties.

In some embodiments of methods for generating a spatial array, the substrate further includes a substantially complementary oligonucleotide hybridized to the first oligonucleotide.

In some embodiments of methods for generating a spatial array, the first oligonucleotide has a length of at least about 2 nucleotides, 5 nucleotides, 8 nucleotides, 10 nucleotides, 15 nucleotides, 18 nucleotides, 20 nucleotides, 22 nucleotides, 25 nucleotides, 27 nucleotides, 30 nucleotides, 33 nucleotides, or 35 nucleotides. In some embodiments of methods for generating a spatial array, the first oligonucleotide has a length of about 2 to 45 nucleotides, 5 to 40 nucleotides, 15 to 40 nucleotides, 25 to 40 nucleotides, 25 to 35 nucleotides, or 27 to 33 nucleotides.

In some embodiments of methods for generating a spatial array, the first oligonucleotide is prepared by synthesis off of the substrate and the first oligonucleotide is subsequently attached to the substrate.

In some embodiments of methods for generating a spatial array, the phosphodiester and exocyclic amine moieties of the first oligonucleotide are protected prior to attachment of the first oligonucleotide to the substrate. In some embodiments of methods for generating a spatial array, the phosphodiester and exocyclic amine moieties of the first oligonucleotide are protected after attachment of the first oligonucleotide to the substrate.

In some embodiments of methods for generating a spatial array, the first oligonucleotide is prepared by in situ synthesis on the substrate. In some embodiments of methods for generating a spatial array, the in situ synthesis is not light-directed synthesis. In some embodiments of methods for generating a spatial array, the in situ synthesis is not spatially-directed synthesis.

In some embodiments of methods for generating a spatial array, the first oligonucleotide includes a sequence including a cleavage site. In some embodiments of methods for generating a spatial array, the first oligonucleotide is attached to the substrate through a linker. In some embodiments of methods for generating a spatial array, a chemical group including: silane, amine, peptide, polyethylene glycol, biotin, desthiobiotin, streptavidin, thiol, acrydite, azide, digoxigenin, hexynyl, or a combination thereof. In some embodiments of methods for generating a spatial array, the linker is a branched linker or a dendrimeric linker.

In some embodiments of methods for generating a spatial array, the third oligonucleotide is attached to the second oligonucleotide by ligation.

In some embodiments of methods for generating a spatial array, any protected moieties of the first and second oligonucleotides are deprotected prior to ligating the third oligonucleotide to the second oligonucleotide.

In some embodiments of methods for generating a spatial array, the plurality of third oligonucleotides have a length of at least about 5 nucleotides, 7 nucleotides, 9 nucleotides, 13 nucleotides, 20 nucleotides, 25 nucleotides, 27 nucleotides, 30 nucleotides, 33 nucleotides, or 35 nucleotides. In some embodiments of methods for generating a spatial array, the plurality of third oligonucleotides have a length of about 5 to 40 nucleotides, 5 to 20 nucleotides, 5 to 10 nucleotides, 10 to 35 nucleotides, 15 to 30 nucleotides, 25 to 35 nucleotides, or 27 to 33 nucleotides.

In some embodiments of methods for generating a spatial array, the third oligonucleotide includes a capture domain of at least 6 nucleotides in length at the 3'-end. In some embodiments of methods for generating a spatial array, the capture domain includes a poly-T sequence. In some embodiments of methods for generating a spatial array, the third oligonucleotide includes a random sequence of 6 to 20 nucleotides in length.

In another aspect, provided herein are compositions including a plurality of oligonucleotides attached to a plurality of regions on a substrate, where an oligonucleotide of the plurality of oligonucleotides includes: a first oligonucleotide of 2 to 50 nucleotides in length attached to the substrate through its 3'-end or its 5'-end, and a second oligonucleotide of 8 to 30 nucleotides in length that is attached to an unattached end of the first oligonucleotide, where the second oligonucleotide includes a spatial barcode.

In another aspect, provided herein are compositions where the first oligonucleotide and the second oligonucleotide include protected phosphodiester and exocyclic amine moieties.

In another aspect, provided herein are compositions where the first oligonucleotide is attached to the substrate through its 5'-end and the second oligonucleotide is attached to the 3'-end of the first oligonucleotide.

In another aspect, provided herein are compositions where the first oligonucleotide is attached to the substrate through its 3'-end and the second oligonucleotide is attached to the 5'-end of the first oligonucleotide.

In some embodiments, compositions where the first oligonucleotide is attached to the substrate through its 3'-end and the second oligonucleotide is attached to the 5'-end of the first oligonucleotide further include a third oligonucleotide of 5 to 40 nucleotides in length that is attached to an unattached end of the second oligonucleotide, where the third oligonucleotide includes a capture domain.

In some embodiments, compositions where the first oligonucleotide is attached to the substrate through its 3'-end and the second oligonucleotide is attached to the 5'-end of the first oligonucleotide, the second oligonucleotide has a length selected from 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

In some embodiments, compositions where the first oligonucleotide is attached to the substrate through its 3'-end and the second oligonucleotide is attached to the 5'-end of the first oligonucleotide, the regions are less than about 2500 $\mu m^2$, less than about 1600 $\mu m^2$, less than about 400 $\mu m^2$, less than about 100 $\mu m^2$, less than about 50 $\mu m^2$, less than about 25 $\mu m^2$, less than about 15 $\mu m^2$, less than about 10 $\mu m^2$, less than about 5 $\mu m^2$, or less than about 1 $\mu m^2$.

In some embodiments, compositions where the first oligonucleotide is attached to the substrate through its 3'-end and the second oligonucleotide is attached to the 5'-end of the first oligonucleotide, the length of the oligonucleotide in each of the regions is at least 15 nucleotides, at least 20 nucleotides, at least 40 nucleotides, at least 50 nucleotides, or at least 60 nucleotides.

In some embodiments, compositions where the first oligonucleotide is attached to the substrate through its 3'-end and the second oligonucleotide is attached to the 5'-end of the first oligonucleotide, each of the regions is from 15 to 100 nucleotides, 20 to 100 nucleotides, 40 to 100 nucleotides, from 50 to 90 nucleotides, or from 60 to 80 nucleotides.

In another aspect, provided herein are methods of preparing a spatial array including (a) providing a substrate, (b) immobilizing a plurality of sets of primers on the substrate, where a first set of the plurality of sets of primers includes a first primer and a second primer, (c) providing a template oligonucleotide including a reverse complement of a spatial barcode domain, a reverse complement of a capture domain, a first hybridization domain capable of hybridizing to the first primer, and a second hybridization domain, where a reverse complement of the second hybridization domain is capable of hybridizing to the second primer, (d) hybridizing the template oligonucleotide to the first primer, (e) extending the first primer using the template oligonucleotide as a template to generate a capture probe including the first primer, the spatial barcode, and the capture domain, which capture probe is immobilized on the substrate, and (f) releasing the template oligonucleotide from the capture probe, thereby producing the spatial array.

In some embodiments, methods of preparing a spatial array further include amplifying the capture probe to create a cluster of one or more capture probes.

In some embodiments of methods of preparing a spatial array, amplifying includes (a) hybridizing the capture probe to the second primer, (b) extending the second primer using the capture probe as a template to generate a copy of the template oligonucleotide that is immobilized on the substrate, (c) hybridizing the copy of the template oligonucleotide to a first primer of a second set of the plurality of primers, and (d) extending the first primer of the second set of the plurality of primers using the copy of template oligonucleotide as a template to generate a copy of the capture probe that is immobilized on the substrate, where the cluster of capture probes includes the capture probe and the copy of the capture probe.

In some embodiments of methods of preparing a spatial array, the template oligonucleotide includes a reverse complement of a unique molecular identifier (UMI), and where the generated capture probe includes the UMI.

In some embodiments of methods of preparing a spatial array, the first primer is affixed to the substrate at a 5' end of the first primer. In some embodiments of methods of preparing a spatial array, the first primer includes a sequence that is complementary to the template oligonucleotide. In some embodiments of methods of preparing a spatial array, the first primer includes a poly (A) domain. In some embodiments of methods of preparing a spatial array, the first primer includes cleavage domain.

In some embodiments of methods of preparing a spatial array, the second primer is affixed to the substrate at a 5' end of the second primer. In some embodiments of methods of preparing a spatial array, the second primer includes a cleavage domain.

In some embodiments of methods of preparing a spatial array, the copy of the template oligonucleotide is released by cleaving the cleavage domain after the copy of the capture probe is generated. In some embodiments of methods of preparing a spatial array, the template oligonucleotide is attached to a bead.

In some embodiments of methods of preparing a spatial array, detaching the bead from the template oligonucleotide after the step of extending the first primer using the template oligonucleotide as a template to generate a capture probe including the first primer, the spatial barcode, and the capture domain, which capture probe is immobilized on the substrate.

In some embodiments of methods of preparing a spatial array, the bead is a gel bead. In some embodiments of methods of preparing a spatial array, the bead is 2 microns or less in diameter. In some embodiments of methods of preparing a spatial array, the bead is 1 micron or less in diameter. In some embodiments of methods of preparing a spatial array, the bead is removed prior to the step of extending the first primer. In some embodiments of methods of preparing a spatial array, the bead is removed after the step of extending the first primer.

In some embodiments of methods of preparing a spatial array, all or a portion of the sequence of the generated capture probe is determined. In some embodiments of methods of preparing a spatial array, all or a portion of the sequence of the generated capture probe is determined after the template oligonucleotide is released.

In some embodiments of methods of preparing a spatial array, all or a portion of the sequence of the generated capture probe is determined in situ. In some embodiments of methods of preparing a spatial array, all or a portion of the sequence of the generated capture probe is determined by in situ sequencing. In some embodiments of methods of preparing a spatial array, the in situ sequencing is performed via sequencing-by-synthesis (SBS), sequential fluorescence hybridization, sequencing by ligation, nucleic acid hybridization, or high-throughput digital sequencing techniques.

In some embodiments of methods of preparing a spatial array, the capture domain includes a sequence complementary to an analyte of interest. In some embodiments of methods of preparing a spatial array, the capture domain includes a poly(T) domain.

In some embodiments of methods of preparing a spatial array, the substrate includes a glass slide. In some embodiments of methods of preparing a spatial array, the glass slide is a treated glass slide.

In another aspect, provided herein are methods for determining a location of an analyte in a biological sample including (a) preparing a spatial array using any of the variety of methods described herein, (b) decoding the one or more capture probes by determining all or a portion of the sequence of the spatial barcode of the one or more capture probes, thereby associating the spatial barcode of the one or more capture probe with a location on the spatial array, (c) contacting the biological sample to the spatial array under conditions where the analyte specifically binds to capture probe(s), (d) extending the one or more capture probes via a polymerization reaction using the analyte as a template to generate an extended one or more capture probes including the one or more capture probes and the reverse complement of the analyte, and (e) determining the sequence of the extended one or more capture probes, and associating the spatial barcode of the one or more capture probes with the analyte, thereby determining the location of the analyte in the biological sample.

In some embodiments of methods for determining a location of an analyte in a biological sample, one or more capture probes includes a template oligonucleotide and a bead. In some embodiments, methods for determining a location of an analyte in a biological sample further include detaching the bead from the template oligonucleotide after the step of extending the one or more capture probes via a polymerization reaction using the analyte as a template to generate an extended one or more capture probes including the one or more capture probes and the reverse complement of the analyte.

In some embodiments of methods for determining a location of an analyte in a biological sample, the first primer and the second primer are at a ratio of between 1:1.5 and 1.5:1. In some embodiments of methods for determining a location of an analyte in a biological sample, the first primer and the second primer are less than 5 µm apart.

In another aspect, provided herein are spatial arrays produced by any of the methods described herein.

In another aspect, provided herein are spatial array including (a) a substrate, and (b) a plurality of sets of primers immobilized on the substrate, where a first set of the plurality of sets of primers includes a first primer and a second primer, and where the first primer includes a sequence that is complementary to a capture probe.

In some embodiments, the spatial array further includes a template oligonucleotide including a reverse complement of a unique molecular identifier (UMI), and where the capture probe includes the UMI.

In some embodiments of spatial arrays provided herein, the first primer is affixed to the substrate at a 5' end of the first primer. In some embodiments of spatial arrays provided herein, the first primer includes a sequence that is complementary to the template oligonucleotide. In some embodiments of spatial arrays provided herein, the first primer includes poly (A) domain. In some embodiments of spatial arrays provided herein, the first primer includes a cleavage domain.

In some embodiments of spatial arrays provided herein, the second primer is affixed to the substrate at a 5' end of the second primer. In some embodiments of spatial arrays provided herein, the second primer includes a cleavage domain.

In some embodiments of spatial arrays provided herein, the template oligonucleotide is attached to a bead. In some embodiments of spatial arrays provided herein, the bead is a gel bead. In some embodiments of spatial arrays provided herein, the bead is 2 microns or less in diameter. In some embodiments of spatial arrays provided herein, the bead is 1 micron or less in diameter.

In some embodiments of spatial arrays provided herein, the substrate includes a glass slide. In some embodiments of spatial arrays provided herein, the glass slide is a treated glass slide.

In some embodiments of spatial arrays provided herein, the first primer and the second primer are at a ratio of between 1:1.5 and 1.5:1. In some embodiments of spatial arrays provided herein, the first primer and the second primer are less than 5 µm apart.

In another aspect, provided herein are methods of generating a spatial array including (a) providing a substrate including an arrayed plurality of acceptor oligonucleotides, where an acceptor oligonucleotide of the plurality of acceptor oligonucleotides includes a spatial barcode and a first ligation handle, and where the 5' end of the acceptor oligonucleotide is attached to the substrate, (b) providing a splint oligonucleotide including a sequence complementary to the first ligation handle and a sequence complementary to a donor oligonucleotide, and (c) ligating a donor oligonucleotide including a capture domain to the 3' end the acceptor oligonucleotide to generate a capture probe, thereby generating a spatial array.

In some embodiments of methods of generating a spatial array, the acceptor oligonucleotides further includes a cleavage domain, a unique molecular identifier, a functional sequence, or any combination thereof.

In some embodiments of methods of generating a spatial array, the sequence complementary to the capture domain of splint oligonucleotide is a poly(A) sequence. In some embodiments, the sequence complementary to the capture domain of the splint oligonucleotide is a gene-specific sequence. In some embodiments, the gene-specific sequence is a Penk-specific sequence. In some embodiments, the sequence complementary to the capture domain of the splint oligonucleotide is a random sequence. In some embodiments, the random sequence is a hexamer.

In some embodiments, methods of generating a spatial array further include contacting a biological sample to the spatial array after step (c). In some embodiments, methods of generating a spatial array further include permeabilizing the biological sample to allow the analyte in the biological sample to interact with the capture probe.

In some embodiments, methods of generating a spatial array further include migrating the analyte in the biological sample to the plurality of capture probes. In some embodiments of methods of generating a spatial array, the migrating includes passive migration. In some embodiments of methods of generating a spatial array, the migrating includes active migration.

In another aspect, provided herein are methods of generating a spatial array including (a) providing a substrate including an arrayed plurality of acceptor oligonucleotides, where an acceptor oligonucleotide of the plurality of acceptor oligonucleotides includes a spatial barcode and a first ligation handle, and where the 5' end of the acceptor oligonucleotide is attached to the substrate, (b) providing a splint oligonucleotide including a sequence complementary to the first ligation handle and a sequence complementary to a second ligation handle, and (c) ligating a donor oligonucleotide including the second ligation handle and a capture domain to the 3' end the acceptor oligonucleotide to generate a capture probe, thereby generating a spatial array.

In some embodiments of methods of generating a spatial array, the acceptor oligonucleotides further includes a cleavage domain, a unique molecular identifier, a functional sequence, or any combination thereof.

In some embodiments of methods of generating a spatial array, the capture domain includes a poly(T) sequence. In some embodiments of methods of generating a spatial array, the capture domain includes a gene-specific sequence. In some embodiments of methods of generating a spatial array, the gene-specific sequence is a Penk-specific sequence. In some embodiments of methods of generating a spatial array, the capture domain includes a random sequence. In some embodiments of methods of generating a spatial array, the random sequence is a hexamer.

In some embodiments, methods of generating a spatial array further include contacting a biological sample to the spatial array after step (c). In some embodiments, methods of generating a spatial array further include permeabilizing the biological sample to allow an analyte in the biological sample to interact with the capture probe.

In some embodiments, methods of generating a spatial array further include migrating the analyte in the biological sample to the capture probe. In some embodiments of methods of generating a spatial array, the migrating includes passive migration. In some embodiments of methods of generating a spatial array, the migrating includes active migration.

In another aspect, provided herein are methods of generating a capture probe bound to substrate including dispensing a second solution onto a portion of a surface of a substrate coated with a first solution, where after the dispensing, molecules within the first solution and the second solution do not substantially mix with each other, where the second solution includes a capture probe, and the dispensing results in attachment of the capture probe to the surface of the substrate.

In some embodiments, methods of generating a capture probe bound to substrate further include: curing the second solution, and removing the first solution from the substrate, where the cured second solution is retained on the surface of the substrate.

In some embodiments of methods of generating a capture probe bound to substrate, the surface of the substrate to which the capture probe is attached has an area that is smaller than a corresponding area generated by dispensing the second solution onto the surface of the substrate in the absence of the first solution. In some embodiments of methods of generating a capture probe bound to substrate, the surface of the substrate to which the capture probe is attached has an area that is about two-fold less than the corresponding area generated by dispensing the second solution onto the surface of the substrate in the absence of the first solution.

In some embodiments, methods of generating a capture probe bound to substrate further include curing the first and second solutions on the substrate, thus generating a matrix. In some embodiments of methods of generating a capture probe bound to substrate, the first and second solutions are cured by chemical means. In some embodiments of methods of generating a capture probe bound to substrate, the first and second solutions are cured by photo-reactive means.

In some embodiments, methods of generating a capture probe bound to substrate further include shrinking the matrix, thus generating a shrunken matrix having an area to which the capture probe is attached, where the area in the shrunken matrix is reduced as compared to a corresponding area in the matrix.

In some embodiments, methods of generating a capture probe bound to substrate further include prior to the step of dispensing the second solution: curing the first solution to form a first solution matrix, where the first solution matrix can be reversibly expanded along one or more of its axes. In some embodiments of methods of generating a capture probe bound to substrate, the step of dispensing the second solution onto the portion of the substrate including dispensing the second solution onto a surface of the first solution matrix in an expanded state. In some embodiments, methods of generating a capture probe bound to substrate further includes, after the dispensing step: shrinking the first solution matrix along the one or more axes of the surface of the substrate.

In some embodiments of methods of generating a capture probe bound to substrate, the first solution has a viscosity that is about 0.1×-fold, 0.2×-fold, 0.3×-fold, 0.4×-fold, 0.5×-fold, 0.6×-fold, 0.7×-fold, 0.8×-fold, 0.9×-fold, 1.0×-fold, 1.1×-fold, 1.2×-fold, 1.3×-fold, 1.4-fold, 1.5×-fold, 1.6×-fold, 1.7×-fold, 1.8×-fold, 1.9×-fold, 2.0×-fold, 2.5×-fold, 3.0×-fold, 4.0×-fold, 5.0× fold, 6.0×-fold, 7.0×-fold, 8.0× fold, 9.0×-fold or 10×-fold greater than the viscosity of the second solution.

In some embodiments of methods of generating a capture probe bound to substrate, the first solution has a lower nucleic acid diffusivity as compared to the second solution.

In some embodiments of methods of generating a capture probe bound to substrate, the capture probe includes a spatial barcode. In some embodiments, the capture probe includes a unique molecular identifier. In some embodiments of methods of generating a capture probe bound to substrate, the capture probe includes a functional domain. In some embodiments of methods of generating a capture probe bound to substrate, the capture probe includes a cleavage domain, a spatial barcode, a unique molecular identifier, a functional domain, and a capture domain.

In another aspect, provided herein are methods of generating an array of capture probes bound to a substrate including dispensing a droplet of a second solution onto a portion of a surface of a substrate coated with a first solution, where after the dispensing, molecules within the first solution and the droplet of the second solution do not substantially mix with each other, where the second solution includes a capture probe, and the dispensing results in attachment of the capture probe to the surface of the substrate.

In some embodiments, methods of generating an array of capture probes bound to a substrate further include: curing the second solution, and removing the first solution from the substrate, where the cured second solution is retained on the surface of the substrate.

In some embodiments of methods of generating an array of capture probes bound to a substrate, the surface of the substrate to which the capture probe is attached has an area that is smaller than a corresponding area generated by dispensing the second solution onto the surface of the substrate in the absence of the first solution. In some embodiments of methods of generating an array of capture probes bound to a substrate, the surface of the substrate to which the capture probe is attached has an area that is about two-fold less than the corresponding area generated by dispensing the second solution onto the surface of the substrate in the absence of the first solution.

In some embodiments, methods of generating an array of capture probes bound to a substrate further include curing the first and second solutions on the substrate, thus generating a matrix. In some embodiments of methods of generating an array of capture probes bound to a substrate, the first solution and the second solutions are cured by chemical means. In some embodiments of methods of generating an array of capture probes bound to a substrate, the first and second solutions are cured by photo-reactive means.

In some embodiments, methods of generating an array of capture probes bound to a substrate further include shrinking the matrix, thus generating a shrunken matrix having an area to which the capture probe is attached, where the area in the shrunken matrix is reduced as compared to a corresponding area in the matrix.

In some embodiments, methods of generating an array of capture probes bound to a substrate further include, prior to the step of dispensing the second solution: curing the first solution to form a first solution matrix, where the first solution matrix can be reversibly expanded along one or more of its axes. In some embodiments of methods of generating an array of capture probes bound to a substrate, the step of dispensing the second solution onto the portion of the substrate including dispensing the second solution onto a surface of the first solution matrix in an expanded state.

In some embodiments, methods of generating an array of capture probes bound to a substrate further include after the dispensing step: shrinking the first solution matrix along the one or more axes of the surface of the substrate.

In some embodiments of methods of generating an array of capture probes bound to a substrate, the first solution has a viscosity that is about 0.1×-fold, 0.2×-fold, 0.3×-fold, 0.4×-fold, 0.5×-fold, 0.6×-fold, 0.7×-fold, 0.8×-fold, 0.9×-fold, 1.0×-fold, 1.1×-fold, 1.2×-fold, 1.3×-fold, 1.4×-fold, 1.5×-fold, 1.6×-fold, 1.7×-fold, 1.8×-fold, 1.9×-fold, 2.0×-fold, 2.5×-fold, 3.0×-fold, 4.0×-fold, 5.0× fold, 6.0×-fold, 7.0×-fold, 8.0× fold, 9.0×-fold or 10×-fold greater than the viscosity of the second solution.

In some embodiments of methods of generating an array of capture probes bound to a substrate, the first solution has a lower nucleic acid diffusivity as compared to the second solution.

In some embodiments of methods of generating an array of capture probes bound to a substrate, the capture probe includes a spatial barcode. In some embodiments of methods of generating an array of capture probes bound to a substrate, the at least one of the capture probes includes a unique molecular identifier. In some embodiments of methods of generating an array of capture probes bound to a substrate, the capture probe includes a functional domain. In some embodiments of methods of generating an array of capture probes bound to a substrate, the capture probe includes a cleavage domain, a spatial barcode, a unique molecular identifier, a functional domain, and a capture domain.

In another aspect, provided herein are methods for spatially profiling an analyte in a biological sample including (a) dispensing a droplet of a second solution onto a portion of a surface of a substrate coated with a the first solution, where after the dispensing, molecules within the first solution and the droplet of the second solution do not substantially mix with each other, where the second solution includes a capture probe, and the dispensing results in attachment of the capture probe to the surface of the substrate, (b) contacting the biological sample with the spatial array such that the analyte present in the biological sample is captured by the capture probes, thereby determining the spatial profile of the captured analyte.

In some embodiments of methods for spatially profiling an analyte in a biological sample, at least one of the capture probes includes a cleavage domain, a spatial barcode, a unique molecular identifier, a functional domain, and a capture domain.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 3 shows an exemplary spatial analysis workflow.
FIG. 4 shows an exemplary spatial analysis workflow.

FIG. 16 shows an example of a microfluidic channel structure 1600 for partitioning dissociated sample (e.g., biological particles or individual cells from a sample).

FIG. 17A shows an example of a microfluidic channel structure 1700 for delivering spatial barcode carrying beads to droplets.

FIGS. 31A-C depict an illustrative embodiment of the methods for preparing a spatial array of the present disclosure. FIG. 31A depicts a substrate provided with first oligonucleotides attached thereto in a 5'-to-3' orientation, wherein the phosphodiester and exocyclic amine groups are protected. FIG. 31B depicts 5'-to-3 light-directed spatial synthesis of second oligonucleotides to the free 3'-ends of the first oligonucleotide on the substrate, wherein the second oligonucleotide have different sequences in the two different regions. FIG. 31C depicts ligation of a third oligonucleotide to the free 3'-ends of the two different second oligonucleotides.

FIGS. 32A-C depict an illustrative embodiment of the methods for preparing a spatial array of the present disclosure. FIG. 32A depicts ex situ solid phase synthesis of a first oligonucleotide in 3'-to-5' direction followed by cleavage from the feature with the phosphodiester and exocyclic amine groups protected. FIG. 32B depicts coupling of the ex situ synthesized first oligonucleotide to a substrate in a 5'-to-3' orientation. FIG. 32C depicts 5'-to-3' light-directed spatial synthesis of second oligonucleotides to the free 3'-ends of the first oligonucleotide on the substrate, wherein the second oligonucleotides have different sequences in the two different regions.

FIG. 33A depicts a first oligonucleotide with phosphodiester and exocyclic amine protecting groups attached to a substrate in a 5'-to-3' orientation, wherein the first oligonucleotide has been in situ synthesized on the surface of the substrate.

FIG. 33B depicts 5'-to-3 light-directed spatial synthesis of second oligonucleotides to the free 3'-ends of the first oligonucleotide (with first segment phosphodiester and exocyclic amine protecting groups in place) on the substrate, wherein the second oligonucleotides have different sequences in the two different regions.

FIGS. 34A-B depict an illustrative embodiment of the methods for preparing a spatial array of the present disclosure. FIG. 34A depicts a first oligonucleotide phosphodiester and exocyclic amine protecting groups attached to a substrate in a 5'-to-3' orientation, wherein the first oligonucleotide has been synthesized on the surface of the substrate using 5'-to-3' light-directed spatial synthesis. FIG. 34B depicts 5'-to-3 light-directed spatial synthesis of second oligonucleotides to the free 3'-ends of the first oligonucleotide (with first oligonucleotide phosphodiester and exocyclic amine protecting groups in place) on the substrate, wherein the second oligonucleotides have different sequences in the two different regions.

FIGS. 35A-C depict an illustrative embodiment of the methods for preparing a spatial array of the present disclosure. FIG. 35A depicts coupling of an ex situ synthesized first oligonucleotide in 3'-to-5' direction without phosphodiester and exocyclic amine groups protected. FIG. 35B depicts in situ protection of the phosphodiester and exocyclic amine groups of the first oligonucleotide. FIG. 35C depicts 5'-to-3 light-directed spatial synthesis of second oligonucleotides to the free 3'-ends of the first oligonucleotide the substrate, wherein the second oligonucleotides have different sequences in the two different regions.

FIGS. 36A-C depict an illustrative embodiment of the methods for preparing a spatial array of the present disclosure. FIG. 36A depicts coupling of an ex situ synthesized first oligonucleotide in 3'-to-5' direction without phosphodiester and exocyclic amine groups protected. FIG. 36B depicts in situ hybridization of a complementary oligonucleotide to the first oligonucleotide, whereby the phosphodiester and exocyclic amine groups of the first oligonucleotide are protected. FIG. 36C depicts 5'-to-3 light-directed spatial synthesis of second oligonucleotides to the free 3'-ends of the first oligonucleotide on the substrate while the first oligonucleotide is hybridized to a complementary oligonucleotide, and wherein the synthesized second oligonucleotides have different sequences in the two different regions.

FIG. 43 is a fluorescent image showing detection of Penk mRNA with a Penk specific capture probe generated by the method shown in FIG. 41 compared to a control tissue optimization slide.

DETAILED DESCRIPTION

I. Introduction

Figure 1:
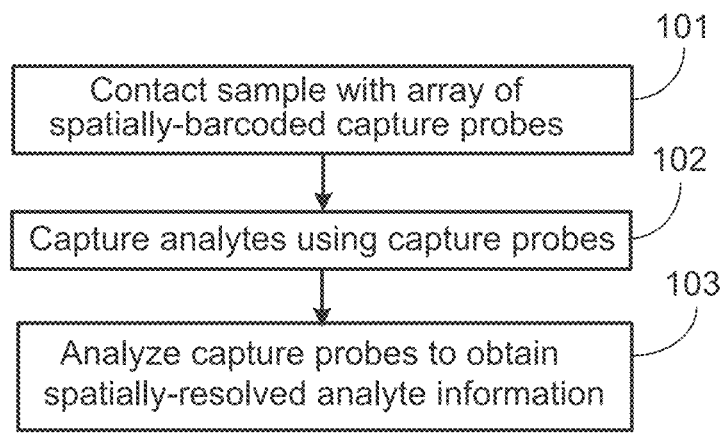
FIG. 1 shows an exemplary spatial analysis workflow.

This disclosure describes apparatus, systems, methods, and compositions for spatial analysis of biological samples. This section describes certain general terminology, analytes, sample types, and preparative steps that are referred to in later sections of the disclosure.

(a) Spatial Analysis

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue. Differences in analyte levels within different cells in a tissue of a mammal can also provide information on drug resistance mechanisms and the development of the same in a tissue of a mammal. Differences in the presence or absence of analytes within different cells in a tissue of a multicellular organism (e.g., a mammal) can provide information on drug resistance mechanisms and the development of the same in a tissue of a multicellular organism.

The spatial analysis methodologies herein provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. Spatial RNA assays traditionally relied on staining for a limited number of RNA species. In contrast, single-cell RNA-sequencing allows for deep profiling of cellular gene expression (including non-coding RNA), but the established methods separate cells from their native spatial context.

Current spatial analysis methodologies provide a vast amount of analyte level and/or expression data for a variety of multiple analytes within a sample at high spatial resolution, e.g., while retaining the native spatial context. Spatial analysis methods include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore or a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate including an analyte, a binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), a photolabile bond, a thermosensitive bond, or a chemical-sensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein). For example, capture probes can be encapsulated or disposed within a permeable bead (e.g., a gel bead). In some examples, capture probes can be encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe can be directed to interact with a cell or a tissue sample using a variety of methods, e.g., inclusion of a lipid anchoring agent in the capture probe, inclusion of an agent that binds specifically to, or forms a covalent bond with a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodrigues et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, and can be used herein in any combination. Further non-limiting aspects of spatial analysis methodologies are described herein.

(b) General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*.

(vi) Genome

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

(vii) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(viii) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(ix) Primer

A "primer" is a single-stranded nucleic acid sequence having a 3' end that can be used as a chemical substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases.

(x) Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension.

Enzymatic extension can be performed by an enzyme including, but not limited to, a polymerase and/or a reverse transcriptase.

(xi) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(xii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(xiii) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia*, *Bacillus*, *Thermophilus*, or *Pyrococcus*.

Suitable examples of DNA polymerases that can be used include, but are not limited to: E. coli DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g., DNA polymerase activity of the wild-type sequence. Mutations can affect the activity profile of the enzymes, e.g., enhance or reduce the rate of polymerization, under different reaction conditions, e.g., temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, Mass.), and Ampligase™ (available from Epicentre Biotechnologies, Madison, Wis.). Derivatives, e.g., sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g., reverse transcriptase, activity of the wild-type sequence. The reverse transcriptase enzyme can be provided as part of a composition that includes other components, e.g., stabilizing components that enhance or improve the activity of the reverse transcriptase enzyme, such as RNase inhibitor(s), inhibitors of DNA-dependent DNA synthesis, e.g., actinomycin D. Many sequence-modified derivative or mutants of reverse transcriptase enzymes, e.g., M-MLV, and compositions including unmodified and modified enzymes are commercially available, e.g., ArrayScript™ MultiScribe™, ThermoScript™, and SuperScript® I, II, III, and IV enzymes.

Certain reverse transcriptase enzymes (e.g., Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g., an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xiv) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also include single domain antibodies (VHH domains and VNAR domains), scFvs, and Fab fragments.

(xv) Affinity Group

An "affinity group" is a molecule or molecular moiety which has a high affinity or preference for associating or binding with another specific or particular molecule or moiety. The association or binding with another specific or particular molecule or moiety can be via a non-covalent interaction, such as hydrogen bonding, ionic forces, and van der Waals interactions. An affinity group can, for example, be biotin, which has a high affinity or preference to associate or bind to the protein avidin or streptavidin. An affinity group, for example, can also refer to avidin or streptavidin which has an affinity to biotin. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

(xvi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a capture probe or analyte. The detectable label can be directly detectable by itself (e.g., radioisotope labels or fluorescent labels) or, in the case of an enzymatic label, can be indirectly detectable, e.g., by catalyzing chemical alterations of a chemical substrate compound or composition, which chemical substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, C1-NERF (low pH), CPM, 6-CR 6G, CTC Formazan, Cy2®, Cy3®, Cy3.5®, Cy5®, Cy5.5®, Cy7®, Cychrome (PE-Cy5), Dansyl amine, Dansyl cadaverine, Dansylchloride, DAPI, Dapoxyl, DCFH, DHR, DiA (4-Di-16-ASP), DiD (Di1C18 (5)), DIDS, Di1 (Di1C18(3)), DiO (DiOC18(3)), DiR (Di1C18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluoroscein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1, 5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™ Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66 W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate chemical substrates (e.g., an oxidizing reagent plus a chemiluminescent compound). A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and—methoxy substituents, oxalates such as oxalyl active esters, p-nitrophenyl, N-alkyl acridinum esters, luciferins, lucigenins, or acridinium esters.

(xvii) Template Switching Oligonucleotide

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

(xviii) Splint Oligonucleotide

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

(c) Analytes

The apparatus, systems, methods, and compositions described in this disclosure can be used to detect and analyze a wide variety of different analytes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte can be an organelle (e.g., nuclei or mitochondria).

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Additional examples of analytes include mRNA and cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a miRNA, a physical environmental (e.g., temperature change), or any other known perturbation agents.

Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The generated cDNA can then be barcoded using a capture probe, featuring a barcode sequence (and optionally, a UMI sequence) that hybridizes with at least a portion of the generated cDNA. In some embodiments, a template switching oligonucleotide hybridizes to a poly(C) tail added to a 3' end of the cDNA by a reverse transcriptase enzyme. The original mRNA template and template switching oligonucleotide can then be denatured from the cDNA and the barcoded capture probe can then hybridize with the cDNA and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, filed Oct. 18, 2017, and U.S. patent application Ser. No. 15/825,740, filed Nov. 29, 2017, both of which are incorporated herein by reference in their entireties. V(D)J analysis can also be completed with the use of one or more labelling agents that bind to particular surface features of immune cells and associated with barcode sequences. The one or more labelling agents can include an MHC or MHC multimer.

As described above, the analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the analyte (e.g., a sequence that can hybridize to the CRISPR RNA (crRNA), single guide RNA (sgRNA), or an adapter sequence engineered into a crRNA or sgRNA).

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate. Methods for performing multiplexed assays to analyze two or more different analytes will be discussed in a subsequent section of this disclosure.

(d) Biological Samples (i) Types of Biological Samples

A "biological sample" is obtained from the subject for analysis using any of a variety of techniques including, but not limited to, biopsy, surgery, and laser capture microscopy (LCM), and generally includes cells and/or other biological material from the subject. In addition to the subjects described above, a biological sample can be obtained from non-mammalian organisms (e.g., a plants, an insect, an arachnid, a nematode (e.g., *Caenorhabditis elegans*), a fungi, an amphibian, or a fish (e.g., zebrafish)). A biological sample can be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from a eukaryote, such as a patient derived organoid (PDO) or patient derived xenograft (PDX). The biological sample can include organoids, a miniaturized and simplified version of an organ produced in vitro in three dimensions that shows realistic micro-anatomy. Organoids can be generated from one or more cells from a tissue, embryonic stem cells, and/or induced pluripotent stem cells, which can self-organize in three-dimensional culture owing to their self-renewal and differentiation capacities. In some embodiments, an organoid is a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, or a retinal organoid. Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Cell-free biological samples can include extracellular polynucleotides. Extracellular polynucleotides can be isolated from a bodily sample, e.g., blood, plasma, serum, urine, saliva, mucosal excretions, sputum, stool, and tears.

As discussed above, a biological sample can include a single analyte of interest, or more than one analyte of interest. Methods for performing multiplexed assays to analyze two or more different analytes in a single biological sample is discussed in a subsequent section of this disclosure.

(ii) Preparation of Biological Samples

A variety of steps can be performed to prepare a biological sample for analysis. Except where indicated otherwise, the preparative steps described below can generally be combined in any manner to appropriately prepare a particular sample for analysis.

(1) Tissue Sectioning

A biological sample can be harvested from a subject (e.g., via surgical biopsy, whole subject sectioning), grown in vitro on a growth substrate or culture dish as a population of cells, or prepared as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(2) Freezing

In some embodiments, the biological sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., −80° C. −90° C., −100° C., −110° C., −120° C., −130° C., −140° C., −150° C., −160° C., −170° C., −180° C., −190° C., or −200° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C. A sample can be snap frozen in isopentane and liquid nitrogen. Frozen samples can be stored in a sealed container prior to embedding.

(3) Formalin Fixation and Paraffin Embedding

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

(4) Fixation

As an alternative to formalin fixation described above, a biological sample can be fixed in any of a variety of other fixatives to preserve the biological structure of the sample prior to analysis. For example, a sample can be fixed via immersion in ethanol, methanol, acetone, formaldehyde (e.g., 2% formaldehyde), paraformaldehyde-Triton, glutaraldehyde, or combinations thereof.

In some embodiments, acetone fixation is used with fresh frozen samples, which can include, but are not limited to, cortex tissue, mouse olfactory bulb, human brain tumor, human post-mortem brain, and breast cancer samples. In some embodiments, a compatible fixation method is chosen and/or optimized based on a desired workflow. For example, formaldehyde fixation may be chosen as compatible for workflows using IHC/IF protocols for protein visualization. As another example, methanol fixation may be chosen for workflows emphasizing RNA/DNA library quality. Acetone fixation may be chosen in some applications to permeabilize the tissue. When acetone fixation is performed, pre-permeabilization steps (described below) may not be performed. Alternatively, acetone fixation can be performed in conjunction with permeabilization steps.

(5) Embedding

As an alternative to paraffin embedding described above, a biological sample can be embedded in any of a variety of other embedding materials to provide a substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

(6) Staining

To facilitate visualization, biological samples can be stained using a wide variety of stains and staining techniques. In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin.

The sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destined by washing the sample in HCl. In some embodiments, destaining can include 1, 2, 3, or more washes in HCl. In some embodiments, destaining can include adding HCl to a downstream solution (e.g., permeabilization solution). As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(7) Hydrogel Embedding

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus. A "hydrogel" as described herein can include a cross-linked 3D network of hydrophilic polymer chains. A "hydrogel subunit" can be a hydrophilic monomer, a molecular precursor, or a polymer that can be polymerized (e.g., cross-linked) to form a three-dimensional (3D) hydrogel network.

A hydrogel can swell in the presence of water. In some embodiments, a hydrogel comprises a natural material. In some embodiments, a hydrogel includes a synthetic material. In some embodiments, a hydrogel includes a hybrid material, e.g., the hydrogel material comprises elements of both synthetic and natural polymers. Any of the materials used in hydrogels or hydrogels comprising a polypeptide-based material described herein can be used. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art. For example, the biological sample can be immobilized in the hydrogel by polyacrylamide crosslinking. Further, analytes of a biological sample can be immobilized in a hydrogel by crosslinking (e.g., polyacrylamide crosslinking).

The composition and application of the hydrogel to a biological sample typically depends on the nature and preparation of the biological sample (e.g., sectioned, non-sectioned, fresh-frozen tissue, type of fixation). A hydrogel can be any appropriate hydrogel where upon formation of the hydrogel on the biological sample the biological sample becomes anchored to or embedded in the hydrogel. Non-limiting examples of hydrogels are described herein or are known in the art. As one example, where the biological sample is a tissue section, the hydrogel can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel are formed in compartments, including but not limited to devices used to culture, maintain, or transport the cells. For example, hydrogels can be formed with monomer solution plus APS/TEMED added to the compartment to a depth ranging from about 0.1 µm to about 5 mm.

In some embodiments, a hydrogel includes a linker that allows anchoring of the biological sample to the hydrogel. In some embodiments, a hydrogel includes linkers that allow anchoring of biological analytes to the hydrogel. In such cases, the linker can be added to the hydrogel before, contemporaneously with, or after hydrogel formation. Non-limiting examples of linkers that anchor nucleic acids to the hydrogel can include 6-((Acryloyl)amino) hexanoic acid (Acryloyl-X SE) (available from ThermoFisher, Waltham, Mass.), Label-IT Amine (available from MirusBio, Madison, Wis.) and Label X).

In some embodiments, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., capture probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, an analyte capture agent is added to the hydrogel before, contemporaneously with, and/or after polymerization. In some embodiments, a cell-penetrating agent is added to the hydrogel before, contemporaneously with, and/or after polymerization.

In some embodiments, a biological sample is embedded in a hydrogel to facilitate sample transfer to another location (e.g., to an array). For example, archived biological samples (e.g., FFPE tissue sections) can be transferred from storage to a spatial array to perform spatial analysis. In some embodiments, a biological sample on a substrate can be covered with any of the prepolymer solutions described herein. In some embodiments, the prepolymer solution can be polymerized such that a hydrogel is formed on top of and/or around the biological sample. Hydrogel formation can occur in a manner sufficient to anchor (e.g., embed) the biological sample to the hydrogel. After hydrogel formation, the biological sample is anchored to (e.g., embedded in) the hydrogel wherein separating the hydrogel from the substrate (e.g., glass slide) results in the biological sample separating from the substrate along with the hydrogel. The biological sample contained in the hydrogel can then be contacted with a spatial array, and spatial analysis can be performed on the biological sample.

Any variety of characteristics can determine the transfer conditions required for a given biological sample. Non-limiting examples of characteristics likely to impact transfer conditions include the sample (e.g., thickness, fixation, and cross-linking) and/or the analyte of interest (different conditions to preserve and/or transfer different analytes (e.g., DNA, RNA, and protein)).

In some embodiments, the hydrogel is removed after contacting the biological sample with the spatial array. For example, methods described herein can include an event-dependent (e.g., light or chemical) depolymerizing hydrogel, wherein upon application of the event (e.g., external stimuli) the hydrogel depolymerizes. In one example, a biological sample can be anchored to a DTT-sensitive hydrogel, where addition of DTT can cause the hydrogel to depolymerize and release the anchored biological sample.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored in a medium before or after clearing of hydrogel (e.g., a mounting medium, methylcellulose, or other semi-solid mediums).

In some embodiments, the hydrogel chemistry can be tuned to specifically bind (e.g., retain) particular species of analytes (e.g., RNA, DNA, protein, etc.). In some embodiments, a hydrogel includes a linker that allows anchoring of the biological sample to the hydrogel. In some embodiments, a hydrogel includes linkers that allow anchoring of biological analytes to the hydrogel. In such cases, the linker can be added to the hydrogel before, contemporaneously with, or after hydrogel formation. Non-limiting examples of linkers that anchor nucleic acids to the hydrogel can include 6-((Acryloyl)amino) hexanoic acid (Acryloyl-X SE), Label- IT Amine and Label X. Non-limiting examples of characteristics likely to impact transfer conditions include the sample (e.g., thickness, fixation, and cross-linking) and/or the analyte of interest (different conditions to preserve and/or transfer different analytes (e.g., DNA, RNA, and protein)).

Additional methods and aspects of hydrogel embedding of biological samples are described for example in Chen et al., Science 347(6221):543-548, 2015, the entire contents of which are incorporated herein by reference.

(8) Biological Sample Transfer

In some embodiments, a biological sample immobilized on a substrate (e.g., a biological sample prepared using methanol fixation or formalin-fixation and paraffin-embedding (FFPE)) is transferred to a spatial array using a hydrogel. In some embodiments, a hydrogel is formed on top of a biological sample on a substrate (e.g., glass slide). For example, hydrogel formation can occur in a manner sufficient to anchor (e.g., embed) the biological sample to the hydrogel. After hydrogel formation, the biological sample is anchored to (e.g., embedded in) the hydrogel wherein separating the hydrogel from the substrate results in the biological sample separating from the substrate along with the hydrogel. The biological sample can then be contacted with a spatial array, thereby allowing spatial profiling of the biological sample. In some embodiments, the hydrogel is removed after contacting the biological sample with the spatial array. For example, methods described herein can include an event-dependent (e.g., light or chemical) depolymerizing hydrogel, wherein upon application of the event (e.g., external stimuli) the hydrogel depolymerizes. In one example, a biological sample can be anchored to a DTT-sensitive hydrogel, where addition of DTT can cause the hydrogel to depolymerize and release the anchored biological sample. A hydrogel can be any appropriate hydrogel where upon formation of the hydrogel on the biological sample the biological sample becomes anchored to or embedded in the hydrogel. Non-limiting examples of hydrogels are described herein or are known in the art. In some embodiments, a hydrogel includes a linker that allows anchoring of the biological sample to the hydrogel. In some embodiments, a hydrogel includes linkers that allow anchoring of biological analytes to the hydrogel. In such cases, the linker can be added to the hydrogel before, contemporaneously with, or after hydrogel formation. Non-limiting examples of linkers that anchor nucleic acids to the hydrogel can include 6-((Acryloyl)amino) hexanoic acid (Acryloyl-X SE) (available from ThermoFisher, Waltham, Mass.), Label-IT Amine (available from MirusBio, Madison, Wis.) and Label X). Any variety of characteristics can determine the transfer conditions required for a given biological sample. Non-limiting examples of characteristics likely to impact transfer conditions include the sample (e.g., thickness, fixation, and cross-linking) and/or the analyte of interest (different conditions to preserve and/or transfer different analytes (e.g., DNA, RNA, and protein)). In some embodiments, hydrogel formation can occur in a manner sufficient to anchor the analytes (e.g., embed) in the biological sample to the hydrogel. In some embodiments, the hydrogel can be imploded (e.g., shrunk) with the anchored analytes (e.g., embedded in the hydrogel) present in the biological sample. In some embodiments, the hydrogel can be expanded (e.g., isometric expansion) with the anchored analytes (e.g., embedded in the hydrogel) present in the biological sample. In some embodiments, the hydrogel can be imploded (e.g., shrunk) and subsequently expanded with anchored analytes (e.g., embedded in the hydrogel) present in the biological sample.

(9) Isometric Expansion

In some embodiments, a biological sample embedded in a hydrogel can be isometrically expanded. Isometric expansion methods that can be used include hydration, a preparative step in expansion microscopy, as described in Chen et al., Science 347(6221):543-548, 2015; Asano et al. Current Protocols. 2018, 80:1, doi:10.1002/cpcb.56 and Gao et al. BMC Biology. 2017, 15:50, doi:10.1186/s12915-017-0393-3, Wassie, A. T., et al, Expansion microscopy: principles and uses in biological research, Nature Methods, 16(1): 33-41 (2018), each of which is incorporated by reference in its entirety.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the expanded biological sample with a spatially barcoded array (e.g., spatially barcoded capture probes on a substrate).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, Mass.), Label-IT Amine (available from MirusBio, Madison, Wis.) and Label X (described for example in Chen et al., Nat. Methods 13:679-684, 2016, the entire contents of which are incorporated herein by reference).

Isometric expansion of the sample can increase the spatial resolution of the subsequent analysis of the sample. For example, isometric expansion of the biological sample can result in increased resolution in spatial profiling (e.g., single-cell profiling). The increased resolution in spatial profiling can be determined by comparison of an isometrically expanded sample with a sample that has not been isometrically expanded.

In some embodiments, a biological sample is isometrically expanded to a volume at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded volume. In some embodiments, the sample is isometrically expanded to at least 2× and less than 20× of its non-expanded volume.

In some embodiments, a biological sample embedded in a hydrogel is isometrically expanded to a volume at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded volume. In some embodiments, the biological sample embedded in a hydrogel is isometrically expanded to at least 2× and less than 20× of its non-expanded volume.

(10) Substrate Attachment

In some embodiments, the biological sample can be attached to a substrate. Examples of substrates suitable for this purpose are described in detail below. Attachment of the biological sample can be irreversible or reversible, depending upon the nature of the sample and subsequent steps in the analytical method.

In certain embodiments, the sample can be attached to the substrate reversibly by applying a suitable polymer coating to the substrate, and contacting the sample to the polymer coating. The sample can then be detached from the substrate using an organic solvent that at least partially dissolves the polymer coating. Hydrogels are examples of polymers that are suitable for this purpose.

More generally, in some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

(11) Unaggregated Cells

In some embodiments, the biological sample corresponds to cells (e.g., derived from a cell culture or a tissue sample). In a cell sample with a plurality of cells, individual cells can be naturally unaggregated. For example, cells can be derived from a suspension of cells and/or disassociated or disaggregated cells from a tissue or tissue section.

Alternatively, the cells in the sample may be aggregated, and may be disaggregated into individual cells using, for example, enzymatic or mechanical techniques. Examples of enzymes used in enzymatic disaggregation include, but are not limited to, dispase, collagenase, trypsin, or combinations thereof. Mechanical disaggregation can be performed, for example, using a tissue homogenizer.

In some embodiments of unaggregated cells or disaggregated cells, the cells are distributed onto the substrate such that at least one cell occupies a distinct spatial feature on the substrate. The cells can be immobilized on the substrate (e.g., to prevent lateral diffusion of the cells). In some embodiments, a cell immobilization agent can be used to immobilize a non-aggregated or disaggregated sample on a spatially-barcoded array prior to analyte capture. A "cell immobilization agent" can refer to an antibody, attached to a substrate, which can bind to a cell surface marker. In some embodiments, the distribution of the plurality of cells on the substrate follows Poisson statistics.

In some embodiments, cells from a plurality of cells are immobilized on a substrate. In some embodiments, the cells are immobilized to prevent lateral diffusion, for example, by adding a hydrogel and/or by the application of an electric field.

(12) Suspended and Adherent Cells

In some embodiments, the biological sample can be derived from a cell culture grown in vitro. Samples derived from a cell culture can include one or more suspension cells which are anchorage-independent within the cell culture. Examples of such cells include, but are not limited to, cell lines derived from hematopoietic cells, and from the following cell lines: Colo205, CCRF-CEM, HL-60, K562, MOLT-4, RPMI-8226, SR, HOP-92, NCI-H322M, and MALME-3M.

Samples derived from a cell culture can include one or more adherent cells which grow on the surface of the vessel that contains the culture medium. Non-limiting examples of adherent cells include DU145 (prostate cancer) cells, H295R (adrenocortical cancer) cells, HeLa (cervical cancer) cells, KBM-7 (chronic myelogenous leukemia) cells, LNCaP (prostate cancer) cells, MCF-7 (breast cancer) cells, MDA-MB-468 (breast cancer) cells, PC3 (prostate cancer) cells, SaOS-2 (bone cancer) cells, SH-SY5Y (neuroblastoma, cloned from a myeloma) cells, T-47D (breast cancer) cells, THP-1 (acute myeloid leukemia) cells, U87 (glioblastoma) cells, National Cancer Institute's 60 cancer cell line panel (NCI60), vero (African green monkey Chlorocebus kidney epithelial cell line) cells, MC3T3 (embryonic calvarium) cells, GH3 (pituitary tumor) cells, PC12 (pheochromocytoma) cells, dog MDCK kidney epithelial cells, *Xenopus* A6 kidney epithelial cells, zebrafish AB9 cells, and Sf9 insect epithelial cells.

Additional examples of adherent cells are shown in Table 1 and catalogued, for example, in "A Catalog of in Vitro Cell Lines, Transplantable Animal and Human Tumors and Yeast," The Division of Cancer Treatment and Diagnosis (DCTD), National Cancer Institute (2013), and in Abaan et al., "The exomes of the NCI-60 panel: a genomic resource for cancer biology and systems pharmacology," *Cancer Research* 73(14):4372-82, 2013, the entire contents of each of which are incorporated by reference herein.

TABLE 1

Examples of adherent cells

| Cell Line | Species | Organ of Origin | Disease |
| --- | --- | --- | --- |
| BT549 | Human | Breast | Ductal Carcinoma |
| HS 578T | Human | Breast | Carcinoma |
| MCF7 | Human | Breast | Adenocarcinoma |
| MDA-MB-231 | Human | Breast | Adenocarcinoma |
| MDA-MB-468 | Human | Breast | Adenocarcinoma |
| T-47D | Human | Breast | Ductal Carcinoma |
| SF268 | Human | CNS | Anaplastic Astrocytoma |
| SF295 | Human | CNS | Glioblastoma-Multiforme |
| SF539 | Human | CNS | Glioblastoma |
| SNB-19 | Human | CNS | Glioblastoma |
| SNB-75 | Human | CNS | Astrocytoma |
| U251 | Human | CNS | Glioblastoma |
| Colo205 | Human | Colon | Dukes' type D, Colorectal adenocarcinoma |
| HCC 2998 | Human | Colon | Carcinoma |
| HCT-116 | Human | Colon | Carcinoma |
| HCT-15 | Human | Colon | Dukes' type C, Colorectal adenocarcinoma |
| HT29 | Human | Colon | Colorectal adenocarcinoma |
| KM12 | Human | Colon | Adenocarcinoma, Grade III |
| SW620 | Human | Colon | Adenocarcinoma |
| 786-O | Human | Kidney | renal cell adenocarcinoma |
| A498 | Human | Kidney | Adenocarcinoma |
| ACHN | Human | Kidney | renal cell adenocarcinoma |
| CAKI | Human | Kidney | clear cell carcinoma |
| RXF 393 | Human | Kidney | Poorly Differentiated Hypernephroma |
| SN12C | Human | Kidney | Carcinoma |
| TK-10 | Human | Kidney | Spindle Cell carcinoma |
| UO-31 | Human | Kidney | Carcinoma |
| A549 | Human | Lung | Adenocarcinoma |
| EKVX | Human | Lung | Adenocarcinoma |
| HOP-62 | Human | Lung | Adenocarcinoma |
| HOP-92 | Human | Lung | Large Cell, Undifferentiated |
| NCI-H226 | Human | Lung | squamous cell carcinoma; mesothelioma |
| NCI-H23 | Human | Lung | adenocarcinoma; non-small cell lung cancer |
| NCI-H460 | Human | Lung | carcinoma; large cell lung cancer |
| NCI-H522 | Human | Lung | adenocarcinoma; non-small cell lung cancer |
| LOX IMVI | Human | Melanoma | Malignant Amelanotic melanoma |
| M14 | Human | Melanoma | malignant melanoma |
| MALME-3M | Human | Melanoma | malignant melanoma |
| MDA-MB-435 | Human | Melanoma | Adenocarcinoma |

TABLE 1-continued

Examples of adherent cells

| Cell Line | Species | Organ of Origin | Disease |
|---|---|---|---|
| SK-MEL-2 | Human | Melanoma | malignant melanoma |
| SK-MEL-28 | Human | Melanoma | malignant melanoma |
| SK-MEL-5 | Human | Melanoma | malignant melanoma |
| UACC-257 | Human | Melanoma | malignant melanoma |
| UACC-62 | Human | Melanoma | malignant melanoma |
| IGROV1 | Human | Ovary | Cystoadenocarcinoma |
| OVCAR-3 | Human | Ovary | Adenocarcinoma |
| OVCAR-4 | Human | Ovary | Adenocarcinoma |
| OVCAR-5 | Human | Ovary | Adenocarcinoma |
| OVCAR-8 | Human | Ovary | Adenocarcinoma |
| SK-OV-3 | Human | Ovary | Adenocarcinoma |
| NCI-ADR-RES | Human | Ovary | Adenocarcinoma |
| DU145 | Human | Prostate | Carcinoma |
| PC-3 | Human | Prostate | grade IV, adenocarcinoma |

In some embodiments, the adherent cells are cells that correspond to one or more of the following cell lines: BT549, HS 578T, MCF7, MDA-MB-231, MDA-MB-468, T-47D, SF268, SF295, SF539, SNB-19, SNB-75, U251, Colo205, HCC 2998, HCT-116, HCT-15, HT29, KM12, SW620, 786-O, A498, ACHN, CAKI, RXF 393, SN12C, TK-10, UO-31, A549, EKVX, HOP-62, HOP-92, NCI-H226, NCI-H23, NCI-H460, NCI-H522, LOX IMVI, M14, MALME-3M, MDA-MB-435, SK-, EL-2, SK-MEL-28, SK-MEL-5, UACC-257, UACC-62, IGROV1, OVCAR-3, OVCAR-4, OVCAR-5, OVCAR-8, SK-OV-3, NCI-ADR-RES, DU145, PC-3, DU145, H295R, HeLa, KBM-7, LNCaP, MCF-7, MDA-MB-468, PC3, SaOS-2, SH-SY5Y, T-47D, THP-1, U87, vero, MC3T3, GH3, PC12, dog MDCK kidney epithelial, *Xenopus* A6 kidney epithelial, zebrafish AB9, and Sf9 insect epithelial cell lines.

(13) Tissue Permeabilization

In some embodiments, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). In some embodiments, the biological sample can be permeabilized using any of the methods described herein (e.g., using any of the detergents described herein, e.g., SDS and/or N-lauroylsarcosine sodium salt solution) before or after enzymatic treatment (e.g., treatment with any of the enzymes described herein, e.g., trypin, proteases (e.g., pepsin and/or proteinase K)).

In some embodiments, a biological sample can be permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS) and/or N-lauroylsarcosine or N-lauroylsarcosine sodium salt. In some embodiments, a biological sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0% w/v % to about 14.0 w/v %, about 10.0 w/v % to about 12.0 w/v %, or about 12.0 w/v % to about 14.0 w/v %) SDS and/or N-lauroylsarcosine salt solution and/or proteinase K (e.g., at a temperature of about 4% to about 35° C., about 4° C. to about 25° C., about 4° C. to about 20° C., about 4° C. to about 10° C., about 10° C. to about 25° C., about 10° C. to about 20° C., about 10° C. to about 15° C., about 35° C. to about 50° C., about 35° C. to about 45° C., about 35° C. to about 40° C., about 40° C. to about 50° C., about 40° C. to about 45° C., or about 45° C. to about 50° C.).

In some embodiments, the biological sample can be incubated with a permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference.

Lysis Reagents

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Proteases

In some embodiments, a medium, solution, or permeabilization solution may contain one or more proteases. In some embodiments, a biological sample treated with a protease capable of degrading histone proteins can result in the generation of fragmented genomic DNA. The fragmented genomic DNA can be captured using the same capture domain (e.g., capture domain having a poly(T) sequence) used to capture mRNA. In some embodiments, a biological sample is treated with a protease capable of degrading histone proteins and an RNA protectant prior to spatial profiling in order to facilitate the capture of both genomic DNA and mRNA.

In some embodiments, a biological sample is permeabilized by exposing the sample to a protease capable of degrading histone proteins. As used herein, the term "histone protein" typically refers to a linker histone protein (e.g., H1) and/or a core histone protein (e.g., H2A, H2B, H3, and H4). In some embodiments, a protease degrades linker histone proteins, core histone proteins, or linker histone proteins and core histone proteins. Any suitable protease capable of degrading histone proteins in a biological sample can be used. Non-limiting examples of proteases capable of degrading histone proteins include proteases inhibited by leupeptin and TLCK (Tosyl-L-lysyl-chloromethane hydrochloride), a protease encoded by the EUO gene from *Chlamydia trachomatis* serovar A, granzyme A, a serine protease (e.g., trypsin or trypsin-like protease, neutral serine protease, elastase, cathepsin G), an aspartyl protease (e.g., cathepsin D), a peptidase family C1 enzyme (e.g., cathepsin L), pepsin, proteinase K, a protease that is inhibited by the diazomethane inhibitor Z-Phe-Phe-CHN(2) or the epoxide inhibitor E-64, a lysosomal protease, or an azurophilic enzyme (e.g., cathepsin G, elastase, proteinase 3, neutral serine protease). In some embodiments, a serine protease is a trypsin enzyme, trypsin-like enzyme or a functional variant or derivative thereof (e.g., P00761; C0HK48; Q8IYP2; Q8BW11; Q6IE06; P35035; P00760; P06871; Q90627; P16049; P07477; P00762; P35031; P19799; P35036; Q29463; P06872; Q90628; P07478; P07146; P00763; P35032; P70059; P29786; P35037; Q90629; P35030; P08426; P35033; P35038; P12788; P29787; P35039; P35040; Q8NHM4; P35041; P35043; P35044; P54624; P04814; P35045; P32821; P54625; P35004; P35046; P32822; P35047; C0HKA5; C0HKA2; P54627; P35005; C0HKA6; C0HKA3; P52905; P83348; P00765; P35042; P81071; P35049; P51588; P35050; P35034; P35051; P24664; P35048; P00764; P00775; P54628; P42278; P54629; P42279; Q91041; P54630; P42280; C0HKA4) or a combination thereof. In some embodiments, a trypsin enzyme is P00761, P00760, Q29463, or a combination thereof. In some embodiments, a protease capable of degrading one or more histone proteins comprises an amino acid sequence with at least 80% sequence identity to P00761, P00760, or Q29463. In some embodiments, a protease capable of degrading one or more histone proteins comprises an amino acid sequence with at least 85%, 90%, 91%, 92%, 93%, 94%, 95%, 96%, 97%, 98%, or 99% identity to P00761, P00760, or Q29463. A protease may be considered a functional variant if it has at least 50% e.g., at least 60%, 70%, 80%, 90%, 95%, 96%, 97%, 98%, 99%, or 100% of the activity relative to the activity of the protease in condition optimum for the enzyme. In some embodiments, the enzymatic treatment with pepsin enzyme, or pepsin like enzyme, can include: P03954/PEPA1_MACFU; P28712/PEPA1_RABIT; P27677/PEPA2_MACFU; P27821/PEPA2_RABIT; P0DJD8/PEPA3_HUMAN; P27822/PEPA3_RABIT; P0DJD7/PEPA4_HUMAN; P27678/PEPA4_MACFU; P28713/PEPA4_RABIT; P0DJD9/PEPA5_HUMAN; Q9D106/PEPA5_MOUSE; P27823/PEPAF_RABIT; P00792/PEPA_BOVIN; Q9N2D4/PEPA_CALJA; Q9GMY6/PEPA_CANLF; P00793/PEPA_CHICK; P11489/PEPA_MACMU; P00791/PEPA_PIG; Q9GMY7/PEPA_RHIFE; Q9GMY8/PEPA_SORUN; P81497/PEPA_SUNMU; P13636/PEPA_URSTH and functional variants and derivatives thereof, or a combination thereof. In some embodiments, the pepsin enzyme can include: P00791/PEPA_PIG; P00792/PEPA_BOVIN, functional variants, derivatives, or combinations thereof.

Additionally, the protease may be contained in a reaction mixture (solution), which also includes other components (e.g., buffer, salt, chelator (e.g., EDTA), and/or detergent (e.g., SDS, N-Lauroylsarcosine sodium salt solution)). The reaction mixture may be buffered, having a pH of about 6.5-8.5, e.g., about 7.0-8.0. Additionally, the reaction mixture may be used at any suitable temperature, such as about 10-50° C., e.g., about 10-44° C., 11-43° C., 12-42° C., 13-41° C., 14-40° C., 15-39° C., 16-38° C., 17-37° C., e.g., about 10° C., 12° C., 15° C., 18° C., 20° C., 22° C., 25° C., 28° C., 30° C., 33° C., 35° C. or 37° C., preferably about 35-45° C., e.g., about 37° C.

Other Reagents

In some embodiments, a permeabilization solution can contain additional reagents or a biological sample may be treated with additional reagents in order to optimize biological sample permeabilization. In some embodiments, an additional reagent is an RNA protectant. As used herein, the term "RNA protectant" typically refers to a reagent that protects RNA from RNA nucleases (e.g., RNases). Any appropriate RNA protectant that protects RNA from degradation can be used. A non-limiting example of a RNA protectant includes organic solvents (e.g., at least 60%, 65%, 70%, 75%, 80%, 85%, 90%, or 95% v/v organic solvent), which include, without limitation, ethanol, methanol, propan-2-ol, acetone, trichloroacetic acid, propanol, polyethylene glycol, acetic acid, or a combination thereof. In some embodiments, a RNA protectant includes ethanol, methanol and/or propan-2-ol, or a combination thereof. In some embodiments, a RNA protectant includes RNAlater ICE (ThermoFisher Scientific). In some embodiments, the RNA protectant comprises at least about 60% ethanol. In some embodiments, the RNA protectant comprises about 60-95% ethanol, about 0-35% methanol and about 0-35% propan-2-ol, wherein the total amount of organic solvent in the medium is not more than about 95%. In some embodiments, the RNA protectant comprises about 60-95% ethanol, about 5-20% methanol and about 5-20% propan-2-ol, wherein the total amount of organic solvent in the medium is not more than about 95%.

In some embodiments, the RNA protectant includes a salt. The salt may include ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate and zinc sulfate. In some embodiments, the salt is a sulfate salt, for example, ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate, or zinc sulfate. In some embodiments, the salt is ammonium sulfate. The salt may be present at a concentration of about 20 g/100 ml of medium or less, such as about 15 g/100 ml, 10 g/100 ml, 9 g/100 ml, 8 g/100 ml, 7 g/100 ml, 6 g/100 ml, 5 g/100 ml or less, e.g., about 4 g, 3 g, 2 g or 1 g/100 ml.

Additionally, the RNA protectant may be contained in a medium that further includes a chelator (e.g., EDTA), a buffer (e.g., sodium citrate, sodium acetate, potassium citrate, or potassium acetate, preferably sodium acetate), and/or buffered to a pH between about 4-8 (e.g., about 5).

In some embodiments, the biological sample is treated with one or more RNA protectants before, contemporaneously with, or after permeabilization. For example, a biological sample is treated with one or more RNA protectants prior to treatment with one or more permeabilization reagents (e.g., one or more proteases). In another example, a biological sample is treated with a solution including one or more RNA protectants and one or more permeabilization reagents (e.g., one or more proteases). In yet another example, a biological sample is treated with one or more RNA protectants after the biological sample has been treated with one or more permeabilization reagents (e.g., one or more proteases). In some embodiments, a biological sample is treated with one or more RNA protectants prior to fixation.

In some embodiments, identifying the location of the captured analyte in the biological sample includes a nucleic acid extension reaction. In some embodiments where a capture probe captures a fragmented genomic DNA molecule, a nucleic acid extension reaction includes DNA polymerase. For example, a nucleic acid extension reaction includes using a DNA polymerase to extend the capture probe that is hybridized to the captured analyte (e.g., fragmented genomic DNA) using the captured analyte (e.g., fragmented genomic DNA) as a template. The product of the extension reaction includes a spatially-barcoded analyte (e.g., spatially-barcoded fragmented genomic DNA). The spatially-barcoded analyte (e.g., spatially-barcoded fragmented genomic DNA) can be used to identify the spatial location of the analyte in the biological sample. Any DNA polymerase that is capable of extending the capture probe using the captured analyte as a template can be used for the methods described herein. Non-limiting examples of DNA polymerases include T7 DNA polymerase; Bsu DNA polymerase; and *E. coli* DNA Polymerase pol I.

Diffusion-Resistant Media

In some embodiments, a diffusion-resistant medium, typically used to limit diffusion of analytes, can include at least one permeabilization reagent. For example, the diffusion-resistant medium (e.g., a hydrogel) can include wells (e.g., micro-, nano-, or picowells or pores) containing a permeabilization buffer or reagents. In some embodiments, the diffusion-resistant medium (e.g., a hydrogel) is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (e.g., hydrogel) is covalently attached to a solid substrate (e.g., an acrylated glass slide).

In some embodiments, the hydrogel can be modified to both deliver permeabilization reagents and contain capture. For example, a hydrogel film can be modified to include spatially-barcoded capture probes. The spatially-barcoded hydrogel film is then soaked in permeabilization buffer before contacting the spatially-barcoded hydrogel film to the sample. In another example, a hydrogel can be modified to include spatially-barcoded capture probes and designed to serve as a porous membrane (e.g., a permeable hydrogel) when exposed to permeabilization buffer or any other biological sample preparation reagent. The permeabilization reagent diffuses through the spatially-barcoded permeable hydrogel and permeabilizes the biological sample on the other side of the hydrogel. The analytes then diffuse into the spatially-barcoded hydrogel after exposure to permeabilization reagents. In such cases, the spatially-barcoded hydrogel (e.g., porous membrane) is facilitating the diffusion of the biological analytes in the biological sample into the hydrogel. In some embodiments, biological analytes diffuse into the hydrogel before exposure to permeabilization reagents (e.g., when secreted analytes are present outside of the biological sample or in instances where a biological sample is lysed or permeabilized by other means prior to addition of permeabilization reagents). In some embodiments, the permeabilization reagent is flowed over the hydrogel at a variable flow rate (e.g., any flow rate that facilitates diffusion of the permeabilization reagent across the spatially-barcoded hydrogel). In some embodiments, the permeabilization reagents are flowed through a microfluidic chamber or channel over the spatially-barcoded hydrogel. In some embodiments, after using flow to introduce permeabilization reagents to the biological sample, biological sample preparation reagents can be flowed over the hydrogel to further facilitate diffusion of the biological analytes into the spatially-barcoded hydrogel. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, wherein a target analyte diffuses through the permeabilization reagent/buffer and to the spatially-barcoded capture probes. In some embodiments, resolution loss may be proportional to gap thickness (e.g., the amount of permeabilization buffer between the sample and the capture probes). In some embodiments, the diffusion-resistant medium (e.g., hydrogel) is between approximately 50-500 micrometers thick including 500, 450, 400, 350, 300, 250, 200, 150, 100, or 50 micrometers thick, or any thickness within 50 and 500 micrometers.

In some embodiments, a biological sample is exposed to a porous membrane (e.g., a permeable hydrogel) to aid in permeabilization and limit diffusive analyte losses, while allowing permeabilization reagents to reach a sample. Membrane chemistry and pore volume can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, the porous membrane is a permeable hydrogel. For example, a hydrogel is permeable when permeabilization reagents and/or biological sample preparation reagents can pass through the hydrogel using diffusion. Any suitable permeabilization reagents and/or biological sample preparation reagents described herein can be used under conditions sufficient to release analytes (e.g., nucleic acid, protein, metabolites, lipids, etc.) from the biological sample. In some embodiments, a hydrogel is exposed to the biological sample on one side and permeabilization reagent on the other side. The permeabilization reagent diffuses through the permeable hydrogel and permeabilizes the biological sample on the other side of the hydrogel. In some embodiments, permeabilization reagents are flowed over the hydrogel at a variable flow rate (e.g., any flow rate that facilitates diffusion of the permeabilization reagent across the hydrogel). In some embodiments, the permeabilization reagents are flowed through a microfluidic chamber or channel over the hydrogel. Flowing permeabilization reagents across the hydrogel enables control of the concentration of reagents. In some embodiments, hydrogel chemistry and pore volume can be tuned to enhance permeabilization and limit diffusive analyte losses.

In some embodiments, a porous membrane is sandwiched between a spatially-barcoded array and the sample, wherein permeabilization solution is applied over the porous membrane. The permeabilization reagents diffuse through the pores of the membrane and into the biological sample. In some embodiments, the biological sample can be placed on a substrate (e.g., a glass slide). Biological analytes then diffuse through the porous membrane and into to the space containing the capture probes. In some embodiments, the porous membrane is modified to include capture probes. For example, the capture probes can be attached to a surface of the porous membrane using any of the methods described herein. In another example, the capture probes can be embedded in the porous membrane at any depth that allows interaction with a biological analyte. In some embodiments, the porous membrane is placed onto a biological sample in a configuration that allows interaction between the capture probes on the porous membrane and the biological analytes from the biological sample. For example, the capture probes are located on the side of the porous membrane that is proximal to the biological sample. In such cases, permeabilization reagents on the other side of the porous membrane diffuse through the porous membrane into the location containing the biological sample and the capture probes in order to facilitate permeabilization of the biological sample (e.g., also facilitating capture of the biological analytes by the capture probes). In some embodiments, the porous membrane is located between the sample and the capture probes. In some embodiments, the permeabilization reagents are flowed through a microfluidic chamber or channel over the porous membrane.

Selective Permeabilization/Selective Lysis

In some embodiments, biological samples can be processed to selectively release an analyte from a subcellular region of a cell according to established methods. In some embodiments, a method provided herein can include detecting at least one biological analyte present in a subcellular region of a cell in a biological sample. As used herein, a "subcellular region" can refer to any subcellular region. For example, a subcellular region can refer to cytosol, a mitochondria, a nucleus, a nucleolus, an endoplasmic reticulum, a lysosome, a vesicle, a Golgi apparatus, a plastid, a vacuole, a ribosome, cytoskeleton, or combinations thereof. In some embodiments, the subcellular region comprises at least one of cytosol, a nucleus, a mitochondria, and a microsome. In some embodiments, the subcellular region is cytosol. In some embodiments, the subcellular region is a nucleus. In some embodiments, the subcellular region is a mitochondria. In some embodiments, the subcellular region is a microsome.

For example, a biological analyte can be selectively released from a subcellular region of a cell by selective permeabilization or selective lysing. In some embodiments, "selective permeabilization" can refer to a permeabilization method that can permeabilize a membrane of a subcellular region while leaving a different subcellular region substantially intact (e.g., biological analytes are not released from subcellular region due to the applied permeabilization method). Non-limiting examples of selective permeabilization methods include using electrophoresis and/or applying a permeabilization reagent. In some embodiments, "selective lysing" can refer to a lysis method that can lyse a membrane of a subcellular region while leaving a different subcellular region substantially intact (e.g., biological analytes are not released from subcellular region due to the applied lysis method). Several methods for selective permeabilization or lysis are known to one of skill in the art including the methods described in Lu et al. *Lab Chip.* 2005 January; 5(1):23-9; Niklas et al. *Anal Biochem.* 2011 Sep. 15; 416(2):218-27; Cox and Emili. *Nat Protoc.* 2006; 1(4): 1872-8; Chiang et al. *J Biochem. Biophys. Methods.* 2000 Nov. 20; 46(1-2):53-68; and Yamauchi and Herr et al. *Microsyst. Nanoeng.* 2017; 3. pii: 16079; each of which is incorporated herein by reference in its entirety.

In some embodiments, "selective permeabilization" or "selective lysis" refer to the selective permeabilization or selective lysis of a specific cell type. For example, "selective permeabilization" or "selective lysis" can refer to lysing one cell type while leaving a different cell type substantially intact (e.g., biological analytes are not released from the cell due to the applied permeabilization or lysis method). A cell that is a "different cell type" than another cell can refer to a cell from a different taxonomic kingdom, a prokaryotic cell versus a eukaryotic cell, a cell from a different tissue type, etc. Many methods are known to one of skill in the art for selectively permeabilizing or lysing different cell types. Non-limiting examples include applying a permeabilization reagent, electroporation, and/or sonication. See, e.g., International Application No. WO 2012/168003; Han et al. *Microsyst Nanoeng.* 2019 Jun. 17; 5:30; Gould et al. *Oncotarget.* 2018 Mar. 20; 9(21): 15606-15615; Oren and Shai. *Biochemistry.* 1997 Feb. 18; 36(7):1826-35; Algayer et al. *Molecules.* 2019 May 31; 24(11). pii: E2079; Hipp et al.

*Leukemia.* 2017 October; 31(10):2278; International Application No. WO 2012/168003; and U.S. Pat. No. 7,785,869; all of which are incorporated by reference herein in their entireties.

In some embodiments, applying a selective permeabilization or lysis reagent comprises contacting the biological sample with a hydrogel comprising the permeabilization or lysis reagent.

In some embodiments, the biological sample is contacted with two or more arrays (e.g., flexible arrays, as described herein). For example, after a subcellular region is permeabilized and a biological analyte from the subcellular region is captured on a first array, the first array can be removed, and a biological analyte from a different subcellular region can be captured on a second array.

(14) Selective Enrichment of RNA Species

In some embodiments, where RNA is the analyte, one or more RNA analyte species of interest can be selectively enriched (e.g., Adiconis, et. al., Comparative analysis of RNA sequencing methods for degraded and low-input samples, *Nature*, vol. 10, July 2013, 623-632, herein incorporated by reference in its entirety). For example, one or more species of RNA can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. For example, biotinylated oligonucleotides with sequence complementary to one or more cDNAs of interest binds to the cDNA and can be selected using biotinylation-streptavidin affinity using any of a variety of methods known to the field (e.g., streptavidin beads).

Alternatively, one or more species of RNA (e.g., ribosomal and/or mitochondrial RNA) can be down-selected (e.g., removed, depleted) using any of a variety of methods. Non-limiting examples of a hybridization and capture method of ribosomal RNA depletion include RiboMinus™, RiboCop™, and Ribo-Zero™. Another non-limiting RNA depletion method involves hybridization of complementary DNA oligonucleotides to unwanted RNA followed by degradation of the RNA/DNA hybrids using RNase H. Non-limiting examples of a hybridization and degradation method include NEBNext® rRNA depletion, NuGEN AnyDeplete, TruSeq™. Another non-limiting ribosomal RNA depletion method includes ZapR™ digestion, for example SMARTer. In the SMARTer method, random nucleic acid adapters are hybridized to RNA for first-strand synthesis and tailing by reverse transcriptase, followed by template switching and extension by reverse transcriptase. Additionally, first round PCR amplification adds full-length Illumina sequencing adapters (e.g., Illumina indexes). Ribosomal RNA is cleaved by ZapR v2 and R probes v2. A second round of PCR is performed, amplifying non-rRNA molecules (e.g., cDNA). Parts or steps of these ribosomal depletion protocols/kits can be further combined with the methods described herein to optimize protocols for a specific biological sample.

In depletion protocols, probes can be administered to a sample that selectively hybridize to ribosomal RNA (rRNA), thereby reducing the pool and concentration of rRNA in the sample. Probes can be administered to a biological sample that selectively hybridize to mitochondria RNA (mtRNA), thereby reducing the pool and concentration of mtRNA in the sample. In some embodiments, probes complementary to mitochondrial RNA can be added during cDNA synthesis, or probes complementary to both ribosomal and mitochondrial RNA can be added during cDNA synthesis. Subsequent application of capture probes to the sample can result in improved capture of other types of RNA due to a reduction in non-specific RNA (e.g., down-selected RNA) present in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques,* 53(6) 373-80, (2012), the entire contents of which are incorporated herein by reference).

(15) Other Reagents

Additional reagents can be added to a biological sample to perform various functions prior to analysis of the biological sample. In some embodiments, nuclease inhibitors such as DNase and RNase inactivating agents or protease inhibitors, and/or chelating agents such as EDTA, can be added to the biological sample. In other embodiments nucleases, such as DNase or RNAse, or proteases, such as pepsin or proteinase K, are added to the sample. In some embodiments, additional reagents may be dissolved in a solution or applied as a medium to the sample. In some embodiments, additional reagents (e.g., pepsin) may be dissolved in HCl prior to applying to the sample.

In some embodiments, the biological sample can be treated with one or more enzymes. For example, one or more endonucleases to fragment DNA, DNA polymerase enzymes, and dNTPs used to amplify nucleic acids can be added. Other enzymes that can also be added to the biological sample include, but are not limited to, polymerase, transposase, ligase, and DNAse, and RNAse.

In some embodiments, reverse transcriptase enzymes can be added to the sample, including enzymes with terminal transferase activity, primers, and template switch oligonucleotides (TSOs). Template switching can be used to increase the length of a cDNA, e.g., by appending a predefined nucleic acid sequence to the cDNA. In some embodiments, the appended nucleic acid sequence comprises one or more ribonucleotides.

In some embodiments, additional reagents can be added to improve the recovery of one or more target molecules (e.g., cDNA molecules, mRNA transcripts). For example, addition of carrier RNA to a RNA sample workflow process can increase the yield of extracted RNA/DNA hybrids from the biological sample. In some embodiments, carrier molecules are useful when the concentration of input or target molecules is low as compared to remaining molecules. Generally, single target molecules cannot form a precipitate, and addition of the carrier molecules can help in forming a precipitate. Some target molecule recovery protocols use carrier RNA to prevent small amounts of target nucleic acids present in the sample from being irretrievably bound. In some embodiments, carrier RNA can be added immediately prior to a second strand synthesis step. In some embodiments, carrier RNA can be added immediately prior to a second strand cDNA synthesis on oligonucleotides released from an array. In some embodiments, carrier RNA can be added immediately prior to a post in vitro transcription clean-up step. In some embodiments, carrier RNA can be added prior to amplified RNA purification and quantification. In some embodiments, carrier RNA can be added before RNA quantification. In some embodiments, carrier RNA can be added immediately prior to both a second strand cDNA synthesis and a post in vitro transcription clean-up step.

(16) Pre-Processing for Capture Probe Interaction

In some embodiments, analytes in a biological sample can be pre-processed prior to interaction with a capture probe. For example, prior to interaction with capture probes, polymerization reactions catalyzed by a polymerase (e.g., DNA polymerase or reverse transcriptase) are performed in the biological sample. In some embodiments, a primer for the polymerization reaction includes a functional group that enhances hybridization with the capture probe. The capture probes can include appropriate capture domains to capture biological analytes of interest (e.g., poly(dT) sequence to capture poly(A) mRNA).

In some embodiments, biological analytes are pre-processed for library generation via next generation sequencing. For example, analytes can be pre-processed by addition of a modification (e.g., ligation of sequences that allow interaction with capture probes). In some embodiments, analytes (e.g., DNA or RNA) are fragmented using fragmentation techniques (e.g., using transposases and/or fragmentation buffers).

Fragmentation can be followed by a modification of the analyte. For example, a modification can be the addition through ligation of an adapter sequence that allows hybridization with the capture probe. In some embodiments, where the analyte of interest is RNA, poly(A) tailing is performed. Addition of a poly(A) tail to RNA that does not contain a poly(A) tail can facilitate hybridization with a capture probe that includes a capture domain with a functional amount of poly(dT) sequence.

In some embodiments, prior to interaction with capture probes, ligation reactions catalyzed by a ligase are performed in the biological sample. In some embodiments, ligation can be performed by chemical ligation. In some embodiments, the ligation can be performed using click chemistry as further described below. In some embodiments, the capture domain includes a DNA sequence that has complementarity to a RNA molecule, where the RNA molecule has complementarity to a second DNA sequence, and where the RNA-DNA sequence complementarity is used to ligate the second DNA sequence to the DNA sequence in the capture domain. In these embodiments, direct detection of RNA molecules is possible.

In some embodiments, prior to interaction with capture probes, target-specific reactions are performed in the biological sample. Examples of target specific reactions include, but are not limited to, ligation of target specific adaptors, probes and/or other oligonucleotides, target specific amplification using primers specific to one or more analytes, and target-specific detection using in situ hybridization, DNA microscopy, and/or antibody detection. In some embodiments, a capture probe includes capture domains targeted to target-specific products (e.g., amplification or ligation).

II. General Spatial Array-Based Analytical Methodology

Provided herein are methods, apparatus, systems, and compositions for spatial array-based analysis of biological samples.

(a) Spatial Analysis Methods

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of each analyte within the biological sample. The spatial location of each analyte within the biological sample is determined based on the feature to which each analyte is bound on the array, and the feature's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to promote analytes out of a cell and towards the spatially-barcoded array. FIG. 1 depicts an exemplary embodiment of this general method. In FIG. 1, the spatially-barcoded array populated with capture probes (as described further herein) is contacted with a biological sample 101, and biological sample is permeabilized, allowing the analyte to migrate away from the sample and toward the array. The analyte interacts with a capture probe on the spatially-barcoded array 102. Once the analyte hybridizes/is bound to the capture probe, the sample is optionally removed from the array and the capture probes are analyzed in order to obtain spatially-resolved analyte information 103.

Figure 2:
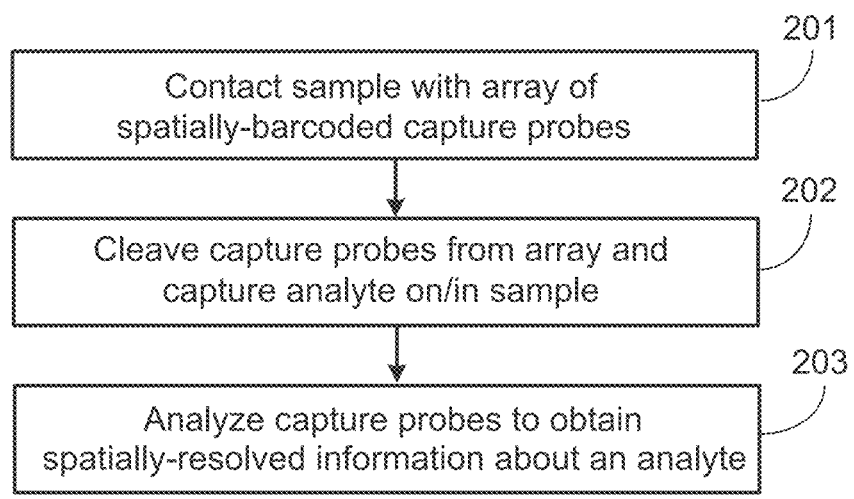
FIG. 2 shows an exemplary spatial analysis workflow.

Another general method is to cleave the spatially-barcoded capture probes from an array, and promote the spatially-barcoded capture probes towards and/or into or onto the biological sample. FIG. 2 depicts an exemplary embodiment of this general method, the spatially-barcoded array populated with capture probes (as described further herein) can be contacted with a sample 201. The spatially-barcoded capture probes are cleaved and then interact with cells within the provided biological sample 202. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell 203.

FIG. 3 shows an exemplary workflow that includes preparing a biological sample on a spatially-barcoded array 301. Sample preparation may include placing the sample on a slide, fixing the sample, and/or staining the biological sample for imaging. The stained sample can be then imaged on the array 302 using both brightfield (to image the sample hematoxylin and eosin stain) and fluorescence (to image features) modalities. Optionally, the sample can be destained prior to permeabilization. In some embodiments, analytes are then released from the sample and capture probes forming the spatially-barcoded array hybridize or bind the released analytes 303. The sample is then removed from the array 304 and the capture probes cleaved from the array 305. The biological sample and array are then optionally imaged a second time in both modalities 305B while the analytes are reverse transcribed into cDNA, and an amplicon library is prepared 306 and sequenced 307. The two sets of images are then spatially-overlaid in order to correlate spatially-identified biological sample information 308. When the sample and array are not imaged a second time, 305B, a spot coordinate file is supplied instead. The spot coordinate file replaces the second imaging step 305B. Further, amplicon library preparation 306 can be performed with a unique PCR adapter and sequenced 307.

FIG. 4 shows another exemplary workflow that utilizes a spatially-barcoded array on a substrate, where spatially-barcoded capture probes are clustered at areas called features. The spatially-barcoded capture probes can include a cleavage domain, one or more functional domains, a spatial barcode, a unique molecular identifier, and a capture domain. The spatially-barcoded capture probes can also include a 5' end modification for reversible attachment to the substrate. The spatially-barcoded array is contacted with a biological sample 401, and the sample is permeabilized through application of permeabilization reagents 402. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte 403. The biological sample can be optionally removed from the array 404.

The capture probes can be optionally cleaved from the array 405, and the captured analytes can be spatially-barcoded by performing a reverse transcriptase first strand cDNA reaction. A first strand cDNA reaction can be optionally performed using template switching oligonucleotides. For example, a template switching oligonucleotide can hybridize to a poly(C) tail added to a 3' end of the cDNA by a reverse transcriptase enzyme in a template independent manner. The original mRNA template and template switching oligonucleotide can then be denatured from the cDNA and the spatially-barcoded capture probe can then hybridize with the cDNA and a complement of the cDNA can be generated. The first strand cDNA can then be purified and collected for downstream amplification steps. The first strand cDNA can be amplified using PCR 406, where the forward and reverse primers flank the spatial barcode and analyte regions of interest, generating a library associated with a particular spatial barcode. In some embodiments, the cDNA comprises a sequencing by synthesis (SBS) primer sequence. The library amplicons are sequenced and analyzed to decode spatial information 407.

Using the methods, compositions, systems, kits, and devices described herein, RNA transcripts present in biological samples (e.g., tissue samples) can be used for spatial transcriptome analysis. In particular, in some cases, the barcoded oligonucleotides may be configured to prime, replicate, and consequently yield barcoded extension products from an RNA template, or derivatives thereof. For example, in some cases, the barcoded oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcoded oligonucleotides. Reverse transcriptases (RTs) can use an RNA template and a primer complementary to the 3' end of the RNA template to direct the synthesis of the first strand complementary DNA (cDNA). Many RTs can be used in this reverse transcription reactions, including, for example, avian myeloblastosis virus (AMV) reverse transcriptase, moloney murine leukemia virus (M-MuLV or MMLV), and other variants thereof. Some recombinant M-MuLV reverse transcriptase, such as, for example, PROTOSCRIPT® II reverse transcriptase, can have reduced RNase H activity and increased thermostability when compared to its wild type counterpart, and provide higher specificity, higher yield of cDNA and more full-length cDNA products with up to 12 kilobase (kb) in length. In some embodiments, the reverse transcriptase enzyme is a mutant reverse transcriptase enzyme such as, but not limited to, mutant MMLV reverse transcriptase. In another embodiment, the reverse transcriptase is a mutant MMLV reverse transcriptase such as, but not limited to, one or more variants described in US Patent Publication No. 20180312822, which is incorporated herein by reference in its entirety.

Figure 5:
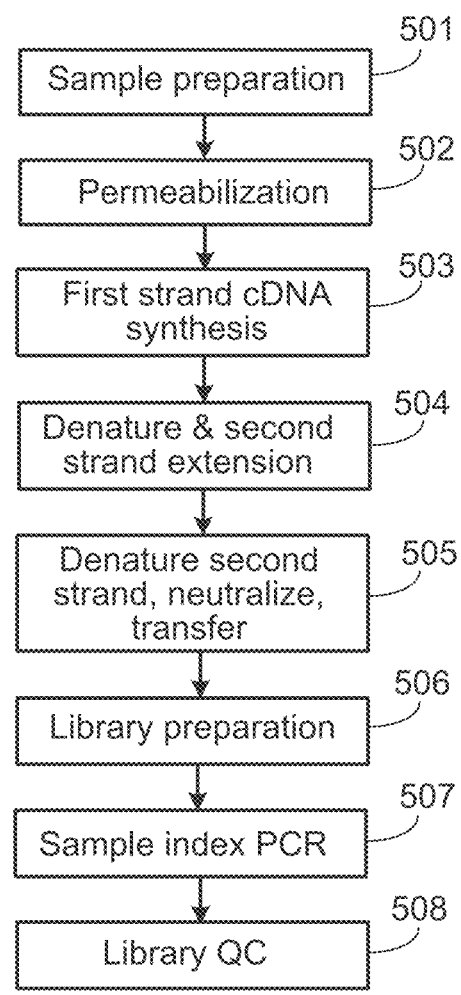
FIG. 5 shows an exemplary spatial analysis workflow.

FIG. 5 depicts an exemplary workflow where the biological sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes. In this embodiment, sample preparation 501 and permeabilization 502 are performed as described elsewhere herein. Once the capture probes capture the analyte(s), first strand cDNA created by template switching and reverse transcriptase 503 is then denatured and the second strand is then extended 504. The second strand cDNA is then denatured from the first strand cDNA, neutralized, and transferred to a tube 505. cDNA quantification and amplification can be performed using standard techniques discussed herein. The cDNA can then be subjected to library preparation 506 and indexing 507, including fragmentation, end-repair, and a-tailing, and indexing PCR steps.

In a non-limiting example of the workflows described above, a biological sample (e.g., tissue section), can be fixed with methanol, stained with hematoxylin and eosin, and imaged. Optionally, the sample can be destained prior to permeabilization. The images can be used to map spatial gene expression patterns back to the biological sample. A permeabilization enzyme can be used to permeabilize the biological sample directly on the slide. Analytes (e.g., polyadenylated mRNA) released from the overlying cells of the biological sample can be captured by capture probes within a capture area on a substrate. Reverse transcription (RT) reagents can be added to permeabilized biological samples. Incubation with the RT reagents can produce spatially-barcoded full-length cDNA from the captured analytes (e.g., polyadenylated mRNA). Second strand reagents (e.g., second strand primers, enzymes) can be added to the biological sample on the slide to initiate second strand synthesis. The resulting cDNA can be denatured from the capture probe template and transferred (e.g., to a clean tube) for amplification, and/or library construction. The spatially-barcoded, full-length cDNA can be amplified via PCR prior to library construction. The cDNA can then be enzymatically fragmented and size-selected in order to optimize the cDNA amplicon size. P5, P7, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites.

In some embodiments, performing correlative analysis of data produced by this workflow, and other workflows described herein, can yield over 95% correlation of genes expressed across two capture areas (e.g., 95% or greater, 96% or greater, 97% or greater, 98% or greater, or 99% or greater). When performing the described workflows using single cell RNA sequencing of nuclei, in some embodiments, correlative analysis of the data can yield over 90% (e.g., over 90%, 91%, 92%, 93%, 94%, 95%, 96%, 97%, 98%, or 99%) correlation of genes expressed across two capture areas.

In some embodiments, after cDNA is generated (e.g., by reverse transcription) the cDNA can be amplified directly on the substrate surface. Generating multiple copies of the cDNA (e.g., cDNA synthesized from captured analytes) via amplification directly on the substrate surface can improve final sequencing library complexity. Thus, in some embodiments, cDNA can be amplified directly on the substrate surface by isothermal nucleic acid amplification. In some embodiments, isothermal nucleic acid amplification can amplify RNA or DNA.

In some embodiments, isothermal amplification can be faster than a standard PCR reaction. In some embodiments, isothermal amplification can be linear amplification (e.g., asymmetrical with a single primer), or exponential amplification (e.g., with two primers). In some embodiments, isothermal nucleic acid amplification can be performed by a template-switching oligonucleotide primer. In some embodiments, the template switching oligonucleotide adds a common sequence onto the 5' end of the RNA being reverse transcribed. For example, after a capture probe interacts with an analyte (e.g., mRNA) and reverse transcription is performed such that additional nucleotides are added to the end of the cDNA creating a 3' overhang as described herein. In some embodiments, a template switching oligonucleotide hybridizes to untemplated poly(C) nucleotides added by a reverse transcriptase to continue replication to the 5' end of the template switching oligonucleotide, thereby generating full-length cDNA ready for further amplification. In some embodiments, the template switching oligonucleotide adds a common 5' sequence to full-length cDNA that is used for cDNA amplification (e.g., a reverse complement of the template switching oligonucleotide).

In some embodiments, once a full-length cDNA molecule is generated, the template switching oligonucleotide can serve as a primer in a cDNA amplification reaction (e.g., with a DNA polymerase). In some embodiments, double stranded cDNA (e.g., first strand cDNA and second strand reverse complement cDNA) can be amplified via isothermal amplification with either a helicase or recombinase, followed by a strand displacing DNA polymerase. The strand displacing DNA polymerase can generate a displaced second strand resulting in an amplified product.

In any of isothermal amplification methods described herein, barcode exchange (e.g., spatial barcode) can occur after the first amplification cycle where there are unused capture probes on the substrate surface. In some embodiments, the free 3'OH end of the unused capture probes can be blocked by any suitable 3' OH blocking method. In some embodiments, the 3'OH can be blocked by hairpin ligation.

Isothermal nucleic acid amplification can be used in addition to, or as an alternative to standard PCR reactions (e.g., a PCR reaction that requires heating to about 95° C. to denature double stranded DNA). Isothermal nucleic acid amplification generally does not require the use of a thermocycler, however in some embodiments, isothermal amplification can be performed in a thermocycler. In some embodiments, isothermal amplification can be performed from about 35° C. to about 75° C. In some embodiments, isothermal amplification can be performed from about 40° C., about 45° C., about 50° C., about 55° C., about 60° C., about 65° C., or about 70° C. or anywhere in between depending on the polymerase and auxiliary enzymes used.

Isothermal nucleic acid amplification techniques are known in the art, and can be used alone or in combination with any of the spatial methods described herein. For example, non-limiting examples of suitable isothermal nucleic acid amplification techniques include transcription mediated amplification, nucleic acid sequence-based amplification, signal mediated amplification of RNA technology, strand displacement amplification, rolling circle amplification, loop-mediated isothermal amplification of DNA (LAMP), isothermal multiple displacement amplification, recombinase polymerase amplification, helicase-dependent amplification, single primer isothermal amplification, and circular helicase-dependent amplification (See, e.g., Gill and Ghaemi, Nucleic acid isothermal amplification technologies: a review, *Nucleosides, Nucleotides*, & *Nucleic Acids*, 27(3), 224-43, doi: 10.1080/15257770701845204 (2008), which is incorporated herein by reference in its entirety).

In some embodiments, the isothermal nucleic acid amplification is helicase-dependent nucleic acid amplification. Helicase-dependent isothermal nucleic acid amplification is described in Vincent, et. al., Helicase-dependent isothermal DNA amplification, *EMBO Rep.*, 795-800 (2004) and U.S. Pat. No. 7,282,328, which are both incorporated herein by reference in their entireties. Further, helicase-dependent nucleic acid amplification on a substrate (e.g., on-chip) is described in Andresen, et. al., Helicase-dependent amplification: use in OnChip amplification and potential for point-of-care diagnostics, *Expert Rev Mol Diagn.*, 9, 645-650, doi: 10.1586/erm.09.46 (2009), which is incorporated herein by reference in its entirety. In some embodiments, the isothermal nucleic acid amplification is recombinase polymerase nucleic acid amplification. Recombinase polymerase nucleic acid amplification is described in Piepenburg, et al., DNA Detection Using Recombinant Proteins, *PLoS Biol.*, 4, 7 e204 (2006) and Li, et. al., Review: a comprehensive summary of a decade development of the recombinase polymerase amplification, *Analyst*, 144, 31-67, doi: 10.1039/C8AN01621F (2019), both of which are incorporated herein by reference in their entireties.

Generally, isothermal amplification techniques use standard PCR reagents (e.g., buffer, dNTPs etc.) known in the art. Some isothermal amplification techniques can require additional reagents. For example, helicase dependent nucleic acid amplification uses a single-strand binding protein and an accessory protein. In another example, recombinase polymerase nucleic acid amplification uses recombinase (e.g., T4 UvsX), recombinase loading factor (e.g., TF UvsY), single-strand binding protein (e.g., T4 gp32), crowding agent (e.g., PEG-35K), and ATP.

After isothermal nucleic acid amplification of the full-length cDNA described by any of the methods herein, the isothermally amplified cDNAs (e.g., single-stranded or double-stranded) can be recovered from the substrate, and optionally followed by amplification with typical cDNA PCR in microcentrifuge tubes. The sample can then be used with any of the spatial methods described herein.

(i) Immunohistochemistry and Immunofluorescence

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 min at 4° C.) before being stained with fluorescent primary antibodies (1:100 in 3×SSC, 2% BSA, 0.1% Triton X, 1 U/µl RNAse inhibitor for 30 min at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

As used herein, an "antigen retrieval buffer" can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases unspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

In some embodiments, additional steps or optimizations can be included in performing IF/IHC protocols in conjunction with spatial arrays. Additional steps or optimizations can be included in performing spatially-tagged analyte capture agent workflows discussed herein.

In some embodiments, provided herein are methods for spatially detecting an analyte (e.g., detecting the location of an analyte, e.g., a biological analyte) from a biological sample (e.g., an analyte present in a biological sample, such as a tissue section) that include: (a) providing a biological sample on a substrate; (b) staining the biological sample on the substrate, imaging the stained biological sample, and selecting the biological sample or subsection of the biological sample (e.g., region of interest) to subject to analysis; (c) providing an array comprising one or more pluralities of capture probes on a substrate; (d) contacting the biological sample with the array, thereby allowing a capture probe of the one or more pluralities of capture probes to capture the analyte of interest; and (e) analyzing the captured analyte, thereby spatially detecting the analyte of interest. Any variety of staining and imaging techniques as described herein or known in the art can be used in accordance with methods described herein. In some embodiments, the staining includes optical labels as described herein, including, but not limited to, fluorescent, radioactive, chemiluminescent, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain such as hematoxylin and eosin (H&E) or periodic acid-schiff (PAS). In some embodiments, significant time (e.g., days, months, or years) can elapse between staining and/or imaging the biological sample and performing analysis. In some embodiments, reagents for performing analysis are added to the biological sample before, contemporaneously with, or after the array is contacted to the biological sample. In some embodiments, step (d) includes placing the array onto the biological sample. In some embodiments, the array is a flexible array where the plurality of spatially-barcoded features (e.g., a substrate with capture probes, a bead with capture probes) are attached to a flexible substrate. In some embodiments, measures are taken to slow down a reaction (e.g., cooling the temperature of the biological sample or using enzymes that preferentially perform their primary function at lower or higher temperature as compared to their optimal functional temperature) before the array is contacted with the biological sample. In some embodiments, step (e) is performed without bringing the biological sample out of contact with the array. In some embodiments, step (e) is performed after the biological sample is no longer in contact with the array. In some embodiments, the biological sample is tagged with an analyte capture agent before, contemporaneously with, or after staining and/or imaging of the biological sample. In such cases, significant time (e.g., days, months, or years) can elapse between staining and/or imaging and performing analysis. In some embodiments, the array is adapted to facilitate biological analyte migration from the stained and/or imaged biological sample onto the array (e.g., using any of the materials or methods described herein). In some embodiments, a biological sample is permeabilized before being contacted with an array. In some embodiments, the rate of permeabilization is slowed prior to contacting a biological sample with an array (e.g., to limit diffusion of analytes away from their original locations in the biological sample). In some embodiments, modulating the rate of permeabilization (e.g., modulating the activity of a permeabilization reagent) can occur by modulating a condition that the biological sample is exposed to (e.g., modulating temperature, pH, and/or light). In some embodiments, modulating the rate of permeabilization includes use of external stimuli (e.g., small molecules, enzymes, and/or activating reagents) to modulate the rate of permeabilization. For example, a permeabilization reagent can be provided to a biological sample prior to contact with an array, which permeabilization reagent is inactive until a condition (e.g., temperature, pH, and/or light) is changed or an external stimulus (e.g., a small molecule, an enzyme, and/or an activating reagent) is provided.

In some embodiments, provided herein are methods for spatially detecting an analyte (e.g., detecting the location of an analyte, e.g., a biological analyte) from a biological sample (e.g., present in a biological sample such as a tissue section) that include: (a) providing a biological sample on a substrate; (b) staining the biological sample on the substrate, imaging the stained biological sample, and selecting the biological sample or subsection of the biological sample (e.g., a region of interest) to subject to spatial transcriptomic analysis; (c) providing an array comprising one or more pluralities of capture probes on a substrate; (d) contacting the biological sample with the array, thereby allowing a capture probe of the one or more pluralities of capture probes to capture the biological analyte of interest; and (e) analyzing the captured biological analyte, thereby spatially detecting the biological analyte of interest.

(b) Capture Probes

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 6:
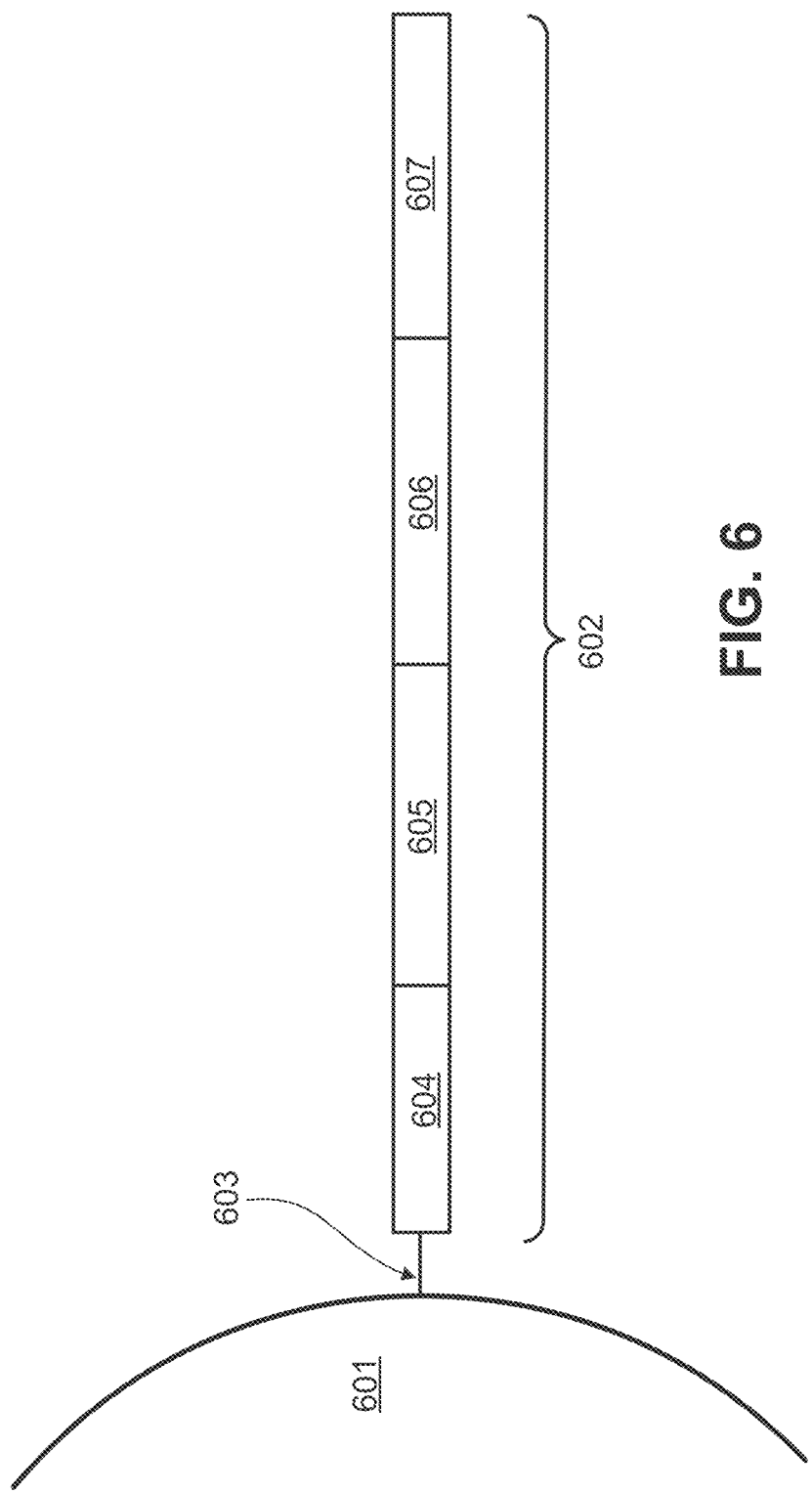
FIG. 6 is a schematic diagram showing an example of a barcoded capture probe, as described herein.

FIG. 6 is a schematic diagram showing an example of a capture probe, as described herein. As shown, the capture probe 602 is optionally coupled to a feature 601 by a cleavage domain 603, such as a disulfide linker. The capture probe can include functional sequences that are useful for subsequent processing, such as functional sequence 604, which can include a sequencer specific flow cell attachment sequence, e.g., a P5 sequence, as well as functional sequence 606, which can include sequencing primer sequences, e.g., a R1 primer binding site. In some embodiments, sequence 604 is a P7 sequence and sequence 606 is a R2 primer binding site. A spatial barcode 605 can be included within the capture probe for use in barcoding the target analyte. The functional sequences can generally be selected for compatibility with any of a variety of different sequencing systems, e.g., 454 Sequencing, Ion Torrent Proton or PGM, Illumina X10, PacBio, Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Roche 454 sequencing, Ion Torrent Proton or PGM sequencing, Illumina X10 sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 605, functional sequences 604 (e.g., flow cell attachment sequence) and 606 (e.g., sequencing primer sequences) can be common to all of the probes attached to a given feature. The spatial barcode can also include a capture domain 607 to facilitate capture of a target analyte.

(i) Capture Domain

As discussed above, each capture probe includes at least one capture domain. The "capture domain" can be an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence, which poly(T) sequences are configured to interact with messenger RNA (mRNA) molecules via the poly (A) tail of an mRNA transcript. In some embodiments, the functional nucleic acid sequence is the binding target of a protein (e.g., a transcription factor, a DNA binding protein, or a RNA binding protein), where the analyte of interest is a protein.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single-stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide.

In some embodiments, the capture domain is located at the 3' end of the capture probe and includes a free 3' end that can be extended, e.g., by template dependent polymerization, to form an extended capture probe as described herein. In some embodiments, the capture domain includes a nucleotide sequence that is capable of hybridizing to nucleic acid, e.g., RNA or other analyte, present in the cells of the biological sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, e.g., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, a capture probe includes a capture domain having a sequence that is capable of binding to mRNA and/or genomic DNA. For example, the capture probe can include a capture domain that includes a nucleic acid sequence (e.g., a poly(T) sequence) capable of binding to a poly(A) tail of an mRNA and/or to a poly(A) homopolymeric sequence present in genomic DNA. In some embodiments, a homopolymeric sequence is added to an mRNA molecule or a genomic DNA molecule using a terminal transferase enzyme in order to produce an analyte that has a poly(A) or poly(T) sequence. For example, a poly(A) sequence can be added to an analyte (e.g., a fragment of genomic DNA) thereby making the analyte capable of capture by a poly(T) capture domain.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g., at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes poly(T)-like sequence and the capture domain of one or more capture probes includes random sequences. In some embodiments, a pool of two or more capture probes form a mixture where the capture domain of one or more capture probes includes a poly(T)-random sequences and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes are used when the nucleic acid in the biological sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes, partially double stranded probes, or complementary sequences. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3' Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, e.g., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

(ii) Cleavage Domain

Each capture probe can optionally include at least one cleavage domain. The cleavage domain represents the portion of the probe that is used to reversibly attach the probe to an array feature, as will be described further herein. Further, one or more segments or regions of the capture probe can optionally be released from the array feature by cleavage of the cleavage domain. As an example, spatial barcodes and/or universal molecular identifiers (UMIs) can be released by cleavage of the cleavage domain.

Figure 7:
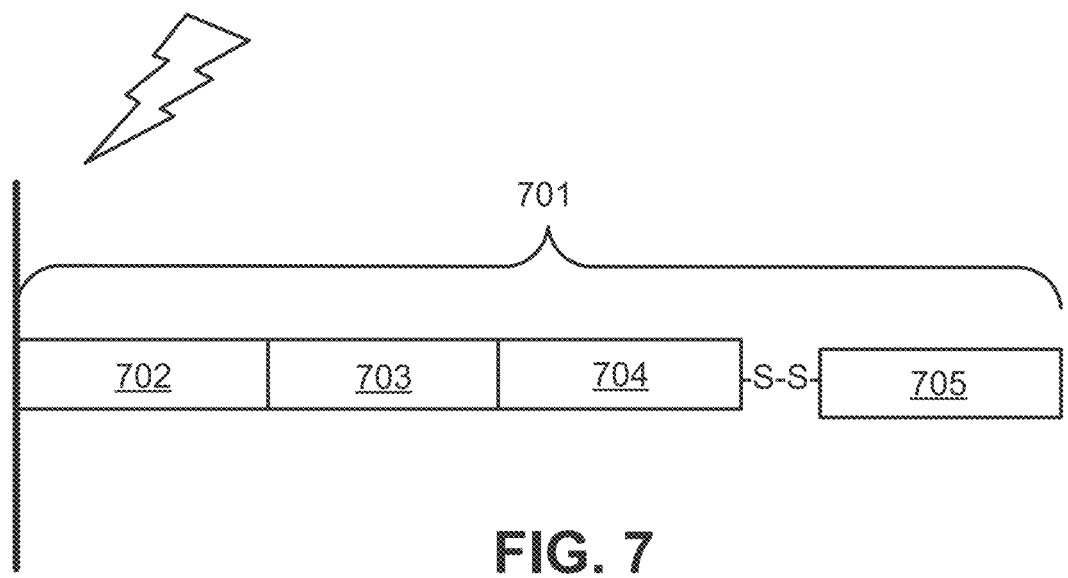
FIG. 7 is a schematic illustrating a cleavable capture probe, wherein the cleaved capture probe can enter into a non-permeabilized cell and bind to target analytes within the sample.

FIG. 7 is a schematic illustrating a cleavable capture probe, wherein the cleaved capture probe can enter into a non-permeabilized cell and bind to analytes within the sample. The capture probe 701 contains a cleavage domain 702, a cell penetrating peptide 703, a reporter molecule 704, and a disulfide bond (—S—S—). 705 represents all other parts of a capture probe, for example a spatial barcode and a capture domain.

In some embodiments, the cleavage domain linking the capture probe to a feature is a disulfide bond. A reducing agent can be added to break the disulfide bonds, resulting in release of the capture probe from the feature. As another example, heating can also result in degradation of the cleavage domain and release of the attached capture probe from the array feature. In some embodiments, laser radiation is used to heat and degrade cleavage domains of capture probes at specific locations. In some embodiments, the cleavage domain is a photo-sensitive chemical bond (e.g., a chemical bond that dissociates when exposed to light such as ultraviolet light).

Oligonucleotides with photo-sensitive chemical bonds (e.g., photo-cleavable linkers) have various advantages. They can be cleaved efficiently and rapidly (e.g., in nanoseconds and milliseconds). In some cases, photo-masks can be used such that only specific regions of the array are exposed to cleavable stimuli (e.g., exposure to UV light, exposure to light, exposure to heat induced by laser). When a photo-cleavable linker is used, the cleavable reaction is triggered by light, and can be highly selective to the linker and consequently biorthogonal. Typically, wavelength absorption for the photocleavable linker is located in the near-UV range of the spectrum. In some embodiments, $\lambda_{max}$ of the photocleavable linker is from about 300 nm to about 400 nm, or from about 310 nm to about 365 nm. In some embodiments, $\lambda_{max}$ of the photocleavable linker is about 300 nm, about 312 nm, about 325 nm, about 330 nm, about 340 nm, about 345 nm, about 355 nm, about 365 nm, or about 400 nm.

Non-limiting examples of a photo-sensitive chemical bond that can be used in a cleavage domain include those described in Leriche et al. *Bioorg Med Chem.* 2012 Jan. 15; 20(2):571-82 and U.S. Publication No. 2017/0275669, both of which are incorporated by reference herein in their entireties. For example, linkers that comprise photo-sensitive chemical bonds include 3-amino-3-(2-nitrophenyl)propionic acid (ANP), phenacyl ester derivatives, 8-quinolinyl benzenesulfonate, dicoumarin, 6-bromo-7-alkixycoumarin-4-ylmethoxycarbonyl, a bimane-based linker, and a bis-arylhydrazone based linker. In some embodiments, the photo-sensitive bond is part of a cleavable linker such as an ortho-nitrobenzyl (ONB) linker below:

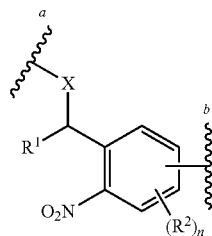

wherein:
X is selected from O and NH;
$R^1$ is selected from H and $C_{1-3}$ alkyl;
$R^2$ is selected from H and $C_{1-3}$ alkoxy;
n is 1, 2, or 3; and
a and b each represent either the point of attachment of the linker to the substrate, or the point of attachment of the linker to the capture probe.

In some embodiments, at least one spacer is included between the substrate and the ortho-nitrobenzyl (ONB) linker, and at least one spacer is included between the ortho-nitrobenzyl (ONB) linker and the capture probe. In some aspects of these embodiments, the spacer comprises at least one group selected from C1-6 alkylene, C2-6 alkenylene, C2-6 alkynylene, C=O, O, S, NH, —(C=O)O—, —(C=O)NH—, —S—S—, ethylene glycol, polyethyleneglycol, propylene glycol, and polypropyleneglycol, or any combination thereof. In some embodiments, X is O. In some embodiments, X is NH. In some embodiments, $R^1$ is H. In some embodiments, $R^1$ is $C_{1-3}$ alkyl. In some embodiments, $R^1$ is methyl. In some embodiments, $R^2$ is H. In some embodiments, $R^2$ is $C_{1-3}$ alkoxy. In some embodiments, $R^2$ is methoxy. In some embodiments, $R^1$ is H and $R^2$ is H. In some embodiments, $R^1$ is H and $R^2$ is methoxy. In some embodiments, $R^1$ is methyl and $R^2$ is H. In some embodiments, $R^1$ is methyl and $R^2$ is methoxy.

In some embodiments, the photocleavable linker has formula:

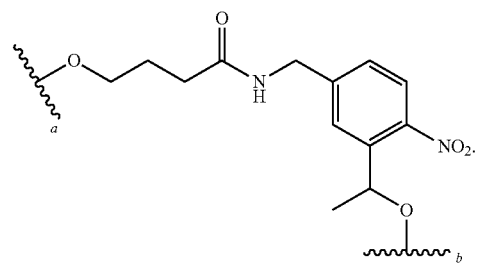 [SMILES: *OCCCC(=O)NCc1ccc([N+](=O)[O-])c(C(C)O*)c1]

In some embodiments, the photocleavable linker has formula:

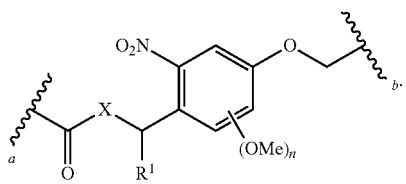

In some embodiments, the photocleavable linker has formula:

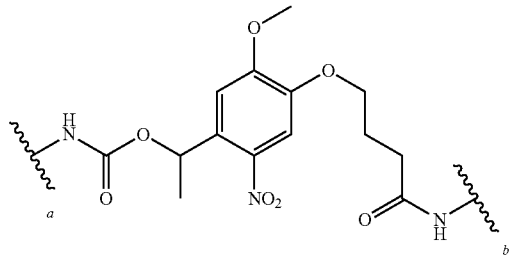

In some embodiments, the photocleavable linker has formula:

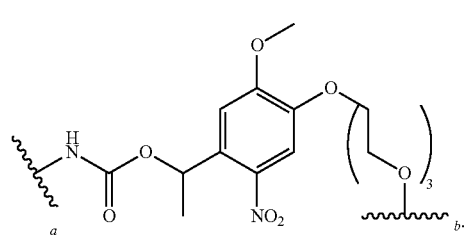

In some embodiments, the photocleavable linker has formula:

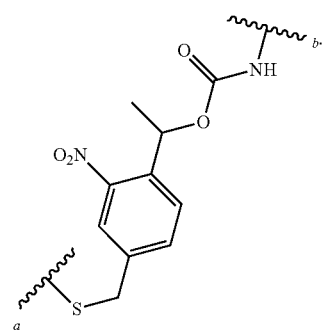 [SMILES: *NC(=O)OC(C)c1ccc(CS*)cc1[N+](=O)[O-]]

Without being bound to any particular theory, it is believed that excitation of the ortho-nitrobenzyl (ONB) linker leads to Norrish-type hydrogen abstraction in the γ-position, followed by formation of azinic acid, which is highly reactive and rearranges into nitroso compound, resulting in the complete cleavage of the linker, as shown on the following scheme:

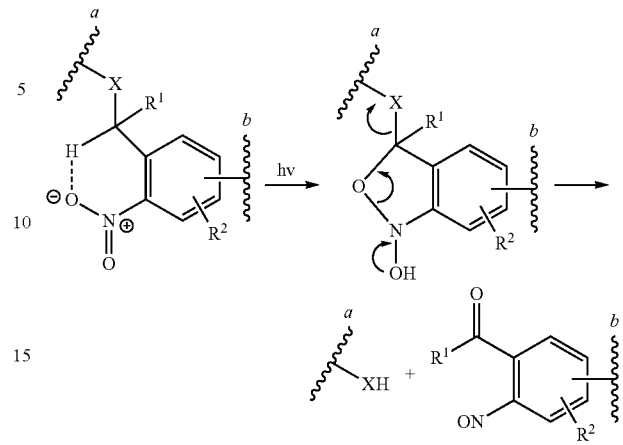

In some embodiments, the photocleavable linker is 3-amino-3-(2-nitrophenyl)propionic acid (ANP) linker:

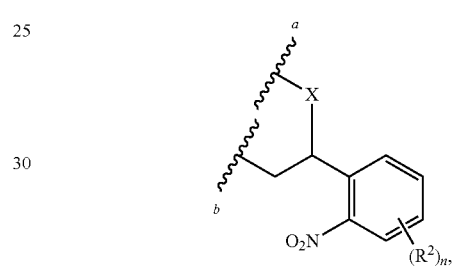

wherein X, $R^2$, n, a, and b are as described herein for the ortho-nitrobenzyl (ONB) linker.

In some embodiments, the photocleavable linker has formula:

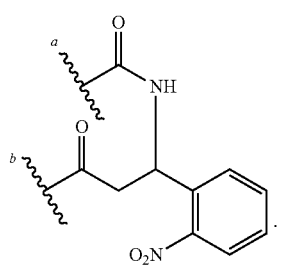 [SMILES: *C(=O)CC(NC(*)=O)c1ccccc1[N+](=O)[O-]]

In some embodiments, the photocleavable linker is phenacyl ester linker:

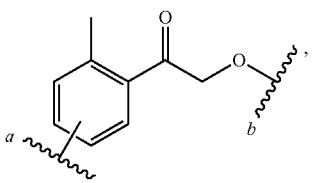

wherein a and b are as described herein for the ortho-nitrobenzyl (ONB) linker.

Other examples of photo-sensitive chemical bonds that can be used in a cleavage domain include halogenated nucleosides such as bromodeoxyuridine (BrdU). Brdu is an analog of thymidine that can be readily incorporated into oligonucleotides (e.g., in the cleavage domain of a capture probe), and is sensitive to UVB light (280-320 nm range). Upon exposure to UVB light, a photo-cleavage reaction occurs (e.g., at a nucleoside immediately 5' to the site of Brdu incorporation (Doddridge et al. Chem. Comm., 1998, 18:1997-1998 and Cook et al. Chemistry and Biology. 1999, 6:451-459)) that results in release of the capture probe from the feature.

Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), an abasic or apurinic/apyrimidinic (AP) site (e.g., cleavable with an alkali or an AP endonuclease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, e.g., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a feature.

In some embodiments, where the capture probe is attached indirectly to a substrate, e.g., via a surface probe, the cleavage domain includes one or more mismatch nucleotides, so that the complementary parts of the surface probe and the capture probe are not 100% complementary (for example, the number of mismatched base pairs can be one, two, or three base pairs). Such a mismatch is recognized, e.g., by the MutY and T7 endonuclease I enzymes, which results in cleavage of the nucleic acid molecule at the position of the mismatch. As described herein a "surface probe" can be any moiety present on the surface of the substrate capable of attaching to an agent (e.g., a capture probe). In some embodiments, the surface probe is an oligonucleotide. In some embodiments, the surface probe is part of the capture probe.

In some embodiments, where the capture probe is attached (e.g., immobilized) to a feature indirectly, e.g., via a surface probe, the cleavage domain includes a nickase recognition site or sequence. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is attached (e.g., immobilized) to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is incorporated herein by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, a cleavage domain is absent from the capture probe. Examples of substrates with attached capture probes lacking a cleavage domain are described for example in Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

(iii) Functional Domain

Each capture probe can optionally include at least one functional domain. Each functional domain typically includes a functional nucleotide sequence for a downstream analytical step in the overall analysis procedure.

In some embodiments, the capture probe can include a functional domain for attachment to a sequencing flow cell, such as, for example, a P5 sequence for Illumina® sequencing. In some embodiments, the capture probe or derivative thereof can include another functional domain, such as, for example, a P7 sequence for attachment to a sequencing flow cell for Illumina® sequencing. The functional domains can be selected for compatibility with a variety of different sequencing systems, e.g., 454 Sequencing, Ion Torrent Proton or PGM, Illumina X10, etc., and the requirements thereof.

In some embodiments, the functional domain includes a primer. The primer can include an R1 primer sequence for Illumina® sequencing, and in some embodiments, an R2 primer sequence for Illumina® sequencing. Examples of such capture probes and uses thereof are described in U.S. Patent Publication Nos. 2014/0378345 and 2015/0376609, the entire contents of each of which are incorporated herein by reference.

(iv) Spatial Barcode

As discussed above, the capture probe can include one or more spatial barcodes (e.g., two or more, three or more, four or more, five or more) spatial barcodes. A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate.

A spatial barcode can be part of an analyte, or independent from an analyte (e.g., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter.

These nucleotides can be completely contiguous, e.g., in a single stretch of adjacent nucleotides, or they can be separated into two or more separate subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer. In some embodiments, the spatial barcode subsequence can be at least about 4, 5, 6, 7, 8, 9, 10, 11, 12, 13, 14, 15, 16 nucleotides or longer. In some embodiments, the spatial barcode subsequence can be at most about 4, 5, 6, 7, 8, 9, 10, 11, 12, 13, 14, 15, 16 nucleotides or shorter.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 8:
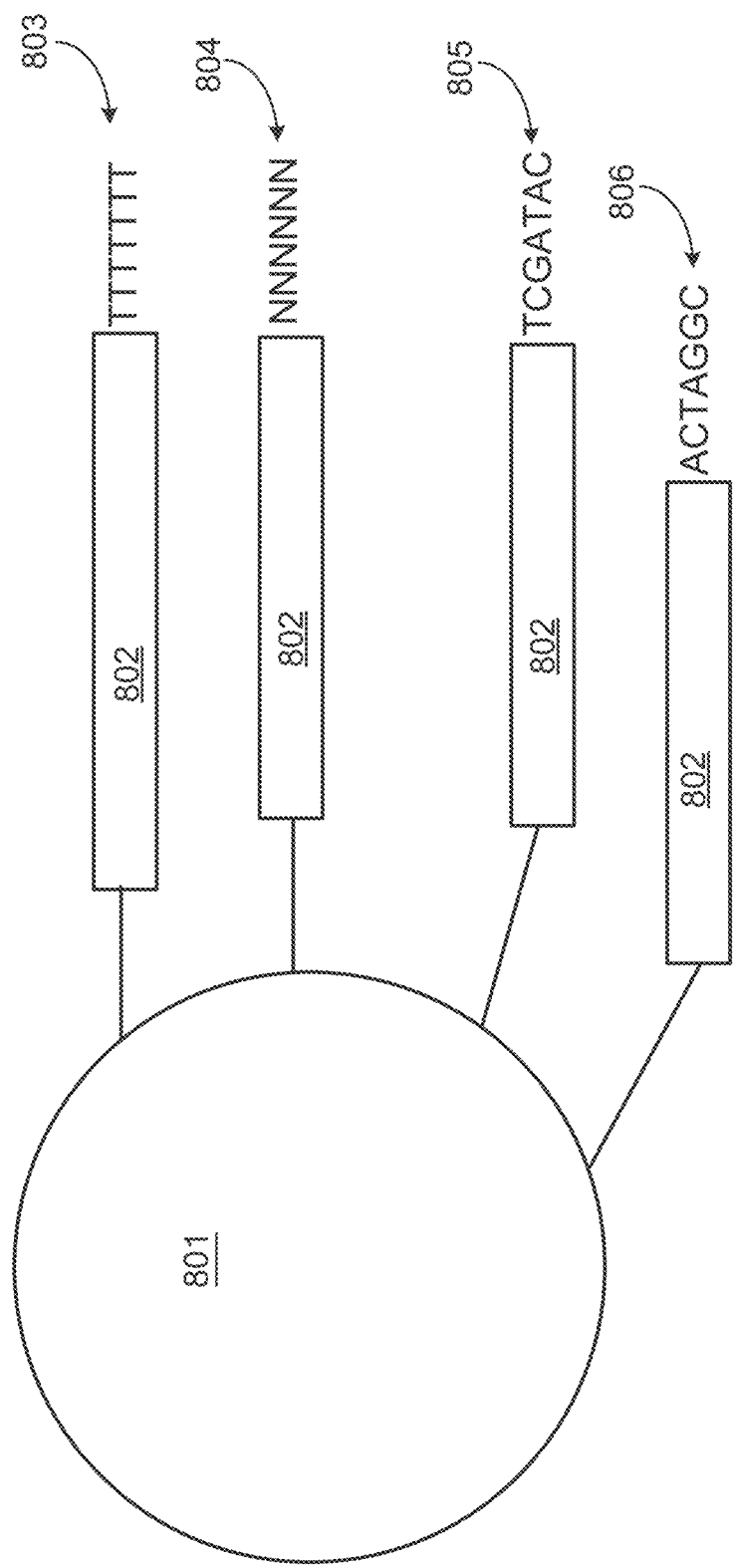
FIG. 8 is a schematic diagram of an exemplary multiplexed spatially-barcoded feature.

FIG. 8 is a schematic diagram of an exemplary multiplexed spatially-barcoded feature. In FIG. 8, the feature 801 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 802. One type of capture probe associated with the feature includes the spatial barcode 802 in combination with a poly(T) capture domain 803, designed to capture mRNA target analytes. A second type of capture probe associated with the feature includes the spatial barcode 802 in combination with a random N-mer capture domain 804 for gDNA analysis. A third type of capture probe associated with the feature includes the spatial barcode 802 in combination with a capture domain complementary to the capture domain on an analyte capture agent capture agent barcode domain 805. A fourth type of capture probe associated with the feature includes the spatial barcode 802 in combination with a capture probe that can specifically bind a nucleic acid molecule 806 that can function in a CRISPR assay (e.g., CRISPR/Cas9). While only four different capture probe-barcoded constructs are shown in FIG. 8, capture-probe barcoded constructs can be tailored for analyses of any given analyte associated with a nucleic acid and capable of binding with such a construct. For example, the schemes shown in FIG. 8 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

(v) Unique Molecular Identifier

The capture probe can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can be unique. A UMI can include one or more specific polynucleotides sequences, one or more random nucleic acid and/or amino acid sequences, and/or one or more synthetic nucleic acid and/or amino acid sequences.

In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The UMI can include from about 6 to about 20 or more nucleotides within the sequence of the capture probes. In some embodiments, the length of a UMI sequence can be about 6, 7, 8, 9, 10, 11, 12, 13, 14, 15, 16, 17, 18, 19, 20 nucleotides or longer. In some embodiments, the length of a UMI sequence can be at least about 6, 7, 8, 9, 10, 11, 12, 13, 14, 15, 16, 17, 18, 19, 20 nucleotides or longer. In some embodiments, the length of a UMI sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated UMI subsequences can be from about 4 to about 16 nucleotides in length. In some embodiments, the UMI subsequence can be about 4, 5, 6, 7, 8, 9, 10, 11, 12, 13, 14, 15, 16 nucleotides or longer. In some embodiments, the UMI subsequence can be at least about 4, 5, 6, 7, 8, 9, 10, 11, 12, 13, 14, 15, 16 nucleotides or longer. In some embodiments, the UMI subsequence can be at most about 4, 5, 6, 7, 8, 9, 10, 11, 12, 13, 14, 15, 16 nucleotides or shorter.

In some embodiments, a UMI is attached to an analyte in a reversible or irreversible manner. In some embodiments, a UMI is added to, for example, a fragment of a DNA or RNA sample before, during, and/or after sequencing of the analyte. In some embodiments, a UMI allows for identification and/or quantification of individual sequencing-reads. In some embodiments, a UMI is a used as a fluorescent barcode for which fluorescently labeled oligonucleotide probes hybridize to the UMI.

(vi) Other Aspects of Capture Probes

For capture probes that are attached to an array feature, an individual array feature can include one or more capture probes. In some embodiments, an individual array feature includes hundreds or thousands of capture probes. In some embodiments, the capture probes are associated with a particular individual feature, where the individual feature contains a capture probe including a spatial barcode unique to a defined region or location on the array.

In some embodiments, a particular feature can contain capture probes including more than one spatial barcode (e.g., one capture probe at a particular feature can include a spatial barcode that is different than the spatial barcode included in another capture probe at the same particular feature, while both capture probes include a second, common spatial barcode), where each spatial barcode corresponds to a particular defined region or location on the array. For example, multiple spatial barcode sequences associated with one particular feature on an array can provide a stronger address or attribution to a given location by providing duplicate or independent confirmation of the location. In some embodiments, the multiple spatial barcodes represent increasing specificity of the location of the particular array point. In a non-limiting example, a particular array point can be coded with two different spatial barcodes, where each spatial barcode identifies a particular defined region within the array, and an array point possessing both spatial barcodes identifies the sub-region where two defined regions overlap, e.g., such as the overlapping portion of a Venn diagram.

In another non-limiting example, a particular array point can be coded with three different spatial barcodes, where the first spatial barcode identifies a first region within the array, the second spatial barcode identifies a second region, where the second region is a subregion entirely within the first region, and the third spatial barcode identifies a third region, where the third region is a subregion entirely within the first and second subregions.

In some embodiments, capture probes attached to array features are released from the array features for sequencing. Alternatively, in some embodiments, capture probes remain attached to the array features, and the probes are sequenced while remaining attached to the array features (e.g., via in situ sequencing). Further aspects of the sequencing of capture probes are described in subsequent sections of this disclosure.

In some embodiments, an array feature can include different types of capture probes attached to the feature. For example, the array feature can include a first type of capture probe with a capture domain designed to bind to one type of analyte, and a second type of capture probe with a capture domain designed to bind to a second type of analyte. In general, array features can include one or more (e.g., two or more, three or more, four or more, five or more, six or more, eight or more, ten or more, 12 or more, 15 or more, 20 or more, 30 or more, 50 or more) different types of capture probes attached to a single array feature.

In some embodiments, the capture probe is nucleic acid. In some embodiments, the capture probe is attached to the array feature via its 5' end. In some embodiments, the capture probe includes from the 5' to 3' end: one or more barcodes (e.g., a spatial barcode and/or a UMI) and one or more capture domains. In some embodiments, the capture probe includes from the 5' to 3' end: one barcode (e.g., a spatial barcode or a UMI) and one capture domain. In some embodiments, the capture probe includes from the 5' to 3' end: a cleavage domain, a functional domain, one or more barcodes (e.g., a spatial barcode and/or a UMI), and a capture domain. In some embodiments, the capture probe includes from the 5' to 3' end: a cleavage domain, a functional domain, one or more barcodes (e.g., a spatial barcode and/or a UMI), a second functional domain, and a capture domain. In some embodiments, the capture probe includes from the 5' to 3' end: a cleavage domain, a functional domain, a spatial barcode, a UMI, and a capture domain. In some embodiments, the capture probe does not include a spatial barcode. In some embodiments, the capture probe does not include a UMI. In some embodiments, the capture probe includes a sequence for initiating a sequencing reaction.

In some embodiments, the capture probe is immobilized on a feature via its 3' end. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain.

In some embodiments, a capture probe includes an in situ synthesized oligonucleotide. The in situ synthesized oligonucleotide can be attached to a substrate, or to a feature on a substrate. In some embodiments, the in situ synthesized oligonucleotide includes one or more constant sequences, one or more of which serves as a priming sequence (e.g., a primer for amplifying target nucleic acids). The in situ synthesized oligonucleotide can, for example, include a constant sequence at the 3' end that is attached to a substrate, or attached to a feature on a substrate. Additionally or alternatively, the in situ synthesized oligonucleotide can include a constant sequence at the free 5' end. In some embodiments, the one or more constant sequences can be a cleavable sequence. In some embodiments, the in situ synthesized oligonucleotide includes a barcode sequence, e.g., a variable barcode sequence. The barcode can be any of the barcodes described herein. The length of the barcode can be approximately 8 to 16 nucleotides (e.g., 8, 9, 10, 11, 12, 13, 14, 15, or 16 nucleotides). The length of the in situ synthesized oligonucleotide can be less than 100 nucleotides (e.g., less than 90, 80, 75, 70, 60, 50, 45, 40, 35, 30, 25 or 20 nucleotides). In some instances, the length of the in situ synthesized oligonucleotide is about 20 to about 40 nucleotides. Exemplary in situ synthesized oligonucleotides are produced by Affymetrix. In some embodiments, the in situ synthesized oligonucleotide is attached to a feature of an array.

Additional oligonucleotides can be ligated to an in situ synthesized oligonucleotide to generate a capture probe. For example, a primer complementary to a portion of the in situ synthesized oligonucleotide (e.g., a constant sequence in the oligonucleotide) can be used to hybridize an additional oligonucleotide and extend (using the in situ synthesized oligonucleotide as a template e.g., a primer extension reaction) to form a double stranded oligonucleotide and to further create a 3' overhang. In some embodiments, the 3' overhang can be created by template-independent ligases (e.g., terminal deoxynucleotidyl transferase (TdT) or poly (A) polymerase). An additional oligonucleotide comprising one or more capture domains can be ligated to the 3' overhang using a suitable enzyme (e.g., a ligase) and a splint oligonucleotide, to generate a capture probe. Thus, in some embodiments, a capture probe is a product of two or more oligonucleotide sequences, (e.g., the in situ synthesized oligonucleotide and the additional oligonucleotide) that are ligated together. In some embodiments, one of the oligonucleotide sequences is an in situ synthesized oligonucleotide.

In some embodiments, the capture probe can be prepared using a splint oligonucleotide (e.g., any of the splint oligonucleotides described herein). Two or more oligonucleotides can be ligated together using a splint oligonucleotide and any variety of ligases known in the art or described herein (e.g., SplintR ligase).

One of the oligonucleotides can include, for example, a constant sequence (e.g., a sequence complementary to a portion of a splint oligonucleotide), a degenerate sequence, and/or a capture domain (e.g., as described herein). One of the oligonucleotides can also include a sequence compatible for ligating or hybridizing to an analyte of interest in the biological sample. An analyte of interest (e.g., an mRNA) can also be used as a splint oligonucleotide to ligate further oligonucleotides onto the capture probe. In some embodiments, the capture probe is generated by having an enzyme add polynucleotides at the end of an oligonucleotide sequence. The capture probe can include a degenerate sequence, which can function as a unique molecular identifier.

A degenerate sequence, which is a sequence in which some positions of a nucleotide sequence contain a number of possible bases. A degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 10, 15, 20, 25, or more degenerate positions within the nucleotide sequence. In some embodiments, the degenerate sequence is used as a UMI.

In some embodiments, a capture probe includes a restriction endonuclease recognition sequence or a sequence of nucleotides cleavable by specific enzyme activities. For example, uracil sequences can be enzymatically cleaved from a nucleotide sequence using uracil DNA glycosylase (UDG) or Uracil Specific Excision Reagent (USER). As another example, other modified bases (e.g., modified by methylation) can be recognized and cleaved by specific endonucleases. The capture probes can be subjected to an enzymatic cleavage, which removes the blocking domain and any of the additional nucleotides that are added to the 3' end of the capture probe during the modification process. Removal of the blocking domain reveals and/or restores the free 3' end of the capture domain of the capture probe. In some embodiments, additional nucleotides can be removed to reveal and/or restore the 3' end of the capture domain of the capture probe.

In some embodiments, a blocking domain can be incorporated into the capture probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

(vii) Extended Capture Probes

An "extended capture probe" is a capture probe with an enlarged nucleic acid sequence. For example, where the capture probe includes nucleic acid, an "extended 3' end" indicates that further nucleotides were added to the most 3' nucleotide of the capture probe to extend the length of the capture probe, for example, by standard polymerization reactions utilized to extend nucleic acid molecules including templated polymerization catalyzed by a polymerase (e.g., a DNA polymerase or reverse transcriptase).

In some embodiments, extending the capture probe includes generating cDNA from the captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending the capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, the capture domain of the capture probe includes a primer for producing the complementary strand of the nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g., cDNA, molecule is generated. In some embodiments, a "full-length" DNA molecule refers to the whole of the captured nucleic acid molecule. However, if the nucleic acid, e.g., RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, Wis.). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Epicentre Biotechnologies, Madison, Wis.), and SplintR (available from New England Biolabs, Ipswich, Mass.). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to an array feature specific for the affinity group. In some embodiments, the substrate can include an antibody or antibody fragment. In some embodiments, the array feature includes avidin or streptavidin and the affinity group includes biotin. In some embodiments, the array feature includes maltose and the affinity group includes maltose-binding protein. In some embodiments, the array feature includes maltose-binding protein and the affinity group includes maltose. In some embodiments, amplifying the extended capture probes can function to release the extended probes from the array feature, insofar as copies of the extended probes are not attached to the array feature.

In some embodiments, the extended capture probe or complement or amplicon thereof is released from an array feature. The step of releasing the extended capture probe or complement or amplicon thereof from an array feature can be achieved in a number of ways. In some embodiments, an extended capture probe or a complement thereof is released from the feature by nucleic acid cleavage and/or by denaturation (e.g., by heating to denature a double-stranded molecule).

In some embodiments, the extended capture probe or complement or amplicon thereof is released from the array feature by physical means. For example, methods for inducing physical release include denaturing double stranded nucleic acid molecules. Another method for releasing the extended capture probes is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the array feature. In some embodiments, a formamide solution can be used to destabilize the interaction between nucleic acid molecules to release the extended capture probe from the array feature.

(viii) Analyte Capture Agents

This disclosure also provides methods and materials for using analyte capture agents for spatial profiling of biological analytes (e.g., mRNA, genomic DNA, accessible chromatin, and cell surface or intracellular proteins and/or metabolites). As used herein, an "analyte capture agent" (also referred to previously at times as a "cell labelling" agent") refers to an agent that interacts with an analyte (e.g., an analyte in a sample) and with a capture probe (e.g., a capture probe attached to a substrate) to identify the analyte. In some embodiments, the analyte capture agent includes an analyte binding moiety and a capture agent barcode domain.

Figure 9:
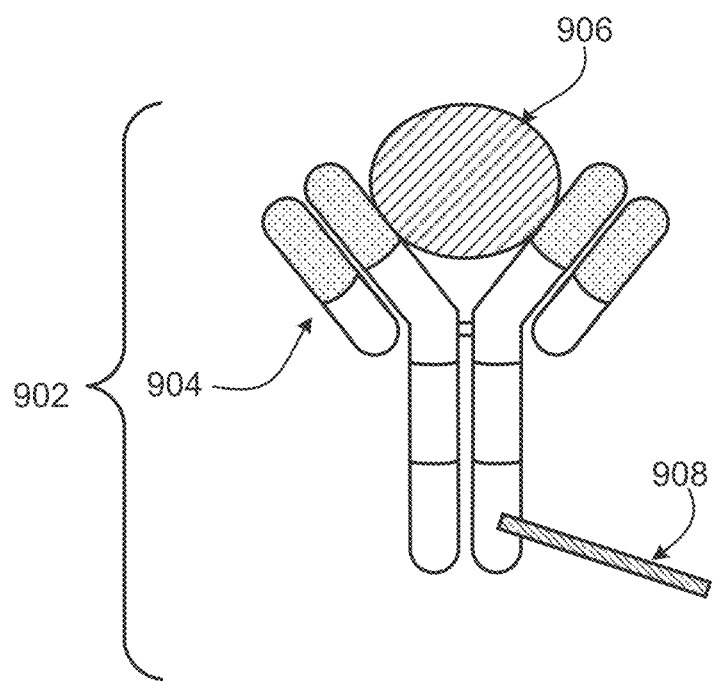
FIG. 9 is a schematic diagram of an exemplary analyte capture agent.

FIG. 9 is a schematic diagram of an exemplary analyte capture agent 902 comprised of an analyte binding moiety 904 and a capture agent barcode domain 908. An analyte binding moiety 904 is a molecule capable of binding to an analyte 906 and interacting with a spatially-barcoded capture probe. The analyte binding moiety can bind to the analyte 906 with high affinity and/or with high specificity. The analyte capture agent can include a capture agent barcode domain 908, a nucleotide sequence (e.g., an oligonucleotide), which can hybridize to at least a portion or an entirety of a capture domain of a capture probe. The analyte binding moiety 904 can include a polypeptide and/or an aptamer (e.g., an oligonucleotide or peptide molecule that binds to a specific target analyte). The analyte binding moiety 904 can include an antibody or antibody fragment (e.g., an antigen-binding fragment).

As used herein, the term "analyte binding moiety" refers to a molecule or moiety capable of binding to a macromolecular constituent (e.g., an analyte, e.g., a biological analyte). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

In some embodiments, an analyte binding moiety of an analyte capture agent includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

An analyte capture agent can include an analyte binding moiety. The analyte binding moiety can be an antibody. Exemplary, non-limiting antibodies that can be used as analyte binding moieties in an analyte capture agent or that can be used in the IHC/IF applications disclosed herein include any of the following including variations thereof: A-ACT, A-AT, ACTH, Actin-Muscle-specific, Actin-Smooth Muscle (SMA), AE1, AE1/AE3, AE3, AFP, AKT Phosphate, ALK-1, Amyloid A, Androgen Receptor, Annexin A1, B72.3, BCA-225, BCL-1 (Cyclin D1), BCL-1/CD20, BCL-2, BCL-2/BCL-6, BCL-6, Ber-EP4, Beta-amyloid, Beta-catenin, BG8 (Lewis Y), BOB-1, CA 19.9, CA 125, CAIX, Calcitonin, Caldesmon, Calponin, Calretinin, CAM 5.2, CAM 5.2/AE1, CD1a, CD2, CD3 (M), CD3 (P), CD3/CD20, CD4, CD5, CD7, CD8, CD10, CD14, CD15, CD20, CD21, CD22, CD 23, CD25, CD30, CD31, CD33, CD34, CD35, CD43, CD45 (LCA), CD45RA, CD56, CD57, CD61, CD68, CD71, CD74, CD79a, CD99, CD117 (c-KIT), CD123, CD138, CD163, CDX-2, CDX-2/CK-7, CEA (M), CEA (P), Chromogranin A, Chymotrypsin, CK-5, CK-5/6, CK-7, CK-7/TTF-1, CK-14, CK-17, CK-18, CK-19, CK-20, CK-HMW, CK-LMW, COLL-IV, COX-2, D2-40, DBA44, Desmin, DOG1, EBER-ISH, EBV (LMP1), E-Cadherin, EGFR, EMA, ER, ERCC1, Factor VIII (vWF), Factor XIIIa, Fascin, FLI-1, FHS, Galectin-3, Gastrin, GCDFP-15, GFAP, Glucagon, Glycophorin A, Glypican-3, Granzyme B, Growth Hormone (GH), GST, HAM 56, HMBE-1, HBP, HCAg, HCG, Hemoglobin A, HEP B CORE (HBcAg), HEP B SURF, (HBsAg), HepParl, HER2, Herpes I, Herpes II, HLA-DR, HMB 45, HPL, HPV-IHC, HPV (6/11)-ISH, HPV (16/18)-ISH, HPV (31/33)-ISH, HPV WSS-ISH, HPV High-ISH, HPV Low-ISH, HPV High & Low-ISH, IgA, IgD, IgG, IgG4, IgM, Inhibin, Insulin, JC Virus-ISH, Kappa-ISH, KER PAN, Ki-67, Lambda-IHC, Lambda-ISH, LH, Lipase, Lysozyme (MURA), Mammaglobin, MART-1, MBP, M-Cell Tryptase, MEL-5, Melan-A, Melan-A/Ki-67, Mesothelin, MiTF, MLH-1, MOC-31, MPO, MSH-2, MSH-6, MUC1, MUC2, MUC4, MUCSAC, MUM-1, MYO D1, Myogenin, Myoglobin, Myoin Heavy Chain, Napsin A, NB84a, NEW-N, NF, NK1-C3, NPM, NSE, OCT-2, OCT-3/4, OSCAR, p16, p21, p27/Kip1, p53, p57, p63, p120, P504S, Pan Melanoma, PANC.POLY, Parvovirus B19, PAX-2, PAX-5, PAX-5/CD43, PAX=5/CD5, PAX-8, PC, PD1, Perforin, PGP 9.5, PLAP, PMS-2, PR, Prolactin, PSA, PSAP, PSMA, PTEN, PTH, PTS, RB, RCC, S6, S100, Serotonin, Somatostatin, Surfactant (SP-A), Synaptophysin, Synuclein, TAU, TCL-1, TCR beta, TdT, Thrombomodulin, Thyroglobulin, TIA-1, TOXO, TRAP, TriView™ breast, TriView™ prostate, Trypsin, TS, TSH, TTF-1, Tyrosinase, Ubiqutin, Uroplakin, VEGF, Villin, Vimentin (VIM), VIP, VZV, WT1 (M) N-Terminus, WT1 (P) C-Terminus, ZAP-70.

Further, exemplary, non-limiting antibodies that can be used as analyte binding moieties in an analyte capture agent or that can be used in the IHC/IF applications disclosed herein include any of the following antibodies (and variations thereof) to: cell surface proteins, intracellular proteins, kinases (e.g., AGC kinase family (e.g., AKT1, AKT2, PDK1, Protein Kinase C, ROCK1, ROCK2, SGK3), CAMK kinase family (e.g., AMPK1, AMPK2, CAMK, Chk1, Chk2, Zip), CK1 kinase family, TK kinase family (e.g., Ab12, AXL, CD167, CD246/ALK, c-Met, CSK, c-Src, EGFR, ErbB2 (HER2/neu), ErbB3, ErbB4, FAK, Fyn, LCK, Lyn, PKT7, Syk, Zap70), STE kinase family (e.g., ASK1, MAPK, MEK1, MEK2, MEK3 MEK4, MEK5, PAK1, PAK2, PAK4, PAK6), CMGC kinase family (e.g., Cdk2, Cdk4, Cdk5, Cdk6, Cdk7, Cdk9, Erk1, GSK3, Jnk/MAPK8, Jnk2/MAPK9, JNK3/MAPK10, p38/MAPK), and TKL kinase family (e.g., ALK1, ILK1, IRAK1, IRAK2, IRAK3, IRAK4, LIMK1, LIMK2, M3K11, RAF1, RIP1, RIP3, VEGFR1, VEGFR2, VEGFR3), Aurora A kinase, Aurora B kinase, IKK, Nemo-like kinase, PINK, PLK3, ULK2, WEE1, transcription factors (e.g., FOXP3, ATF3, BACH1, EGR, ELF3, FOXA1, FOXA2, FOX01, GATA), growth factor receptors, tumor suppressors (e.g., anti-p53, anti-BLM, anti-Cdk2, anti-Chk2, anti-BRCA-1, anti-NBS1, anti-BRCA-2, anti-WRN, anti-PTEN, anti-WT1, anti-p38).

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety and its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies or aptamers) as well as being readily detected, (e.g., using sequencing or array technologies).

In some embodiments, the capture agent barcode domain of an analyte capture agent includes an analyte capture sequence. As used herein, the term "analyte capture sequence" refers to a region or moiety configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent, the capture agent barcode domain can be directly coupled to the analyte binding moiety, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties can be achieved through any of a variety of direct or indirect, covalent or non-covalent associations or attachments. For example, in the case of a capture agent barcode domain coupled to an analyte binding moiety that includes an antibody or antigen-binding fragment, such capture agent barcode domains can be covalently attached to a portion of the antibody or antigen-binding fragment using chemical conjugation techniques (e.g., Lightning-Link® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker(s), coupled to oligonucleotides with an avidin or streptavidin linker.) Antibody and oligonucleotide biotinylation techniques can be used, and are described for example in Fang et al., *Nucleic Acids Res.* (2003), 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG4-NHS ester reaction, or the like, can be used to couple capture agent barcode domains to analyte binding moieties. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH2). The reactive moiety on the analyte binding moiety can be a chemical compound or group that binds to the reactive moiety on the analyte binding moiety. Exemplary strategies to conjugate the analyte binding moiety to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety is an antibody, the antibody can be modified prior to or contemporaneously with conjugation of the oligonucleotide. For example, the antibody can be glycosylated with a chemical substrate-permissive mutant of β-1,4-galactosyltransferase, GalT (Y289L) and azide-bearing uridine diphosphate-N-acetylgalactosamine analog uridine diphosphate-GalNAz. The modified antibody can be conjugated to an oligonucleotide with a dibenzocyclooctyne-PEG4-NHS group. In some embodiments, certain steps (e.g., COOH activation (e.g., EDC) and homobifunctional cross linkers) can be avoided to prevent the analyte binding moieties from conjugating to themselves. In some embodiments of any of the spatial profiling methods described herein, the analyte capture agent (e.g., analyte binding moiety coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins. An analyte capture agent can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent to couple with intracellular constituents (such as, without limitation, intracellular proteins, metabolites, and nuclear membrane proteins). Following intracellular delivery, analyte capture agents can be used to analyze intracellular constituents as described herein.

In some embodiments of any of the spatial profiling methods described herein, the capture agent barcode domain coupled to an analyte capture agent can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1',2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent bound to the cell surface protein can be bound to a capture probe (e.g., a capture probe on an array), which capture probe includes a capture domain that interacts with an analyte capture sequence present on the capture agent barcode domain of the analyte capture agent. All or part of the capture agent barcode domain (including the analyte binding moiety barcode) can be copied with a polymerase using a 3' end of the capture domain as a priming site, generating an extended capture probe that includes the all or part of complementary sequence that corresponds to the capture probe (including a spatial barcode present on the capture probe) and a copy of the analyte binding moiety barcode. In some embodiments, an analyte capture agent with an extended capture agent barcode domain that includes a sequence complementary to a spatial barcode of a capture probe is called a "spatially-tagged analyte capture agent."

In some embodiments, the spatial array with spatially-tagged analyte capture agents can be contacted with a sample, where the analyte capture agent(s) associated with the spatial array capture the target analyte(s). The analyte capture agent(s) containing the extended capture probe(s), which includes a sequence complementary to the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g., single cells) and analyzed by the single cell/droplet methods described herein. The spatially-tagged analyte capture agent can be sequenced to obtain the nucleic acid sequence of the spatial barcode of the capture probe and the analyte binding moiety barcode of the analyte capture agent. The nucleic acid sequence of the extended capture probe can thus be associated with an analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a feature (e.g., a feature at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

Figure 10:
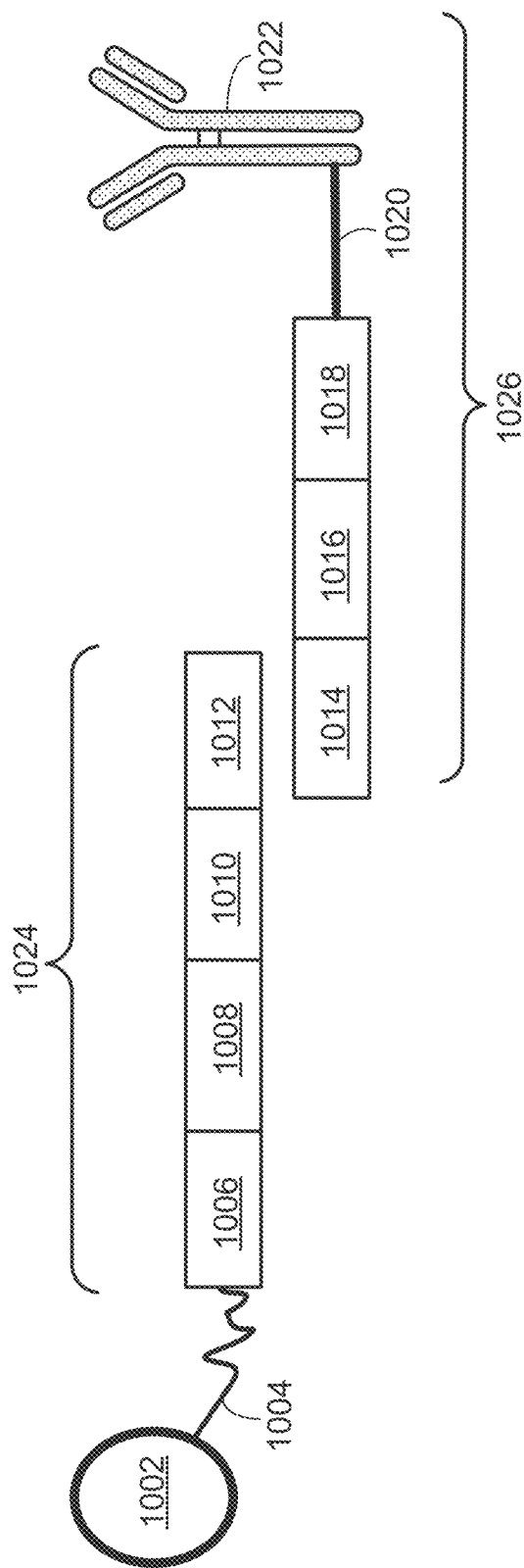
FIG. 10 is a schematic diagram depicting an exemplary interaction between a feature-immobilized capture probe 1024 and an analyte capture agent 1026.

FIG. 10 is a schematic diagram depicting an exemplary interaction between a feature-immobilized capture probe 1024 and an analyte capture agent 1026. The feature-immobilized capture probe 1024 can include a spatial barcode 1008 as well as one or more functional sequences 1006 and 1010, as described elsewhere herein. The capture probe can also include a capture domain 1012 that is capable of binding to an analyte capture agent 1026. The analyte capture agent 1026 can include a functional sequence 1018, capture agent barcode domain 1016, and an analyte capture sequence 1014 that is capable of binding to the capture domain 1012 of the capture probe 1024. The analyte capture agent can also include a linker 1020 that allows the capture agent barcode domain 1016 to couple to the analyte binding moiety 1022.

In some embodiments of any of the spatial profiling methods described herein, the methods are used to identify immune cell profiles. Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (MHC) molecules. The TCR is generally a heterodimer of two chains, each of which is a member of the immunoglobulin superfamily, possessing an N-terminal variable (V) domain, and a C terminal constant domain. In humans, in 95% of T cells, the TCR consists of an alpha (α) and beta (β) chain, whereas in 5% of T cells, the TCR consists of gamma and delta (γ/δ) chains. This ratio can change during ontogeny and in diseased states as well as in different species. When the TCR engages with antigenic peptide and MHC (peptide/MHC or pMHC), the T lymphocyte is activated through signal transduction.

Each of the two chains of a TCR contains multiple copies of gene segments—a variable 'V' gene segment, a diversity 'D' gene segment, and a joining 1' gene segment. The TCR alpha chain (TCRa) is generated by recombination of V and J segments, while the beta chain (TCRb) is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity, and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 1' gene segment. Each light chain gene contains multiple copies of two different gene segments for the variable region of the protein—a variable 'V' gene segment and a joining 1' gene segment.

The recombination can generate a molecule with one of each of the V, D, and J segments. Furthermore, several bases can be deleted and others added (called N and P nucleotides) at each of the two junctions, thereby generating further diversity. After B cell activation, a process of affinity maturation through somatic hypermutation occurs. In this process, progeny cells of the activated B cells accumulate distinct somatic mutations throughout the gene with higher mutation concentration in the CDR regions leading to the generation of antibodies with higher affinity to the antigens.

In addition to somatic hypermutation, activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA, and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

Certain methods described herein are utilized to analyze the various sequences of TCRs and BCRs from immune cells, for example, various clonotypes. In some embodiments, the methods are used to analyze the sequence of a TCR alpha chain, a TCR beta chain, a TCR delta chain, a TCR gamma chain, or any fragment thereof (e.g., variable regions including V(D)J or VJ regions, constant regions, transmembrane regions, fragments thereof, combinations thereof, and combinations of fragments thereof). In some embodiments, the methods described herein can be used to analyze the sequence of a B cell receptor heavy chain, B cell receptor light chain, or any fragment thereof (e.g., variable regions including V(D)J or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions can include gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

In some embodiments, the analyte binding moiety is based on the Major Histocompatibility Complex (MHC) class I or class II. In some embodiments, the analyte binding moiety is an MHC multimer including, without limitation, MHC dextramers, MEW tetramers, and MEW pentamers (see, for example, U.S. Patent Application Publication Nos. US 2018/0180601 and US 2017/0343545, the entire contents of each of which are incorporated herein by reference. MHCs (e.g., a soluble MHC monomer molecule), including full or partial MHC-peptides, can be used as analyte binding moieties of analyte capture agents that are coupled to capture agent barcode domains that include an analyte binding moiety barcode that identifies its associated MEW (and, thus, for example, the MHC's TCR binding partner). In some embodiments, MHCs are used to analyze one or more cell-surface features of a T-cell, such as a TCR. In some cases, multiple MHCs are associated together in a larger complex (MHC multi-mer) to improve binding affinity of MHCs to TCRs via multiple ligand binding synergies.

Figure 11A:
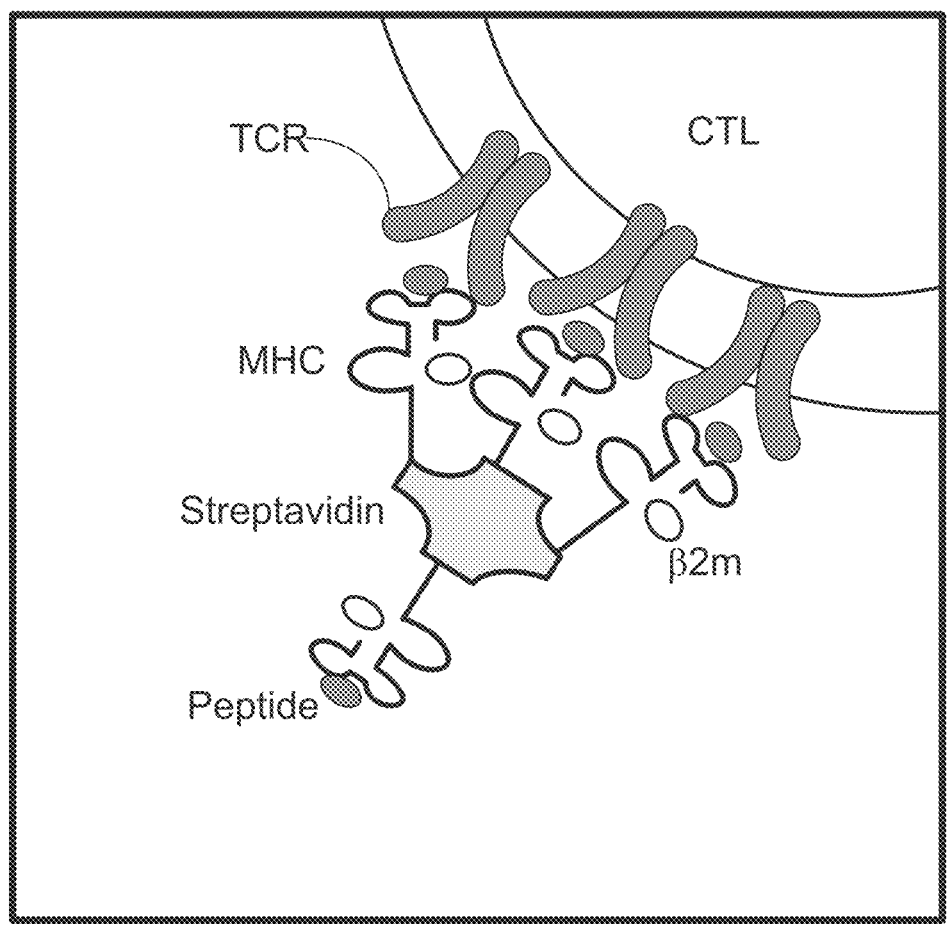
FIGS. 11A, 11B, and 11C are schematics illustrating how streptavidin cell tags can be utilized in an array-based system to produce a spatially-barcoded cells or cellular contents.
Figure 11B:
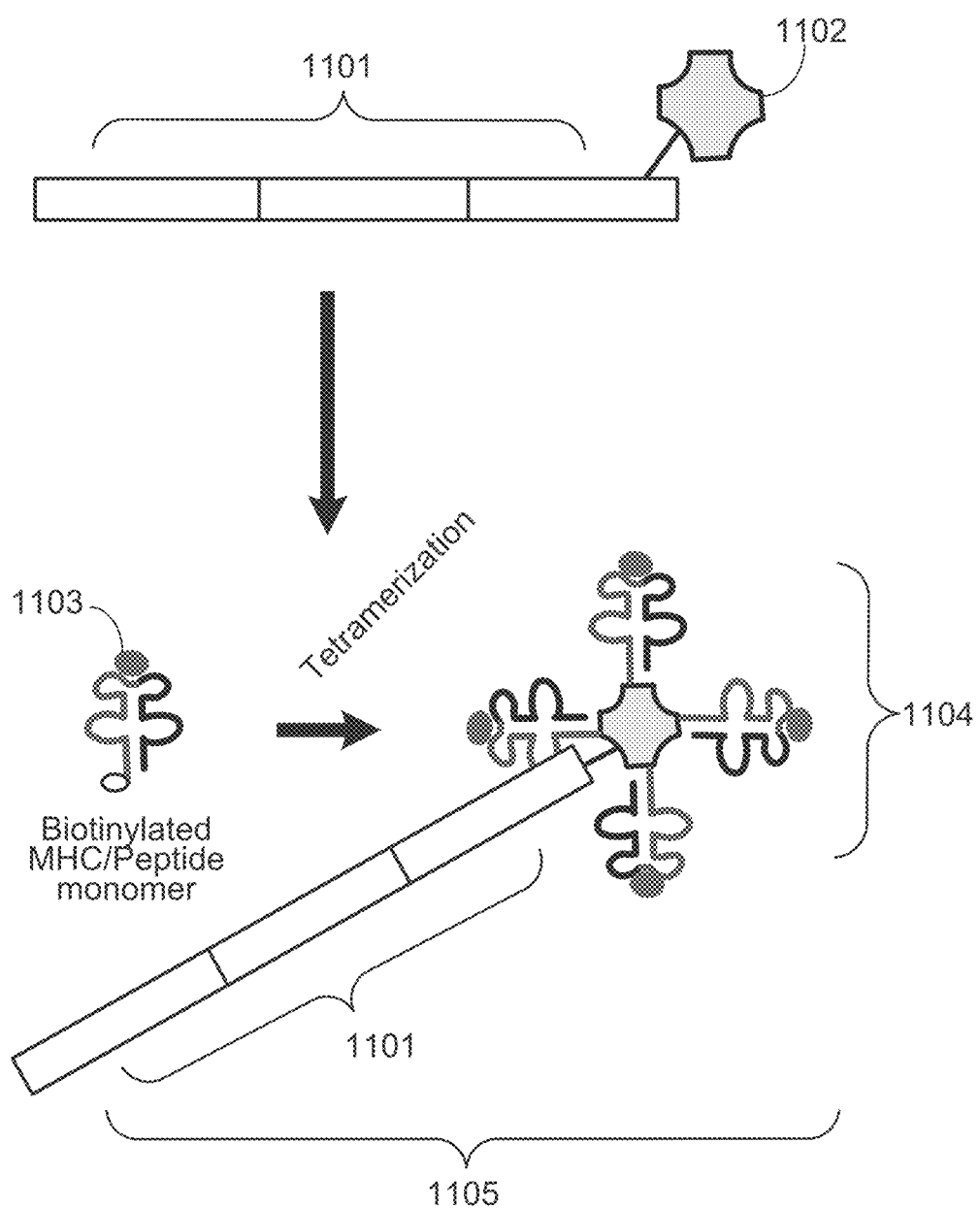
Figure 11C:
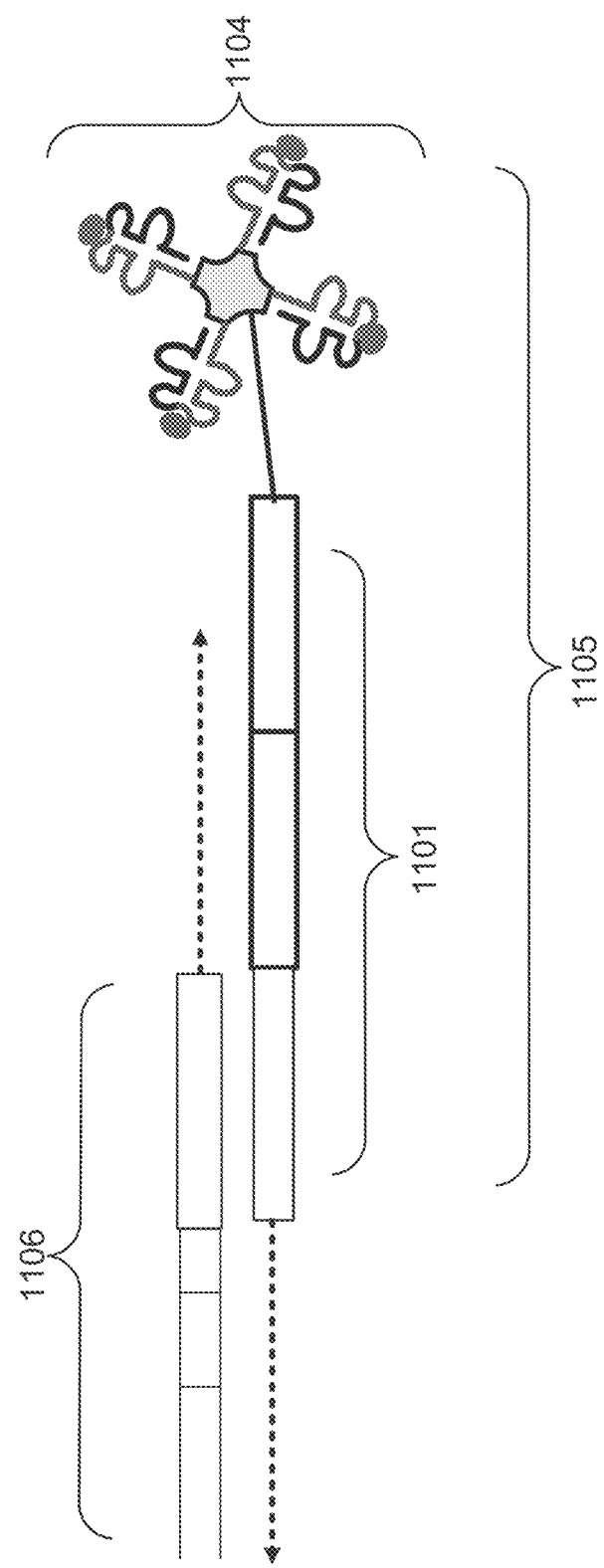

FIGS. 11A, 11B, and 11C are schematics illustrating how streptavidin cell tags can be utilized in an array-based system to produce a spatially-barcoded cell or cellular contents. For example, as shown in FIG. 11, peptide-bound major histocompatibility complex (pMHCs) can be individually associated with biotin and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 11B, a capture agent barcode domain 1101 can be modified with streptavidin 1102 and contacted with multiple molecules of biotinylated MHC 1103 (such as a pMHC) such that the biotinylated MEW 1103 molecules are coupled with the streptavidin conjugated capture agent barcode domain 1101. The result is a barcoded MHC multimer complex 1105. As shown in FIG. 11B, the capture agent barcode domain sequence 1101 can identify the MHC as its associated label and also includes optional functional sequences such as sequences for hybridization with other oligonucleotides. As shown in FIG. 11C, one example oligonucleotide is capture probe 1106 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1")), a flow cell attachment sequence (e.g., P5 or P7 or partial sequences thereof)), etc. In some cases, capture probe 1106 may at first be associated with a feature (e.g., a gel bead) and released from the feature. In other embodiments, capture probe 1106 can hybridize with a capture agent barcode domain 1101 of the MHC-oligonucleotide complex 1105. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 1106 or capture agent barcode domain 1101. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 1106 spatial barcode sequence may be used to identify a feature and the sequence derived from spatial barcode sequence on the capture agent barcode domain 1101 may be used to identify the particular peptide MHC complex 1104 bound on the surface of the cell (e.g., when using MHC-peptide libraries for screening immune cells or immune cell populations).

(c) Substrates

For the spatial array-based analytical methods described herein, a substrate functions as a support for direct or indirect attachment of capture probes to features of the array. In addition, in some embodiments, a substrate (e.g., the same substrate or a different substrate) can be used to provide support to a biological sample, particularly, for example, a thin tissue section. Accordingly, a "substrate" is a support that is insoluble in aqueous liquid and which allows for positioning of biological samples, analytes, features, and/or capture probes on the substrate.

Further, a "substrate" as used herein, and when not preceded by the modifier "chemical", refers to a member with at least one surface that generally functions to provide physical support for biological samples, analytes, and/or any of the other chemical and/or physical moieties, agents, and structures described herein. Substrates can be formed from a variety of solid materials, gel-based materials, colloidal materials, semi-solid materials (e.g., materials that are at least partially cross-linked), materials that are fully or partially cured, and materials that undergo a phase change or transition to provide physical support. Examples of substrates that can be used in the methods and systems described herein include, but are not limited to, slides (e.g., slides formed from various glasses, slides formed from various polymers), hydrogels, layers and/or films, membranes (e.g., porous membranes), flow cells, cuvettes, wafers, plates, or combinations thereof. In some embodiments, substrates can optionally include functional elements such as recesses, protruding structures, microfluidic elements (e.g., channels, reservoirs, electrodes, valves, seals), and various markings, as will be discussed in further detail below.

(i) Substrate Attributes

A substrate can generally have any suitable form or format. For example, a substrate can be flat, curved, e.g., convexly or concavely curved towards the area where the interaction between a biological sample, e.g., tissue sample, and a substrate takes place. In some embodiments, a substrate is flat, e.g., planar, chip, or slide. A substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or crosstable). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a substrate can be modified so that discrete sites are formed that can only have or accommodate a single feature. In some embodiments, the surface of a substrate can be modified so that features adhere to random sites.

In some embodiments, the surface of a substrate is modified to contain one or more wells, using techniques such as (but not limited to) stamping, microetching, or molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate (e.g., wells or features) can each bear a different capture probe. Different capture probes attached to each structure can be identified according to the locations of the structures in or on the surface of the substrate. Exemplary substrates include arrays in which separate structures are located on the substrate including, for example, those having wells that accommodate features.

In some embodiments where the substrate is modified to contain one or more structures, including but not limited to, wells, projections, ridges, features, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites. In some embodiments where the substrate is modified to contain various structures, including but not limited to wells, projections, ridges, features, or markings, the structures are applied in a pattern. Alternatively, the structures can be randomly distributed.

The substrate (e.g., or a bead or a feature on an array) can include tens to hundreds of thousands or millions of individual oligonucleotide molecules (e.g., at least about 10,000, 50,000, 100,000, 500,000, 1,000,000, 10,000,000, 100,000,000, 1,000,000,000, or 10,000,000,000 oligonucleotide molecules).

In some embodiments, a substrate includes one or more markings on a surface of a substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducial markers can be included on a substrate. Such markings can be made using techniques including, but not limited to, printing, sandblasting, and depositing on the surface.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., *Applied Optics* 46:421-427, 2007), the entire contents of which are incorporated herein by reference. In some embodiments, a fiducial marker can be a physical particle (e.g., a nanoparticle, a microsphere, a nanosphere, a bead, or any of the other exemplary physical particles described herein or known in the art).

In some embodiments, a fiducial marker can be present on a substrate to provide orientation of the biological sample. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of features on the substrate. In some embodiments, a quantum dot can be coupled to the substrate to aid in the orientation of the biological sample. In some examples, a quantum dot coupled to a substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the tissue sample is stained to visualize or image the tissue section. Although not required, it can be advantageous to use a marker that can be detected using the same conditions (e.g., imaging conditions) used to detect a labelled cDNA.

In some embodiments, fiducial markers are included to facilitate the orientation of a tissue sample or an image thereof in relation to an immobilized capture probes on a substrate. Any number of methods for marking an array can be used such that a marker is detectable only when a tissue section is imaged. For instance, a molecule, e.g., a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be randomly placed in the field of view. For example, an oligonucleotide containing a fluorophore can be randomly printed, stamped, synthesized, or attached to a substrate (e.g., a glass slide) at a random position on the substrate. A tissue section can be contacted with the substrate such that the oligonucleotide containing the fluorophore contacts, or is in proximity to, a cell from the tissue section or a component of the cell (e.g., an mRNA or DNA molecule). An image of the substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a substrate). In this instance, a fiducial marker can be stamped, attached, or synthesized on the substrate and contacted with a biological sample. Typically, an image of the sample and the fiducial marker is taken, and the position of the fiducial marker on the substrate can be confirmed by viewing the image.

In some embodiments, a fiducial marker can be an immobilized molecule (e.g., a physical particle) attached to the substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye.

As noted herein, any of the fiducial markers described herein (e.g., microspheres, beads, or any of the other physical particles described herein) can be located at a portion (e.g., corner) of an array in a specific pattern or design (e.g., hexagonal design) to aid in orientation of a biological sample on an array of features on the substrate. In some embodiments, the fiducial markers located at a portion (e.g., corner) of an array (e.g., an array on a substrate) can be patterned or designed in at least 1, at least 2, at least 3, or at least 4 unique patterns. In some examples, the fiducial markers located at the corners of the array (e.g., an array on a substrate) can have four unique patterns of fiducial markers.

In some examples, fiducial markers can surround the array. In some embodiments the fiducial markers allow for detection of, e.g., mirroring. In some embodiments, the fiducial markers may completely surround the array. In some embodiments, the fiducial markers may not completely surround the array. In some embodiments, the fiducial markers identify the corners of the array. In some embodiments, one or more fiducial markers identify the center of the array. In some embodiments, the fiducial markers comprise patterned spots, wherein the diameter of one or more patterned spot fiducial markers is approximately 100 micrometers. The diameter of the fiducial markers can be any useful diameter including, but not limited to, 50 micrometers to 500 micrometers in diameter. The fiducial markers may be arranged in such a way that the center of one fiducial marker is between 100 micrometers and 200 micrometers from the center of one or more other fiducial markers surrounding the array. In some embodiments, the array with the surrounding fiducial markers is approximately 8 mm by 8 mm. In some embodiments, the array without the surrounding fiducial markers is smaller than 8 mm by 50 mm.

In some embodiments, an array can be enclosed within a frame. Put another way, the perimeter of an array can have fiducial markers such that the array is enclosed, or substantially enclosed. In some embodiments, the perimeter of an array can be fiducial markers (e.g., any fiducial marker described herein). In some embodiments, the perimeter of an array can be uniform. For example, the fiducial markings can connect, or substantially connect, consecutive corners of an array in such a fashion that the non-corner portion of the array perimeter is the same on all sides (e.g., four sides) of the array. In some embodiments, the fiducial markers attached to the non-corner portions of the perimeter can be pattered or designed to aid in the orientation of the biological sample on the array. In some embodiments, the particles attached to the non-corner portions of the perimeter can be patterned or designed in at least 1, at least 2, at least 3, or at least 4 patterns. In some embodiments, the patterns can have at least 2, at least 3, or at least 4 unique patterns of fiducial markings on the non-corner portion of the array perimeter.

In some embodiments, an array can include at least two fiducial markers (e.g., at least 3, at least 4, at least 5, at least 6, at least 7, at least 8, at least 9, at least 10, at least 12, at least 15, at least 20, at least 30, at least 40, at least 50, at least 60, at least 70, at least 80, at least 90, at least 100 fiducial markers or more (e.g., several hundred, several thousand, or tens of thousands of fiducial markers)) in distinct positions on the surface of a substrate. Fiducial markers can be provided on a substrate in a pattern (e.g., an edge, one or more rows, one or more lines, etc.).

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon", cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene polycarbonate, or combinations thereof.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In another example, a substrate can be a flow cell. Flow cells can be formed of any of the foregoing materials, and can include channels that permit reagents, solvents, features, and analytes to pass through the flow cell. In some embodiments, a hydrogel embedded biological sample is assembled in a flow cell (e.g., the flow cell is utilized to introduce the hydrogel to the biological sample). In some embodiments, a hydrogel embedded biological sample is not assembled in a flow cell. In some embodiments, the hydrogel embedded biological sample can then be prepared and/or isometrically expanded as described herein.

(ii) Conductive Substrates

Conductive substrates (e.g., electrophoretic compatible arrays) generated as described herein can be used in the spatial detection of analytes. For example, an electrophoretic field can be applied to facilitate migration of analytes towards the barcoded oligonucleotides (e.g., capture probes) on the array (e.g., capture probes immobilized on paper, capture probes immobilized in a hydrogel film, or capture probes immobilized on a glass slide having a conductive coating). In some embodiments, an electrophoresis assembly can be arranged. For example, an anode and a cathode can be arranged such that an array of capture probes (e.g., capture probes immobilized on paper, capture probes immobilized in a hydrogel film, or capture probes immobilized on a glass slide having a conductive coating) and a biological sample are positioned between the anode and the cathode. In such embodiments, analytes in the biological sample are actively migrated toward the capture probes on the conductive substrate and captured. The biological sample can be prepared (e.g., permeabilized) according to any method described herein. In some embodiments, after electrophoretic-assisted capture of the analytes, the barcoded oligonucleotides (e.g., capture probes) and captured analytes can be collected, processed, and/or analyzed (e.g., sequenced) using any of the methods described herein.

In some embodiments, a conductive substrate can include glass (e.g., a glass slide) that has been coated with a substance or otherwise modified to confer conductive properties to the glass. In some embodiments, a glass slide can be coated with a conductive coating. In some embodiments, a conductive coating includes tin oxide (TO) or indium tin oxide (ITO). In some embodiments, a conductive coating includes a transparent conductive oxide (TCO). In some embodiments, a conductive coating includes aluminum doped zinc oxide (AZO). In some embodiments, a conductive coating includes fluorine doped tin oxide (FTO).

In some embodiments, arrays that are spotted or printed with oligonucleotides (e.g., capture probes, e.g., any of the variety of capture probes described herein) can be generated on a conductive substrate (e.g., any of the conductive substrates described herein). For example, the arrays described herein can be compatible with active analyte capture methods (e.g., any of the analyte capture methods described herein, including without limitation, electrophoretic capture methods). In some embodiments, a conductive substrate is a porous medium. Non-limiting examples of porous media that can be used in methods described herein that employ active analyte capture include a nitrocellulose or nylon membrane. In some embodiments, a porous medium that can be used in methods described herein that employ active analyte capture includes paper. In some embodiments, the oligonucleotides can be printed on a paper substrate. In some embodiments, the printed oligonucleotides can interact with the substrate (e.g., interact with fibers of the paper). In some embodiments, printed oligonucleotides can covalently bind the substrate (e.g., to fibers of the paper). In some embodiments, oligonucleotides in a molecular precursor solution can be printed on a conductive substrate (e.g., paper). In some embodiments, a molecular precursor solution can polymerize, thereby generating gel pads on the conductive substrate (e.g., paper). In some embodiments, a molecular precursor solution can be polymerized by light (e.g., photocured). In some embodiments, gel beads (e.g., any of the variety of gel beads described herein) containing oligonucleotides (e.g., barcoded oligonucleotides such as capture probes) can be printed on a conductive substrate (e.g., paper). In some embodiments, the printed oligonucleotides can be covalently attached into the gel matrix.

(iii) Coatings

In some embodiments, a surface of a substrate can be coated with a cell-permissive coating to allow adherence of live cells. A "cell-permissive coating" is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly (L)-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen. A cell-permissive coating can be used to culture adherent cells on a spatially-barcoded array, or to maintain cell viability of a tissue sample or section while in contact with a spatially-barcoded array.

In some embodiments, a substrate is coated with a surface treatment such as poly(L)-lysine. Additionally or alternatively, the substrate can be treated by silanation, e.g., with epoxy-silane, amino-silane, and/or by a treatment with polyacrylamide.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents is incorporated herein by reference.

Treatment can include adding a functional group that is reactive or capable of being activated such that it becomes reactive after application of a stimulus (e.g., photoreactive functional groups). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

A "conditionally removable coating" is a coating that can be removed from the surface of a substrate upon application of a releasing agent. In some embodiments, a conditionally removable coating includes a hydrogel as described herein, e.g., a hydrogel including a polypeptide-based material. Non-limiting examples of a hydrogel featuring a polypeptide-based material include a synthetic peptide-based material featuring a combination of spider silk and a transmembrane segment of human muscle L-type calcium channel (e.g., PEPGEL®), an amphiphilic 16 residue peptide containing a repeating arginine-alanine-aspartate-alanine sequence (RADARADARADARADA) (e.g., PURAIVIATRIX®), EAK16 (AEAEAKAKAEAEAKAK), KLD12 (KLDLKLDLKLDL), and PGMATRIX™.

In some embodiments, the hydrogel in the conditionally removable coating is a stimulus-responsive hydrogel. A stimulus-responsive hydrogel can undergo a gel-to-solution and/or gel-to-solid transition upon application of one or more external triggers (e.g., a releasing agent). See, e.g., Willner, *Acc. Chem. Res.* 50:657-658, 2017, which is incorporated herein by reference in its entirety. Non-limiting examples of a stimulus-responsive hydrogel include a thermoresponsive hydrogel, a pH-responsive hydrogel, a light-responsive hydrogel, a redox-responsive hydrogel, an analyte-responsive hydrogel, or a combination thereof. In some embodiments, a stimulus-responsive hydrogel can be a multi-stimuli-responsive hydrogel.

A "releasing agent" or "external trigger" is an agent that allows for the removal of a conditionally removable coating from a substrate when the releasing agent is applied to the conditionally removable coating. An external trigger or releasing agent can include physical triggers such as thermal, magnetic, ultrasonic, electrochemical, and/or light stimuli as well as chemical triggers such as pH, redox reactions, supramolecular complexes, and/or biocatalytically driven reactions. See e.g., Echeverria, et al., *Gels* (2018), 4, 54; doi:10.3390/gels4020054, which is incorporated herein by reference in its entirety. The type of "releasing agent" or "external trigger" can depend on the type of conditionally removable coating. For example, a conditionally removable coating featuring a redox-responsive hydrogel can be removed upon application of a releasing agent that includes a reducing agent such as dithiothreitol (DTT). As another example, a pH-responsive hydrogel can be removed upon the application of a releasing agent that changes the pH.

(iv) Gel Substrates

In some embodiments, a hydrogel can form a substrate. The term "hydrogel" herein refers to a macromolecular polymer gel including a network. Within the network, some polymer chains can optionally be cross-linked, although cross-linking does not always occur. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, features, projections, and/or markings) located on a substrate. Where the substrate includes a gel (e.g., a hydrogel or gel matrix), oligonucleotides within the gel can attach to the substrate.

In some embodiments, a hydrogel can include hydrogel subunits. The hydrogel subunits can include any convenient hydrogel subunits, such as, but not limited to, acrylamide, bis-acrylamide, polyacrylamide and derivatives thereof, poly(ethylene glycol) and derivatives thereof (e.g., PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, or combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which is incorporated herein by reference.

In some embodiments, cross-linkers and/or initiators are added to hydrogel subunits. Examples of cross-linkers include, without limitation, bis-acrylamide and diazirine. Examples of initiators include, without limitation, azobisisobutyronitrile (AIBN), riboflavin, and L-arginine. Inclusion of cross-linkers and/or initiators can lead to increased covalent bonding between interacting biological macromolecules in later polymerization steps.

In some embodiments, hydrogels can have a colloidal structure, such as agarose, or a polymer mesh structure, such as gelatin. In some embodiments, the hydrogel is a homopolymeric hydrogel. In some embodiments, the hydrogel is a copolymeric hydrogel. In some embodiments, the hydrogel is a multipolymer interpenetrating polymeric hydrogel.

In some embodiments, some hydrogel subunits are polymerized (e.g., undergo "formation") covalently or physically cross-linked, to form a hydrogel network. For example, hydrogel subunits can be polymerized by any method including, but not limited to, thermal crosslinking, chemical crosslinking, physical crosslinking, ionic crosslinking, photo-crosslinking, free-radical initiation crosslinking, an addition reaction, condensation reaction, water-soluble crosslinking reactions, irradiative crosslinking (e.g., x-ray, electron beam), or combinations thereof. Techniques such as lithographic photopolymerization can also be used to form hydrogels.

In some embodiments, gel beads containing oligonucleotides (e.g., barcoded oligonucleotides such as capture probes) can be deposited on a substrate (e.g., a glass slide). In some embodiments, gel pads can be deposited on a substrate (e.g., a glass slide). In some embodiments, gel pads or gel beads are deposited on a substrate in an arrayed format. In some embodiments in which gel pads or gel beads are deposited on a substrate in an arrayed format, a hydrogel molecular precursor solution can be applied on top of the array (e.g., the array of gel pads or gel beads on a glass slide). In some embodiments, a hydrogel molecular precursor solution can be polymerized such that the deposited gel pads or gel beads are immobilized within the polymerized hydrogel. Any suitable method of polymerization can be used or (e.g., any of the variety of methods described herein). In some embodiments, a polymerized hydrogel that includes the gel pads or gel beads can be removed (e.g., peeled) from the substrate (e.g., glass slide) such that the gel beads or gel pads are secured in the hydrogel. In some embodiments, a polymerized hydrogel that includes the gel pads or gel beads is a conductive substrate (as described herein) that can be used in accordance with any of the variety of analyte capture methods described herein (e.g., electrophoretic migration of analytes for capture).

Arrays can be prepared by depositing features (e.g., droplets, beads) on a substrate surface to produce a spatially-barcoded array. Methods of depositing (e.g., droplet manipulation) features are known in the art (see, U.S. Patent Application Publication No. 2008/0132429, Rubina, A. Y., et al., *Biotechniques*. 2003 May; 34(5):1008-14, 1016-20, 1022 and Vasiliskov et al. *Biotechniques*. 1999 September; 27(3):592-4, 596-8, 600 passim. each herein incorporated by reference in its entirety). A feature can be printed or deposited at a specific location on the substrate (e.g., inkjet printing). In some embodiments, each feature can have a unique oligonucleotide that functions as a spatial barcode. In some embodiments, each feature can have capture probes for multiplexing (e.g., capturing multiple analytes or multiple types of analytes, e.g., proteins and nucleic acids). In some embodiments, a feature can be printed or deposited at the specific location using an electric field. A feature can contain a photo-crosslinkable polymer precursor and an oligonucleotide. In some embodiments, the photo-crosslinkable polymer precursor can be deposited into a patterned feature on the substrate (e.g., well).

A "photo-crosslinkable polymer precursor" refers to a compound that cross-links and/or polymerizes upon exposure to light. In some embodiments, one or more photoinitiators may also be included to induce and/or promote polymerization and/or cross-linking. See, e.g., Choi et al. *Biotechniques*. 2019 January; 66(1):40-53, which is incorporated herein by reference in its entirety.

Non-limiting examples of photo-crosslinkable polymer precursors include polyethylene (glycol) diacrylate (PEGDA), gelatin-methacryloyl (GelMA), and methacrylated hyaluronic acid (MeHA). In some embodiments, a photo-crosslinkable polymer precursor comprises polyethylene (glycol) diacrylate (PEGDA), gelatin-methacryloyl (GelMA), methacrylated hyaluronic acid (MeHA), or a combination thereof. In some embodiments, a photo-crosslinkable polymer precursor (e.g., PAZAM) can be covalently linked (e.g., cross-linked) to a substrate. In some embodiments, a photo-crosslinkable polymer precursor is not covalently linked to a substrate surface. For example, a silane-free acrylamide can be used (See U.S. Patent Application Publication No. 2011/0059865, herein incorporated by reference in its entirety). The photo-crosslinkable polymer precursor in a feature (e.g., droplet or bead) can be polymerized by any known method. The oligonucleotides can be polymerized in a cross-linked gel matrix (e.g., copolymerized or simultaneously polymerized). In some embodiments, the features containing the photo-crosslinkable polymer precursor deposited on the substrate surface can be exposed to UV light. The UV light can induce polymerization of the photo-crosslinkable polymer precursor and result in the features becoming a gel matrix (e.g., gel pads) on the substrate surface (e.g., array).

Polymerization methods for hydrogel subunits can be selected to form hydrogels with different properties (e.g., pore volume, swelling properties, biodegradability, conduction, transparency, and/or permeability of the hydrogel). For example, a hydrogel can include pores of sufficient volume to allow the passage of macromolecules, (e.g., nucleic acids, proteins, chromatin, metabolites, gRNA, antibodies, carbohydrates, peptides, metabolites, and/or small molecules) to/from the sample (e.g., tissue section). It is known that pore volume generally decreases with increasing concentration of hydrogel subunits and generally increases with an increasing ratio of hydrogel subunits to cross-linker. Therefore, a hydrogel composition can be prepared that includes a concentration of hydrogel subunits that allows the passage of such biological macromolecules.

In some embodiments, hydrogel formation on a substrate occurs before, contemporaneously with, or after features (e.g., beads) are attached to the substrate. For example, when a capture probe is attached (e.g., directly or indirectly) to a substrate, hydrogel formation can be performed on the substrate already containing the capture probes.

(d) Arrays

In many of the methods described herein, features (as described further below) are collectively positioned on a substrate. An "array" is a specific arrangement of a plurality of features that is either irregular or forms a regular pattern. Individual features in the array differ from one another based on their relative spatial locations. In general, at least two of the plurality of features in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given feature in the array. In some embodiments, a given feature in the array includes two or more species of oligonucleotides (e.g., capture probes). In some embodiments, the two or more species of oligonucleotides (e.g., capture probes) attached directly or indirectly to a given feature on the array include a common (e.g., identical) spatial barcode.

(i) Arrays for Analyte Capture

In some embodiments, an array can include a capture probe attached directly or indirectly to the substrate. The capture probe can include a capture domain (e.g., a nucleotide sequence) that can specifically bind (e.g., hybridize) to a target analyte (e.g., mRNA, DNA, or protein) within a sample. In some embodiments, the binding of the capture probe to the target (e.g., hybridization) can be detected and quantified by detection of a visual signal, e.g., a fluorophore, a heavy metal (e.g., silver ion), or chemiluminescent label, which has been incorporated into the target. In some embodiments, the intensity of the visual signal correlates with the relative abundance of each analyte in the biological sample. Since an array can contain thousands or millions of capture probes (or more), an array can interrogate many analytes in parallel.

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or feature using a variety of techniques. In some embodiments, the capture probe is directly attached to a feature that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g., a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, the capture probe is a nucleic acid. In some embodiments, the capture probe is immobilized on a substrate or feature via its 5' end. In some embodiments, the capture probe is immobilized on a substrate or feature via its 5' end and includes from the 5' to 3' end: one or more barcodes (e.g., a spatial barcode and/or a UMI) and one or more capture domains. In some embodiments, the capture probe is immobilized on a substrate or feature via its 5' end and includes from the 5' to 3' end: one barcode (e.g., a spatial barcode or a UMI) and one capture domain. In some embodiments, the capture probe is immobilized on a substrate or feature via its 5' end and includes from the 5' to 3' end: a cleavage domain, a functional domain, one or more barcodes (e.g., a spatial barcode and/or a UMI), and a capture domain.

In some embodiments, the capture probe is immobilized on a substrate or feature via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a substrate or feature via its 5' end and includes from the 5' to 3' end: a cleavage domain, a functional domain, a spatial barcode, a UMI, and a capture domain. In some embodiments, the capture probe is immobilized on a substrate or feature via its 5' end and does not include a spatial barcode. In some embodiments, the capture probe is immobilized on a substrate or feature via its 5' end and does not include a UMI. In some embodiments, the capture probe includes a sequence for initiating a sequencing reaction.

In some embodiments, the capture probe is immobilized on a substrate or feature via its 3' end. In some embodiments, the capture probe is immobilized on a substrate or feature via its 3' end and includes from the 3' to 5' end: one or more barcodes (e.g., a spatial barcode and/or a UMI) and one or more capture domains. In some embodiments, the capture probe is immobilized on a substrate or feature via its 3' end and includes from the 3' to 5' end: one barcode (e.g., a spatial barcode or a UMI) and one capture domain. In some embodiments, the capture probe is immobilized on a substrate or feature via its 3' end and includes from the 3' to 5' end: a cleavage domain, a functional domain, one or more barcodes (e.g., a spatial barcode and/or a UMI), and a capture domain. In some embodiments, the capture probe is immobilized on a substrate or feature via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g., the functional group can be placed at the 5' or 3' end of the capture probe or within the sequence of the capture probe. In some embodiments, a capture probe can further include a substrate. A typical substrate for a capture probe to be immobilized includes moieties which are capable of binding to such capture probes, e.g., to amine-functionalized nucleic acids. Examples of such substrates are carboxy, aldehyde, or epoxy substrates.

In some embodiments, the substrates on which capture probes can be immobilized can be chemically activated, e.g., by the activation of functional groups available on the substrate. The term "activated substrate" relates to a material in which interacting or reactive chemical functional groups are established or enabled by chemical modification procedures. For example, a substrate including carboxyl groups can be activated before use. Furthermore, certain substrates contain functional groups that can react with specific moieties already present in the capture probes.

In some embodiments, a covalent linkage is used to directly couple a capture probe to a substrate. In some embodiments a capture probe is indirectly coupled to a substrate through a linker separating the "first" nucleotide of the capture probe from the substrate, e.g., a chemical linker. In some embodiments, a capture probe does not bind directly to the substrate, but interacts indirectly, for example by binding to a molecule which itself binds directly or indirectly to the substrate. In some embodiments, the capture probe is indirectly attached to a substrate (e.g., attached to a substrate via a solution including a polymer).

In some embodiments where the capture probe is immobilized on a feature of the array indirectly, e.g., via hybridization to a surface probe capable of binding the capture probe, the capture probe can further include an upstream sequence (5' to the sequence that hybridizes to the nucleic acid, e.g., RNA of the tissue sample) that is capable of hybridizing to 5' end of a surface probe. Alone, the capture domain of the capture probe can be seen as a capture domain oligonucleotide, which can be used in the synthesis of the capture probe in embodiments where the capture probe is immobilized on the array indirectly.

In some embodiments, a substrate is comprised of an inert material or matrix (e.g., glass slides) that has been functionalized by, for example, treating the substrate with a material comprising reactive groups which enable immobilization of capture probes. See, for example, WO 2017/019456, the entire contents of which is herein incorporated by reference. Non-limiting examples include polyacrylamide hydrogels supported on an inert substrate (e.g., glass slide; see WO 2005/065814 and U.S. Patent Application No. 2008/0280773, the entire contents of which is incorporated herein by reference).

In some embodiments, functionalized biomolecules (e.g., capture probes) are immobilized on a functionalized substrate using covalent methods. Methods for covalent attachment include, for example, condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. Methods for covalent attachment also include, for example, click chemistry reactions, including [3+2] cycloaddition reactions (e.g., Huisgen 1,3-dipolar cycloaddition reaction and copper(I)-catalyzed azide-alkyne cycloaddition (CuAAC)); thiol-ene reactions; the Diels-Alder reaction and inverse electron demand Diels-Alder reaction; [4+1] cycloaddition of isonitriles and tetrazines; and nucleophilic ring-opening of small carbocycles (e.g., epoxide opening with amino oligonucleotides). Methods for covalent attachment also include, for example, maleimides and thiols; and para-nitrophenyl ester—functionalized oligonucleotides and polylysine-functionalized substrate. Methods for covalent attachment also include, for example, disulfide reactions; radical reactions (see, e.g., U.S. Pat. No. 5,919,626, the entire contents of which are herein incorporated by reference); and hydrazide-functionalized substrate (e.g., wherein the hydrazide functional group is directly or indirectly attached to the substrate) and aldehyde-functionalized oligonucleotides (see, e.g., Yershov et al. (1996) *Proc. Natl. Acad. Sci. USA* 93, 4913-4918, the entire contents of which are herein incorporated by reference).

In some embodiments, functionalized biomolecules (e.g., capture probes) are immobilized on a functionalized substrate using photochemical covalent methods. Methods for photochemical covalent attachment include, for example, immobilization of antraquinone-conjugated oligonucleotides (see, e.g., Koch et al. (2000) *Bioconjugate Chem.* 11, 474-483, the entire contents of which is herein incorporated by reference).

In some embodiments, functionalized biomolecules (e.g., capture probes) are immobilized on a functionalized substrate using non-covalent methods. Methods for non-covalent attachment include, for example, biotin-functionalized oligonucleotides and streptavidin-treated substrates (see, e.g., Holmstrom et al. (1993) *Analytical Biochemistry* 209, 278-283 and Gilles et al. (1999) *Nature Biotechnology* 17, 365-370, the entire contents of which are herein incorporated by reference).

In some embodiments, an oligonucleotide (e.g., a capture probe) can be attached to a substrate or feature according to the methods set forth in U.S. Pat. Nos. 6,737,236, 7,259,258, 7,375,234, 7,427,678, 5,610,287, 5,807,522, 5,837,860, and 5,472,881; U.S. Patent Application Publication Nos. 2008/0280773 and 2011/0059865; Shalon et al. (1996) *Genome Research*, 639-645; Rogers et al. (1999) *Analytical Biochemistry* 266, 23-30; Stimpson et al. (1995) *Proc. Natl. Acad. Sci. USA* 92, 6379-6383; Beattie et al. (1995) *Clin. Chem.* 45, 700-706; Lamture et al. (1994) *Nucleic Acids Research* 22, 2121-2125; Beier et al. (1999) *Nucleic Acids Research* 27, 1970-1977; Joos et al. (1997) *Analytical Biochemistry* 247, 96-101; Nikiforov et al. (1995) *Analytical Biochemistry* 227, 201-209; Timofeev et al. (1996) *Nucleic Acids Research* 24, 3142-3148; Chrisey et al. (1996) *Nucleic Acids Research* 24, 3031-3039; Guo et al. (1994) *Nucleic Acids Research* 22, 5456-5465; Running and Urdea (1990) *BioTechniques* 8, 276-279; Fahy et al. (1993) *Nucleic Acids Research* 21, 1819-1826; Zhang et al. (1991) 19, 3929-3933; and Rogers et al. (1997) *Gene Therapy* 4, 1387-1392. The entire contents of each of the foregoing documents is incorporated herein by reference.

(ii) Generation of Capture Probes in an Array Format

Arrays can be prepared by a variety of methods. In some embodiments, arrays are prepared through the synthesis (e.g., in situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., "Basic concepts of microarrays and potential applications in clinical microbiology." *Clinical Microbiology Reviews* 22.4 (2009): 611-633; US201314111482A; U.S. Pat. No. 9,593,365B2; US2019203275; and WO2018091676, which are each incorporated herein by reference in its entirety.

(1) Spotting or Printing

In some embodiments, oligonucleotides (e.g., capture probes) can be "spotted" or "printed" onto a substrate to form an array. The oligonucleotides can be applied by either noncontact or contact printing. A noncontact printer can use the same method as computer printers (e.g., bubble jet or inkjet) to expel small droplets of probe solution onto the substrate. The specialized inkjet-like printer can expel nanoliter to picoliter volume droplets of oligonucleotide solution, instead of ink, onto the substrate. In contact printing, each print pin directly applies the oligonucleotide solution onto a specific location on the surface. The oligonucleotides can be attached to the substrate surface by the electrostatic interaction of the negative charge of the phosphate backbone of the DNA with a positively charged coating of the substrate surface or by UV-cross-linked covalent bonds between the thymidine bases in the DNA and amine groups on the treated substrate surface. In some embodiments, the substrate is a glass slide. In some embodiments, the oligonucleotides (e.g., capture probes) are attached to a substrate by a covalent bond to a chemical matrix, e.g., epoxy-silane, amino-silane, lysine, polyacrylamide, etc.

(2) In Situ Synthesis

Capture probes arrays can be prepared by in situ synthesis. In some embodiments, capture probe arrays can be prepared using photolithography. Photolithography typically relies on UV masking and light-directed combinatorial chemical synthesis on a substrate to selectively synthesize probes directly on the surface of an array, one nucleotide at a time per spot, for many spots simultaneously. In some embodiments, a substrate contains covalent linker molecules that have a protecting group on the free end that can be removed by light. UV light is directed through a photolithographic mask to deprotect and activate selected sites with hydroxyl groups that initiate coupling with incoming protected nucleotides that attach to the activated sites. The mask is designed in such a way that the exposure sites can be selected, and thus specify the coordinates on the array where each nucleotide can be attached. The process can be repeated, a new mask is applied activating different sets of sites and coupling different bases, allowing different oligonucleotides to be constructed at each site. This process can be used to synthesize hundreds of thousands of different oligonucleotides. In some embodiments, maskless array synthesizer technology can be used. Programmable micromirrors can create digital masks that reflect the desired pattern of UV light to deprotect the features.

In some embodiments, the inkjet spotting process can also be used for in situ oligonucleotide synthesis. The different nucleotide precursors plus catalyst can be printed on the substrate, and are then combined with coupling and deprotection steps. This method relies on printing picoliter volumes of nucleotides on the array surface in repeated rounds of base-by-base printing that extends the length of the oligonucleotide probes on the array.

(3) Electric Fields

Arrays can also be prepared by active hybridization via electric fields to control nucleic acid transport. Negatively charged nucleic acids can be transported to specific sites, or features, when a positive current is applied to one or more test sites on the array. The surface of the array can contain a binding molecule, e.g., streptavidin, which allows for the formation of bonds (e.g., streptavidin-biotin bonds) once electrically addressed biotinylated probes reach their targeted location. The positive current is then removed from the active features, and new test sites can be activated by the targeted application of a positive current. The process are repeated until all sites on the array are covered.

(4) Ligation

In some embodiments, an array comprising barcoded probes can be generated through ligation of a plurality of oligonucleotides. In some instances, an oligonucleotide of the plurality contains a portion of a barcode, and the complete barcode is generated upon ligation of the plurality of oligonucleotides. For example, a first oligonucleotide containing a first portion of a barcode can be attached to a substrate (e.g., using any of the methods of attaching an oligonucleotide to a substrate described herein), and a second oligonucleotide containing a second portion of the barcode can then be ligated onto the first oligonucleotide to generate a complete barcode. Different combinations of the first, second and any additional portions of a barcode can be used to increase the diversity of the barcodes. In instances where the second oligonucleotide is also attached to the substrate prior to ligation, the first and/or the second oligonucleotide can be attached to the substrate via a surface linker which contains a cleavage site. Upon ligation, the ligated oligonucleotide can be linearized by cleaving at the cleavage site.

To increase the diversity of the barcodes, a plurality of second oligonucleotides comprising two or more different barcode sequences can be ligated onto a plurality of first oligonucleotides that comprise the same barcode sequence, thereby generating two or more different species of barcodes. To achieve selective ligation, a first oligonucleotide attached to a substrate containing a first portion of a barcode can initially be protected with a protective group (e.g., a photocleavable protective group), and the protective group can be removed prior to ligation between the first and second oligonucleotide. In instances where the barcoded probes on an array are generated through ligation of two or more oligonucleotides, a concentration gradient of the oligonucleotides can be applied to a substrate such that different combinations of the oligonucleotides are incorporated into a barcoded probe depending on its location on the substrate.

Probes can be generated by directly ligating additional oligonucleotides onto existing oligonucleotides via a splint oligonucleotide. In some embodiments, oligonucleotides on an existing array can include a recognition sequence that can hybridize with a splint oligonucleotide. The recognition sequence can be at the free 5' end or the free 3' end of an oligonucleotide on the existing array. Recognition sequences useful for the methods of the present disclosure may not contain restriction enzyme recognition sites or secondary structures (e.g., hairpins), and may include high contents of Guanine and Cytosine nucleotides.

(5) Polymerases

Barcoded probes on an array can also be generated by adding single nucleotides to existing oligonucleotides on an array, for example, using polymerases that function in a template-independent manner. Single nucleotides can be added to existing oligonucleotides in a concentration gradient, thereby generating probes with varying length, depending on the location of the probes on the array.

(6) Modification of Existing Capture Probes

Arrays can also be prepared by modifying existing arrays, for example, by modifying oligonucleotides already attached to an arrays. For instance, capture probes can be generated on an array that already comprises oligonucleotides that are attached to the array (or features on the array) at the 3' end and have a free 5' end. In some instances, an array is any commercially available array (e.g., any of the arrays available commercially as described herein). The oligonucleotides can be in situ synthesized using any of the in situ synthesis methods described herein. The oligonucleotide can include a barcode and one or more constant sequences. In some instances, the constant sequences are cleavable sequences. The length of the oligonucleotides attached to the substrate (e.g., array) can be less than 100 nucleotides (e.g., less than 90, 80, 75, 70, 60, 50, 45, 40, 35, 30, 25, 20, 15, or 10 nucleotides). To generate probes using oligonucleotides, a primer complementary to a portion of an oligonucleotide (e.g., a constant sequence shared by the oligonucleotides) can hybridize to the oligonucleotide and extend the oligonucleotide (using the oligonucleotide as a template) to form a duplex and to create a 3' overhang. The 3' overhang can be created by template-independent ligases (e.g., terminal deoxynucleotidyl transferase (TdT) or poly (A) polymerase). The 3' overhang allows additional nucleotides or oligonucleotides to be added to the duplex, for example, by an enzyme. For instance, a capture probe can be generated by adding additional oligonucleotides to the end of the 3' overhang (e.g., via splint oligonucleotide mediated ligation), where the additional oligonucleotides can include a sequence or a portion of sequence of one or more capture domains, or a complement thereof.

The additional oligonucleotide (e.g., a sequence or a portion of sequence of a capture domain) can include a degenerate sequence (e.g., any of the degenerate sequences as described herein). The additional oligonucleotide (e.g., a sequence or a portion of sequence of a capture domain) can include a sequence compatible for hybridizing or ligating with an analyte of interest in a biological sample. An analyte of interest can also be used as a splint oligonucleotide to ligate additional oligonucleotides onto a probe. When using a splint oligonucleotide to assist in the ligation of additional oligonucleotides, an additional oligonucleotide can include a sequence that is complementary to the sequence of the splint oligonucleotide. Ligation of the oligonucleotides can involve the use of an enzyme, such as, but not limited to, a ligase. Non-limiting examples of suitable ligases include Tth DNA ligase, Taq DNA ligase, *Thermococcus* sp. (strain 9oN) DNA ligase (9oN™ DNA ligase, New England Biolabs), Ampligase™ (available from Epicentre Biotechnologies, Madison, Wis.), and SplintR (available from New England Biolabs, Ipswich, Mass.). An array generated as described above is useful for spatial analysis of a biological sample. For example, the one or more capture domains can be used to hybridize with the poly(A) tail of an mRNA molecule. Reverse transcription can be carried out using a reverse transcriptase to generate cDNA complementary to the captured mRNA. The sequence and location of the captured mRNA can then be determined (e.g., by sequencing the capture probe that contains the barcode as well as the complementary cDNA).

An array for spatial analysis can be generated by various methods as described herein. In some embodiments, the array has a plurality of capture probes comprising spatial barcodes. These spatial barcodes and their relationship to the locations on the array can be determined. In some cases, such information is readily available, because the oligonucleotides are spotted, printed, or synthesized on the array with a pre-determined pattern. In some cases, the spatial barcode can be decoded by methods described herein, e.g., by in situ sequencing, by various labels associated with the spatial barcodes etc. In some embodiments, an array can be used as a template to generate a daughter array. Thus, the spatial barcode can be transferred to the daughter array with a known pattern.

(iii) Features

A "feature" is an entity that acts as a support or repository for various molecular entities used in sample analysis. In some embodiments, some or all of the features in an array are functionalized for analyte capture. In some embodiments, functionalized features include one or more capture probe(s). Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

In addition to those above, a wide variety of other features can be used to form the arrays described herein. For example, in some embodiments, features that are formed from polymers and/or biopolymers that are jet printed, screen printed, or electrostatically deposited on a substrate can be used to form arrays. Jet printing of biopolymers is described, for example, in PCT Patent Application Publication No. WO 2014/085725. Jet printing of polymers is described, for example, in de Gans et al., *Adv Mater.* 16(3): 203-213 (2004). Methods for electrostatic deposition of polymers and biopolymers are described, for example, in Hoyer et al., *Anal. Chem.* 68(21): 3840-3844 (1996). The entire contents of each of the foregoing references are incorporated herein by reference.

As another example, in some embodiments, features are formed by metallic micro- or nanoparticles. Suitable methods for depositing such particles to form arrays are described, for example, in Lee et al., *Beilstein J. Nanotechnol.* 8: 1049-1055 (2017), the entire contents of which are incorporated herein by reference.

As a further example, in some embodiments, features are formed by magnetic particles that are assembled on a substrate. Examples of such particles and methods for assembling arrays are described in Ye et al., *Scientific Reports* 6: 23145 (2016), the entire contents of which are incorporated herein by reference.

As another example, in some embodiments, features correspond to regions of a substrate in which one or more optical labels have been incorporated, and/or which have been altered by a process such as permanent photobleaching. Suitable substrates to implement features in this manner include a wide variety of polymers, for example. Methods for forming such features are described, for example, in Moshrefzadeh et al., *Appl. Phys. Lett.* 62: 16 (1993), the entire contents of which are incorporated herein by reference.

As yet another example, in some embodiments, features can correspond to colloidal particles assembled (e.g., via self-assembly) to form an array. Suitable colloidal particles are described for example in Sharma, *Resonance* 23(3): 263-275 (2018), the entire contents of which are incorporated herein by reference.

As a further example, in some embodiments, features can be formed via spot-array photopolymerization of a monomer solution on a substrate. In particular, two-photon and three-photon polymerization can be used to fabricate features of relatively small (e.g., sub-micron) dimensions. Suitable methods for preparing features on a substrate in this manner are described for example in Nguyen et al., *Materials Today* 20(6): 314-322 (2017), the entire contents of which are incorporated herein by reference.

In some embodiments, features are directly or indirectly attached or fixed to a substrate that is liquid permeable. In some embodiments, features are directly or indirectly attached or fixed to a substrate that is biocompatible. In some embodiments, features are directly or indirectly attached or fixed to a substrate that is a hydrogel.

Figure 12:
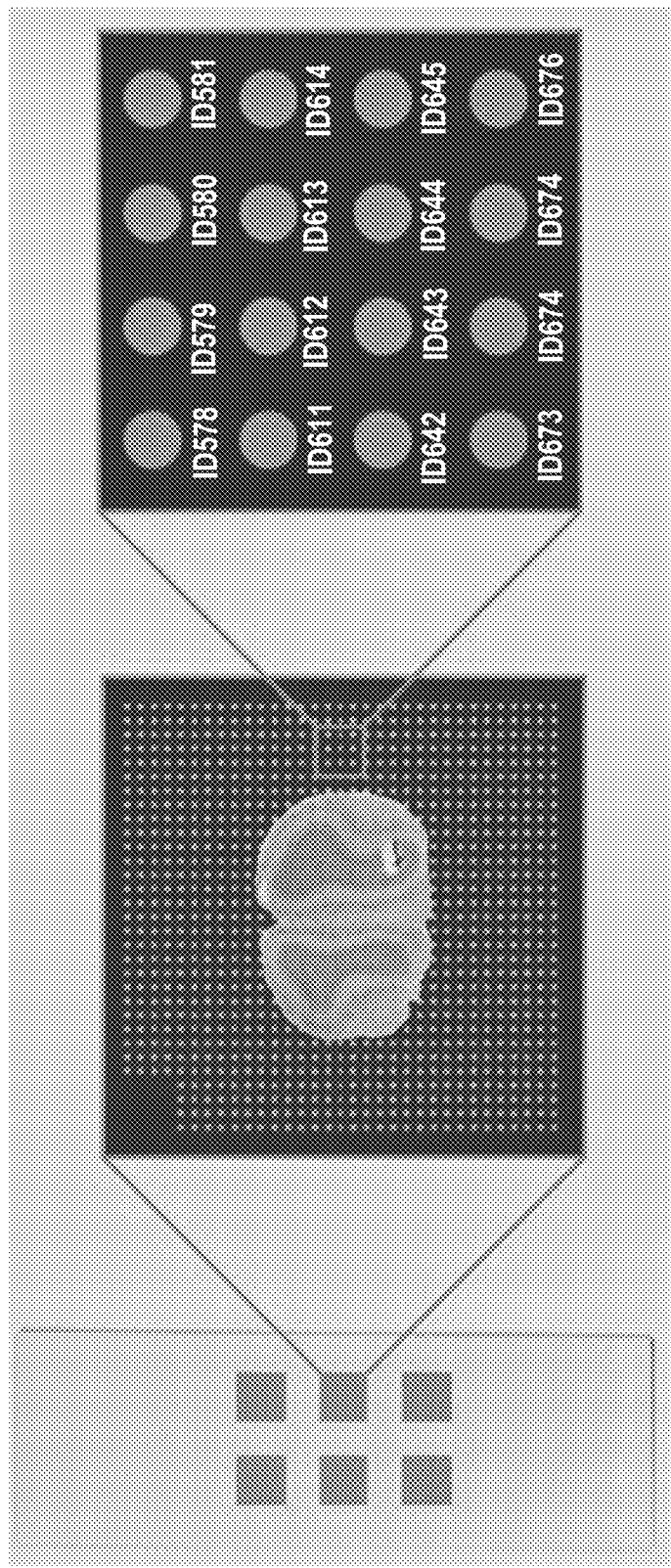
FIG. 12 is a schematic showing the arrangement of barcoded features within an array.

FIG. 12 depicts an exemplary arrangement of barcoded features within an array. From left to right, FIG. 12 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

(1) Beads

A "bead" can be a particle. A bead can be porous, non-porous, solid, semi-solid, and/or a combination thereof. In some embodiments, a bead can be dissolvable, disruptable, and/or degradable, whereas in certain embodiments, a bead is not degradable. A semi-solid bead can be a liposomal bead. Solid beads can include metals including, without limitation, iron oxide, gold, and silver. In some embodiments, the bead can be a silica bead. In some embodiments, the bead can be rigid. In some embodiments, the bead can be flexible and/or compressible.

The bead can be a macromolecule. The bead can be formed of nucleic acid molecules bound together. The bead can be formed via covalent or non-covalent assembly of molecules (e.g., macromolecules), such as monomers or polymers. Polymers or monomers can be natural or synthetic. Polymers or monomers can be or include, for example, nucleic acid molecules (e.g., DNA or RNA).

A bead can be rigid, or flexible and/or compressible. A bead can include a coating including one or more polymers. Such a coating can be disruptable or dissolvable. In some embodiments, a bead includes a spectral or optical label (e.g., dye) attached directly or indirectly (e.g., through a linker) to the bead. For example, a bead can be prepared as a colored preparation (e.g., a bead exhibiting a distinct color within the visible spectrum) that can change color (e.g., colorimetric beads) upon application of a desired stimulus (e.g., heat and/or chemical reaction) to form differently colored beads (e.g., opaque and/or clear beads).

A bead can include natural and/or synthetic materials. For example, a bead can include a natural polymer, a synthetic polymer or both natural and synthetic polymers. Examples of natural polymers include, without limitation, proteins, sugars such as deoxyribonucleic acid, rubber, cellulose, starch (e.g., amylose, amylopectin), enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include, without limitation, acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., copolymers) thereof. Beads can also be formed from materials other than polymers, including for example, lipids, micelles, ceramics, glass-ceramics, material composites, metals, and/or other inorganic materials.

In some embodiments, a bead is a degradable bead. A degradable bead can include one or more species (e.g., disulfide linkers, primers, other oligonucleotides, etc.) with a labile bond such that, when the bead/species is exposed to the appropriate stimuli, the labile bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, upon exposure of a polyacrylamide gel bead including cystamine cross-linkers to a reducing agent, the disulfide bonds of the cystamine can be broken and the bead degraded.

Degradation can refer to the disassociation of a bound or entrained species (e.g., disulfide linkers, primers, other oligonucleotides, etc.) from a bead, both with and without structurally degrading the physical bead itself. For example, entrained species can be released from beads through osmotic pressure differences due to, for example, changing chemical environments. By way of example, alteration of bead pore volumes due to osmotic pressure differences can generally occur without structural degradation of the bead itself. In some embodiments, an increase in pore volume due to osmotic swelling of a bead can permit the release of entrained species within the bead. In some embodiments, osmotic shrinking of a bead can cause a bead to better retain an entrained species due to pore volume contraction.

Any suitable agent that can degrade beads can be used. In some embodiments, changes in temperature or pH can be used to degrade thermo-sensitive or pH-sensitive bonds within beads. In some embodiments, chemical degrading agents can be used to degrade chemical bonds within beads by oxidation, reduction or other chemical changes. For example, a chemical degrading agent can be a reducing agent, such as DTT, where DTT can degrade the disulfide bonds formed between a cross-linker and gel precursors, thus degrading the bead. In some embodiments, a reducing agent can be added to degrade the bead, which can cause the bead to release its contents. Examples of reducing agents can include, without limitation, dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof.

Any of a variety of chemical agents can be used to trigger the degradation of beads. Examples of chemical agents include, but are not limited to, pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as N,N'-bis-(acryloyl)cystamine (BAC) or cystamine. Degradation of such degradable cross-linkers can be accomplished through any variety of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof.

In some embodiments, exposure to an aqueous solution, such as water, can trigger hydrolytic degradation, and thus degradation of the bead. Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In some embodiments, heat can increase the internal pressure of the bead components such that the bead ruptures or explodes. Heat can also act upon heat-sensitive polymers used as materials to construct beads.

Where degradable beads are used, it can be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads include reducible cross-linking groups, such as disulfide groups, it will be desirable to avoid contacting such beads with reducing agents, e.g., DTT or other disulfide cleaving reagents. In such embodiments, treatment of the beads described herein will, in some embodiments be provided free of reducing agents, such as DTT. Because reducing agents are often provided in commercial enzyme preparations, it can be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that can be used to treat the beads described herein. The terms "reducing agent free" or "DTT free" preparations refer to a preparation having less than about 1/10th, less than about 1/50th, or less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or less than about 0.0001 mM DTT. In some embodiments, the amount of DTT can be undetectable.

A degradable bead can be useful to more quickly release an attached capture probe (e.g., a nucleic acid molecule, a spatial barcode sequence, and/or a primer) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a capture probe having one or more spatial barcodes can be attached, via a disulfide bond, to a polyacrylamide bead including cystamine. Upon exposure of the spatially-barcoded bead to a reducing agent, the bead degrades and the capture probe having the one or more spatial barcode sequences is released upon breakage of both the disulfide linkage between the capture probe and the bead and the disulfide linkages of the cystamine in the bead.

The addition of multiple types of labile bonds to a bead can result in the generation of a bead capable of responding to varied stimuli. Each type of labile bond can be sensitive to an associated stimulus (e.g., chemical stimulus, light, temperature, pH, enzymes, etc.) such that release of reagents attached to a bead via each labile bond can be controlled by the application of the appropriate stimulus. Some non-limiting examples of labile bonds that can be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond can be cleavable via other nucleic acid molecule targeting enzymes, such as restriction enzymes (e.g., restriction endonucleases). Such functionality can be useful in controlled release of reagents from a bead. In some embodiments, another reagent including a labile bond can be linked to a bead after gel bead formation via, for example, an activated functional group of the bead as described above. In some embodiments, a gel bead including a labile bond is reversible. In some embodiments, a gel bead with a reversible labile bond is used to capture one or more regions of interest of a biological sample. For example, without limitation, a bead including a thermolabile bond can be heated by a light source (e.g., a laser) that causes a change in the gel bead that facilitates capture of a biological sample in contact with the gel bead. Capture probes having one or more spatial barcodes that are releasably, cleavably, or reversibly attached to the beads described herein include capture probes that are released or releasable through cleavage of a linkage between the capture probe and the bead, or that are released through degradation of the underlying bead itself, allowing the capture probes having the one or more spatial barcodes to be accessed or become accessible by other reagents, or both.

Beads can have different physical properties. Physical properties of beads can be used to characterize the beads. Non-limiting examples of physical properties of beads that can differ include volume, shape, circularity, density, symmetry, and hardness. For example, beads can be of different volumes. Beads of different diameters can be obtained by using microfluidic channel networks configured to provide beads of a specific volume (e.g., based on channel sizes, flow rates, etc.). In some embodiments, beads have different hardness values that can be obtained by varying the concentration of polymer used to generate the beads. In some embodiments, a spatial barcode attached to a bead can be made optically detectable using a physical property of the capture probe. For example, a nucleic acid origami, such as a deoxyribonucleic acid (DNA) origami, can be used to generate an optically detectable spatial barcode. To do so, a nucleic acid molecule, or a plurality of nucleic acid molecules, can be folded to create two- and/or three-dimensional geometric shapes. The different geometric shapes can be optically detected.

In some embodiments, special types of nanoparticles with more than one distinct physical property can be used to make the beads physically distinguishable. For example, Janus particles with both hydrophilic and hydrophobic surfaces can be used to provide unique physical properties.

A bead can generally be of any suitable shape. Examples of bead shapes include, but are not limited to, spherical, non-spherical, oval, oblong, amorphous, circular, cylindrical, cuboidal, hexagonal, and variations thereof. In some embodiments, non-spherical (e.g., hexagonal, cuboidal, shaped beads can assemble more closely (e.g., tighter) than spherical shaped beads. In some embodiments, beads can self-assemble into a monolayer. A cross section (e.g., a first cross-section) can correspond to a diameter or maximum cross-sectional dimension of the bead. In some embodiments, the bead can be approximately spherical. In such embodiments, the first cross-section can correspond to the diameter of the bead. In some embodiments, the bead can be approximately cylindrical. In such embodiments, the first cross-section can correspond to a diameter, length, or width along the approximately cylindrical bead.

Beads can be of uniform size or heterogeneous size. "Polydispersity" generally refers to heterogeneity of sizes of molecules or particles. The polydispersity index (PDI) of a bead can be calculated using the equation PDI=Mw/Mn, where Mw is the weight-average molar mass and Mn is the number-average molar mass. In certain embodiments, beads can be provided as a population or plurality of beads having a relatively monodisperse size distribution. Where it can be desirable to provide relatively consistent amounts of reagents, maintaining relatively consistent bead characteristics, such as size, can contribute to the overall consistency.

In some embodiments, the beads provided herein can have size distributions that have a coefficient of variation in their cross-sectional dimensions of less than 50%, less than 40%, less than 30%, less than 20%, less than 15%, less than 10%, less than 5%, or lower. In some embodiments, a plurality of beads provided herein has a polydispersity index of less than 50%, less than 45%, less than 40%, less than 35%, less than 30%, less than 25%, less than 20%, less than 15%, less than 10%, less than 5%, or lower.

In some embodiments, the bead can have a diameter or maximum dimension no larger than 100 µm (e.g., no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm.)

In some embodiments, a plurality of beads has an average diameter no larger than 100 µm. In some embodiments, a plurality of beads has an average diameter or maximum dimension no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm.

In some embodiments, the volume of the bead can be at least about 1 µm$^3$, e.g., at least 1 µm$^3$, 2 µm$^3$, 3 µm$^3$, 4 µm$^3$, 5 µm$^3$, 6 µm$^3$, 7 µm$^3$, 8 µm$^3$, 9 µm$^3$, 10 µm$^3$, 12 µm$^3$, 14 µm$^3$, 16 µm$^3$, 18 µm$^3$, 20 µm$^3$, 25 µm$^3$, 30 µm$^3$, 35 µm$^3$, 40 µm$^3$, 45 µm$^3$, 50 µm$^3$, 55 µm$^3$, 60 µm$^3$, 65 µm$^3$, 70 µm$^3$, 75 µm$^3$, 80 µm³, 85 µm³, 90 µm³, 95 µm³, 100 µm³, 125 µm³, 150 µm³, 175 µm³, 200 µm³, 250 µm³, 300 µm³, 350 µm³, 400 µm³, 450 µm³, µm³, 500 µm³, 550 µm³, 600 µm³, 650 µm³, 700 µm³, 750 µm³, 800 µm³, 850 µm³, 900 µm³, 950 µm³, 1000 µm³, 1200 µm³, 1400 µm³, 1600 µm³, 1800 µm³, 2000 µm³, 2200 µm³, 2400 µm³, 2600 µm³, 2800 µm³, 3000 µm³, or greater.

In some embodiments, the bead can have a volume of between about 1 µm³ and 100 µm³, such as between about 1 µm³ and 10 µm³, between about 10 µm³ and 50 µm³, or between about 50 µm³ and 100 µm³. In some embodiments, the bead can include a volume of between about 100 µm³ and 1000 µm³, such as between about 100 µm³ and 500 µm³ or between about 500 µm³ and 1000 µm³. In some embodiments, the bead can include a volume between about 1000 µm³ and 3000 µm³, such as between about 1000 µm³ and 2000 µm³ or between about 2000 µm³ and 3000 µm³. In some embodiments, the bead can include a volume between about 1 µm³ and 3000 µm³, such as between about 1 µm³ and 2000 µm³, between about 1 µm³ and 1000 µm³, between about 1 µm³ and 500 µm³, or between about 1 µm³ and 250 µm³.

The bead can include one or more cross-sections that can be the same or different. In some embodiments, the bead can have a first cross-section that is different from a second cross-section. The bead can have a first cross-section that is at least about 0.0001 micrometer, 0.001 micrometer, 0.01 micrometer, 0.1 micrometer, or 1 micrometer. In some embodiments, the bead can include a cross-section (e.g., a first cross-section) of at least about 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 millimeter (mm), or greater. In some embodiments, the bead can include a cross-section (e.g., a first cross-section) of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, the bead can include a cross-section (e.g., a first cross-section) of between about 1 µm and 100 µm. In some embodiments, the bead can have a second cross-section that is at least about 1 µm. For example, the bead can include a second cross-section of at least about 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 millimeter (mm), or greater. In some embodiments, the bead can include a second cross-section of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, the bead can include a second cross-section of between about 1 µm and 100 µm.

In some embodiments, beads can be of a nanometer scale (e.g., beads can have a diameter or maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). A plurality of beads can have an average diameter or average maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). In some embodiments, a bead has a diameter or volume that is about the diameter of a single cell (e.g., a single cell under evaluation).

In some embodiments, a bead is able to identify multiple analytes (e.g., nucleic acids, proteins, chromatin, metabolites, drugs, gRNA, and lipids) from a single cell. In some embodiments, a bead is able to identify a single analyte from a single cell (e.g., mRNA).

A bead can have a tunable pore volume. The pore volume can be chosen to, for instance, retain denatured nucleic acids. The pore volume can be chosen to maintain diffusive permeability to exogenous chemicals such as sodium hydroxide (NaOH) and/or endogenous chemicals such as inhibitors. A bead can be formed of a biocompatible and/or biochemically compatible material, and/or a material that maintains or enhances cell viability. A bead can be formed from a material that can be depolymerized thermally, chemically, enzymatically, and/or optically.

In some embodiments, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. Swelling of the beads can be accomplished, for instance, by placing the beads in a thermodynamically favorable solvent, subjecting the beads to a higher or lower temperature, subjecting the beads to a higher or lower ion concentration, and/or subjecting the beads to an electric field.

The swelling of the beads can be accomplished by various swelling methods. In some embodiments, swelling is reversible (e.g., by subjecting beads to conditions that promote de-swelling). In some embodiments, the de-swelling of the beads is accomplished, for instance, by transferring the beads in a thermodynamically unfavorable solvent, subjecting the beads to lower or higher temperatures, subjecting the beads to a lower or higher ion concentration, and/or adding or removing an electric field. The de-swelling of the beads can be accomplished by various de-swelling methods. In some embodiments, de-swelling is reversible (e.g., subject beads to conditions that promote swelling). In some embodiments, the de-swelling of beads can include transferring the beads to cause pores in the bead to shrink. The shrinking can then hinder reagents within the beads from diffusing out of the interiors of the beads. The hindrance created can be due to steric interactions between the reagents and the interiors of the beads. The transfer can be accomplished microfluidically. For instance, the transfer can be achieved by moving the beads from one co-flowing solvent stream to a different co-flowing solvent stream. The swellability and/or pore volume of the beads can be adjusted by changing the polymer composition of the bead.

A bead can include a polymer that is responsive to temperature so that when the bead is heated or cooled, the characteristics or dimensions of the bead can change. For example, a polymer can include poly(N-isopropylacrylamide). A gel bead can include poly(N-isopropylacrylamide) and when heated the gel bead can decrease in one or more dimensions (e.g., a cross-sectional diameter, multiple cross-sectional diameters). A temperature sufficient for changing one or more characteristics of the gel bead can be, for example, at least about 0 degrees Celsius (° C.), 1° C., 2° C., 3° C., 4° C., 5° C., 10° C., or higher. For example, the temperature can be about 4° C. In some embodiments, a temperature sufficient for changing one or more characteristics of the gel bead can be, for example, at least about 25° C., 30° C., 35° C., 37° C., 40° C., 45° C., 50° C., or higher. For example, the temperature can be about 37° C.

Functionalization of beads for attachment of capture probes can be achieved through a wide range of different approaches, including, without limitation, activation of chemical groups within a polymer, incorporation of active or activatable functional groups in the polymer structure, or attachment at the pre-polymer or monomer stage in bead production. The bead can be functionalized to bind to targeted analytes, such as nucleic acids, proteins, carbohydrates, lipids, metabolites, peptides, or other analytes.

In some embodiments, a bead can contain molecular precursors (e.g., monomers or polymers), which can form a polymer network via polymerization of the molecular precursors. In some embodiments, a precursor can be an already polymerized species capable of undergoing further polymerization via, for example, a chemical cross-linkage. In some embodiments, a precursor can include one or more of an acrylamide or a methacrylamide monomer, oligomer, or polymer. In some embodiments, the bead can include pre-polymers, which are oligomers capable of further polymerization. For example, polyurethane beads can be prepared using prepolymers. In some embodiments, a bead can contain individual polymers that can be further polymerized together (e.g., to form a co-polymer). In some embodiments, a bead can be generated via polymerization of different precursors, such that they include mixed polymers, co-polymers, and/or block co-polymers. In some embodiments, a bead can include covalent or ionic bonds between polymeric precursors (e.g., monomers, oligomers, and linear polymers), nucleic acid molecules (e.g., oligonucleotides), primers, and other entities. In some embodiments, covalent bonds can be carbon-carbon bonds or thioether bonds.

Cross-linking of polymers can be permanent or reversible, depending upon the particular cross-linker used. Reversible cross-linking can allow the polymer to linearize or dissociate under appropriate conditions. In some embodiments, reversible cross-linking can also allow for reversible attachment of a material bound to the surface of a bead. In some embodiments, a cross-linker can form a disulfide linkage. In some embodiments, a chemical cross-linker forming a disulfide linkage can be cystamine or a modified cystamine.

For example, where the polymer precursor material includes a linear polymer material, such as a linear polyacrylamide, PEG, or other linear polymeric material, the activation agent can include a cross-linking agent, or a chemical that activates a cross-linking agent within formed droplets. Likewise, for polymer precursors that include polymerizable monomers, the activation agent can include a polymerization initiator. For example, in certain embodiments, where the polymer precursor includes a mixture of acrylamide monomer with a N,N'-bis-(acryloyl)cystamine (BAC) comonomer, an agent such as tetraethylmethylenediamine (TEMED) can be provided, which can initiate the copolymerization of the acrylamide and BAC into a cross-linked polymer network, or other conditions sufficient to polymerize or gel the precursors. The conditions sufficient to polymerize or gel the precursors can include exposure to heating, cooling, electromagnetic radiation, and/or light.

Following polymerization or gelling, a polymer or gel can be formed. The polymer or gel can be diffusively permeable to chemical or biochemical reagents. The polymer or gel can be diffusively impermeable to macromolecular constituents. The polymer or gel can include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel can include any other polymer or gel.

In some embodiments, disulfide linkages can be formed between molecular precursor units (e.g., monomers, oligomers, or linear polymers) or precursors incorporated into a bead and nucleic acid molecules (e.g., oligonucleotides, capture probes). Cystamine (including modified cystamines), for example, is an organic agent including a disulfide bond that can be used as a cross-linker agent between individual monomeric or polymeric precursors of a bead. Polyacrylamide can be polymerized in the presence of cystamine or a species including cystamine (e.g., a modified cystamine) to generate polyacrylamide gel beads including disulfide linkages (e.g., chemically degradable beads including chemically-reducible cross-linkers). The disulfide linkages can permit the bead to be degraded (or dissolved) upon exposure of the bead to a reducing agent.

In some embodiments, chitosan, a linear polysaccharide polymer, can be cross-linked with glutaraldehyde via hydrophilic chains to form a bead. Crosslinking of chitosan polymers can be achieved by chemical reactions that are initiated by heat, pressure, change in pH, and/or radiation.

In some embodiments, a bead can include an acrydite moiety, which in certain aspects can be used to attach one or more capture probes to the bead. In some embodiments, an acrydite moiety can refer to an acrydite analogue generated from the reaction of acrydite with one or more species (e.g., disulfide linkers, primers, other oligonucleotides, etc.), such as, without limitation, the reaction of acrydite with other monomers and cross-linkers during a polymerization reaction. Acrydite moieties can be modified to form chemical bonds with a species to be attached, such as a capture probe. Acrydite moieties can be modified with thiol groups capable of forming a disulfide bond or can be modified with groups already including a disulfide bond. The thiol or disulfide (via disulfide exchange) can be used as an anchor point for a species to be attached or another part of the acrydite moiety can be used for attachment. In some embodiments, attachment can be reversible, such that when the disulfide bond is broken (e.g., in the presence of a reducing agent), the attached species is released from the bead. In some embodiments, an acrydite moiety can include a reactive hydroxyl group that can be used for attachment of species.

In some embodiments, precursors (e.g., monomers or cross-linkers) that are polymerized to form a bead can include acrydite moieties, such that when a bead is generated, the bead also includes acrydite moieties. The acrydite moieties can be attached to a nucleic acid molecule (e.g., an oligonucleotide), which can include a priming sequence (e.g., a primer for amplifying target nucleic acids, random primer, primer sequence for messenger RNA) and/or one or more capture probes. The one or more capture probes can include sequences that are the same for all capture probes coupled to a given bead and/or sequences that are different across all capture probes coupled to the given bead. The capture probe can be incorporated into the bead. In some embodiments, the capture probe can be incorporated or attached to the bead such that the capture probe retains a free 3' end. In some embodiments, the capture probe can be incorporated or attached to the bead such that the capture probe retains a free 5' end. In some embodiments, beads can be functionalized such that each bead contains a plurality of different capture probes. For example, a bead can include a plurality of capture probes e.g., Capture Probe 1, Capture Probe 2, and Capture Probe 3, and each of Capture Probes 1, Capture Probes 2, and Capture Probes 3 contain a distinct capture domain (e.g., capture domain of Capture Probe 1 includes a poly(dT) capture domain, capture domain of Capture Probe 2 includes a gene-specific capture domain, and capture domain of Capture Probe 3 includes a CRISPR-specific capture domain). By functionalizing beads to contain a plurality of different capture domains per bead, the level of multiplex capability for analyte detection can be improved.

In some embodiments, precursors (e.g., monomers or cross-linkers) that are polymerized to form a bead can include a functional group that is reactive or capable of being activated such that when it becomes reactive it can be polymerized with other precursors to generate beads including the activated or activatable functional group. The functional group can then be used to attach additional species (e.g., disulfide linkers, primers, other oligonucleotides, etc.) to the beads. For example, some precursors including a carboxylic acid (COOH) group can co-polymerize with other precursors to form a bead that also includes a COOH functional group. In some embodiments, acrylic acid (a species including free COOH groups), acrylamide, and bis(acryloyl)cystamine can be co-polymerized together to generate a bead including free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC NHS or DMTMM are used for activation). The activated COOH groups can then react with an appropriate species (e.g., a species including an amine functional group where the carboxylic acid groups are activated to be reactive with an amine functional group) as a functional group on a moiety to be linked to the bead.

Beads including disulfide linkages in their polymeric network can be functionalized with additional species (e.g., disulfide linkers, primers, other oligonucleotides, etc.) via reduction of some of the disulfide linkages to free thiols. The disulfide linkages can be reduced via, for example, the action of a reducing agent (e.g., DTT, TCEP, etc.) to generate free thiol groups, without dissolution of the bead. Free thiols of the beads can then react with free thiols of a species or a species including another disulfide bond (e.g., via thiol-disulfide exchange) such that the species can be linked to the beads (e.g., via a generated disulfide bond). In some embodiments, free thiols of the beads can react with any other suitable group. For example, free thiols of the beads can react with species including an acrydite moiety. The free thiol groups of the beads can react with the acrydite via Michael addition chemistry, such that the species including the acrydite is linked to the bead. In some embodiments, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control can be exerted, for example, by controlling the concentration of a reducing agent used to generate free thiol groups and/or concentration of reagents used to form disulfide bonds in bead polymerization. In some embodiments, a low concentration of reducing agent (e.g., molecules of reducing agent:gel bead ratios) of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, or less than or equal to about 1:10,000) can be used for reduction. Controlling the number of disulfide linkages that are reduced to free thiols can be useful in ensuring bead structural integrity during functionalization. In some embodiments, optically-active agents, such as fluorescent dyes can be coupled to beads via free thiol groups of the beads and used to quantify the number of free thiols present in a bead and/or track a bead.

In some embodiments, addition of moieties to a bead after bead formation can be advantageous. For example, addition of a capture probe after bead formation can avoid loss of the species (e.g., disulfide linkers, primers, other oligonucleotides, etc.) during chain transfer termination that can occur during polymerization. In some embodiments, smaller precursors (e.g., monomers or cross linkers that do not include side chain groups and linked moieties) can be used for polymerization and can be minimally hindered from growing chain ends due to viscous effects. In some embodiments, functionalization after bead synthesis can minimize exposure of species (e.g., oligonucleotides) to be loaded with potentially damaging agents (e.g., free radicals) and/or chemical environments. In some embodiments, the generated hydrogel can possess an upper critical solution temperature (UCST) that can permit temperature driven swelling and collapse of a bead. Such functionality can aid in oligonucleotide (e.g., a primer) infiltration into the bead during subsequent functionalization of the bead with the oligonucleotide. Post-production functionalization can also be useful in controlling loading ratios of species in beads, such that, for example, the variability in loading ratio is minimized. Species loading can also be performed in a batch process such that a plurality of beads can be functionalized with the species in a single batch.

Reagents can be encapsulated in beads during bead generation (e.g., during polymerization of precursors). Such reagents can or cannot participate in polymerization. Such reagents can be entered into polymerization reaction mixtures such that generated beads include the reagents upon bead formation. In some embodiments, such reagents can be added to the beads after formation. Such reagents can include, for example, capture probes (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, chemical substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such reagents can include one or more enzymes described herein, including without limitation, polymerase, reverse transcriptase, restriction enzymes (e.g., endonuclease), transposase, ligase, proteinase K, DNAse, etc. Such reagents can also or alternatively include one or more reagents such as lysis agents, inhibitors, inactivating agents, chelating agents, stimulus agents. Trapping of such reagents can be controlled by the polymer network density generated during polymerization of precursors, control of ionic charge within the bead (e.g., via ionic species linked to polymerized species), or by the release of other species. Encapsulated reagents can be released from a bead upon bead degradation and/or by application of a stimulus capable of releasing the reagents from the bead. In some embodiments, the beads or bead arrangements can be incubated in permeabilization reagents as described herein.

In some embodiments, the beads can also include (e.g., encapsulate or have attached thereto) a plurality of capture probes that include spatial barcodes, and the optical properties of the spatial barcodes can be used for optical detection of the beads. For example, the absorbance of light by the spatial barcodes can be used to distinguish the beads from one another. In some embodiments, a detectable label can directly or indirectly attach to a spatial barcode and provide optical detection of the bead. In some embodiments, each bead in a group of one or more beads has a unique detectable label, and detection of the unique detectable label determines the location of the spatial barcode sequence associated with the bead.

Optical properties giving rise to optical detection of beads can be due to optical properties of the bead surface (e.g., a detectable label attached to the bead), or optical properties from the bulk region of the bead (e.g., a detectable label incorporated during bead formation or an optical property of the bead itself). In some embodiments, a detectable label can be associated with a bead or one or more moieties coupled to the bead.

In some embodiments, the beads include a plurality of detectable labels. For example, a fluorescent dye can be attached to the surface of the beads and/or can be incorporated into the beads. Different intensities of the different fluorescent dyes can be used to increase the number of optical combinations that can be used to differentiate between beads. For example, if N is the number of fluorescent dyes (e.g., between 2 and 10 fluorescent dyes, such as 4 fluorescent dyes) and M is the possible intensities for the dyes (e.g., between 2 and 50 intensities, such as 20 intensities), then $M^N$ are the possible distinct optical combinations. In one example, 4 fluorescent dyes with 20 possible intensities can be used to generate 160,000 distinct optical combinations.

One or more optical properties of the beads or biological contents, such as cells or nuclei, can be used to distinguish the individual beads or biological contents from other beads or biological contents. In some embodiments, the beads are made optically detectable by including a detectable label having optical properties to distinguish the beads from one another.

In some embodiments, optical properties of the beads can be used for optical detection of the beads. For example, without limitation, optical properties can include absorbance, birefringence, color, fluorescence, luminosity, photosensitivity, reflectivity, refractive index, scattering, or transmittance. For example, beads can have different birefringence values based on degree of polymerization, chain length, or monomer chemistry.

In some embodiments, nanobeads, such as quantum dots or Janus beads, can be used as optical labels or components thereof. For example, a quantum dot can be attached to a spatial barcode of a bead.

Optical labels of beads can provide enhanced spectral resolution to distinguish (e.g., identify) between beads with unique spatial barcodes (e.g., beads including unique spatial barcode sequences). That is, the beads are manufactured in a way that the optical labels and the barcodes on the beads (e.g., spatial barcodes) are correlated with each other. In some aspects, the beads can be loaded into a flowcell such that beads are arrayed in a closely packed manner (e.g., single-cell resolution). Imaging can be performed, and the spatial location of the barcodes can be determined (e.g., based on information from a look-up table (LUT)). The optical labels for spatial profiling allow for quick deconvolution of bead-barcode (e.g., spatial barcode) identify.

In some examples, a lookup table (LUT) can be used to associate a property (e.g., an optical label, such as a color and/or intensity) of the bead with the barcode sequence. The property may derive from the particle (e.g., bead) or an optical label associated with the bead. The beads can be imaged to obtain optical information of the bead, including, for example, the property (e.g., color and/or intensity) of the bead or the optical label associated with the bead, and optical information of the biological sample. For example, an image can include optical information in the visible spectrum, non-visible spectrum, or both. In some embodiments, multiple images can be obtained across various optical frequencies.

In some embodiments, a first bead includes a first optical label and spatial barcodes each having a first spatial barcode sequence. A second bead includes a second optical label and spatial barcodes each having a second spatial barcode sequence. The first optical label and second optical label can be different (e.g., provided by two different fluorescent dyes or the same fluorescent dye at two different intensities). The first and second spatial barcode sequences can be different nucleic acid sequences. In some embodiments, the beads can be imaged to identify the first and second optical labels, and the first and second optical labels can then be used to associate the first and second optical labels with the first and second spatial barcode sequences, respectively. In some embodiments, the nucleic acid containing the spatial barcode can further have a capture domain for analytes (e.g., mRNA). In some embodiments, the nucleic acid (e.g., nucleic acid containing the spatial barcode) can have a unique molecular identifier, a cleavage domain, a functional domain, or combinations thereof.

In some embodiments, the optical label has a characteristic electromagnetic spectrum. As used herein, the "electromagnetic spectrum" refers to the range of frequencies of electromagnetic radiation. In some embodiments, the optical label has a characteristic absorption spectrum. As used herein, the "absorption spectrum" refers to the range of frequencies of electromagnetic radiation that are absorbed. The "electromagnetic spectrum" or "absorption spectrum" can lead to different characteristic spectrum. In some embodiments, the peak radiation or the peak absorption occurs at 380-450 nm (Violet), 450-485 nm (Blue), 485-500 nm (Cyan), 500-565 nm (Green), 565-590 nm (Yellow), 590-625 nm (Orange), or 625-740 nm (Red). In some embodiments, the peak radiation or the peak absorption occurs around 400 nm, 460 nm, or 520 nm.

Optical labels included on the beads can identify the associated spatial barcode on the bead. Due to the relative limited diversity of optical labels it can be advantageous to limit the size of the spatial array for deconvolution. For example, the substrate can be partitioned into two or more partitions (e.g., bins). In some embodiments, the substrate can be partitioned into three or more partitions. In some embodiments, the substrate can be partitioned into four or more partitions (e.g., bins). In some embodiments, a set of beads are deposited to the partition. Within each set of beads, one or more beads (e.g., equal to or more than 10, 20, 30, 40, 50, 60, 70, 80, 90, 100, 150, 200, 250, 300, 350, 400, 450, 500, 600, 700, 800, 900, 1000, 2000, 3000, 4000, or 5000 beads) can have an unique optical label.

In some cases, beads within the same partition can have different coordinates on the substrate. These coordinates can be determined e.g., by various imaging techniques, such as observation through microscope under an appropriate condition. In some embodiments, the beads within the same partition can share the same spatial barcode. In some embodiments, the beads (e.g., beads having capture probes with barcodes, e.g., spatial barcodes or UMI) are different from each other for different partition bins. In some embodiments, the beads having capture probes with barcodes (e.g., spatial barcodes or UMI) can have different barcodes. For example, in some cases, within each set of beads, which beads are associated with a capture probe, the capture probes on individual beads can have a unique barcode. In some cases, among all beads (e.g., within two or more sets of beads), individual beads can have capture probes with a unique barcode.

In some aspects, the present disclosure provides a substrate. The substrate can have 1, 2, 3, 4, 5, 6, 7, 8, 9, 10, 20, 30, 40, 50, 60, 70, 80, 90, 100, 110, 120, 130, 140, 150, 160, 170, 180, 190, 200, 300, 400, 500, 600, 700, 800, 900, 1000, or more than 1000 partitions (e.g., bins, or pre-defined area). The partitions can have the same shape or different shapes. In some embodiments, the substrate has only one partition (e.g., bin or pre-defined area).

In some embodiments, the first partition (e.g., the first pre-defined area, or the only bin on the substrate) can have a first set of beads. In some embodiments, at least one bead from the first set of beads comprises an optical label, and a capture probe (e.g., an oligonucleotide capture probe) comprising a barcode and a capture domain. At least one of the beads can have a unique optical label among the first set of beads. In some embodiments, at least 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% of the beads in the first set of beads have a unique optical label. In some embodiments, each bead in the first set of beads has a unique optical label.

In some embodiments, the substrate can have a second partition (e.g., the second pre-defined area, or the second bin). The second partition can have a second set of beads. In some embodiments, at least one bead from the second set of beads comprises an optical label, and a capture probe (e.g., an oligonucleotide capture probe) comprising a barcode and a capture domain. At least one of the beads can have a unique optical label among the second set of beads. In some embodiments, at least 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% of the beads in the second set of beads have a unique optical label. In some embodiments, each bead in the second set of beads has a unique optical label.

In some embodiments, the substrate can have a third partition, a fourth partition, a fifth partition, a sixth partition, a seventh partition, an eighth partition, a ninth partition, or a tenth partition, etc. In some embodiments, the substrate can have multiple partitions. In some cases, each of these partitions has properties that are similar to the first or the second partitions described herein. For example, at least one bead from each set of beads comprises an optical label, and a capture probe (e.g., an oligonucleotide capture probe) comprising a barcode and a capture domain. At least one of these beads can have a unique optical label among each set of beads. In some embodiments, at least 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% of the beads in each set of beads have a unique optical label. In some embodiments, each bead in each set of beads has a unique optical label.

In some embodiments, the beads are deposited on the substrate. In some embodiments, the beads can be deposited directly on or into a biological sample. Thus, in some cases, the biological sample can be fixed or attached on the substrate before beads are deposited onto the substrate.

In some embodiments, the beads are only deposited to areas of interest (e.g., specific locations on the substrate, specific cell types, and specific tissue structures). Thus, the deposited beads do not necessarily cover the entire biological sample. In some embodiments, one or more regions of a substrate can be masked or modified (e.g., capped capture domains) such that the masked regions do not interact with a corresponding region of the biological sample.

In some embodiments, two or more than two sets of beads (e.g., 2, 3, 4, 5, 6, 7, 8, 9, 10, or more than 10 sets) are deposited at two or more than two partitions (e.g., 2, 3, 4, 5, 6, 7, 8, 9, 10, or more than 10 partitions). These partitions do not need to be adjacent to each other. As long as the location of the partitions on the substrate is recorded, the identity of the beads can be determined from the optical labels.

In some embodiments, a set of beads can have equal to or more than 1, 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 2000, 3000, 4000, or 5000 beads. In some embodiments, a set 25 of beads can have less than 5, 6, 7, 8, 9, 10, 20, 30, 40, 50, 60, 70, 80, 90, 100, 150, 200, 250, 300, 350, 400, 450, 500, 600, 700, 800, 900, 1000, 2000, 3000, 4000, or 5000 beads.

Optical labels can be included while generating the beads. For example, optical labels can be included in the polymer structure of a gel bead, or attached at the pre-polymer or monomer stage in bead production. In some embodiments, the beads include moieties that attach to one or more optical labels (e.g., at a surface of a bead and/or within a bead). In some embodiments, optical labels can be loaded into the beads with one or more reagents. For example, reagents and optical labels can be loaded into the beads by diffusion of the reagents (e.g., a solution of reagents including the optical labels). In some embodiments, optical labels can be included while preparing spatial barcodes. For example, spatial barcodes can be prepared by synthesizing molecules including barcode sequences (e.g., using a split pool or combinatorial approach). Optical labels can be attached to spatial barcodes prior to attaching the spatial barcodes to a bead. In some embodiments, optical labels can be included after attaching spatial barcodes to a bead. For example, optical labels can be attached to spatial barcodes coupled to the bead. In some embodiments, spatial barcodes or sequences thereof can be releasably or cleavably attached to the bead. Optical labels can be releasably or non-releasably attached to the bead. In some embodiments, a first bead (e.g., a bead including a plurality of spatial barcodes) can be coupled to a second bead including one or more optical labels. For example, the first bead can be covalently coupled to the second bead via a chemical bond. In some embodiments, the first bead can be non-covalently associated with the second bead.

The first and/or second bead can include a plurality of spatial barcodes. The plurality of spatial barcodes coupled to a given bead can include the same barcode sequences. Where both the first and second beads include spatial barcodes, the first and second beads can include spatial barcodes including the same barcode sequences or different barcode sequences.

Bead arrays containing captured analytes can be processed in bulk or partitioned into droplet emulsions for preparing sequencing libraries. In some embodiments, next generation sequencing reads are clustered and correlated to the spatial position of the spatial barcode on the bead array. For example, the information can be computationally superimposed over a high-resolution image of the tissue section to identify the location(s), where the analytes were detected.

In some embodiments, de-cross linking can be performed to account for de-crosslinking chemistries that may be incompatible with certain barcoding/library prep biochemistry (e.g., presence of proteases). For example, a two-step process is possible. In the first step, beads can be provided in droplets such that DNA binds to the beads after the conventional de-crosslinking chemistry is performed. In the second step, the emulsion is broken and beads collected and then re-encapsulated after washing for further processing.

In some embodiments, beads can be affixed or attached to a substrate using photochemical methods. For example, a bead can be functionalized with perfluorophenylazide silane (PFPA silane), contacted with a substrate, and then exposed to irradiation (see, e.g., Liu et al. (2006) *Journal of the American Chemical Society* 128, 14067-14072). For example, immobilization of antraquinone-functionalized substrates (see, e.g., Koch et al. (2000) *Bioconjugate Chem.* 11, 474-483, the entire contents of which are herein incorporated by reference).

The arrays can also be prepared by bead self-assembly. Each bead can be covered with hundreds of thousands of copies of a specific oligonucleotide. In some embodiments, each bead can be covered with about 1,000 to about 1,000,000 oligonucleotides. In some embodiments, each bead can be covered with about 1,000,000 to about 10,000,000 oligonucleotides. In some embodiments, each bead can covered with about 2,000,000 to about 3,000,000, about 3,000,000 to about 4,000,000, about 4,000,000 to about 5,000,000, about 5,000,000 to about 6,000,000, about 6,000,000 to about 7,000,000, about 7,000,000 to about 8,000,000, about 8,000,000 to about 9,000,000, or about 9,000,000 to about 10,000,000 oligonucleotides. In some embodiments, each bead can be covered with about 10,000,000 to about 100,000,000 oligonucleotides. In some embodiments, each bead can be covered with about 100,000,000 to about 1,000,000,000 oligonucleotides. In some embodiments, each bead can be covered with about 1,000,000,000 to about 10,000,000,000 oligonucleotides. The beads can be irregularly distributed across etched substrates during the array production process. During this process, the beads can be self-assembled into arrays (e.g., on a fiber-optic bundle substrate or a silica slide substrate). In some embodiments, the beads irregularly arrive at their final location on the array. Thus, the bead location may need to be mapped or the oligonucleotides may need to be synthesized based on a predetermined pattern.

Beads can be affixed or attached to a substrate covalently, non-covalently, with adhesive, or a combination thereof. The attached beads can be, for example, layered in a monolayer, a bilayer, a trilayer, or as a cluster. As defined herein, a "monolayer" generally refers to an arrayed series of probes, beads, spots, dots, features, micro-locations, or islands that are affixed or attached to a substrate, such that the beads are arranged as one layer of single beads. In some embodiments, the beads are closely packed.

As defined herein, the phrase "substantial monolayer" or "substantially form(s) a monolayer" generally refers to (the formation of) an arrayed series of probes, beads, microspheres, spots, dots, features, micro-locations, or islands that are affixed or attached to a substrate, such that about 50% to about 99% (e.g., about 50% to about 98%) of the beads are arranged as one layer of single beads. This arrangement can be determined using a variety of methods, including microscopic imaging.

In some embodiments, the monolayer of beads is a located in a predefined area on the substrate. For example, the predefined area can be partitioned with physical barriers, a photomask, divots in the substrate, or wells in the substrate.

As used herein, the term "reactive element" generally refers to a molecule or molecular moiety that can react with another molecule or molecular moiety to form a covalent bond. Reactive elements include, for example, amines, aldehydes, alkynes, azides, thiols, haloacetyls, pyridyl disulfides, hydrazides, carboxylic acids, alkoxyamines, sulfhydryls, maleimides, Michael acceptors, hydroxyls, and active esters. Some reactive elements, for example, carboxylic acids, can be treated with one or more activating agents (e.g., acylating agents, isourea-forming agents) to increase susceptibility of the reactive element to nucleophilic attack. Non-limiting examples of activating agents include N-hydroxysuccinimide, N-hydroxysulfosuccinimide, 1-ethyl-3-(3-dimethylaminopropyl)carbodiimide, dicyclohexylcarbodiimide, diisopropylcarbodiiimide, 1-hydroxybenzotriazole, (benzotriazol-1-yloxy)tripyrrolidinophosphonium hexfluorophosphate, (benzotriazol-1-yl)-N,N,N',N'-tetramethyluronium hexafluorophosphate, 4-(N,N-dimethylamino)pyridine, and carbonyldiimidazole.

In some embodiments, the reactive element is bound directly to a bead. For example, hydrogel beads can be treated with an acrylic acid monomer to form acrylic acid-functionalized hydrogel beads. In some cases, the reactive element is bound indirectly to the bead via one or more linkers. As used herein, a "linker" generally refers to a multifunctional (e.g., bifunctional, trifunctional) reagent used for conjugating two or more chemical moieties. A linker can be a cleavable linker that can undergo induced dissociation. For example, the dissociation can be induced by a solvent (e.g., hydrolysis and solvolysis); by irradiation (e.g., photolysis); by an enzyme (e.g., enzymolysis); or by treatment with a solution of specific pH (e.g., pH 4, 5, 6, 7, or 8).

In some embodiments, the reactive element is bound directly to a substrate. For example, a glass slide can be coated with (3-aminopropyl)triethoxysilane. In some embodiments, the reactive element is bound indirectly to a substrate via one or more linkers.

Gel/Hydrogel Beads

In some embodiments, the bead can be a gel bead. A "gel" is a semi-rigid material permeable to liquids and gases. Exemplary gels include, but are not limited to, those having a colloidal structure, such as agarose; polymer mesh structures, such as gelatin; hydrogels; and cross-linked polymer structures, such as polyacrylamide, SFA (see, for example, U.S. Patent Application Publication No. 2011/0059865, which is incorporated herein by reference in its entirety) and PAZAM (see, for example, U.S. Patent Application Publication No. 2014/0079923, which is incorporated herein by reference in its entirety).

A gel can be formulated into various shapes and dimensions depending on the context of intended use. In some embodiments, a gel is prepared and formulated as a gel bead (e.g., a gel bead including capture probes attached or associated with the gel bead). A gel bead can be a hydrogel bead. A hydrogel bead can be formed from molecular precursors, such as a polymeric or monomeric species.

In some cases, a bead comprises a polymer or hydrogel. The polymer or hydrogel may determine one or more characteristics of the hydrogel bead, such as the volume, fluidity, porosity, rigidity, organization, or one or more other features of the hydrogel bead. In some embodiments, a hydrogel bead can include a polymer matrix (e.g., a matrix formed by polymerization or cross-linking). A polymer matrix can include one or more polymers (e.g., polymers having different functional groups or repeat units). Cross-linking can be via covalent, ionic, and/or inductive interactions, and/or physical entanglement.

A polymer or hydrogel may be formed, for example, upon cross-linking one or more cross-linkable molecules within the hydrogel bead. For example, a hydrogel may be formed upon cross-linking one or more molecules within the hydrogel bead. The hydrogel may be formed upon polymerizing a plurality of monomers within the hydrogel bead. The hydrogel may be formed upon polymerizing a plurality of polymers within the hydrogel bead. Polymeric or hydrogel precursors may be provided to the hydrogel bead and may not form a polymer or hydrogel without application of a stimulus (e.g., as described herein). In some cases, the hydrogel bead may be encapsulated within the polymer or hydrogel. Formation of a hydrogel bead may take place following one or more other changes to the cell that may be brought about by one or more other conditions.

The methods described herein may be applied to a single hydrogel bead or a plurality of hydrogel beads. A method of processing a plurality of hydrogel beads may comprise providing the plurality of hydrogel beads within a vessel and subjecting the plurality of hydrogel beads to conditions sufficient to change one or more characteristics of the hydrogel bead. For example, plurality of hydrogel beads may be subjected to a first condition or set of conditions comprising a chemical species, and a cross-section of the hydrogel beads of the plurality of hydrogel beads may change from a first cross-section to a second cross-section, which second cross-section is less than the first cross-section. The chemical species may comprise, for example, an organic solvent such as ethanol, methanol, or acetone. The plurality of hydrogel beads may then be subjected to a second condition or set of conditions comprising a chemical species, and crosslinks may form within each of the hydrogel beads. The chemical species may comprise, for example, a cross-linking agent. The plurality of processed hydrogel beads may be provided in an aqueous fluid. In some instances, the second cross-section of the plurality of hydrogel beads is substantially maintained in the aqueous fluid. The plurality of processed hydrogel beads may be partitioned within a plurality of partitions. The partitions may be, for example, aqueous droplets included in a water-in-oil emulsion. The partitions may be, for example, a plurality of wells. The plurality of fixed hydrogel beads may be co-partitioned with one or more reagents. In some cases, the plurality of fixed hydrogel beads may be co-partitioned with one or more beads, where each bead comprises a plurality of nucleic acid barcode molecules attached thereto. The nucleic acid barcode molecules attached to a given bead may comprise a common barcode sequence, and the nucleic acid barcode molecules attached to each different bead may comprise a sequence comprising a different common barcode sequence. The nucleic acid barcode molecules, or portions thereof, may then be used in reactions with target molecules associated with hydrogel beads of the plurality of hydrogel beads.

Core/Shell Beads

In some embodiments, the bead is a core/shell bead that comprises an inner core (e.g., a nanosphere or microsphere) and an outer shell (e.g., a hydrogel coating the nanosphere or microsphere). In some embodiments, the inner core can be a solid nanoparticle or solid microparticle. In some embodiments, the inner core can be a silica inner core (e.g., a silica nanoparticle or silica microparticle). In some embodiments, the inner core of the core/shell bead can have an average diameter of about 1 micron. In some embodiments, the inner core can have an average diameter of about 2 microns. In some embodiments, the inner core can have an average diameter of about 3 microns. In some embodiments, the inner core can have an average diameter of about 4 microns. In some embodiments, the inner core can have an average diameter of about 5 microns. In some embodiments, the inner core can have an average diameter of about 6 microns. In some embodiments, the inner core can have an average diameter of about 7 microns. In some embodiments, the inner core can have an average diameter of about 8 microns. In some embodiments, the inner core can have an average diameter of about 9 microns. In some embodiments, the inner core can have an average diameter of about 10 microns. In some embodiments, the inner core can have an average diameter of about 100 nanometers to about 10 microns.

In some embodiments, the core/shell bead can decrease its outer shell volume by removing solvents, salts, or water (e.g., dehydrated, desiccated, dried, exsiccated) from the outer shell to form a shrunken core/shell bead. In another example, the core/shell bead can decrease its outer shell volume by adjusting temperature or pH, as described above. In some embodiments, the core/shell bead can expand its outer shell volume, for example by the addition of solvents, salts, or water (e.g., rehydration) to form an expanded core/shell bead. In some embodiments, the outer shell (e.g., coating the inner core) can have an average thickness of about 1 micron. In some embodiments, the outer shell can have an average thickness of about 2 microns. In some embodiments, the outer shell can have an average thickness of about 3 microns. In some embodiments, the outer shell can have an average thickness of about 4 microns. In some embodiments, the outer shell can have an average thickness of about 5 microns.

In some embodiments, the core/shell bead can have an average diameter of about 1 micron to about 10 microns. In some embodiments, the core/shell bead can have an average diameter of about 1 micron. In some embodiments, the core/shell bead can have an average diameter of about 2 microns. In some embodiments, the core/shell bead can have an average diameter of about 3 microns. In some embodiments, the core/shell bead can have an average diameter of about 4 microns. In some embodiments, the core/shell bead can have an average diameter of about 5 microns. In some embodiments, the core/shell bead can have an average diameter of about 6 microns. In some embodiments, the core/shell bead can have an average diameter of about 7 microns. In some embodiments, the core/shell bead can have an average diameter of about 8 microns. In some embodiments, the core/shell bead can have an average diameter of about 9 microns. In some embodiments, the core/shell bead can have an average diameter of about 10 microns.

(2) Methods for Covalently Bonding Features to a Substrate

Provided herein are methods for the covalent bonding of features (e.g., optically labeled beads, hydrogel beads, microsphere beads) to a substrate.

In some embodiments, the features (e.g., beads) are coupled to a substrate via a covalent bond between a first reactive element and a second reactive element. In some embodiments, the covalently-bound beads substantially form a monolayer of features (e.g., hydrogel beads, microsphere beads) on the substrate.

In some embodiments, the features (e.g., beads) are functionalized with a first reactive element, which is directly bound to the features. In some embodiments, the features are functionalized with a first reactive element, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is functionalized with a second reactive element, which is directly bound to the substrate. In some embodiments, the substrate is functionalized with a second reactive element, which is indirectly bound to the beads via a linker. In some embodiments, the linker is a benzophenone. For example, the linker can be benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is a glass slide. In some embodiments, the substrate is a pre-functionalized glass slide.

In some embodiments, about 99% of the covalently-bound beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the covalently-bound beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the covalently-bound beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the covalently-bound beads for a monolayer of beads on the substrate.

In some embodiments, at least one of the first reactive element and the second reactive element is selected from the group consisting of:

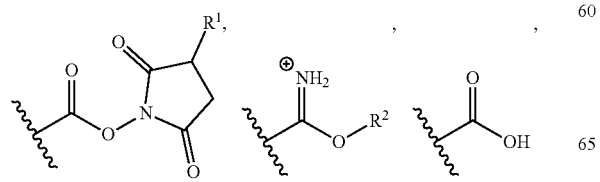

-continued

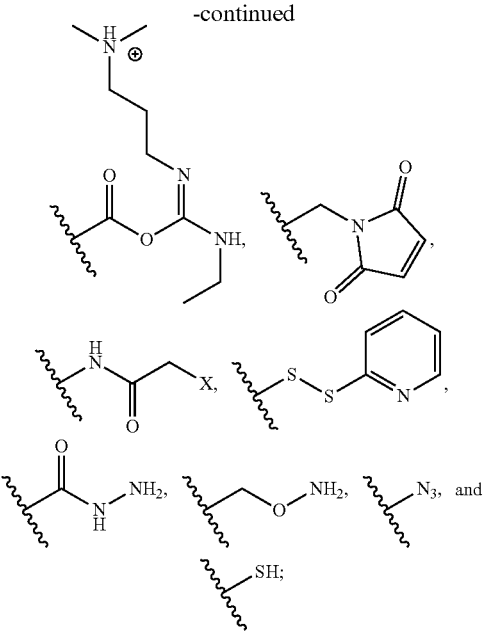

wherein

R$^1$ is selected from H, C$_1$-C$_6$ alkyl, or —SO$_3$;

R$^2$ is C$_1$-C$_6$ alkyl; and

X is a halo moiety.

In some embodiments, at least one of the first reactive element or the second reactive element comprises

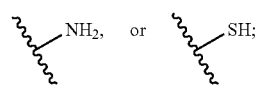

wherein the ⌇ indicates the point of attachment of the first reactive element or the second reactive element to the bead (e.g., hydrogel bead or microsphere bead) or to the substrate.

In some embodiments, at least one of the first reactive element or the second reactive element is selected from the group consisting of:

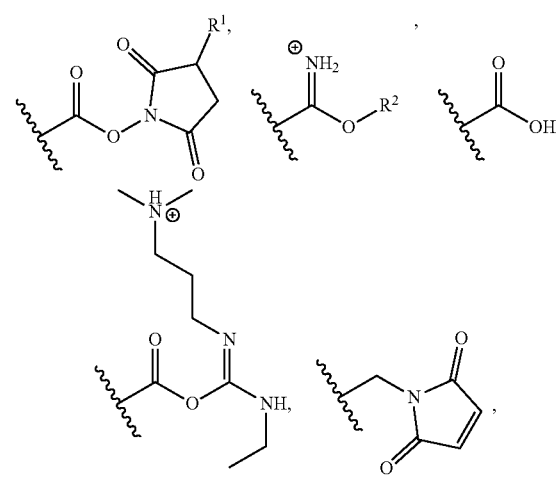

-continued

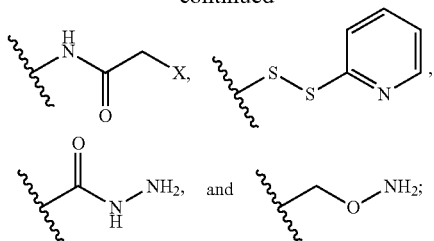

wherein

R¹ is selected from H, $C_1$-$C_6$ alkyl, or —$SO_3$;

R² is $C_1$-$C_6$ alkyl; and

X is a halo moiety.

In some embodiments, at least one of the first reactive element or the second reactive element comprises

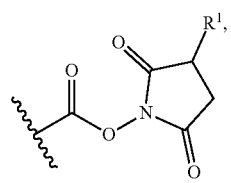

wherein R¹ is selected from H, $C_1$-$C_6$ alkyl, or —$SO_3$. In some embodiments, R¹ is H. In some embodiments, R¹ is $C_1$-$C_6$ alkyl. In some embodiments, R¹ is —$SO_3$.

In some embodiments, at least one of the first reactive element or the second reactive element comprises

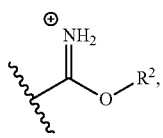

wherein R² is $C_1$-$C_6$ alkyl. In some embodiments, R² is methyl.

In some embodiments, at least one of the first reactive element or the second reactive element comprises

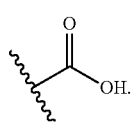

Is some embodiments,

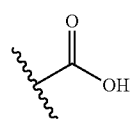

can be reacted with an activating agent to form an active ester. In some embodiments, the active ester is

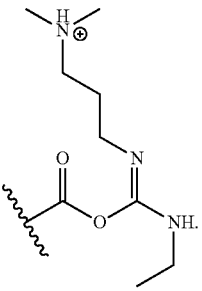

In some embodiments, the activating agent is an acylating agent (e.g., N-hydroxysuccinimide and N-hydroxysulfosuccinimide). In some embodiments, the activating agent is an O-acylisourea-forming agent (e.g., 1-ethyl-3-(3-dimethylaminopropyl)carbodiimide (EDC), dicyclohexylcarbodiimide, and diisopropylcarbodiimide). In some embodiments, the activating agent is a combination of at least one acylating agent and at least one O-isourea-forming agents (e.g., N-hydroxysuccinimide (NHS), 1-ethyl-3-(3-dimethylaminopropyl)carbodiimide (EDC), N-hydroxysulfosuccinimide (sulfo-NHS), and a combination thereof).

In some embodiments, at least one of the first reactive element or the second reactive element comprises

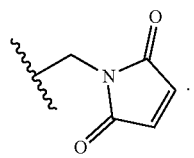 [SMILES: *CN1C(=O)C=CC1=O]

In some embodiments, at least one of the first reactive element or the second reactive element comprises

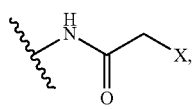

wherein X is a halo moiety. For example, X is chloro, bromo, or iodo.

In some embodiments, at least one of the first reactive element or the second reactive element comprises

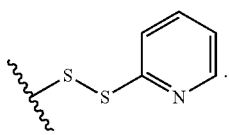 [SMILES: *SSc1ccccn1 ; "."]

In some embodiments, at least one of the first reactive element or the second reactive element comprises

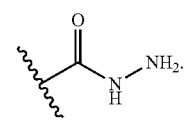

In some embodiments, at least one of the first reactive element or the second reactive element comprises

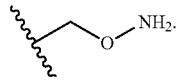

In some embodiments, at least one of the first reactive element or the second reactive element is selected from the group consisting of:

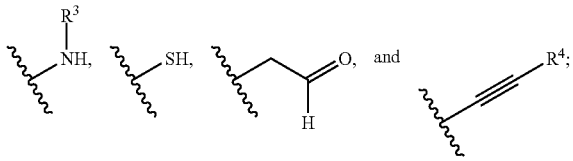

wherein
R³ is H or C₁-C₆ alkyl; and
R⁴ is H or trimethylsilyl.

In some embodiments, at least one of the first reactive element or the second reactive element comprises

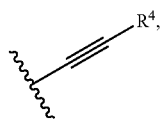

wherein R⁴ is H or trimethylsilyl. In some embodiments, R⁴ is H.

In some embodiments, at least one of the first reactive element or the second reactive element is selected from the group consisting of:

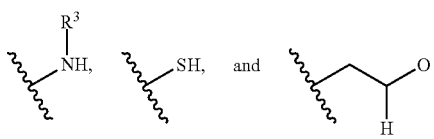

wherein R³ is H or C₁-C₆ alkyl. In some embodiments, R³ is H. In some embodiments, R³ is C₁-C₆ alkyl.

In some embodiments, at least one of the first reactive element or the second reactive element comprises

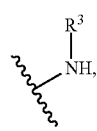

wherein R³ is H or C₁-C₆ alkyl. In some embodiments, R³ is H. In some embodiments, R³ is C₁-C₆ alkyl.

In some embodiments, at least one of the first reactive elements or the second reactive elements comprises

In some embodiments, at least one of the first reactive elements or the second reactive elements comprises

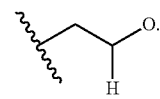

In some embodiments, one of the first reactive elements or the second reactive elements is selected from the group consisting of:

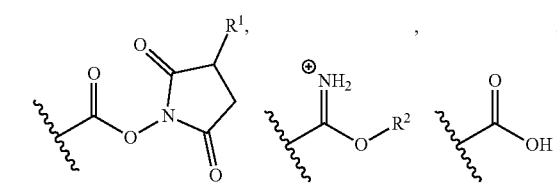

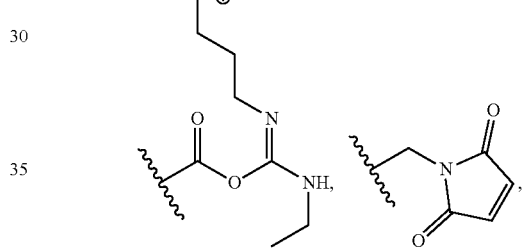

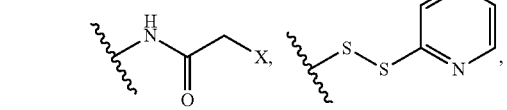

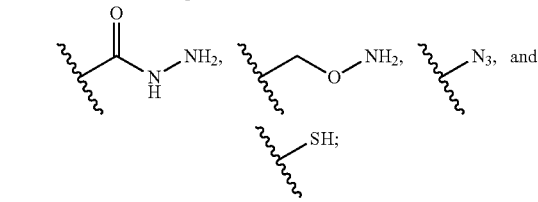

wherein
R¹ is selected from H, C₁-C₆ alkyl, or —SO₃;
R² is C₁-C₆ alkyl;
X is a halo moiety;
and the other of the first reactive element or the second reactive element is selected from the group consisting of:

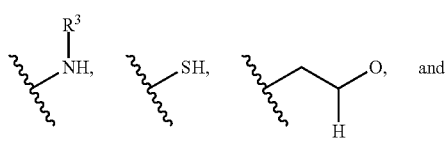

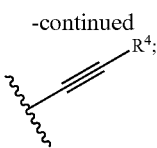

wherein

R³ is H or C₁-C₆ alkyl; and

R⁴ is H or trimethylsilyl.

In some embodiments, one of the first reactive elements or the second reactive elements is selected from the group consisting of

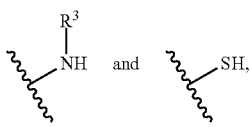

wherein R³ is H or C₁-C₆ alkyl;

and the other of the first reactive element or the second reactive element is

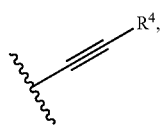

wherein R⁴ is H or trimethylsilyl. In some embodiments, R³ is H. In some embodiments, R³ is C₁-C₆ alkyl. In some embodiments, R⁴ is H. In some embodiments, R⁴ is trimethylsilyl.

In some embodiments, one of the first reactive element or the second reactive element is selected from the group consisting of:

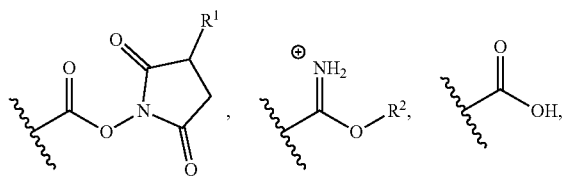

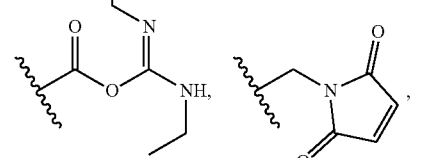

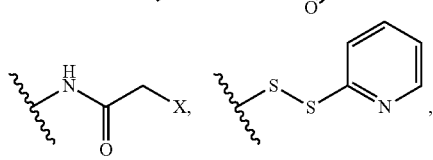

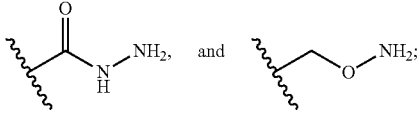

wherein

R¹ is selected from H, C₁-C₆ alkyl, or —SO₃;

R² is C₁-C₆ alkyl;

X is a halo moiety;

and the other of the first reactive element or the second reactive element is selected from the group consisting of:

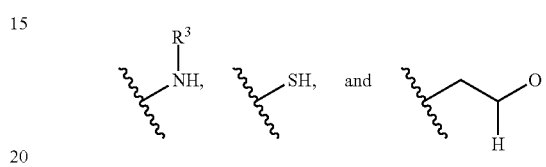

wherein R³ is H or C₁-C₆ alkyl. In some embodiments, R¹ is H. In some embodiments, R¹ is C₁-C₆ alkyl. In some embodiments, R¹ is —SO₃. In some embodiments, R² is methyl. In some embodiments, X is iodo. In some embodiments, R³ is H. In some embodiments, R³ is C₁-C₆ alkyl.

In some embodiments, one of the first reactive elements or the second reactive elements is selected from the group consisting of:

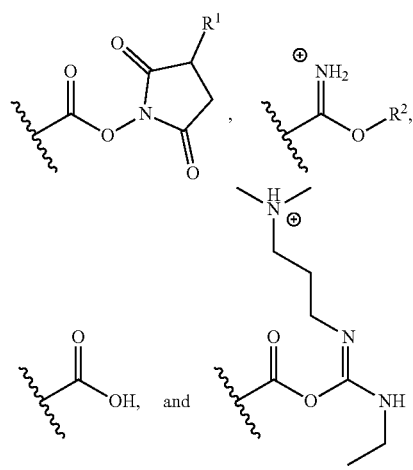

wherein

R¹ is selected from H, C₁-C₆ alkyl, or —SO₃;

R² is C₁-C₆ alkyl;

and the other of the first reactive elements or the second reactive elements comprises

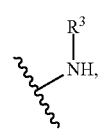

wherein R³ is H or C₁-C₆ alkyl. In some embodiments, R¹ is H. In some embodiments, R¹ is C₁-C₆ alkyl. In some embodiments, R¹ is —SO₃. In some embodiments, R² is methyl. In some embodiments, R³ is H. In some embodiments, R³ is C₁-C₆ alkyl.

In some embodiments, one of the first reactive element or the second reactive element is selected from the group consisting of:

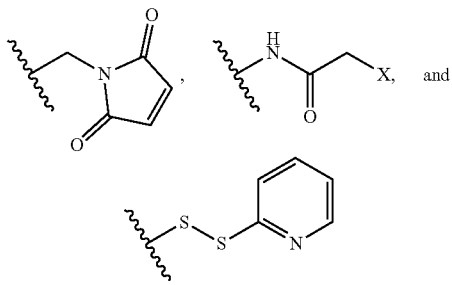

wherein X is a halo moiety;
and the other of the first reactive element or the second reactive element comprises

In some embodiments, X is bromo. In some embodiments, X is iodo.

In some embodiments, one of the first reactive element or the second reactive element is selected from the group consisting of

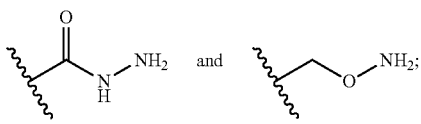

and the other of the first reactive element or the second reactive element comprises

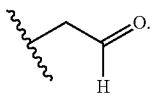

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, and the like.

(3) Methods for Non-Covalently Bonding Features to a Substrate

Provided herein are methods for the non-covalent bonding of features (e.g., optically-labeled beads, hydrogel beads, or microsphere beads) to a substrate.

In some embodiments, features (e.g., beads) are coupled to a substrate via a non-covalent bond between a first affinity group and a second affinity group. In some embodiments, the non-covalently-bound features (e.g., beads) substantially form a monolayer of beads (e.g., hydrogel beads, microsphere beads) on the substrate.

In some embodiments, the features are functionalized with a first affinity group, which is directly bound to the features. In some embodiments, the features are functionalized with a first affinity group, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is functionalized with a second affinity group, which is directly bound to the substrate. In some embodiments, the substrate is functionalized with a second affinity group, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments the first affinity group or the second affinity group is biotin, and the other of the first affinity group or the second affinity group is streptavidin.

In some embodiments, about 99% of the non-covalently-bound beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the non-covalently-bound beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the non-covalently-bound beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the non-covalently-bound beads for a monolayer of beads on the substrate.

In some embodiments, the monolayer of beads is a formed in a predefined area on the substrate. In some embodiments, the predefined area is partitioned with physical barriers. For example, divots or wells in the substrate. In some embodiments, the predefined area is partitioned using a photomask. For example, the substrate is coated with a photo-activated solution, dried, and then irradiated under a photomask. In some embodiments, the photo-activated solution is UV-activated.

As used herein, an "adhesive" generally refers to a substance used for sticking objects or materials together. Adhesives include, for example, glues, pastes, liquid tapes, epoxy, bioadhesives, gels, and mucilage. In some embodiments, an adhesive is liquid tape. In some embodiments, the adhesive is glue.

In some embodiments, beads are adhered to a substrate using an adhesive (e.g., liquid tape, glue, paste). In some embodiments, the adhered beads substantially form a monolayer of beads on the substrate (e.g., a glass slide). In some embodiments, the beads are hydrogel beads. In some embodiments, the beads are microsphere beads. In some embodiments, the beads are coated with the adhesive, and then the beads are contacted with the substrate. In some embodiments, the substrate is coated with the adhesive, and then the substrate is contacted with the beads. In some embodiments, both the substrate is coated with the adhesive and the beads are coated with the adhesive, and then the beads and substrate are contacted with one another.

In some embodiments, about 99% of the adhered beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the adhered beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the adhered beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the adhered beads for a monolayer of beads on the substrate.

In some embodiments, beads can be deposited onto a biological sample such that the deposited beads form a monolayer of beads on the biological sample (e.g., over or under the biological sample). In some embodiments, beads deposited on the substrate can self-assemble into a monolayer of beads that saturate the intended surface area of the biological sample under investigation. In this approach, bead arrays can be designed, formulated, and prepared to evaluate a plurality of analytes from a biological sample of any size or dimension. In some embodiments, the concentration or density of beads (e.g., gel beads) applied to the biological sample is such that the area as a whole, or one or more regions of interest in the biological sample, is saturated with a monolayer of beads. In some embodiments, the beads are contacted with the biological sample by pouring, pipetting, spraying, and the like, onto the biological sample. Any suitable form of bead deposition can be used.

In some embodiments, the biological sample can be confined to a specific region or area of the array. For example, a biological sample can be affixed to a glass slide and a chamber, gasket, or cage positioned over the biological sample to act as a containment region or frame within which the beads are deposited. As will be apparent, the density or concentration of beads needed to saturate an area or biological sample can be readily determined by one of ordinary skill in the art (e.g., through microscopic visualization of the beads on the biological sample). In some embodiments, the bead array contains microfluidic channels to direct reagents to the spots or beads of the array.

(4) Feature Geometric Attributes

Features on an array can have a variety of sizes. In some embodiments, a feature of an array can have an average diameter or maximum dimension between 500 nm μm to 100 μm. For example, between 500 nm to 2 μm, 1 μm to 3 μm, 1 μm to 5 μm, 1 μm to 10 μm, 1 μm to 20 μm, 1 μm to 30 μm, 1 μm to 40 μm, 1 μm to 50 μm, 1 μm to 60 μm, 1 μm to 70 μm, 1 μm to 80 μm, 1 μm to 90 μm, 90 μm to 100 μm, 80 μm to 100 μm, 70 μm to 100 μm, 60 μm to 100 μm, 50 μm to 100 μm, 40 μm to 100 μm, 30 μm to 100 μm, 20 μm to 100 μm, 10 μm to 100 μm, about 40 μm to about 70 μm, or about 50 μm to about 60 μm. In some embodiments, the feature has an average diameter or maximum dimension between 30 μm to 100 μm, 40 μm to 90 μm, 50 μm to 80 μm, 60 μm to 70 μm, or any range within the disclosed subranges. In some embodiments, the feature has an average diameter or maximum dimension no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm. In some embodiments, the feature has an average diameter or maximum dimension of approximately 65 μm. In some embodiments, the feature has an average diameter or maximum distance of approximately 55 μm.

In some embodiments, the size and/or shape of a plurality of features of an array are approximately uniform. In some embodiments, the size and/or shape of a plurality of features of an array is not uniform. For example, in some embodiments, features in an array can have an average cross-sectional dimension, and a distribution of cross-sectional dimensions among the features can have a full-width and half-maximum value of 0% or more (e.g., 5% or more, 10% or more, 20% or more, 30% or more, 40% or more, 50% or more, 70% or more, or 100% or more) of the average cross-sectional dimension for the distribution.

In certain embodiments, features in an array can have an average cross-sectional dimension of between about 1 μm and about 10 μm. This range in average feature cross-sectional dimension corresponds to the approximate diameter of a single mammalian cell. Thus, an array of such features can be used to detect analytes at, or below, mammalian single-cell resolution.

In some embodiments, a plurality of features has a mean diameter or mean maximum dimension of about 0.1 μm to about 100 μm (e.g., about 0.1 μm to about 5 μm, about 1 μm to about 10 μm, about 1 μm to about 20 μm, about 1 μm to about 30 μm, about 1 μm to about 40 μm, about 1 μm to about 50 μm, about 1 μm to about 60 μm, about 1 μm to about 70 μm, about 1 μm to about 80 μm, about 1 μm to about 90 μm, about 90 μm to about 100 μm, about 80 μm to about 100 µm, about 70 µm to about 100 µm, about 60 µm to about 100 µm, about 50 µm to about 100 µm, about 40 µm to about 100 µm, about 30 µm to about 100 µm, about 20 µm to about 100 µm, or about 10 µm to about 100 µm). In some embodiments, the plurality of features has a mean diameter or mean maximum dimension between 30 µm to 100 µm, 40 µm to 90 µm, 50 µm to 80 µm, 60 µm to 70 µm, or any range within the disclosed sub-ranges. In some embodiments, the plurality of features has a mean diameter or a mean maximum dimension no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm. In some embodiments, the plurality of features has a mean average diameter or a mean maximum dimension of approximately 65 µm, approximately 60 µm, approximately 55 µm, approximately 50 µm, approximately 45 µm, approximately 40 µm, approximately 35 µm, approximately 30 µm, approximately 25 µm, approximately 20 µm, approximately 15 µm, approximately 10 µm, approximately 5 µm, approximately 4 µm, approximately 3 µm, approximately 2 µm, or approximately 1 µm.

(iv) Array Geometric Attributes

In some embodiments, an array includes a plurality of features. For example, an array includes between 4,000 and 50,000 features, or any range within 4,000 to 40,000 features. For example, an array includes between 4,000 to 35,000 features, 4,000 to 30,000 features, 4,000 to 25,000 features, 4,000 to 20,000 features, 4,000 to 15,000 features, 4,000 to 10,000 features, 4,000 to 6,000 features, or 4,400 to 6,000 features. In some embodiments, the array includes between 4,100 and 5,900 features, between 4,200 and 5,800 features, between 4,300 and 5,700 features, between 4,400 and 5,600 features, between 4,500 and 5,500 features, between 4,600 and 5,400 features, between 4,700 and 5,300 features, between 4,800 and 5,200 features, between 4,900 and 5,100 features, or any range within the disclosed sub-ranges. For example, the array can include about 4,000 features, about 4,200 features, about 4,400 features, about 4,800 features, about 5,000 features, about 5,200 features, about 5,400 features, about 5,600 features, or about 6,000 features, about 10,000 features, about 20,000 features, about 30,000 features, about 40,000 features, or about 50,000 features. In some embodiments, the array comprises at least 4,000 features. In some embodiments, the array includes approximately 5,000 features.

In some embodiments, features within an array have an irregular arrangement or relationship to one another, such that no discernable pattern or regularity is evident in the geometrical spacing relationships among the features. For example, features within an array may be positioned randomly with respect to one another. Alternatively, features within an array may be positioned irregularly, but the spacings may be selected deterministically to ensure that the resulting arrangement of features is irregular.

In some embodiments, features within an array are positioned regularly with respect to one another to form a pattern. A wide variety of different patterns of features can be implemented in arrays. Examples of such patterns include, but are not limited to, square arrays of features, rectangular arrays of features, hexagonal arrays of features (including hexagonal close-packed arrays), radial arrays of features, spiral arrays of features, triangular arrays of features, and more generally, any array in which adjacent features in the array are reached from one another by regular increments in linear and/or angular coordinate dimensions.

In some embodiments, features within an array are positioned with a degree of regularity with respect to one another such that the array of features is neither perfectly regular nor perfectly irregular (i.e., the array is "partially regular"). For example, in some embodiments, adjacent features in an array can be separated by a displacement in one or more linear and/or angular coordinate dimensions that is 10% or more (e.g., 20% or more, 30% or more, 40% or more, 50% or more, 60% or more, 70% or more, 80% or more, 90% or more, 100% or more, 110% or more, 120% or more, 130% or more, 140% or more, 150% or more, 160% or more, 170% or more, 180% or more, 190% or more, 200% or more) of an average displacement or a nominal displacement between adjacent features in the array. In certain embodiments, the distribution of displacements (linear and/or angular) between adjacent features in an array has a full-width at half-maximum of between 0% and 200% (e.g., between 0% and 100%, between 0% and 75%, between 0% and 50%, between 0% and 25%, between 0% and 15%, between 0% and 10%) of an average displacement or nominal displacement between adjacent features in the array.

In some embodiments, arrays of features can have a variable geometry. For example, a first subset of features in an array can be arranged according to a first geometrical pattern, and a second subset of features in the array can be arranged according to a second geometrical pattern that is different from the first pattern. Any of the patterns described above can correspond to the first and/or second geometrical patterns, for example.

In general, arrays of different feature densities can be prepared by adjusting the spacing between adjacent features in the array. In some embodiments, the geometric center-to-center (e.g., pitch) spacing between adjacent features in an array is between 100 nm to 10 µm, 500 nm to 2 µm, 1 µm to 5 µm, and 20 µm to 200 µm. For example, the center-to-center spacing can be between 100 nm to 10 µm, 500 nm to 2 µm, 1 µm, to 5 µm, 20 µm to 40 µm, 20 µm to 60 µm, 20 µm to 80 µm, 80 µm to 100 µm, 100 µm to 120 µm, 120 µm to 140 µm, 140 µm to 160 µm, 160 µm to 180 µm, 180 µm to 200 µm, 60 µm to 100 µm, or 40 µm to 100 µm, 50 µm to 150 µm, 80 µm to 120 µm, or 90 µm to 110 µm. In some embodiments, the pitch between adjacent array features is between 30 µm and 100 µm, 40 µm and 90 µm, 50 µm and 80 µm, 60 µm and 70 µm, 80 µm and 120 µm, or any range within the disclosed sub-ranges. In some embodiments, the pitch between adjacent array features of an array is approximately 65 µm, approximately 60 µm, approximately 55 µm, approximately 50 µm, approximately 45 µm, approximately 40 µm, approximately 35 µm, approximately 30 µm, approximately 25 µm, approximately 20 µm, approximately 15 µm, approximately 10 µm, approximately 5 µm, approximately 4 µm, approximately 3 µm, approximately 2 µm, or approximately 1 µm. In some embodiments, the pitch between adjacent array features of an array is less than 100 µm.

An array of features can have any appropriate resolution. In some embodiments, an array of features can have a spatially constant (e.g., within a margin of error) resolution. In general, an array with a spatially consistent resolution is an array in which the pitch between adjacent features in the array is constant (e.g., within a margin of error). Such arrays can be useful in a variety of applications. In some embodiments, an array of features can have a spatially varying resolution. In general, an array with a spatially varying resolution is an array in which the center-to-center spacing (e.g., pitch) (along linear, angular, or both linear and angular coordinate dimensions) between adjacent features in the array varies. Such arrays can be useful in a variety of applications. For example, in some embodiments, depending upon the spatial resolution at which the sample is to be investigated, the sample can be selectively associated with the portion of the array that corresponds approximately to the desired spatial resolution of the measurement.

In some embodiments, it may be useful to describe the resolution of an array of features by functional aspects, for example, the number of reads that can be carried out per feature (which can be a proxy for sequencing saturation), the number of transcripts that can be detected per feature, or the number of genes that can be detected per feature. For example, in some embodiments, the number of reads that can be performed per feature is between 50,000 and 1,000,000. For example, the number of reads that can be performed per feature can be between 50,000 and 100,000, 50,000 and 150,000, 50,000 and 200,000, 50,000 and 250,000, 50,000 and 300,000, 50,000 and 350,000, 50,000 and 400,000, 50,000 and 500,000, 50,000 and 550,000, 50,000 and 600,000, 50,000 and 650,000, 50,000 and 700,000, 50,000 and 750,000, 50,000 and 800,000, 50,000 and 850,000, 50,000 and 900,000, 50,000 and 950,000, 50,000 and 1,000,000, 100,000 to 500,000, 150,000 to 500,000, 200,000 to 500,000, 250,000 to 500,000, 300,000 and 500,000, 350,000 and 500,000, 400,000 and 500,000, 450,000 and 500,000, 150,000 to 250,000, or 300,000 to 400,000. In some embodiments, the number of reads that can be performed per feature is about 70,000. In some embodiments, the number of reads that can be performed per feature is about 170,000. In some embodiments, the number reads that can be performed per feature is about 330,000. In some embodiments, the number reads that can be performed per feature is about 500,000. In some embodiments, the number reads that can be performed per feature is about 800,000.

In some embodiments, the number of transcripts that can be detected per feature is between 20,000 and 200,000. For example, in some embodiments, the number of transcripts that can be detected per feature can be between 20,000 and 30,000, 20,000 and 40,000, 20,000 and 50,000, 30,000 and 60,000, 40,000 and 60,000, 50,000 and 60,000, 20,000 and 100,000, 30,000 and 100,000, 40,000 and 200,000, 50,000 and 200,000, or 30,000 and 200,000. In some embodiments, the number of transcripts that can be detected per feature is about 40,000. In some embodiments, the number of transcripts that can be detected per feature is about 60,000. In some embodiments, the number of transcripts that can be detected per feature is about 80,000. In some embodiments, the number of transcripts that can be detected per feature is about 100,000.

In some embodiments, the number of genes that can be detected per feature is between 1,000 and 5,000. For example, the number of genes that can be detected per feature can be between 1,000 and 1,500, 1,000 and 2,000, 1,000 and 2,500, 1,000 and 3,000, 1,000 and 3,500, 1,000 and 4,000, 1,000 and 4,500, 1,500 and 5,000, 2,000 and 5,000, 2,500 and 5,000, 3,000 and 5,000, 3,500 and 5,000, 4,000 and 5,000, 4,500 and 5,000, 1,500 and 2,500, 2,500 and 3,500, or 3,500 and 4,000. In some embodiments, the number of genes that can be detected per feature is about 2,000. In some embodiments, the number of genes that can be detected per feature is about 3,000. In some embodiments, the number of genes that can be detected per feature is about 4,000.

In some embodiments, it may be useful to describe the resolution of an array of features by functional aspects, for example, the number of UMI counts per feature. For example, in some embodiments, the number of UMI counts that can be performed per feature is between 1,000 and 50,000. In some embodiments, the number of UMI counts can be averaged to obtain a mean UMI per feature. In some embodiments, the number of UMI counts can be averaged to obtain a median UMI count per feature. For example, the median UMI count per feature can be between 1,000 and 50,000, 1,000 and 40,000, 1,000 and 30,000, 1,000 and 20,000, 1,000 and 10,000, 1,000 and 5,000. In some embodiments, the median UMI count per feature is about 5,000. In some embodiments, the median UMI count per feature is about 10,000.

These components can be used to determine the sequencing saturation of the array. The sequencing saturation can be a measure of the library complexity and sequencing depth. For example, different cell types will have different amounts of RNA, thus different number of transcripts, influencing library complexity. Additionally, sequencing depth is related to the number of sequencing reads. In some embodiments, the inverse of sequencing saturation is the number of additional reads it would take to detect a new transcript. One way of measuring the sequencing saturation of an array is to determine the number of reads to detect a new UMI. For example, if a new UMI is detected every 2 reads of the feature, the sequencing saturation would be 50%. As another example, if a new UMI is detected every 10 reads of a feature, the sequencing saturation would be 90%.

Arrays of spatially varying resolution can be implemented in a variety of ways. In some embodiments, for example, the pitch between adjacent features in the array varies continuously along one or more linear and/or angular coordinate directions. Thus, for a rectangular array, the spacing between successive rows of features, between successive columns of features, or between both successive rows and successive columns of features, can vary continuously.

In certain embodiments, arrays of spatially varying resolution can include discrete domains with populations of features. Within each domain, adjacent features can have a regular pitch. Thus, for example, an array can include a first domain within which adjacent features are spaced from one another along linear and/or angular coordinate dimensions by a first set of uniform coordinate displacements, and a second domain within which adjacent features are spaced from one another along linear and/or angular coordinate dimensions by a second set of uniform coordinate displacements. The first and second sets of displacements differ in at least one coordinate displacement, such that adjacent features in the two domains are spaced differently, and the resolution of the array in the first domain is therefore different from the resolution of the array in the second domain.

In some embodiments, the pitch of array features can be sufficiently small such that array features are effectively positioned continuously or nearly continuously along one or more array dimensions, with little or no displacement between array features along those dimensions. For example, in a feature array where the features correspond to regions of a substrate (i.e., oligonucleotides are directly bound to the substrate), the displacement between adjacent oligonucleotides can be very small—effectively, the molecular width of a single oligonucleotide. In such embodiments, each oligonucleotide can include a distinct spatial barcode such that the spatial location of each oligonucleotide in the array can be determined during sample analysis. Arrays of this type can have very high spatial resolution, but may only include a single oligonucleotide corresponding to each distinct spatial location in a sample.

In general, the size of the array (which corresponds to the maximum dimension of the smallest boundary that encloses all features in the array along one coordinate direction) can be selected as desired, based on criteria such as the size of the sample, the feature diameter, and the density of capture probes within each feature. For example, in some embodiments, the array can be a rectangular or square array for which the maximum array dimension along each coordinate direction is 10 mm or less (e.g., 9 mm or less, 8 mm or less, 7 mm or less, 6 mm or less, 5 mm or less, 4 mm or less, 3 mm or less). Thus, for example, a square array of features can have dimensions of 8 mm by 8 mm, 7 mm by 7 mm, 5 mm by 5 mm, or be smaller than 5 mm by 5 mm.

(v) Bead Arrays

As used herein, the term "bead array" refers to an array that includes a plurality of beads as the features in the array. In some embodiments, two or more beads are dispersed onto a substrate to create an array, where each bead is a feature on the array. In some embodiments, the beads are attached to a substrate. For example, the beads can optionally attach to a substrate such as a microscope slide and in proximity to a biological sample (e.g., a tissue section that includes cells). The beads can also be suspended in a solution and deposited on a surface (e.g., a membrane, a tissue section, or a substrate (e.g., a microscope slide)). Beads can optionally be dispersed into wells on a substrate, e.g., such that only a single bead is accommodated per well.

Examples of arrays of beads on or within a substrate include beads located in wells such as the BeadChip array (available from Illumina Inc., San Diego, Calif.), arrays used in sequencing platforms from 454 LifeSciences (a subsidiary of Roche, Basel, Switzerland), and array used in sequencing platforms from Ion Torrent (a subsidiary of Life Technologies, Carlsbad, Calif.). Examples of bead arrays are described in, e.g., U.S. Pat. Nos. 6,266,459; 6,355,431; 6,770,441; 6,859,570; 6,210,891; 6,258,568; and 6,274,320; U.S. Pat. Application Publication Nos. 2009/0026082; 2009/0127589; 2010/0137143; 2019/0177777; and 2010/0282617; and PCT Patent Application Publication Nos. WO 00/063437 and WO 2016/162309, the entire contents of each of which is incorporated herein by reference.

In some embodiments, the bead array includes a plurality of beads. For example, the bead array can include at least 10,000 beads (e.g., at least 100,000 beads, at least 1,000,000 beads, at least 5,000,000 beads, at least 10,000,000 beads). In some embodiments, the plurality of beads includes a single type of bead (e.g., substantially uniform in volume, shape, and other physical properties, such as translucence). In some embodiments, the plurality of beads includes two or more types of different beads.

Bead arrays can be generated by attaching beads (e.g., barcoded beads) to a substrate in a regular pattern, or an irregular arrangement. In some embodiments, the barcode sequences are known before attaching them to the substrate. In some embodiments, the barcode sequences are not known before attaching them to the substrate. Beads can be attached to selective regions on a substrate by, e.g., selectively activating regions on the substrate to allow for attachment of the beads. Activating selective regions on the substrate can include activating or degrading a coating (e.g., a conditionally removable coating as described herein) at the selective regions where the coating has been applied on the substrate, rendering the selective regions more permissive to bead attachment as compared to regions outside of the selected regions. The regions that are rendered more permissive for bead attachment can be configured to fit only one bead or multiple beads (e.g., limited by well size or surface patterning, such as fabrication techniques). Beads bound to the selected regions can form a two-dimensional array on the substrate. The substrate can be uniformly or non-uniformly coated with the coating. The beads can be any suitable beads described herein, including beads that are attached to one or more spatial barcodes. Beads can be attached to the selected regions according to any of the methods suitable for attaching beads to substrates described herein, such as through covalent bonds, non-covalent bonds, or chemical linkers.

Any variety of suitable patterning techniques can be used to attach beads to a substrate surface. In some embodiments, in a non-limiting way, physical techniques such as inkjet printing, optical and optoelectronic cell trapping, laser-based patterning, acoustic patterning, dielectrophoresis, or magnetic techniques can be used to pattern the substrate. Alternatively, chemical and/or physiochemical techniques can be used such as, in a non-limiting way, surface chemistry methods, microcontact printing, microwells and filtration, DUV patterning, or patterning in microfluidic devices combined with microcontact printing (See, e.g., Martinez-Rivas, A., Methods of micropatterning and manipulation of cells for biomedical applications, Micromachines (Basel) 8, (2017), which in is incorporated herein by reference).

The coating can be photoreactive, and selectively activating or degrading the coating involves exposing selected regions of the coating to light or radiation. Selectivity can be achieved through the application of photomasks. Regions of the coating that are exposed to light can be rendered more permissive for bead attachment (e.g., more adhesive), as compared to regions not exposed to light (e.g., regions protected from the light by a photomask). When applied to the substrate, the beads thus preferentially attach to the more permissive regions on the substrate, and un-attached beads can optionally be removed from the substrate. The light source and/or the photomask can be adjusted to allow further sites on the substrate to become more permissive for bead attachment, allowing additional beads to be attached at these sites. Alternatively, a different light source, or a different photomask can be applied. The process of photopatterning thus allows beads to be attached at pre-determined locations on the substrate, thereby generating a bead array.

Beads can be attached iteratively, e.g., a subset of the beads can be attached at one time, and the process can be repeated to attach one or more additional subsets of beads. In some embodiments, the size of the activated spot (e.g., spot on the substrate) is smaller than the size of a bead. For example, a bead can be attached to the activated substrate (e.g., spot) such that only a single bead attaches to the activated substrate. In some embodiments, the substrate can be washed to remove unbound beads. In some embodiments, the substrate can be activated in a second location and a second bead can be attached to the activated substrate surface. This process can be done iteratively to attach beads to the entire substrate, or a portion thereof. Alternatively, beads can be attached to the substrate all in one step. Furthermore, methods of attaching beads to a substrate are known in the art. Any suitable method can be used, including, in a non-limiting way, specific chemical bonds, non-specific chemical bonds, linkers, physically trapping the beads (e.g., polymer, hydrogel), or any of the methods described herein.

An exemplary workflow for generating a bead array can include selectively rendering a first set of one or more selected regions on a coated substrate to be more permissive for bead attachment as compared to regions outside of the selected regions, applying a plurality of beads to the array and allowing the beads to attach to the first set of selected regions, optionally removing un-attached beads, rendering a second set of one or more selected regions more permissive to bead attachment as compared to regions outside the second set of selected regions, applying a plurality of beads and allowing the beads to attach to the second set of selected regions, and optionally removing the un-attached beads. This iterative process can be carried out for any number of times to generate a patterned bead array.

Another exemplary process includes activating a first region on a coated substrate and exposing the activated first region to a plurality of barcoded beads, so that a first set of one or more beads are bound to the first region; and activating a second region on the coated substrate and exposing the activated second region to a plurality of barcoded beads, so that a second set of one or more beads are bound to the second region, wherein the first set of one or more beads comprise an identical first oligonucleotide sequence unique to the first region of the surface of the substrate, and the second set of one or more beads comprise an identical second oligonucleotide sequence unique to the second region of the surface of the substrate, and wherein the first and second oligonucleotide sequences are different. Additional regions on the coated substrate may be activated and exposed to additional barcoded beads. Each set of barcoded beads can include an oligonucleotide sequence that is different from all other sets of barcoded beads and that is unique to the location of the activated region. Additionally, the first set of one or more beads and the second set of one or more beads can be different. In other words, the first set of one or more beads and the second set of one or more beads can have different surface chemistries, different compositions (e.g., solid bead, gel bead, silica bead) (e.g., nanoparticles vs microparticles), and/or physical volumes. In some embodiments, a third set of one or more beads, a fourth set of one or more beads, a fifth set of one or more beads or more can have different surface chemistries, different compositions (e.g., solid bead, gel bead, silica bead) (e.g., nanoparticles vs microparticles), and/or physical volumes can be attached to the substrate surface. The methods may include removing the beads that do not bind to the first, second, and/or any of the additional regions. In some embodiments, removing the beads comprise washing the beads off the surface of the substrate. The removing may be carried out after each round of or after several rounds of activating a region (e.g., first, second or additional regions) on the surface of the substrate), and binding of beads to the activated region. In some instances, each bead is bound to the substrate at a single location. The beads bound to the first, second, and additional regions can form a two-dimensional array of beads on the substrate.

A photoreactive coating can comprise a plurality of photoreactive molecules, which can undergo a chemical reaction (e.g., hydrolysis, oxidation, photolysis) when exposed to light of certain wavelengths or range of wavelengths. A photo-reactive molecule can become reactive when exposed to light and can react with other molecules and form chemical bonds with other molecules.

The coating can comprise a polymer, and activating selected regions on the substrate include modifying the polymer at the respective regions. Modifying the polymer includes, for example, photochemically modifying the polymer by exposing the polymer to radiation or light. Alternatively or additionally, modifying the polymer can include chemically modifying the polymer by contacting the polymer with one or more chemical reagents. In some instances, the coating is a hydrogel. In some instances, the coating comprises a photoreactive polymer. Exemplary photo-reactive polymers include poly(ethylene glycol) (PEG)-based polymers, poly(L-lysine) (PLL)-based polymer, copolymer comprising functionalized or unfunctionalized units of PEG and PLL (e.g., poly-L-lysine-grafted-polyethylene glycol (PLL-g-PEG)), and methacrylated gelatin (GelMA) polymers.

Beads can also be attached to selective regions on a substrate by selectively crosslinking beads to a coating that has been applied on the substrate. For example, a plurality of beads can be applied to a substrate having a photocrosslinkable coating, and upon crosslinking of a subset of the beads to the coating, the non-cross-linked beads can be removed, leaving only the cross-linked beads on the substrate. The process can be repeated multiple times. The coating can include a photo-crosslinkable polymer. Exemplary photo-crosslinkable polymers are described, e.g., in Shirai, *Polymer Journal* 46:859-865 (2014), Ravve, *Photocrosslinkable Polymers*, Light-Associated Reactions of Synthetic Polymers. Springer, New York, N.Y. (2006), and Ferreira et al. *Photocrosslinkable Polymers for Biomedical Applications, Biomedical Engineering—Frontiers and Challenges*, Prof. Reza Fazel (Ed.), ISBN: 978-953-307-309-5 (2011), each of which are herein incorporated by reference in its entirety.

Suitable light sources for activating, degrading or crosslinking the coating as described herein include, but are not limited to, Ultraviolet (UV) light (e.g., 250-350 nm or 350-460 nm UV light) and visible light (e.g., broad spectrum visible light). A Digital Micromirror Device (DMD) can also be used to provide the light source.

The distance between a first pair of adjacent selected regions according to the methods described herein can be the same or different from a second pair of adjacent selected regions.

Barcoded beads, or beads comprising a plurality of barcoded probes, can be generated by first preparing a plurality of barcoded probes on a substrate, depositing a plurality of beads on the substrate, and generating probes attached to the beads using the probes on the substrate as a template.

Large scale commercial manufacturing methods allow for millions of oligonucleotides to be attached to an array. Commercially available arrays include those from Roche NimbleGen, Inc., (Wisconsin) and Affymetrix (ThermoFisher Scientific).

In some embodiments, arrays can be prepared according to the methods set forth in WO 2012/140224, WO 2014/060483, WO 2016/162309, WO 2017/019456, WO 2018/091676, and WO 2012/140224, and U.S. Patent Application No. 2018/0245142. The entire contents of each of the foregoing documents are herein incorporated by reference.

In some embodiments, a bead array is formed when beads are embedded in a hydrogel layer where the hydrogel polymerizes and secures the relative bead positions. The bead-arrays can be pre-equilibrated and combined with reaction buffers and enzymes (e.g., reverse-transcription mix). In some embodiments, the bead arrays can be stored (e.g., frozen) long-term (e.g., days) prior to use.

(vi) Flexible Arrays

A "flexible array" includes a plurality of spatially-barcoded features attached to, or embedded in, a flexible substrate (e.g., a membrane, a hydrogel, or tape) placed onto, or proximal to, a biological sample. In some embodiments, a flexible array includes a plurality of spatially-barcoded features embedded within a hydrogel.

Flexible arrays can be highly modular. In some embodiments, spatially-barcoded features (e.g., beads) can be loaded onto a substrate (e.g., a slide) to produce a high-density self-assembled array. In some embodiments, the features (e.g., beads) can be loaded onto the substrate with a flow cell. In some embodiments, the features (e.g., beads) are embedded in a hydrogel (e.g., a hydrogel pad or layer placed on top of the self-assembled features). In some embodiments, the hydrogel can polymerize, thereby securing the features in the hydrogel. In some embodiments, the hydrogel containing the features can be removed from the substrate and used as a flexible array. In some embodiments, the flexible array can be deconvolved by optical sequencing or any other method described herein. In some embodiments, the features (e.g., beads) can be about 1 µm to about 25 µm in diameter. In some embodiments, about 25 µm diameter features in the flexible array can provide for approximately 1000 DPI and about 1 megapixel resolution. In some embodiments, the features (e.g., beads) can be about 13.2 µm in diameter. In some embodiments, the about 13.2 µm beads in the flexible array can provide for approximately 1920×1080 resolution.

Flexible arrays generated according to any of the methods described herein (e.g., beads embedded within a hydrogel) can contain a thermolabile polymer. In some embodiments, flexible arrays having thermolabile beads can be contacted with a biological sample. In some embodiments, a region of interest in the biological sample can be identified such that an infrared laser can be used to select a region of interest. In some embodiments, the infrared laser can cause the flexible array (e.g., thermolabile beads) to deform and become adhesive. In some embodiments, the adhesive portion of the flexible array can adhere (e.g., bind) to the region of interest (e.g., cells) directly above or underneath. The process of identifying a region of interest, applying an infrared laser to the region of interest, and adhering the underlying biological sample (e.g., cells) to the flexible array can iteratively repeated. In some embodiments, the flexible array can be removed such that only the adhered biological sample (e.g., cells) from the one or more regions of interest can also be removed with the flexible array. In some embodiments, the flexible array and the adhered biological sample can be further processed (e.g., amplified, quantitated, and/or sequenced) according to any method described herein.

Flexible arrays can be pre-equilibrated with reaction buffers and enzymes at functional concentrations (e.g., a reverse-transcription mix). In some embodiments, the flexible arrays can be stored for extended periods (e.g., days) or frozen until ready for use. In some embodiments, permeabilization of biological samples (e.g., a tissue section) can be performed with the addition of enzymes/detergents prior to contact with the flexible array. In some embodiments, the flexible array can be placed directly on the sample, or placed in indirect contact with the sample (e.g., with an intervening layer or substance between the biological sample and the flexible bead-array). In some embodiments, the flexible array can be mechanically applied (e.g., pressed downward or compressed between two surfaces) on the biological sample to enhance analyte capture. In some embodiments, a flexible array can be applied to the side of a biological sample. For example, a biological sample can be cut (e.g., sliced) in any direction and a flexible array can be applied to the exposed analytes. In some embodiments, the flexible array can be dissolvable (e.g., via heat, chemical, or enzymatic disruption). In some embodiments, once a flexible array is applied to the sample, reverse transcription and targeted capture of analytes can be performed on microspheres, or beads of a first volume and beads of a second volume, or any of the beads described herein. In some embodiments once a flexible array is applied to the biological sample and allowed to capture analytes, the flexible array can be removed (e.g., peeled) from the biological sample for further processing (e.g., amplification, quantitation, and/or sequencing) according to any method described herein.

Flexible arrays can also be used with any of the methods (e.g., active capture methods such as electrophoresis) described herein. For example, flexible arrays can be contacted with a biological sample on a conductive substrate (e.g., an indium tin oxide coated glass slide), such that an electric field can be applied to the conductive substrate to facilitate migration of analytes through, across, within, or in the direction of the flexible array. Additionally and alternatively, flexible arrays can be contacted to a biological sample in an electrophoretic assembly (e.g., electrophoretic chamber), such that an electric field can be applied to migrate analytes in the direction of the flexible array or across, through, or within the flexible array.

In some embodiments, a flexible array can be generated with the assistance of a substrate holder (e.g., any array alignment device). For example, a spatially-barcoded bead array can be placed in one placeholder of the substrate holder and second substrate (e.g., a glass slide) can be placed in the second placeholder of the substrate holder. In some embodiments, the array is optionally optically decoded and a gel prepolymer solution is introduced between the spatially-barcoded bead array and second substrate. In some embodiments, the substrate holder is closed such that the second substrate is on top (e.g., above, parallel to) the spatially-barcoded bead array. The gel prepolymer solution can be polymerized by any method described herein and result in spatially-barcoded features cross-linked in the hydrogel, thereby generating a flexible array. In some embodiments, the substrate holder can be opened and the second substrate with the hydrogel and the spatially-barcoded cross-linked features can be removed from the substrate holder (the flexible array optionally can be removed from the second substrate) for use in spatial analysis by any of the methods described herein.

(vii) Shrinking Hydrogel Features/Arrays

As used herein "shrinking" or "reducing the size" of a hydrogel refers to any process causing the hydrogel to physically contract and/or the size of the hydrogel to decrease in volume. For example, the scaffold of the gel may shrink or "implode" upon solvent removal (see, e.g., Long and Williams. *Science.* 2018; 362(6420):1244-1245, and Oran et al. *Science* 2018; 362(6420): 1281-1285; each of which is incorporated herein by reference in its entirety). As another example, the process to shrink or reduce the volume of a hydrogel may be one that removes water (i.e., a dehydrating process) from the hydrogel. There are many methods known to one of skill in the art for shrinking or reducing the volume of a hydrogel. Non-limiting examples of a method to shrink or reduce the volume of a hydrogel include exposing the hydrogel to one or more of: a dehydrating solvent, a salt, heat, a vacuum, lyophilization, desiccation, filtration, air-drying, or combinations thereof.

In some embodiments, a hydrogel bead can be decreased in volume (e.g., shrunken hydrogel bead) before being attached to or embedded in a hydrogel. In some embodiments, a hydrogel bead can be decreased in volume (e.g., shrunken hydrogel bead) after being attached to or embedded in a hydrogel. In some embodiments, one or more hydrogel beads can be attached to or embedded in a hydrogel. In some embodiments, one or more hydrogel beads can be decreased in volume (e.g., one or more shrunken hydrogel beads) before being attached to or embedded in a hydrogel. In some embodiments, one or more hydrogel beads can be decreased in volume (e.g., one or more shrunken hydrogel beads) after being attached to or embedded in a hydrogel. In some embodiments, one or more hydrogel beads attached to or embedded in a hydrogel can be decreased in volume. For example, the one or more hydrogel beads and the hydrogel that the hydrogel beads are attached to or embedded in are decreased in volume at the same time (e.g., shrunken hydrogel bead-containing hydrogel). In some embodiments, one or more hydrogel beads attached to or embedded in a hydrogel can be isometrically decreased in volume.

In some embodiments, one or more hydrogel beads attached to or embedded in a hydrogel can be decreased in volume from about 3 fold to about 4 fold. For example, one or more hydrogel beads attached to or embedded in a hydrogel can be decreased in volume by removing or exchanging solvents, salts, or water (e.g., dehydration). In another example, one or more hydrogel beads attached to or embedded in a hydrogel can be decreased in volume by controlling temperature or pH. See e.g., Ahmed, E. M. J. of Advanced Research. 2015 March; 6(2):105-121, which is incorporated herein by reference in its entirety. In some embodiments, one or more hydrogel beads attached to or embedded in a hydrogel can be decreased in volume by removing water.

In some embodiments, decreasing the volume of one or more hydrogel beads attached to or embedded in a hydrogel can increase the spatial resolution of the subsequent analysis of the sample. The increased resolution in spatial profiling can be determined by comparison of the spatial analysis of the sample using one or more shrunken hydrogel beads attached to or embedded in a hydrogel with one or more non-shrunken hydrogel beads attached to or embedded in a hydrogel.

In some embodiments, a hydrogel bead is not decreased in volume. In some embodiments, a hydrogel bead can be decreased in volume (e.g., shrunken hydrogel bead). In some embodiments, a shrunken hydrogel gel bead is stabilized. For example, the hydrogel bead can be decreased in volume by removing solvents, salts, or water (e.g., dehydrated, desiccated, dried, exsiccated) from the hydrogel bead to form a shrunken hydrogel bead. In another example, the hydrogel bead can be decreased in volume by controlling temperature or pH. See e.g., Ahmed, E. M. J. of Advanced Research. 2015 March; 6(2):105-121, which is incorporated herein by reference in its entirety. Non-limiting examples of solvents that may be used to form a shrunken hydrogel bead or shrunken hydrogel bead array include a ketone, such as methyl ethyl ketone (MEK), isopropanol (IPA), acetone, 1-butanol, methanol (MeOH), dimethyl sulfoxide (DMSO), glycerol, propylene glycol, ethylene glycol, ethanol, (k) 1,4-dioxane, propylene carbonate, furfuryl alcohol, N,N-dimethylformamide (DMF), acetonitrile, aldehyde, such as formaldehyde or glutaraldehyde, or any combinations thereof.

In some embodiments, the hydrogel bead or hydrogel bead array is shrunken or stabilized via a cross-linking agent. For example, the cross-linking agent may comprise disuccinimidyl suberate (DSS), dimethylsuberimidate (DMS), formalin, and dimethyladipimidate (DMA), dithiobis(-succinimidyl propionate) (DSP), disuccinimidyl tartrate (DST), and ethylene glycol bis(succinimidyl succinate) (EGS).

In some embodiments, the hydrogel bead or hydrogel bead array is processed with salts to form a shrunken hydrogel bead or shrunken hydrogel bead array. Non-limiting examples of salts that may be used to form a shrunken hydrogel bead or shrunken hydrogel bead array are inorganic salts including aluminum, ammonium, barium, beryllium, calcium, cesium, lithium, magnesium, potassium, rubidium, sodium, and strontium salts. Further non-limiting examples of inorganic salts include sodium chloride, potassium chloride, lithium chloride, cesium chloride, sodium fluoride, sodium bromide, sodium iodide, sodium nitrite, potassium sulfate, potassium nitrate, potassium carbonate, potassium bicarbonate, sodium sulfate, sodium nitrate, sodium carbonate, sodium bicarbonate, calcium sulfate, copper oxychloride, calcium chloride, calcium carbonate, calcium bicarbonate, magnesium sulfate, magnesium nitrate, magnesium chloride, magnesium carbonate, magnesium bicarbonate, ammonium sulfate, ammonium chloride, ammonium nitrate, ammonium carbonate, ammonium bicarbonate, trisodium phosphate, tripotassium phosphate, calcium phosphate, copper(II) sulfate, sodium sulfide, potassium sulfide, calcium sulfide, potassium permanganate, iron (II) chloride, iron(III) chloride, iron (2+) sulfate, iron(III) sulfate, iron(II) nitrate, iron(III) nitrate, manganese(II) chloride, manganese(III) chloride, manganese(II) sulfate, manganese(II) nitrate, zinc chloride, zinc nitrate, zinc sulfate, ammonium orthomolybdate, monopotassium phosphate, nickel(II) sulfate, nickel(II) nitrate, sodium metavanadate, sodium paravanadate, potassium dichromate, ammonium dichromate, antipyonin, ammonium nitrite, potassium fluoride, sodium fluoride, ammonium fluoride, calcium fluoride, chrome alum, potassium alum, potassium iodide, sodium hypochlorite, tin(II) sulfate, tin(II) nitrate, gold selenite, dicesium chromate, potassium perchlorate, calcium perchlorate, aluminum sulphate, lead(II) bisulfate, barium phosphate, barium hydrogen orthophosphate, barium dihydrogen phosphate, silver dichromate, potassium bromate, sodium bromate, sodium iodate, sodium silicate, diammonium phosphate, ammonium phosphate, ammonium dihydrogen phosphate, chromium orthophosphate, copper(II) chloride, copper(I) chloride, sodium tetrametaphosphate, potassium heptafluoroniobate, zinc phosphate, sodium sulfite, copper (I) nitrate, copper(II) nitrate, potassium silicate, copper(II) carbonate basic, copper(II) carbonate salts of acrylic acid and sulfopropyl acrylate.

In some embodiments, the removal of water comprises an acid. Non-limiting examples of an acid include: HCl, HI, HBr, HClO4, HClO3, HNO3, H2SO4, phosphoric acid, phosphorous acid, acetic acid, oxalic acid, ascorbic acid, carbonic acid, sulfurous acid, tartaric acid, citric acid, malonic acid, phthalic acid, barbituric acid, cinnamic acid, glutaric acid, hexanoic acid, malic acid, folic acid, propionic acid, stearic acid, trifluoroacetic acid, acetylsalicylic acid, glutamic acid, azelaic acid, benzilic acid, fumaric acid, gluconic acid, lactic acid, oleic acid, propiolic acid, rosolic acid, tannic acid, uric acid, gallic acid, and combinations of two or more thereof. In some embodiments, the hydrogel is exposed to a different pH environment. For example, the hydrogel can be exposed to an acidic pH or a basic pH. In some embodiments, the hydrogel is exposed to a pH of less than about 6.5, e.g., a pH of about 6, about 5.5, about 5, about 4.5, about 4, about 3.5, about 3, about 2.5, about 2, about 1.5, or about 1. In some embodiments, the hydrogel is exposed to a pH of greater than about 7.5, e.g., a pH of about 8, about 8.5, about 9, about 9.5, about 10, about 10.5, about 11, about 11.5, about 12, about 12.5, about 13, about 13.5, or about 14.

In some embodiments, the removal of water comprises a dehydrating process such as heat, a vacuum, lyophilization, desiccation, filtration, and air-drying. In some embodiments, the hydrogel bead or hydrogel bead array undergoes an alteration in pH to form a shrunken hydrogel bead or shrunken hydrogel bead array (e.g., an alteration from about pH 7 to about pH 5, from about pH 7 to about pH 5.5, from about pH 7 to about pH 6, from about pH 7 to about pH 6.5, from about pH 6.5 to about pH 5, from about pH 6 to about pH 5, from about pH 6 to about pH 5.5, or any pH alteration encompassed within these ranges).

In some embodiments, the hydrogel bead or hydrogel bead array undergoes an alteration in temperature (e.g., an alteration from about 37° C., 38° C., 39° C., 40° C., 41° C., 42° C., 43° C., 44° C., 45° C., 46° C., 47° C., 48° C., 49° C. to about 50° C., 51° C., 52° C., 53° C., 54° C., 55° C., 56° C., 57° C., 58° C., 59° C. 60° C., 61° C., 62° C., 63° C., 64° C., 65° C., 66° C., 67° C., 68° C., 69° C., 70° C., or higher, or any temperature alteration encompassed within these ranges) to form a shrunken hydrogel bead or shrunken hydrogel bead array.

In some embodiments, a hydrogel bead can be decreased in size in linear dimension by about 2 fold, about 3 fold, about 4 fold, about 5 fold, about 6 fold, about 7 fold, about 8 fold, about 9 fold, or any intervals therein. In some embodiments, a hydrogel bead can be decreased in volume by about 1 fold, about 5 fold, about 10 fold, about 15 fold, about 20 fold, about 25 fold, about 30 fold, about 35 fold, about 40 fold, about 45 fold, about 50 fold, about 55 fold, about 60 fold, about 65 fold about 70 fold, about 75 fold, about 80 fold, or any intervals therein. In some embodiments, a hydrogel bead can be decreased in size such that the hydrogel bead has an average diameter of about 1 μm to about 15 μm.

In some embodiments, a plurality of hydrogel beads can be decreased in size in linear dimension by about 2 fold, about 3 fold, about 4 fold, about 5 fold, about 6 fold, about 7 fold, about 8 fold, about 9 fold, or any intervals therein. In some embodiments, a plurality of hydrogel beads can be decreased in size such that the average diameter of a hydrogel bead is about 1 μm to about 15 μm. In some embodiments, a plurality of hydrogel beads can be decreased in volume by about 1 fold, about 5 fold, about 10 fold, about 15 fold, about 20 fold, about 25 fold, about 30 fold, about 35 fold, about 40 fold, about 45 fold, about 50 fold, about 55 fold, about 60 fold, about 65 fold about 70 fold, about 75 fold, about 80 fold, or any intervals therein.

In some embodiments, a plurality of hydrogel beads can be decreased in volume such that the hydrogel bead has an average diameter of about 1 μm to about 15 μm. In some embodiments, a plurality of shrunken hydrogel beads has an average diameter of about 15 μm. In some embodiments, a plurality of shrunken hydrogel beads has an average diameter of about 14 μm. In some embodiments, a plurality of shrunken hydrogel beads has an average diameter of about 13 μm. In some embodiments, a plurality of shrunken hydrogel beads has an average diameter of about 12 μm. In some embodiments, a plurality of shrunken hydrogel beads has an average diameter of about 11 μm. In some embodiments, a plurality of shrunken hydrogel beads has an average diameter of about 10 μm. In some embodiments, a plurality of shrunken hydrogel beads has an average diameter of about 9 μm. In some embodiments, a plurality of shrunken hydrogel beads has an average diameter of about 8 μm. In some embodiments, a plurality of shrunken hydrogel beads has an average diameter of about 7 μm. In some embodiments, a plurality of shrunken hydrogel beads has an average diameter of about 6 μm. In some embodiments, a plurality of shrunken hydrogel beads has an average diameter of about 5 μm. In some embodiments, a plurality of shrunken hydrogel beads has an average diameter of about 4 μm. In some embodiments, a plurality of shrunken hydrogel beads has an average diameter of about 3 μm. In some embodiments, a plurality of shrunken hydrogel beads has an average diameter of about 2 μm. In some embodiments, a plurality of shrunken hydrogel beads has an average diameter of about 1 μm. In some embodiments, a plurality of shrunken hydrogel beads has an average diameter of about 14-15 μm. In some embodiments, a plurality of shrunken hydrogel beads has an average diameter of about 13-15 μm. In some embodiments, a plurality of shrunken hydrogel beads has an average diameter of about 12-15 μm. In some embodiments, a plurality of shrunken hydrogel beads has an average diameter of about 11-15 μm. In some embodiments, a plurality of shrunken hydrogel beads has an average diameter of about 10-15 μm. In some embodiments, a plurality of shrunken hydrogel beads has an average diameter of about 9-15 μm. In some embodiments, a plurality of shrunken hydrogel beads has an average diameter of about 8-15 μm. In some embodiments, a plurality of shrunken hydrogel beads has an average diameter of about 7-15 μm. In some embodiments, a plurality of shrunken hydrogel beads has an average diameter of about 6-15 μm. In some embodiments, a plurality of shrunken hydrogel beads has an average diameter of about 1-10 μm. In some embodiments, a plurality of shrunken hydrogel beads has an average diameter of about 1-5 μm. In some embodiments, a plurality of shrunken hydrogel beads has an average diameter of about 1-3 μm. In some embodiments, a plurality of shrunken hydrogel beads has an average diameter of about 13-14 μm. In some embodiments, a plurality of shrunken hydrogel beads has an average diameter of about 12-14 μm. In some embodiments, a plurality of shrunken hydrogel beads has an average diameter of about 11-14 μm. In some embodiments, a plurality of shrunken hydrogel beads has an average diameter of about 10-14 μm. In some embodiments, a plurality of shrunken hydrogel beads has an average diameter of about 9-14 μm. In some embodiments, a plurality of shrunken hydrogel beads has an average diameter of about 8-14 μm. In some embodiments, a plurality of shrunken hydrogel beads has an average diameter of about 7-14 μm. In some embodiments, a plurality of shrunken hydrogel beads has an average diameter of about 6-14 μm. In some embodiments, a plurality of shrunken hydrogel beads has an average diameter of about 5-14 μm. In some embodiments, a plurality of shrunken hydrogel beads has an average diameter of about 12-13 μm. In some embodiments, a plurality of shrunken hydrogel beads has an average diameter of about 11-13 μm. In some embodiments, a plurality of shrunken hydrogel beads has an average diameter of about 10-13 μm. In some embodiments, a plurality of shrunken hydrogel beads has an average diameter of about 9-13 μm. In some embodiments, a plurality of shrunken hydrogel beads has an average diameter of about 8-13 μm. In some embodiments, a plurality of shrunken hydrogel beads has an average diameter of about 7-13 μm. In some embodiments, a plurality of shrunken hydrogel beads has an average diameter of about 6-13 μm. In some embodiments, a plurality of shrunken hydrogel beads has an average diameter of about 5-13 μm. In some embodiments, a plurality of shrunken hydrogel beads has an average diameter of about 11-12 μm. In some embodiments, a plurality of shrunken hydrogel beads has an average diameter of about 10-12 μm. In some embodiments, a plurality of shrunken hydrogel beads has an average diameter of about 9-12 μm. In some embodiments, a plurality of shrunken hydrogel beads has an average diameter of about 8-12 μm. In some embodiments, a plurality of shrunken hydrogel beads has an average diameter of about 7-12 µm. In some embodiments, a plurality of shrunken hydrogel beads has an average diameter of about 6-12 µm. In some embodiments, a plurality of shrunken hydrogel beads has an average diameter of about 5-12 µm. In some embodiments, a plurality of shrunken hydrogel beads has an average diameter of about 10-11 µm. In some embodiments, a plurality of shrunken hydrogel beads has an average diameter of about 9-11 µm. In some embodiments, a plurality of shrunken hydrogel beads has an average diameter of about 8-11 µm. In some embodiments, a plurality of shrunken hydrogel beads has an average diameter of about 7-11 µm. In some embodiments, a plurality of shrunken hydrogel beads has an average diameter of about 6-11 µm. In some embodiments, a plurality of shrunken hydrogel beads has an average diameter of about 5-11 µm. In some embodiments, a plurality of shrunken hydrogel beads has an average diameter of about 9-10 µm. In some embodiments, a plurality of shrunken hydrogel beads has an average diameter of about 8-10 µm. In some embodiments, a plurality of shrunken hydrogel beads has an average diameter of about 7-10 µm. In some embodiments, a plurality of shrunken hydrogel beads has an average diameter of about 6-10 µm. In some embodiments, a plurality of shrunken hydrogel beads has an average diameter of about 5-10 µm. In some embodiments, a plurality of shrunken hydrogel beads has an average diameter of about 8-9 µm. In some embodiments, a plurality of shrunken hydrogel beads has an average diameter of about 7-9 µm. In some embodiments, a plurality of shrunken hydrogel beads has an average diameter of about 6-9 µm. In some embodiments, a plurality of shrunken hydrogel beads has an average diameter of about 5-9 µm. In some embodiments, a plurality of shrunken hydrogel beads has an average diameter of about 7-8 µm. In some embodiments, a plurality of shrunken hydrogel beads has an average diameter of about 6-8 µm. In some embodiments, a plurality of shrunken hydrogel beads has an average diameter of about 5-8 µm. In some embodiments, a plurality of shrunken hydrogel beads has an average diameter of about 6-7 µm. In some embodiments, a plurality of shrunken hydrogel beads has an average diameter of about 5-7 µm. In some embodiments, a plurality of shrunken hydrogel beads has an average diameter of about 5-6 µm.

In some embodiments, one or more hydrogel beads can be decreased in volume at the same time. In some embodiments, one or more hydrogel beads can be decreased in volume at different times. In some embodiments, one or more hydrogel beads can be assembled into an array before decreasing the volume of the one or more hydrogel beads. In some embodiments, one or more hydrogel beads can be assembled into an array after decreasing the volume of the one or more hydrogel beads. In some embodiments, the one or more shrunken hydrogel beads can be reversibly attached to a substrate. In some embodiments, the one or more shrunken hydrogel beads can be irreversibly attached to a substrate. In some embodiments, the one or more shrunken hydrogel beads can be re-expanded. In some embodiments, the one or more shrunken hydrogel beads can be isometrically re-expanded. In some embodiments, the one or more shrunken hydrogel beads can be re-expanded primarily in the z-dimension. In some embodiments, the one or more shrunken hydrogel beads attached to a substrate (e.g., reversibly or irreversibly) can be re-expanded primarily in the z-dimension. In some embodiments, the one or more shrunken hydrogel beads attached to a substrate (e.g., reversibly or irreversibly) can be isometrically re-expanded primarily in the z-dimension.

In some embodiments, decreasing the volume of the hydrogel bead (e.g., shrunken hydrogel bead) can increase the spatial resolution of the subsequent analysis of the sample. The increased resolution in spatial profiling can be determined by comparison of spatial analysis of the sample using a shrunken hydrogel bead with a non-shrunken hydrogel bead. For example, in some embodiments, the subsequent analysis of the sample can include any array-based spatial analysis method disclosed herein.

In some embodiments, one or more physical parameters or dimensions and/or one or more other characteristics of the hydrogel bead may be changed. For example, a cross-section of the hydrogel bead may be changed from a first cross-section to a second cross-section. The first cross-section may be smaller or larger than the second cross-section. Alternatively, or in addition, one or more other characteristics of the hydrogel bead may be changed. For example, the fluidity, density, rigidity, porosity, refractive index, polarity, and/or other characteristic of the hydrogel bead or one or more components thereof may be changed. In a non-limiting example, the hydrogel bead includes a hydrogel. In another example, the hydrogel bead hydrogel may form crosslinks within the bead. The same or different conditions may be used to change or affect different characteristics of the hydrogel bead at the same or different times. In some cases, a first condition or set of conditions may be used to change a first characteristic or set of characteristics of the hydrogel bead (e.g., a cross-section) and a second condition or set of conditions may be used to change a second characteristic or set of characteristics of the hydrogel bead. The first condition or set of conditions may be applied at the same or a different time as the second condition or set of conditions. For example, a first characteristic or set of characteristics may be changed under a first condition or set of conditions, after which a second characteristic or set of characteristics may be changed under a second condition or set of conditions.

A characteristic or set of characteristics of the hydrogel bead may be changed by one or more conditions. A condition suitable for changing a characteristic or set of characteristics of the hydrogel bead may be, for example, a temperature, a pH, an ion or salt concentration, a pressure, chemical species, any combinations thereof, or another condition. For example, hydrogel bead may be exposed to a chemical species that may bring about a change in one or more characteristics of the hydrogel bead. In some cases, a stimulus may be used to change one or more characteristics of the hydrogel bead. For example, upon application of the stimulus, one or more characteristics of the hydrogel bead may be changed. The stimulus may be, for example, a thermal stimulus, a photo stimulus, a chemical stimulus, or another stimulus. A temperature sufficient for changing one or more characteristics of the hydrogel bead may be, for example, at least about 0 degrees Celsius (° C.), 1° C., 2° C., 3° C., 4° C., 5° C., 10° C., or higher. For example, the temperature may be about 4° C. In other cases, a temperature sufficient for changing one or more characteristics of the hydrogel bead may be, for example, at least about 25° C., 30° C., 35° C., 37° C., 40° C., 45° C., 50° C., or higher. For example, the temperature may be about 37° C. A pH sufficient for changing one or more characteristics of the hydrogel bead may be, for example, between about 5 and 8, such as between about 6 and 7.

In some cases, a chemical species or a chemical stimulus may be used to change one or more characteristics of the hydrogel bead. For example, a chemical species or a chemical stimulus may be used to change a dimension of a hydrogel bead (e.g., a cross-section, diameter, or volume). In some cases, a chemical species or a chemical stimulus may be used to change a dimension of a hydrogel bead (e.g., a cross-sectional diameter) from a first dimension to a second dimension (e.g., a second cross-sectional dimeter), where the second dimension is reduced compared to the first dimension. The chemical species may comprise an organic solvent, such as an alcohol, ketone, or aldehyde. For example, the chemical species may comprise acetone, methanol, ethanol, formaldehyde, or glutaraldehyde. The chemical species may comprise a cross-linking agent. For example, the cross-linking agent may comprise disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS), and any combinations thereof. In some cases, a cross-linking agent may be a photo-cleavable cross-linking agent. In some cases, a chemical stimulus may be used to change one or more characteristics of the hydrogel bead (e.g., a dimension of a hydrogel bead), where the chemical stimulus comprises one or more chemical species. For example, the chemical stimulus may comprise a first chemical species and a second chemical species, where the first chemical species is an organic solvent and the second chemical species is a cross-linking agent. In some cases, a chemical stimulus may comprise a chemical species that is a fixation agent that is capable of fixing or preserving a hydrogel bead. For example, an organic solvent such as an alcohol (e.g., ethanol or methanol), ketone (e.g., acetone), or aldehyde (e.g., formaldehyde or glutaraldehyde), or any combinations thereof may act as a fixation agent. Alternatively, or in addition, a cross-linking agent may act as a fixation agent. In some cases, a fixation agent may comprise disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and/or ethylene glycol bis(succinimidyl succinate) (EGS), and any combinations thereof. In some cases, a first chemical species and/or fixation agent may be provided to or brought into contact with the hydrogel bead to bring about a change in a first characteristic or set of characteristics of the hydrogel bead, and a second chemical species and/or fixation agent may be provided to or brought into contact with the hydrogel bead to bring about a change in a second characteristic or set of characteristics of the hydrogel bead. For example, a first chemical species and/or fixation agent may be provided to or brought into contact with the hydrogel bead to bring about a change in a dimension of a hydrogel bead (e.g., a reduction in cross-sectional diameter), and a second chemical species and/or fixation agent may be provided to or brought into contact with the hydrogel bead to bring about a change in a second characteristic or set of characteristics of the hydrogel bead (e.g., forming crosslinks within and/or surrounding the hydrogel bead). The first and second chemical species and/or fixation agents may be provided to or brought into contact with the hydrogel bead at the same or different times.

In some embodiments, fixation may affect one or more parameters or characteristics of the hydrogel bead. For example, fixation may result in shrinkage or volumetric reduction of the hydrogel bead. Fixation may include dehydration of the hydrogel bead. Providing a fixation agent to the hydrogel bead may result in a change in a dimension of the hydrogel bead. For example, providing a fixation agent to the hydrogel bead may result in a change in the volume or diameter of the hydrogel bead. Providing a fixation agent to the hydrogel bead may result in a change in a cross-section of the hydrogel bead (e.g., a cross-sectional diameter). For example, a first cross-section of the hydrogel bead prior to fixation may be different (e.g., larger) than a second cross-section of the hydrogel bead following fixation. In an example, an approximately spherical hydrogel bead may comprise a first cross section (e.g., a cross-sectional diameter) prior to fixation that is reduced in size to a second cross-section following fixation. Providing a fixation agent to the hydrogel bead may result in a second cross-section that is reduced by at least about 5% compared to the first cross-section. In some cases, the second cross-section may be reduced by at least 6%, 8%, 10%, 15%, 25%, 30%, 35%, 40%, 45%, 50%, or more relative to the first cross-section. For example, the second cross-section may be reduced by at least about 10%, 15%, 25%, or 50% relative to the first cross-section. Fixation may also affect other features of the hydrogel bead. For example, fixation may result in a change in the porosity of a membrane or wall of a hydrogel bead, reorganization of components of the hydrogel bead, a change in hydrogel bead fluidity or rigidity, or other changes. In an example, a first fixation agent that is an organic solvent is provided to the hydrogel bead to change a first characteristic (e.g., hydrogel bead volume) and a second fixation agent that is a cross-linking agent is provided to the hydrogel bead to change a second characteristic (e.g., hydrogel bead fluidity or rigidity). The first fixation agent may be provided to the hydrogel bead before the second fixation agent.

In some instances, an approximately spherical hydrogel bead may comprise a first diameter prior to fixation (e.g., by an organic solvent) that is reduced in volume compared to a second diameter following fixation when maintained in a non-aqueous environment. Following fixation and reduction in volume to said second diameter, when maintained in an aqueous environment, the hydrogel bead may increase in volume to have a diameter substantially similar to the first diameter. In some cases, an approximately spherical hydrogel bead may include a first diameter prior to fixation (e.g., by an organic solvent) that is reduced in volume compared to a second diameter following fixation. Following fixation and reduction in volume to said second diameter, the hydrogel bead may be cross-linked by a second fixative, wherein the second diameter is substantially maintained in an aqueous environment following cross-linking by the second fixative.

A change to a characteristic or set of characteristics of the hydrogel bead may be reversible or irreversible. In some cases, a change to a characteristic or set of characteristics of the hydrogel bead may be irreversible, such that the change cannot be readily undone. For example, the volume, morphology, or other feature of the hydrogel bead may be altered in a way that cannot be readily reversed. In an example, the change from a first cross-section of the hydrogel bead to a second cross-section of the hydrogel bead is irreversible. In some cases, an irreversible change may be at least partially reversed upon the application of appropriate conditions and/or over a period of time. In other cases, a change to a characteristic or set of characteristics of the hydrogel bead may be reversible. For example, the volume of a hydrogel bead may be reduced upon being subjected to a first condition or set of conditions, and the volume of a hydrogel bead may be increased to approximately the original volume upon being subjected to a second condition or set of conditions. Thus, the change from a first cross-section of the hydrogel bead to the second cross-section may be reversible. A reversible change (e.g., a reversible volume reduction) may be useful in, for example, providing a hydrogel bead of a given volume to a given location, such as a partition. In some cases, a change to a characteristic or set of characteristics of the hydrogel bead may be only partially reversible. For example, the volume of a hydrogel bead may be reduced (e.g., by dehydration), and the reduction in hydrogel bead volume may be accompanied by reorganization of components within the hydrogel bead. Upon reversal of the volume of the hydrogel bead (e.g., by rehydration), the arrangement of one or more components may not revert to the original arrangement of the hydrogel bead prior to the volume reduction. A change to a characteristic or set of characteristics of the hydrogel bead, such as a cross-section of the hydrogel bead, may be reversible upon application of a stimulus. The stimulus may be, for example, a thermal stimulus, a photo stimulus, or a chemical stimulus. In some cases, the stimulus may comprise a change in pH and/or application of a reducing agent such as dithiothreitol. Application of the stimulus may reverse, wholly or in part, a change from, for example, a first cross-section to a second cross-section.

In some embodiments, a plurality of hydrogel beads can be shrunken hydrogel beads generated by removing water from a plurality of first hydrogel beads. In some embodiments, the plurality of shrunken hydrogel beads has an average diameter no larger than about 15 microns. For example, the plurality of shrunken hydrogel beads has an average diameter no larger than about 15, 14, 13, 12, 11, 10, 9, 8, 7, 6, 5, 4, 3, 2, or 1 micron. In some embodiments, each member of the plurality of shrunken hydrogel beads has a diameter no larger than about 15 microns. For example, each member of the plurality of shrunken hydrogel beads can have a diameter no larger than about 15, 14, 13, 12, 11, 10, 9, 8, 7, 6, 5, 4, 3, 2, or 1 micron. In some embodiments, the plurality of shrunken hydrogel beads has an average diameter no larger than 10 microns. In some embodiments, each member of the plurality of shrunken hydrogel beads has a diameter no larger than 10 microns. In some embodiments, the plurality of shrunken hydrogel beads has an average diameter no larger than 5 microns. In some embodiments, each member of the plurality of shrunken hydrogel beads has a diameter no larger than 5 microns. In some embodiments, the plurality of shrunken hydrogel beads has an average diameter no larger than 1 micron. In some embodiments, each member of the plurality of shrunken hydrogel beads has a diameter no larger than 1 micron. In some embodiments, the plurality of shrunken hydrogel beads has an average diameter no larger than the diameter of a cell (e.g., a mammalian cell, a plant cell, or a fungal cell). In some embodiments, each member of the plurality of shrunken hydrogel beads has a diameter no larger than the diameter of a cell (e.g., a mammalian cell, a plant cell, or a fungal cell).

In some embodiments, the plurality of shrunken hydrogel beads has a polydispersity index of less than about 25%. For example, the plurality of shrunken hydrogel beads can have a polydispersity index of less than about 25%, 20%, 15%, 10%, 9%, 8%, 7%, 6%, 5%, 4%, 3%, 2%, or 1%. In some embodiments, the plurality of shrunken hydrogel beads has a polydispersity index of less than 15%. In some embodiments, the plurality of shrunken hydrogel beads has an average diameter of about 8 to about 13 microns. In some embodiments, the plurality of shrunken hydrogel beads has an average diameter of about 10 to about 12 microns. In some embodiments, the plurality of shrunken hydrogel beads has an average diameter of about the diameter of a cell (e.g., a mammalian cell, a plant cell, or a fungal cell). In some embodiments, the plurality of shrunken hydrogel beads has an average diameter of less than the diameter of a cell (e.g., a mammalian cell, a plant cell, or a fingal cell). In some embodiments, the plurality of capture probes on the plurality of shrunken gel beads bind cellular analytes at single-cell resolution. In some embodiments, the plurality of capture probes on the plurality of shrunken gel beads bind cellular analytes at higher than single-cell resolution (e.g., at a resolution that is at a higher density than the diameter of a cell).

In some embodiments, bead arrays having a plurality of hydrogel beads disposed on a substrate are generated by patterning or self-assembly of larger gel beads, after which the array of larger gel beads is shrunken (e.g., by any of the variety of methods provided herein). In some embodiments, the larger gel beads are not small enough for single-cell resolution, while the shrunken gel beads are small enough for single-cell resolution. In some embodiments, bead arrays having a plurality of hydrogel beads disposed on a substrate are generated by patterning or self-assembly of shrunken gel beads that have previously been generated by shrinking larger gel beads (e.g., by any of the variety of methods provided herein). Beads can be spatially confined by any of a variety of methods, including without limitation, reversible or irreversible crosslinking.

In some embodiments, bead arrays include spatially-confined gel beads with high aspect ratios (e.g., pillared arrays). For example, bead arrays having a plurality of hydrogel beads disposed on a substrate can be generated by any of the variety of methods described herein (e.g., by patterning or self-assembly of shrunken gel beads or by patterning or self-assembly of larger gel beads followed by shrinking), after which the high-density bead array is expanded (or re-expanded). When expanding, spatial constraints direct the beads to expand primarily in the Z dimension (away from the substrate), resulting in pillar arrays. In some embodiments, the gel beads of the pillar arrays have high aspect ratios. In some embodiments, aspect ratio of the expanded plurality of spatially-confined shrunken hydrogel beads is at least 2. In other embodiments, the aspect ratio of the expanded plurality of spatially-confined shrunken hydrogel beads is at least 3. In some embodiments, the plurality of spatially-confined shrunken hydrogel beads has an average aspect ratio of at least 4, 5, 6, 7, 8 or more.

In some embodiments, the method for the removal of water from a hydrogel is the same for each hydrogel (e.g., the first hydrogel, the second hydrogel, or the third hydrogel). In some embodiments, the method for the removal of water from one hydrogel (e.g., the first hydrogel) is different from the method for the removal of water for at least one other hydrogel (e.g., a second hydrogel, a third hydrogel, or a fourth hydrogel). For example, the method for the removal of water from one hydrogel can be different from the method for the removal of water for the other hydrogels (e.g., a second hydrogel, a third hydrogel, or a fourth hydrogel). In some embodiments, the method for the removal of water is different for each hydrogel (e.g., the first hydrogel, the second hydrogel, the third hydrogel, and the fourth hydrogel).

In some embodiments, the shrunken hydrogel is at least about 2-fold smaller in a linear dimension (e.g., along one axis) than the pre-shrunk hydrogel. For example, at least about 2.5, about 3, about 4, about 5, about 6, about 7, about 8, about 9, about 10, or more fold smaller in a linear dimension than the pre-shrunk hydrogel.

In some embodiments, the size of the hydrogel is reduced along more than one axes, e.g., along 2 or 3 axes. In some embodiments, each axis intersects each other axis at 90 degrees. In some embodiments, the size of the hydrogel along the first axis is about 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the size of the hydrogel along the second axis is about 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the size of the hydrogel along the third axis is about 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the reduction in the volume of the hydrogel is isometric.

In some embodiments, the volume of each hydrogel (e.g., a first hydrogel, a second hydrogel, a third hydrogel, or a fourth hydrogel) is the same. In some embodiments, the volume of at least one hydrogel is different. For example, in some embodiments, one hydrogel is different in volume from the other hydrogels (e.g., a second hydrogel, a third hydrogel, or a fourth hydrogel). In some embodiments, every hydrogel is different in volume from every other hydrogel.

In some embodiments, members of the plurality of features are cross-linked to a hydrogel (e.g., a first hydrogel, a second hydrogel, a third hydrogel, or a fourth hydrogel).

In one embodiment, features of an array can be copied into a hydrogel, and the volume of the hydrogel is reduced by removing water. These steps can be performed multiple times. For example, a method for preparing a high-density spatially-barcoded flexible array can include copying a plurality of spatially-barcoded features from an array into a first hydrogel, wherein the first hydrogel is in contact with the array; reducing the volume of the first hydrogel including the copied features by removing water, forming a first shrunken hydrogel including the copied features; copying the features in the first shrunken hydrogel into a second hydrogel, where the second hydrogel is in contact with the first hydrogel; and reducing the volume of the second hydrogel including the copied features by removing water, forming a second shrunken hydrogel including the copied features, thus generating a high-density spatially-barcoded array. The process of copying spatially-barcoded features from an array to a first hydrogel, removing water from the first hydrogel to form a first shrunken hydrogel, and copying spatially-barcoded features from the first shrunken hydrogel to one or more subsequent hydrogels can be performed multiple times (e.g., 2, 3, 4, 5, 6, 7, 8, 9, or 10 times). The result is a high-density flexible array including spatially-barcoded features.

In some embodiments, copying members of the plurality of features from an array includes copy by PCR. In some embodiments, the hydrogel (e.g., a first hydrogel, a second hydrogel, a third hydrogel, and/or a fourth hydrogel) comprises PCR reagents as described herein. In some embodiments, members of the plurality of features are copied using replica plating techniques (see, e.g., Mitra and Church, *Nucleic Acids Res.* 1999 Dec. 15; 27(24):e34, which is incorporated by reference herein in its entirety). In some embodiments, after copying a plurality of features from an array into a first hydrogel, the features of the array are amplified in the first hydrogel (e.g., clonal amplification). In some embodiments, members of the plurality of features are copied into the first hydrogel such that the pattern of the plurality of features of the first hydrogel is the same or substantially similar (e.g., at least 80%) to the pattern of the plurality of features of the array.

In some embodiments, one or more pluralities of features of the array are partitioned. For example, each partition can comprise a plurality of features different from the plurality of features of other partitions. For example, the members of the plurality of features are partitioned similar to the partitions of the plurality of features of the array. In some embodiments, the features of the array are copied into the first hydrogel, such that the volume or diameter of the pre-shrunk first hydrogel features are similar to the volume or diameter of the array features.

In some embodiments, the volume of a hydrogel comprising copied features is reduced, thus increasing the density of the copied features. In some embodiments, the copied features within a hydrogel further increases in density with each subsequent hydrogel copy and shrinking. For example, the density of the copied features of a second shrunken hydrogel is higher than the density of the copied features of a first shrunken hydrogel. Similarly, the density of the copied features of a third shrunken hydrogel is higher than the density of the copied features of a second shrunken hydrogel. Similarly, the density of the copied features of a fourth shrunken hydrogel is higher than the density of the copied features of a third shrunken hydrogel. In some embodiments, the volume of a partition of members of the plurality of features in a hydrogel is reduced when the volume of the hydrogel is reduced.

In some embodiments of the methods described herein, an array comprises shrunken gel features (e.g., beads). In some embodiments, the methods described herein generate shrunken gel bead arrays. In some embodiments, the shrunken gel beads of the array are shrunken hydrogel beads.

A "shrunken array" includes a plurality of spatially-barcoded features attached to, or embedded in, a substrate that have been reduced in volume (e.g., reduction in diameter or volume). A biological sample can be contacted with a shrunken array and further contacted with a solution capable of rehydrating the shrunken array. In some embodiments, analyte transfer and capture is driven by molecular diffusion. The process of rehydrating the shrunken array by providing a permeabilization solution or tissue stain to the sample can promote analytes (e.g., transcripts) present in the biological sample towards the spatially-barcoded features, thereby improving capture efficiency of the analytes. See, e.g., J. Vlassakis, A. E. Herr. "Effect of Polymer Hydration State on In-Gel Immunoassays." *Anal. Chem.* 2015, 87(21): 11030-8, herein incorporated by reference in its entirety.

A shrunken array can be generated with features (e.g., beads) containing spatial barcodes from an existing array. For example, an array (e.g., hydrogel bead array) described and prepared by any method herein can be contacted with reagents capable of dehydrating (e.g., removing water) the features (e.g., beads) to generate a shrunken array (e.g., a shrunken bead array). Methods of dehydrating features (e.g., beads) are known in the art. Any suitable method of dehydration (e.g., removing water) can be used. For example, in a non-limiting way, features (e.g., beads) can be dehydrated by a ketone, such as methyl ethyl ketone (MEK), isopropanol (IPA), acetone, 1-butanol, methanol (MeOH), dimethyl sulfoxide (DMSO), glycerol, propylene glycol, ethylene glycol, ethanol, (k) 1,4-dioxane, propylene carbonate, furfuryl alcohol, N,N-dimethylformamide (DMF), acetonitrile, aldehyde, such as formaldehyde or glutaraldehyde, or any combinations thereof. Additional dehydration agents include various salts, including inorganic salts (See, e.g., Ahmed, E. M., Hydrogel: Preparation, characterization, and applications: A review, *Journal of Advanced Research*, 6 (2) 105-121 (2015), which is incorporated herein by reference).

In some embodiments, the dehydrated features (e.g., beads) can create a shrunken array (e.g., shrunken bead array or shrunken hydrogel array) where the average diameter of the dehydrated features (e.g., beads) can be smaller than the average diameter of the features prior to dehydration. In some embodiments, the dehydrated features (e.g., beads) can have an average diameter at least two-fold smaller than the average diameter of the features prior to dehydration. In some embodiments, the dehydrated features (e.g., beads) can have an average diameter at least three-fold smaller than the average diameter of the features prior to dehydration. In some embodiments, the dehydrated features (e.g., beads) can have an average diameter at least four-fold or smaller than the average diameter of the features (e.g., beads) prior to dehydration.

After generating a shrunken array, a biological sample (e.g., tissue sample) can be contacted with the shrunken array (e.g., shrunken bead array). A rehydrating solution can be provided to the biological sample and the shrunken array by any suitable method (e.g., by pipetting). The rehydrating solution can contain reagents to rehydrate (e.g., water or buffers) the features (e.g., beads) of the shrunken array. In some embodiments, the rehydrating solution can be applied to the entire biological sample. In some embodiments, the rehydrating solution can be selectively applied (e.g., to a region of interest). In some embodiments, absorbing water from the rehydrating solution can increase the diameter of at least one feature (e.g., bead) in the shrunken array. In some embodiments, the rehydrating solution can increase the diameter of at least one feature (e.g., bead) by at least two-fold. In some embodiments, the rehydrating solution can increase the diameter of at least one feature (e.g., bead) by at least three-fold. In some embodiments, the rehydrating solution can increase the diameter of at least one feature (e.g., bead) by at least four-fold. In some embodiments, the rehydrating solution can increase the diameter of at least one feature (e.g., bead) by at least five-fold or more.

In some embodiments, the rehydrating solution can contain permeabilization reagents. The biological sample can be permeabilized using permeabilization reagents and techniques known in the art or otherwise described herein. Biological samples from different sources (e.g., brain, liver, ovaries, kidney, breast, colon, etc.) can require different permeabilization treatments. For example, permeabilizing the biological sample (e.g., using a protease) can facilitate the migration of analytes to the substrate surface (e.g., spatially-barcoded features). In some embodiments, the permeabilization reagents can be a detergent (e.g., saponin, Triton X-100™, Tween-20™). In some embodiments, an organic solvent (e.g., methanol, acetone) can permeabilize cells of the biological sample. In some embodiments, an enzyme (e.g., trypsin) can permeabilize the biological sample. In another embodiment, an enzyme (e.g., collagenase) can permeabilize the biological sample.

In some embodiments the solution can permeabilize the biological sample and rehydrate the features (e.g., beads) of the shrunken array (e.g., shrunken hydrogel). In some embodiments, the rehydrating solution can stain the biological sample and rehydrate the features of the shrunken array (e.g., beads).

In some embodiments, the rehydrating solution (e.g., permeabilization or stain solution) can diffuse through the biological sample. In some embodiments, the rehydrating solution can reduce diffusion of analytes away from the substrate. In some embodiments, while diffusing through the biological sample, the rehydrating solution can migrate analytes toward the substrate surface and improve the efficiency of analyte capture.

(viii) Microcapillary Arrays

A "microcapillary array" is an arrayed series of features that are partitioned by microcapillaries. A "microcapillary channel" is an individual partition created by the microcapillaries. For example, microcapillary channels can be fluidically isolated from other microcapillary channels, such that fluid or other contents in one microcapillary channel in the array are separated from fluid or other contents in a neighboring microcapillary channel in the array. The density and order of the microcapillary channels can be any suitable density or order of discrete sites.

In some embodiments, microcapillary arrays are treated to generate conditions that facilitate loading. An example is the use of a corona wand (BD-20AC, Electro Technic Products) to generate a hydrophilic surface. In some embodiments, a feature (e.g., a bead with capture probes attached) is loaded onto a microcapillary array such that the exact position of the feature within the array is known. For example, a capture probe containing a spatial barcode can be placed into a microcapillary channel so that the spatial barcode can enable identification of the location from which the barcoded nucleic acid molecule was derived.

In some embodiments, when random distribution is used to distribute features, empirical testing can be performed to generate loading/distribution conditions that facilitate a single feature per microcapillary. In some embodiments, it can be desirable to achieve distribution conditions that facilitate only a single feature (e.g., bead) per microcapillary channel. In some embodiments, it can be desirable to achieve distribution conditions that facilitate more than one feature (e.g., bead) per microcapillary channel, by flowing the features through the microcapillary channel.

In some embodiments, the microcapillary array is placed in contact with a sample (e.g., on top or below) so that microcapillaries containing a feature (e.g., a bead, which can include a capture probe) are in contact with the biological sample. In some embodiments, a biological sample is placed onto an exposed side of a microcapillary array and mechanical compression is applied, moving the biological sample into the microcapillary channel to create a fluidically isolated reaction chamber containing the biological sample.

In some embodiments, a biological sample is partitioned by contacting a microcapillary array to the biological sample, thereby creating microcapillary channels including a bead and a portion of the biological sample. In some embodiments, a portion of a biological sample contained in a microcapillary channel is one or more cells. In some embodiments, a feature is introduced into a microcapillary array by flow after one or more cells are added to a microcapillary channel.

In some embodiments, reagents are added to the microcapillary array. The reagents can include enzymatic reagents or reagent mixtures for performing amplification of a nucleic acid. In some embodiments, the reagents include a reverse transcriptase, a ligase, one or more nucleotides, or any combinations thereof. One or more microcapillary channels can be sealed after reagents are added to the microcapillary channels, e.g., by using silicone oil, mineral oil, a non-porous material, or lid.

In some embodiments, a reagent solution is removed from each microcapillary channel following an incubation for an amount of time and at a certain temperature or range of (ix) Hydrogel/Well Arrays In some embodiments are methods for generating patterned hydrogel arrays using wells (e.g., a nanowell or microwell array). In some embodiments, the well is a 3-dimensional structure. In some embodiments, the top view of a well is any suitable 2-dimensional shape, which when extended along the z-axis, produces a 3-dimensional structure capable of containing one or more features (e.g., beads) and/or reagents. Non-limiting examples of wells which may form an array include a triangular prism, a square or rectangular prism, a pentagonal prism, a hexagonal prism, a heptagonal prism, an octagonal prism, an n-sided prism, or a cylindrical array (e.g., "microcapillary array"). In some embodiments, a well of the well array shares at least one well wall (or a portion of the well wall, if a microcapillary array) with an adjacent well. In some embodiments, a well does not share any walls or portion of a wall in common with another well of the array. In some embodiments, the well array is attached to a substrate, such that the wells of the well array are fluidically isolated from each other. In some embodiments, one end of the well array is open (e.g., exposed), wherein the open end can be used to distribute features or reagents into the well.

In some embodiments, the method includes providing shrunken (e.g., dehydrated) hydrogel features (e.g., beads) to a well array. The hydrogel features can be dehydrated (e.g., removing water) by any of the variety of methods described herein. The features, described elsewhere herein, can be provided such that the number of features is less than the number of wells of the array, the features can be provided such that the number of features equals the number of wells of the array, or the features can be provided in excess of the number of wells of the array. In some embodiments, the well array is manipulated such that one or more shrunken hydrogel features move from the top surface of the array down into a well. For example, a well array can be placed on a shaker for a length of time necessary for the features to distribute into the wells. Other, non-limiting examples of manipulations that can cause a shrunken hydrogel feature to enter a well are physically shaking, tilting, or rolling the well array, or a combination thereof, using forced air to blow features into a well, using a magnet to pull down hydrogel features comprising magnetic particles, using microfluidic systems to distribute features into wells, using a printer to deposit a feature into a well, or any other method to distribute features into wells. In some embodiments, once a well contains a feature, the well cannot accept or retain another feature. In other embodiments, a well can contain more than one feature.

In some embodiments, the method includes rehydrating (e.g., adding water) the shrunken hydrogel features, wherein the shrunken hydrogel features are located in the wells. Rehydrating shrunken hydrogel features can be accomplished by any method described herein. Rehydrating a shrunken hydrogel feature in the well can cause the shrunken hydrogel feature to expand. In some embodiments, the shrunken hydrogel feature expands to fill the well. In some embodiments, the shrunken hydrogel feature expands in a z direction, such that the feature expands out of the unenclosed (i.e. open) end of the well. The exposed area of the rehydrated feature can create a patterned hydrogel array (e.g., a well array). A rehydrated feature contained within a well can be stable. In some embodiments, a rehydrated feature (e.g., a rehydrated shrunken hydrogel feature) is immobilized within a well, such that typical array usage does not dissociate the rehydrated feature from the well. The patterned hydrogel array can be used for analyte capture according to the methods described herein.

(x) Bead Tethering

"Bead tethering" can refer to an arrangement of beads, wherein the arrangement may or may not form an array. The tethered beads can be contacted with a sample and processed according to methods described herein. Further, contacting a biological sample with a single bead or beads tethered together in various arrangements can allow for more precise spatial detection of analytes, e.g., a region of interest. Methods for tethering beads together are known in the art. Some suitable, non-limiting, methods of tethering beads together can be, e.g., chemical linkers, proximity ligation, or any other method described herein. In some embodiments, beads can be tethered together independent of a substrate. In some embodiments, beads can be tethered in various arrangements on an existing substrate. In some embodiments, a substrate (e.g., a hydrogel) can be formed around existing tethered beads. In some embodiments, the beads or bead arrangement can contact a portion of the biological sample. In some embodiments, the bead or bead arrangement can contact a region of interest. In some embodiments, the beads or bead arrangement can contact the entire biological sample. In some embodiments, the beads or bead arrangements are contacted to random positions on the biological sample. In some embodiments, the beads are contacted to according to a specific pattern on the biological sample.

Beads can be tethered together in various arrangements. In some embodiments, a single (e.g., one) bead can be contacted with a biological sample. In some embodiments, two or more beads can be tethered (e.g., connected to each other), in various arrangements. For example, in a non-limiting way, beads can be tethered together to form a cluster, a row, or arranged on a mesh (e.g., a net). In some embodiments, at least three beads can be tethered together in a two-dimensional (2D) array (e.g., a cluster). In some embodiments, at least two beads can be tethered together in a one-dimensional (1D) array (e.g., a row). In such embodiments, the beads are arranged in such fashion that the beads can contact each other directly. In some embodiments, at least two beads can be tethered together in a string arrangement. In such embodiments, the beads are arranged in such fashion that the beads can contact each other indirectly (e.g., beads are connected via linker). In some embodiments, at least two beads can be tethered together in a mesh arrangement (e.g., net). In some embodiments, beads tethered together in a 2D array, a 1D array, the beads on a string arrangement, and the beads on the mesh arrangement can be used in any combination with each other on the biological sample.

In some embodiments, at least about 2 to about 10 beads can be tethered together in various arrangements. In some embodiments at least about 3, about 4, about 5, about 6, about 7, about 8, about 9, or more beads can be tethered together. In some embodiments, about 10 to about 100 beads can be tethered together in various arrangements. In some embodiments, about 10, about 20, about 30, about 40, about 50, about 60, about 70, about 80, about 90, or more beads can be tethered together in various arrangements. In some embodiments, about 100 to about 1,000 beads can be tethered together in various arrangements. In some embodiments, about 100, about 200, about 300, about 400, about 500, about 600, about 700, about 800, or about 900 or more beads can be tethered together in various arrangements. In some embodiments, about 1000 to about 10000 beads can be tethered together in various arrangements. In some embodiments, about 1000, about 2000, about 3000, about 4000, about 5000, about 6000, about 7000, about 8000, about 9000, about 10000 or more beads can be tethered together.

In some embodiments, the tethered beads can have capture probes comprising spatial barcodes, functional domains, unique molecular identifiers, cleavage domains, and capture domains, or combinations thereof. In some embodiments, each bead can be associated with a unique spatial barcode. In some embodiments, the spatial barcode is known prior to contacting the bead or bead arrangement to the biological sample. In some embodiments, the spatial barcode is not known prior to contacting the bead or bead arrangement to the biological sample. The identity of each bead (e.g., spatial barcode) in the array can be deconvolved, for example, by direct optical sequencing, as discussed herein.

(xi) Printing Arrays in Liquid

In some embodiments, an array can be printed in liquid. The resolution of conventionally-printed arrays can be limited, due to the diffusion of printed solutions. Printing the array in a highly viscous liquid can increase resolution by preventing the diffusion of the printed solution. Thus, disclosed herein are various methods and materials for attaching and/or introducing a capture probe (e.g., a nucleic acid capture probe) having a barcode (e.g., a spatial barcode) to a substrate (e.g., a slide), wherein the attaching (e.g., printing) is performed in liquid.

In some aspects, capture probes are printed on a substrate (e.g., a slide or bead). In some aspects, the substrate is a slide. In some aspects, the substrate is a 96-well microtiter plate. In some aspects, methods provided herein can also be applied to other substrates commonly used for nucleic acid analyses, including but not limited to beads, particles, membranes, filters, dipsticks, slides, plates, and microchips. In some aspects, such substrates may be composed of a number of materials known to be compatible with nucleic acid analysis, including but not limited to agarose, styrene, nylon, glass, and silicon.

(1) First Solution

In some embodiments, provided herein are methods of printing arrays on substrates using one or more liquid solution(s) (e.g., two or more solutions that include distinct capture probes). In some aspects, methods of printing arrays on substrates using one or more solution(s) can improve the resolution of the printed array. In some aspects, methods provided herein include dispensing a first solution (e.g., bulk solution) onto a substrate. In some aspects, the first solution (e.g., bulk solution) has a lower Reynolds Number relative to a second solution (e.g., a second solution that includes capture probes to be attached to the substrate). The Reynolds Number represents an inverse relationship between the density and velocity of a fluid and its viscosity in a channel of given length. More viscous, less dense, and/or slower moving fluids will have a lower Reynolds Number, and are easier to divert, stop, start, or reverse without turbulence. In some embodiments, the first solution and the second solution are immiscible.

In some aspects, the first (e.g., bulk) solution is hydrophobic. In some aspects, after dispensing the first (e.g., bulk) solution onto the slide, the first (e.g., bulk) solution remains on the slide in discrete spatial areas on the slide. In some aspects, the first (e.g., bulk) solution is made of a solution that does not denature one or more probes and/or does not inhibit probe-to-substrate binding. In some embodiments, the bulk solution can include an aqueous solution, a high viscosity solution, or a low nucleic acid diffusivity solution. In some aspects, the first (e.g., bulk) solution is a gel. In some aspects, the first (e.g., bulk) solution is a hydrogel. In some aspects, the first (e.g., bulk) solution includes natural polymers, including for example, glycerol, collagen, gelatin, sugars such as starch, alginate, and agarose, or any combinations thereof. In some aspects, the first (e.g., bulk) solution includes a synthetic polymer. In some aspects, the synthetic polymer is prepared by any method known in the art, including for example, chemical polymerization methods. In some aspects, the gel or polymer is hydrophobic. In some aspects, the gel or polymer is hydrophilic. In some aspects, the gel or polymer is aqueous. In some aspects, the gel or polymer shrinks at room temperature. In some aspects, the gel or polymer shrinks when heated. In some aspects, the polymer is a film that shrinks when heated.

In some aspects, the first (e.g., bulk) solution includes glycerol. In some aspects, glycerol is present in the first (e.g., bulk) solution at a concentration of 5-100%. In some aspects, glycerol is present in the solution at a concentration of 5%, 10%, 15%, 20%, 25%, 30%, 35%, 40%, 45%, 50%, 55%, 60%, 65%, or 70%.

In some aspects, the first (e.g., bulk) solution includes sugar. In some aspects, the sugar is a monosaccharide, a disaccharide, a polysaccharide, or combinations thereof. In some aspects, the sugar is glucose, fructose, mannose, galactose, ribose, sorbose, ribulose, lactose, maltose, sucrose, raffinose, starch cellulose, or combinations thereof. In some aspects, sugar is sourced from complex compounds such as molasses or other by-products from sugar refinement. In some aspects, sugar is present in the first (e.g., bulk) solution at a concentration of 5-100%. In some aspects, sugar is present in the solution at a concentration of 5%, 10%, 15%, 20%, 25%, 30%, 35%, 40%, 45%, 50%, 55%, 60%, 65%, or 70%.

In some aspects, the first (e.g., bulk) solution has a viscosity that is about 0.1×-fold, 0.2×-fold, 0.3×-fold, 0.4×-fold, 0.5×-fold, 0.6×-fold, 0.7×-fold, 0.8×-fold, 0.9×-fold, 1.0×-fold, 1.1×-fold, 1.2×-fold, 1.3×-fold, 1.4-fold, 1.5×-fold, 1.6×-fold, 1.7×-fold, 1.8×-fold, 1.9×-fold, 2.0×-fold, 2.5×-fold, 3.0×-fold, 4.0×-fold, 5.0× fold, 6.0×-fold, 7.0×-fold, 8.0× fold, 9.0×-fold, or 10×-fold greater than the viscosity of the second solution.

(2) Second Solution

In some embodiments, printing arrays on substrates using two or more solutions includes using a second solution. In some embodiments, the second solution can include one or more capture probes. In some embodiments, the second solution is dispensed in the form of a droplet. Some embodiments include a plurality of second solutions, wherein each member of the plurality includes one or more capture probes comprising a spatial barcode unique to that particular droplet. In some embodiments, the second solution is dispensed onto a substrate covered or partially covered with the first (e.g., bulk) solution. In some embodiments, the first (e.g., bulk) solution reduces or prevents the diffusion of one or more capture probes from the second solution. In some aspects, the one or more capture probes remain entirely within the second solution when printed onto a substrate covered or partially covered with the first (e.g., bulk) solution.

In some aspects, the second solution includes one or more capture probes (e.g., any of the capture probes disclosed herein). In some aspects, the second solution includes one spatially-barcoded capture probe. In some aspects the second solution includes at least 5, at least 10, at least 20, at least 30 at least 40, at least 50, at least 75, at least 100, at least 200, at least 300, at least 400, at least 500, at least 600, at least 700, at least 800, at least 900, at least 1,000, at least 1,500, at least 2,000, at least 3,000, at least 4,000, or at least 5,000 spatially-barcoded capture probes. In some aspects, the second solution includes compounds that facilitate binding of the one or more capture probes to the substrate. In some aspects, the second solution does not inhibit the one or more capture probes from binding the substrate and/or does not denature the one or more capture probes. In some aspects, the second solution is less viscous than the first (e.g., bulk) solution. In some aspects, the second solution and the first (e.g., bulk) solution are wholly or substantially immiscible (e.g., they do not mix). In some aspects, the second solution is an aqueous solution. In some aspects, the second solution is a hydrophilic solution.

(3) Dispensing

In some embodiments, spot printing a high-density pattern of features can include dispensing the oligonucleotides and/or features, in the form of a liquid droplet, onto the surface of the substrate in the presence of a bulk solution. In some embodiments, the second solution droplet(s) (e.g., oligonucleotides and/or feature droplet(s)) and the first (e.g., bulk) solution does not substantially mix with each other. In some aspects, the printing methods disclosed herein that include dispensing a second solution including one or more spatially-barcoded capture probes onto a substrate in the presence (e.g., through) a first (e.g., bulk) solution result in a spot size of the second solution (e.g., a cross-sectional spot size of the second solution on the plane of the substrate) that is smaller compared to the spot size that would be obtained by dispensing the same second solution onto the substrate in the absence of the first (e.g., bulk) solution. In some aspects, the spot size (e.g., the cross-sectional spot size of the second solution on the plane of the substrate) of the second solution does not increase after printing the second solution onto the substrate in the presence of the first (e.g., bulk) solution. In some aspects, the area of the spot of the second solution does not change after printing the second onto the substrate in the presence of the first (e.g., bulk) solution. In some aspects, printing of the second solution onto the substrate in the presence of the first (e.g., bulk) solution results in a desired pattern on the substrate surface. For example, a plurality of second solutions can be printed onto the substrate in the presence of the first solution such that the locations where the plurality of second solutions are printed results in a desired pattern on the substrate. In some embodiments, two or more members of a plurality of second solutions printed onto a substrate include distinct populations of capture probes, which capture probes attach to the substrate, such that an array of capture probes is generated.

(4) Density

In some embodiments, the cross-sectional area of the oligonucleotide and/or feature droplet(s) on the substrate is smaller than a corresponding cross-sectional area of the oligonucleotide and/or feature droplet(s) that would be generated by dispensing the oligonucleotides and/or features onto the surface of the substrate in the absence of the bulk solution. In some embodiments, the cross-sectional area of the oligonucleotide and/or feature droplet(s) on the substrate is about two-fold smaller than the corresponding cross-sectional area of the oligonucleotide and/or feature droplet(s) that would be generated by dispensing the oligonucleotide and/or feature droplet(s) onto the surface of the substrate in the absence of the bulk solution.

In some aspects, the cross-sectional area of the second solution on the substrate generated by dispensing the second solution onto the surface of the substrate in the presence of the first solution is smaller than a corresponding cross-sectional area of the second solution that would be generated by dispensing the second solution onto the surface of the substrate in the absence of the first solution. In some aspects, the cross-sectional area of the second solution on the substrate generated by dispensing the second solution onto the surface of the substrate in the presence of the first solution is about two-fold, about three-fold, about four-fold, or about five-fold, about 10-fold, about 20-fold, about 30-fold, about 40-fold, about 50-fold, about 60-fold, about 70-fold, about 80-fold, about 90-fold, or about 100-fold smaller than the corresponding cross-sectional area of the second solution that would be generated by dispensing the second solution onto the surface of the substrate in the absence of the first solution.

(5) Curing

Any suitable technique or condition can be used to cure the first solution, the second solution, and/or the spot formed by the second solution after the second solution (including the capture probes) is dispensed onto the substrate. As used herein, the term "curing" and related terms can refer to treating a solution (e.g., a first solution, a second solution, or both) with an agent and/or condition that transforms a solution from a liquid state to a solid state (e.g., transformed into a matrix), wherein the solution retains a three dimensional shape after the curing process. Suitable examples of curing techniques and/or conditions include ultraviolet (UV) radiation, infrared (IR) radiation, thermal radiation, microwave radiation, visible radiation, narrow-wavelength radiation, laser light, natural light, humidity, or combinations thereof. Suitable examples of a curing source include, for example, a UV light, a heating device, a radiation device, a microwave device, a plasma device, or combinations thereof.

In some embodiments, the first solution and/or the second solution is chemically cured. In some embodiments, the oligonucleotide and/or feature droplet(s) are chemically cured. In some embodiments, the bulk solution is chemically cured. In some aspects, the spot formed by the second solution after the second solution (including the capture probes) is dispensed onto the substrate is chemically cured. In some embodiments, the oligonucleotides and/or features and the bulk solution are attached to the substrate (e.g., by curing), thus generating a feature and bulk solution-matrix. In some aspects, the matrix (e.g., the first and second solution-matrix) is chemically cured. Chemically curing a solution can be accomplished by any means known in the art. For example, a solution can include one or more hydrogel subunits that can be chemically polymerized (e.g., cross-linked) to form a three-dimensional (3D) hydrogel network. Features dispensed, in the form of a liquid droplet, onto the surface of a substrate in the presence of a bulk solution can be polymerized. In some embodiments, the features are co-polymerized with the bulk solution to create a gel feature in hydrogel flexible array, whereas in other embodiments the gel pad or feature is polymerized and the bulk solution is removed leaving a spot or bead array. Non-limiting examples of hydrogel subunits include acrylamide, bis-acrylamide, polyacrylamide and derivatives thereof, poly(ethylene glycol) and derivatives thereof (e.g., PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, or combinations thereof. Other materials and techniques useful in forming and/or cross-linking hydrogels are described in more detail herein.

In some aspects, the first solution and/or second solution is photo-reactively cured. In some embodiments, the oligonucleotide and/or feature droplet(s) are photo-reactively cured. In some embodiments, the bulk solution is photo-reactively cured. In some aspects, the spot formed by the second solution after the second solution including the capture probe is dispensed onto the substrate is photo-reactively cured. In some aspects, the matrix (e.g., the first and second solution-matrix) is photo-reactively cured. Photo-reactive curing can be accomplished by any means known in the art.

In some aspects, methods disclosed herein include curing the first (e.g., bulk) and/or second solution. In some aspects, methods disclosed herein include curing the spot formed by the second solution after the second solution (e.g., a second solution including the capture probe) is dispensed onto the substrate. In some aspects, methods disclosed herein include curing the first solution and the second solution after both are dispensed onto the slide. In some embodiments, curing the first and second solutions results in a first-and-second solution matrix. In some aspects, methods disclosed herein include curing the second solution followed by removal of the uncured first solution from the substrate. In some aspects, the methods disclosed herein include curing the first and second solutions on the substrate, thus generating a matrix (e.g., a first and second solution-matrix).

(6) Expanding Matrices

In some embodiments, prior to dispensing the second solution droplet(s) (e.g., oligonucleotide and/or feature droplet(s)) onto the surface of a substrate in the presence of a first (e.g., bulk) solution, the first (e.g., bulk) solution is cured to form a bulk solution-matrix, and the bulk solution matrix is reversibly expanded along one or more axes (e.g., one or more axes of a matrix or a substrate surface). In some embodiments, second solution droplet(s) can be dispensed in the presence of expanded first (e.g., bulk) solution-matrix.

In some embodiments, dispensing a plurality of second solution droplet(s) (e.g., including different capture probes having different spatial barcodes) onto a substrate covered with a first (e.g., bulk) solution, wherein the first solution is initially stretched along one or more axes. In some embodiments, the stretched first solution is cured. In some embodiments, the stretched first solution is partially cured. In some embodiments, the stretched first solution is uncured and is dispensed on a surface that itself is stretched. In some aspects, the volume (e.g., cross-sectional area) of the second solution droplet(s) is decreased after being dispensed into a first solution that is initially stretched. In some aspects, disclosed herein are methods of preparing an array including (i) providing a gel or polymer (e.g., a cured or partially cured solution) onto a substrate, (2) stretching the gel or polymer, (3) dispensing a droplet of the second solution onto the substrate while the gel or polymer is stretched, and (4) allowing the gel or polymer to relax, thereby decreasing the overall area (e.g., cross-sectional area) of the second solution droplet(s) on the substrate. In some aspects, the stretching step includes reversibly expanding the gel or polymer along one or more axes coplanar with the surface of the substrate.

(7) Removing Solution

In some embodiments, the first (e.g., bulk) solution can be removed from the substrate after the oligonucleotide and/or feature droplet(s) are attached to the substrate. In some aspects, the first (e.g., bulk) solution is removed after the second solution including the one or more capture probes (e.g., plurality of second solutions that include different capture probes) is dispensed onto the substrate. Methods of removing the first (e.g., bulk) solution are known in the art. In some aspects, removal of the first (e.g., bulk) solution results in complete removal of the first solution, leaving only the second solution including the one or more capture probes (e.g., plurality of second solutions that include different capture probes) on the substrate. In some aspects, removal of the first (e.g., bulk) solution does not change the surface area of the second solution (e.g., plurality of second solutions that include different capture probes) in contact with the substrate. In some aspects, removal of the first (e.g., bulk) solution does not change the shape of the droplet of the second solution (e.g., plurality of second solutions that include different capture probes) in contact with the substrate. In some aspects, prior to removal of the first (e.g., bulk) solution, the second solution including the one or more probes (e.g., plurality of second solutions that include different capture probes) is cured by methods disclosed herein but that the first (e.g., bulk) solution is not cured. For example, the first and second solutions can be subjected to agents and/or conditions under which the second solution (e.g., plurality of second solutions that include different capture probes) is cured, while the first (e.g., bulk) solution is not cured. In some embodiments, the second solution (e.g., plurality of second solutions that include different capture probes) includes one or more hydrogel subunits that can be polymerized (e.g., cross-linked) to form a three-dimensional (3D) hydrogel network, while the first (e.g., bulk) solution does not include such one or more hydrogel subunits. Upon subjecting the first and second solutions to curing conditions, only the second solution(s) will be cured, allowing the first solution to be removed.

In some embodiments, the first (e.g., bulk) solution is not removed from the substrate after the oligonucleotides and/or features are attached to the substrate.

(8) Shrinking Droplet/Feature Arrays

In some embodiments, an expanded first (e.g., bulk) solution-matrix containing a second solution (e.g., oligonucleotide and/or feature droplet(s)) can be shrunk along one or more axes (e.g., of the matrix or of the substrate surface) such that the cross-sectional area of the second solution droplet(s) (e.g., oligonucleotide and/or feature droplet(s)) is smaller than a corresponding cross-sectional area of a second solution droplet(s) e.g., oligonucleotide and/or feature droplet(s)) that would be generated if the first (e.g., bulk) solution-matrix containing the second solution droplet(s) (e.g., oligonucleotide and/or feature droplet(s)) were not shrunk along the one or more axes. In some embodiments, shrinking the matrix (e.g., the first-and-second solution matrix) generates a shrunken matrix (e.g., a shrunken first-and-second solution matrix), wherein the volume of a second solution droplet (e.g., a plurality of second solution droplets) of the matrix is reduced as compared to the volume of the second solution droplet in a non-shrunken matrix. In some aspects, shrinking two or more second solutions (e.g., droplets of second solutions) results in a higher density of the two or more second solutions. In some embodiments, the second solution droplet(s) (e.g., oligonucleotide and/or feature droplet(s)) and first (e.g., bulk) solution-matrix can be shrunk by any method disclosed herein. In some embodiments, the shrinking can include removing water. In some aspects, the resolution of the array is increased after the droplet is shrunk. In some aspects, shrinking the second solution droplet results in a decrease in the cross-sectional area of the droplet (e.g., the cross-sectional area in the plane of the substrate onto which the second solution droplet is printed or dispensed). In some aspects, after shrinking the droplet, the concentration of probes on the substrate will be increased, thereby improving sensitivity.

The spatial array is contacted to the biological sample, wherein the biological sample can be any described herein (e.g., a FFPE tissue section). Once the spatial array has been placed on the biological sample, a cellular and/or nuclear permeabilization reaction can occur, such that the biological analytes (e.g., DNA, RNA, proteins, metabolites, small molecules, lipids, and the like) are released and captured onto the spatial array, preserving their spatial information. The spatial array is removed, and the molecular information therein is determined (e.g., by performing library construction for next generation sequencing). Sequencing can be followed by correlation of the expression value (e.g., gene expression of the analyte) with the feature.

In some aspects, the cross-sectional area of a second solution droplet is decreased upon shrinking by about 10%, by about 20%, by about 30%, by about 40%, by about 50%, by about 60%, by about 70%, by about 80%, or by about 90% compared to the cross-sectional area of a second solution droplet that is printed or dispensed onto the substrate. In some aspects, the cross-sectional area of a second solution droplet is decreased by about 1.0-fold, by about 1.1-fold, by about 1.2-fold, by about 1.3-fold, by about 1.4 fold, by about 1.5-fold, by about 2-fold, by about 3-fold, by about 4-fold, or by about 5-fold compared to the cross-sectional area of a second solution droplet that is printed or dispensed onto the substrate.

In some aspects, disclosed herein are methods of preparing an array including dispensing a plurality of second solution droplets of (e.g., including different capture probes having different spatial barcodes) onto the substrate covered with a first (e.g., bulk) solution, curing the first and second solutions to generate a matrix (e.g., a first and second solution-matrix), wherein the volume and shape of the plurality of second solution droplets in the matrix are substantially the same as when the plurality of second solution droplets was dispensed, and shrinking the matrix, thereby decreasing the overall volume (e.g., cross-sectional area) of the plurality of second solution droplets. In some aspects, shrinking can be accomplished using any of the variety of shrinking agents or conditions described herein. In some aspects, shrinking can be accomplished by dehydrating the matrix.

In some aspects, after the second solution is dispensed, the area of the second solution is shrunk along the one or more axes of coplanar with the surface of the substrate such that the cross-sectional area of the second solution on the substrate (e.g., the slide) is smaller than a corresponding cross-sectional area of the second solution that would be generated if the first solution matrix including the second solution were not shrunk along the one or more axes of the surface of the substrate.

With respect to orientation, shrinkage need not be equal in any two orthogonal directions on the substrate. However, in some aspects, the shrinkage of a second solution droplet is substantially uniform in shrinkage. In some aspects, a second solution droplet shrinks in substantially the same amount in each direction, regardless of position on the substrate plane.

In some aspects, after preparing the substrate with the one or more capture probes (e.g., a spatial array that includes the capture probes), disclosed herein are methods for spatially profiling an analyte (e.g., a plurality of analytes) in a biological sample, including (a) generating a spatial array including a plurality of capture probes bound to a substrate; wherein (i) at least a portion of the substrate is coated with a first solution; and (ii) a plurality of second solutions, in the form of a liquid droplets, are dispensed onto the surface of the substrate in the presence of the first solution, wherein the first solution and the plurality of second solutions do not substantially mix with each other, wherein at least two members of the plurality of the second solutions include one or more different capture probes having different spatial barcodes, and wherein at least one of the one or more capture probes of at least two members of the plurality of second solutions is bound to the substrate; (b) contacting the biological sample with the spatial array such that the analyte(s) present in the biological sample are captured by one or more of the capture probes; and (c) determining the spatial profile of the captured analyte(s) in the biological sample.

(xii) Array/Feature Preservation

In some embodiments, the biological sample can be preserved after completion of an assay with a feature or arrangement of features for additional rounds of spatial detection of analytes. In some embodiments, the biological sample, features, array, or any combination thereof can be preserved after the spatial profiling. In some embodiments, the biological sample, features, array, or combinations thereof can be protected from dehydration (e.g., drying, desiccation). In some embodiments, the biological sample, features, array, or combinations thereof, can be protected from evaporation. Methods of preserving and/or protecting biological samples, features, or arrays are known in the art. For example, in a non-limiting way, the biological sample, features, array, or combinations thereof can be covered by a reversible sealing agent. Any suitable reversible sealing agent can be used. Methods of reversible sealing are known in the art (See, e.g., WO 2019/104337, which is incorporated herein by reference). In a non-limiting way, suitable reversible sealing agents can include non-porous materials, membranes, lids, or oils (e.g., silicone oil, mineral oil). In further non-limiting examples, the biological sample, features, array, or combinations thereof can be preserved in an environmental chamber (e.g., hermetically sealed) and removed for additional rounds of spatial analysis at a later time.

(e) Analyte Capture

In this section, general aspects of methods and systems for capturing analytes are described. Individual method steps and system features can be present in combination in many different embodiments; the specific combinations described herein do not in any way limit other combinations of steps or features.

(i) Conditions for Capture

Generally, analytes can be captured when contacting a biological sample with a substrate including capture probes (e.g., substrate with capture probes embedded, spotted, printed on the substrate or a substrate with features (e.g., beads, wells) comprising capture probes).

As used herein, "contact," "contacted," and/or "contacting," a biological sample with a substrate refers to any contact (e.g., direct or indirect) such that capture probes can interact (e.g., capture) with analytes from the biological sample. For example, a substrate may be near or adjacent to the biological sample without direct physical contact, yet capable of capturing analytes from the biological sample. In some embodiments a biological sample is in direct physical contact with a substrate. In some embodiments, a biological sample is in indirect physical contact with a substrate. For example, a liquid layer may be between the biological sample and the substrate. In some embodiments, analytes diffuse through a liquid layer. In some embodiments capture probes diffuse through a liquid layer. In some embodiments reagents may be delivered via a liquid layer between a biological sample and a substrate. In some embodiments, indirect physical contact may include a second substrate (e.g., a hydrogel, a film, a porous membrane) between the biological sample and the first substrate comprising capture probes. In some embodiments, reagents may be delivered by a second substrate to a biological sample.

In some embodiments, a cell immobilization agent can be used to contact a biological sample with a substrate (e.g., by immobilizing non-aggregated or disaggregated sample on a spatially-barcoded array prior to analyte capture). A "cell immobilization agent" as used herein can refer to an agent (e.g., an antibody), attached to a substrate, which can bind to a cell surface marker. Non-limiting examples of a cell surface marker include CD45, CD3, CD4, CD8, CD56, CD19, CD20, CD11c, CD14, CD33, CD66b, CD34, CD41, CD61, CD235a, CD146, and epithelial cellular adhesion molecule (EpCAM). A cell immobilization agent can include any probe or component that can bind to (e.g., immobilize) a cell or tissue when on a substrate. A cell immobilization agent attached to the surface of a substrate can be used to bind a cell that has a cell surface maker. The cell surface marker can be a ubiquitous cell surface marker, wherein the purpose of the cell immobilization agent is to capture a high percentage of cells within the sample. The cell surface marker can be a specific, or more rarely expressed, cell surface marker, wherein the purpose of the cell immobilization agent is to capture a specific cell population expressing the target cell surface marker. Accordingly, a cell immobilization agent can be used to selectively capture a cell expressing the target cell surface marker from a population of cells that do not have the same cell surface marker.

Capture probes on a substrate (or on a feature on the substrate) may interact with released analytes through a capture domain, described elsewhere, to capture analytes. In some embodiments, certain steps are performed to enhance the transfer or capture of analytes to the capture probes of the array. Examples of such modifications include, but are not limited to, adjusting conditions for contacting the substrate with a biological sample (e.g., time, temperature, orientation, pH levels, pre-treating of biological samples, etc.), using force to transport analytes (e.g., electrophoretic, centrifugal, mechanical, etc.), performing amplification reactions to increase the amount of biological analytes (e.g., PCR amplification, in situ amplification, clonal amplification), and/or using labeled probes for detecting of amplicons and barcodes.

In some embodiments, an array is adapted in order to facilitate biological analyte migration. Non-limiting examples of adapting an array to facilitate biological analyte migration include arrays with substrates containing nanopores, nanowells, and/or microfluidic channels; arrays with porous membranes; and arrays with substrates that are made of hydrogel. In some cases, the array substrate is liquid permeable. In some cases, the array is a coverslip or slide that includes nanowells or patterning, (e.g., via fabrication). In some cases where the substrate includes nanopores, nanowells, and/or microfluidic channels, these structures can facilitate exposure of the biological sample to reagents (e.g., reagents for permeabilization, biological analyte capture, and/or a nucleic acid extension reaction), thereby increasing analyte capture efficiency as compared to a substrate lacking such characteristics.

In some embodiments, analyte capture is facilitated by treating a biological sample with permeabilization reagents. If a biological sample is not permeabilized sufficiently, the amount of analyte captured on a substrate can be too low to enable adequate analysis. Conversely, if a biological sample is too permeable, an analyte can diffuse away from its origin in the biological sample, such that the relative spatial relationship of the analytes within the biological sample is lost. Hence, a balance between permeabilizing the biological sample enough to obtain good signal intensity while still maintaining the spatial resolution of the analyte distribution in the biological sample is desired. Methods of preparing biological samples to facilitate analyte capture are known in the art and can be modified depending on the biological sample and how the biological sample is prepared (e.g., fresh frozen, FFPE, etc.).

(ii) Substrate Holder

Described herein are methods in which an array with capture probes located on a substrate and a biological sample located on a different substrate, are contacted such that the array is in contact with the biological sample (e.g., the substrates are sandwiched together). In some embodiments, the array and the biological sample can be contacted (e.g., sandwiched), without the aid of a substrate holder. In some embodiments, the array and biological sample substrates can be placed in a substrate holder (e.g., an array alignment device) designed to align the biological sample and the array. For example, the substrate holder can have placeholders for two substrates. In some embodiments, an array including capture probes can be positioned on one side of the substrate holder (e.g., in a first substrate placeholder). In some embodiments, a biological sample can be placed on the adjacent side of the substrate holder in a second placeholder. In some embodiments, a hinge can be located between the two substrate placeholders that allows the substrate holder to close, e.g., make a sandwich between the two substrate placeholders. In some embodiments, when the substrate holder is closed the biological sample and the array with capture probes are contacted with one another under conditions sufficient to allow analytes present in the biological sample to interact with the capture probes of the array. For example, dried permeabilization reagents can be placed on the biological sample and rehydrated. A permeabilization solution can be flowed through the substrate holder to permeabilize the biological sample and allow analytes in the biological sample to interact with the capture probes. Additionally, the temperature of the substrates or permeabilization solution can be used to initiate or control the rate of permeabilization. For example, the substrate including the array, the substrate including the biological sample, or both substrates can be held at a low temperature to slow diffusion and permeabilization efficiency. Once sandwiched, in some embodiments, the substrates can be heated to initiate permeabilization and/or increase diffusion efficiency. Transcripts that are released from the permeabilized tissue can diffuse to the array and be captured by the capture probes. The sandwich can be opened, and cDNA synthesis can be performed on the array.

Any of the variety of combinations described herein where a sandwich including an array with capture probes and a biological sample on two different substrates can be placed in a substrate holder designed to align the biological sample and the array. For example, the substrate holder can have placeholders for two substrates. In some embodiments, an array including capture probes can be positioned on one side of the substrate holder (e.g., in a first substrate placeholder). In some embodiments, a biological sample can be placed on the adjacent side of the substrate holder in a second placeholder. In some embodiments, in between the two substrate placeholders can be a hinge that allows the substrate holder to close, e.g., make a sandwich between the two substrate placeholders. In some embodiments, when the substrate holder is closed the biological sample and the array with capture probes can be contacted with one another under conditions sufficient to allow analytes present in the biological sample to interact with the capture probes of the array for spatial analysis by any method described herein. For example, dried permeabilization reagents can be placed on the biological sample and rehydrated. Additionally, a permeabilization solution can be flowed through the substrate holder to permeabilize the biological sample and allow analytes in the biological sample to interact with the capture probes.

In some embodiments, a flexible array described herein can be placed in the substrate holder, and sandwiched with a biological sample. In some embodiments, the flexible array can include spatially-barcoded cross-linked features. In some embodiments, the flexible array can be presoaked in permeabilization reagents before being placed into the substrate holder. In some embodiments, the flexible array can be soaked in permeabilization reagents after being placed in the substrate holder. In some embodiments, the substrate holder including a biological sample in one placeholder and a flexible array can be closed (e.g., form a sandwich) such that the permeabilization reagents allow analytes present in the biological sample to interact with capture probes of the flexible array (e.g., capture probes on the spatially-barcoded features).

In some embodiments, the substrate holder can be heated or cooled to regulate permeabilization and/or diffusion efficiency.

(iii) Passive Capture Methods

In some embodiments, analytes can be migrated from a sample to a substrate. Methods for facilitating migration can be passive (e.g., diffusion) and/or active (e.g., electrophoretic migration of nucleic acids). Non-limiting examples of passive migration can include simple diffusion and osmotic pressure created by the rehydration of dehydrated objects.

Passive migration by diffusion uses concentration gradients. Diffusion is movement of untethered objects toward equilibrium. Therefore, when there is a region of high object concentration and a region of low object concentration, the object (e.g., a capture probe, an analyte, etc.) moves to an area of lower concentration. In some embodiments, untethered analytes move down a concentration gradient.

In some embodiments, different reagents may be added to the biological sample, such that the biological sample is rehydrated while improving capture of analytes. In some embodiments, the biological sample can be contacted with a shrunken array as described herein. In some embodiments, the biological sample and/or the shrunken array can be rehydrated with permeabilization reagents. In some embodiments, the biological sample and/or the shrunken array can be rehydrated with a staining solution (e.g., hematoxylin and eosin stain).

(iv) Diffusion-Resistant Media/Lids

To increase efficiency by encouraging analyte diffusion toward the spatially-barcoded capture probes, a diffusion-resistant medium can be used. In general, molecular diffusion of biological analytes occurs in all directions, including toward the capture probes (i.e., toward the spatially-barcoded array), and away from the capture probes (i.e., into the bulk solution). Increasing diffusion toward the spatially-barcoded array reduces analyte diffusion away from the spatially-barcoded array and increases the capturing efficiency of the capture probes.

In some embodiments, a biological sample is placed on the top of a spatially-barcoded substrate and a diffusion-resistant medium is placed on top of the biological sample. For example, the diffusion-resistant medium can be placed onto an array that has been placed in contact with a biological sample. In some embodiments, the diffusion-resistant medium and spatially-barcoded array are the same component. For example, the diffusion-resistant medium can contain spatially-barcoded capture probes within or on the diffusion-resistant medium (e.g., coverslip, slide, hydrogel, or membrane). In some embodiments, a sample is placed on a substrate and a diffusion-resistant medium is placed on top of the biological sample. Additionally, a spatially-barcoded capture probe array can be placed in close proximity over a diffusion-resistant medium. For example, a diffusion-resistant medium may be sandwiched between a spatially-barcoded array and a sample on a substrate. In some embodiments, a diffusion-resistant medium is disposed or spotted onto a sample. In other embodiments, a diffusion-resistant medium is placed in close proximity to a sample.

In general, a diffusion-resistant medium can be any material known to limit diffusivity of biological analytes. For example, a diffusion-resistant medium can be a solid lid (e.g., coverslip or glass slide). In some embodiments, a diffusion-resistant medium may be made of glass, silicon, paper, hydrogel polymer monoliths, or other material. In some embodiments, the glass side can be an acrylated glass slide. In some embodiments, the diffusion-resistant medium is a porous membrane. In some embodiments, the material may be naturally porous. In some embodiments, the material may have pores or wells etched into solid material. In some embodiments, the pore volume can be manipulated to minimize loss of target analytes. In some embodiments, the membrane chemistry can be manipulated to minimize loss of target analytes. In some embodiments, the diffusion-resistant medium (e.g., hydrogel) is covalently attached to a substrate (e.g., glass slide). In some embodiments, a diffusion-resistant medium can be any material known to limit diffusivity of poly(A) transcripts. In some embodiments, a diffusion-resistant medium can be any material known to limit the diffusivity of proteins. In some embodiments, a diffusion-resistant medium can be any material know to limit the diffusivity of macromolecular constituents.

In some embodiments, a diffusion-resistant medium includes one or more diffusion-resistant media. For example, one or more diffusion-resistant media can be combined in a variety of ways prior to placing the media in contact with a biological sample including, without limitation, coating, layering, or spotting. As another example, a hydrogel can be placed onto a biological sample followed by placement of a lid (e.g., glass slide) on top of the hydrogel.

In some embodiments, a force (e.g., hydrodynamic pressure, ultrasonic vibration, solute contrasts, microwave radiation, vascular circulation, or other electrical, mechanical, magnetic, centrifugal, and/or thermal forces) is applied to control diffusion and enhance analyte capture. In some embodiments, one or more forces and one or more diffusion-resistant media are used to control diffusion and enhance capture. For example, a centrifugal force and a glass slide can used contemporaneously. Any of a variety of combinations of a force and a diffusion-resistant medium can be used to control or mitigate diffusion and enhance analyte capture.

In some embodiments, a diffusion-resistant medium, along with the spatially-barcoded array and sample, is submerged in a bulk solution. In some embodiments, a bulk solution includes permeabilization reagents. In some embodiments, a diffusion-resistant medium includes at least one permeabilization reagent. In some embodiments, a diffusion-resistant medium (i.e. hydrogel) is soaked in permeabilization reagents before contacting the diffusion-resistant medium to the sample. In some embodiments, a diffusion-resistant medium can include wells (e.g., micro-, nano-, or picowells) containing a permeabilization buffer or reagents. In some embodiments, a diffusion-resistant medium can include permeabilization reagents. In some embodiments, a diffusion-resistant medium can contain dried reagents or monomers to deliver permeabilization reagents when the diffusion-resistant medium is applied to a biological sample. In some embodiments, a diffusion-resistant medium is added to the spatially-barcoded array and sample assembly before the assembly is submerged in a bulk solution. In some embodiments, a diffusion-resistant medium is added to the spatially-barcoded array and sample assembly after the sample has been exposed to permeabilization reagents. In some embodiments, permeabilization reagents are flowed through a microfluidic chamber or channel over the diffusion-resistant medium. In some embodiments, the flow controls the sample's access to the permeabilization reagents. In some embodiments, target analytes diffuse out of the sample and toward a bulk solution and get embedded in a spatially-barcoded capture probe-embedded diffusion-resistant medium. In some embodiments, a free solution is sandwiched between the biological sample and a diffusion-resistant medium.

Figure 13:
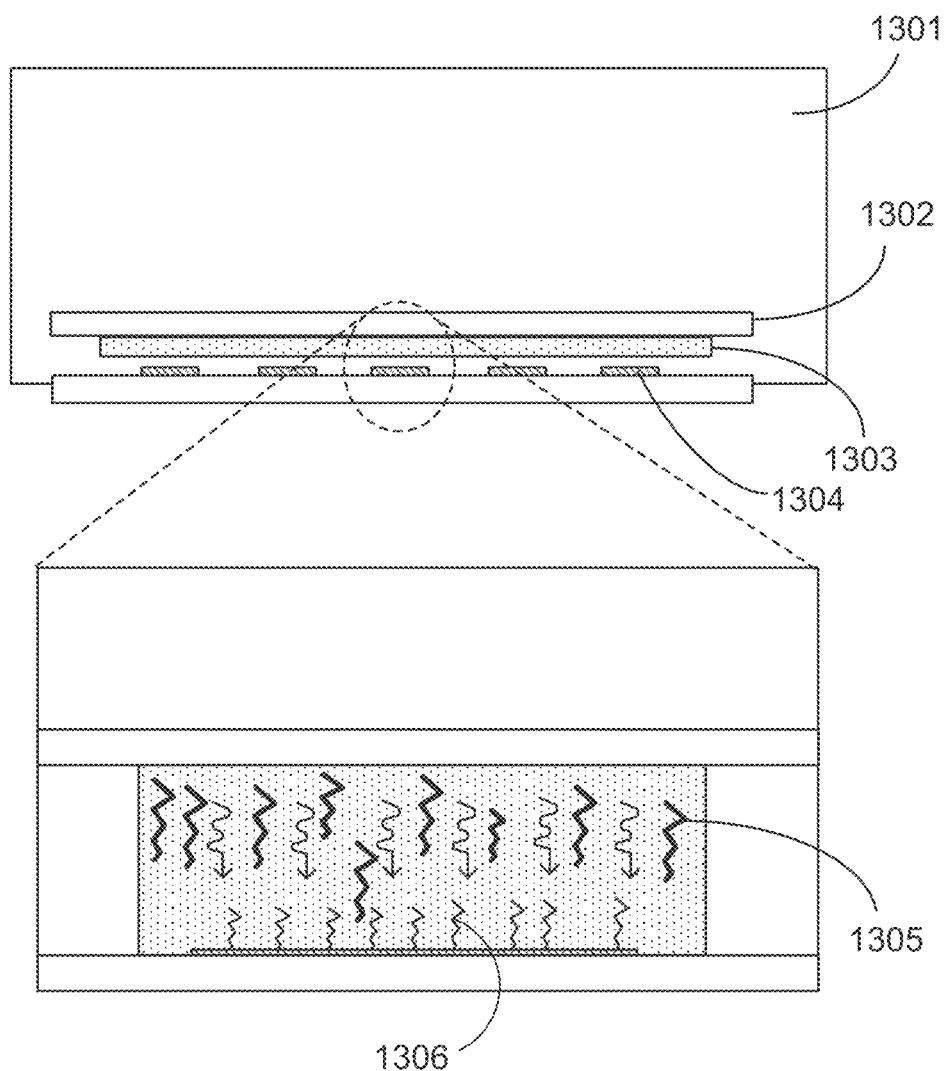
FIG. 13 is a schematic illustrating a side view of a diffusion-resistant medium, e.g., a lid.

FIG. 13 is an illustration of an exemplary use of a diffusion-resistant medium. A diffusion-resistant medium 1302 can be contacted with a sample 1303. In FIG. 13, a glass slide 1304 is populated with spatially-barcoded capture probes 1306, and the sample 1303, 1305 is contacted with the array 1304, 1306. A diffusion-resistant medium 1302 can be applied to the sample 1303, wherein the sample 1303 is sandwiched between a diffusion-resistant medium 1302 and a capture probe coated slide 1304. When a permeabilization solution 1301 is applied to the sample, using the diffusion-resistant medium/lid 1302 directs migration of the analytes 1305 toward the capture probes 1306 by reducing diffusion of the analytes out into the medium. Alternatively, the lid may contain permeabilization reagents.

(v) Active Capture Methods

In some of the methods described herein, an analyte in a biological sample (e.g., in a cell or tissue section) can be transported (e.g., passively or actively) to a capture probe (e.g., a capture probe affixed to a substrate (e.g., a substrate or bead)).

For example, analytes can be transported to a capture probe (e.g., an immobilized capture probe) using an electric field (e.g., using electrophoresis), pressure, fluid flow, gravity, temperature, and/or a magnetic field. For example, analytes can be transported through, e.g., a gel (e.g., hydrogel), a fluid, or a permeabilized cell, to a capture probe (e.g., an immobilized capture probe) using a pressure gradient, a chemical concentration gradient, a temperature gradient, and/or a pH gradient. For example, analytes can be transported through a gel (e.g., hydrogel), a fluid, or a permeabilized cell, to a capture probe (e.g., an immobilized capture probe).

In some examples, an electrophoretic field can be applied to analytes to facilitate migration of analytes towards a capture probe. In some examples, a sample containing analytes contacts a substrate having capture probes fixed on the substrate (e.g., a slide, cover slip, or bead), and an electric current is applied to promote the directional migration of charged analytes towards capture probes on a substrate. An electrophoresis assembly (e.g., an electrophoretic chamber), where a biological sample is in contact with a cathode and capture probes (e.g., capture probes fixed on a substrate), and where the capture probes are in contact with the biological sample and an anode, can be used to apply the current.

In some embodiments, methods utilizing an active capture method can employ a conductive substrate (e.g., any of the conductive substrates described herein). In some embodiments, a conductive substrate includes paper, a hydrogel film, or a glass slide having a conductive coating. In some embodiments, a conductive substrate (e.g., any of the conductive substrates described herein) includes one or more capture probes.

In some embodiments, electrophoretic transfer of analytes can be performed while retaining the relative spatial locations of analytes in a biological sample while minimizing passive diffusion of an analyte away from its location in a biological sample. In some embodiments, an analyte captured by a capture probe (e.g., capture probes on a substrate) retains the spatial location of the analyte present in the biological sample from which it was obtained (e.g., the spatial location of the analyte that is captured by a capture probe on a substrate when the analyte is actively migrated to the capture probe by electrophoretic transfer can be more precise or representative of the spatial location of the analyte in the biological sample than when the analyte is not actively migrated to the capture probe). In some embodiments, electrophoretic transport and binding process is described by the Damköhler number (Da), which is a ratio of reaction and mass transport rates. The fraction of analytes bound and the shape of the biological sample will depend on the parameters in the Da. There parameters include electromigration velocity $U_e$ (depending on analyte electrophoretic mobility $\mu_e$ and electric field strength E), density of capture probes (e.g., barcoded oligonucleotides) $p_0$, the binding rate between probes (e.g., barcoded oligonucleotides) and analytes $k_{on}$, and capture area thickness L.

$$Da \sim \frac{k_{on} p_0 L}{\mu_e E}$$

Fast migration (e.g., electromigration) can reduce assay time and can minimize molecular diffusion of analytes.

In some embodiments, electrophoretic transfer of analytes can be performed while retaining the relative spatial alignment of the analytes in the sample. As such, an analyte captured by the capture probes (e.g., capture probes on a substrate) retains the spatial information of the cell or the biological sample from which it was obtained. Applying an electrophoretic field to analytes can also result in an increase in temperature (e.g., heat). In some embodiments, the increased temperature (e.g., heat) can facilitate the migration of the analytes towards a capture probe.

In some examples, a spatially-addressable microelectrode array is used for spatially-constrained capture of at least one charged analyte of interest by a capture probe. For example, a spatially-addressable microelectrode array can allow for discrete (e.g., localized) application of an electric field rather than a uniform electric field. The spatially-addressable microelectrode array can be independently addressable. In some embodiments, the electric field can be applied to one or more regions of interest in a biological sample. The electrodes may be adjacent to each other or distant from each other. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

A high density of discrete sites on a microelectrode array can be used. The surface can include any suitable density of discrete sites (e.g., a density suitable for processing the sample on the conductive substrate in a given amount of time). In one embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 20,000, about 40,000, about 60,000, about 80,000, about 100,000, or about 500,000 sites per 1 $mm^2$. In some embodiments, the surface has a density of discrete sites of at least about 200, at least about 300, at least about 400, at least about 500, at least about 600, at least about 700, at least about 800, at least about 900, at least about 1,000, at least about 2,000, at least about 3,000, at least about 4,000, at least about 5,000, at least about 6,000, at least about 7,000, at least about 8,000, at least about 9,000, at least about 10,000, at least about 20,000, at least about 40,000, at least about 60,000, at least about 80,000, at least about 100,000, or at least about 500,000 sites per 1 $mm^2$.

Figure 14A:
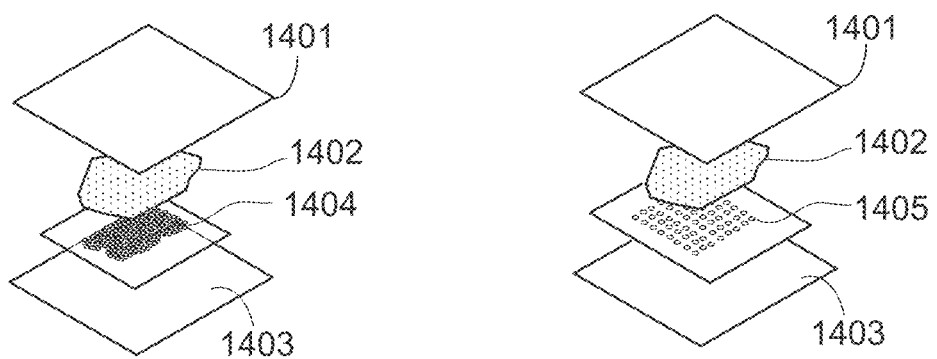
FIGS. 14A and 14B are schematics illustrating expanded FIG. 14A and side views FIG. 14B of an electrophoretic transfer system configured to direct transcript analytes toward a spatially-barcoded capture probe array.
Figure 14B:
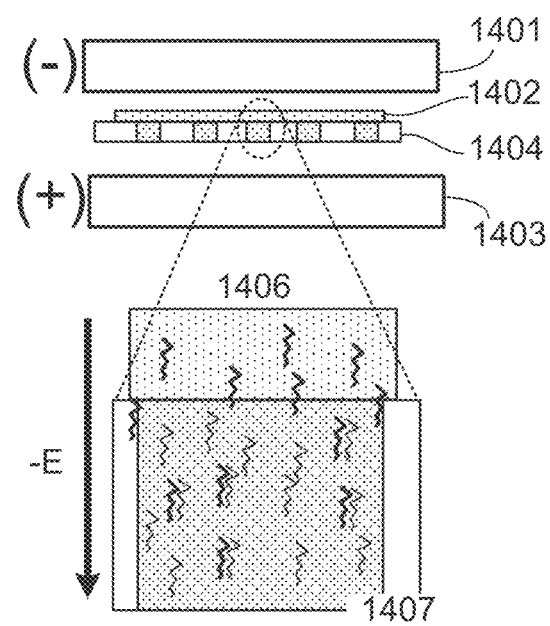

Schematics illustrating an electrophoretic transfer system configured to direct nucleic acid analytes (e.g., mRNA transcripts) toward a spatially-barcoded capture probe array are shown in FIG. 14A and FIG. 14B. In this exemplary configuration of an electrophoretic system, a sample 1402 is sandwiched between the cathode 1401 and the spatially-barcoded capture probe array 1404, 1405, and the spatially-barcoded capture probe array 1404, 1405 is sandwiched between the sample 1402 and the anode 1403, such that the sample 1402, 1406 is in contact with the spatially-barcoded capture probes 1407. When an electric field is applied to the electrophoretic transfer system, negatively charged nucleic acid analytes 1406 will be pulled toward the positively charged anode 1403 and into the spatially-barcoded array 1404, 1405 containing the spatially-barcoded capture probes 1407. The spatially-barcoded capture probes 1407 interact with the nucleic acid analytes (e.g., mRNA transcripts hybridize to spatially-barcoded nucleic acid capture probes forming DNA/RNA hybrids) 1406, making the analyte capture more efficient. The electrophoretic system set-up may change depending on the target analyte. For example, proteins may be positive, negative, neutral, or polar depending on the protein as well as other factors (e.g., isoelectric point, solubility, etc.). The skilled practitioner has the knowledge and experience to arrange the electrophoretic transfer system to facilitate capture of a particular target analyte.

Figure 15:
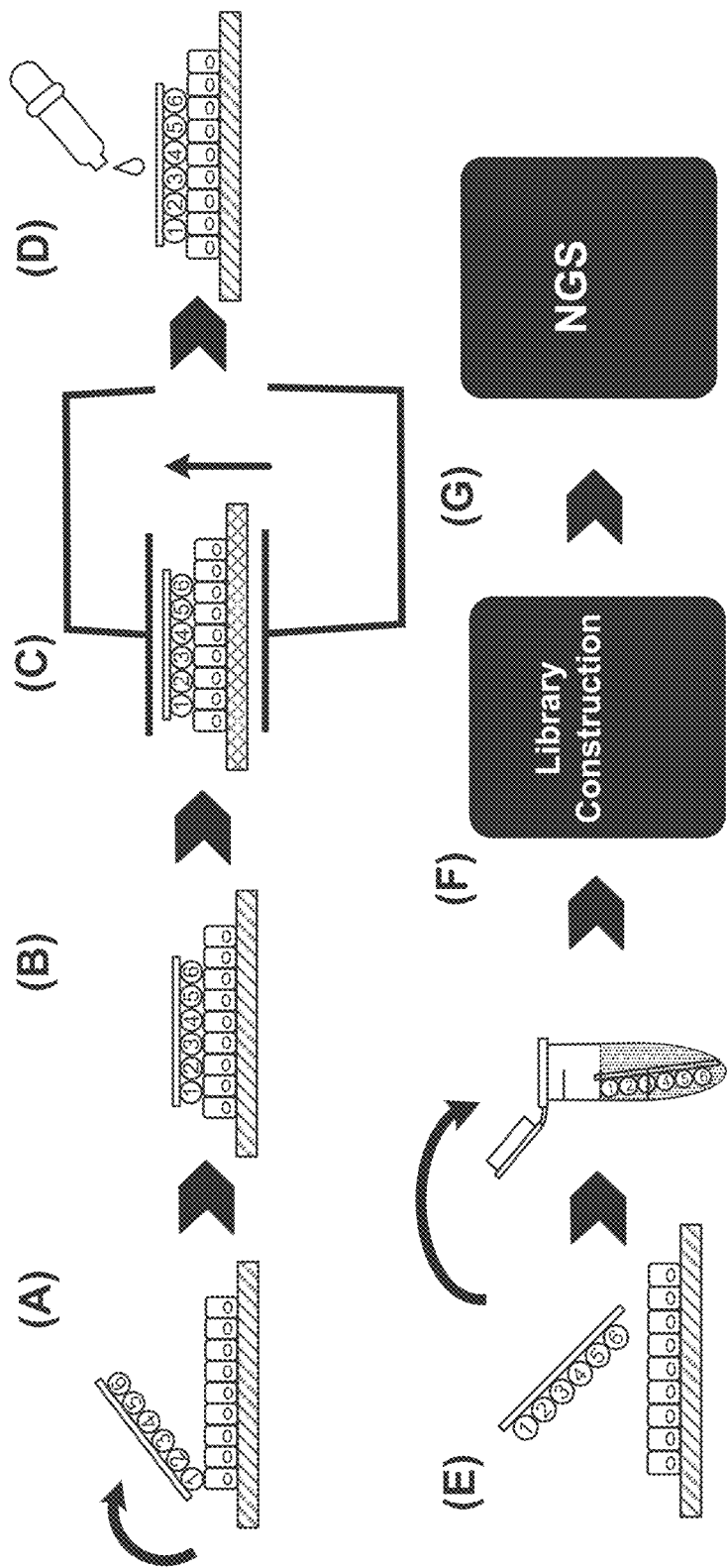
FIG. 15 is a schematic illustrating an exemplary workflow protocol utilizing an electrophoretic transfer system.

FIG. 15 is an illustration showing an exemplary workflow protocol utilizing an electrophoretic transfer system. In the example, Panel A depicts a flexible spatially-barcoded feature array being contacted with a sample. The sample can be a flexible array, wherein the array is immobilized on a hydrogel, membrane, or other flexible substrate. Panel B depicts contact of the array with the sample and imaging of the array-sample assembly. The image of the sample/array assembly can be used to verify sample placement, choose a region of interest, or any other reason for imaging a sample on an array as described herein. Panel C depicts application of an electric field using an electrophoretic transfer system to aid in efficient capture of a target analyte. Here, negatively charged mRNA target analytes migrate toward the positively charged anode. Panel D depicts application of reverse transcription reagents and first strand cDNA synthesis of the captured target analytes. Panel E depicts array removal and preparation for library construction (Panel F) and next-generation sequencing (Panel G).

(vi) Targeted Analysis

In some aspects, arrays (e.g., glass slides) include a plurality of capture probes that bind to one or more specific biological targets in a sample. The capture probes can be directly or indirectly attached to a substrate. The capture probe can be or include, for example, DNA or RNA. In some aspects, the capture probes on an array can be immobilized, e.g., attached or bound, to the array via their 5' or 3' ends, depending on the chemical matrix of the array. In some aspects, the probes are attached via a 3' linkage, thereby leaving a free 5' end. In some aspects, the probes are attached via a 5' linkage, thereby leaving a free 3' end. In some aspects, the probes are immobilized indirectly. For example, a probe can be attached to a bead, which bead can be deposited on a substrate. A capture probe as disclosed in this section can include any of the various components of a capture probe as provided throughout this disclosure (e.g., spatial barcodes, UMIs, functional domains, cleavage domains, etc.).

In some aspects, a capture probe or plurality of capture probes interact with an analyte specific for a particular species or organism (e.g., host or pathogen). In some aspects, the probe or plurality of probes can be used to detect a viral, bacterial, or plant protein or nucleic acid. In some aspects, the capture probe or plurality of capture probes can be used to detect the presence of a pathogen (e.g., bacteria or virus) in the biological sample. In some aspects, the capture probe or plurality of capture probes can be used to detect the expression of a particular nucleic acid associated with a pathogen (e.g., presence of 16S ribosomal RNA or Human Immunodeficiency Virus (HIV) RNA in a human sample).

In some aspects, the capture domain in the capture probe can interact with one or more specific analytes (e.g., an analyte or a subset of analytes out of the pool of total analytes). The specific analyte(s) to be detected can be any of a variety of biological molecules including but not limited to proteins, nucleic acids, lipids, carbohydrates, ions, small molecules, subcellular targets, or multicomponent complexes containing any of the above. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes.

In some aspects, analytes from a biological sample interact with one or more capture probes (e.g., one or more capture probes immobilized directly or indirectly on a substrate), and the capture probes interact with specific analytes in the biological sample. In some aspects, the capture probes are allowed to interact with (e.g., hybridize to) specific analytes, e.g., under appropriate conditions where oligonucleotide capture probes can hybridize to the target nucleic acids. In some aspects, analytes that did not hybridize to capture probes are removed (e.g., analytes that do not interact with capture domains of the capture probes). In some embodiments, removal of analytes that did not interact with a capture probe can be accomplished by, e.g., washing the sample to remove such analytes.

In some aspects, a capture probe or plurality of capture probes includes a capture domain that interacts with an analyte or analytes present in a biological sample. In some aspects, the capture probe or plurality of capture probes includes a capture domain that detects the presence or level amount (e.g., expression level) of a particular analyte or analytes of interest. The capture domain of a capture probe (immobilized directly or indirectly on a substrate) can be capable of binding selectively to a desired subtype or subset of nucleic acid. In some aspects, for example, the capture domain binds to a subset of nucleic acids in a genome or a subset of nucleic acids in a transcriptome. In some aspects, the analyte(s) can include one or more nucleic acids. In some aspects, the capture probe or plurality of capture probes can be used to detect the expression of a particular transcript (e.g., a particular mRNA). In some aspects, a capture probe or plurality of capture probes can be specific for (e.g., binds to) an individual change in a nucleic acid or protein (e.g., a mutation or single nucleotide polymorphism (SNP)).

In some aspects, the biological sample includes an analyte that is or includes a nucleic acid. The nucleic acid can be RNA or DNA. In some aspects, the capture probe or plurality of capture probes detects DNA copy number of a particular set of nucleic acid analyte or analytes. For example, capture probe or plurality of capture probes provided herein can be used to detect DNA copy number of nucleic acids that share homology to each other.

In some aspects, the capture probe or plurality of capture probes includes a capture domain that detects the presence or level amount (e.g., expression level) of one or more RNA transcripts (e.g., specific RNA transcripts). In some aspects, the capture probe or plurality of capture probes includes a capture domain that detects the presence or amount (e.g., expression level) of one or more non-coding RNAs (e.g., microRNA, transfer RNA (tRNA), ribosomal RNA (rRNA), small interfering RNA (siRNA) and small nucleolar RNA (snoRNA). In some aspects, the probe or plurality of probes includes a capture domain that detects the presence or level amount (e.g., expression level) of one or more proteins (e.g., proteins expressed of a nucleic acid of interest).

In some aspects, the capture probe or plurality of capture probes can be specific for a particular protein. In some aspects, the capture probe or plurality of capture probes can be used to detect the presence of a particular protein of interest. In some aspects, the capture probe or plurality of capture probes can be used to detect translation of a particular protein. In some aspects, the capture probe or plurality of capture probes can specifically interact with an active region of an enzyme, a binding domain of an immunoglobulin, defined domains of proteins, whole proteins, synthetic peptides, peptides with introduced mutations, aptamer, or any combination thereof. In some aspects, the analyte(s) can include one or more proteins. In some aspects, the analyte(s) can include one or more nucleic acids and one or more proteins.

In some aspects, the capture probe or plurality of capture probes can be used to detect particular post-translational modifications of a particular protein. In such embodiments, analyte capture agents can be specific for cell surface analytes having a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some aspects, the capture probe or plurality of capture probes can be specific for a particular set of nucleic acids (e.g., nucleic acids that are associated with a specific cellular pathway or pathways). In some aspects, the set of nucleic acids is DNA. In some aspects, the set of nucleic acids is RNA. In some aspects, the set of nucleic acids has similar and/or homologous sequences. In some aspects, the set of nucleic acids encodes for analytes that function in a similar cellular pathway. In some aspects, the set of nucleic acids encodes for analytes that are expressed in a certain pathological state (e.g., cancer, Alzheimer's, or Parkinson's disease). In some aspects, the set of nucleic acids encodes for analytes that are over-expressed in a certain pathological state. In some aspects, the set of nucleic acids encodes for analytes that are under-expressed in a certain pathological state.

In some aspects, the capture probe or plurality of capture probes can be specific for a particular nucleic acid, or detection or expression of a particular set of proteins (e.g., in a similar cellular pathway). In some aspects, the set of proteins has similar functional domains. In some aspects, the set of proteins functions in a similar cellular pathway. In some aspects, the set of proteins is expressed in a certain pathological state (e.g., cancer, Alzheimer's or Parkinson's disease). In some aspects, the set of proteins is over-expressed in a certain pathological state. In some aspects, the set of proteins is under-expressed in a certain pathological state.

In some embodiments, a capture probe includes a capture domain that is capable of binding to more than one analyte. In some embodiments, a capture domain can bind to one or more analytes that are about 80% identical, about 85% identical, about 90% identical, about 95% identical, about 96% identical, about 97% identical, about 98% identical, about 99% identical, 100% identical to the target analyte. In some aspects, the capture probe can bind to an analyte that is about 80% identical, about 85% identical, about 90% identical, about 95% identical, about 96% identical, about 97% identical, about 98% identical, or about 99% identical to each other. In some embodiments, a capture domain can bind to a conserved region of one or more analytes, in which the conserved regions are about 80% identical, about 85% identical, about 90% identical, about 95% identical, about 96% identical, about 97% identical, about 98% identical, about 99% identical, 100% identical to the target analyte.

In some aspects, a capture probe or plurality of capture probes interacts with two or more analytes (e.g., nucleic acids or proteins) that are not similar in sequence and/or do not share a conserved domain. In some embodiments, a capture probe includes two or more capture domains, each of which interacts with a different analyte. In such embodiments, members of the two or more capture domains can be adjacent to each other in the capture probe and/or members of the two or more capture domains can be separated from each other in the capture probe by one or more domains (e.g., nucleic acid domains). For example, in some aspects, the sets of analytes that are detected include mutational changes in the targeted nucleic acids or proteins. In some aspects, the capture probe or plurality of capture probes detects sets of nucleic acids or proteins (e.g., non-homologous nucleic acids or proteins) that are individually mutated during a pathogenic state. In some aspects, the pathogenic state is cancer.

In some aspects, a capture probe or plurality of capture probes include capture domains that can be used to detect analytes that are typically detected using diagnostic panels. In some aspects, the capture probe or plurality of capture probes are used to detect changes in one or more analytes. In some aspects, the analyte changes include one or more of increased analyte expression, decreased analyte expression, mutated nucleic acid sequences, or any combination thereof. In some aspects, the changes in the analytes are associated with and/or lead to manifestation of a pathogenic state in a subject. In some aspects, the detected changes are compared to a reference analyte or analytes.

(vii) Polypeptide Capture

Provided herein are methods and materials for identifying the location of a polypeptide in a biological sample. In some embodiments, an analyte (e.g., a polypeptide analyte) can be directly captured on a substrate. For example, polypeptide analytes can be captured by amine groups on a functionalized substrate. In other examples, an analyte (e.g., a polypeptide analyte) can be captured via an analyte binding moiety directly attached to a substrate. In some embodiments, the substrate may be populated with analyte minding moieties directly attached to the substrate as well as spatially-barcoded capture probes directly attached to the substrate. In other embodiments, an analyte (e.g., a polypeptide analyte) can be captured via an analyte binding moiety indirectly attached to a substrate. In an example, the substrate may be populated with capture probes that are bound to an analyte capture agent, wherein the analyte capture domain of the analyte capture agent binds to the capture domain of the capture probe and the analyte binding moiety binds the polypeptide analyte.

In some embodiments, an analyte (e.g., a polypeptide analyte) can be directly captured or immobilized on a substrate. Direct immobilization may be achieved by covalently coupling the polypeptide analyte to the substrate via amide bonds between the carboxylic acid of the C-terminal amino acid residue and a functionalized substrate surface. For example, a substrate (e.g., a glass coverslip or slide) can be functionalized through amino-silanization with aminopropyltriethoxysilane. The substrate surfaces are further passivated by overnight incubation with polyethylene glycol (PEG)-NHS solution, and functionalized slides can be stored in a vacuum desiccator until use. The t-butyloxycarbonyl protecting groups can be removed by incubating the substrate with 90% TFA (v/v in water) for 5 hours before use, thus exposing free amine groups for peptide immobilization. The resulting functionalized substrate is stable to multiple cycles of Edman degradation and washing steps.

In some embodiments, methods for capturing polypeptides in a biological sample include providing a substrate where an analyte binding moiety is directly immobilized on the substrate. In some embodiments, direct immobilization is achieved through chemical modification of the substrate and/or chemical modification of the analyte binding moiety. For example, a substrate can be prepared with free amines on the surface. When exposed to an analyte binding moiety with a free carboxylic acid on the C-terminal residue, the free amines can form amide bonds with the carboxylic acid thereby covalently coupling the analyte binding moiety to the substrate. Substrates and/or analyte binding moieties can be modified in any manner that facilitates covalent bonding of the analyte binding moiety to the substrate. Non-limiting examples of chemical modification that can be used to covalently bind the analyte binding moiety to the substrate include are described herein.

In some embodiments, methods for capturing analyte polypeptides include providing a substrate (e.g., an array) where the analyte binding moiety is indirectly attached to the substrate. For example, an analyte binding moiety can be indirectly attached to a substrate via an oligonucleotide (e.g., a capture agent barcode domain or capture agent barcode domain hybridized to a capture probe) or other domain capable of binding to both the substrate and the analyte binding domain. The capture agent barcode domain is described elsewhere herein. The capture agent barcode domain can be modified to include a cleavage domain, which can attach to a substrate using any of the chemistries described herein. In some embodiments, the capture agent barcode domain can include an analyte capture sequence as described herein, wherein the analyte capture sequence can hybridize to the capture domain of a capture probe. In some embodiments, a substrate (e.g., an array) containing capture probes can be modified to capture polypeptide analytes by hybridizing the analyte capture sequence of the analyte capture agent to the capture domain of a capture probe.

In some embodiments, methods for capturing analyte polypeptides include providing a substrate (e.g., an array) and providing an analyte capture agent to the biological sample. For example, after drying and fixing sectioned tissue samples, the tissue samples can be positioned on a substrate (e.g., a spatial array), rehydrated, blocked, and permeabilized (e.g., 3×SSC, 2% BSA, 0.1% Triton X, 1 U/µl RNAse inhibitor for 10 min at 4° C.) before being stained with fluorescent primary antibodies (1:100) and a pool of analyte capture agents (in 3×SSC, 2% BSA, 0.1% Triton X, 1 U/µl RNAse inhibitor for 30 min at 4° C.). The biological sample can be washed, coverslipped (in glycerol+1 U/µl RNAse inhibitor), imaged for detected analytes (e.g., using a confocal microscope or other apparatus capable of fluorescent detection), and washed again. The analyte-bound analyte capture agents can be released from the biological sample (e.g., the biological sample can be treated with proteinase, e.g., proteinase K) and migrated to the spatial array. An analyte capture sequence of the analyte-bound analyte capture agent can be captured by a capture probe capture domain, and the capture agent barcode domain can be extended to produce a spatially-tagged analyte capture agent. The spatially-tagged analyte capture agents can be processed according to spatial workflows described herein.

In some embodiments, methods for capturing analyte polypeptides include providing blocking probes to analyte capture agents before introducing the analyte capture agents to a biological sample. In some embodiments, the blocking probes can be alternatively or additionally provided in any of the rehydrating or blocking buffers provided herein. In some embodiments, the analyte capture agent analyte capture sequence can be blocked prior to binding to the capture probe capture domain using a blocking probe sequence complementary to the analyte capture sequence. Blocking the capture agent barcode domain, particularly the free 3' end of the capture agent barcode domain (e.g., analyte capture sequence), prior to contacting the analyte capture agents with the biological sample and/or substrate, can prevent binding of the analyte capture sequence of the capture agent barcode domains, e.g., prevents the binding of a poly(A) tail to the capture probe capture domain. In some embodiments, blocking the analyte capture agent analyte capture domain reduces non-specific background staining. In some embodiments, the blocking probes are reversible, such that the blocking probes can be removed from the analyte capture sequence during or after the time that analyte capture agents are in contact with the biological sample. In some embodiments, the blocking probe can be removing with RNAse treatment (e.g., RNAse H treatment).

In some embodiments, methods for capturing polypeptides in a biological sample include active transfer (e.g., electrophoresis). For example, the biological sample is placed on a conductive substrate and contacted with a spatial array including one or more analyte binding moieties. An electric filed can be applied to the conductive substrate to promote migration of the polypeptides towards the analyte binding moieties, as described herein.

In some embodiments, methods for identifying the spatial location of a polypeptide in a biological sample include determining the sequence of a captured polypeptide. In some embodiments, the sequence of the captured polypeptide is determined through detection of amino acid residues labeled with a detectable label (e.g., radiolabel of a fluorophore). Non-limiting examples of detectable labels that can be used for labelling the captured polypeptide include fluorophores and radiolabels. In some embodiments, the polypeptides are labeled at specific amino acid residues only (e.g., not all amino acid residues are labeled). In some embodiments, the polypeptide is labeled prior to contacting the biological sample with the substrate. In some embodiments, a captured polypeptide is labeled with fluorophores using standard coupling schemes (see Hernandez et al., *New J. Chem.* 41:462-469 (2017)). For example, polypeptides may be labeled by reaction with Atto647N-NHS, Atto647Niodoacetamide, TMR-NHS, or JF549-NHS, as appropriate, to label lysines (via NHS) or cysteines (via iodoacetamide). In addition, serine or threonine phosphorylation sites may be selectively labeled via beta elimination followed by conjugate addition via thiols to substitute thiol-linked fluorophores in place of phosphates (see Stevens et al., *Rapid Commun. Mass Specrtom.*, 15: 2157-2162 (2005)). The number of fluorophores incorporated into a polypeptide is any number that may be spectrally resolved. In some instances, four or more fluorophores are utilized.

In some embodiments, a captured polypeptide is radiolabeled. In some embodiments, specific amino acids can be labeled with an isotope. Non-limiting examples of isotopes used to label amino acids include $^3$H, $^{14}$C, $^{15}$N, $^{32}$P, and $^{125}$I. In some embodiments, the isotope is incorporated into the selected amino acid prior to incorporation into a polypeptide. In some embodiments, the radiolabeled amino acid can be incorporated into the polypeptide after polypeptide formation.

In some embodiments, the sequence of the captured polypeptide is determined using Edman degradation (and in some embodiments successive rounds of Edman degradation). In such cases, a polypeptide is captured, and the polypeptide sequence can be resolved by imaging the substrate following repeated rounds of Edman degradation. For example, the substrate is imaged following each Edman reaction in order to capture the detectable labels that are produced due to the removal of amino acids that are a byproduct of the reaction. The information obtained by the Edman degradation can be complied to identify a polypeptide. In some embodiments, the biological sample is visualized or imaged using light or fluorescence microscopy.

(viii) Enrichment of Captured Analytes after Capture

In some aspects, spatial analysis of targeted analytes includes an enrichment step or steps post-capture to enrich the captured analytes for the targeted analyte. For example, the capture domain can be selected or designed for the selective capture of more analytes than the practitioner desires to analyze. In some embodiments, capture probes that include random sequences (e.g., random hexamers or similar sequences) that form all or part of the capture domain can be used to capture nucleic acids from a biological sample in an unbiased way. For example, capture probes having capture domains that include random sequences can be used to generically capture DNA, RNA, or both from a biological sample. Alternatively, capture probes can include capture domains can that capture mRNA generally. As is well known in the art, this can be on the basis of hybridization to the poly-A tail of mRNAs. In some embodiments, the capture domain includes a sequence that interacts with (e.g., hybridizes to) the poly-A tail of mRNAs. Non-limiting examples of such sequences include poly-T DNA sequences and poly-U RNA sequences. In some embodiments, random sequences can be used in conjunction with poly-T (or poly-T analogue etc.) sequences. Thus, where a capture domain includes a poly-T (or a "poly-T-like") oligonucleotide, it can also include a random oligonucleotide sequence.

In some aspects, after capture of more analytes than the practitioner desires to analyze, methods disclosed herein include enrichment of particular captured analytes. In some aspects, methods include enrichment of analytes that include mutations (e.g., SNPs) of interest, nucleic acid(s) of interest, and/or proteins(s) of interest.

In some embodiments, methods of spatial analysis provided herein include selectively enriching one or more analytes of interest (e.g., target analytes) after analyte capture. For example, one or more analytes of interest can be enriched by addition of one or more oligonucleotides to the pool of captured analytes. In some embodiments, one or more analytes of interest can be enriched by addition of one or more oligonucleotides to the pool of captured analytes on the array. In some embodiments, one or more analytes of interest can be enriched by addition of one or more oligonucleotides to the pool of captured analytes where the pool of captured analytes have been released (e.g., removed) from the array. In some embodiments, when captured analytes have been released from the array the one or more nucleotides can be complementary to a portion of a TSO and R1 sequence, or portion thereof. In some embodiments, the additional oligonucleotide(s) include a sequence used for priming a reaction by a polymerase. For example, one or more primer sequences with sequence complementarity to one or more analytes of interest can be used to amplify the one or more analyte(s) of interest, thereby selectively enriching these analytes. In some embodiments, one or more primer sequences can be complementary to other domains on the capture probe (e.g., R1 sequence, or portion thereof, as above), and not complementary to the analyte. In some embodiments, enrichment by amplification (e.g., PCR) occurs by using a first primer complementary to an analyte or analytes of interest (or another domain in the capture probe and the TSO), or complement thereof, and a second primer complementary to a region of the capture probe, or complement thereof. In some embodiments, the region of the capture probe, or complement thereof, is distal to a spatial barcode from the capture domain, such that enrichment by amplification amplifies both the captured analyte or analytes and its or their associated spatial barcodes, thus permitting spatial analysis of the enriched analyte or analytes.

In some embodiments, two or more capture probes capture two or more distinct analytes, which analytes are enriched (e.g., simultaneously or sequentially) from the pool of captured analytes. In some embodiments, enrichment by PCR amplification includes multiple rounds of amplification. For example, enrichment by PCR amplification can include nested PCR reactions using different primers that are specific for the analyte or analytes of interest. In some embodiments, enrichment by amplification can be performed using an amplification method that is not PCR. A non-limiting example of a non-PCR amplification method is rolling circle amplification. Other non-PCR amplification methods are known in the art.

In some embodiments, an oligonucleotide with sequence complementarity to a captured analyte or analytes of interest, or complement thereof, can be used to enrich the captured analyte or analytes of interest from the pool of captured analytes. In some embodiments, an oligonucleotide with sequence complementarity to a captured analyte or analytes of interest (or another domain the capture probe), or complement thereof, can include one or more functional moieties that are useful in the enrichment process. For example, biotinylated oligonucleotides with sequence complementary to one or more analytes interest, or complements thereof, can bind to the analyte(s) of interest and can be selected using biotinylation-strepavidin affinity using any of a variety of methods known in the art (e.g., streptavidin beads). In some embodiments, oligonucleotides with sequence complementary to one or more analytes interest, or complements thereof, include a magnetic moiety (e.g., a magnetic bead) that can be used in the enrichment process.

Additionally or alternatively, one or more species of analyte (e.g., mitochondrial DNA or RNA) can be down-selected (e.g., removed) using any of a variety of methods. In some embodiments, such down-selection of analytes that are not of interest can result in improved capture of other types of analytes that are of interest. For example, probes can be administered to a sample that selectively hybridize to ribosomal RNA (rRNA), thereby reducing the pool and concentration of rRNA in the sample. In some embodiments, such down-selection can result in improved capture of other types of RNA due to the reduction in non-specific RNA present in the sample. Additionally or alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which is incorporated herein by reference). In some embodiments, hydroxyapatite chromatography can be used to remove abundant species (e.g., rRNA).

(ix) RNA-Templated Ligation

In some embodiments of methods provided here, RNA-templated ligation is used to interrogate spatial gene expression in a biological sample (e.g., an FFPE tissue section). RNA-templated ligation enables sensitive measurement of specific nucleic acid analytes of interest that otherwise might be analyzed less sensitively with a whole transcriptomic approach. It provides advantages of compatibility with common histochemical stains and suitability for analysis of decade-old materials (e.g., FFPE samples) and exceedingly small microdissected tissue fragments.

In some aspects, the steps of RNA-templated ligation include: (1) hybridization of pairs of probes (e.g., DNA probes) to RNA (e.g., formalin fixed RNA) within a tissue section; (2) ligation of adjacently annealed probe pairs in situ; (3) RNase H treatment that (i) releases RNA-templated ligation products from the tissue (e.g., into solution) for downstream analysis and (ii) destroys unwanted DNA-templated ligation products; and optionally, (4) amplification of RNA-templated ligation products (e.g., by multiplex PCR).

In some aspects, disclosed herein are methods of direct detection of RNA target-DNA probe duplexes without first converting RNA to cDNA by reverse transcription. In some aspects, RNA-templated ligation can include a DNA ligase. In some aspects, RNA-templated ligation can include RNA ligase. In some aspects, RNA-templated ligation can include T4 RNA ligase.

In some aspects, RNA-templated ligation is used for detection of RNA, determination of RNA sequence identity, and/or expression monitoring and transcript analysis. In some aspects, RNA-templated ligation allows for detection of a particular change in a nucleic acid (e.g., a mutation or single nucleotide polymorphism (SNP)), detection or expression of a particular nucleic acid, or detection or expression of a particular set of nucleic acids (e.g., in a similar cellular pathway or expressed in a particular pathology). In some embodiments, the methods that include RNA-templated ligation are used to analyze nucleic acids, e.g., by genotyping, quantitation of DNA copy number or RNA transcripts, localization of particular transcripts within samples, and the like. In some aspects, systems and methods provided herein that include RNA-templated ligation identify single nucleotide polymorphisms (SNPs). In some aspects, such systems and methods identify mutations.

In some aspects, disclosed herein are methods of detecting RNA expression that include bringing into contact a first probe, a second probe, and ligase (e.g., T4 RNA ligase). In some embodiments, the first probe and the second probe are designed to hybridize to a target sequence such that the 5' end of the first probe and the 3' end of the second probe are adjacent and can be ligated, wherein at least the 5'-terminal nucleotide of the first probe and at least the 3'-terminal nucleotide of the second probe are deoxyribonucleotides (DNA), and wherein the target sequence includes (e.g., is composed of) ribonucleotides (RNA). After hybridization, a ligase (e.g., T4 RNA ligase) ligates the first probe and the second probe if the target sequence is present in the target sample, but does not ligate the first probe and the second probe if the target sequence is not present in the target sample. The presence or absence of the target sequence in the biological sample can be determined by determining whether or not the first and second probes were ligated in the presence of ligase. Any of a variety of methods can be used to determine whether or not the first and second probes were ligated in the presence of ligase, including but not limited to, sequencing the ligated product, hybridizing the ligated product with a detection probe that hybridizes only when the first and second probes were ligated in the presence of ligase, restriction enzyme analysis, and other methods known in the art.

In some aspects, two or more RNA analytes are analyzed using methods that include RNA-templated ligation. In some aspects, when two or more analytes are analyzed, a first and second probe that is specific for (e.g., specifically hybridizes to) each RNA analyte are used.

In some aspects, three or more probes are used in RNA-templated ligation methods provided herein. In some embodiments, the three or more probes are designed to hybridize to a target sequence such that the three or more probes hybridize adjacent to each other such that the 5' and 3' ends of adjacent probes can be ligated. In some embodiments, the presence or absence of the target sequence in the biological sample can be determined by determining whether or not the three or more probes were ligated in the presence of ligase.

In some aspects, the first probe is a DNA probe. In some aspects, the first probe is a chimeric DNA/RNA probe. In some aspects, the second probe is a DNA probe. In some aspects, the second probe is a chimeric DNA/RNA probe.

In some aspects, methods of RNA-templated ligation utilize the T4 RNA Ligase 2 to efficiently join adjacent chimeric RNA-DNA probe pairs hybridized in situ on fixed RNA target sequences. Subsequent treatment with RNase H releases RNA-templated ligation products (e.g., into solution) for downstream analysis.

(x) Region of Interest

A biological sample can have regions that show morphological feature(s) that may indicate the presence of disease or the development of a disease phenotype. For example, morphological features at a specific site within a tumor biopsy sample can indicate the aggressiveness, therapeutic resistance, metastatic potential, migration, stage, diagnosis, and/or prognosis of cancer in a subject. A change in the morphological features at a specific site within a tumor biopsy sample often correlate with a change in the level or expression of an analyte in a cell within the specific site, which can, in turn, be used to provide information regarding the aggressiveness, therapeutic resistance, metastatic potential, migration, stage, diagnosis, and/or prognosis of cancer in a subject. A region or area within a biological sample that is selected for specific analysis (e.g., a region in a biological sample that has morphological features of interest) is often described as "a region of interest." A region of interest in a biological sample can be used to analyze a specific area of interest within a biological sample, and thereby, focus experimentation and data gathering to a specific region of a biological sample (rather than an entire biological sample). This results in increased time efficiency of the analysis of a biological sample.

A region of interest can be identified in a biological sample using a variety of different techniques, e.g., expansion microscopy, bright field microscopy, dark field microscopy, phase contrast microscopy, electron microscopy, fluorescence microscopy, reflection microscopy, interference microscopy, confocal microscopy, and visual identification (e.g., by eye), and combinations thereof. For example, the staining and imaging of a biological sample can be performed to identify a region of interest. In some examples, the region of interest can correspond to a specific structure of cytoarchitecture. In some embodiments, a biological sample can be stained prior to visualization to provide contrast between the different regions of the biological sample. The type of stain can be chosen depending on the type of biological sample and the region of the cells to be stained. In some embodiments, more than one stain can be used to visualize different aspects of the biological sample, e.g., different regions of the sample, specific cell structures (e.g., organelles), or different cell types. In other embodiments, the biological sample can be visualized or imaged without staining the biological sample.

In some embodiments, staining and imaging a biological sample prior to contacting the biological sample with a spatial array is performed to select samples for spatial analysis. In some embodiments, the staining includes applying a fiducial marker as described herein, including fluorescent, radioactive, chemiluminescent, or colorimetric detectable markers. In some embodiments, the staining and imaging of biological samples allows the user to identify the specific sample (or region of interest) the user wishes to assess.

In some examples, an array (e.g., any of the exemplary arrays described herein) can be contacted with only a portion of a biological sample (e.g., a cell, a tissue section, or a region of interest). In some examples, a biological sample is contacted with only a portion of an array (e.g., any of the exemplary arrays described herein). In some embodiments, capture probes on an array corresponding to regions of interest of a biological sample (e.g., proximal to the region of interest) can be selectively cleaved and analyzed. For example, capture probes on an array may be deactivated or eliminated outside of areas corresponding to regions of interest of a biological sample. In some embodiments, capture probes including a photocleavable bond and on the array in areas corresponding to regions of interest of a biological sample can be selectively cleaved by using light. A mirror, mirror array, a lens, a moving stage, and/or a photomask can be used to direct the light to regions of the array that correspond areas outside one or more regions of interest in the biological sample. Some embodiments include deactivating or eliminating capture probes, e.g., capture probes comprising a photocleavable bond as described herein, using light. In some embodiments, a laser, e.g., a scanning laser, can be used to deactivate or eliminate capture probes. In some embodiments, the eliminated member of the plurality of capture probes can be washed away. In some embodiments, regions of interest can be labeled with different heavy metals, and a laser can sequentially ablate these regions of interest before mass spectrometry identification. A laser can, for example, deactivate or eliminate capture probes through UV light destruction of DNA, heat, inducing a chemical reaction that prevents the capture probes from moving to the next step, inducing photocleavage of a photocleavable bond, or a combination thereof. In some examples, a portion of the array can be deactivated such that it does not interact with the analytes in the biological sample (e.g., optical deactivation, chemical deactivation, heat deactivation, or blocking of the capture probes in the array (e.g., using blocking probes)). In some examples, a region of interest can be removed from a biological sample and then the region of interest can be contacted to the array (e.g., any of the arrays described herein). A region of interest can be removed from a biological sample using microsurgery, laser capture microdissection, chunking, a microtome, dicing, trypsinization, labelling, and/or fluorescence-assisted cell sorting, and the like.

In some examples, a region of interest can be permeabilized or lysed while areas outside the region of interest are not permeabilized or lysed (e.g., Kashyap et al. *Sci Rep.* 2016; 6: 29579, herein incorporated by reference in its entirety). For example, in some embodiments, a region of interest can be contacted with a hydrogel comprising a permeabilization or lysing reagent. In some embodiments, the area(s) outside the region of interest are not contacted with the hydrogel comprising the permeabilization or lysing reagent.

(f) Partitioning

As discussed above, in some embodiments, the sample can optionally be separated into single cells, cell groups, or other fragments/pieces that are smaller than the original, unfragmented sample. Each of these smaller portions of the sample can be analyzed to obtain spatially-resolved analyte information for the sample.

For samples that have been separated into smaller fragments—and particularly, for samples that have been disaggregated, dissociated, or otherwise separated into individual cells—one method for analyzing the fragments involves separating the fragments into individual partitions (e.g., fluid droplets), and then analyzing the contents of the partitions. In general, each partition maintains separation of its own contents from the contents of other partitions. The partition can be a droplet in an emulsion, for example.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle volume, particle concentration, etc.), microfluidic architectures (e.g., channel geometry, etc.), and other parameters can be adjusted to control the occupancy of the resulting partitions (e.g., number of analytes per partition, number of beads per partition, etc.). For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

In addition to cells and/or analytes, a partition can include additional components, and in particular, one or more beads. A partition can include a single gel bead, a single cell bead, or both a single cell bead and single gel bead. A variety of different beads can be incorporated into partitions. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead. For example, a nucleic acid molecule (e.g., an oligonucleotide), can be coupled to a bead by a releasable linkage (e.g., a disulfide linker), wherein the nucleic acid molecule can be or include a barcode. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead. The same bead can be coupled (e.g., via releasable linkage) to one or more other nucleic acid molecules.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly(T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead. In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

In some embodiments, barcoded nucleic acid molecules can be initially associated with a microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well. As described above, FIG. 16 shows an example of a microfluidical channel structure for partitioning individual analytes (e.g., cells) into discrete partitions.

FIG. 16 shows an example of a microfluidic channel structure for partitioning individual analytes (e.g., cells) into discrete partitions. The channel structure can include channel segments 1601, 1602, 1603, and 1604 communicating at a channel junction 1605. In operation, a first aqueous fluid 1606 that includes suspended biological particles (or cells) 1607 may be transported along channel segment 1601 into junction 1605, while a second fluid 1608 that is immiscible with the aqueous fluid 1606 is delivered to the junction 1605 from each of channel segments 1602 and 1603 to create discrete droplets 1609, 1610 of the first aqueous fluid 1606 flowing into channel segment 1604, and flowing away from junction 1605. The channel segment 1604 may be fluidically coupled to an outlet reservoir where the discrete droplets can be stored and/or harvested. A discrete droplet generated may include an individual biological particle 1607 (such as droplets 1609). A discrete droplet generated may include more than one individual biological particle 1607. A discrete droplet may contain no biological particle 1607 (such as droplet 1610). Each discrete partition may maintain separation of its own contents (e.g., individual biological particle 1607) from the contents of other partitions.

FIG. 17A shows another example of a microfluidic channel structure 1700 for delivering beads to droplets. The channel structure includes channel segments 1701, 1702, 1703, 1704 and 1705 communicating at a channel junction 1706. During operation, the channel segment 1701 can transport an aqueous fluid 1707 that includes a plurality of beads 1708 along the channel segment 1701 into junction 1706. The plurality of beads 1708 can be sourced from a suspension of beads. For example, the channel segment 1701 can be connected to a reservoir that includes an aqueous suspension of beads 1708. The channel segment 1702 can transport the aqueous fluid 1707 that includes a plurality of particles 1709 (e.g., cells) along the channel segment 1702 into junction 1706. In some embodiments, the aqueous fluid 1707 in either the first channel segment 1701 or the second channel segment 1702, or in both segments, can include one or more reagents, as further described below.

A second fluid 1710 that is immiscible with the aqueous fluid 1707 (e.g., oil) can be delivered to the junction 1706 from each of channel segments 1703 and 1704. Upon meeting of the aqueous fluid 1707 from each of channel segments 1701 and 1702 and the second fluid 1710 from each of channel segments 1703 and 1704 at the channel junction 1706, the aqueous fluid 1707 can be partitioned as discrete droplets 1711 in the second fluid 1710 and flow away from the junction 1706 along channel segment 1705. The channel segment 1705 can deliver the discrete droplets to an outlet reservoir fluidly coupled to the channel segment 1705, where they can be harvested.

As an alternative, the channel segments 1701 and 1702 can meet at another junction upstream of the junction 1706. At such junction, beads and biological particles can form a mixture that is directed along another channel to the junction 1706 to yield droplets 1711. The mixture can provide the beads and biological particles in an alternating fashion, such that, for example, a droplet includes a single bead and a single biological particle.

The second fluid 1710 can include an oil, such as a fluorinated oil, that includes a fluorosurfactant for stabilizing the resulting droplets, for example, inhibiting subsequent coalescence of the resulting droplets 1711.

The partitions described herein can include small volumes, for example, less than about 10 microliters (L), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

In the foregoing discussion, droplets with beads were formed at the junction of different fluid streams. In some embodiments, droplets can be formed by gravity-based partitioning methods.

Figure 17B:
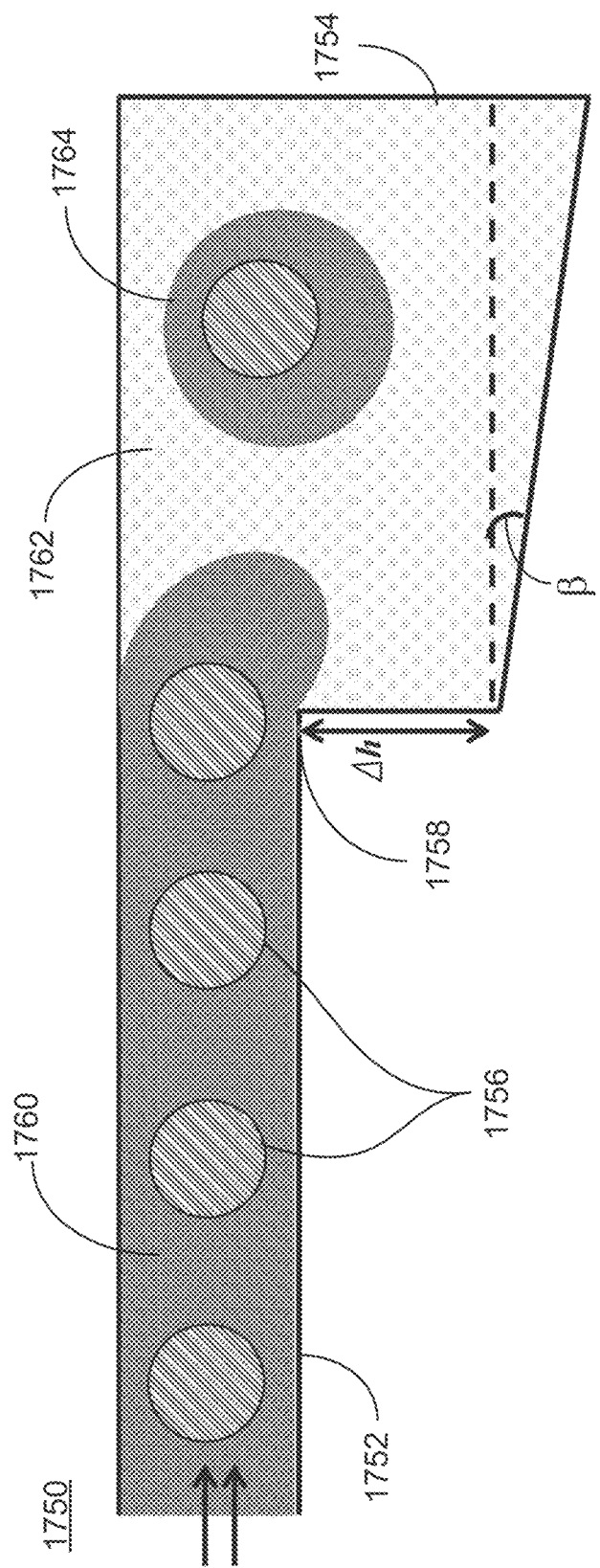
FIG. 17B shows a cross-section view of another example of a microfluidic channel structure 1750 with a geometric feature for controlled partitioning.

FIG. 17B shows a cross-section view of another example of a microfluidic channel structure 1750 with a geometric feature for controlled partitioning. A channel structure 1750 can include a channel segment 1752 communicating at a channel junction 1758 (or intersection) with a reservoir 1754. In some instances, the channel structure 1750 and one or more of its components can correspond to the channel structure 1700 and one or more of its components.

An aqueous fluid 1760 comprising a plurality of particles 1756 may be transported along the channel segment 1752 into the junction 1758 to meet a second fluid 1762 (e.g., oil, etc.) that is immiscible with the aqueous fluid 1760 in the reservoir 1754 to create droplets 1764 of the aqueous fluid 1760 flowing into the reservoir 1754. At the junction 1758 where the aqueous fluid 1760 and the second fluid 1762 meet, droplets can form based on factors such as the hydrodynamic forces at the junction 1758, relative flow rates of the two fluids 1760, 1762, fluid properties, and certain geometric parameters (e.g., Δh, etc.) of the channel structure 1750. A plurality of droplets can be collected in the reservoir 1754 by continuously injecting the aqueous fluid 1760 from the channel segment 1752 at the junction 1758.

A discrete droplet generated may comprise one or more particles of the plurality of particles 1756. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 1760 can have a substantially uniform concentration or frequency of particles 1756. As described elsewhere herein, the particles 1756 (e.g., beads) can be introduced into the channel segment 1752 from a separate channel (not shown in FIG. 17). The frequency of particles 1756 in the channel segment 1752 may be controlled by controlling the frequency in which the particles 1756 are introduced into the channel segment 1752 and/or the relative flow rates of the fluids in the channel segment 1752 and the separate channel. In some instances, the particles 1756 can be introduced into the channel segment 1752 from a plurality of different channels, and the frequency controlled accordingly. In some instances, different particles may be introduced via separate channels. For example, a first separate channel can introduce beads and a second separate channel can introduce biological particles into the channel segment 1752. The first separate channel introducing the beads may be upstream or downstream of the second separate channel introducing the biological particles.

In some instances, the second fluid 1762 may not be subjected to and/or directed to any flow in or out of the reservoir 1754. For example, the second fluid 1762 may be substantially stationary in the reservoir 1754. In some instances, the second fluid 1762 may be subjected to flow within the reservoir 1754, but not in or out of the reservoir 1754, such as via application of pressure to the reservoir 1754 and/or as affected by the incoming flow of the aqueous fluid 1760 at the junction 1758. Alternatively, the second fluid 1762 may be subjected and/or directed to flow in or out of the reservoir 1754. For example, the reservoir 1754 can be a channel directing the second fluid 1762 from upstream to downstream, transporting the generated droplets.

The channel structure 1750 at or near the junction 1758 may have certain geometric features that at least partly determine the volumes and/or shapes of the droplets formed by the channel structure 1750. The channel segment 1752 can have a first cross-section height, h1, and the reservoir 1754 can have a second cross-section height, h2. The first cross-section height, h1, and the second cross-section height, h2, may be different, such that at the junction 1758, there is a height difference of Δh. The second cross-section height, h2, may be greater than the first cross-section height, h1. In some instances, the reservoir may thereafter gradually increase in cross-section height, for example, the more distant it is from the junction 1758. In some instances, the cross-section height of the reservoir may increase in accordance with expansion angle, β, at or near the junction 1758. The height difference, Δh, and/or expansion angle, β, can allow the tongue (portion of the aqueous fluid 1760 leaving channel segment 1752 at junction 1758 and entering the reservoir 1754 before droplet formation) to increase in depth and facilitate decrease in curvature of the intermediately formed droplet. For example, droplet volume may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 1760 entering the junction 1758 can be between about 0.04 microliters (μL)/minute (min) and about 40 μL/min. In some instances, the flow rate of the aqueous fluid 1760 entering the junction 1758 can be between about 0.01 microliters (μL)/minute (min) and about 100 μL/min. Alternatively, the flow rate of the aqueous fluid 1760 entering the junction 1758 can be less than about 0.01 μL/min. alternatively, the flow rate of the aqueous fluid 1760 entering the junction 1758 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 1760 entering the junction 1758. The second fluid 1762 may be stationary, or substantially stationary, in the reservoir 1754. Alternatively, the second fluid 1762 may be flowing, such as at the above flow rates described for the aqueous fluid 1760.

While FIG. 17B illustrates the height difference, Δh, being abrupt at the junction 1758 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 1758, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIG. 17B illustrates the expanding reservoir cross-section height as linear (e.g., constant expansion angle, p), the cross-section height may expand non-linearly. For example, the reservoir may be defined at least partially by a dome-like (e.g., hemispherical) shape having variable expansion angles. The cross-section height may expand in any shape.

Figure 17C:
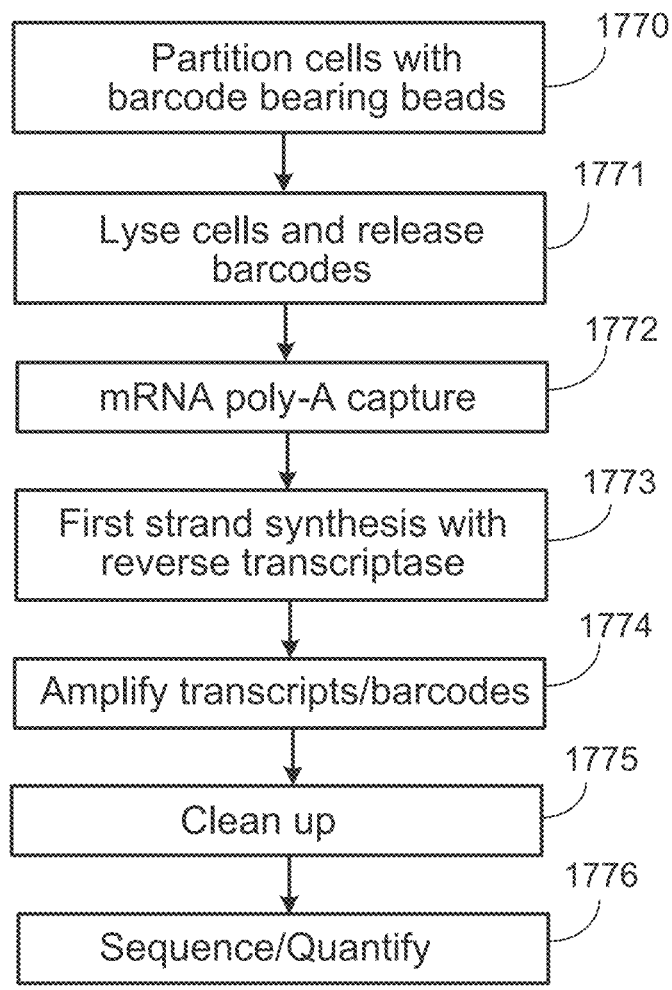
FIG. 17C shows an example of a workflow schematic.

FIG. 17C depicts a workflow wherein cells are partitioned into droplets along with barcode-bearing beads 1770. See FIG. 17A. The droplet forms an isolated reaction chamber wherein the cells can be lysed 1771 and target analytes within the cells can then be captured 1772 and amplified 1773, 1774 according to previously described methods. After sequence library preparation clean-up 1775, the material is sequenced and/or quantified 1776 according to methods described herein.

It should be noted that while the example workflow in FIG. 17C includes steps specifically for the analysis of mRNA, analogous workflows can be implemented for a wide variety of other analytes, including any of the analytes described previously.

By way of example, in the context of analyzing sample RNA as shown in FIG. 17C, the poly(T) segment of one of the released nucleic acid molecules (e.g., from the bead) can hybridize to the poly(A) tail of a mRNA molecule. Reverse transcription can result in a cDNA transcript of the mRNA, which transcript includes each of the sequence segments of the nucleic acid molecule. If the nucleic acid molecule includes an anchoring sequence, it will more likely hybridize to and prime reverse transcription at the sequence end of the poly(A) tail of the mRNA.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, partitions include precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

A degradable bead can include one or more species with a labile bond such that, when the bead/species is exposed to the appropriate stimulus, the bond is broken and the bead degrades within the partition. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet. The free species (e.g., oligonucleotides, nucleic acid molecules) can interact with other reagents contained in the partition.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore volumes due to osmotic pressure differences can generally occur without structural degradation of the bead itself. In some cases, an increase in pore volume due to osmotic swelling of a bead can permit the release of entrained species within the bead. In some embodiments, osmotic shrinking of a bead can cause a bead to better retain an entrained species due to pore volume contraction.

Numerous chemical triggers can be used to trigger the degradation of beads within partitions. Examples of these chemical changes can include, but are not limited to, pH-mediated changes to the integrity of a component within the bead, degradation of a component of a bead via cleavage of cross-linked bonds, and depolymerization of a component of a bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, Mo.), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore size of the encapsulate is sufficiently small to retain nucleic acid fragments of a given volume, following cellular disruption.

Examples of other species that can be co-partitioned with analytes in the partitions include, but are not limited to, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA.

Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; bridged nucleic acids, modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a miRNA, a physical environmental (e.g., temperature change), or any other known perturbation agents.

Additionally, in some embodiments, the unaggregated cell or disaggregated cells introduced and processed within partitions or droplets as described herein, can be removed from the partition, contacted with a spatial array, and spatially-barcoded according to methods described herein. For example, single cells of an unaggregated cell sample can be partitioned into partitions or droplets as described herein. The partitions or droplets can include reagents to permeabilize a cell, barcode targeted cellular analyte(s) with a cellular barcode, and amplify the barcoded analytes. The partitions or droplets can be contacted with any of the spatial arrays described herein. In some embodiments, the partition can be dissolved, such that the contents of the partition are placed in contact with the capture probes of the spatial array. The capture probes of the spatial array can then capture target analytes from the ruptured partitions or the droplets, and processed by the spatial workflows described herein.

(g) Analysis of Captured Analytes (i) Sample Removal from an Array

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes selecting a region of interest in the biological sample to subject to spatial transcriptomic analysis. In some embodiments, one or more of the one or more capture probes include a capture domain. In some embodiments, one or more of the one or more capture probe pluralities comprise a unique molecular identifier (UMI). In some embodiments, one or more of the one or more capture probe pluralities comprise a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

(ii) Extended Capture Probes

In some embodiments, a capture probe can be extended (an "extended capture probe," e.g., as described herein (e.g., Section II (b) (vii))). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, Wis.). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Epicentre Biotechnologies, Madison, Wis.), and SplintR (available from New England Biolabs, Ipswich, Mass.). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by a applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

(iii) Cleavage Domain

Capture probes can optionally include a "cleavage domain," where one or more segments or regions of the capture probe (e.g., spatial barcodes and/or UMIs) can be releasably, cleavably, or reversibly attached to a feature, or some other substrate, so that spatial barcodes and/or UMIs can be released or be releasable through cleavage of a linkage between the capture probe and the feature, or released through degradation of the underlying substrate or chemical substrate, allowing the spatial barcode(s) and/or UMI(s) of the cleaved capture probe to be accessed or be accessible by other reagents, or both. Non-limiting aspects of cleavage domains are described herein (e.g., in Section II (b) (ii)).

In some embodiments, the capture probe is linked, (e.g., via a disulfide bond), to a feature. In some embodiments, the capture probe is linked to a feature via a propylene group (e.g., Spacer C3). A reducing agent can be added to break the various disulfide bonds, resulting in release of the capture probe including the spatial barcode sequence. In another example, heating can also result in degradation and release of the attached capture probe. In some embodiments, the heating is done by laser (e.g., laser ablation) and features at specific locations can be degraded. In addition to thermally cleavable bonds, disulfide bonds, photo-sensitive bonds, and UV sensitive bonds, other non-limiting examples of labile bonds that can be coupled to a capture probe (e.g., spatial barcode) include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. In some embodiments, the cleavage domain can be a single U. In some embodiments, the cleavage domain can be an abasic site that can be cleaved with an abasic site-specific endonuclease (e.g., Endonuclease IV or Endonuclease VIII).

In some embodiments, the cleavage domain of the capture probe is a nucleotide sequence within the capture probe that is cleaved specifically, e.g., physically by light or heat, chemically or enzymatically. The location of the cleavage domain within the capture probe will depend on whether or not the capture probe is immobilized on the substrate such that it has a free 3' end capable of functioning as an extension primer (e.g., by its 5' or 3' end). For example, if the capture probe is immobilized by its 5' end, the cleavage domain will be located 5' to the spatial barcode and/or UMI, and cleavage of said domain results in the release of part of the capture probe including the spatial barcode and/or UMI and the sequence 3' to the spatial barcode, and optionally part of the cleavage domain, from a feature. Alternatively, if the capture probe is immobilized by its 3' end, the cleavage domain will be located 3' to the capture domain (and spatial barcode) and cleavage of said domain results in the release of part of the capture probe including the spatial barcode and the sequence 3' to the spatial barcode from a feature. In some embodiments, cleavage results in partial removal of the cleavage domain. In some embodiments, cleavage results in complete removal of the cleavage domain, particularly when the capture probes are immobilized via their 3' end as the presence of a part of the cleavage domain can interfere with the hybridization of the capture domain and the target nucleic acid and/or its subsequent extension.

(iv) Sequencing

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g., sequencing), i.e., can directly take part in the sequence analysis reaction or process (e.g., the sequencing reaction or sequencing process, or be the molecule which is sequenced or otherwise identified). Alternatively, the barcoded nucleic acid molecule can be subjected to a step of second strand synthesis or amplification before sequence analysis (e.g., sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g., barcoded nucleic acid molecules) can be analyzed (e.g., sequenced). To perform single molecule sequencing, the nucleic acid strand can be modified at the 3' end.

Massively parallel pyrosequencing techniques can be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., *Anal. Biochem.* 242(1), 84-9 (1996); Ronaghi, *Genome Res.* 11(1), 3-11 (2001); Ronaghi et al. *Science* 281 (5375), 363

(1998); and U.S. Pat. Nos. 6,210,891, 6,258,568, and 6,274,320, the entire contents of each of which are incorporated herein by reference.

In some embodiments, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in situ. In situ sequencing methods are particularly useful, for example, when the biological sample remains intact after analytes on the sample surface (e.g., cell surface analytes) or within the sample (e.g., intracellular analytes) have been barcoded. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, the entire contents of each of which are incorporated herein by reference.

In addition, examples of methods and systems for performing in situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Exemplary techniques for in situ sequencing include, but are not limited to, STARmap (described for example in Wang et al., (2018) *Science,* 361(6499) 5691), MERFISH (described for example in Moffitt, (2016) *Methods in Enzymology,* 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid features are present in a double stranded form these can be processed to provide single stranded nucleic acid templates using methods well known in the art, for example by denaturation, cleavage, etc. The sequencing primers which are hybridized to the nucleic acid template and used for primer extension are preferably short oligonucleotides, for example, 15 to 25 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010, 251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged.

In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., *Trends Biotechnol.* 18, 14 7-151 (2000); Deamer et al., *Acc. Chem.* Res. 35:817-825 (2002); Li et al., *Nat. Mater.* 2:611-615 (2003); Soni et al., *Clin. Chem.* 53, 1996-2001 (2007); Healy et al., *Nanomed.* 2, 459-481 (2007); Cockroft et al., *J. Am. Chem. Soc.* 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeq™ technology by Illumina, Inc., San Diego, Calif.), HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.), and sequencing of DNA nanoballs (Complete Genomics, Inc., Mountain View, Calif.).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181. The entire contents of each of the foregoing references are incorporated herein by reference herein.

(v) Temporal Analysis

In some embodiments, the methods described herein can be used to assess analyte levels and/or expression in a cell or a biological sample over time (e.g., before or after treatment with an agent or different stages of differentiation). In some examples, the methods described herein can be performed on multiple similar biological samples or cells obtained from the subject at a different time points (e.g., before or after treatment with an agent, different stages of differentiation, different stages of disease progression, different ages of the subject, before or after physical perturbation, before or after treatment with a perturbation agent as described herein, or before or after development of resistance to an agent). As described herein, a "perturbation agent" or "perturbation reagent" can be a small molecule, an antibody, a drug, an aptamer, a nucleic acid (e.g., miRNA), a CRISPR crRNA/sgRNA, TALEN, zinc finger nuclease, antisense oligonucleotide a physical environmental (e.g., temperature change), and/or any other known perturbation agents where the agent alters equilibrium or homeostasis.

In some embodiments, the methods described herein can be performed on multiple similar biological samples or cells obtained from the subject at 2, 3, 4, 5, 6, 7, 8, 9, 10, or more times. For example, the multiple similar biological samples can be repetitive samples from the same subject, the same tissue, the same organoid, the same cell suspension, or any other biological sample described herein. In some embodiments, the methods described herein can be performed on the same biological sample or cells obtained from the subject at a different time points (e.g., before or after treatment with a perturbation agent, different stages of differentiation, different stages of disease progression, different ages of the subject, or before or after development of resistance to an agent). In some embodiments, a perturbation agent can be small-molecules, antibodies, nucleic acids, peptides, and/or other external stimuli (e.g., temperature change). In some embodiments, the biological sample is contacted with a different array at each time point.

In some embodiments, a sample can be placed in a controlled environment permissive for cellular growth and/or maintenance, and/or to prevent hypoxia. In some embodiments, a controlled environment allows a sample to be analyzed at different time points. Barcoded arrays can be placed proximal to (e.g., on top of) the sample and imaged using a microscope or other suitable instrument to register the relative position of the biological sample to the barcoded array, optionally using optically encoded fiducial markers. An electric field can be applied for a period of time, such that biological analytes (e.g., DNA, RNA, proteins, metabolites, small molecules, lipids, and the like) are released from the sample and captured by capture probes on the spatially-barcoded array, preserving spatial information of the sample. The barcoded array can be removed, and the spatial and molecular information therein is determined (e.g., by performing library construction for next generation sequencing or in situ sequencing). Sequencing can be followed by computational analysis to correlate the molecular information (e.g., gene expression values with the spatial barcode). These steps can be repeated one or more times to capture the spatial information of analytes at different time-points.

In some embodiments, methods as described herein can be combined with a cell migration assay. A cell migration assay can comprise one or more microprinted lines, or suspended 3D nanofibers, on which the cells migrate. Migration using these assays can be measured by imaging cell migration and/or contacting migrated cells with a spatially-barcoded array. An array used in a cell migration assay can comprise one or more channels on the substrate of the array, e.g., to confine cell migration to one dimension along the substrate. Additionally, the channels can direct the migration of a cell such that it does not contact another cell on the array (e.g., the channels do not overlap with each other), and in some embodiments, the channels are about the same width as or wider than a cell (e.g., for a mammalian cell, a channel can have a width of about 2 μm to about 10 μm). Cellular location on the spatially-barcoded array can be identified using any method described herein.

In some embodiments, cells can be disposed on an array as described herein and allowed to migrate. Cell migration in cell migration assays can be used to measure target phenotypes (e.g., phenotype for invasiveness). In some embodiments, the cell migration distance can be measured and correlated to a biological analyte. Reagents can be added to the array to facilitate cell migration. For example, the array can be coated with one or more extracellular matrix (ECM) components (e.g., basement membrane extract (BME), laminin I, collagen I, collagen IV, fibronectin, vitronectin, elastin), a cell culture medium, a chemoattractant, a chemorepellant, or a combination thereof. In some embodiments, a reagent such as a chemoattractant or chemorepellant can be disposed on only a portion of the array, present as a gradient along the one or more axis or channels of the array, or a combination thereof.

(vi) Spatially Resolving Analyte Information

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate a nucleic acid barcode molecule with a feature. In some embodiments, an optical label of a feature can permit associating the feature with a biological particle (e.g., cell or nuclei). The association of a feature with a biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell or in a cell at a specific location of the biological sample).

In some embodiments, a feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

As discussed above, analytes obtained from a sample, such as RNA, DNA, peptides, lipids, and proteins, can be further processed. In particular, the contents of individual cells from the sample can be provided with unique spatial barcode sequences such that, upon characterization of the analytes, the analytes can be attributed as having been derived from the same cell. More generally, spatial barcodes can be used to attribute analytes to corresponding spatial locations in the sample. For example, hierarchical spatial positioning of multiple pluralities of spatial barcodes can be used to identify and characterize analytes over a particular spatial region of the sample. In some embodiments, the spatial region corresponds to a particular spatial region of interest previously identified, e.g., a particular structure of cytoarchitecture previously identified. In some embodiments, the spatial region corresponds to a small structure or group of cells that cannot be seen with the naked eye. In some embodiments, a unique molecular identifier can be used to identify and characterize analytes at a single cell level.

The analyte can include a nucleic acid molecule, which can be barcoded with a barcode sequence of a nucleic acid barcode molecule. In some embodiments, the barcoded analyte can be sequenced to obtain a nucleic acid sequence. In some embodiments, the nucleic acid sequence can include genetic information associated with the sample. The nucleic acid sequence can include the barcode sequence, or a complement thereof. The barcode sequence, or a complement thereof, of the nucleic acid sequence can be electronically associated with the property (e.g., color and/or intensity) of the analyte using the LUT to identify the associated feature in an array.

(vii) Proximity Capture

In some embodiments, two- or three-dimensional spatial profiling of one or more analytes present in a biological sample can be performed using a proximity capture reaction, which is a reaction that detects two analytes that are spatially close to each other and/or interacting with each other. For example, a proximity capture reaction can be used to detect sequences of DNA that are close in space to each other, e.g., the DNA sequences can be within the same chromosome, but separated by about 700 bp or less. As another example, a proximity capture reaction can be used to detect protein associations, e.g., two proteins that interact with each other. A proximity capture reaction can be performed in situ to detect two analytes that are spatially close to each other and/or interacting with each other inside a cell. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). Examples of such methods are described, for example, in Miele et al., *Methods Mol Biol*. (2009), 464, Simonis et al., *Nat. Genet*. (2006), 38(11): 1348-54, Raab et al., *Embo. J*. (2012), 31(2): 330-350, and Eagen et al., *Trends Biochem. Sci*. (2018) 43(6): 469-478, the entire contents of each of which is incorporated herein by reference.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Soderberg et al., *Methods*. (2008), 45(3): 227-32, the entire contents of which are incorporated herein by reference. In some embodiments, proximity ligation can include chromosome conformation capture methods.

In some embodiments, the proximity capture reaction is performed on analytes within about 400 nm distance (e.g., about 300 nm, about 200 nm, about 150 nm, about 100 nm, about 50 nm, about 25 nm, about 10 nm, or about 5 nm) from each other. In general, proximity capture reactions can be reversible or irreversible.

(viii) Feature Removal from an Array

A spatially-barcoded array can be contacted with a biological sample to spatially detect analytes present in the biological sample. In some embodiments, the features (e.g., gel pads, beads) can be removed from the substrate surface for additional analysis (e.g., imaging, sequencing, or quantification). In some embodiments, the features (e.g., gel pads, beads) can be removed mechanically (e.g., scraping), by an enzymatic reaction, or by a chemical reaction. In some embodiments, the features (e.g., gel pads, beads) can be aspirated. In some embodiments, after the features are removed (by any method), the features can be combined with a uniquely barcoded bead. In some embodiments, the oligonucleotides within a feature can be ligated or hybridized to the barcode sequence on the barcoded bead. For example, the spatial barcode oligonucleotide within a feature can be ligated to the barcode sequence on the barcoded bead. Additionally, the capture probes can be ligated to the barcode sequence on the barcoded bead. In some embodiments, the features and the bead can be partitioned. In some embodiments, the features (e.g., gels pads, beads) and the uniquely barcoded bead can be partitioned into a vesicle. In some embodiments, the vesicle can have a lipid bilayer. In some embodiments, the features and the bead can be encapsulated. In some embodiments, the features and the bead can be encapsulated in an oil emulsion. In some embodiments, the features and the bead can be encapsulated in a water-in-oil emulsion. Once partitioned, the features (e.g., gel pads, beads) can be processed for further analysis (e.g., sequencing) according to any method described herein.

(ix) Other Applications

The spatial analysis methods described herein can be used to detect and characterize the spatial distribution of one or more haplotypes in a biological sample. As used in the present disclosure, a haplotype is used to describe one or more mutations, DNA variations, polymorphisms in a given segment of the genome, which can be used to classify the genetic segment, or a collection of alleles or genetic segments containing single nucleotide polymorphisms (SNPs). Haplotype association studies are used to inform a greater understanding of biological conditions. For example, identifying and characterizing haplotype variants at or associated with putative disease loci in humans can provide a foundation for mapping genetic causes underlying disease susceptibility. The term "locus" (plural "loci"), as used in the art, can be a fixed location on a chromosome, including the location of a gene or a genetic marker, which can contain a plurality of haplotypes, including alleles and SNPs.

Variant haplotype detection is a technique used to identify heterozygous cells in single cell studies. In combination with spatial analysis, variant haplotype detection can further provide novel information on the distribution of heterozygous cells in biological samples (e.g., tissues) affected by or exhibiting a variety of biological conditions. These data may reveal causal relationships between variant haplotypes and disease outcomes, to aid in identification of disease-associated variants, or to reveal heterogeneity within a biological sample.

In some embodiments, variant haplotype detection is a technique that can be used in combination with, in addition to, or as a part of, the spatial analysis methods described herein. Briefly, variant haplotype detection can include providing inputs for executing an algorithm on a computer system, and performing an analysis to identify and determine the spatial distribution of haplotypes. One input can be a plurality of sequence reads obtained from a two-dimensional spatial array in contact with a biological sample and subsequently aligned to a genome. The sequence reads can also contain spatial barcodes with positional information, such that the sequence reads can be mapped to a location on the biological sample. Other inputs can include electronic data files of gene sequence variations, or haplotypes, and a reference genome. For each locus, the corresponding sequence reads and variant haplotypes are aligned to determine the haplotype identity of each sequence read. The haplotype identity and the spatial barcode of the sequence reads are then categorized to determine the spatial distribution of haplotypes within the biological sample. As described above, this spatial distribution can be used to characterize a biological condition of the sample. In some embodiments, sequence reads are obtained by in situ sequencing of the two-dimensional array of positions on the substrate, while in some embodiments, sequence reads are obtained by high-throughput sequencing. In some embodiments, other methods for generating sequence reads described herein are used, such as paired end sequencings.

In some embodiments, a respective loci in the plurality of loci is bi-allelic and the corresponding set of haplotypes for the respective loci consists of a first allele and a second allele. In some such embodiments, the respective loci includes a heterozygous single nucleotide polymorphism (SNP), a heterozygous insert, or a heterozygous deletion.

In some embodiments, analytes captured by any of the spatial analysis methods described herein can be analyzed (e.g., sequenced) via in situ sequencing methods. For example, a substrate including a plurality of capture probes (e.g., an array), attached either directly or indirectly (e.g., via a feature), that include a spatial barcode and a capture domain. In some embodiments, the capture domain can be configured to interact (e.g., hybridize) with an analyte (e.g., mRNA). In some embodiments, a biological sample can be contacted to the array such that the capture domain of the capture probe interacts with (e.g., hybridizes) the analyte. In some embodiments, the capture probe can function as a template for a hybridization or ligation reaction with the captured analyte. For example, a reverse transcription reaction can be performed to extend the 3' end of a capture probe hybridized to the analyte using any of the exemplary reverse transcriptases described herein, thereby generating an extended capture probe (e.g., an extended capture probe including the spatial barcode and a sequence that is complementary to a sequence in the analyte). After the extended capture probe is synthesized, a second strand that is complementary to the extended capture probe can be synthesized. In some embodiments, second strand synthesis can be performed using any of the methods described herein. In some embodiments, amine-modified nucleotides can be used when generating the extended capture probe or the second strand, or both. For example, the amine-modified nucleotides can be aminoallyl (aa)-dUTP, aa-dCTP, aa-dGTP, and/or aa-dATP.

In some embodiments, after generation of the extended capture probe, the second strand, or both the extended capture probe and/or the second strand can be released from the surface of the substrate. For example, the extended capture probe and/or the second strand can be released by any of the methods described herein (e.g., heat or cleavage via a cleavage domain). In some embodiments, the amine-modified nucleotides incorporated into the extended capture probe can be cross-linked to the surface of a substrate or cross-linked to the biological sample using its amine-modified nucleotides. In some embodiments, the surface of the substrate can be coated in a hydrogel. In some embodiments, the surface of the substrate can be coated in a protein matrix. In some embodiments, the cross-linking can be irreversible. In some embodiments, the cross-linked extended capture probe and/or second strand can be circularized. For example, circular template ligation can be performed by a DNA ligase (e.g., T4 DNA ligase) or circular template-free ligation can be performed by a template independent ligase (e.g., CircLigase). In some embodiments, the extended capture probe is circularized with CircLigase. In some embodiments, the circularized extended capture probe can be amplified. For example, rolling circle amplification can be performed with a suitable DNA polymerase (e.g., phi29). In some embodiments, the capture probe includes a functional domain (e.g., sequencing adapter). In some embodiments, rolling circle amplification can be performed with a primer complementary to the functional domain (e.g., sequencing adapter). In some embodiments, the rolling circle amplification can be performed to generate two or more amplicons (e.g., one or more amplicons including any of the amine-modified nucleotides described herein). In some embodiments, the two or more amplicons produced by the rolling circle amplification can be cross-linked to the surface of the substrate and/or cross-linked to the biological sample. In some embodiments, the two or more amplicons can be sequenced in situ. The in situ sequencing can be performed by any method described herein (See, Lee, J. H., Fluorescent in situ sequencing (FISSEQ) of RNA for gene expression profiling, *Nat Protoc.*, 10(3): 442-458, doi:10.1038/nprot.2014.191 (2015), which is incorporated herein by reference). In some embodiments, the two or more amplicons can be imaged.

In some embodiments, spatial analysis by any of the methods described herein can be performed on ribosomal RNA (rRNA), including, endogenous ribosomal RNA (e.g., native to the biological sample), and/or exogenous RNA (e.g., microbial ribosomal RNA and/or viral RNA also present in the biological sample). As used herein, "metagenomics," can refer to the study of exogenous nucleic acids (e.g., DNA, RNA, or other nucleic acids described herein) present in a biological sample. As used herein, "spatial metagenomics," can refer to the study of the spatial location of exogenous nucleic acid present in a biological sample. Spatial metagenomics can also refer to the identification of one or more species (e.g., viral or microbial) present in the biological sample and/or the study of identifying patterns of proximity (e.g., co-localization) amongst species.

In some embodiments, microbial rRNA can be spatially detected, quantified, and/or amplified from a biological sample. In some embodiments, rRNA (e.g., 16S ribosomal RNA) can be associated with a particular microbial species. For example, microbial ribosomal RNA (e.g., 16S ribosomal RNA) can be used to identify one or more species of microbe present in the biological sample (See e.g., Kolbert, C. P., and Persing, D. H., Ribosomal DNA sequencing as a tool for identification of bacterial pathogens, *Current Opinion in Microbiology.* 2 (3): 299-305. doi:10.1016/S1369-5274(99)80052-6. PMID 10383862 (1999), which is incorporated herein by reference). In some embodiments, identification of microbial species in proximity to one or more other microbial species can be identified.

In some embodiments, a substrate can be covered (e.g., coated) with a photo-crosslinkable coating (e.g., conditionally dissolvable polymer, e.g., DTT sensitive hydrogel). A biological sample can be contacted with the photo-crosslinkable coated substrate. In some embodiments, the biological sample and photo-crosslinkable substrate are assembled into a flow-cell and the photo-crosslinkable polymer can be incubated with the biological sample. The biological sample can be cross-linked into hydrogel-voxels of defined dimensions using a light source and a photomask. In some embodiments, the flow-cell can be dismantled and washed to remove unpolymerized hydrogel. The photo-crosslinkable coating can be treated with DTT to yield single-cell partitions or approximately single-cell partitions.

In some embodiments, the single-cell or approximately single-cell partitions can be encapsulated in a vesicle. The vesicle can contain a barcoded feature (e.g., a bead), and the barcoded feature can contain a capture domain. In some embodiments, the capture domain can capture microbial rRNA (e.g., microbial 16S rRNA). In some embodiments, the captured microbial rRNA can be amplified and analyzed (e.g., sequenced) by any of the methods described herein. In some embodiments, the amplified and sequenced microbial rRNA can identify microbial species and/or patterns of proximity (e.g., co-localization) of one or more species.

Alternatively, spatial analysis can be performed on exogenous rRNA (e.g., microbial or viral) with a plurality of capture probes on a substrate (e.g., an array), wherein the capture probes include a spatial barcode and a capture domain. In some embodiments, the capture domain can be configured to interact (e.g., hybridize) with microbial rRNA present in the biological sample. The capture probe can be configured to interact with any microbial rRNA. In some embodiments, the capture probe is configured to interact with microbial 16S rRNA. The biological sample can be treated (e.g., permeabilized) such that the capture domain and the analyte (e.g., microbial rRNA) interact (e.g., hybridize). In some embodiments, the captured analyte (e.g., microbial rRNA) can be reverse transcribed generating a first strand cDNA, followed by second strand cDNA synthesis as described herein. The first stand cDNA and/or the second strand cDNA can include a portion or all of a capture probe sequence, or a complement thereof. The capture probe sequence, or complement thereof, can include the spatial barcode, or complement thereof. In some embodiments, the first strand cDNA, and optionally, the second strand cDNA can be amplified by any method described herein. The amplified capture probes and analytes can be analyzed (e.g., sequenced) by any method described herein. The spatial information of the spatially-barcoded features can be used to determine the spatial location of the captured analytes (e.g., microbial rRNA) in the biological sample. In some embodiments, the captured analyte can identify the microbial species present in the biological sample. In some embodiments, the spatial information and identity of microbial species present in the biological sample can be correlated with one another, thus revealing whether certain microbial species may be found in proximity (e.g., co-localize) with one another.

Provided herein are methods for spatially profiling analytes within a biological sample. Profiles of biological samples (e.g., individual cells, populations of cells, tissue sections, etc.) can be compared to profiles of other cells, e.g., "normal," or "healthy," biological samples. In some embodiments of any the methods for spatially profiling analytes described herein, the method can provide for diagnosis of a disease (e.g., cancer, Alzheimer's disease, Parkinson's disease). In some embodiments of any the methods for spatially profiling analytes described herein, the methods can be used in drug screening. In some embodiments of any the methods for spatially profiling analytes described herein, the methods can be used to perform drug screening with an organoid. In some embodiments of any the methods for spatially profiling analytes described herein, the methods can be used to detect changes in (e.g., altered) cellular signaling. In some embodiments of any the methods for spatially profiling analytes described herein, the methods can include the introduction of a pathogen to the biological sample and evaluation of the response of the biological sample to the pathogen. In some embodiments of any the methods for spatially profiling analytes described herein, the methods include exposing the biological sample to a perturbation agent (e.g., any of the perturbation agents described herein) and evaluating the response of the biological sample to the perturbation agent. In some embodiments of any the methods for spatially profiling analytes described herein, the methods include monitoring cell differentiation in a biological sample (e.g., an organoid). In some embodiments of any the methods for spatially profiling analytes described herein, the methods include analyzing tissue morphogenesis. In some embodiments of any the methods for spatially profiling analytes described herein, the methods include identifying spatial heterogeneity in a biological sample (e.g., identifying different cell types or populations in a biological sample). In some embodiments of any the methods for spatially profiling analytes described herein, the methods include analyzing the spatiotemporal order (e.g., timing) of molecular events. For example, the methods for spatially profiling analytes can include monitoring expression levels over the course of a disease.

The methods provided herein can also be used to determine a relative level of inflammation in a subject (e.g., determine an inflammatory score) or a subject's response to treatment or the development of resistance to treatment. The methods described herein can also be used to identify candidate targets for potential therapeutic intervention and/ or to identify biomarkers associated with different disease states in a subject.

(h) Quality Control

(i) Control Sample

As used herein, the term "control sample" typically refers to a substrate that is insoluble in aqueous liquid and that allows for an accurate and traceable positioning of test analytes on the substrate. The control sample can be any suitable substrate known to the person skilled in the art. Exemplary control samples comprise a semi-porous material. Non-limiting examples of a semi-porous material include a nitrocellulose membrane, a hydrogel, and a nylon filter.

A control sample can be of any appropriate dimension or volume (e.g., size or shape). In some embodiments, a control sample is a regular shape (e.g., a square, circle, or a rectangle). In some embodiments, a surface of a control sample has any appropriate form or format. For example, the surface of a control sample can be flat or curved (e.g., convexly or concavely curved towards the area where the interaction between the substrate and the control sample takes place). In some embodiments, a control sample has rounded corners (e.g., for increased safety or robustness). In some embodiments, a control sample has one or more cut-off corners (e.g., for use with a slide clamp or cross-table).

A control sample can comprise a plurality of test analytes. In some embodiments, the members of the plurality of test analytes are disposed on the substrate in a known amount and in a known location. For example, a plurality of test analytes are disposed at a known amount on the control sample at one or more locations. In some embodiments, the plurality of test analytes are disposed on the substrate in a defined pattern (e.g., an x-y grid pattern). In some embodiments, the defined pattern includes one or more locations or spots.

In some embodiments, each location comprises a plurality of the same species of test analyte. In some embodiments, each location comprises a plurality of one or more different species of test analytes. In some embodiments, each location on the control sample represents a different region of a biological sample, e.g., a tissue sample. In some embodiments, an area on the control sample that does not comprise a plurality of test analytes represents an area where no biological sample is present.

In some embodiments, the plurality of test analytes comprises one or more test analytes, e.g., a first test analyte, a second test analyte, a third test analyte, a fourth test analyte, etc. In some embodiments, the plurality of test analytes comprises nucleic acids. In some embodiments, each location or feature comprises a population of nucleic acid sequences. In some embodiments, the nucleic acid sequence of a first test analyte differs from the nucleic acid sequence of a second test analyte by a single nucleic acid residue. In some embodiments, each location or feature comprises a population of RNA transcripts and one or more specific surface marker proteins or one or more CRISPR guide RNAs. In some embodiments, the plurality of test analytes comprises a bacterial artificial chromosomes (BAC). In some embodiments, each location on the control sample comprises a unique blend of BACs. In some embodiments, proteins are cross-linked to the BACs, for example, to mimic histone binding on DNA.

In some embodiments, the concentration of a first test analyte differs from the concentration of a second test analyte at a different location or feature on the control sample. In some embodiments, the first test analyte and the second test analyte comprise an identical nucleotide sequence.

(ii) Spatial RNA Integrity Number (sRIN)

As used herein, the term "spatial RNA Integrity Number" or "sRIN" refers to the in situ indication of RNA quality based on an integrity score. Higher sRIN scores correlate with higher data quality in the spatial profiling assays described herein. For example, a first biological sample with a high sRIN score will have higher data quality compared to a second biological sample with sRIN score lower than the first biological sample. In some embodiments, a sRIN is calculated for a tissue section, one or more regions of a tissue section, or a single cell.

In some embodiments, one or more sRINs for a given biological sample (e.g., tissue section, one or more regions of a tissue, or a single cell) are calculated by: (a) providing (i) a spatial array including a plurality of capture probes on a substrate, where a capture probe comprises a capture domain and (ii) a tissue stained with a histology stain (e.g., any of the stains described herein); (b) contacting the spatial array with the biological sample (e.g., tissue); (c) capturing a biological analyte (e.g., an 18S rRNA molecule) from the biological sample (e.g., tissue) with the capture domain; (d) generating a cDNA molecule from the captured biological analyte (e.g., 18S rRNA); (e) hybridizing one or more labeled oligonucleotide probes to the cDNA; (f) imaging the labeled cDNA and the histology stain (e.g., any of the stains described herein), and (g) generating a spatial RNA integrity number for a location in the spatial array, wherein the spatial RNA integrity number comprises an analysis of a labeled cDNA image and a histology stain (e.g., any of the stains described herein) image for the location.

In some embodiments, the biological sample (e.g., tissue) is stained with a histology stain. As used herein, a "histology stain" can be any stain described herein. For example, the biological sample can be stained with IF/IHC stains described herein. For example, the biological sample (e.g., tissue) can be stained with Hematoxylin & Eosin ("H&E"). In some embodiments, the biological sample (e.g., tissue) is stained with a histology stain (e.g., any of the stains described herein) before, contemporaneously with, of after labelling of the cDNA with labeled oligonucleotide probes. In some embodiments, the stained biological sample can be, optionally, destained (e.g., washed in HCl). For example, Hematoxylin, from the H&E stain, can be optionally removed from the biological sample by washing in dilute HCl (0.01M) prior to further processing. In some embodiments, the stained biological sample can be optionally destained after imaging and prior to permeabilization.

In some embodiments, the spatial array includes a plurality of capture probes immobilized on a substrate where the capture probes include at least a capture domain. In some embodiments, the capture domain includes a poly(T) sequence. For example, a capture domain includes a poly(T) sequence that is capable of capturing an 18S rRNA transcript from a biological sample.

In some embodiments, calculating one or more spatial RNA Integrity Numbers for a biological sample includes hybridizing at least one (e.g., at least two, at least three, at least four, or at least five) labeled oligonucleotide probes to the cDNA generated from the 18s rRNA. In some embodiments, a labeled oligonucleotide probe includes a sequence that is complementary to a portion of the 18S cDNA. In some embodiments, four labeled oligonucleotide probes (P1-P4) are designed to hybridize at four different locations spanning the entire gene body of the 18S rRNA. In some embodiments, a labeled oligonucleotide probe can include any of the detectable labels as described herein. For example, an oligonucleotide labeled probe can include a fluorescent label (e.g., Cy3). In some embodiments, one or more of the labeled oligonucleotide probes designed with complementarity to different locations within the 18S cDNA sequence include the same detectable label. For example, four labeled oligonucleotide probes, (P1-P4) each designed to have complementarity to a different location within the 18S cDNA sequence can all have the same detectable label (e.g., Cy3). In some embodiments, one or more of the labeled oligonucleotide probes designed with complementarity to different locations within the 18S cDNA sequence include a different detectable label. For example, four labeled oligonucleotide probes, (P1-P4) each designed to have complementarity to a different location within the 18S cDNA sequence can include different detectable labels.

In some embodiments, determining a spatial RNA Integrity Number for a biological sample (e.g., tissue section, one or more regions of a tissue, or a single cell) includes analyzing the images taken from a spatial array and a histology stain (e.g., any of the stains described herein) for the same location. For example, for the spatial array, all images are generated by scanning with a laser (e.g., a 532 nm wavelength) after the fluorescently labeled (e.g., Cy3) oligonucleotide probes have been hybridized to the 18S cDNA. One image is generated per probe (P1-P4) and one image is generated where no fluorescently labeled probes were hybridized (P0). Normalization of Fluorescence Units (FU) data is performed by subtraction of the auto-fluorescence recorded with P0 and division with P1. After alignment, the five images (one image from each probe, P1-P4, and one image from an area without bound probe) are loaded into a script. The script generates two different plots, one heat-map of spatial RIN values and one image alignment error plot, which combines the histology stain (e.g., any of the stains described herein) image. The image alignment error plot is used to visualize which pixels and positions should be excluded from the analysis due to alignment errors between the images from P0-P4.

III. General Spatial Cell-Based Analytical Methodology

(a) Barcoding a Biological Sample

In some embodiments, provided herein are methods and materials for attaching and/or introducing a molecule (e.g., a peptide, a lipid, or a nucleic acid molecule) having a barcode (e.g., a spatial barcode) to a biological sample (e.g., to a cell in a biological sample) for use in spatial analysis. In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis.

Figure 18:
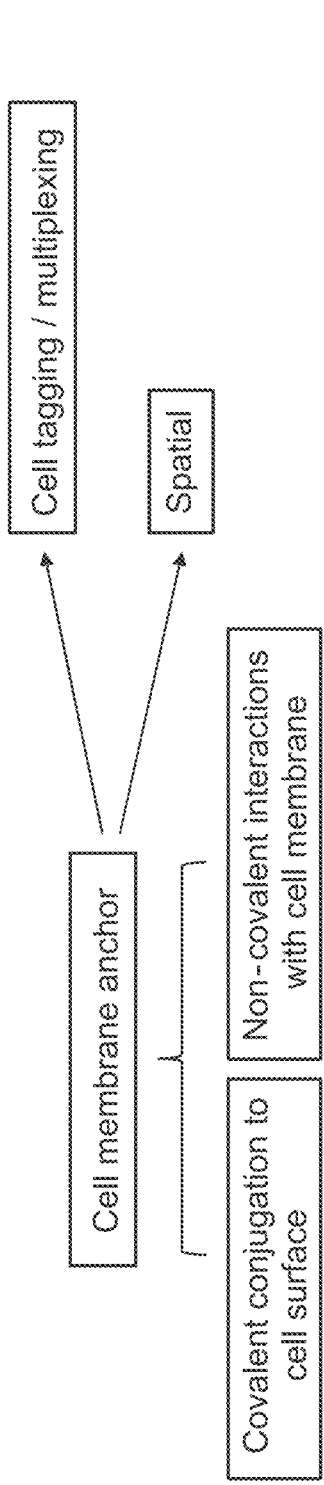
FIG. 18 is a schematic depicting cell tagging using either covalent conjugation of the analyte binding moiety to the cell surface or non-covalent interactions with cell membrane elements.

FIG. 18 is a schematic diagram depicting cell tagging using either covalent conjugation of an analyte binding moiety to a cell surface or non-covalent interactions with cell membrane elements. FIG. 18 lists non-exhaustive examples of a covalent analyte binding moiety/cell surface interactions, including protein targeting, amine conjugation using NHS chemistry, cyanuric chloride, thiol conjugation via maleimide addition, as well as targeting glycoproteins/glycolipids expressed on the cell surface via click chemistry. Non-exhaustive examples of non-covalent interactions with cell membrane elements include lipid modified oligos, biocompatible anchor for cell membrane (BAM, e.g., oleyl-PEG-NHS), lipid modified positive neutral polymer, and antibody to membrane proteins. A cell tag can be used in combination with an analyte capture agent and cleavable or non-cleavable spatially-barcoded capture probes for spatial and multiplexing applications.

In some embodiments, a plurality of molecules (e.g., a plurality of lipid or nucleic acid molecules) having a plurality of barcodes (e.g., a plurality of spatial barcodes) are introduced to a biological sample (e.g., to a plurality of cells in a biological sample) for use in spatial analysis, wherein the plurality of molecules are introduced to the biological sample in an arrayed format. In some embodiments, a plurality of molecules (e.g., a plurality of lipid or nucleic acid molecules) having a plurality of barcodes are provided on a substrate (e.g., any of the variety of substrates described herein) in any of the variety of arrayed formats described herein, and the biological sample is contacted with the molecules on the substrate such that the molecules are introduced to the biological sample. In some embodiments, the molecules that are introduced to the biological sample are cleavably attached to the substrate, and are cleaved from the substrate and released to the biological sample when contacted with the biological sample. In some embodiments, the molecules introduced to the biological sample are covalently attached to the substrate prior to cleavage. In some embodiments, the molecules that are introduced to the biological sample are non-covalently attached to the substrate (e.g., via hybridization), and are released from the substrate to the biological sample when contacted with the biological sample.

In some embodiments, a plurality of molecules (e.g., a plurality of lipid or nucleic acid molecules) having a plurality of barcodes (e.g., a plurality of spatial barcodes) are migrated or transferred from a substrate to cells of a biological sample. In some embodiments, migrating a plurality of molecules from a substrate to cells of a biological sample includes applying a force (e.g., mechanical, centrifugal, or electrophoretic) to the substrate and/or the biological sample to facilitate migration of the plurality of molecules from the substrate to the biological sample.

In some embodiments of any of the spatial analysis methods described herein, physical force is used to facilitate attachment to or introduction of a molecule (e.g., a nucleic acid molecule) having a barcode (e.g., a spatial barcode) into a biological sample (e.g., a cell present in a biological sample). As used herein, "physical force" refers to the use of a physical force to counteract the cell membrane barrier in facilitating intracellular delivery of molecules. Examples of physical force instruments and methods that can be used in accordance with materials and methods described herein include the use of a needle, ballistic DNA, electroporation, sonoporation, photoporation, magnetofection, hydroporation, and combinations thereof.

(i) Introducing a Cell-Tagging Agent to the Surface of a Cell

In some embodiments, biological samples (e.g., cells in a biological sample) can be labelled using cell-tagging agents where the cell-tagging agents facilitate the introduction of the molecules (e.g., nucleic acid molecules) having barcodes (e.g., spatial barcodes) into the biological sample (e.g., into cells in a biological sample). As used herein, the term "cell-tagging agent" refers to a molecule having a moiety that is capable of attaching to the surface of a cell (e.g., thus attaching the barcode to the surface of the cell) and/or penetrating and passing through the cell membrane (e.g., thus introducing the barcode to the interior of the cell). In some embodiments, a cell-tagging agent includes a barcode (e.g., a spatial barcode). The barcode of a barcoded cell-tagging agent can be any of the variety of barcodes described herein. In some embodiments, the barcode of a barcoded cell-tagging agent is a spatial barcode. In some embodiments, a cell-tagging agent comprises a nucleic acid molecule that includes the barcode (e.g., the spatial barcode). In some embodiments, the barcode of a barcoded cell-tagging agent identifies the associated molecule, where each barcode is associated with a particular molecule. In some embodiments, one or more molecules are applied to a sample. In some embodiments, a nucleic acid molecule that includes the barcode is covalently attached to the cell-tagging agent. In some embodiments, a nucleic acid molecule that includes the barcode is non-covalently attached to the cell-tagging agent. A non-limiting example of non-covalent attachment includes hybridizing the nucleic acid molecule that includes the barcode to a nucleic acid molecule on the cell-tagging agent (which nucleic acid molecule on the cell-tagging agent can be bound to the cell-tagging agent covalently or non-covalently). In some embodiments, a nucleic acid molecule attached to a cell-tagging agent that includes a barcode (e.g., a spatial barcode) also includes one or more additional domains. Such additional domains include, without limitation, a PCR handle, a sequencing priming site, a domain for hybridizing to another nucleic acid molecule, and combinations thereof.

In some embodiments, a cell-tagging agent attaches to the surface of a cell. When the cell-tagging agent includes a barcode (e.g., a nucleic acid that includes a spatial barcode), the barcode is also attached to the surface of the cell. In some embodiments of any of the spatial analysis methods described herein, a cell-tagging agent attaches covalently to the cell surface to facilitate introduction of the spatial analysis reagents. In some embodiments of any of the spatial analysis methods described herein, a cell-tagging agent attaches non-covalently to the cell surface to facilitate introduction of the spatial analysis reagents.

In some embodiments, once a cell or cells in a biological sample is spatially tagged with a cell-tagging agent(s), spatial analysis of analytes present in the biological sample is performed. In some embodiments, such spatial analysis includes dissociating the spatially-tagged cells of the biological sample (or a subset of the spatially-tagged cells of the biological sample) and analyzing analytes present in those cells on a cell-by-cell basis. Any of a variety of methods for analyzing analytes present in cells on a cell-by-cell basis can be used. Non-limiting examples include any of the variety of methods described herein and methods described in PCT Application Publication No. WO 2019/113533A1, the content of which is incorporated herein by reference in its entirety. For example, the spatially-tagged cells can be encapsulated with beads comprising one or more nucleic acid molecules having a barcode (e.g., a cellular barcode) (e.g., an emulsion). The nucleic acid present on the bead can have a domain that hybridizes to a domain on a nucleic acid present on the tagged cell (e.g., a domain on a nucleic acid that is attached to a cell-tagging agent), thus linking the spatial barcode of the cell to the cellular barcode of the bead. Once the spatial barcode of the cell and the cellular barcode of the bead are linked, analytes present in the cell can be analyzed using capture probes (e.g., capture probes present on the bead). This allows the nucleic acids produced (using these methods) from specific cells to be amplified and sequenced separately (e.g., within separate partitions or droplets).

In some embodiments, once a cell or cells in a biological sample is spatially tagged with a cell-tagging agent(s), spatial analysis of analytes present in the biological sample is performed in which the cells of the biological sample are not dissociated into single cells. In such embodiments, various methods of spatial analysis such as any of those provided herein can be employed. For example, once a cell or cells in a biological sample is spatially tagged with a cell-tagging agent(s), analytes in the cells can be captured and assayed. In some embodiments, cell-tagging agents include both a spatial barcode and a capture domain that can be used to capture analytes present in a cell. For example, cell-tagging agents that include both a spatial barcode and a capture domain can be introduced to cells of the biological sample in a way such that locations of the cell-tagging agents are known (or can be determined after introducing them to the cells). One non-limiting example of introducing cell-tagging agents to a biological sample is to provide the cell-tagging agents in an arrayed format (e.g., arrayed on a substrate such as any of the variety of substrates and arrays provided herein), where the positions of the cell-tagging agents on the array are known at the time of introduction (or can be determined after introduction). The cells can be permeabilized as necessary (e.g., using permeabilization agents and methods described herein), reagents for analyte analysis can be provided to the cells (e.g., a reverse transcriptase, a polymerase, nucleotides, etc., in the case where the analyte is a nucleic acid that binds to the capture probe), and the analytes can be assayed. In some embodiments, the assayed analytes (and/or copies thereof) can be released from the substrate and analyzed. In some embodiments, the assayed analytes (and/or copies thereof) are assayed in situ.

Non-limiting examples of cell-tagging agents and systems that attach to the surface of a cell (e.g., thus introducing the cell-tagging agent and any barcode attached thereto to the exterior of the cell) that can be used in accordance with materials and methods provided herein for spatially analyzing an analyte or analytes in a biological sample include: lipid tagged primers/lipophilic-tagged moieties, positive or neutral oligo-conjugated polymers, antibody-tagged primers, streptavidin-conjugated oligonucleotides, dye-tagged oligonucleotides, click-chemistry, receptor-ligand systems, covalent binding systems via amine or thiol functionalities, and combinations thereof.

(ii) Introducing a Cell-Tagging Agent to the Interior of a Cell

Non-limiting examples of cell-tagging agents and systems that penetrate and/or pass through the cell membrane (e.g., thus introducing the cell-tagging agent and any barcode attached thereto to the interior of the cell) that can be used in accordance with materials and methods provided herein for spatially profiling an analyte or analytes in a biological sample include: a cell-penetrating agent (e.g., a cell-penetrating peptide), a nanoparticle, a liposome, a polymersome, a peptide-based chemical vector, electroporation, sonoporation, lentiviral vectors, retroviral vectors, and combinations thereof.

Figure 19:
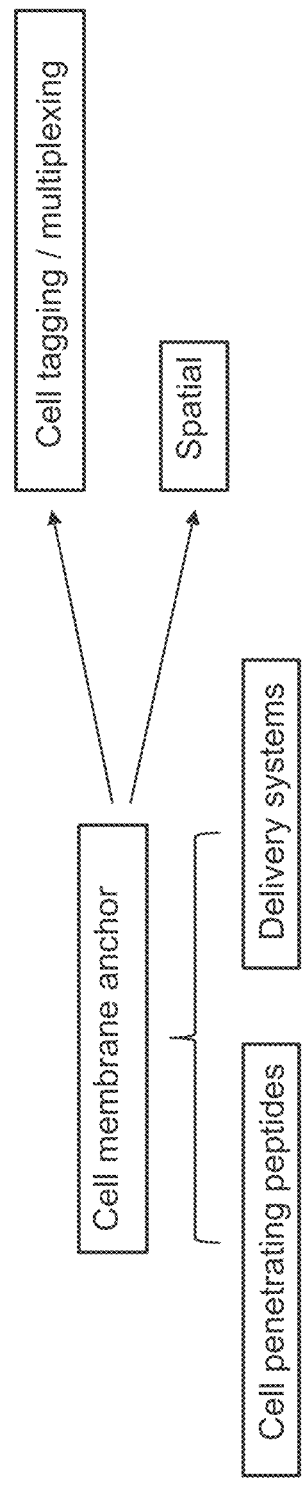
FIG. 19 is a schematic depicting cell tagging using either cell-penetrating peptides or delivery systems.

FIG. 19 is a schematic showing an exemplary cell tagging method. Non-exhaustive examples of oligo delivery vehicles may include a cell penetrating peptide or a nanoparticle. Non-exhaustive examples of the delivery systems can include lipid-based polymeric and metallic nanoparticles or oligos that can be conjugated or encapsulated within the delivery system. The cell tag can be used in combination with a capture agent barcode domain and a cleavable or non-cleavable spatially-barcoded capture probes for spatial and multiplexing applications.

1. Cell-Penetrating Agent

In some embodiments of any of the spatial profiling methods described herein, identification of a biological analyte by a molecule (e.g., a nucleic acid molecule) having a barcode (e.g., a spatial barcode) and a capture domain is facilitated by a cell-penetrating agent. In some embodiments, a molecule (e.g., a nucleic acid molecule) having a barcode (e.g., a spatial barcode) and a capture domain is coupled to a cell-penetrating agent, and the cell-penetrating agent allows the molecule to interact with an analyte inside the cell. A "cell-penetrating agent" as used herein can refer to an agent capable of facilitating the introduction of a molecule (e.g., a nucleic acid molecule) having a barcode (e.g., a spatial barcode) and a capture domain into a cell of a biological sample (see, e.g., Lovatt et al. Nat Methods. 2014 February; 11(2):190-6, which is incorporated herein by reference in its entirety). In some embodiments, a cell-penetrating agent is a cell-penetrating peptide. A "cell-penetrating peptide" as used herein refers to a peptide (e.g., a short peptide, e.g., a peptide not usually exceeding 30 residues) that has the capacity to cross cellular membranes. In some embodiments, cell-penetrating agents or cell penetrating peptides may be covalently or non-covalently coupled to a molecule (e.g., a barcoded nucleic acid molecule), likely at the 5' end of the molecule. A cell-penetrating peptide may direct the barcoded nucleic acid molecule to a specific organelle.

In some embodiments of any of the spatial profiling methods described herein, a cell-penetrating peptide coupled to a molecule (e.g., a nucleic acid molecule) having a barcode (e.g., a spatial barcode) and a capture domain can cross a cellular membrane using an energy dependent or an energy independent mechanism. For example, a cell-penetrating peptide can cross a cellular membrane through direct translocation through physical perturbation of the plasma membrane, endocytosis (e.g., mediated via clathrin), adaptive translocation, pore-formation, electroporation-like permeabilization, and/or entry at microdomain boundaries. Non-limiting examples of a cell-penetrating peptide include: penetratin, tat peptide, pVEC, transportan, MPG, Pep-1, a polyarginine peptide, MAP, R6W3, (D-Arg)9, Cys(Npys)-(D-Arg)9, Anti-BetaGamma (MPS-Phosducin-like protein C terminus), Cys(Npys) antennapedia, Cys(Npys)-(Arg)9, Cys(Npys)-TAT (47-57), HIV-1 Tat (48-60), KALA, mastoparan, penetratin-Arg, pep-1-cysteamine, TAT (47-57) GGG-Cys(Npys), Tat-NR2Bct, transdermal peptide, SynBI, SynB3, PTD-4, PTD-5, FHV Coat-(35-49), BMV Gag-(7-25), HTLV-II Rex-(4-16), R9-tat, SBP, FBP, MPG, MPG (ΔNLS), Pep-2, MTS, plsl, and a polylysine peptide (see, e.g., Bechara et al. FEBS Lett. 2013 Jun. 19; 587(12):1693-702, which is incorporated by reference herein in its entirety).

In some embodiments, there could be two orientations for cell-penetrating peptide (CPP) conjugation. For example, one orientation can be (N-terminus)-CPP-Cys-(C-terminus)-linker-NH2C6-5'-oligo-3'; 3'-oligo-5'-NH2C6-linker-(N-terminus)-Cys-CPP-(C-terminus). The methods herein can be performed with other CPP conjugations and orientations.

2. Nanoparticles

In some embodiments of any of the spatial profiling methods described herein, capture of a biological analyte by a molecule (e.g., a nucleic acid molecule) having a barcode (e.g., a spatial barcode) and a capture domain is facilitated by an inorganic particle (e.g., a nanoparticle). In some embodiments, a molecule (e.g., a nucleic acid molecule) having a barcode (e.g., a spatial barcode) and a capture domain is coupled to an inorganic particle (e.g., a nanoparticle), and the molecule (e.g., a nucleic acid molecule) having a barcode (e.g., a spatial barcode) and a capture domain uses the nanoparticle to get access to analytes inside the cell. Non-limiting examples of nanoparticles that can be used in embodiments herein to deliver a molecule (e.g., a nucleic acid molecule) having a barcode (e.g., a spatial barcode) and a capture domain into a cell and/or cell bead include inorganic nanoparticles prepared from metals, (e.g., iron, gold, and silver), inorganic salts, and ceramics (e.g., phosphate or carbonate salts of calcium, magnesium, or silicon). The surface of a nanoparticle can be coated to facilitate binding of the molecule (e.g., a nucleic acid molecule) having a barcode (e.g., a spatial barcode) and a capture domain, or the surface can be chemically modified to facilitate attachment of the molecule (e.g., a nucleic acid molecule) having a barcode (e.g., a spatial barcode) and a capture domain. Magnetic nanoparticles (e.g., supermagnetic iron oxide), fullerenes (e.g., soluble carbon molecules), carbon nanotubes (e.g., cylindrical fullerenes), quantum dots, and supramolecular systems can also be used.

3. Liposomes

In some embodiments of any of the spatial analysis methods described herein, capture of a biological analyte by a molecule (e.g., a nucleic acid molecule) having a barcode (e.g., a spatial barcode) and a capture domain is facilitated by a liposome. Various types of lipids, including cationic lipids, can be used in liposome delivery. In some cases, a molecule (e.g., a nucleic acid molecule) having a barcode (e.g., a spatial barcode) and a capture domain is delivered to a cell via a lipid nano-emulsion. A lipid emulsion refers to a dispersion of one immiscible liquid in another stabilized by emulsifying agent. Labeling cells can comprise use of a solid lipid nanoparticle.

4. Polymersomes

In some embodiments of any of the spatial analysis methods described herein, capture of a biological analyte by a molecule (e.g., a nucleic acid molecule) having a barcode (e.g., a spatial barcode) and a capture domain is facilitated by a polymersome. In some embodiments, a molecule (e.g., a nucleic acid molecule) having a barcode (e.g., a spatial barcode) and a capture domain is contained in the polymersome, and the molecule (e.g., a nucleic acid molecule) having a barcode (e.g., a spatial barcode) and a capture domain uses the polymersome to get access to analytes inside the cell. A "polymersome" as referred to herein is an artificial vesicle. For example, a polymersome can be a vesicle similar to a liposome, but the membrane comprises amphiphilic synthetic block copolymers (see, e.g., Rideau et al. Chem. Soc. Rev., 2018, 47, 8572-8610, which is incorporated by reference herein in its entirety). In some embodiments, polymersomes comprise di-(AB) or tri-block copolymers (e.g., ABA or ABC), where A and C are a hydrophilic block and B is a hydrophobic block. In some embodiments, a polymersome comprises poly(butadiene)-b-poly(ethylene oxide), poly(ethyl ethylene)-b-poly(ethylene oxide), polystyrene-b-poly(ethylene oxide), poly(2-vinylpyridine)-b-poly(ethylene oxide), polydimethylsiloxane-b-poly(ethylene oxide), polydimethylsiloxane-g-poly(ethylene oxide), polycaprolactone-b-poly(ethylene oxide), polyisobutylene-b-poly(ethylene oxide), polystyrene-b-polyacrylic acid, polydimethylsiloxane-b-poly-2-methyl-2-oxazoline, or a combination thereof (wherein b=block and g=grafted).

5. Peptide-Based Chemical Vectors

In some embodiments of any of the spatial analysis methods described herein, capture of a biological analyte by a molecule (e.g., a nucleic acid molecule) having a barcode (e.g., a spatial barcode) and a capture domain is facilitated by a peptide-based chemical vector, e.g., a cationic peptide-based chemical vector. Cationic peptides can be rich in basic residues like lysine and/or arginine. In some embodiments of any of the spatial analysis methods described herein, capture of a biological analyte by a molecule (e.g., a nucleic acid molecule) having a barcode (e.g., a spatial barcode) and a capture domain is facilitated by a polymer-based chemical vector. Cationic polymers, when mixed with a molecule (e.g., a nucleic acid molecule) having a barcode (e.g., a spatial barcode) and a capture domain, can form nanosized complexes called polyplexes. Polymer based vectors can comprise natural proteins, peptides and/or polysaccharides. Polymer based vectors can comprise synthetic polymers. In some embodiments, a polymer-based vector comprises polyethylenimine (PEI). PEI can condense DNA into positively-charged particles, which bind to anionic cell surface residues and are brought into the cell via endocytosis. In some embodiments, a polymer-based chemical vector comprises poly(L)-lysine (PLL), poly (DL-lactic acid) (PLA), poly (DL-lactide-co-glycoside) (PLGA), polyornithine, polyarginine, histones, protamines, or a combination thereof. Polymer-based vectors can comprise a mixture of polymers, for example, PEG and PLL. Other non-limiting examples of polymers include dendrimers, chitosans, synthetic amino derivatives of dextran, and cationic acrylic polymers.

6. Electroporation

In some embodiments of any of the spatial analysis methods described herein, capture of a biological analyte by a molecule (e.g., a nucleic acid molecule) having a barcode (e.g., a spatial barcode) and a capture domain is facilitated by electroporation. With electroporation, a biological analyte by a molecule (e.g., a nucleic acid molecule) having a barcode (e.g., a spatial barcode) and a capture domain can enter a cell through one or more pores in the cellular membrane formed by applied electricity. The pore of the membrane can be reversible based on the applied field strength and pulse duration.

7. Sonoporation

In some embodiments of any of the spatial analysis methods described herein, capture of a biological analyte by a molecule (e.g., a nucleic acid molecule) having a barcode (e.g., a spatial barcode) and a capture domain is facilitated by sonoporation. Cell membranes can be temporarily permeabilized using sound waves, allowing cellular uptake of a biological analyte by a molecule (e.g., a nucleic acid molecule) having a barcode (e.g., a spatial barcode) and a capture domain.

8. Lentiviral Vectors and Retroviral Vectors

In some embodiments of any of the spatial analysis methods described herein, capture of a biological analyte by a molecule (e.g., a nucleic acid molecule) having a barcode (e.g., a spatial barcode) and a capture domain is facilitated by vectors. For example, a vector as described herein can be an expression vector where the expression vector includes a promoter sequence operably linked to the sequence encoding the molecule (e.g., a nucleic acid molecule) having a barcode (e.g., a spatial barcode) and a capture domain. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, for example, include sufficient cis-acting elements for expression where other elements for expression can be supplied by the host mammalian cell or in an in vitro expression system. Skilled practitioners will be capable of selecting suitable vectors and mammalian cells for introducing any of spatial profiling reagents described herein.

9. Other Methods and Cell-Tagging Agents for Intracellular Introduction of a Molecule In some embodiments of any of the spatial analysis methods described herein, capture of a biological analyte by a molecule (e.g., a nucleic acid molecule) having a barcode (e.g., a spatial barcode) and a capture domain is facilitated by the use of a needle, for example for injection (e.g., microinjection), particle bombardment, photoporation, magnetofection, and/or hydroporation. For example, with particle bombardment, a molecule (e.g., a nucleic acid molecule) having a barcode (e.g., a spatial barcode) and a capture domain can be coated with heavy metal particles and delivered to a cell at a high speed. In photoporation, a transient pore in a cell membrane can be generated using a laser pulse, allowing cellular uptake of a molecule (e.g., a nucleic acid molecule) having a barcode (e.g., a spatial barcode) and a capture domain. In magnetofection, a molecule (e.g., a nucleic acid molecule) having a barcode (e.g., a spatial barcode) and a capture domain can be coupled to a magnetic particle (e.g., magnetic nanoparticle, nanowires, etc.) and localized to a target cell via an applied magnetic field. In hydroporation, a molecule (e.g., a nucleic acid molecule) having a barcode (e.g., a spatial barcode) and a capture domain can be delivered to a cell and/or cell bead via hydrodynamic pressure.

(iii) Lipid Tagged Primers/Lipophilic-Tagged Moieties

In some embodiments of any of the spatial profiling methods described herein, a molecule (e.g., a nucleic acid molecule) having a barcode (e.g., a spatial barcode) is coupled to a lipophilic molecule. In some embodiments, the lipophilic molecule enables delivery of the lipophilic molecule to the cell membrane or the nuclear membrane. In some embodiments, a molecule (e.g., a nucleic acid molecule) having a barcode (e.g., a spatial barcode) coupled to a lipophilic molecule can associate with and/or insert into lipid membranes such as cell membranes and nuclear membranes. In some cases, the insertion can be reversible. In some cases, the association between the lipophilic molecule and the cell may be such that the cell retains the lipophilic molecule (e.g., and associated components, such as nucleic acid barcode molecules) during subsequent processing (e.g., partitioning, cell permeabilization, amplification, pooling, etc.). In some embodiments, a molecule (e.g., a nucleic acid molecule) having a barcode (e.g., a spatial barcode) coupled to a lipophilic molecule may enter into the intracellular space and/or a cell nucleus.

Non-limiting examples of lipophilic molecules that can be used in embodiments described herein include sterol lipids such as cholesterol, tocopherol, steryl, palmitate, lignoceric acid, and derivatives thereof. In some embodiments, the lipophilic molecules are neutral lipids that are conjugated to hydrophobic moieties (e.g., cholesterol, squalene, or fatty acids) (See Raouane et al. *Bioconjugate Chem.*, 23(6):1091-1104 (2012) which is herein incorporated by reference in its entirety). In some embodiments, a molecule (e.g., a nucleic acid molecule) having a barcode (e.g., a spatial barcode) may be attached to the lipophilic moiety via a linker, using covalent or direct attachment. In some embodiments, the linker is a tetra-ethylene glycol (TEG) linker. Other exemplary linkers include, but are not limited to, Amino Linker C6, Amino Linker C12, Spacer C3, Spacer C6, Spacer C12, Spacer 9, and Spacer 18. In some embodiments, a molecule (e.g., a nucleic acid molecule) having a barcode (e.g., a spatial barcode) is indirectly coupled (e.g., via hybridization or ligand-ligand interactions, such as biotin-streptavidin) to a lipophilic molecule. In some embodiments, the lipophilic moiety can be attached to a capture probe, spatial barcode, or other DNA sequence, at either the 5' or 3' end of the specified DNA sequence. In some embodiments, the lipophilic moiety can be coupled to a capture probe, spatial barcode, or other DNA sequence in a lipid-dependent manner. Other lipophilic molecules that may be used in accordance with methods provided herein include amphiphilic molecules wherein the headgroup (e.g., charge, aliphatic content, and/or aromatic content) and/or fatty acid chain length (e.g., C12, C14, C16, or C18) can be varied. For instance, fatty acid side chains (e.g., C12, C14, C16, or C18) can be coupled to glycerol or glycerol derivatives (e.g., 3-t-butyldiphenylsilylglycerol), which can also comprise, e.g., a cationic head group. In some embodiments, a molecule (e.g., a nucleic acid molecule) having a barcode (e.g., a spatial barcode) disclosed herein can then be coupled (either directly or indirectly) to these amphiphilic molecules. In some embodiments, a molecule (e.g., a nucleic acid molecule) having a barcode (e.g., a spatial barcode) coupled to an amphiphilic molecule may associate with and/or insert into a membrane (e.g., a cell, cell bead, or nuclear membrane). In some cases, an amphiphilic or lipophilic moiety may cross a cell membrane and provide a molecule (e.g., a nucleic acid molecule) having a barcode (e.g., a spatial barcode) to an internal region of a cell and/or cell bead.

In some embodiments, additives can be added to supplement lipid-based modifications. In some embodiments, the additive is low density lipoprotein (LDL). In some embodiments, the additive is the cholesterol trafficking inhibitor U-18666A. In some embodiments, U-18666A inhibits cholesterol transport from late endosomes at micromolar concentrations and/or lysosomes to the endoplasmic reticulum (ER) at nanomolar concentrations. In some embodiments, U-18666A can inhibit oxidosqualene cyclase, a key enzyme in the cholesterol biosynthesis pathway, at sufficiently high concentrations (e.g., at or about >0.5 mM).

In some embodiments, wherein the molecule (e.g., with a nucleic acid sequence) has an amino group within the molecule, the molecule (e.g., a nucleic acid molecule) having a barcode (e.g., a spatial barcode) and an amino group can be coupled to an amine-reactive lipophilic molecule. For example, a molecule (e.g., a nucleic acid molecule) having a barcode (e.g., a spatial barcode) and an amino group can be conjugated to DSPE-PEG (2000)-cyanuric chloride (1,2-distearoyl-sn-glycero-3-phosphoethanolamine-N-[cyanur(polyethylene glycol)-2000]).

In some embodiments, a cell-tagging agent can attach to a surface of a cell through a combination of lipophilic and covalent attachment. For example, a cell-tagging agent can include an oligonucleotide attached to a lipid to target the oligonucleotide to a cell membrane, and an amine group that can be covalently linked to a cell surface protein(s) via any number of chemistries described herein. In these embodiments, the lipid can increase the surface concentration of the oligonucleotide and can promote the covalent reaction.

As used herein, an "anchor oligonucleotide" and/or "co-anchor oligonucleotide" can include a lipid-conjugated oligonucleotide, wherein the lipid is capable of becoming embedded within a cell membrane. In some embodiments, the lipid capable of becoming embedded within a cell membrane includes but is not limited to, sterol lipids such as cholesterol, tocopherol, steryl, palmitate, lignoceric acid, and derivatives thereof. In some embodiments, the sterol lipid of the anchor oligonucleotide and/or co-anchor oligonucleotide can be attached to either the 5' or 3' end of the oligonucleotide portion. In some embodiments, the anchor oligonucleotide and/or the co-anchor oligonucleotide can integrate into the cell membrane of a cell in a biological sample (e.g., the sterol lipid of the anchor oligonucleotide and/or co-anchor oligonucleotide).

In some embodiments, a sterol lipid (e.g., lignoceric acid) anchor oligonucleotide is attached to the 5' end of the oligonucleotide. In some embodiments, the anchor oligonucleotide can have a constant sequence. In some embodiments the constant sequence of the anchor oligonucleotide can be about 15 to about 30 nucleotides long. In some embodiments, the anchor oligonucleotide can have an additional domain 3' to the constant sequence. In some embodiments, the additional domain can be an adapter sequence (e.g., sequencing adapter). In some embodiments, the adapter sequence can be about 15 to about 35 nucleotides long.

In some embodiments, the lipid (e.g., sterol lipid) of the co-anchor oligonucleotide (e.g., palmitic acid), is attached to the 3' end of the oligonucleotide. In some embodiments, the co-anchor oligonucleotide can have a constant sequence. For example, the constant sequence of the co-anchor oligonucleotide can be a reverse complement of the constant sequence from the anchor oligonucleotide. In some embodiments, the constant sequence of the anchor oligonucleotide and the constant sequence of the co-anchor oligonucleotide can bind (e.g., hybridize) to each other. In some embodiments, the lipid (e.g., sterol lipid) of the anchor oligonucleotide and the co-anchor oligonucleotide can integrate into a cell membrane in the biological sample and the respective constant sequences can hybridize to each other at the same time. In some embodiments, a barcoded oligonucleotide, which can include several domains, can be introduced to the integrated anchor oligonucleotide and co-anchor oligonucleotide hybridized to each other. The barcoded oligonucleotide can include, in a 5' to 3' direction, a functional domain (e.g., a sequencing adapter domain), a unique molecular identifier, a sample barcode, a second unique molecular identifier, and the reverse complement of a constant sequence. For example, after tagging a cell with any of the cell-tagging agents described herein the cells can be partitioned (e.g., encapsulated in a vesicle) with a barcoded feature (e.g., a bead). In some embodiments, the reverse complement of the constant sequence of the barcoded oligonucleotide can interact (e.g., hybridize) with the constant sequence (e.g., a portion of the sequence) on the barcoded feature.

(iv) Intracellular Cleavage Domain

As used herein, capture probes can optionally include an "intracellular cleavage domain," wherein one or more segments or regions of the capture probe (e.g., capture domains, spatial barcodes, and/or UMIs) can be releasably or cleavably attached to one or more other segments or regions of the capture probe, such as a cell-penetrating agent, such that the capture domain, spatial barcode, and/or UMI can be released or be releasable through cleavage of a linkage between the capture domain, spatial barcode, and/or UMI and the cell-penetrating agent and/or cell penetration tag. In some embodiments, the cleavage of the linkage between the capture domain, spatial barcode, and/or UMI and the cell-penetrating agent is induced in an intracellular environment (e.g., the intracellular cleavage domain is cleaved after the capture probes is introduced into the cell). For example, the linkage between the capture domain, spatial barcode, and/or UMI and the cell-penetrating agent can be a disulfide bond that is cleaved by the reducing conditions in the cell, for example, when the intracellular cleavage domain comprises a disulfide bond. Any other suitable linker can be used to release or cleave the intracellular cleavage domain of the capture probe.

(v) Positive or Neutral Oligo-Conjugated Polymers

In some embodiments of any of the spatial analysis methods described herein, a molecule (e.g., a nucleic acid molecule) having a barcode (e.g., a spatial barcode) can be coupled to a glycol chitosan derivative. In some embodiments, the glycol chitosan derivative can be coupled with two or more molecules (e.g., nucleic acid molecules) having a barcode (e.g., a spatial barcode). In some embodiments, the glycol chitosan derivative can be coupled with about 3, about 4, about 5, about 6, about 7, about 8, about 9, about 10 or more molecules. The glycol chitosan derivative (e.g., glycol chitosan-cholesterol) can serve as a hydrophobic anchor (see Wang et al. *J. Mater. Chem. B.*, 30:6165 (2015), which is herein incorporated by reference in its entirety). Non-limiting examples of chitosan derivatives that can be coupled to a molecule (e.g., a nucleic acid molecule) having a barcode (e.g., a spatial barcode) can be found in Cheung et al., *Marine Drugs*, 13(8): 5156-5186 (2015), which is herein incorporated by reference in its entirety.

(vi) Bifunctional NHS Linker Cell-Tagging

In some embodiments of any of the spatial analysis methods described herein, a molecule (e.g., a nucleic acid molecule) having a barcode (e.g., a spatial barcode) can be coupled to a bifunctional NHS linker. In some embodiments, the coupled bifunctional NHS linker (e.g., bifunctional linker and the molecule having a barcode) can facilitate the attachment of the spatial barcode to the surface of the cell. In some embodiments, after facilitating attachment to the surface of the cell, excess NHS linker can be removed (e.g., washed away). In some embodiments, the process of coupling the molecule having a barcode can be performed under non-anhydrous conditions to maintain the activity of unreacted bifunctional NHS. In some embodiments, the non-anhydrous condition can be in the presence of DMSO. In some embodiments, the non-anhydrous condition can be in the presence of DMF.

(vii) Antibody-Tagged Primers

In some embodiments of any of the spatial analysis methods described herein, a molecule (e.g., a nucleic acid molecule) having a barcode (e.g., a spatial barcode) can be coupled to an antibody or antigen binding fragment thereof in a manner that facilitates attachment of the molecule (e.g., a nucleic acid molecule) having a barcode (e.g., a spatial barcode) to the surface of a cell. In some embodiments, facilitating attachment to the cell surface facilitates introduction of the molecule (e.g., a nucleic acid molecule) having a barcode (e.g., a spatial barcode) into the cell. In some embodiments, the molecule (e.g., a nucleic acid molecule) having a barcode (e.g., a spatial barcode) can be coupled to an antibody that is directed to an antigen that is present on the surface of a cell. In some embodiments, the molecule (e.g., a nucleic acid molecule) having a barcode (e.g., a spatial barcode) can be coupled to an antibody that is directed to an antigen that is present on the surface of a plurality of cells (e.g., a plurality of cells in a biological sample). In some embodiments, the molecule (e.g., a nucleic acid molecule) having a barcode (e.g., a spatial barcode) can be coupled to an antibody that is directed to an antigen that is present on the surface of a cell, a plurality of cells, or substantially all the cells present in a biological sample. In some embodiments, the barcoded-antibody is directed to an intracellular antigen. Any of the exemplary methods described herein of attaching a molecule (e.g., a nucleic acid molecule) having a barcode (e.g., a spatial barcode) to another molecule (e.g., an antibody or antigen fragment thereof) can be used.

(viii) Streptavidin-Conjugated Oligonucleotides

In some embodiments of any of the spatial analysis methods described herein, a molecule (e.g., a nucleic acid molecule) having a barcode (e.g., a spatial barcode) can attach to the surface of a cell using biotin-streptavidin. In some embodiments, primary amines in the side chain of lysine residues of cell surface polypeptides are labelled with NHS-activated biotin reagents. For example, the N-terminus of a polypeptide can react with NHS-activated biotin reagents to form stable amide bonds. In some embodiments, cell-tagging agents include molecules (e.g., a nucleic acid molecule) having barcodes (e.g., a spatial barcode) conjugated to streptavidin. In some cases, streptavidin can be conjugated to the molecule (e.g., a nucleic acid molecule) having a barcode (e.g., a spatial barcode) using click chemistry (e.g., maleimide modification) as described herein. In some embodiments, a cell containing NHS-activated biotin incorporated into lysine side chains of a cell surface protein forms a non-covalent bond with the streptavidin conjugated to the molecule (e.g., a nucleic acid molecule) having a barcode (e.g., a spatial barcode). In some embodiments, the molecule (e.g., a nucleic acid molecule) having a barcode (e.g., a spatial barcode) conjugated to streptavidin is itself part of a cell-tagging agent.

(ix) Dye-Tagged Oligonucleotides

In some embodiments of any of the spatial analysis methods described herein, a molecule (e.g., a nucleic acid molecule) having a barcode (e.g., a spatial barcode) is directly linked to a detectable label. In some embodiments, the detectable label is any of the detectable labels described herein. In some embodiments the detectable label is a fluorescent tag. In some embodiments, the physical properties of the fluorescent tags (e.g., a fluorescent tag having hydrophobic properties) can overcome the hydrophilic nature of the molecule (e.g., a nucleic acid molecule) having a barcode (e.g., a spatial barcode). For example, in some embodiments, wherein the molecule is a nucleic acid molecule, a fluorescent tag (e.g., BODIPY, Cy3, Atto 647N, and Rhodamine Red C2) can be coupled to a 5' end of the nucleic acid molecule having a barcode (e.g., a spatial barcode). In some embodiments, wherein the molecule is a nucleic acid molecule, any fluorescent tag having hydrophobic properties can be coupled to the nucleic acid molecule having a barcode (e.g., a spatial barcode) in a manner that overcomes the hydrophilic nature of the nucleic acid molecule. Non-limiting examples of fluorescent tags with hydrophobic properties include BODIPY, Cy3, Atto 647N, and Rhodamine Red C2.

(x) Click-Chemistry

In some embodiments of any of the spatial analysis methods described herein, molecules (e.g., a nucleic acid molecule) having barcodes (e.g., a spatial barcode) are coupled to click-chemistry moieties. As used herein, the term "click chemistry," generally refers to reactions that are modular, wide in scope, give high yields, generate byproducts, such as those that can be removed by nonchromatographic methods, and are stereospecific (but not necessarily enantioselective) (see, e.g., Angew. *Chem. Int. Ed.*, 2001, 40(11):2004-2021, which is incorporated herein by reference in its entirety). In some cases, click chemistry can describe pairs of functional groups that can selectively react with each other in mild, aqueous conditions.

An example of a click chemistry reaction is the Huisgen 1,3-dipolar cycloaddition of an azide and an alkyne, i.e., copper-catalyzed reaction of an azide with an alkyne to form the 5-membered heteroatom ring 1,2,3-triazole. The reaction is also known as a Cu(I)-Catalyzed Azide-Alkyne Cycloaddition (CuAAC), a Cu(I) click chemistry or a Cu+ click chemistry. Catalysts for the click chemistry include, but are not limited to, Cu(I) salts, or Cu(I) salts made in situ by reducing Cu(II) reagents to Cu(I) reagents with a reducing reagent (*Pharm Res.* 2008, 25(10): 2216-2230, which is incorporated herein by reference in its entirety). Known Cu(II) reagents for the click chemistry can include, but are not limited to, the Cu(II)-(TBTA) complex and the Cu(II) (THPTA) complex. TBTA, which is tris-[(1-benzyl-1H-1,2, 3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, is another example of a stabilizing agent for Cu(I). Other conditions can also be used to construct the 1,2,3-triazole ring from an azide and an alkyne using copper-free click chemistry, such as the Strain-promoted Azide-Alkyne Click chemistry reaction (SPAAC) (see, e.g., *Chem. Commun.*, 2011, 47:6257-6259 and *Nature*, 2015, 519(7544): 486-90, each of which is incorporated herein by reference in its entirety).

(xi) Receptor-Ligand Systems

In some embodiments of any of the spatial analysis methods described herein, a molecule (e.g., a nucleic acid molecule) having a barcode (e.g., a spatial barcode) can be coupled to a ligand, wherein the ligand is part of a receptor-ligand interaction on the surface of a cell. For example, a molecule (e.g., a nucleic acid molecule) having a barcode (e.g., a spatial barcode) can be coupled to a ligand that interacts selectively with a cell surface receptor thereby targeting the molecule (e.g., a nucleic acid molecule) having a barcode (e.g., a spatial barcode) to a specific cell. Non-limiting examples of receptor-ligand systems that can be used include integrin receptor-ligand interactions, GPCR receptor-ligand interactions, RTK receptor-ligand interactions, and TLR-ligand interactions (see Juliano, *Nucleic Acids Res.*, 44(14): 6518-6548 (2016), which is incorporated herein by reference in its entirety). Any of the methods described herein for attaching a molecule (e.g., a nucleic acid molecule) having a barcode (e.g., a spatial barcode) to a ligand (e.g., any of the methods described herein relating to attaching a molecule (e.g., a nucleic acid molecule) having a barcode (e.g., a spatial barcode) to an antibody) can be used.

(xii) Covalent Binding Systems Via Amine or Thiol Functionalities

In some embodiments of any of the spatial analysis methods described herein, a molecule (e.g., a nucleic acid molecule) having a barcode (e.g., a spatial barcode) can incorporate reactive functional groups at sites within the molecule (e.g., with a nucleic acid sequence). In such cases, the reactive functional groups can facilitate conjugation to ligands and/or surfaces. In some embodiments, a molecule (e.g., a nucleic acid molecule) having a barcode (e.g., a spatial barcode) can include thiol modifiers that are designed to react with a broad array of activated accepting groups (e.g., maleimide and gold microspheres). For example, a molecule (e.g., a nucleic acid molecule) having a barcode (e.g., a spatial barcode) having thiol modifiers can interact with a maleimide-conjugated peptide thereby resulting in labelling of the peptide. In some embodiments, maleimide-conjugated peptides are present on the surface of a cell whereupon interaction with the thiol-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. Non-limiting examples of thiol modifiers include: 5' thiol modifier C6 S—S, 3' thiol modifier C3 S—S, dithiol, 3' thiol modifier oxa 6-S—S, and dithiol serinol.

In some embodiments of any of the spatial analysis methods described herein, a molecule (e.g., a nucleic acid molecule) having a barcode (e.g., a spatial barcode) can include amine modifiers, e.g., amine modifiers that are designed to attach to another molecule in the presence of an acylating agent. In some embodiments, a molecule (e.g., a nucleic acid molecule) having a barcode (e.g., a spatial barcode) can include amine modifiers that are designed to attach to a broad array of linkage groups (e.g., carbonyl amide, thiourea, sulfonamide, and carboxamide). For example, a molecule (e.g., a nucleic acid molecule) having a barcode (e.g., a spatial barcode) and an amine modifier can interact with a sulfonamide-conjugated peptide thereby resulting in labelling of the peptide. In some embodiments, sulfonamide-conjugated peptides are present on the surface of a cell whereupon interaction with the amine-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. Non-limiting example of amine modifiers include: DMS(O)MT-Amino-Modifier-C6, Amino-Modifier-C3-TFA, Amino-Modifier-C12, Amino-Modifier-C6-TFA, Amino-dT, Amino-Modifier-5, Amino-Modifier-C2-dT, Amino-Modifier-C6-dT, and 3'-Amino-Modifier-C7.

As another example, a molecule (e.g., a nucleic acid molecule) having a barcode (e.g., a spatial barcode) can incorporate reactive functional groups at sites within the molecule (e.g., with a nucleic acid sequence) such as N-hydroxysuccinimide (NHS). In some embodiments, amines (e.g., amine-containing peptides) are present on the surface of a cell whereupon interaction with the NHS-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. In some embodiments, a molecule (e.g., a nucleic acid molecule) having a barcode (e.g., a spatial barcode) is reacted with a bifunctional NHS linker to form an NHS-modified molecule (e.g., a nucleic acid molecule) having a barcode (e.g., a spatial barcode).

In some embodiments, a molecule (e.g., a nucleic acid molecule) having a barcode (e.g., a spatial barcode) can be coupled to a biocompatible anchor for cell membrane (BAM). For example, a BAM can include molecules that comprise an oleyl group and PEG. The oleyl group can facilitate anchoring the molecule (e.g., a nucleic acid molecule) having a barcode (e.g., a spatial barcode) to a cell, and the PEG can increase water solubility. In some embodiments, oleyl-PEG-NHS can be coupled to a molecule (e.g., a nucleic acid molecule) having a barcode (e.g., a spatial barcode) using NHS chemistry.

(xiii) Azide-Based Systems

In some embodiments, wherein the molecule (e.g., with a nucleic acid sequence) incorporates reactive functional groups at sites within the molecule, a molecule (e.g., a nucleic acid molecule) having a barcode (e.g., a spatial barcode) can be coupled to an azide group on a cell surface. In some embodiments, the reactive functional group is an alkynyl group. In some embodiments, click chemistry as described herein can be used to attach the alkynyl-modified molecule (e.g., a nucleic acid molecule) having a barcode (e.g., a spatial barcode) to an azide group on the cell surface. An azide group can be attached to the cell surface through a variety of methods. For example, NHS chemistry can be used to attach an azide group to the cell surface. In some embodiments, N-azidoacetylmannosamine-tetraacylated (Ac4ManNAz), which contains an azide group, can react with sialic acid on the surface of a cell to attach azide to the cell surface. In some embodiments, azide is attached to the cell surface by bio-orthogonal expression of azide. For example, azide is incubated with the cells. In some embodiments, the alkynyl-modified molecule (e.g., a nucleic acid molecule) having a barcode (e.g., a spatial barcode) can attach to the surface of a cell via an azide group in the presence of copper. In some embodiments, the alkynyl-modified molecule (e.g., a nucleic acid molecule) having a barcode (e.g., a spatial barcode) can attach to the surface of a cell via an azide group in the absence of copper.

(xiv) Lectin-Based Systems

In some embodiments of any of the spatial analysis methods described herein, a molecule (e.g., a nucleic acid molecule) having a barcode (e.g., a spatial barcode) can be coupled to a lectin that facilitates attachment of the molecule (e.g., a nucleic acid molecule) having a barcode (e.g., a spatial barcode) to a cell surface. Lectin can bind to glycans, e.g., glycans on the surface of cells. In some embodiments, the molecule (e.g., a nucleic acid molecule) having a barcode (e.g., a spatial barcode) has an incorporated reactive functional group such as an azide group. In some embodiments, the molecule (e.g., a nucleic acid molecule) having a barcode (e.g., a spatial barcode) and an azide group is reacted with a modified lectin, e.g., a lectin modified using NHS chemistry to introduce an azide reactive group. In some embodiments, a live cell is labelled with a lectin-modified molecule (e.g., a nucleic acid molecule) having a barcode (e.g., a spatial barcode). In some embodiments, a fixed cell is labelled with a lectin-modified molecule (e.g., a nucleic acid molecule) having a barcode (e.g., a spatial barcode). In some embodiments, a permeabilized cell is labelled with a lectin-modified molecule (e.g., a nucleic acid molecule) having a barcode (e.g., a spatial barcode). In some embodiments, organelles in the secretory pathway can be labelled with a lectin-modified molecule (e.g., a nucleic acid molecule) having a barcode (e.g., a spatial barcode).

(b) Methods for Separating a Sample into Single Cells or Cell Groups

Some embodiments of any of the methods described herein can include separating a biological sample into single cells, cell groups, types of cells, or a region or regions of interest. For example, a biological sample can be separated into single cells, cell groups, types of cells, or a region or regions of interest before being contacted with one or more capture probes. In other examples, a biological sample is first contacted with one or more capture probes, and then separated into single cells, cell groups, types of cells, or a region or regions of interest.

In some embodiments, a biological sample can be separated into chucks using pixelation. Pixelation can include the steps of providing a biological sample, and punching out one or more portions of the biological sample. The punched out portions of the biological sample can then be used to perform any of the methods described herein. In some embodiments, the punched-out portions of the biological sample can be in a random pattern or a designed pattern. In some embodiments, the punched-out portions of the biological sample can be focused on a region of interest or a subcellular structure in the biological sample.

Figure 20A:
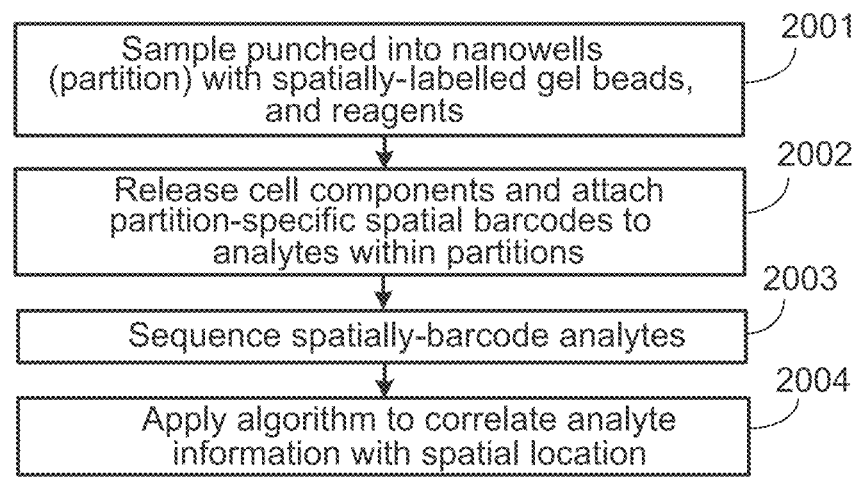
FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

Figure 20B:
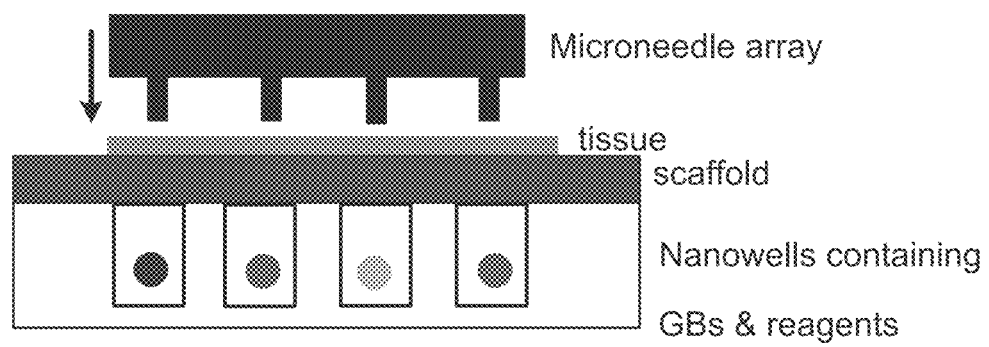
FIG. 20B is a schematic depicting multi-needle pixilation, wherein an array of needles punched through a sample on a scaffold and into nanowells containing gel beads and reagents below. Once the needle is in the nanowell, the cell(s) are ejected.

FIG. 20B is a schematic depicting multi-needle pixelation, wherein an array of needles is punched through a sample on a scaffold, into nanowells containing beads (e.g., gel beads) and reagents. Once the needle is in the nanowell, the cell(s) are ejected.

In some embodiments, a biological sample (e.g., a tissue sample or tissue section) is divided into smaller portions as compared to the original biological sample size ("chunks") before performance of any of the spatial analysis methods described herein. In some embodiments, the methods can include spatial barcoding of FFPE "chunks" via barcodes applied in a spatially well-defined pattern (e.g., array printing). In order to associate a spatial barcode with a particular "chunk" of biological sample, the barcode (e.g., a spatial barcode) can be of a sufficient length to prevent diffusion of the barcode in subsequent steps, or the spatial barcode can be covalently applied to the FFPE sample. In some embodiments, the spatial barcode is unique to each FFPE chunk. In some embodiments, spatial barcodes can be embedded onto an FFPE slide (e.g., within a matrix, such as a wax or a hydrogel). In some embodiments, the FFPE slide is heated (e.g., wax is heated) prior to addition of the spatial barcodes. In some embodiments, after addition of the spatial barcodes, the FFPE slide can be cooled and cut or dissociated into chunks. Methods of chunking (e.g., cutting) biological samples are known in the art. For example, in a non-limiting example, chunking of biological samples can be done in various ways such as laser microdissection, mechanical means, acoustic (e.g., sonication) means, or any other method described herein. In some embodiments, fluorophores/Qdots, etc. can be embedded in the chunk to preserve spatial information about the biological sample. Barcoding at this step enables massively parallel encapsulation of chunks while retaining local spatial information (e.g., tumor versus normal/healthy cells). In some embodiments, chunking of a biological sample (e.g., a tissue section) can result in single-cell chunks of the biological sample. In other embodiments, chunking of a biological sample can be performed to obtain chunks that correspond to diseased portions of the biological sample. In another embodiment, chunking of biological samples can be performed to obtain discrete chunks of the biological sample that correspond to diseased or healthy portions of the biological sample. In some embodiments, chunking of biological samples can be performed to obtain chunks that correspond to specific cell types (e.g., chunking based on fluorescent or chemiluminescent imaging of antibodies bound to target proteins) in the biological sample.

In some embodiments, the spatially-barcoded chunks can be further processed. For example, the spatially-barcoded chunk can be individually encapsulated (e.g., a matrix, emulsion, or hydrogel). In some embodiments, the spatially-barcoded chunk can be encapsulated in a partition (e.g., a well, droplet, channel, or vesicle). In some embodiments, the spatially-barcoded chunk can be encapsulated in a vesicle. In some embodiments, the vesicle can comprise a lipid bilayer. In some embodiments, the spatially-barcoded FFPE chunk can be encapsulated with a uniquely barcoded bead. In some embodiments, the uniquely barcoded bead can have a functional domain, a cleavage domain, a unique molecular identifier, and a capture domain, or combinations thereof. In some embodiments, the encapsulated spatially-barcoded FFPE chunk and the uniquely barcoded bead can be heated to deparaffinize the FFPE sample. In some embodiments, the encapsulated spatially-barcoded FFPE chunk and the uniquely barcoded bead can be treated with xylene to deparaffinize the FFPE sample. In some embodiments, the deparaffinized sample can be treated to de-crosslink methylene bridges in a single step. In some embodiments, additional steps can be performed when, for example, de-crosslinking chemistry is incompatible with barcoding or library preparation steps. In some embodiments, after de-crosslinking methylene bridges, the nucleic acids originating or present in the chunk can bind to the uniquely barcoded bead. In some embodiments, after the spatial barcode binds the uniquely barcoded bead, the encapsulation can be disrupted (e.g., lysed, melted, or removed) and the barcoded beads can be collected. In some embodiments, the collected barcoded beads can be washed and re-encapsulated. In some embodiments, the nucleic acids associated with the bead (e.g., spatial barcode, unique barcode, analyte transcript) can be amplified (e.g., PCR amplified) and processed (e.g., sequenced) according to any of the methods described herein.

In some embodiments, a biological sample can be divided or portioned using laser capture microdissection (e.g., highly-multiplexed laser capture microdissection).

(c) Release and Amplification of Analytes

In some embodiments, lysis reagents can be added to the sample to facilitate release of analyte(s) from a sample. Examples of lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes. Other lysis agents can additionally or alternatively be co-partitioned with the biological sample to cause the release of the sample's contents into the partitions. In some embodiments, surfactant-based lysis solutions can be used to lyse cells, although these can be less desirable for emulsion-based systems where the surfactants can interfere with stable emulsions. Lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of biological materials that can be in addition to or in place of droplet partitioning, where any pore volume of the encapsulate is sufficiently small to retain nucleic acid fragments of a given size, following cellular disruption.

In addition to the permeabilization agents, other reagents can also be added to interact with the biological sample, including, for example, DNase and RNase inactivating agents or inhibitors or chelating agents, such as EDTA, and other reagents to allow for subsequent processing of analytes from the sample. In other embodiments, nucleases, such as DNase or RNAse, or proteases, such as pepsin or proteinase K, are added to the sample.

Further reagents that can be added to a sample, include, for example, endonucleases to fragment DNA, DNA polymerase enzymes, and dNTPs used to amplify nucleic acids. Other enzymes that can also be added to the sample include, but are not limited to, polymerase, transposase, ligase, proteinase K, and DNAse, etc. Additional reagents can also include reverse transcriptase enzymes, including enzymes with terminal transferase activity, primers, and switch oligonucleotides. In some embodiments, template switching can be used to increase the length of a cDNA, e.g., by appending a predefined nucleic acid sequence to the cDNA.

If a tissue sample is not permeabilized sufficiently, the amount of analyte captured on the substrate can be too low to enable adequate analysis. Conversely, if the tissue sample is too permeable, the analyte can diffuse away from its origin in the tissue sample, such that the relative spatial relationship of the analytes within the tissue sample is lost. Hence, a balance between permeabilizing the tissue sample enough to obtain good signal intensity while still maintaining the spatial resolution of the analyte distribution in the tissue sample is desired.

In some embodiments, where the biological sample includes live cells, permeabilization conditions can be modified so that the live cells experience only brief permeabilization (e.g., through short repetitive bursts of electric field application), thereby allowing one or more analytes to migrate from the live cells to the substrate while retaining cellular viability.

In some embodiments, after contacting a biological sample with a substrate that include capture probes, a removal step is performed to remove all or a portion of the biological sample from the substrate. In some embodiments, the removal step includes enzymatic or chemical degradation of the permeabilized cells of the biological sample. For example, the removal step can include treating the biological samples with an enzyme (e.g., proteinase K) to remove at least a portion of the biological sample from the first substrates. In some embodiments, the removal step can include ablation of the tissue (e.g., laser ablation).

In some embodiments, where RNA is captured from cells in a sample, one or more RNA species of interest can be selectively enriched. For example, one or more species of RNA of interest can be selected by addition of one or more oligonucleotides. One or more species of RNA can be selectively down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved RNA capture due to the reduction in non-specific RNA present in the sample. In some embodiments, the additional oligonucleotide is a sequence used for priming a reaction by a polymerase. For example, one or more primer sequences with sequence complementarity to one or more RNAs of interest, can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. In one non-limiting example, biotinylated oligonucleotides with sequence complementary to one or more cDNA of interest binds to the cDNA and can be selected using biotinylation-strepavidin affinity in any number of methods known to the field (e.g., streptavidin beads).

In some embodiments, any of the spatial analysis methods described herein can include modulating the rate of interaction between biological analytes from the biological sample and the capture probes on the array. In some embodiments, modulating the rate of interaction can occur by modulating the biological sample (e.g., modulating temperature or pH). In some embodiments, modulating the rate of interaction includes using external stimuli. Non-limiting examples of external stimuli that can be used to modulate the rate of interaction include light, temperature, small molecules, enzymes, and/or an activating reagent. In one example, light can be used to activate a polymerase in a nucleic acid extension reaction. In another example, temperature can be used to modulate hybridization between two complementary nucleic acid molecules.

Nucleic acid analytes can be amplified using a polymerase chain reaction (e.g., digital PCR, quantitative PCR, or real time PCR), isothermal amplification, or any nucleic acid amplification or extension reactions described herein, or known in the art.

(d) Partitioning

As discussed above, in some embodiments, the sample can optionally be separated into single cells, cell groups (e.g., based on cell sub-type or gene expression profile), or other fragments/pieces that are smaller than the original sample. Each of these smaller portions of the sample can be analyzed to obtain spatially-resolved analyte information from the sample. Non-limiting partitioning methods are described herein.

For samples that have been separated into smaller fragments—and particularly, for samples that have been disaggregated, dissociated, or otherwise separated into individual cells—one method for analyzing the fragments involves partitioning the fragments into individual partitions (e.g., fluid droplets), and then analyzing the contents of the partitions. In general, each partition maintains separation of its own contents from the contents of other partitions. For example, the partition can be a droplet in an emulsion.

The methods described herein provide for the compartmentalization or partitioning of a cell (e.g., a cell) from a sample into discrete compartments or voxels. As used herein, each "voxel" represents a 3-dimensional volumetric unit. In some embodiments, a voxel maintains separation of its own contents from the contents of other voxels. A voxel can be one partition of an array of partitions of volume. For example, a voxel can be one partition of an array of discrete partitions into which a 3-dimensional object is divided. As another example, members of a plurality of photo-crosslinkable polymer precursors can be cross-linked into voxels that are part of an array of the photo-crosslinked polymer covering the substrate or a portion of the substrate. Unique identifiers, e.g., barcodes, may be previously, subsequently, or concurrently delivered to the cell, in order to allow for the later attribution of the characteristics of the cell to the particular voxel. In some embodiments, a voxel has defined dimensions. In some embodiments, a voxel comprises a single cell.

For example, a substrate can be coated with a DTT-sensitive hydrogel and then contacted with a biological sample. Optionally, capture probes attached to the substrate are released from the substrate such that the released capture probes are introduced into the biological sample and at least one released capture probe interacts with at least one biological analyte present in the biological sample via the capture domain. The biological sample and substrate can be assembled into a flow-cell and a photo-crosslinkable polymer precursor added. The cells of the biological sample can be then crosslinked into hydrogel-voxels of defined dimensions using a light source. The flow-cell can be dismantled and washed to remove unpolymerized polymer precursors. The coating can be treated with DTT to yield single-cell partitions for use in downstream applications. The capture probes/biological analytes can be analyzed, and the spatial information of the spatially-barcoded features can be used to determine the spatial location of the captured biological analytes in the biological sample.

In addition to analytes, a partition can include additional components, and in particular, one or more beads. A partition can include a single gel bead, a single cell bead, or both a single cell bead and single gel bead.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters can be adjusted to control the occupancy of the resulting partitions (e.g., number of analytes per partition, number of beads per partition, etc.) For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

A partition can include one or more unique identifiers, such as barcodes. Barcodes can be previously, subsequently, or concurrently delivered to the partitions that hold the compartmentalized or partitioned biological particle. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead.

In some embodiments, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well.

Figure 21:
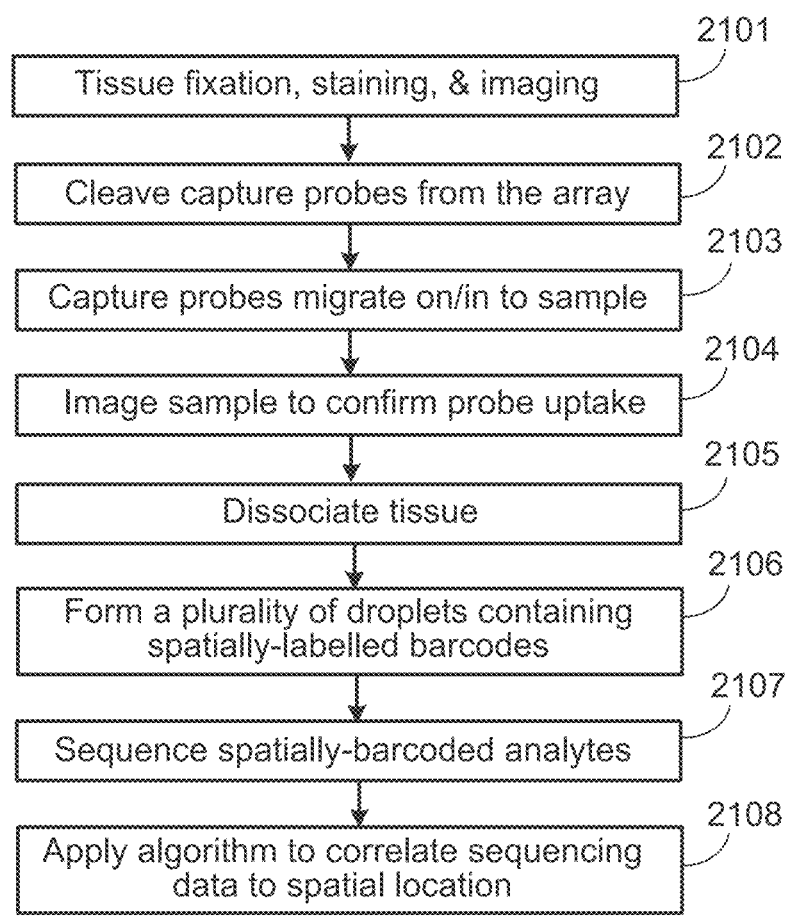
FIG. 21 shows a workflow schematic illustrating exemplary, non-limiting, non-exhaustive steps for dissociating a spatially-barcoded sample for analysis via droplet or flow cell analysis methods.

FIG. 21 depicts an exemplary workflow, where a sample is contacted with a spatially-barcoded capture probe array and the sample is fixed, stained, and imaged 2101, as described elsewhere herein. The capture probes can be cleaved from the array 2102 using any method as described herein. The capture probes can diffuse toward the cells by either passive or active migration as described elsewhere herein. The capture probes may then be introduced to the sample 2103 as described elsewhere herein, wherein the capture probe is able to gain entry into the cell in the absence of cell permeabilization, using one of the cell penetrating peptides or lipid delivery systems described herein. The sample can then be optionally imaged in order to confirm probe uptake, via a reporter molecule incorporated within the capture probe 2104. The sample can then be separated from the array and undergo dissociation 2105, wherein the sample is separated into single cells or small groups of cells. Once the sample is dissociated, the single cells can be introduced to an oil-in water droplet 2106, wherein a single cell is combined with reagents within the droplet and processed so that the spatial barcode that penetrated the cell labels the contents of that cell within the droplet. Other cells undergo separately partitioned reactions concurrently. The contents of the droplet is then sequenced 2107 in order to associate a particular cell or cells with a particular spatial location within the sample 2108.

As described above, FIG. 16 shows an example of a microfluidic channel structure for partitioning individual analytes (e.g., cells) into discrete partitions. FIGS. 17A and 17C also show other examples of microfluidic channel structures that can be used for delivering beads to droplets.

A variety of different beads can be incorporated into partitions as described above. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. For example, a nucleic acid molecule, such as an oligonucleotide, can be coupled to a bead by a releasable linkage, such as, for example, a disulfide linker. The same bead can be coupled (e.g., via releasable linkage) to one or more other nucleic acid molecules. The nucleic acid molecule can be or include a barcode. As noted elsewhere herein, the structure of the barcode can include a number of sequence elements.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly (T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead.

In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up, and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

In some embodiments, a degradable bead can be introduced into a partition, such that the bead degrades within the partition and any associated species (e.g., oligonucleotides) are released within the droplet when the appropriate stimulus is applied. The free species (e.g., oligonucleotides, nucleic acid molecules) can interact with other reagents contained in the partition. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

A degradable bead can include one or more species with a labile bond such that, when the bead/species is exposed to the appropriate stimulus, the bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, upon exposure of a polyacrylamide gel bead that includes cystamine cross-linkers to a reducing agent, the disulfide bonds of the cystamine can be broken and the bead degraded.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore volumes due to osmotic pressure differences can generally occur without structural degradation of the bead itself. In some cases, an increase in pore volume due to osmotic swelling of a bead can permit the release of entrained species within the bead. In some embodiments, osmotic shrinking of a bead can cause a bead to better retain an entrained species due to pore volume contraction.

Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, Mo.), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore volume of the encapsulate is sufficiently small to retain nucleic acid fragments of a given size, following cellular disruption.

Examples of other species that can be co-partitioned with analytes in the partitions include, but are not limited to, DNase and RNase inactivating agents or inhibitors or chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA.

Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a nucleic acid (e.g., miRNA), a physical environmental (e.g., temperature change), or any other known perturbation agents.

(e) Sequencing Analysis

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g., sequencing), i.e., can directly take part in the sequence analysis reaction or process (e.g., the sequencing reaction or sequencing process, or be the molecule which is sequenced or otherwise identified). Alternatively, the barcoded nucleic acid molecule can be subjected to a step of second strand synthesis or amplification before sequence analysis (e.g., sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g., barcoded nucleic acid molecules) can be analyzed (e.g., sequenced). To perform single molecule sequencing, the nucleic acid strand can be modified at the 3' end.

In some embodiments, massively parallel pyrosequencing techniques can be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., *Anal. Biochem.* 242(1), 84-9 (1996); Ronaghi, *Genome Res.* 11(1), 3-11 (2001); Ronaghi et al. *Science* 281 (5375), 363 (1998); and U.S. Pat. Nos. 6,210,891, 6,258,568, and 6,274,320, the entire contents of each of which are incorporated herein by reference.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (e.g., by bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in situ. In situ sequencing methods are particularly useful, for example, when the biological sample remains intact after analytes on the sample surface (e.g., cell surface analytes) or within the sample (e.g., intracellular analytes) have been barcoded. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, the entire contents of each of which are incorporated herein by reference.

In addition, examples of methods and systems for performing in situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Example techniques for in situ sequencing include, but are not limited to, STARmap (described for example in Wang et al., (2018) *Science,* 361(6499) 5691), MERFISH (described for example in Moffitt, (2016) *Methods in Enzymology,* 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid features are present in a double stranded form these can be processed to provide single stranded nucleic acid templates using methods well known in the art, for example by denaturation, cleavage, etc. The sequencing primers which are hybridized to the nucleic acid template and used for primer extension are preferably short oligonucleotides, for example, 15 to 25 nucleotides in length. The sequencing primers can be greater than 25 nucleotides in length as well. For example, sequencing primers can be about 20 to about 60 nucleotides in length, or more than 60 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010, 251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., *Trends Biotechnol.* 18, 14 7-151 (2000); Deamer et al., *Acc. Chem. Res.* 35:817-825 (2002); Li et al., *Nat. Mater.* 2:611-615 (2003); Soni et al., *Clin. Chem.* 53, 1996-2001 (2007); Healy et al., *Nanomed.* 2, 459-481 (2007); Cockroft et al., *J. Am. Chem. Soc.* 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeq™ technology by Illumina, Inc., San Diego, Calif.), HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.), and sequencing of DNA nanoballs (Complete Genomics, Inc., Mountain View, Calif.).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes. The entire contents of each of the foregoing references are incorporated herein by reference.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181. The entire contents of each of the foregoing references are herein incorporated by reference.

IV. Multiplexing (a) Multiplexing Generally

In various embodiments of spatial analysis as described herein, features can include different types of capture probes for analyzing both intrinsic and extrinsic information for individual cells. For example, a feature can include one or more of the following: 1) a capture probe featuring a capture domain that binds to one or more endogenous nucleic acids in the cell; 2) a capture probe featuring a capture domain that binds to one or more exogenous nucleic acids in the cell (e.g., nucleic acids from a microorganism (e.g., a virus, a bacterium)) that infects the cell, nucleic acids introduced into the cell (e.g., such as plasmids or nucleic acid derived therefrom), nucleic acids for gene editing (e.g., CRISPR-related RNA such as crRNA, guide RNA); 3) a capture probe featuring a capture domain that binds to an analyte capture agent (e.g., an antibody coupled to a oligonucleotide that includes a capture agent barcode domain having an analyte capture sequence that binds the capture domain), and 4) a capture moiety featuring a domain that binds to a protein (e.g., an exogenous protein expressed in the cell, a protein from a microorganism (e.g., a virus, a bacterium)) that infects the cell, or a binding partner for a protein of the cell (e.g., an antigen for an immune cell receptor).

In some embodiments of any of the spatial analysis methods as described herein, spatial profiling includes concurrent analysis of two different types of analytes. A feature can be a gel bead, which is coupled (e.g., reversibly coupled) to one or more capture probes. The capture probes can include a spatial barcode sequence and a poly(T) priming sequence that can hybridize with the poly(A) tail of an mRNA transcript. The capture probe can also include a UMI sequence that can uniquely identify a given transcript. The capture probe can also include a spatial barcode sequence and a random N-mer priming sequence that is capable of randomly hybridizing with gDNA. In this configuration, capture probes can include the same spatial barcode sequence, which permits association of downstream sequencing reads with the feature.

In some embodiments of any of the spatial analysis methods as described herein, a feature can be a gel bead, which is coupled (e.g., reversibly coupled) to capture probes. The Capture probe can include a spatial barcode sequence and a poly(T) priming sequence that can hybridize with the poly(A) tail of an mRNA transcript. The capture probe can also include a UMI sequence that can uniquely identify a given transcript. The capture probe can include a spatial barcode sequence and a capture domain that is capable of specifically hybridizing with an analyte capture agent. The analyte capture agent can includes an oligonucleotide that includes an analyte capture sequence that interacts with the capture domain coupled to the feature. The oligonucleotide of the analyte capture agent can be coupled to an antibody that is bound to the surface of a cell. The oligonucleotide includes a barcode sequence (e.g., an analyte binding moiety barcode) that uniquely identifies the antibody (and thus, the particular cell surface feature to which it is bound). In this configuration, the capture probes include the same spatial barcode sequence, which permit downstream association of barcoded nucleic acids with the location on the spatial array. In some embodiments of any of the spatial profiling methods described herein, the analyte capture agents can be can be produced by any suitable route, including via example coupling schemes described elsewhere herein.

In some embodiments of any of the spatial analysis methods described herein, other combinations of two or more biological analytes that can be concurrently measured include, without limitation: (a) genomic DNA and cell surface features (e.g., via analyte capture agents that bind to a cell surface feature), (b) mRNA and a lineage tracing construct, (c) mRNA and cell methylation status, (d) mRNA and accessible chromatin (e.g., ATAC-seq, DNase-seq, and/or MNase-seq), (e) mRNA and cell surface or intracellular proteins and/or metabolites, (f) mRNA and chromatin (spatial organization of chromatin in a cell), (g) an analyte capture agent (e.g., any of the MHC multimers described herein) and a V(D)J sequence of an immune cell receptor (e.g., T-cell receptor), (h) mRNA and a perturbation agent (e.g., a CRISPR crRNA/sgRNA, TALEN, zinc finger nuclease, and/or antisense oligonucleotide as described herein), (i) genomic DNA and a perturbation agent, (j) an analyte capture agent and a perturbation agents, (k) accessible chromatin and a perturbation agent, (l) chromatin (e.g., spatial organization of chromatin in a cell) and a perturbation agent, and (m) cell surface or intracellular proteins and/or metabolites and a perturbation agent (e.g., any of the perturbation agents described herein), or any combination thereof.

In some embodiments of any of the spatial analysis methods described herein, the first analyte can include a nucleic acid molecule with a nucleic acid sequence (e.g., mRNA, complementary DNA derived from reverse transcription of mRNA) encoding at least a portion of a V(D)J sequence of an immune cell receptor (e.g., a TCR or BCR). In some embodiments, the nucleic acid molecule with a nucleic acid sequence encoding at least a portion of a V(D)J sequence of an immune cell receptor is cDNA first generated from reverse transcription of the corresponding mRNA, using a poly(T) containing primer. The cDNA that is generated can then be barcoded using a primer, featuring a spatial barcode sequence (and optionally, a UMI sequence) that hybridizes with at least a portion of the cDNA that is generated. In some embodiments, a template switching oligonucleotide in conjunction a terminal transferase or a reverse transcriptase having terminal transferase activity can be employed to generate a priming region on the cDNA to which a barcoded primer can hybridize during cDNA generation. Terminal transferase activity can, for example, add a poly(C) tail to a 3' end of the cDNA such that the template switching oligonucleotide can bind via a poly(G) priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described, for example, in PCT Patent Application Publication No. WO 2018/075693, and in U.S. Patent Application Publication No. 2018/0105808, the entire contents of each of which are incorporated herein by reference.

In some embodiments, V(D)J analysis can be performed using methods similar to those described herein. For example, V(D)J analysis can be completed with the use of one or more analyte capture agents that bind to particular surface features of immune cells and are associated with barcode sequences (e.g., analyte binding moiety barcodes). The one or more analyte capture agents can include an MHC or MHC multimer. A barcoded oligonucleotide coupled to a bead that can be used for V(D)J analysis. The oligonucleotide is coupled to a bead by a releasable linkage, such as a disulfide linker. The oligonucleotide can include functional sequences that are useful for subsequent processing, such as functional sequence, which can include a sequencer specific flow cell attachment sequence, e.g., a P5 sequence, as well as functional sequence, which can include sequencing primer sequences, e.g., a R1 primer binding site. In some embodiments, the sequence can include a P7 sequence and a R2 primer binding site. A barcode sequence can be included within the structure for use in barcoding the template polynucleotide. The functional sequences can be selected for compatibility with a variety of different sequencing systems, e.g., 454 Sequencing, Ion Torrent Proton or PGM, Illumina X10, etc., and the requirements thereof. In some embodiments, the barcode sequence, functional sequences (e.g., flow cell attachment sequence) and additional sequences (e.g., sequencing primer sequences) can be common to all of the oligonucleotides attached to a given bead. The barcoded oligonucleotide can also include a sequence to facilitate template switching (e.g., a poly(G) sequence). In some embodiments, the additional sequence provides a unique molecular identifier (UMI) sequence segment, as described elsewhere herein.

In an exemplary method of cellular polynucleotide analysis using a barcode oligonucleotide, a cell is co-partitioned along with a bead bearing a barcoded oligonucleotide and additional reagents such as a reverse transcriptase, primers, oligonucleotides (e.g., template switching oligonucleotides), dNTPs, and a reducing agent into a partition (e.g., a droplet in an emulsion). Within the partition, the cell can be lysed to yield a plurality of template polynucleotides (e.g., DNA such as genomic DNA, RNA such as mRNA, etc.).

A reaction mixture featuring a template polynucleotide from a cell and (i) the primer having a sequence towards a 3' end that hybridizes to the template polynucleotide (e.g., poly(T)) and (ii) a template switching oligonucleotide that includes a first oligonucleotide towards a 5' end can be subjected to an amplification reaction to yield a first amplification product. In some embodiments, the template polynucleotide is an mRNA with a poly(A) tail and the primer that hybridizes to the template polynucleotide includes a poly(T) sequence towards a 3' end, which is complementary to the poly(A) segment. The first oligonucleotide can include at least one of an adaptor sequence, a barcode sequence, a unique molecular identifier (UMI) sequence, a primer binding site, and a sequencing primer binding site or any combination thereof. In some cases, a first oligonucleotide is a sequence that can be common to all partitions of a plurality of partitions. For example, the first oligonucleotide can include a flow cell attachment sequence, an amplification primer binding site, or a sequencing primer binding site and the first amplification reaction facilitates the attachment the oligonucleotide to the template polynucleotide from the cell. In some embodiments, the first oligonucleotide includes a primer binding site. In some embodiments, the first oligonucleotide includes a sequencing primer binding site.

The sequence towards a 3' end (e.g., poly(T)) of the primer hybridizes to the template polynucleotide. In a first amplification reaction, extension reaction reagents, e.g., reverse transcriptase, nucleoside triphosphates, co-factors (e.g., $Mg^{2+}$ or $Mn^{2+}$), that are also co-partitioned, can extend the primer sequence using the cell's nucleic acid as a template, to produce a transcript, e.g., cDNA, having a fragment complementary to the strand of the cell's nucleic acid to which the primer annealed. In some embodiments, the reverse transcriptase has terminal transferase activity and the reverse transcriptase adds additional nucleotides, e.g., poly(C), to the cDNA in a template independent manner.

The template switching oligonucleotide, for example a template switching oligonucleotide which includes a poly (G) sequence, can hybridize to the cDNA and facilitate template switching in the first amplification reaction. The transcript, therefore, can include the sequence of the primer, a sequence complementary to the template polynucleotide from the cell, and a sequence complementary to the template switching oligonucleotide.

In some embodiments of any of the spatial analysis methods described herein, subsequent to the first amplification reaction, the first amplification product or transcript can be subjected to a second amplification reaction to generate a second amplification product. In some embodiments, additional sequences (e.g., functional sequences such as flow cell attachment sequence, sequencing primer binding sequences, barcode sequences, etc.) are attached. The first and second amplification reactions can be performed in the same volume, such as for example in a droplet. In some embodiments, the first amplification product is subjected to a second amplification reaction in the presence of a barcoded oligonucleotide to generate a second amplification product having a barcode sequence. The barcode sequence can be unique to a partition, that is, each partition can have a unique barcode sequence. The barcoded oligonucleotide can include a sequence of at least a segment of the template switching oligonucleotide and at least a second oligonucleotide. The segment of the template switching oligonucleotide on the barcoded oligonucleotide can facilitate hybridization of the barcoded oligonucleotide to the transcript, e.g., cDNA, to facilitate the generation of a second amplification product. In addition to a barcode sequence, the barcoded oligonucleotide can include a second oligonucleotide such as at least one of an adaptor sequence, a unique molecular identifier (UMI) sequence, a primer binding site, and a sequencing primer binding site, or any combination thereof.

In some embodiments of any of the spatial analysis methods described herein, the second amplification reaction uses the first amplification product as a template and the barcoded oligonucleotide as a primer. In some embodiments, the segment of the template switching oligonucleotide on the barcoded oligonucleotide can hybridize to the portion of the cDNA or complementary fragment having a sequence complementary to the template switching oligonucleotide or that which was copied from the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence using the first amplification product as template. The second amplification product can include a second oligonucleotide, a sequence of a segment of the template polynucleotide (e.g., mRNA), and a sequence complementary to the primer.

In some embodiments of any of the spatial analysis methods described herein, the second amplification product uses the barcoded oligonucleotide as a template and at least a portion of the first amplification product as a primer. The segment of the first amplification product (e.g., cDNA) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence (e.g., first amplification product) using the barcoded oligonucleotide as template. The second amplification product can include the sequence of the primer, a sequence which is complementary to the sequence of the template polynucleotide (e.g., mRNA), and a sequence complementary to the second oligonucleotide.

In some embodiments of any of the spatial analysis methods described herein, three or more classes of biological analytes can be concurrently measured. For example, a feature can include capture probes that can participate in an assay of at least three different types of analytes via three different capture domains. A bead can be coupled to a barcoded oligonucleotide that includes a capture domain that includes a poly(T) priming sequence for mRNA analysis; a barcoded oligonucleotide that includes a capture domain that includes a random N-mer priming sequence for gDNA analysis; and a barcoded oligonucleotide that includes a capture domain that can specifically bind a an analyte capture agent (e.g., an antibody with a spatial barcode), via its analyte capture sequence.

In some embodiments of any of the spatial analysis methods described herein, other combinations of three or more biological analytes that can be concurrently measured include, without limitation: (a) mRNA, a lineage tracing construct, and cell surface and/or intracellular proteins and/or metabolites; (b) mRNA, accessible chromatin (e.g., ATAC-seq, DNase-seq, and/or MNase-seq), and cell surface and/or intracellular proteins and/or metabolites; (c) mRNA, genomic DNA, and a perturbation reagent (e.g., a CRISPR crRNA/sgRNA, TALEN, zinc finger nuclease, and/or antisense oligonucleotide as described herein); (d) mRNA, accessible chromatin, and a perturbation reagent; (e) mRNA, an analyte capture agent (e.g., any of the MHC multimers described herein), and a perturbation reagent; (f) mRNA, cell surface and/or intracellular proteins and/or metabolites, and a perturbation agent; (g) mRNA, a V(D)J sequence of an immune cell receptor (e.g., T-cell receptor), and a perturbation reagent; (h) mRNA, an analyte capture agent, and a V(D)J sequence of an immune cell receptor; (i) cell surface and/or intracellular proteins and/or metabolites, a an analyte capture agent (e.g., the MHC multimers described herein), and a V(D)J sequence of an immune cell receptor; (j) methylation status, mRNA, and cell surface and/or intracellular proteins and/or metabolites; (k) mRNA, chromatin (e.g., spatial organization of chromatin in a cell), and a perturbation reagent; (l) a V(D)J sequence of an immune cell receptor, chromatin (e.g., spatial organization of chromatin in a cell); and a perturbation reagent; and (m) mRNA, a V(D)J sequence of an immune cell receptor, and chromatin (e.g., spatial organization of chromatin in a cell), or any combination thereof.

In some embodiments of any of the spatial analysis methods described herein, four or more classes biological analytes can be concurrently measured. A feature can be a bead that is coupled to barcoded primers that can each participate in an assay of a different type of analyte. The feature is coupled (e.g., reversibly coupled) to a capture probe that includes a capture domain that includes a poly(T) priming sequence for mRNA analysis and is also coupled (e.g., reversibly coupled) to capture probe that includes a capture domain that includes a random N-mer priming sequence for gDNA analysis. Moreover, the feature is also coupled (e.g., reversibly coupled) to a capture probe that binds an analyte capture sequence of an analyte capture agent via its capture domain. The feature can also be coupled (e.g., reversibly coupled) to a capture probe that can specifically bind a nucleic acid molecule that can function as a perturbation agent (e.g., a CRISPR crRNA/sgRNA, TALEN, zinc finger nuclease, and/or antisense oligonucleotide as described herein), via its capture domain.

In some embodiments of any of the spatial analysis methods described herein, each of the various spatially-barcoded capture probes present at a given feature or on a given bead include the same spatial barcode sequence. In some embodiments, each barcoded capture probe can be released from the feature in a manner suitable for analysis of its respective analyte. For example, barcoded constructs A, B, C and D can be generated as described elsewhere herein and analyzed. Barcoded construct A can include a sequence corresponding to the barcode sequence from the bead (e.g., a spatial barcode) and a DNA sequence corresponding to a target mRNA. Barcoded construct B can include a sequence corresponding to the barcode sequence from the bead (e.g., a spatial barcode) and a sequence corresponding to genomic DNA. Barcoded construct C can include a sequence corresponding to the barcode sequence from the bead (e.g., a spatial barcode) and a sequence corresponding to barcode sequence associated with an analyte capture agent (e.g., an analyte binding moiety barcode). Barcoded construct D can include a sequence corresponding to the barcode sequence from the bead (e.g., a spatial barcode) and a sequence corresponding to a CRISPR nucleic acid (which, in some embodiments, also includes a barcode sequence). Each construct can be analyzed (e.g., via any of a variety of sequencing methods) and the results can be associated with the given cell from which the various analytes originated. Barcoded (or even non-barcoded) constructs can be tailored for analyses of any given analyte associated with a nucleic acid and capable of binding with such a construct.

In some embodiments of any of the spatial analysis methods described herein, other combinations of four or more biological analytes that can be concurrently measured include, without limitation: (a) mRNA, a lineage tracing construct, cell surface and/or intracellular proteins and/or metabolites, and gDNA; (b) mRNA, accessible chromatin (e.g., ATAC-seq, DNase-seq, and/or MNase-seq), cell surface and/or intracellular proteins and/or metabolites, and a perturbation agent (e.g., a CRISPR crRNA/sgRNA, TALEN, zinc finger nuclease, and/or antisense oligonucleotide as described herein); (c) mRNA, cell surface and/or intracellular proteins and/or metabolites, an analyte capture agent (e.g., the MHC multimers described herein), and a V(D)J sequence of an immune cell receptor (e.g., T-cell receptor); (d) mRNA, genomic DNA, a perturbation reagent, and accessible chromatin; (e) mRNA, cell surface and/or intracellular proteins and/or metabolites, an analyte capture agent (e.g., the MHC multimers described herein), and a perturbation reagent; (f) mRNA, cell surface and/or intracellular proteins and/or metabolites, a perturbation reagent, and a V(D)J sequence of an immune cell receptor (e.g., T-cell receptor); (g) mRNA, a perturbation reagent, an analyte capture agent (e.g., the MHC multimers described herein), and a V(D)J sequence of an immune cell receptor (e.g., T-cell receptor); (h) mRNA, chromatin (e.g., spatial organization of chromatin in a cell), and a perturbation reagent; (i) a V(D)J sequence of an immune cell receptor, chromatin (e.g., spatial organization of chromatin in a cell); and a perturbation reagent; (j) mRNA, a V(D)J sequence of an immune cell receptor, chromatin (e.g., spatial organization of chromatin in a cell), and genomic DNA; (k) mRNA, a V(D)J sequence of an immune cell receptor, chromatin (e.g., spatial organization of chromatin in a cell), and a perturbation reagent, or any combination thereof.

(b) Construction of Spatial Arrays for Multi-Analyte Analysis

This disclosure also provides methods and materials for constructing a spatial array capable of multi-analyte analysis. In some embodiments, a spatial array includes a plurality of features on a substrate where one or more members of the plurality of features include a plurality of oligonucleotides having a first type functional sequence and oligonucleotides having a second, different type of functional sequence. In some embodiments, a feature can include oligonucleotides with two types of functional sequences. A feature can be coupled to oligonucleotides comprising a TruSeq functional sequence and also to oligonucleotides comprising a Nextera functional sequence. In some embodiments, one or more members of the plurality of features comprises both types of functional sequences. In some embodiments, one or more members of the plurality features includes a first type of functional sequence. In some embodiments, one or more members of the plurality of features includes a second type of functional sequence. In some embodiments, an additional oligonucleotide can be added to the functional sequence to generate a full oligonucleotide where the full oligonucleotide includes a spatial barcode sequence, an optional UMI sequence, a priming sequence, and a capture domain. Attachment of these sequences can be via ligation (including via splint ligation as is described in U.S. Patent Application Publication No. 20140378345, the entire contents of which are incorporated herein by reference), or any other suitable route. As discussed herein, oligonucleotides can be hybridized with splint sequences that can be helpful in constructing complete full oligonucleotides (e.g., oligonucleotides that are capable of spatial analysis).

In some embodiments, the oligonucleotides that hybridize to the functional sequences (e.g., TruSeq and Nextera) located on the features include capture domains capable of capturing different types of analytes (e.g., mRNA, genomic DNA, cell surface proteins, or accessible chromatin). In some examples, oligonucleotides that can bind to the TruSeq functional sequences can include capture domains that include poly(T) capture sequences. In addition to the poly (T) capture sequences, the oligonucleotides that can bind the TruSeq functional groups can also include a capture domain that includes a random N-mer sequence for capturing genomic DNA (e.g., or any other sequence or domain as described herein capable of capturing any of the biological analytes described herein). In such cases, the spatial arrays can be constructed by applying ratios of TruSeq-poly(T) and TruSeq-N-mer oligonucleotides to the features comprising the functional TruSeq sequences. This can produce spatial arrays where a portion of the oligonucleotides can capture mRNA and a different portion of oligonucleotides can capture genomic DNA. In some embodiments, one or more members of a plurality of features include both TruSeq and Nextera functional sequences. In such cases, a feature including both types of functional sequences is capable of binding oligonucleotides specific to each functional sequence. For example, an oligonucleotide capable of binding to a TruSeq functional sequence could be used to deliver an oligonucleotide including a poly(T) capture domain and an oligonucleotide capable of binding to a Nextera functional sequence could be used to deliver an oligonucleotide including an N-mer capture domain for capturing genomic DNA. It will be appreciated by a person of ordinary skill in the art that any combination of capture domains (e.g., capture domains having any of the variety of capture sequences described herein capable of binding to any of the different types of analytes as described herein) could be combined with oligonucleotides capable of binding to TruSeq and Nextera functional sequences to construct a spatial array.

In some embodiments, an oligonucleotide that includes a capture domain (e.g., an oligonucleotide capable of coupling to an analyte) or an analyte capture agent can include an oligonucleotide sequence that is capable of binding or ligating to an assay primer. The adapter can allow the capture probe or the analyte capture agent to be attached to any suitable assay primers and used in any suitable assays. The assay primer can include a priming region and a sequence that is capable of binding or ligating to the adapter. In some embodiments, the adapter can be a non-specific primer (e.g., a 5' overhang) and the assay primer can include a 3' overhang that can be ligated to the 5' overhang. The priming region on the assay primer can be any primer described herein, e.g., a poly (T) primer, a random N-mer primer, a target-specific primer, or an analyte capture agent capture sequence.

In some examples, an oligonucleotide can includes an adapter, e.g., a 5' overhang with 10 nucleotides. The adapter can be ligated to assay primers, each of which includes a 3' overhang with 10 nucleotides that complementary to the 5' overhang of the adapter. The capture probe can be used in any assay by attaching to the assay primer designed for that assay.

Adapters and assay primers can be used to allow the capture probe or the analyte capture agent to be attached to any suitable assay primers and used in any suitable assays. A capture probe that includes a spatial barcode can be attached to a bead that includes a poly(dT) sequence. A capture probe including a spatial barcode and a poly(T) sequence can be used to assay multiple biological analytes as generally described herein (e.g., the biological analyte includes a poly(A) sequence or is coupled to or otherwise is associated with an analyte capture agent comprising a poly (A) sequence as the analyte capture sequence).

A splint oligonucleotide with a poly(A) sequence can be used to facilitate coupling to a capture probe that includes a spatial barcode and a second sequence that facilitates coupling with an assay primer. Assay primers include a sequence complementary to the splint oligo second sequence and an assay-specific sequence that determines assay primer functionality (e.g., a poly(T) primer, a random N-mer primer, a target-specific primer, or an analyte capture agent capture sequence as described herein).

In some embodiments of any of the spatial profiling methods described herein, a feature can include a capture probe that includes a spatial barcode comprising a switch oligonucleotide, e.g., with a 3' end 3rG. For example, a feature (e.g., a gel bead) with a spatial barcode functionalized with a 3rG sequence can be used that enables template switching (e.g., reverse transcriptase template switching), but is not specific for any particular assay. In some embodiments, the assay primers added to the reaction can determine which type of analytes are analyzed. For example, the assay primers can include binding domains capable of binding to target biological analytes (e.g., poly (T) for mRNA, N-mer for genomic DNA, etc.). A capture probe (e.g., an oligonucleotide capable of spatial profiling) can be generated by using a reverse transcriptase enzyme/polymerase to extend, which is followed by template switching onto the barcoded adapter oligonucleotide to incorporate the barcode and other functional sequences. In some embodiments, the assay primers include capture domains capable of binding to a poly(T) sequence for mRNA analysis, random primers for genomic DNA analysis, or a capture sequence that can bind a nucleic acid molecule coupled to an analyte binding moiety (e.g., a an analyte capture sequence of an analyte capture agent) or a nucleic acid molecule that can function in as a perturbation reagent (e.g., a CRISPR crRNA/sgRNA, TALEN, zinc finger nuclease, and/or antisense oligonucleotide as described herein).

V. Systems for Sample Analysis

The methods described above for analyzing biological samples can be implemented using a variety of hardware components. In this section, examples of such components are described. However, it should be understood that in general, the various steps and techniques discussed herein can be performed using a variety of different devices and system components, not all of which are expressly set forth.

Figure 22A:
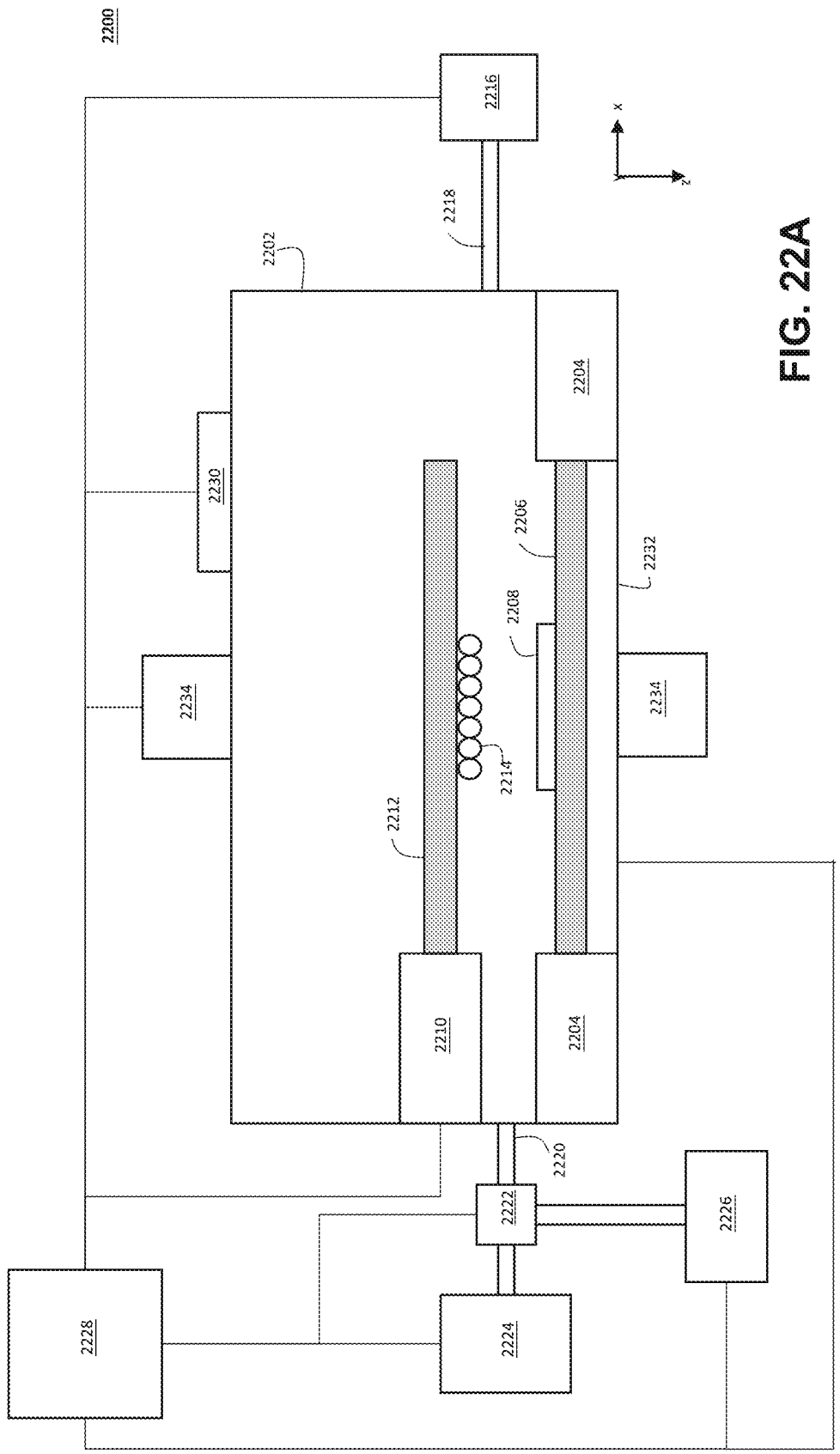
FIG. 22A is a schematic diagram showing an example sample handling apparatus that can be used to implement various steps and methods described herein.

FIG. 22A is a schematic diagram showing an example sample handling apparatus 2200. Sample handling apparatus 2200 includes a sample chamber 2202 that, when closed or sealed, is fluid-tight. Within chamber 2202, a first holder 2204 holds a first substrate 2206 on which a sample 2208 is positioned. Sample chamber 2202 also includes a second holder 2210 that holds a second substrate 2212 with an array of features 2214, as described above.

A fluid reservoir 2216 is connected to the interior volume of sample chamber 2202 via a fluid inlet 2218. Fluid outlet 2220 is also connected to the interior volume of sample chamber 2202, and to valve 2222. In turn, valve 2222 is connected to waste reservoir 2224 and, optionally, to analysis apparatus 2226. A control unit 2228 is electrically connected to second holder 2210, to valve 2222, to waste reservoir 2224, and to fluid reservoir 2216.

During operation of apparatus 2200, any of the reagents, solutions, and other biochemical components described above can be delivered into sample chamber 2202 from fluid reservoir 2216 via fluid inlet 2218. Control unit 2228, connected to fluid reservoir 2216, can control the delivery of reagents, solutions, and components, and adjust the volumes and flow rates according to programmed analytical protocols for various sample types and analysis procedures. In some embodiments, fluid reservoir 2216 includes a pump, which can be controlled by control unit 2228, to facilitate delivery of substances into sample chamber 2202.

In certain embodiments, fluid reservoir 2216 includes a plurality of chambers, each of which is connected to fluid inlet 2218 via a manifold (not shown). Control unit 2228 can selectively deliver substances from any one or more of the multiple chambers into sample chamber 2202 by adjusting the manifold to ensure that the selected chambers are fluidically connected to fluid inlet 2218.

In general, control unit 2228 can be configured to introduce substances from fluid reservoir 2216 into sample chamber 2202 before, after, or both before and after, sample 2208 on first substrate 2206 has interacted with the array of features 2214 on first substrate 2212. Many examples of such substances have been described previously. Examples of such substances include, but are not limited to, permeabilizing agents, buffers, fixatives, staining solutions, washing solutions, and solutions of various biological reagents (e.g., enzymes, peptides, oligonucleotides, primers).

To initiate interaction between sample 2208 and feature array 2214, the sample and array are brought into spatial proximity. To facilitate this step, second holder 2210—under the control of control unit 2228—can translate second substrate 2212 in any of the x-, y-, and z-coordinate directions. In particular, control unit 2228 can direct second holder 2210 to translate second substrate 2212 in the z-direction so that sample 2208 contacts, or nearly contacts, feature array 2214.

In some embodiments, apparatus 2200 can optionally include an alignment sub-system 2230, which can be electrically connected to control unit 2228. Alignment sub-system 2230 functions to ensure that sample 2208 and feature array 2214 are aligned in the x-y plane prior to translating second substrate 2212 in the z-direction so that sample 2208 contacts, or nearly contacts, feature array 2214.

Alignment sub-system 2230 can be implemented in a variety of ways. In some embodiments, for example, alignment sub-system 2230 includes an imaging unit that obtains one or more images showing fiducial markings on first substrate 2206 and/or second substrate 2212. Control unit 2218 analyzes the image(s) to determine appropriate translations of second substrate 2212 in the x- and/or y-coordinate directions to ensure that sample 2208 and feature array 2214 are aligned prior to translation in the z-coordinate direction.

In certain embodiments, control unit 2228 can optionally regulate the removal of substances from sample chamber 2202. For example, control unit 2228 can selectively adjust valve 2222 so that substances introduced into sample chamber 2202 from fluid reservoir 2216 are directed into waste reservoir 2224. In some embodiments, waste reservoir 2224 can include a reduced-pressure source (not shown) electrically connected to control unit 2228. Control unit 2228 can adjust the fluid pressure in fluid outlet 2220 to control the rate at which fluids are removed from sample chamber 2202 into waste reservoir 2224.

In some embodiments, analytes from sample 2208 or from feature array 2214 can be selectively delivered to analysis apparatus 2226 via suitable adjustment of valve 2222 by control unit 2228. As described above, in some embodiments, analysis apparatus 2226 includes a reduced-pressure source (not shown) electrically connected to control unit 2228, so that control unit 2228 can adjust the rate at which analytes are delivered to analysis apparatus 2226. As such, fluid outlet 2220 effectively functions as an analyte collector, while analysis of the analytes is performed by analysis apparatus 2226. It should be noted that not all of the workflows and methods described herein are implemented via analysis apparatus 2226. For example, in some embodiments, analytes that are captured by feature array 2214 remain bound to the array (i.e., are not cleaved from the array), and feature array 2214 is directly analyzed to identify specifically-bound sample components.

In addition to the components described above, apparatus 2200 can optionally include other features as well. In some embodiments, for example, sample chamber 2202 includes a heating sub-system 2232 electrically connected to control unit 2228. Control unit 2228 can activate heating sub-system 2232 to heat sample 2208 and/or feature array 2214, which can help to facilitate certain steps of the methods described herein.

In certain embodiments, sample chamber 2202 includes an electrode 2234 electrically connected to control unit 2228. Control unit 2228 can optionally activate electrode 2234, thereby establishing an electric field between the first and second substrates. Such fields can be used, for example, to facilitate migration of analytes from sample 2208 toward feature array 2214.

Figure 22B:
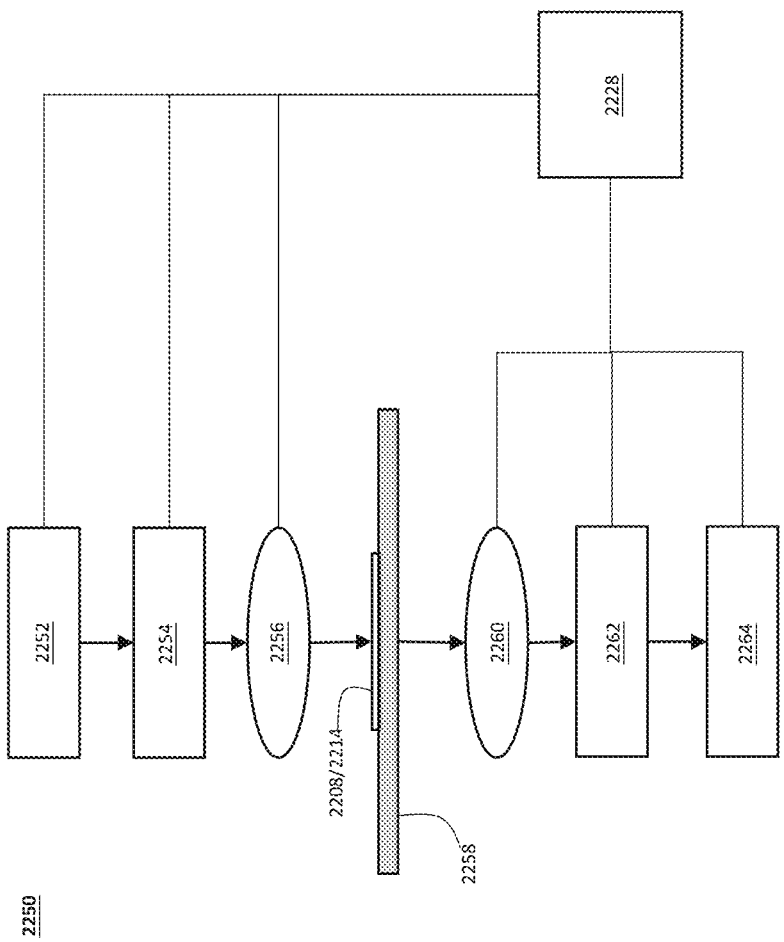
FIG. 22B is a schematic diagram showing an example imaging apparatus that can be used to obtain images of biological samples, analytes, and arrays of features.

In some of the methods described herein, one or more images of a sample and/or a feature array are acquired. Imaging apparatus that is used to obtain such images can generally be implemented in a variety of ways. FIG. 22B shows one example of an imaging apparatus 2250. Imaging apparatus 2250 includes a light source 2252, light conditioning optics 2254, light delivery optics 2256, light collection optics 2260, light adjusting optics 2262, and a detection sub-system 2264. Each of the foregoing components can optionally be connected to control unit 2228, or alternatively, to another control unit. For purposes of explanation below, it will be assumed that control unit 2228 is connected to the components of imaging apparatus 2250.

During operation of imaging apparatus 2250, light source 2252 generates light. In general, the light generated by source 2252 can include light in any one or more of the ultraviolet, visible, and/or infrared regions of the electromagnetic spectrum. A variety of different light source elements can be used to generate the light, including (but not limited to) light emitting diodes, laser diodes, laser sources, fluorescent sources, incandescent sources, and glow-discharge sources.

The light generated by light source 2252 is received by light conditioning optics 2254. In general, light conditioning optics 2254 modify the light generated by light source 2252 for specific imaging applications. For example, in some embodiments, light conditioning optics 2254 modify the spectral properties of the light, e.g., by filtering out certain wavelengths of the light. For this purpose, light conditioning optics 2254 can include a variety of spectral optical elements, such as optical filters, gratings, prisms, and chromatic beam splitters.

In certain embodiments, light conditioning optics 2254 modify the spatial properties of the light generated by light source 2252. Examples of components that can be used for this purpose include (but are not limited to) apertures, phase masks, apodizing elements, and diffusers.

After modification by light conditioning optics 2254, the light is received by light delivery optics 2256 and directed onto sample 2208 or feature array 2214, either of which is positioned on a mount 2258. Light conditioning optics 2254 generally function to collect and direct light onto the surface of the sample or array. A variety of different optical elements can be used for this purpose, and examples of such elements include, but are not limited to, lenses, mirrors, beam splitters, and various other elements having non-zero optical power.

Light emerging from sample 2208 or feature array 2214 is collected by light collection optics 2260. In general, light collection optics 2260 can include elements similar to any of those described above in connection with light delivery optics 2256. The collected light can then optionally be modified by light adjusting optics 2262, which can generally include any of the elements described above in connection with light conditioning optics 2254.

The light is then detected by detection sub-system 2264. Generally, detection sub-system 2264 functions to generate one or more images of sample 2208 or feature array 2214 by detecting light from the sample or feature array. A variety of different imaging elements can be used in detection sub-system 2264, including CCD detectors and other image capture devices.

Each of the foregoing components can optionally be connected to control unit 2228 as shown in FIG. 22B, so that control unit 2228 can adjust various properties of the imaging apparatus. For example, control unit 2228 can adjust the position of sample 2208 or feature array 2214 relative to the position of the incident light, and also with respect to the focal plane of the incident light (if the incident light is focused). Control unit 2228 can also selectively filter both the incident light and the light emerging from the sample.

Imaging apparatus 2250 can typically obtain images in a variety of different imaging modalities. In some embodiments, for example, the images are transmitted light images, as shown in FIG. 22B. In certain embodiments, apparatus 2250 is configured to obtain reflection images. In some embodiments, apparatus 2250 can be configured to obtain birefringence images, fluorescence images, phosphorescence images, multiphoton absorption images, and more generally, any known image type.

In general, control unit 2228 can perform any of the method steps described herein that do not expressly require user intervention by transmitting suitable control signals to the components of sample handling apparatus 2200 and/or imaging apparatus 2250. To perform such steps, control unit 2228 generally includes software instructions that, when executed, cause control unit 2228 to undertake specific steps. In some embodiments, control unit 2228 includes an electronic processor and software instructions that are readable by the electronic processor, and cause the processor to carry out the steps describe herein. In certain embodiments, control unit 2228 includes one or more application-specific integrated circuits having circuit configurations that effectively function as software instructions.

Figure 22C:
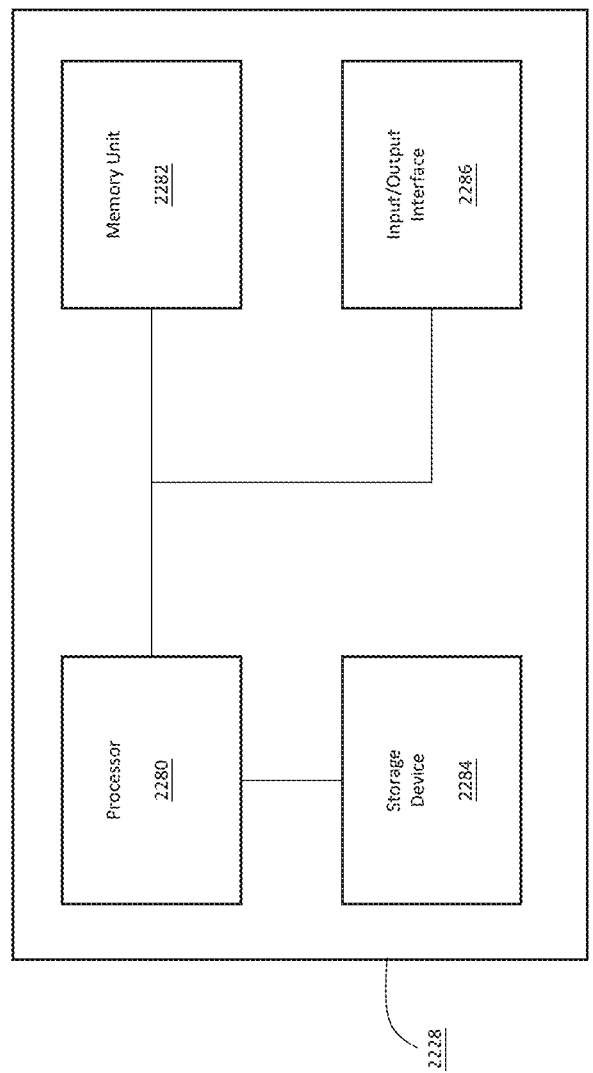
FIG. 22C is a schematic diagram of an example of a control unit of the apparatus of FIGS. 22A and 22B.

Control unit 2228 can be implemented in a variety of ways. FIG. 22C is a schematic diagram showing one example of control unit 2228, including an electronic processor 2280, a memory unit 2282, a storage device 2284, and an input/output interface 2286. Processor 2280 is capable of processing instructions stored in memory unit 2282 or in storage device 2284, and to display information on input/output interface 2286.

Memory unit 2282 stores information. In some embodiments, memory unit 2282 is a computer-readable medium. Memory unit 2282 can include volatile memory and/or non-volatile memory. Storage device 2284 is capable of providing mass storage, and in some embodiments, is a computer-readable medium. In certain embodiments, storage device 2284 may be a floppy disk device, a hard disk device, an optical disk device, a tape device, a solid state device, or another type of writeable medium.

The input/output interface 2286 implements input/output operations. In some embodiments, the input/output interface 2286 includes a keyboard and/or pointing device. In some embodiments, the input/output interface 2286 includes a display unit for displaying graphical user interfaces and/or display information.

Instructions that are executed and cause control unit 2228 to perform any of the steps or procedures described herein can be implemented in digital electronic circuitry, or in computer hardware, firmware, or in combinations of these. The instructions can be implemented in a computer program product tangibly embodied in an information carrier, e.g., in a machine-readable storage device, for execution by a programmable processor (e.g., processor 2280). The computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

Processor 2280 can include any one or more of a variety of suitable processors. Suitable processors for the execution of a program of instructions include, by way of example, both general and special purpose microprocessors, and the sole processor or one of multiple processors of any kind of computer or computing device.

EXEMPLARY EMBODIMENTS

In some non-limiting examples of the workflows described herein, the sample can be immersed in 100% chilled methanol and incubated for 30 minutes at −20° C. After 20 minutes, the sample can be removed and rinsed in ultrapure water. After rinsing the sample, fresh eosin solution is prepared, and the sample can be covered in isopropanol. After incubating the sample in isopropanol for 1 minute, the reagent can be removed by holding the slide at an angle, where the bottom edge of the slide can be in contact with a laboratory wipe and air dried. The sample can be uniformly covered in hematoxylin solution and incubated for 7 minutes at room temperature. After incubating the sample in hematoxylin for 7 minutes, the reagent can be removed by holding the slide at an angle, where the bottom edge of the slide can be in contact with a laboratory wipe.

The slide containing the sample can be immersed in water and the excess liquid can be removed. After that, the sample can be covered with blueing buffer and can be incubated for 2 minutes at room temperature. The slide containing the sample can again be immersed in water, and uniformly covered with eosin solution and incubated for 1 minute at room temperature. The slide can be air-dried for no more than 30 minutes and incubated for 5 minutes at 37° C. The sample can be imaged using brightfield imaging setting.

Further, the biological sample can be processed by the following exemplary steps for sample permeabilization and cDNA generation. The sample can be exposed to a permeabilization enzyme and incubated at 37° C. for the pre-determined permeabilization time (which is tissue type specific). The permeabilization enzyme can be removed and the sample prepared for analyte capture by adding 0.1×SSC buffer. The sample can then subjected to a pre-equilibration thermocycling protocol (e.g., lid temperature and pre-equilibrate at 53° C., reverse transcription at 53° C. for 45 minutes, and then hold at 4° C.) and the SSC buffer can be removed. A Master Mix, containing nuclease-free water, a reverse transcriptase reagent, a template switch oligo, a reducing agent, and a reverse transcriptase enzyme can be added to the biological sample and substrate, and the sample with the Master Mix can be subjected to a thermocycling protocol (e.g., perform reverse transcription at 53° C. for 45 minutes and hold at 4° C.). Second strand synthesis can be performed on the substrate by subjecting the substrate to a thermocycling protocol (e.g., pre-equilibrate at 65° C., second strand synthesis at 65° C. for 15 minutes, then hold at 4° C.). The Master Mix reagents can be removed from the sample and 0.8M KOH can be applied and incubated for 5 minutes at room temperature. The KOH can be removed and elution buffer can be added and removed from the sample. A Second Strand Mix, including a second strand reagent, a second strand primer, and a second strand enzyme, can be added to the sample and the sample can be sealed and incubated. At the end of the incubation, the reagents can be removed and elution buffer can be added and removed from the sample, and 0.8M KOH can be added again to the sample and the sample can be incubated for 10 minutes at room temperature. Tris-HCl can be added and the reagents can be mixed. The sample can be transferred to a new tube, vortexed, and placed on ice.

Further the biological sample can be processed by the following exemplary steps for cDNA amplification and quality control. A qPCR Mix, including nuclease-free water, qPCR Master Mix, and cDNA primers, can be prepared and pipetted into wells in a qPCR plate. A small amount of sample can be added to the plated qPCR Mix, and thermocycled according to a predetermined thermocycling protocol (e.g., step 1: 98° C. for 3 minutes, step 2: 98° C. for 5 seconds, step 3: 63° C. for 30 seconds, step 4: record amplification signal, step 5: repeating 98° C. for 5 seconds, 63° C. for 30 seconds for a total of 25 cycles). After completing the thermocycling, a cDNA amplification mix, including amplification mix and cDNA primers, can be prepared and combined with the remaining sample and mixed. The sample can then be incubated and thermocycled (e.g., lid temperature at 105° C. for ~45-60 minutes; step 1: 98° C. for 3 minutes, step 2: 98° C. for 15 seconds, step 3: 63° C. for 20 seconds, step 4: 72° C. for one minute, step 5: [the number of cycles determined by qPCR Cq Values], step 6: 72° C. for 1 minute, and step 7: hold at 4° C.). The sample can then be stored at 4° C. for up to 72 hours or at −20° C. for up to 1 week, or resuspended in 0.6× SPRIselect Reagent and pipetted to ensure proper mixing. The sample can then be incubated at 5 minutes at room temperature, and cleared by placing the sample on a magnet (e.g., the magnet is in the high position). The supernatant can be removed and 80% ethanol can be added to the pellet, and incubated for 30 seconds. The ethanol can be removed and the pellet can be washed again. The sample can then be centrifuged and placed on a magnet (e.g., the magnet is on the low position). Any remaining ethanol can be removed and the sample can be air dried for up to 2 minutes. The magnet can be removed and elution buffer can be added to the sample, mixed, and incubated for 2 minutes at room temperature. The sample can then be placed on the magnet (e.g., on low position) until the solution clears. The sample can be transferred to a new tube strip and stored at 4° C. for up to 72 hours or at −20° C. for up to 4 weeks. A portion of the sample can be run on an Agilent Bioanalyzer High Sensitivity chip, where a region can be selected and the cDNA concentration can be measured to calculate the total cDNA yield. Alternatively, the quantification can be determined by Agilent Bioanalyzer or Agilent TapeStation.

Further, the biological sample can be processed by the following exemplary steps for spatial gene expression library construction. A Fragmentation Mix, including a fragmentation buffer and fragmentation enzyme, can be prepared on ice. Elution buffer and fragmentation mix can be added to each sample, mixed, and centrifuged. The sample mix can then be placed in a thermocycler and cycled according to a predetermined protocol (e.g., lid temperature at 65° C. for ~35 minutes, pre-cool block down to 4° C. before fragmentation at 32° C. for 5 minutes, End-repair and A-tailing at 65° C. for 30 minutes, and holding at 4° C.). The 0.6× SPRIselect Reagent can be added to the sample and incubated at 5 minutes at room temperature. The sample can be placed on a magnet (e.g., in the high position) until the solution clears, and the supernatant can be transferred to a new tube strip. 0.8× SPRIselect Reagent can be added to the sample, mixed, and incubated for 5 minutes at room temperature. The sample can be placed on a magnet (e.g., in the high position) until the solution clears. The supernatant can be removed and 80% ethanol can be added to the pellet, the pellet can be incubated for 30 seconds, and the ethanol can be removed. The ethanol wash can be repeated and the sample placed on a magnet (e.g., in the low position) until the solution clears. The remaining ethanol can be removed and elution buffer can be added to the sample, mixed, and incubated for 2 minutes at room temperature. The sample can be placed on a magnet (e.g., in the high position) until the solution clears, and a portion of the sample can be moved to a new tube strip. An Adaptor Ligation Mix, including ligation buffer, DNA ligase, and adaptor oligos, can be prepared and centrifuged. The Adaptor Ligation Mix can be added to the sample, pipette-mixed, and centrifuged briefly. The sample can then be thermocycled according to a pre-determined protocol (e.g., lid temperature at 30° C. for ~15 minutes, step 1: 20° C. for 15 minutes, step 2: 4° C. hold). The sample can be vortexed to re-suspend SPRIselect Reagent, additional 0.8× SPRIselect Reagent can be added to the sample and incubated for 5 minutes at room temperature, and placed on a magnet (e.g., in the high position) until the solution clears. The supernatant can be removed and the pellet can be washed with 80% ethanol, incubated for 30 seconds, and the ethanol can be removed. The ethanol wash can be repeated, and the sample can be centrifuged briefly before placing the sample on a magnet (e.g., in the low position). Any remaining ethanol can be removed and the sample can be air dried for a maximum of 2 minutes. The magnet can be removed, and elution buffer can be added to the sample, and the sample can be pipette-mixed, incubated for 2 minutes at room temperature, and placed on a magnet (e.g., in the low position) until the solution clears. A portion of the sample can be transferred to a new tube strip. Amplification mix, can be prepared and combined with the sample. An individual Dual Index TT Set A can be added to the sample, pipette-mixed and subjected to a pre-determined thermocycling protocol (e.g., lid temperature at 105° C. for ~25-40 minutes, step 1: 98° C. for 45 seconds, step 2: 98° C. for 20 seconds, step 3: 54° C. for 30 seconds; step 4: 72° C. for 20 seconds, step 5: reverting to step 2 for a predetermined number of cycles, step 6: 72° C. for 1 minute, and 4° C. on hold). Vortex to re-suspend the SPRIselect Reagent, additional 0.6× SPRIselect Reagent can be added to each sample, mixed, and incubated for 5 minutes at room temperature. The sample can be placed on a magnet (e.g., in the high position) until the solution clears, and the supernatant can be transferred to a new tube strip. The 0.8× SPRIselect Reagent can be added to each sample, pipette-mixed, and incubated for 5 minutes at room temperature. The sample can then be placed on a magnet (e.g., in the high position) until the solution clears. The supernatant can be removed, and the pellet can be washed with 80% ethanol, incubated for 30 seconds, and then the ethanol can be removed. The ethanol wash can be repeated, the sample centrifuged, and placed on a magnet (e.g., in the low position) to remove any remaining ethanol. The sample can be removed from the magnet and Elution Buffer can be added to the sample, pipette-mixed, and incubated at 2 minutes at room temperature. The sample can be placed on a magnet (e.g., in the low position) until the solution clears and a portion of the sample can be transferred to a new tube strip. The sample can be stored at 4° C. for up to 72 hours, or at −20° C. for long-term storage. The average fragment size can be determined using a Bioanalyzer trace or an Agilent TapeStation.

The library can be sequenced using available sequencing platforms, including, MiSeq, NextSeq 500/550, HiSeq 2500, HiSeq 3000/4000, NovaSeq, and iSeq.

In alternate embodiments of the above described workflows, a biological sample can be permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS). In some embodiments, a biological sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0 w/v % to about 14.0 w/v %, about 10.0 w/v % to about 12.0 w/v %, or about 12.0 w/v % to about 14.0 w/v %) SDS and/or proteinase K (e.g., at a temperature of about 35° C. to about 50° C., about 35° C. to about 45° C., about 35° C. to about 40° C., about 40° C. to about 50° C., about 40° C. to about 45° C., or about 45° C. to about 50° C.).

In non-limiting examples of any of the workflows described herein, a nucleic acid molecule is produced that includes a contiguous nucleotide sequence comprising: (a) a first primer sequence (e.g., Read 1); (b) a spatial barcode; (c) a unique molecular sequence (UMI); (d) a capture domain; (e) a sequence complementary to a sequence present in a nucleic acid from a biological sample; (f) a second primer sequence (e.g., Read 2) that is substantially complementary to a sequence of a template switching oligonucleotide (TSO). In some embodiments of these nucleic acid molecules, the nucleic acid molecule is a single-stranded nucleic acid molecule. In some embodiments of these nucleic acid molecules, the nucleic acid molecule is a double-stranded nucleic acid molecule. In some embodiments of these nucleic acid molecules, (a) through (f) are positioned in a 5' to 3' direction in the contiguous nucleotide sequence. In some embodiments of any of these nucleic acid molecules, the nucleic acid molecule is attached to a substrate (e.g., a slide). In some embodiments of any of these nucleic acid molecules, the 5' end of the contiguous nucleic acid sequence is attached to the substrate (e.g., a slide). In some embodiments of any of these nucleic acid molecules, the contiguous nucleotide sequence is a chimeric RNA and DNA sequence. In some embodiments of any of these nucleic acid molecules, the contiguous nucleotide sequence is a DNA sequence.

In non-limiting examples of any of the workflows described herein, a nucleic acid molecule is produced that includes a contiguous nucleotide sequence comprising: (a) a sequence complementary to a first primer sequence (e.g., a sequence complementary to Read 1); (b) a sequence complementary to a spatial barcode; (c) a sequence complementary to a unique molecular sequence; (d) a sequence complementary to a capture domain; (e) a sequence present in a nucleic acid from a biological sample; and (f) a sequence of a template switching oligonucleotide (TSO). In some embodiments of any of these nucleic acid molecules, the nucleic acid molecule is single-stranded. In some embodiments of any of these nucleic acid molecules, the nucleic acid molecule is double-stranded. In some embodiments of any of these nucleic acid molecules, the contiguous nucleotide sequence is a DNA sequence. In some embodiments of any of these nucleic acid molecules, (a) through (f) are positioned in a 3' to 5' direction in the contiguous nucleotide sequence.

In non-limiting examples of any of the workflows described herein, a nucleic acid molecule is produced that includes a contiguous nucleotide sequence comprising: (a) a first primer sequence (e.g., Read 1); (b) a spatial barcode; (c) a unique molecular sequence (UMI); (d) a capture domain; (e) a sequence complementary to a sequence present in a nucleic acid from a biological sample; and (f) a second primer sequence (Read 2). In some embodiments of any of these nucleic acid molecules, the nucleic acid molecule is a single-stranded nucleic acid molecule. In some embodiments of any of these nucleic acid molecules, the nucleic acid molecule is a double-stranded nucleic acid molecule. In some embodiments of any of these nucleic acid molecules, (a) through (f) are positioned in a 5' to 3' direction in the contiguous nucleotide sequence. In some embodiments of any of these nucleic acid molecules, the contiguous nucleotide sequence is a DNA sequence. In some embodiments of any of these nucleic acid molecules, the contiguous nucleotide sequence further comprises 3' to (f): (g) a sequence complementary to a first adaptor sequence; and (h) a sequence complementary to a third primer sequence. In some embodiments of any of the nucleic acid molecules, the first adaptor sequence is an i7 sample index sequence. In some embodiments of any of these nucleic acid molecules, the third primer sequence is a P7 primer sequence. In some embodiments of any of these nucleic acid molecules, (h) is 3' positioned relative to (g) in the contiguous nucleotide sequence. In some embodiments of any of these nucleic acid molecules, the contiguous nucleotide sequence further comprises 5' to (a): (i) a second adaptor sequence; and (ii) a fourth primer sequence. In some embodiments of any of these nucleic acid molecules, the second adaptor sequence is an i5 sample index sequence. In some embodiments of any of these nucleic acid molecules, the fourth primer sequence is a P5 primer sequence. In some embodiments of any of these nucleic acid molecules, (ii) is 5' positioned relative to (i) in the contiguous nucleotide sequence.

In non-limiting examples of any of the workflows described herein, a nucleic acid molecule is produced that includes a contiguous nucleotide sequence comprising: (a) a sequence complementary to a first primer sequence; (b) a sequence complementary to a spatial barcode; (c) a sequence complementary to a unique molecular sequence; (d) a sequence complementary to a capture domain; (e) a sequence present in a nucleic acid from a biological sample; and (f) a sequence complementary to a second primer sequence. In some embodiments of these nucleic acid molecules, a sequence complementary to a first primer sequence is a sequence complementary to Read 1. In some embodiments of these nucleic acid molecules, a sequence complementary to a second primer sequence is a sequence complementary to Read 2. In some embodiments of any of these nucleic acid molecules, the nucleic acid molecule is a single-stranded nucleic acid molecule. In some embodiments of any of these nucleic acid molecules, the nucleic acid molecule is a double-stranded nucleic acid molecule. In some embodiments of any of these nucleic acid molecules, (a) through (f) are positioned in a 3' to 5' direction in the contiguous nucleotide sequence. In some embodiments of any of these nucleic acid molecules, the contiguous nucleotide sequence is a DNA sequence. In some embodiments of any of these nucleic acid molecules, the contiguous nucleotide sequence further comprises 5' to (f): (g) a first adaptor sequence; and (h) a third primer sequence. In some embodiments of any of these nucleic acid molecules, the first adaptor sequence is an i7 sample index sequence. In some embodiments of any of these nucleic acid molecules, the third primer sequence is a P7 primer sequence. In some embodiments of any of these nucleic acid molecules, (h) is 5' positioned relative to (g) in the contiguous nucleotide sequence. In some embodiments of any of these nucleic acid molecules, the contiguous nucleotide sequence further comprises 3' to (a): (i) a sequence complementary to a second adaptor sequence; and (ii) a sequence complementary to a fourth primer sequence. In some embodiments of any of these nucleic acid molecules, the second adaptor sequence is an i5 sample index sequence. In some embodiments of any of these nucleic acid molecules, the fourth primer sequence is a P5 primer sequence. In some embodiments of any of these nucleic acid molecules, (ii) is 3' positioned relative to (i) in the contiguous nucleotide sequence.

Spatial RIN

Provided herein is a non-limiting example of a protocol for determining the spatial RIN in a tissue that can include collecting breast cancer tissue and snap freezing in liquid nitrogen. Tissue can be embedded in OCT and sectioned at 10 or 12 µM thickness at −20° C. and mounted directly on a spatial array including capture probes having an 18S rRNA capture domain. Tissue can be fixed and stained using a Hematoxylin and Eosin (H&E) staining protocol. Briefly, Mayer's Hematoxylin can be added, washed in water, incubated in Bluing buffer, washed in water, stained with Eosin, then washed in water, and finally dried. For visualizing H&E staining, sections can be mounted with 85% glycerol and covered with a coverslip. Bright field imaging can be performed using the Metafer Slide Scanning Platform (Metasystems) where raw images are stitched together with the VSlide software (Metasystems). Glycerol can be removed by holding the spatial array or glass slide in water until the coverslip falls off and then was air dry until the remaining liquid evaporates. Hematoxylin, from the H&E stain, can be optionally removed from the tissue section, for example, by washing in dilute HCl (0.01M) prior to further processing. The tissue sections are then ready for further processing.

Following staining, the 18S rRNA present in the tissue sections are captured by the 18S rRNA specific capture domains on the spatial array. The 18S rRNA is then converted to cDNA in situ. Specifically, reverse transcription is performed on the spatial array in a sealed hybridization cassette by adding 70 µl reaction mixture including 1× First-strand buffer, 5 mM DTT, 1 M Betaine, 6 mM MgCl2, 1 mM dNTPs, 0.2 mg/ml BSA, 50 ng/µl Actinomycin D, 10% DMSO, 20 U/µl SuperScript III Reverse Transcriptase, 2 U/µl RNaseOUT Recombinant Ribonuclease Inhibitor. The reaction is performed overnight at 42° C. overnight. After incubation cDNA synthesis mixture is removed and the tissue was washed with 0.1×SSC buffer.

In order to prepare the spatial array for oligonucleotide probe labeling and imaging, the breast cancer tissue and rRNA is removed. Tissue removal can be performed first by incubation with β-mercaptoethanol in RLT lysis buffer at a 3:100 ratio at 56° C. for 1 hour with continuous shaking at 300 rpm. All tissues can be incubated with a 1:7 ratio of Proteinase K and PKD buffer for 1 hour at 56° C. using short intervals with gentle shaking at 300 rpm. The spatial array is then washed with continuous shaking at 300 rpm as follows: first in 2×SSC with 0.1% SDS at 50° C. for 10 min, then in 0.2×SSC at RT for 1 min and finally in 0.1×SSC at RT for 1 min. The spatial array is then spin-dried and put back into the hybridization cassette. rRNA removal can be performed using a reaction mixture containing the following final concentrations: 1× First-strand buffer, 0.4 mg/ml BSA and 16.3 mU/µl RNase H. The reaction can be performed for 1 hour at 37° C. with gentle shaking at 300 rpm using short intervals. Spatial arrays are then washed with 0.1×SSC buffer and treated with 60% DMSO at room temperature for 5 minutes and then washed three times with 0.1×SSC buffer.

In order to detect the cDNA produced from the 18S rRNA, labeled oligonucleotide probes are generated that had sequence complementarity to the 18S cDNA sequence. Oligonucleotides are identified that have a length between 18-23 nucleotides with an optimum at 20 nucleotides, a melting temperature (Tm) between 38-50° C. with the optimal temperature at 42° C., and a content of guanine and cytosine of 30-60% with an optimum at 50%. The first five bases of the 3'-ends are set to include two of either guanine or cytosine or one of each. Oligonucleotides are checked for quality using Mfold (determination of secondary structure), Oligo Calc: Oligonucleotide Properties Calculator (determination of self-dimerization and hairpin formation), and BLAST (determination of off-target binding). The sequence locations are picked for compatibility with both human (NR_003286.2) and mouse (NR_003278.3) 18S rRNA. Four of the oligonucleotide probes selected include: probe 1 (P1; SEQ ID NO: 4) GAGGAATTCCCAGTAAGT, probe 2 (P2; SEQ ID NO: 5) GAGATTGAGCAATAACAG, probe 3 (P3; SEQ ID NO: 6) GTAGTTCCGACCATAAAC, and probe 4 (P4; SEQ ID NO: 7) GGTGACTCTAGATAACCT. Control oligonucleotide probes can be designed to include complementary sequences of three detection probes at a time with a 20 bases spacer sequence between each probe. The selected oligonucleotide probes can be then designed to incorporate a Cy3 fluorophore.

Next, labeled oligonucleotide probes are hybridized to the spatial array containing cDNA produced from the 18S rRNA or containing control capture probes. This step can include at least 4 successive rounds of hybridization and imaging, with at least one round for each of the four labeled oligonucleotide probes. Following each round of hybridization and imaging, the spatial array can be washed to remove the hybridized probe before continuing with a subsequent round of hybridization and imaging.

Hybridization of labeled oligonucleotide probes includes adding to the spatial arrays a pre-heated (e.g., heated to 50° C.) hybridization mixture (10 mM Tris-HCl, 1 mM EDTA, 50 mM NaCl, and 0.5 µM of fluorescently labelled probe) containing at least 0.5 µM of one of the fluorescently labeled oligonucleotide probes (e.g., one of P1, P2, P3 or P4). The spatial array can be then imaged using a DNA microarray scanner with the following settings: excitation wavelength 532 nm set to gain 70 and 635 nm set to 1. Following imaging, the spatial array is incubated with 60% DMSO at room temperature for 5 minutes and washed three times with 0.1×SSC buffer to remove the hybridized probe. Subsequent rounds of hybridization and imaging are performed with a different labeled oligonucleotide probe used in each round (e.g., round 2 used P2, round 3 used P3, and round 4 used P4). An initial, pre-hybridization round (PO) of imaging are performed in order to assess background fluorescence.

One image is generated per labeled oligonucleotide probe (P1-P4) and also one where no fluorescently labeled probes were hybridized (PO). Normalization of Fluorescence Units (FU) data is done by subtraction of the auto-fluorescence recorded with PO and division with P1. After aligning the five images for a particular location in the tissue (one image from each probe, P1-P4, and one image from the location without labeling), the images are loaded into a script and run in RStudio. The Script can generate two different plots, one heat-map of spatial RIN values and one image alignment error plot.

High quality RNA is defined as full-length (or close to full-length) transcripts, whereas low quality RNA is defined as fragmented transcripts. Spatial RIN values are similar to traditional RIN values in that the RIN values range from 1 to 10, with higher numbers indicating higher quality (e.g., less degraded, less fragmented) RNA samples.

Spatial ATAC Compositions

Provided herein are compositions for identifying the location of an analyte in a biological sample. In some embodiments, a nucleotide molecule composition including a) a spatial barcode b) a unique molecule c) capture domain; d) a functional domain; and e) a splint oligonucleotide. In some embodiments, a partially double-stranded nucleotide molecule composition including: a) a spatial barcode; b) a unique molecular identifier; c) a capture domain; d) a functional domain; and e) a splint oligonucleotide. In some embodiments, a composition including a) a capture probe including i) a spatial barcode; ii) a unique molecular identifier; iii) a capture domain; iv) a functional domain; and v) a splint oligonucleotide and b) fragmented genomic DNA including i) a first adapter sequence comprising a transposon end sequence and a sequence complementary to the capture domain; and ii) a second adapter sequence comprising the transposon end sequence and a second adapter sequence. In some embodiments, a composition including a) a transposase enzyme monomer complexed with a first adapter including i) a transposon end sequence; and ii) a sequence complementary to the capture domain; and b) a transposase enzyme second monomer complexed with a second adapter including i) a transposon end sequence; and ii) a second adapter sequence; c) genomic DNA; and d) a capture probe, including i) a spatial barcode; ii) a unique molecular identifier; iii) a capture domain; iv) a functional domain; and v) a splint oligonucleotide. In some embodiments, a composition including a) a transposase enzyme monomer complexed with a first adapter including i) a transposon end sequence; ii) a sequence complementary to the capture domain; wherein the 5' end of the first adapter is phosphorylated and b) a transposase enzyme second monomer complexed with a second adapter including i) the transposon end sequence; ii) a second adapter sequence; wherein the 5' end of the second adapter is phosphorylated; c) genomic DNA; and d) a capture probe including i) a spatial barcode; ii) a unique molecular identifier; iii) a capture domain; iv) a functional domain; and v) a splint oligonucleotide. In some embodiments, a composition including a) a transposase enzyme dimer including i) a transposase enzyme monomer complexed with a first adapter including 1) a transposon end sequence, 2) a sequence complementary to a capture domain; ii) a transposase enzyme second monomer complexed with a second adapter including 1) the transposon end sequence; 2) a second adapter sequence; b) genomic DNA; c) a capture probe, including i) a spatial barcode; ii) a unique molecular identifier; iii) a capture domain; iv) a functional domain; and v) a splint oligonucleotide. In some embodiments, a composition including a) a transposase enzyme dimer including i) a transposase enzyme monomer complexed with a first adapter including 1) a transposon end sequence, 2) a sequence complementary to a capture domain wherein the 5' end of the first adapter is phosphorylated; ii) a transposase enzyme second monomer complexed with a second adapter including 1) the transposon end sequence; 2) a second adapter sequence wherein the 5' end of the second adapter is phosphorylated; c) genomic DNA; and d) a capture probe, including i) a spatial barcode; ii) a unique molecular identifier; iii) a capture domain; iv) a functional domain; and v) a splint oligonucleotide.

Spatial Transcriptomics

In some embodiments, provided herein are methods for spatially detecting an analyte (e.g., detecting the location of an analyte, e.g., a biological analyte) from a biological sample (e.g., present in a biological sample such as a tissue section) that include: (a) providing a biological sample on a substrate; (b) staining the biological sample on the substrate, imaging the stained biological sample, and selecting the biological sample or subsection of the biological sample to subject to spatial analysis; (c) providing an array comprising one or more pluralities of capture probes on a substrate; (d) contacting the biological sample with the array, thereby allowing a capture probe of the one or more pluralities of capture probes to capture the biological analyte of interest; and (e) analyzing the captured biological analyte, thereby spatially detecting the biological analyte of interest. Any variety of staining and imaging techniques as described herein or known in the art can be used in accordance with methods described herein. In some embodiments, the staining includes optical labels as described herein, including, but not limited to, fluorescent, radioactive, chemiluminescent, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain such as hematoxylin and eosin (H&E) or periodic acid-schiff (PAS). In some embodiments, significant time (e.g., days, months, or years) can elapse between staining and/or imaging the biological sample and performing spatial transcriptomic analysis. In some embodiments, reagents for performing spatial analysis are added to the biological sample before, contemporaneously with, or after the array is contacted to the biological sample. In some embodiments, step (d) includes placing the array onto the biological sample. In some embodiments, the array is a flexible array where the plurality of spatially-barcoded features (e.g., capture probes) are attached to a flexible substrate. In some embodiments, measures are taken to slow down a reaction (e.g., cooling the temperature of the biological sample or using enzymes that preferentially perform their primary function at lower or higher temperature as compared to their optimal functional temperature) before the array is contacted with the biological sample. In some embodiments, step (e) is performed without bringing the biological sample out of contact with the array. In some embodiments, step (e) is performed after the biological sample is no longer in contact with the array. In some embodiments, the biological sample is tagged with an analyte capture agent before, contemporaneously with, or after staining and/or imaging of the biological sample. In such cases, significant time (e.g., days, months, or years) can elapse between staining and/or imaging and performing spatial analysis. In some embodiments, the array is adapted to facilitate biological analyte migration from the stained and/or imaged biological sample onto the array (e.g., using any of the materials or methods described herein). In some embodiments, a biological sample is permeabilized before being contacted with an array. In some embodiments, the rate of permeabilization is slowed prior to contacting a biological sample with an array (e.g., to limit diffusion of analytes away from their original locations in the biological sample). In some embodiments, modulating the rate of permeabilization (e.g., modulating the activity of a permeabilization reagent) can occur by modulating a condition that the biological sample is exposed to (e.g., modulating temperature, pH, and/or light). In some embodiments, modulating the rate of permeabilization includes use of external stimuli (e.g., small molecules, enzymes, and/or activating reagents) to modulate the rate of permeabilization. For example, a permeabilization reagent can be provided to a biological sample prior to contact with an array, which permeabilization reagent is inactive until a condition (e.g., temperature, pH, and/or light) is changed or an external stimulus (e.g., a small molecule, an enzyme, and/or an activating reagent) is provided.

Spatially-Resolved Gene Expression and Clustering in Invasive Ductal Carcinoma

The spatial gene expression of invasive ductal carcinoma tissue from a female patient (ER+, PR−, HER2+) was profiled (BioIVT: Asterand-Case ID 66320; Specimen ID 116899F). As a control, the healthy tissue sections adjacent to the tumor were obtained. 4 replicates were used for each tissue type.

Figure 23A:
FIG. 23A shows a histological section of an invasive ductal carcinoma annotated by a pathologist.
Figure 23B:
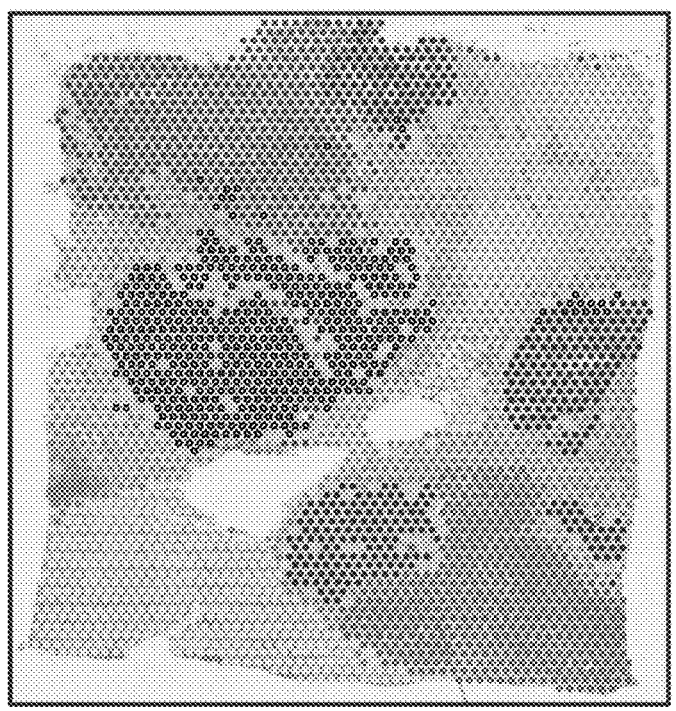
FIG. 23B shows a tissue plot with spots colored by unsupervised clustering.
Figure 23C:
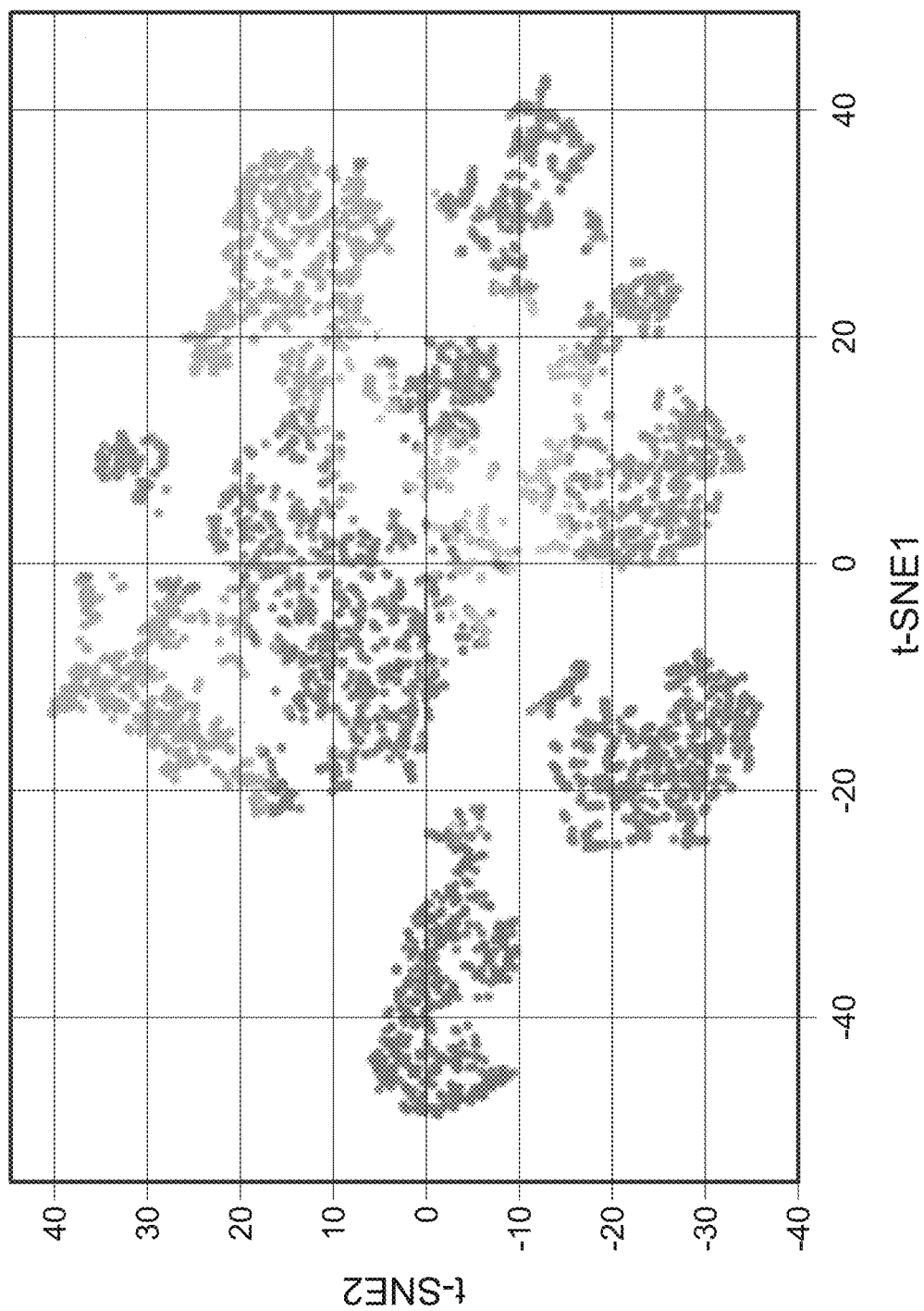
FIG. 23C is a tSNE plot of spots colored by unsupervised clustering.
Figure 23D:
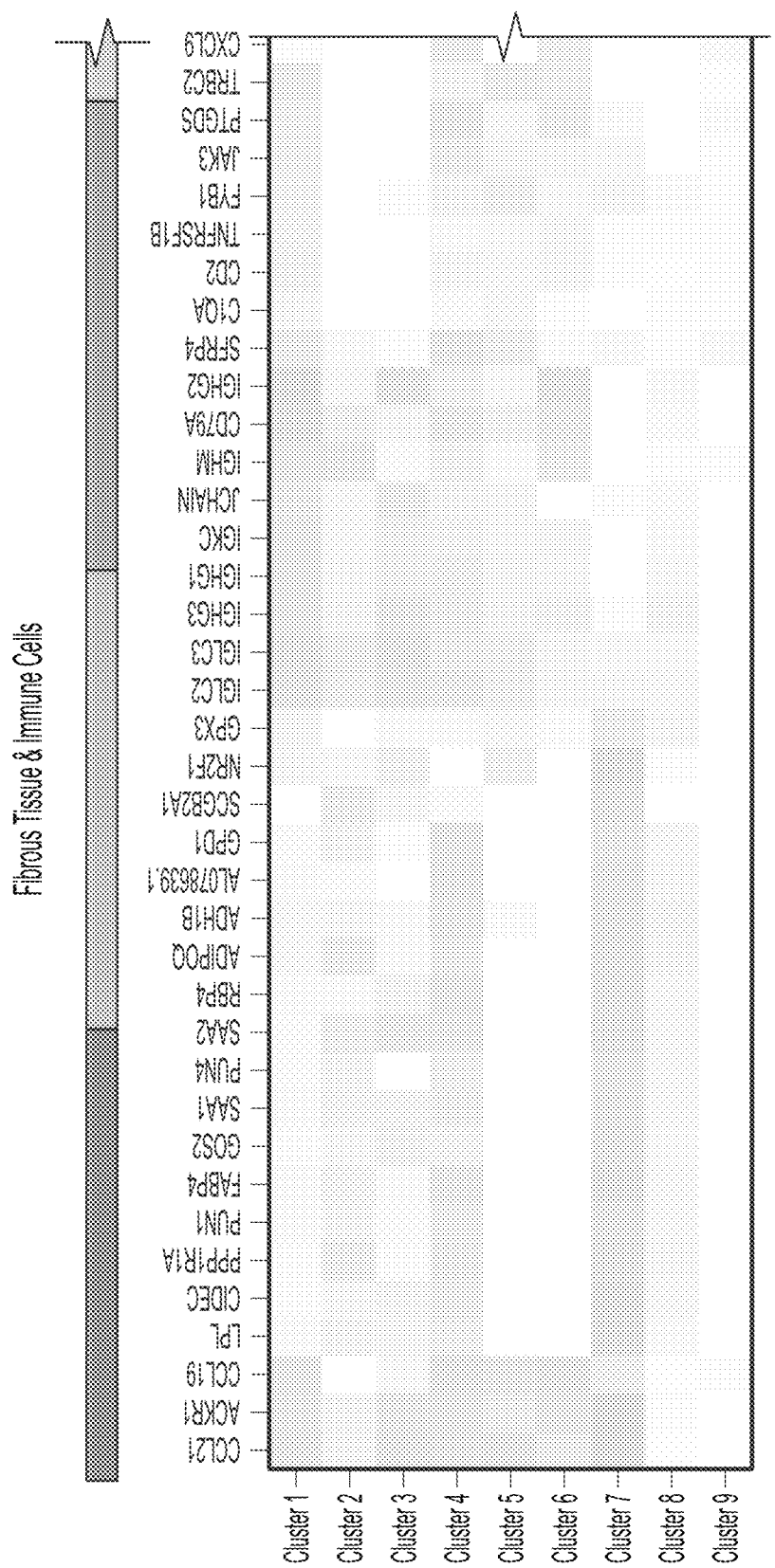
FIG. 23D shows a gene expression heat map of the most variable genes between 9 clusters.

Spatially-resolved gene expression and clustering in invasive ductal carcinoma reveal intra-tumor heterogeneity is shown in FIGS. 23A-H. FIG. 23A shows a histological section of an invasive ductal carcinoma annotated by a pathologist. The section contains a large proportion of invasive carcinoma (22.344 mm$^2$ portion indicated by thick black line (outlined in black in color figure)), three separate ductal cancer in situ regions (portions indicated by medium thickness black line 1.329 mm$^2$, 1.242 mm$^2$, and 0.192 mm$^2$ (outlined in green in color figure)), and fibrous tissue. FIG. 23B shows a tissue plot with spots colored by unsupervised clustering of transcripts. FIG. 23C shows a t-SNE plot of spots colored by unsupervised clustering of transcripts. FIG. 23D shows a gene expression heat map of the most variable genes between the 9 identified clusters. The region defined as fibrous tissue mostly corresponds to clusters 1, 7, and 8. Interestingly, a large region annotated as invasive carcinoma by a pathologist contained spatial spots that were assigned to DCIS (cluster 5). In addition, four subtypes of invasive carcinoma with distinct molecular properties (clusters 2, 3, 4, and 6) were identified, revealing intra-tumor heterogeneity.

Figure 23E:
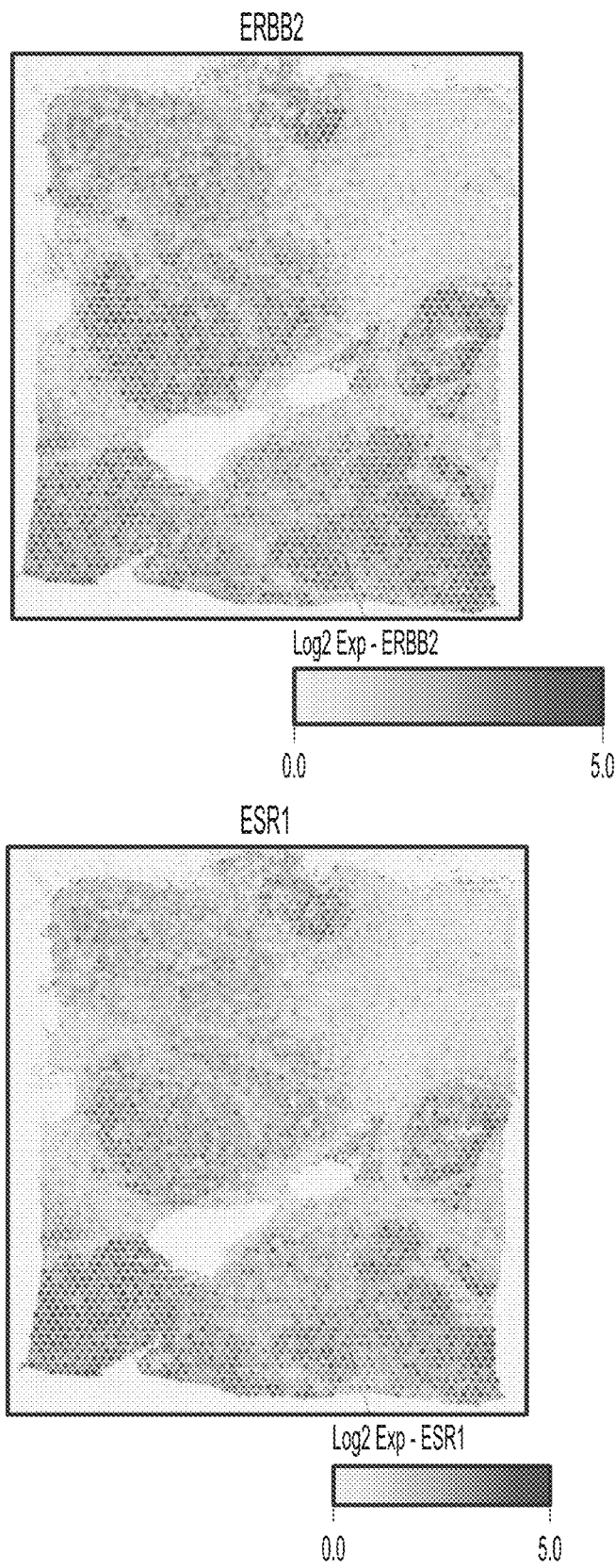
FIG. 23E shows the expression levels of genes corresponding to human epidermal growth factor receptor 2 (Her2), estrogen receptor (ER), and progesterone receptor (PR) in the tissue section.
Figure 23E:
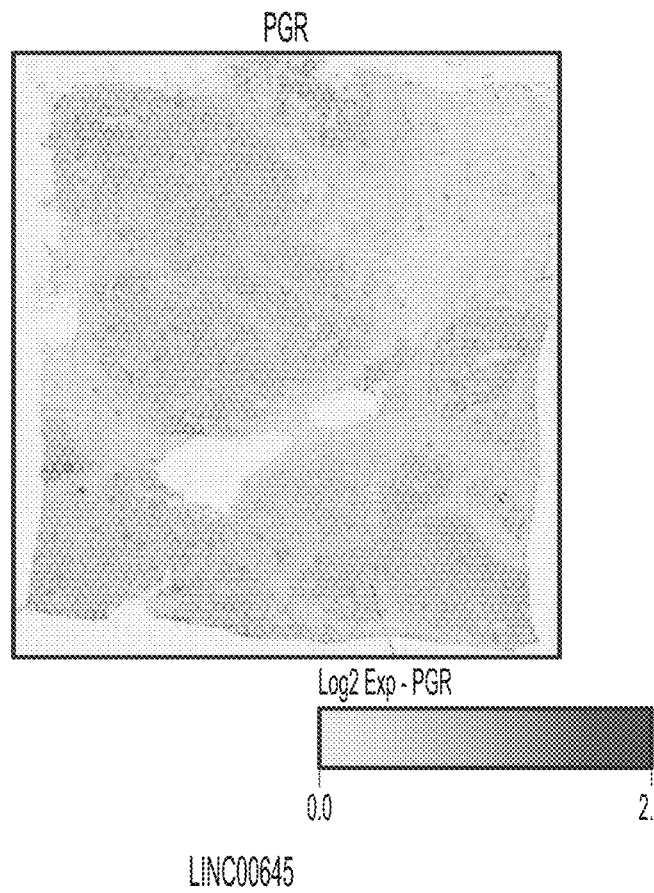
Figure 23F:
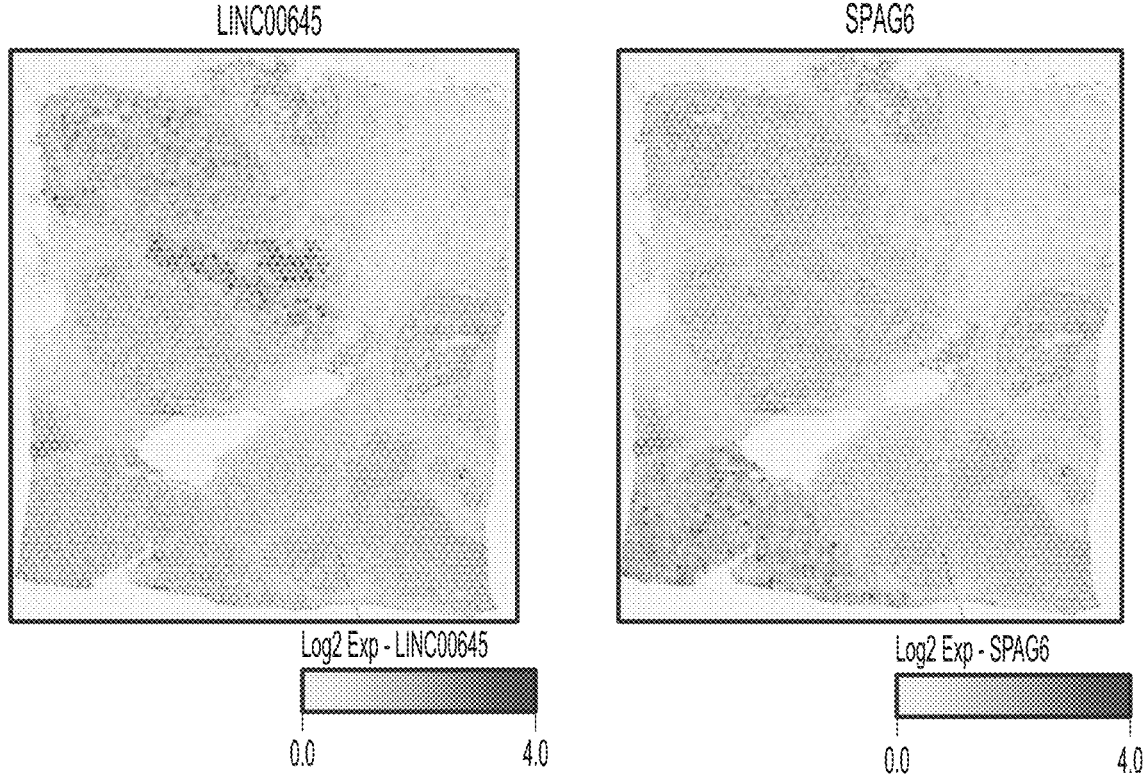
FIG. 23F shows the expression levels of genes of top differentially expressed genes from each of the 9 clusters on individual plots.
Figure 23F:
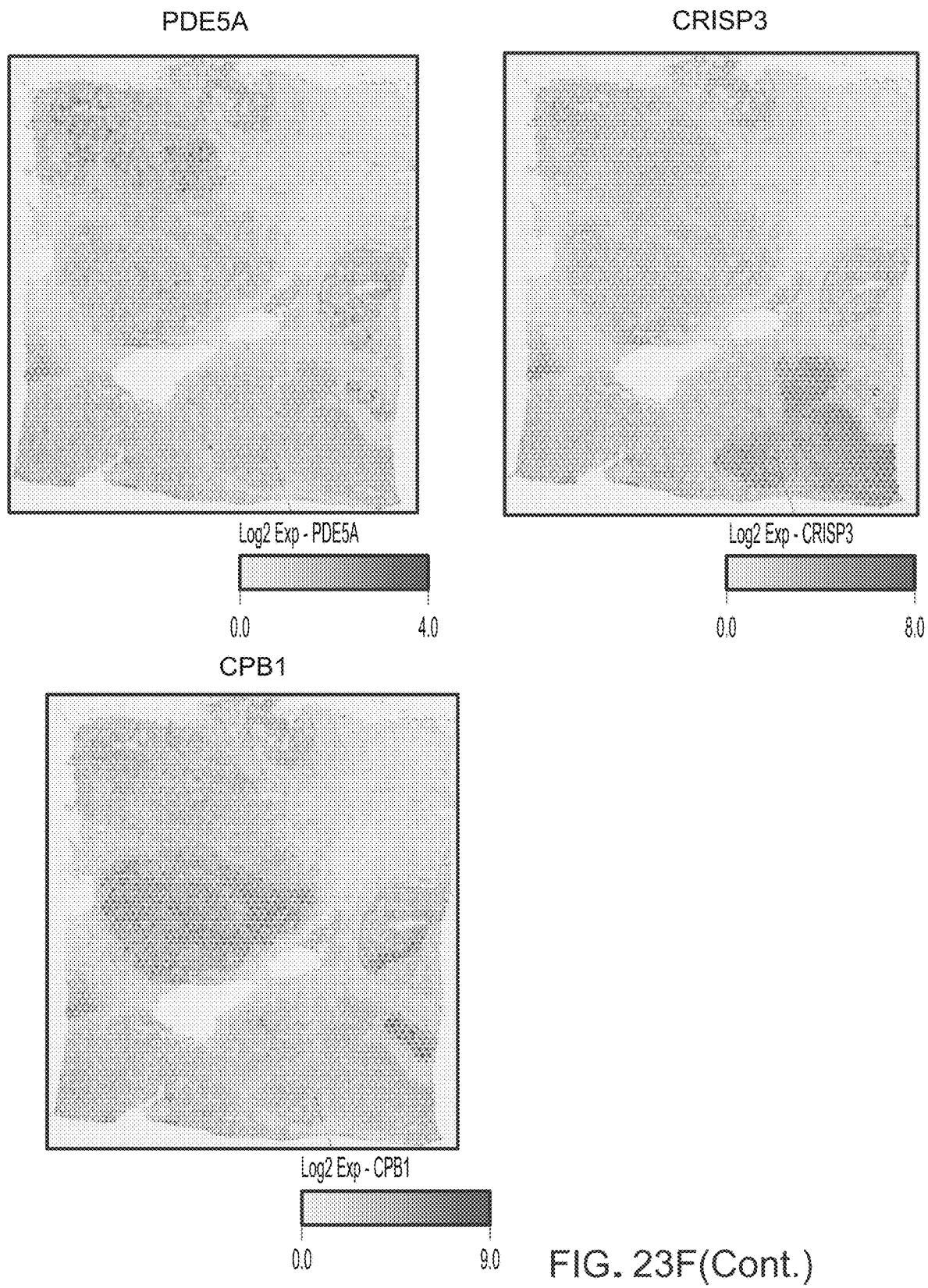
Figure 23G:
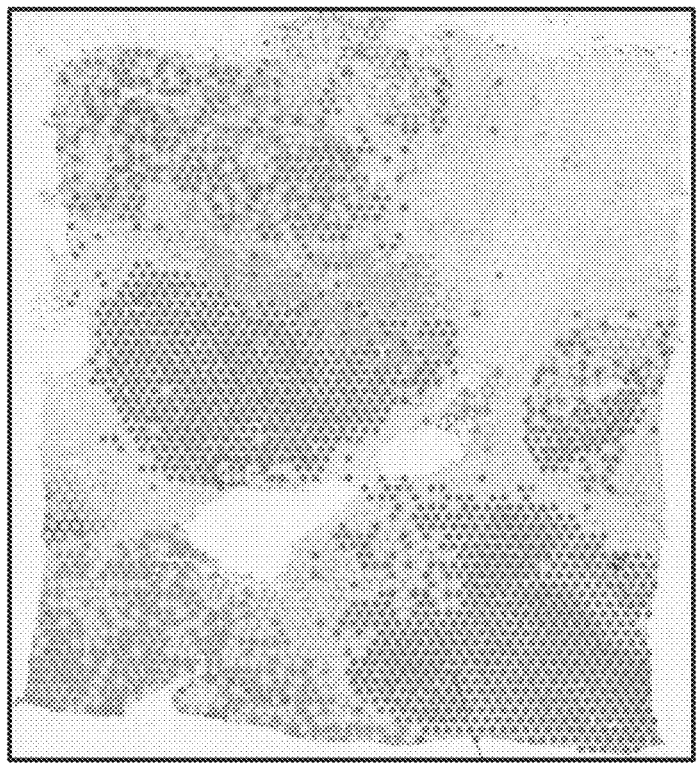
FIG. 23G shows the expression levels of genes of top differentially expressed genes from each of the 9 clusters on a single plot.
Figure 23H:
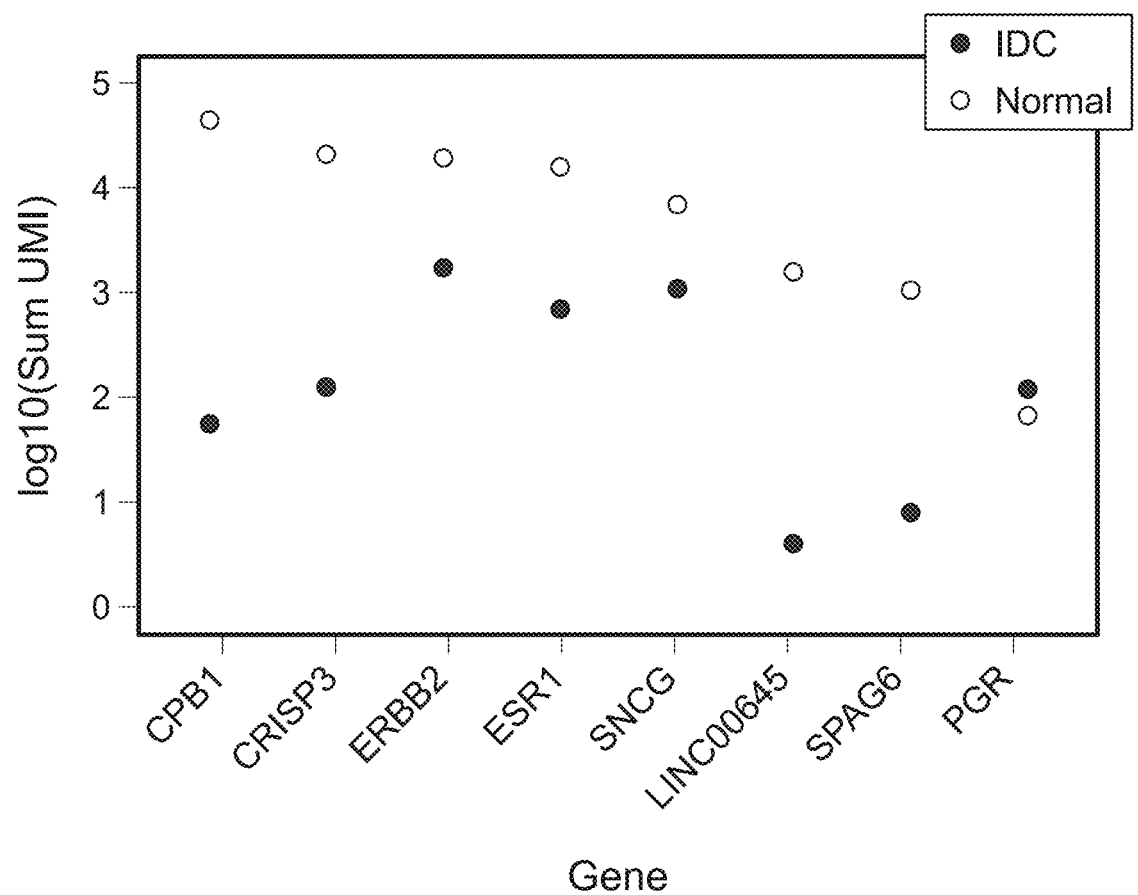
FIG. 23H is a plot of the expression levels of the top differentially expressed genes from each of the 9 clusters in invasive ductal cell carcinoma (IDC) and normal breast tissue.

The expression levels of genes corresponding to human epidermal growth factor receptor 2 (Her2), estrogen receptor (ER), and progesterone receptor (PGR) in the tissue section are shown in FIG. 23E. It is clearly visible that Her2 and ER are highly expressed in the invasive carcinoma and DCIS regions while the expression of PR is absent, consistent with the patient's diagnosis. One of the top differentially expressed genes from each cluster in the invasive carcinoma region was selected (rectangular boxes in FIG. 23D), and its expression levels are located in the tissue as shown in FIG. 23F and overlapped in one plot as shown in FIG. 23G. With the exception of PGR, all of these genes were highly up-regulated in the carcinoma tissue compared to the adjacent normal tissue (FIG. 23H). Analysis revealed that all of these up-regulated genes have implication in cancer progression. Interestingly, in the subset of cluster 3, a long non-coding RNA, of which abnormal expression has recently been implicated in tumor development (see, e.g., Zhang T, et al. Long Non-Coding RNA and Breast Cancer. *Technol Cancer Res* Treat. 2019, 18, 1533033819843889, incorporated herein by reference in its entirety), is one of the top differentially expressed genes. In glioblastoma, LINC00645 promotes epithelial-to-mesenchymal transition by inducing TGF-β (see, e.g., Li, C. et al. Long non-coding RNA linc00645 promotes TGF-β-induced epithelial-mesenchymal transition by regulating miR-205-3p-ZEB1 axis in glioma. *Cell Death & Dis.* 2019, 10, 272, incorporated herein by reference in its entirety).

Figure 23I:
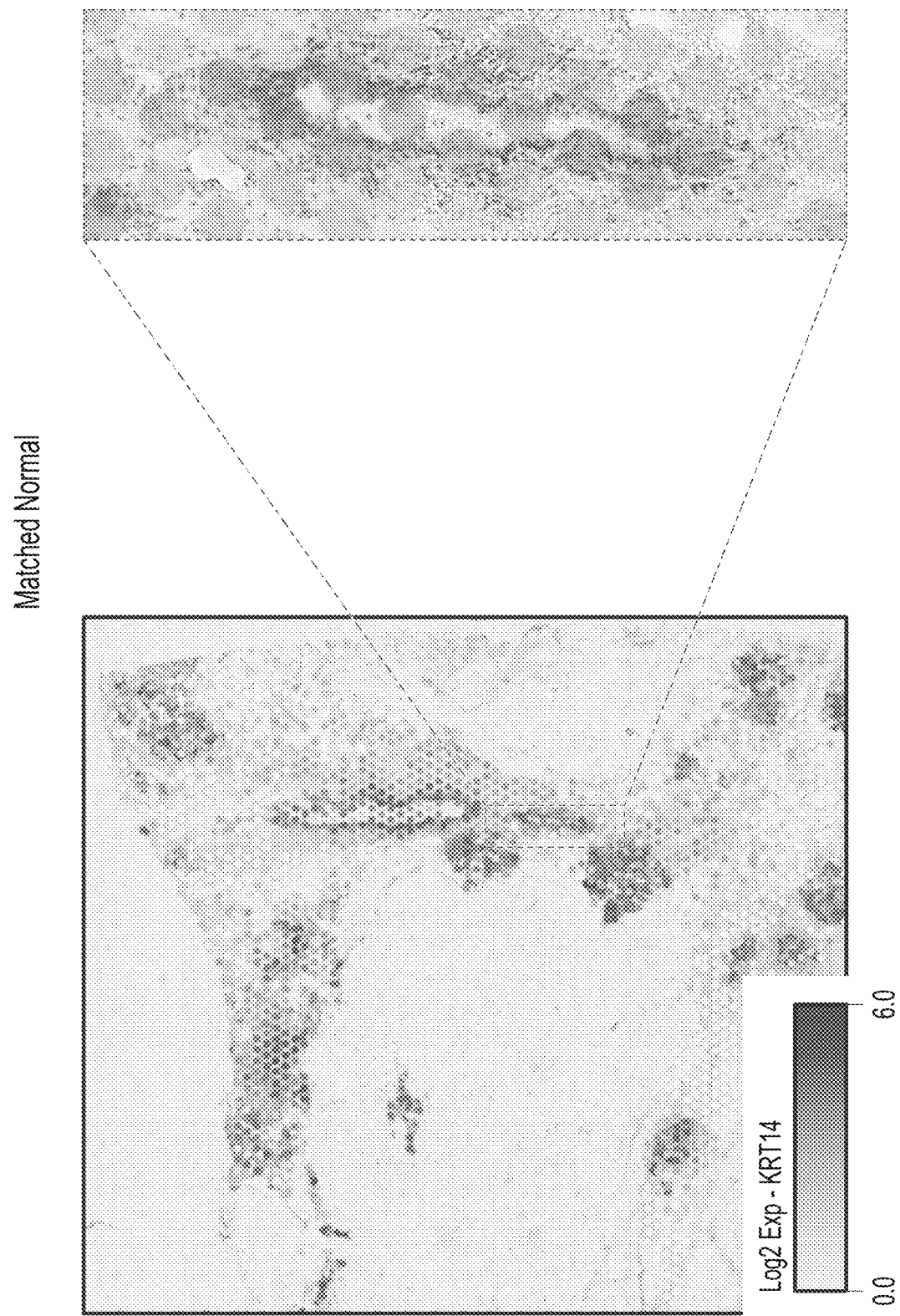
FIG. 23I shows the expression of KRT14 in IDC and match normal tissue.
Figure 23I:
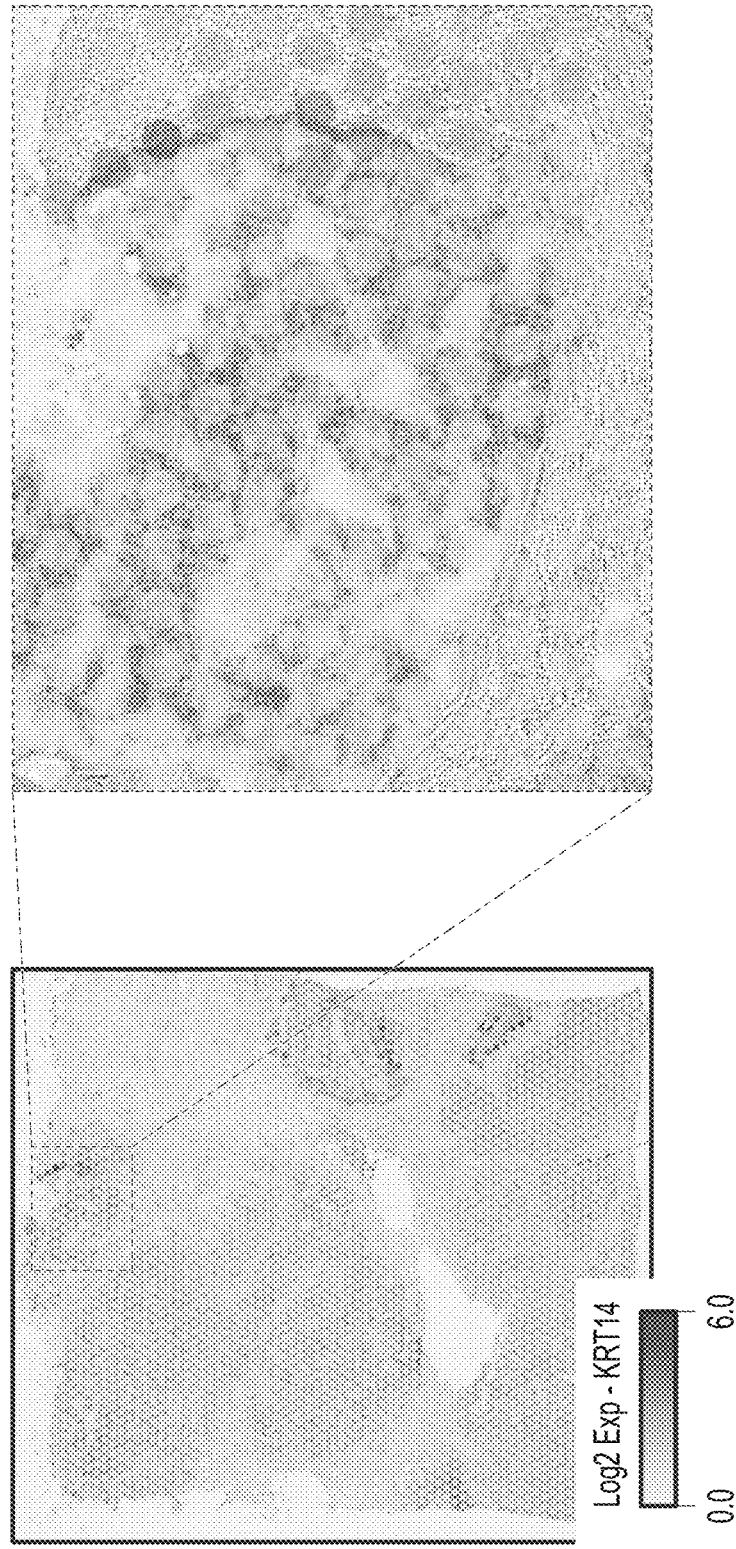
Figure 23J:
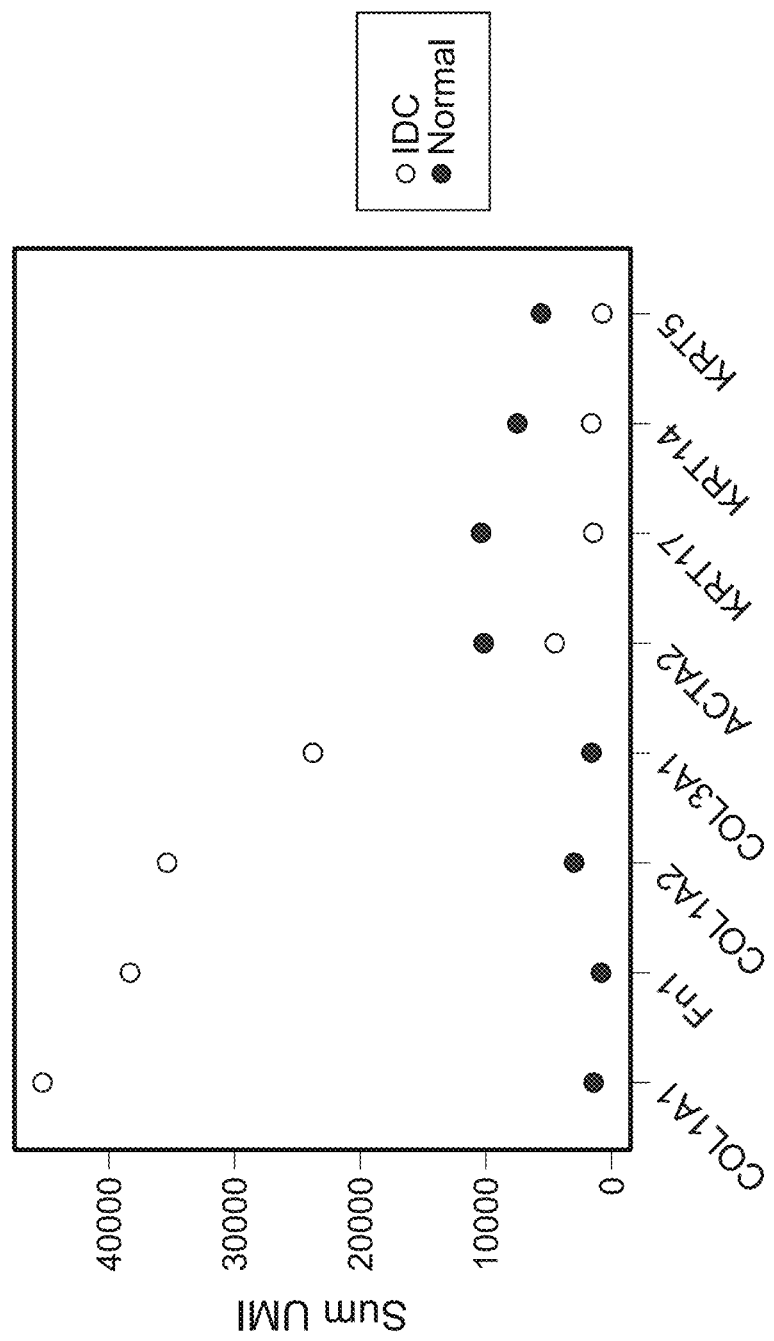
FIG. 23J is a plot of the expression levels of extracellular matrix genes in IDC and normal tissue.

During breast cancer progression, the myoepithelial cells, which continue to surround preinvasive in situ carcinoma, gradually disappear (see, e.g., Gudjonsson, T. et al. Myoepithelial Cells: Their Origin and Function in Breast Morphogenesis and Neoplasia. *J. Mammary Gland Biol. Neoplasia.* 2009, 10, 261, incorporated herein by reference in its entirety). This phenomenon is clearly visualized in FIGS. 23I and 23J where KRT14 (a gene signature of myoepithelial cells) was highly expressed around the lining of the duct in the normal tissue while it was disappearing in the DCIS region in IDC tissue (FIG. 23I). The extracellular matrix genes such as COL1A1 and FN1, key genes associated with invasion and metastasis, were highly upregulated while smooth muscles and basal keratin were down-regulated in IDC (FIG. 23J).

VI. Generation of Spatial Arrays

In some aspects, provided herein are methods for generating arrays for spatial analysis (e.g., spatial arrays). The spatial arrays can have capture probes that can interact with analytes present in a biological sample either directly or indirectly. For example, analytes can be RNA, DNA, protein, lipids, or any other analytes described herein. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain. In some embodiments, a capture probe includes a cleavage domain.

In some embodiments, capture probes are attached to an array feature and an individual array feature can include one or more capture probes. In some embodiments, an individual array feature includes hundreds or thousands of capture probes. In some embodiments, the capture probes are associated with a particular individual feature, where the individual feature contains a capture probe including a spatial barcode unique to the individual feature (e.g., a defined region or location on the array).

In some embodiments, a particular feature can contain capture probes including more than one spatial barcode (e.g., one capture probe at a particular feature can include a non-common spatial barcode that is different than the non-common spatial barcode included in another capture probe at the same particular feature, while both capture probes include a second, common spatial barcode), where the non-common spatial barcodes of the capture probes corresponds to a particular defined region or location on the array. For example, multiple non-common spatial barcode sequences associated with one particular feature on an array can provide a stronger address or attribution to a given location by providing duplicate or independent confirmation of the location. In some embodiments, the multiple non-common spatial barcodes represent increasing specificity of the location of the particular array point As used herein, spatial analyte capture can utilize nucleic acid probes (e.g., capture probes) including spatial barcode sequences, which are immobilized on a substrate (e.g., directly or indirectly) to generate an array. The spatial barcode sequences can correspond to the location of the capture probes on the array. In some embodiments, biological samples, such as tissue sections, are placed onto the array and an analyte from the biological sample is captured. In some embodiments, the captured analyte is a protein. In some embodiments, the captured analyte is a nucleic acid. In some embodiments, the captured analyte is RNA (e.g. messenger RNA). In some embodiments, the captured analyte is DNA (e.g., genomic DNA). In some embodiments, DNA from the biological sample is processed, e.g. fragmented and/or provided with a binding domain that hybridizes to the capture probes on the array. In some embodiments, DNA polymerase extension or ligation reaction is performed in the biological sample on the array. In some embodiments, the probes to which nucleic acids in the biological sample bind are extended using the bound nucleic acid as a template to generate complementary nucleic acid strands, which is immobilized on the surface of the array. In some embodiments, extended probes (e.g., capture probes that are subjected to template-directed nucleic acid polymerization using a captured nucleic acid analyte as a template) carry information about the position of the "captured" analytes in the biological sample, e.g. tissue section. In some embodiments, the extended probes can be released from the surface of the array and analyzed, e.g. sequenced, which results in a "library" of captured nucleic acid analytes that are associated with spatial information. In some embodiments, the sequence data can then be matched to a location in the biological sample, e.g. tissue section. For instance, the biological sample can be visualized or imaged, e.g., stained and/or photographed, before or after analyte capture to facilitate the correlation of the spatial barcode in the capture probe (e.g., an extended capture probe that is associated with a given analyte) with a position within the biological sample and the sequence data can be overlaid on an image of the biological sample, e.g., using a computer, to display the distribution pattern of any analyte of interest across the biological sample. The visualization step is not essential as the tagged analytes can be correlated with a location in the biological sample using other means, e.g., the unique profile of the analytes captured with the same spatial barcode, e.g., at the same position on the array, can enable the analyte to be correlated to a location within the biological sample based on the characteristics of cells or areas of cells within the biological sample (e.g., a tissue section). Any of a variety of analytes can be captured and analyzed in accordance with methods provided herein, including but not limited to RNA, specific sub-types of RNA, proteins, antibodies, genomic DNA, T-cell receptors, small molecules, or other analytes.

Capture Probes via Splint Oligonucleotides

Capture probes for spatial analysis can be generated by different methods. In some embodiments, the capture probe is generated from two or more oligonucleotide sequences. In some embodiments, two or more oligonucleotide sequences are ligated together to generate a capture probe. In some embodiments, capture probe generation can be facilitated by a splint oligonucleotide. In some embodiments, a plurality of oligonucleotides are attached to a feature on the substrate. In some embodiments, the oligonucleotides of the array can be about 20 to about 80 nucleotides long. In some embodiments, the oligonucleotides of the array can be about 30 to about 70 nucleotides long. In some embodiments, the oligonucleotides of the array can be about 40 to about 60 nucleotides long. In some embodiments, the oligonucleotides of the array can be about 45 to about 55 nucleotides long. In some embodiments, the capture probe includes one or more constant sequences (e.g., any of the variety of constant sequences described herein). For example, the oligonucleotide can have a functional domain (e.g. any of the variety of functional domains described herein) and/or a cleavage domain (e.g. any of the variety of cleavage domains described herein).

In some embodiments, a primer can hybridize to an oligonucleotide attached, directly or indirectly to the substrate (e.g., attached to a feature attached to a substrate, e.g., attached via a linker). In some embodiments, the oligonucleotides can be attached, directly or indirectly, to the substrate at the 3' end, resulting in the attaching oligonucleotides having free 5' ends. For example, an array including a plurality of oligonucleotides attached to a substrate at their 3' ends can be contacted with a plurality of primers. In some embodiments, the plurality of primers are complementary or substantially complementary to the oligonucleotides attached to the substrate at their 3' ends, or a portion thereof. In some embodiments the primer can be extended using the oligonucleotide attached to the substrate as a template to generate a first oligonucleotide. In some embodiments, the primer is extended by a reverse transcriptase enzyme. In some embodiments, the primer is extended by a DNA polymerase enzyme. In some embodiments, additional nucleotides can be added (e.g., added by an enzyme) to the end of the first oligonucleotide to generate a 3' overhang. In some embodiments, the enzyme is a template independent polymerase (e.g., any of the variety of template independent polymerases described herein or otherwise known in the art). In some embodiments, the template independent polymerase is terminal nucleotidyl transferase. In some embodiments, the template independent polymerase is a poly(A) polymerase.

In some embodiments, oligonucleotides attached directly or indirectly to the substrate at the 3' end and having free 5' ends can include a sequence that indicates the position of a given oligonucleotide on the substrate. In some embodiments, such a sequence is or can function as a spatial barcode. In some embodiments, different oligonucleotides attached directly or indirectly to the substrate at the 3' end and having free 5' ends can include different sequences that can indicate the position of the different oligonucleotide on the substrate (e.g., the different oligonucleotides can have different spatial barcodes or sequences that act as different spatial barcodes).

In some embodiments, the first oligonucleotide including the 3' overhang generated by the template independent polymerase can be contacted with a splint oligonucleotide. The term "splint oligonucleotide", as used herein, refers to an oligonucleotide that, when hybridized to other polynucleotides, acts as a "splint" to position the polynucleotides (e.g., oligonucleotides) next to one another (e.g., abutting one another) so that they can be ligated together. In some embodiments, the splint oligonucleotide is DNA. In some embodiments, the splint oligonucleotide is RNA. In some embodiments, the splint oligonucleotide includes a nucleotide sequence that is partially complementary to nucleotide sequences from two or more different oligonucleotides. In some embodiments, the splint oligonucleotide is approximately 40 nucleotides in length. In some embodiments, the splint oligonucleotide is between about 10 and about 50 oligonucleotides in length. In some embodiments, the splint oligonucleotide is between about 10 and about 45, about 10 and about 40, about 10 and about 35, about 10 and about 30, about 10 and about 25, or about 10 and about 20 oligonucleotides in length. In some embodiments, the splint oligonucleotide is between about 15 and about 50, about 15 and about 45, about 15 and about 40, about 15 and about 35, about 15 and about 30, about 15 and about 30, or about 15 and about 25 nucleotides in length.

In some embodiments, the splint oligonucleotide provided to the first oligonucleotides can have a sequence that is complementary to the nucleotides of a generated 3' overhang of the first oligonucleotide. A second oligonucleotide can be provided to the array. In some embodiments, the splint oligonucleotide can have another sequence that is complementary or substantially complementary to the second oligonucleotide, or portion thereof. In some embodiments, the splint oligonucleotide can hybridize to both the 3' overhang of the first oligonucleotide and the second oligonucleotide at the same time. In some embodiments, the first oligonucleotide and the second oligonucleotide are ligated together to generate a capture probe. In some embodiments, an RNA ligase is used to ligate the first and second oligonucleotide together. In some embodiments, a DNA ligase is used to ligate the first and second oligonucleotides sequences together. In some embodiments, the DNA ligase is a T4 DNA ligase. In some embodiments the ligase is App ligase.

In some embodiments, the splint oligonucleotide includes a sequence that is complementary to the nucleotides of a generated 3' overhang of the first oligonucleotide, or a portion thereof, and a sequence that is complementary to the second oligonucleotide, or a portion thereof. In some embodiments, the splint oligonucleotide includes a sequence that is perfectly complementary (e.g., is 100% complementary) to the nucleotides of a generated 3' overhang of the first oligonucleotide, or a portion thereof, and/or a sequence that is perfectly complementary to the second oligonucleotide, or a portion thereof. In some embodiments, the splint oligonucleotide includes a sequence that is not perfectly complementary (e.g., is not 100% complementary) to the nucleotides of a generated 3' overhang of the first oligonucleotide, or a portion thereof, and/or a sequence that is not perfectly complementary to the second oligonucleotide, or a portion thereof. In some embodiments, the splint oligonucleotide includes a sequence that is at least 70%, 75%, 80%, 85%, 90%, 95%, 96%, 97%, 98%, or 99% complementary to the nucleotides of a generated 3' overhang of the first oligonucleotide, or a portion thereof, and/or a sequence that is complementary to the second oligonucleotide, or a portion thereof. In some embodiments, the splint oligonucleotide includes a sequence that is perfectly complementary (e.g., is 100% complementary) to the nucleotides of a generated 3' overhang of the first oligonucleotide, or a portion thereof, but is not perfectly complementary to a sequence that is complementary to the second oligonucleotide, or a portion thereof. In some embodiments, the splint oligonucleotide includes a sequence that is not perfectly complementary (e.g., is not 100% complementary) to the nucleotides of a generated 3' overhang of the first oligonucleotide, or a portion thereof, but is perfectly complementary to a sequence that is complementary to the second oligonucleotide, or a portion thereof. So long as the splint oligonucleotide is capable of hybridizing to the nucleotides of a generated 3' overhang of the first oligonucleotide, or a portion thereof, and to a sequence that is complementary to the second oligonucleotide, or a portion thereof, the splint oligonucleotide need not have a sequence that is perfectly complementary to either the generated 3' overhang of the first oligonucleotide or to the second oligonucleotide. The second oligonucleotide can be about 20 to about 80 nucleotides long. In some embodiments, the second oligonucleotide can be about 30 to about 70 nucleotides long. In some embodiments, the second oligonucleotide can be about 40 to about 60 nucleotides long. In some embodiments, the second oligonucleotide can be about 45 to about 55 nucleotides long. The second oligonucleotide can include various domains. For example, the second oligonucleotide can include one or more of a sequence complementary to the splint oligonucleotide, a functional sequence, a unique molecular identifier, and a capture domain (e.g., any of the variety of functional sequences, a unique molecular identifiers, and/or a capture domains described herein). In some embodiments of any of the methods described herein, the capture probes can include a unique molecular identifier. In some embodiments of any of the methods described herein, a unique molecular identifier can be about or at least 5, 6, 7, 8, 9, 10, 11, 12, 13, 14, 15, 16, 17, 18, 19, 20, 25, 30, 35, 40, 45, or 50 nucleotides.

In some embodiments, the capture domain can include a poly(dT) sequence. In some embodiments, the poly(dT) sequence can interact (e.g., hybridize) with poly(A) sequences of analytes (e.g., mRNA). In some embodiments, the capture domain can include a gene specific sequence.

Capture Probes from Hydrogel Arrays

In some aspects, provided herein are methods for preparing a high-density spatially barcoded array, e.g., a high-diversity and high-density spatially barcoded array. For example, methods for preparing a high-density spatially barcoded array can include contacting an array including one or more pluralities of first oligonucleotides with a hydrogel including one or more pluralities of second oligonucleotides. In some embodiments, the first oligonucleotide, the second oligonucleotide, or both, can have include a capture domain. The first oligonucleotide and the second oligonucleotide can be attached to generate capture probes. The hydrogel containing the capture probes can be reduced in size (e.g., shrunk). In some embodiments, methods for preparing a high-density spatially barcoded array can include contacting an array including one or more pluralities of first oligonucleotides with a hydrogel including one or more pluralities of second oligonucleotides; attaching a first oligonucleotide to a second oligonucleotide to generate a capture probe including a capture domain; reducing the size of the hydrogel including the capture probes by dehydration (e.g., removing water), forming a shrunken hydrogel array including the one or more pluralities of capture probes and thus generating a high-density spatially barcoded array (e.g., spatial array). In some embodiments, a capture probe is any of the variety of capture probes described herein. In some embodiments, the one or more pluralities of capture probes are immobilized in the hydrogel.

The term "partition," as used herein, can be a verb or a noun. When used as a verb (e.g., "to partition," or "partitioning"), the term generally refers to the fractionation (subdivision) of a species or sample (e.g., a polynucleotide) such that one fraction (or subdivision) is sequestered from another. Each sequestered section is referred to using the noun "partition." In some embodiments, a partition maintains separation of its own contents from the contents of other partitions. A partition may be any suitable area in which one fraction of a sample is separated or sequestered from another. In some embodiments, a hydrogel can include one or more partitions of a species or sample (e.g., a polynucleotide), wherein the hydrogel matrix maintains the separation of the contents of one partition from the contents of other partitions. In some embodiments, a partition has defined dimensions.

In some embodiments, the one or more pluralities of immobilized first oligonucleotides are partitioned. In some embodiments, the one or more pluralities of immobilized first oligonucleotides are partitioned into a plurality of first oligonucleotide partitions. In some embodiments, a partitioned plurality of immobilized first oligonucleotides is different from another partitioned plurality of immobilized first oligonucleotides. In some embodiments, a partitioned plurality of immobilized first oligonucleotides are partitioned into features on a substrate.

In some embodiments, one or more first pluralities of first oligonucleotides include a barcode sequence (e.g., spatial barcode). In some embodiments, one or more pluralities of first oligonucleotides include a spatial barcode sequence different from the spatial barcode sequence of one or more other pluralities of first oligonucleotides. In some embodiments, one or more first oligonucleotide partitions (e.g., a population) include a plurality of immobilized first oligonucleotides including a spatial barcode sequence different from the spatial barcode sequence of the plurality of immobilized first oligonucleotides of one or more other first oligonucleotide partitions. In some embodiments, a first oligonucleotide of a population of first oligonucleotides in one or more first oligonucleotide partitions includes a spatial barcode. In some embodiments, the first oligonucleotide of a population of first oligonucleotides in one or more first oligonucleotide partitions includes a spatial barcode that is different from the spatial barcode of a first oligonucleotide of a population of first oligonucleotides in another first oligonucleotide partition. In some embodiments, a spatial barcode of the first oligonucleotide of a population of first oligonucleotides in one or more first oligonucleotide partitions is different from a spatial barcode of a second oligonucleotide of a population of second oligonucleotides in one or more second oligonucleotide partitions. In some embodiments, a first oligonucleotide partition comprises a first population of first oligonucleotides comprising a spatial barcode that is different from a spatial barcode of a second population of first oligonucleotides in another first oligonucleotide partition.

In some embodiments, the one or more pluralities of second oligonucleotides are immobilized in the hydrogel. In some embodiments, the immobilized second oligonucleotides are partitioned. In some embodiments, the immobilized second oligonucleotides are partitioned into a first population of immobilized second oligonucleotides (e.g., in a partition). In some embodiments, one or more immobilized second oligonucleotide partitions include another population of immobilized second oligonucleotides different from the first population of immobilized second oligonucleotide partitions. In some embodiments, the first immobilized second oligonucleotide of a partitioned population (e.g., a first population) of immobilized second oligonucleotides is different from a second immobilized second oligonucleotide of another partitioned population of immobilized second oligonucleotides. In some embodiments, the first immobilized second oligonucleotide, the second immobilized second oligonucleotide, or both include a spatial barcode. In some embodiments, the first immobilized second oligonucleotide of a partitioned population of immobilized second oligonucleotides includes a spatial barcode that is different from a spatial barcode of the second immobilized second oligonucleotide of another partitioned population of immobilized second oligonucleotides.

In some embodiments, one or more pluralities of second oligonucleotides include a spatial barcode sequence. In some embodiments, one or more pluralities of second oligonucleotides include a spatial barcode sequence different from the spatial barcode sequence of one or more pluralities of second oligonucleotides. In some embodiments, the spatial barcode sequence of one or more pluralities of first oligonucleotides is different from the spatial barcode sequence of one or more pluralities of second oligonucleotides. In some embodiments, one or more second oligonucleotide partitions include a plurality of second oligonucleotides including a spatial barcode sequence different from the spatial barcode sequence of the plurality of second oligonucleotides of one or more second oligonucleotide partitions.

In some embodiments, each first oligonucleotide from the plurality of first oligonucleotides includes a spatial barcode. In some embodiments, each first oligonucleotide from the plurality of first oligonucleotides includes a unique molecular identifier. In some embodiments, each first oligonucleotide from the plurality of first oligonucleotides includes a cleavage domain, a spatial barcode, a unique molecular identifier, and a capture domain. In some embodiments, at least one first oligonucleotide from the plurality of first oligonucleotides includes a spatial barcode. In some embodiments, at least one first oligonucleotide from the plurality of first oligonucleotides includes a unique molecular identifier. In some embodiments, at least one first oligonucleotide from the plurality of first oligonucleotides includes a cleavage domain, a spatial barcode, a unique molecular identifier, and a capture domain.

A "capture probe" as used herein can refer to a capture probe that is a product of attaching a first oligonucleotide to second oligonucleotide is a hydrogel. For example, one or more domains of the first oligonucleotide can be attached to one or more domains of a second oligonucleotide (e.g., a second oligonucleotide in a hydrogel). "Attaching" the first and second oligonucleotide in a hydrogel can be accomplished by any suitable means described herein. For example, a first oligonucleotide can be ligated to an end of a second oligonucleotide. As another example, PCR can be used to attach one or more domains of a first oligonucleotide to one or more domains of a second oligonucleotide (e.g., a second oligonucleotide in a hydrogel).

In some embodiments, methods provided herein that include attaching a first oligonucleotide to second oligonucleotide is a hydrogel can be used to generate a spatial array of relatively high complexity. In some embodiments, a plurality of first oligonucleotides (e.g., partitioned first oligonucleotides) is attached to a plurality of second oligonucleotides (e.g., partitioned second oligonucleotides) to generate a plurality of capture probes such that the plurality of capture probes exhibits a high complexity (e.g., a high sequence complexity) relative to the complexity of the plurality of first and second oligonucleotides. For example, a plurality of first oligonucleotides can have a plurality of first partial spatial barcodes, and a plurality of second oligonucleotides can have a plurality of second partial spatial barcodes. By attaching the plurality of first and second oligonucleotides to each other in a combinatorial fashion, a plurality of spatial barcodes can be generated, which plurality of generated spatial barcodes can have a higher sequence complexity than the sequence complexity of either of the first or second partial spatial barcodes. As a non-limiting example, if a plurality of first oligonucleotides includes a plurality of M first partial spatial barcodes (e.g., the plurality of first oligonucleotides can be partitioned such that each of the M first partial spatial barcodes is in a different partition) and a plurality of second oligonucleotides includes a plurality of N second partial spatial barcodes (e.g., the plurality of second oligonucleotides can be partitioned such that each of the N second partial spatial barcodes is in a different partition), the plurality of first and second oligonucleotides can be attached in a combinatorial fashion to generate a plurality of spatial barcodes that includes M×N spatial barcodes.

In some embodiments, attaching members of the one or more pluralities of first oligonucleotides to members of the one or more pluralities of second oligonucleotides to form one or more pluralities of capture probes includes using a polymerase chain reaction (PCR). In some embodiments, the hydrogel includes PCR reagents such as a DNA polymerase, a plurality of primers, and a plurality of nucleotides. In some embodiments, members of the plurality of features are amplified (see, e.g., Mitra and Church, *Nucleic Acids Res.* 15; 27(24):e34 (1999) which is herein incorporated by reference in its entirety).

In some embodiments, chemical ligation can be used to ligate two or more oligonucleotides (e.g., a first oligonucleotide and a second oligonucleotide from a hydrogel as described herein). In some embodiments, chemical ligation involves the use of condensing reagents. In some embodiments, condensing reagents are utilized to activate a phosphate group. In some embodiments, condensing reagents may be one or more of 1-25 ethyl-3-(3-dimethylaminopropyl) carbodiimide (EDCI), cyanogen bromide, imidazole derivatives, and 1-hydroxybenzotriazole (HOAt). In some embodiments, functional group pairs selected from one or more of a nucleophilic group and an electrophilic group, or an alkyne and an azide group are used for chemical ligation. In some embodiments, chemical ligation of two or more oligonucleotides requires a template strand that is complementary to the oligonucleotides to be ligated (e.g., a splint oligonucleotide). In some embodiments, the chemical ligation process is similar to oligonucleotide synthesis.

In some embodiments, not all of the domains of a first oligonucleotide are attached to a second oligonucleotide to form a capture probe. For example, a capture probe can include 1, 2, 3, 4, or 5 domains of the original first oligonucleotide. In some embodiments, all the domains of the first oligonucleotide are attached to the second oligonucleotide. For example, the capture probe includes all the domains of the first oligonucleotide.

In some embodiments, members of the one or more pluralities of the first oligonucleotide are cross-linked to a hydrogel.

As used herein "shrinking" or "reducing the size of" a hydrogel refers to any process causing the hydrogel to physically contract and/or the size of the hydrogel to decrease in volume. For example, the scaffold of the gel may shrink or "implode" upon solvent removal (see, e.g., Long and Williams. *Science.* 2018; 362(6420):1244-1245, and Oran et al. *Science.* 2018; 362(6420):1281-1285; each of which is incorporated herein by reference in its entirety). As another example, the process to shrink or reduce the size of a hydrogel may be one that removes water (e.g., a dehydrating process) from the hydrogel. There are many methods known to one of skill in the art for shrinking or reducing the size of a hydrogel. Non-limiting examples of a method to shrink or reduce the size of a hydrogel include exposing the hydrogel to one or more of: a dehydrating solvent, a salt, heat, a vacuum, lyophilization, desiccation, filtration, and air-drying.

In some embodiments, the removal of water includes a dehydrating solvent. Non-limiting examples of a dehydrating solvent include a ketone (such as methyl ethyl ketone (MEK)), isopropanol (IPA), acetone, 1-butanol, methanol (MeOH), dimethyl sulfoxide (DMSO), glycerol, propylene glycol, ethylene glycol, ethanol, (k) 1,4-dioxane, propylene carbonate, furfuryl alcohol, N,N-dimethylformamide (DMF), acetonitrile, and an aldehyde (such as formaldehyde or glutaraldehyde). In some embodiments, the solvent includes at least one of an alcohol, a ketone, an aldehyde, acetonitrile, and a combination thereof. In some embodiments, the solvent includes a solvent selected from the group consisting of: glycerol, ethanol, acetonitrile, acetone, 2-propanol, and a combination thereof.

In some embodiments, the removal of water includes the use of a salt. In some embodiments, the salt includes an inorganic salt. Non-limiting examples of salts that may be used to shrink a hydrogel include inorganic salts such as aluminum, ammonium, barium, beryllium, calcium, cesium, lithium, magnesium, potassium, rubidium, sodium, and strontium salts. Further non-limiting examples of inorganic salts include sodium chloride, potassium chloride, lithium chloride, cesium chloride, sodium fluoride, sodium bromide, sodium iodide, sodium nitrite, potassium sulfate, potassium nitrate, potassium carbonate, potassium bicarbonate, sodium sulfate, sodium nitrate, sodium carbonate, sodium bicarbonate, calcium sulfate, copper oxychloride, calcium chloride, calcium carbonate, calcium bicarbonate, magnesium sulfate, magnesium nitrate, magnesium chloride, magnesium carbonate, magnesium bicarbonate, ammonium sulfate, ammonium chloride, ammonium nitrate, ammonium carbonate, ammonium bicarbonate, trisodium phosphate, tripotassium phosphate, calcium phosphate, copper(II) sulfate, sodium sulfide, potassium sulfide, calcium sulfide, potassium permanganate, iron(II) chloride, iron(III) chloride, iron (2+)

sulfate, iron(III) sulfate, iron(II) nitrate, iron(III) nitrate, manganese(II) chloride, manganese(III) chloride, manganese(II) sulfate, manganese(II) nitrate, zinc chloride, zinc nitrate, zinc sulfate, ammonium orthomolybdate, monopotassium phosphate, nickel(II) sulfate, nickel(II) nitrate, sodium metavanadate, sodium paravanadate, potassium dichromate, ammonium dichromate, antipyonin, ammonium nitrite, potassium fluoride, sodium fluoride, ammonium fluoride, calcium fluoride, chrome alum, potassium alum, potassium iodide, sodium hypochlorite, tin(II) sulfate, tin(II) nitrate, gold selenite, dicesium chromate, potassium perchlorate, calcium perchlorate, aluminium sulphate, lead(II) bisulfate, barium phosphate, barium hydrogen orthophosphate, barium dihydrogen phosphate, silver dichromate, potassium bromate, sodium bromate, sodium iodate, sodium silicate, diammonium phosphate, ammonium phosphate, ammonium dihydrogen phosphate, chromium orthophosphate, copper(II) chloride, copper(I) chloride, sodium tetrametaphosphate, potassium heptafluoroniobate, zinc phosphate, sodium sulfite, copper(I) nitrate, copper(II) nitrate, potassium silicate, copper(II) carbonate basic, copper(II) carbonate salts of acrylic acid and sulfopropyl acrylate.

In some embodiments, the removal of water includes an acid. In some embodiments, the hydrogel is exposed to a different pH environment. For example, the hydrogel can be exposed to an acidic pH or a basic pH. In some embodiments, the hydrogel is exposed to a pH of less than about 6.5, e.g., a pH of about 6, about 5.5, about 5, about 4.5, about 4, about 3.5, about 3, about 2.5, about 2, about 1.5, or about 1. In some embodiments, the hydrogel is exposed to a pH of greater than about 7.5, e.g., a pH of about 8, about 8.5, about 9, about 9.5, about 10, about 10.5, about 11, about 11.5, about 12, about 12.5, about 13, about 13.5, or about 14.

In some embodiments, the removal of water includes a dehydrating process such as heat, a vacuum, lyophilization, desiccation, filtration, and air-drying. In some embodiments, the hydrogel is exposed to an increased temperature, e.g., a higher temperature than about room temperature. For example, a temperature of about 37° C., 38 15° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. 60° C., 61° C., 62° C., 63° C., 64° C., 65° C., 66° C., 67° C., 68° C., 69° C., or 70° C., or higher. As another example, the hydrogel is exposed to an increase in temperature from about 37° C., 38° C., 39° C., 40° C., 41° C., 42° C., 43° C., 44° C., 45° C., 46° C., 47° C., 48° C., or 49° C. to about 50° C., 51 20° C., 52° C., 53° C., 54° C., 55° C., 56° C., 57° C., 58° C., 59° C. 60° C., 61° C., 62° C., 63° C., 64° C., 65° C., 66° C., 67° C., 68° C., 69° C., or 70° C., or higher).

In some embodiments, more than one method to shrink or reduce the size of a hydrogel can be used. For example, a hydrogel can be exposed to an acid and subsequently dehydrated by another method such as heat, a vacuum, lyophilization, desiccation, filtration, or a combination thereof.

In some embodiments, the hydrogel can further include a cross-linking agent. The cross linking agent may help stabilize the hydrogel and/or modulate the extent the hydrogel shrinks. Non-limiting examples of a cross-linking agent include disuccinimidyl suberate (DSS), dimethylsuberimidate (DMS), formalin, dimethyladipimidate (DMA), dithiobis(-succinimidyl propionate) (DSP), disuccinimidyl tartrate (DST), and ethylene glycol bis(succinimidyl succinate) (EGS). In some embodiments, the shrunken hydrogel is at least about 2-fold smaller in a linear dimension (e.g., along one axis) than the pre-shrunk hydrogel. For example, at least about 2.5, about 3, about 4, about 5, about 6, about 7, about 8, about 9, about 10, or more fold smaller in a linear dimension than the pre-shrunk hydrogel. In some embodiments, a shrunken hydrogel is about 2 to about 10 fold smaller in a linear dimension than the pre-shrunk hydrogel. For example, about 2 to about 3, about 2 to about 4, about 2 to about 5, about 2 to about 6, about 2 to about 7, about 2 to about 8, about 2 to about 9, about 9 to about 10, about 8 to about 10, about 7 to about 10, about 6 to about 10, about 5 to about 10, about 4 to about 10, or about 3 to about 10. In some embodiments, a shrunken hydrogel is about 2 to about 4, about 3 to about 5, about 4 to about 6, about 5 to about 7, about 6 to about 8 fold smaller in a linear dimension than the pre-shrunk hydrogel. In some embodiments, a shrunken hydrogel is about 2, about 3, about 4, about 5, about 6, about 7, about 8, about 9, or about 10 fold smaller in a linear dimension than the pre-shrunk hydrogel. In some embodiments, the shrunken hydrogel is about 2 to about 10 fold smaller in a linear dimension than the size of the hydrogel prior to reducing the size of the pre-shrunk hydrogel.

In some embodiments, the size of the hydrogel is reduced along more than one axes, e.g., along 2 or 3 axes. In some embodiments, each axis intersects each other axis at 90 degrees. In some embodiments, the size of the hydrogel along the first axis is about 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the size of the hydrogel along the second axis is about 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the size of the hydrogel along the third axis is about 2 to about 10 or more fold smaller than the preshrunk hydrogel, e.g., about 2, about 3, about 4, about 5, about 6, about 7, about 8, about 9, about 10 or more fold smaller than the pre-shrunk hydrogel. In some embodiments, the reduction in the size of the hydrogel is isometric.

In some embodiments, a hydrogel is prepared from hydrogel subunits including at least one of: acrylamide, bisacrylamide, a poly(ethylene glycol), a polyaliphatic polyurethane, a polyether polyurethane, a polyester polyurethane, a polyethylene copolymer, a polyamide, a polyvinyl alcohol, polypropylene glycol, polytetramethylene oxide, polyvinyl pyrrolidone, polyacrylamide, poly(hydroxyethyl acrylate), poly(hydroxyethyl methacrylate), collagen, hyaluronic acid, chitosan, dextran, agarose, gelatin, alginate, a protein polymer, methylcellulose, and any combination thereof.

In some embodiments, the size of a hydrogel including capture probes is reduced, thus increasing the density of the capture probes. In some embodiments, the volume of a partition of members of the plurality of capture probes in a hydrogel is reduced when the size of the hydrogel is reduced.

In some embodiments, a high-density spatially barcoded array (e.g., a high density spatially barcoded array as described herein) can be used for spatial analysis of analytes present in the biological sample. For example, methods for spatially determining the location of an analyte or a plurality of analytes in a biological sample can include providing a high-density spatially barcoded array as described herein; contacting the biological sample with the high-density spatially barcoded array under conditions such that one or more analytes present in the biological sample are captured by one or more capture probes of the array; and determining the spatial location of the captured analytes by any of the methods described herein.

Methods for Spatial Analysis of Analytes

In some embodiments, a high-density spatially barcoded array (e.g., a high density spatially barcoded array as described herein) can be used for spatial analysis of analytes present in a biological sample. For example, methods for spatially determining a location of an analyte or a plurality of analytes in a biological sample can include providing a high-density spatially barcoded array as described herein; contacting the biological sample with the high-density spatially barcoded array under conditions such that one or more analytes present in the biological sample are captured by one or more capture probes of the array; and determining the spatial location of the captured analyte(s).

In some aspects, provided herein methods for building an array (e.g., a spatial array, e.g. a high-density spatial array). In some embodiments, methods of generating an array comprise: (a) providing an substrate including a plurality of features immobilized on the substrate, wherein the features (e.g., each feature or a substantial portion thereof) comprises a plurality of first oligonucleotides, and wherein the first oligonucleotides (e.g., each first nucleotide or a substantial portion thereof) include a first spatial barcode (e.g., a first partial spatial barcode); (b) selecting one or more first oligonucleotides from the plurality of first oligonucleotides; (c) delivering a second oligonucleotide to the one or more selected first oligonucleotides, wherein the second oligonucleotide includes a second spatial barcode (e.g., a second partial spatial barcode) and a capture domain; and (d) attaching the second oligonucleotide to the one or more selected first oligonucleotides, thereby generating one or more capture probes including the first spatial barcode and the second spatial barcode, thereby generating an array.

In some embodiments, each feature of the plurality of features is associated with one of a number of different first spatial barcodes. In some embodiments, each second oligonucleotide is associated with one of a number of different second barcodes.

In some embodiments, step (d) includes ligating the second oligonucleotide to the one or more selected first oligonucleotides. In some embodiments, the method includes ligating the second oligonucleotide to the one or more selected first oligonucleotides using a ligase. In some embodiments, the second oligonucleotide is attached to the one or more selected first oligonucleotides by a chemical coupling reaction. In some embodiments, one or more of (e.g., each of) the first oligonucleotides includes a 3' end that is masked by a protective group (e.g., a photocleavable protective group). In some embodiments, the method includes removing the photocleavable protective group from the one or more selected first oligonucleotides prior to delivering a second oligonucleotide to the one or more selected first oligonucleotides. In some embodiments, the protective group is a photocleavable protective group (e.g., any of the variety of a photocleavable protective groups described herein or otherwise known in the art). In some embodiments, the protective group is removed by exposing the one or more selected first oligonucleotides to light. In some embodiments, the protective group coupled to the one or more selected first oligonucleotides is a photomask (e.g., any of the variety of a photomasks described herein or otherwise known in the art). In some embodiments, the photomask is removed by exposing the one or more selected first oligonucleotides to light.

In some embodiments, the selected first oligonucleotide(s) are separated from the other first oligonucleotides of the plurality by one or more physical barriers, wherein the one or more physical barriers form one or more chambers, and wherein the second oligonucleotide is delivered to the one or more chambers including the one or more selected first oligonucleotides. In some embodiments, the one or more physical barriers include a hydrophobic surface. In some embodiments, the one or more physical barriers include one or more chamber walls having a tapered end. In some embodiments, the selected first oligonucleotide(s) are separated from the other first oligonucleotides of the plurality, but are not separated by one or more physical barriers. For example, the selected first oligonucleotide(s) can be separated from the other first oligonucleotides of the plurality simply by virtue of their spatial locations. In some embodiments, the second oligonucleotide includes a unique molecular identifier. In some embodiments, the second oligonucleotide includes a 3' end that is masked. In some embodiments, a free 3'-OH group on the capture probes is created.

In some embodiments, methods of generating an array comprise: (a) providing an array including two or more partitions, wherein the partitions (e.g., each partition or a substantial portion thereof) includes a plurality of features immobilized on a substrate, wherein the features (e.g., each feature or a substantial portion thereof) includes a plurality of first oligonucleotides, and wherein the first oligonucleotides (e.g., each first oligonucleotide or a substantial portion thereof) include a first spatial barcode (e.g., a first partial spatial barcode); (b) delivering a second oligonucleotide to a first partition, wherein the second oligonucleotide includes a second barcode (e.g., a second partial spatial barcode) and a capture domain; and (c) attaching the second oligonucleotide to one or more first oligonucleotides in the first partition, thereby generating one or more capture probes including the first spatial barcode and the second spatial barcode in the first partition, thereby generating an array.

In some embodiments, methods provided herein further include: (d) delivering a third oligonucleotide to a second partition of the two or more partitions, wherein the third oligonucleotide includes a third spatial barcode (e.g., a third partial spatial barcode); and (e) attaching the third oligonucleotide to a fourth oligonucleotide in the second partition, wherein the fourth oligonucleotide includes the first spatial barcode (e.g., the first partial spatial barcode), thereby generating capture probes including the first spatial barcode and the third spatial barcode in the second partition. In some embodiments, methods provided herein further include: (d) delivering a third oligonucleotide to a second partition, wherein the third oligonucleotide includes a third spatial barcode (e.g., a third partial spatial barcode); and (e) attaching the third oligonucleotide to a fourth oligonucleotide in the second partition, wherein the fourth oligonucleotide includes the fourth spatial barcode (e.g., a fourth partial spatial barcode) thereby generating capture probes including the fourth spatial barcode and the third spatial barcode in the second partition.

In some embodiments, the two or more partitions are separated by one or more physical barriers. In some embodiments, the one or more physical barriers are printed on the substrate. In some embodiments, the one or more physical barriers form one or more chambers including one or more chamber walls. In some embodiments, the one or more chamber walls include a hydrophobic surface. In some embodiments, the one or more chamber walls include a tapered end in contact with the substrate. In some embodiments, the second oligonucleotide is delivered using a microfluidic device.

Chemical Ligation of Oligonucleotides

In some embodiments, chemical ligation can be used to ligate two or more oligonucleotides. In some embodiments, chemical ligation involves the use of condensing reagents. In some embodiments, condensing reagents are utilized to activate a phosphate group. In some embodiments, condensing reagents may be one or more of 1-ethyl-3-(3-dimethylaminopropyl) carbodiimide (EDCI), cyanogen bromide, imidazole derivatives, and 1-hydroxybenzotriazole (HOAt). In some embodiments, functional group pairs selected from one or more of a nucleophilic group and an electrophilic group, or an alkyne and an azide group are used for chemical ligation. In some embodiments, chemical ligation of two or more oligonucleotides requires a template strand that is complementary to the oligonucleotides to be ligated (e.g., a splint oligonucleotide). In some embodiments, the chemical ligation process is similar to oligonucleotide synthesis.

Photocleavable Protective Groups

In some embodiments, a photocleavable protective group (e.g. any photocleavable, photoremovable, photoreleasable, photoactivatable, or photosensitive protective group described herein or known in the art) can be coupled to one or both ends of an oligonucleotide on a substrate, a surface probe (e.g. any of the surface probes described herein), or a capture probe (e.g., any of the capture probes described herein). In some embodiments, a photocleavable protective group is a chemical modification to a molecule that can be removed with light. In some embodiments, the photocleavable protective group (PPG) is at least one of a nitrobenzyl-based PPG, a carbonyl-based PPG, or a benzyl-based PPG. In some embodiments, the photocleavable protective group is removed from one or more surface probes by exposing the one or more surface probes to a light.

Shallow Sequencing

As used herein, the coverage or depth of sequencing is the number of unique reads that include a given nucleotide in a reconstructed sequence. As used herein, shallow sequencing is a small or low number of unique reads of an identified analyte. In some embodiments, shallow sequencing can be performed to identify a spatial region of interest. In some embodiments, shallow sequencing can be performed on an entire biological sample. In some embodiments, shallow sequencing can be performed on an identified region of a biological sample (e.g., a region of interest). In some embodiments, shallow sequencing can be performed after identifying and/or selecting a region of a biological sample by some other method (e.g., immunostaining).

Target Spatial Barcodes

In some embodiments, a target spatial barcode (e.g., sometimes referred to herein as a target barcode sequence) is a barcode sequence corresponding to a spatial region of interest. In some embodiments, a target spatial barcode is or includes a spatial barcode. In some embodiments, a target spatial barcode is identified by identifying a spatial region of interest and identifying the spatial barcode associated with the spatial region of interest on the array. In some embodiments, a target spatial barcode is identified by performing shallow sequencing, and selecting a spatial barcode based on the captured analytes. As used herein, the coverage or depth of sequencing is the number of unique reads that include a given nucleotide in a reconstructed sequence. As used herein, shallow sequencing is a small or low number of unique reads of an identified analyte. In some embodiments, shallow sequencing can be performed to identify a spatial region of interest. In some embodiments, shallow sequencing can be performed on an entire biological sample. In some embodiments, shallow sequencing can be performed on an identified region of a biological sample (e.g., a region of interest). In some embodiments, shallow sequencing can be performed after identifying and/or selecting a region of a biological sample by some other method (e.g., immunostaining). In some embodiments, a target spatial barcode is identified by a co-localization of a target spatial barcode with one or more additional spatial barcode sequences. In some embodiments, a target spatial barcode is identified by imaging. In some embodiments, imaging includes immunohistochemistry and/or other staining or microscopy methods. In some embodiments, a target spatial barcode is identified manually. In some embodiments, a target spatial barcode is identified using a computer. In some embodiments, a target spatial barcode is identified algorithmically. In some embodiments, the target spatial barcode corresponds to a plurality of spatial barcode sequences that identify a region, a sub-region, a sub-sub-region, or further spatial demarcation. In some embodiments, a target spatial barcode is used to identify and characterize captured analytes at single-cell resolution. In some embodiments, the identifying can include sequencing a plurality of capture probes to generate a plurality of sequencing reads, and analyzing the plurality of sequencing reads to identify the at least one target spatial barcode. In some embodiments, each of the plurality of capture probes can further include one or more functional sequences selected from the group consisting of a sequencing primer sequence and a sequence configured to attach to a flow cell of a sequencer. In some embodiments, the plurality of capture probes can include, from 5' to 3', a first functional domain (e.g., adapter sequence), a sequence derived from a template nucleic acid, and a second adapter sequence. The first adapter sequence can include a first sequence configured to attach to a flow cell of a sequencer, a first sequencing primer sequence, and a spatial barcode. The second adapter sequence can include a second sequencing primer sequence and a second sequence configured to attach to a flow cell of a sequencer. The second adapter sequence can further include an index sequence.

Enriching Barcoded Nucleic Acids

In an aspect, the present disclosure provides methods of enriching a sample for target spatial barcoded nucleic acids. The methods can include providing a plurality of capture probes including a plurality of different spatial barcodes and a target capture probe of the population of captures, identifying at least one target spatial barcode from the plurality of different target spatial barcodes, and enriching the population of target capture probes including the spatial barcode from the plurality of capture probes.

In an aspect, the present disclosure provides methods of enriching a sample for target spatial barcoded nucleic acids. The methods can include providing a plurality of capture probes including a plurality of different spatial barcodes, identifying at least one target spatial barcode from the plurality of different target spatial barcodes, and enriching the analyte detected by (e.g., specifically bound to the capture probe) the capture probes including the at least one target spatial barcode (e.g., sometimes referred to herein as a target barcode sequence). Enriching can be performed by purifying capture probes including the at least one target spatial barcode from a plurality of capture probes. Additionally or alternatively, enriching can be performed by amplifying (e.g., increasing the numbers of) capture probes including the at least one target spatial barcode from a plurality of capture probes. The amplification can include any of the variety of amplification methods described herein, including isothermal amplification and/or PCR. Enriching can be performed by both purifying and amplifying the capture probe including the at least one target spatial barcode from a plurality of capture probes.

Spatial barcodes can be included in capture probes. For example, the capture probes can be co-partitioned into a partition with spatial barcodes to facilitate the barcoding reaction for spatial analysis. The spatial barcodes can be attached to a bead (e.g., in the context of a capture probe). The bead can be a gel bead. In some embodiments, the spatial barcodes are releasably attached to the bead (e.g., gel bead) as described elsewhere herein (e.g., via a cleavage domain). The plurality of capture probes can be spatially barcoded as described elsewhere herein.

In some embodiments, methods provided herein can include enriching nucleic acids including the at least one target spatial barcode (e.g., capture probes that have been extended using a captured analytes as a template). The enriching can include performing a nucleic acid amplification reaction on at least one capture probe including the at least one target spatial barcode to generate an enriched plurality of capture probes including the at least one target spatial barcode. The nucleic acid amplification reaction can be a polymerase chain reaction (PCR). The nucleic acid extension amplification reaction can be an isothermal amplification reaction. The nucleic acid amplification reaction can include a polymerase. The nucleic acid extension reaction can result in amplification of the nucleic acid.

In some embodiments, methods provided herein can further include performing an additional amplification reaction (e.g., PCR) on the enriched plurality of capture probes including the at least one target spatial barcode. The amplification reaction PCR can include use of an additional primer including a sequence specific for the enriched plurality of capture probes including the at least one target spatial barcode sequence. In some embodiments, the additional primer can include a sequence specific for the spatial barcode of the enriched plurality of capture probes including the at least one target spatial barcode. In some embodiments, the additional primer can include a sequence substantially specific for the spatial barcode sequence of the enriched plurality of capture probes including the at least one target spatial barcode. For example, the additional primer can include a sequence having at least 50%, 55%, 60%, 65%, 70%, 75%, 80%, 85%, 90%, 91%, 92%, 93%, 94%, 95%, 96%, 97%, 98%, 99%, 99.5%, 99.9% or more sequence complementarity or sequence identity to the spatial barcode sequence of the enriched plurality of capture probes including the at least one target spatial barcode. In some embodiments, the additional primer can include a sequence specific for a 5' region of a spatial barcode sequence of the enriched plurality of capture probes including the at least one target spatial barcode. In some cases, the additional primer can include a sequence that has no (or low) sequence complementarity or identity to the spatial barcode sequence of the enriched plurality of capture probes including the at least one target spatial barcode.

In some embodiments, the additional primer can include one or more functional sequences that facilitate sequencing of the enriched plurality of capture probes. The one or more functional sequences can include a sequencing primer sequence. The one or more functional sequences can include a sequence configured to attach to a flow cell of a sequencer.

In some embodiments, methods provided herein can further include, subsequent to the nucleic acid amplification reaction, performing a size selection process to remove unincorporated primers. The size selection process can include using a gel or gel-like polymer. The size selection process can use gel electrophoresis. In some cases, the size selection process can include using a substrate. The substrate can be an array.

In some embodiments, the enriched plurality of nucleic acids can include an affinity group. The affinity group can be incorporated to the enriched plurality of the nucleic acid via a polymerization reaction with a primer including the affinity group. The affinity group can be incorporated via enzymatic reaction with a nucleotide and the affinity group. The affinity group may be attached covalently or non-covalently. The method can further include coupling the enriched plurality of capture probes including the affinity group to a substrate specific for the affinity group. The substrate can be an array. The substrate can be a polymer matrix. The substrate can be a glass slide. The substrate can be a resin. In some embodiments, the substrate can include an antibody or antibody fragment. In some embodiments, the substrate includes avidin or streptavidin and the affinity group includes (or is) biotin. In some embodiments, the substrate includes maltose and the affinity group includes (or is) maltose binding protein. In some embodiments, the substrate includes maltose-binding protein and the affinity group includes (or is) maltose.

In some embodiments, prior to the nucleic acid amplification reaction, a first capture probe complementary to a first portion of the at least one target spatial barcode and a second capture probe complementary to a second portion of the at least one target spatial barcode can be hybridized. The first capture probe can be ligated to the second capture probe to generate the primer including the sequence specific for the at least one target spatial barcode. The ligating can include using a DNA ligase.

In some embodiments, the enriching can result in at least 10-fold enrichment of capture probes including the at least one target spatial barcode. In some embodiments, the enriching can result in at least 20-fold enrichment of capture probes including the at least one target spatial barcode. The enrichment of nucleic acids can be observed by an increase in the percentage of nucleic acids including the at least one target spatial barcode in the enriched plurality of capture probes compared to the percent amount of nucleic acids including the at least one target spatial barcode in the plurality of capture probes. The enriching can result in at least 50-fold enrichment of capture probes including the at least one target spatial barcode. The enriching can result in at least 100-fold enrichment of capture probes including the at least one target spatial barcode. The enriching can result in at least 200-fold enrichment of capture probes including the at least one target spatial barcode. The enriching can result in at least 500-fold enrichment of capture probes including the at least one target spatial barcode. The enriching can result in at least 1000-fold enrichment of capture probes including the at least one target spatial barcode.

Primers used for extension or amplification reactions described herein can be a specific length or include a specific number of nucleotides. For example, the primers may be at least about 5, about 6, about 7, about 8, about 9, about 10, about 12, about 14, about 16, about 18, about 20, about 22, about 24, about 25, about 26, about 28, about 30, about 40, about 50 or more nucleotides long. Alternatively or in addition, the primers can be no more than about 50, about 40, about 30, about 28, about 26, about 25, about 24, about 22, about 20, about 18, about 16, about 14, about 12, about 10, about 9, about 8, about 7, about 6, about 5, or fewer nucleotides long.

The primers may have a specific melting temperature. The melting temperature of the primer can be at least about 35 degrees Celsius (° C.), 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. 60° C., 61° C., 62° C., 63° C., 64° C., 65° C., or higher. The melting temperature of the primer can be no more than about 35° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. 60° C., 61° C., 62° C., 63° C., 64° C., 65° C., or lower.

In some cases, primers are ligated together to form a longer primer. The longer primer can be subsequently used for any PCR reactions, as described elsewhere herein. Ligating together shorter primers into a longer primer can increase the stringency of binding such that the targeted spatial barcode is enriched. For example, the shorter primers can be able to distinguish mismatches better and thus bind only to sequences with perfect or near perfect complementarity. The longer primer can be more able to accommodate mismatches in sequences and bind to sequences that are not the targeted barcode. In some cases, more than 2 primers are ligated together to form a longer primer. For example, at least about 3, 4, 5, 6, 7, 8, 9, 10, or more primers can be ligated together to form a longer primer.

In some embodiments, the primer includes an affinity group and the enriched plurality of capture probes includes the affinity group. The affinity group can include biotin. The affinity group can include streptavidin or avidin. The affinity group can include dioxigenin. The affinity group can include a protein or polypeptide. The affinity group can include an antibody or antibody fragment. The affinity group can include a receptor or receptor ligand. The affinity group can includes a sugar, a monosaccharide, a disaccharide, or a polysaccharide. The affinity group can include maltose.

Methods of the present disclosure can be used for various applications, such as, processing a single analyte (e.g., RNA, DNA, or protein) or multiple analytes (e.g., DNA and RNA, DNA and protein, RNA and protein, or RNA, DNA, and protein) from a single cell. For example, multiple analytes from the biological sample can be processed. The multiple analytes can be from the single cell. This can enable, for example, simultaneous proteomic, transcriptomic and genomic analysis of the cell (e.g., multiplexing).

Hierarchal Barcode Enrichment

In some aspects, the present disclosure provides methods of spatially designing or designating spatial barcodes, such that the position of the spatial barcodes are specifically identified. In some embodiments, a particular individual feature on a spatial array (e.g., a spot or bead) can contain more than one spatial barcode, wherein each spatial barcode corresponds to a particular defined region on the spotted array. For example, multiple spatial barcode sequences associated with one particular feature on an array can provide a stronger address or attribution to a given location by providing duplicate or independent confirmation of the location. In some cases, the multiple spatial barcodes represent increasing specificity of the location of the particular feature. In a non-limiting example, a particular feature can be coded with two different spatial barcodes, wherein each spatial barcode identifies a particular defined region within the array, and a feature possessing both spatial barcodes identifies the sub-region where two defined regions overlap, e.g., such as the overlapping portion of a Venn diagram. In another non-limiting example, a particular feature can be coded with three or more different spatial barcodes, wherein the first spatial barcode identifies a first region within the array, the second spatial barcode (e.g., sub region spatial barcode, second common spatial barcode) identifies a second region, wherein the second region is a subregion entirely within the first region (a sub region), and the third spatial barcode (e.g., sub-sub region spatial barcode, third common spatial barcode) identifies a third region, wherein the third region is a subregion entirely within the first and second subregions (a sub region), and so on. In some embodiments, each capture probe has a unique molecular identifier (UMI). In some embodiments, each capture probe has a UMI, as well as one or more target spatial barcodes corresponding to one or more regions or sub regions on an array.

In some embodiments, an array has multiple features (also sometimes referred to as "regions", "spots", or "locations") and subregions. In some embodiments, an array has 10 features or more. In some embodiments, an array has 20, 30, 40, 50, 60, 70, 80, 90, 100 features, or more. In some embodiments, an array has 100, 200, 300, 400, 500, 600, 700, 800, 900, 1000 features or more. In some embodiments, an array has 1000, 2000, 3000, 4000, 5000, 6000, 7000, 8000, 9000, 1000 features or more. In some embodiments, the features are identical in size. In some embodiments, the features are not identical in size. The features may take any shape, including but not limited to square, rectangle, circle, oval, pentagon, hexagon, octagon arc, arches, lens, crescent, and any combinations thereof. In some embodiments, a feature of an array has multiple subregions. In some embodiments, a feature of an array has 10, 20, 30, 40, 50, 60, 70, 80, 90, 100, 200, 300, 400, 500, 600, 700, 800, 900, 1000 subregions or more. In some embodiments, the subregions are identical in size to other subregions. In some embodiments, the subregions are not identical in size to other subregions. In some embodiments, the subregions are completely surrounded by a larger region. In some embodiments, subregions are partially surrounded by a larger region. In some embodiments, different subregions of a feature include different regional spatial barcodes that are characteristic of the given subregions. In some embodiments, different subregions of a feature include different regional spatial barcodes that are characteristic of the given subregions and a common spatial barcode that is characteristic of the feature. Such embodiments permit enrichment of capture analytes having the common spatial barcode and/or one or more regional spatial barcodes (e.g., via any of the variety of enrichment methods described herein). In some embodiments, an array has multiple sub-subregions. In some embodiments, an array has 10, 20, 30, 40, 50, 60, 70, 80, 90, 100, 200, 300, 400, 500, 600, 700, 800, 900, 1000 sub-subregions or more. In some embodiments, the sub-subregions are identical in size to other sub-subregions. In some embodiments, the sub-subregions are not identical in size to other sub-subregions. In some embodiments, sub-subregions are completely surrounded by a larger region. In some embodiments, the larger region is a subregion. In some embodiments, the larger region is a region. In some embodiments, sub-subregions are partially surrounded by a larger subregion. In some embodiments, sub-subregions are partially surrounded by a larger region. In some embodiments, different sub-subregions of a subregion include different sub-regional spatial barcodes that are characteristic of the given sub-subregions. In some embodiments, different sub-subregions of a feature include different sub-regional spatial barcodes that are characteristic of the given subregions and a common regional spatial barcode that is characteristic of the region. In some embodiments, different sub-subregions of a feature include different sub-regional spatial barcodes that are characteristic of the given subregions, a common regional barcode that is characteristic of the region, and a common spatial barcode that is characteristic of the feature. Such embodiments permit enrichment of capture analytes having the common spatial barcode and/or one or more regional spatial barcodes (e.g., via any of the variety of enrichment methods described herein). In some embodiments, individual features or spots or beads include a region. In some embodiments, individual features of spots or beads include a subregion. In some embodiments, individual features or spots or beads include a sub-subregion. In some embodiments, individual features or spots or beads include a region corresponding to single cell resolution of the biological sample.

In some embodiments, the present disclosure provides methods of enriching a sample including more than one analyte specifically bound to the capture probe. The methods can include providing a plurality of capture probes including a plurality of different spatial barcodes, identifying more than one target spatial barcode (e.g., sometimes referred to as a target barcode sequence) from the plurality of different spatial barcodes, and enriching capture probes including the more than one target spatial barcode. Enriching can be performed by purifying capture probes including the more than one target spatial barcode from a plurality of capture probes. Enriching can be performed by amplifying (e.g., increasing the numbers of) capture probes including the more than one target spatial barcode from a plurality of capture probes. Enriching can be performed by both purifying and amplifying the capture probe including the more than one target spatial barcode from a plurality of capture probes. Enriching can be performed using target spatial barcodes associated with smaller regions. Enriching can be performed using target spatial barcodes of increasing specificity to a particular feature or spot or location. For example, enriching can be performed by amplifying and/or purifying a first plurality of capture probes including a target spatial barcode that is associated with a first spatial location (e.g., a first feature, a first subregion, and/or a first sub-subregion). The enriching may further include amplifying and/or purifying a second plurality of capture probes including a target spatial barcode that is associated with a second spatial location (e.g., a second feature, a second subregion, and/or a second sub-subregion) that is partially or completely within the first spatial location. The enriching can further include amplifying and/or purifying a second plurality of capture probes including a target spatial barcode that is associated with a second spatial location that is partially within the first region. The enriching can further include amplifying and/or purifying a second plurality of capture probes including a target spatial barcode that is associated with a second spatial location that is completely within the first spatial location. The enriching can further include amplifying and/or purifying a third plurality of capture probes including a target spatial barcode that is associated with a third spatial location that is partially or completely within the first and second spatial locations. The enriching can further include amplifying and/or purifying a third plurality of capture probes including a target spatial barcode that is associated with a third spatial location that is partially within the first and second spatial locations. The enriching can further include amplifying and/or purifying a third plurality of capture probes including a target spatial barcode that is associated with a third spatial location that is completely within the first and second spatial locations. The enriching can further include amplifying and/or purifying a fourth plurality of capture probes including additional target spatial barcodes that are associated with four or more spatial locations that are partially or completely within the first, second, and third spatial locations. The enriching may further include amplifying and/or purifying a fifth plurality of capture probes including additional target spatial barcodes that are associated with five or more spatial locations that are partially or completely within the first, second, third, and fourth spatial locations. The enriching can further include amplifying and/or purifying additional pluralities of capture probes including additional target spatial barcodes that are associated with 6, 7, 8, 9, 10, or more spatial locations that are partially or completely within the previously identified regions and/or sub regions.

In some embodiments, the method can include enriching nucleic acids including more than one target spatial barcode. The enriching can include performing a nucleic acid extension reaction using a capture probe including more than one target spatial barcode and a primer including a sequence specific for more than one target spatial barcode to generate an enriched plurality of capture probes including more than one target spatial barcode. The nucleic acid extension reaction can be a polymerase chain reaction (PCR). The nucleic acid extension reaction can include a polymerase. The nucleic acid extension reaction can result in amplification of the nucleic acid.

In some embodiments, methods provided herein may further include performing additional rounds of PCR on the enriched plurality of capture probes corresponding to the number of spatial barcode sequences of a given location. The additional rounds of PCR may include use of additional primers including a sequence specific for the additional target spatial barcode (e.g., target spatial barcode associated with a region, a subregion, or sub-subregion of interest). In some embodiments, the additional primers may include a sequence specific for the spatial barcode sequence of the enriched plurality of capture probes including more than one target spatial barcode. In some embodiments, the additional primers may include a sequence substantially specific for an additional target spatial barcode of the enriched plurality of capture probes including more than one target spatial barcode. For example, the additional primer may include a sequence having at least 50%, 55%, 60%, 65%, 70%, 75%, 80%, 85%, 90%, 91%, 92%, 93%, 94%, 95%, 96%, 97%, 98%, 99%, 99.5%, 99.9% or more sequence complementarity or sequence identity to a target spatial barcode of the enriched plurality of capture probes including the more than one target spatial barcode. In some embodiments, the additional primers may include a sequence specific for a 5' region of a spatial barcode sequence of the enriched plurality of capture probes including more than one target spatial barcode. In some cases, the additional primer can includes a sequence that has no (or low) sequence complementarity or identity to one or more spatial barcode sequences of the enriched plurality of capture probes including more than one target spatial barcode.

In some embodiments, each spatial barcode sequence of the plurality of different spatial barcode sequences can identify a capture probe as derived from a single cell. Alternatively or in addition, each spatial barcode sequence of the plurality of different spatial barcode sequences may identify a capture probe as derived from a single partition.

Identifying a Spatial Region of Interest

In some embodiments, identifying a spatial region of interest includes any technique for observing and/or locating an area within a tissue. In some embodiments, identifying a spatial region of interest includes immunostaining techniques, including but not limited to, immunohistochemistry techniques. In some embodiments, identifying a spatial region of interest includes microscopy techniques, including but not limited to, optical microscopy, fluorescence microscopy, and confocal microscopy. In some embodiments, identifying a spatial region of interest includes visual inspection. In some embodiments, identifying a spatial region of interest includes shallow sequencing a spatial region. In some embodiments, identifying a spatial region of interest includes shallow sequencing the entire biological sample. Any of the variety of other methods described herein or otherwise known in the art to identify a spatial region of interest can be used.

Generating Spatial Arrays with Light

In at least one embodiment of the compositions and methods of the present disclosure, a plurality of first oligonucleotide are attached to a substrate by any suitable means that immobilizes the first oligonucleotide by either their 3' or 5' end in a region of the substrate and allows the unattached end to be available for further synthesis. Further synthesis can include in situ base-by-base step-wise synthesis (e.g., phosphoramidite chemistry) or biosynthesis via enzyme reactions (e.g., DNA polymerization or reverse transcription). In some embodiments, the means of attachment is also be suitable to allow at least a portion of the first oligonucleotide to be capable of hybridization.

In at least one embodiment of the compositions and methods of the present disclosure, the plurality of first oligonucleotides are attached to a substrate by a covalent linkage. Accordingly, in at least one embodiment, the plurality of first oligonucleotides are attached to the substrate by a chemical reaction that forms one or more covalent bonds between a functional group on the substrate (or a linker group attached to the substrate) and a functional group on the 3'- or 5'-end of the first oligonucleotide (or a linker group attached to the 3' or 5'-end of the first oligonucleotide). Such functional groups can include a naturally occurring nucleotide functional group, e.g. a terminal hydroxyl group, or a non-natural functional group introduced during oligonucleotide synthesis, such as a 5'-amine group. Reagents and techniques for chemically modifying substrate materials and/or nucleotides with functional groups that are useful in the methods of the present disclosure are well known in the art. For example, functional groups that may be introduced on a substrate that allow for attachment of a first oligonucleotide (e.g., 5'-amine modified oligonucleotide) to a substrate include linkers with available carboxy, aldehyde or epoxy groups. Other functionalized linker compounds are known to the person skilled in the art.

The first oligonucleotide of the plurality of first oligonucleotides to be attached to a substrate in preparing a spatial array of the present disclosure can be understood as having at least three exemplary oligonucleotide: a first oligonucleotide of about 2-mer to about 40-mer that is attached to the substrate through either its 3'-end or its 5'-end; a second oligonucleotide that is attached to the unattached end of the first, and includes a spatial barcode sequence of about 8-mer to about 30-mer in length that indicates the region on the substrate where the second is located (e.g., a spatial barcode); and a plurality of third oligonucleotide s of about 5-mer to about 50-mer attached to the second oligonucleotide, wherein the third oligonucleotide includes a capture sequence at its 3'-end. In some embodiments, the exemplary oligonucleotides include one or more additional sequences. For example, a first oligonucleotide can include a functional domain (e.g., any of the variety of functional domains described herein). In some embodiments, two or more domains present in the exemplary oligonucleotides each include a portion of a domain, such that when the exemplary oligonucleotides are joined, a full domain is generated. For example, a first oligonucleotide can include a first portion of a domain (e.g., a spatial barcode) and a second oligonucleotide can include a second portion of a domain (e.g., a spatial barcode) such that the spatial barcode is generated upon joining the first and second oligonucleotides.

FIGS. 31A-B depict at least one embodiment of a method for preparing an exemplary spatial array composition of the present disclosure. First, as shown in FIG. 31A, a substrate is provided that includes a first oligonucleotide attached through its 5'-end to the substrate. In at least one embodiment, the first oligonucleotide includes a sequence that is identical across all of the plurality of the different oligonucleotides attached to the substrate. In some embodiments, the first oligonucleotide can be understood as a common oligonucleotide "lawn" across the surface of the substrate that does not differ in sequence in the various regions of the substrate. The free, unattached end of the first oligonucleotide, thus, effectively acts as the starting point on the spatial array for the spatially-directed in situ synthesis of the second oligonucleotide that includes the spatial barcode.

In at least one embodiment, the length of the first oligonucleotide is the same across the surface of the substrate. While typically not critical to the function of the spatial array, in at least one embodiment, the length of the first oligonucleotide sequence should be at least about 2 nucleotides in length. Furthermore, in some embodiments the length of the first oligonucleotide is at least about 5 nucleotides in length, at least about 10 nucleotides in length, at least about 15 nucleotides in length, at least about 20 nucleotides in length, at least about 25 nucleotides in length, at least about 27 nucleotides in length, at least about 30 nucleotides in length, at least about 33 nucleotides in length, or at least about 35 nucleotides in length. Similarly, in some embodiments the first oligonucleotide has a length of about 2 nucleotides in length to about 40 nucleotides in length, about 5 nucleotides in length to about 40 nucleotides in length, about 10 nucleotides in length to about 30 nucleotides in length, about 25 nucleotides in length to about 35 nucleotides in length, about 20 nucleotides in length to about 40 nucleotides in length, about 25 nucleotides in length to about 40 nucleotides in length, about 25 nucleotides in length to about 35 nucleotides in length, or about 27 nucleotides in length to about 33 nucleotides in length.

As further depicted in FIG. 31A, in at least one embodiment, the first oligonucleotide can include phosphodiester and exocyclic amine moieties that are protected. Protection of the phosphodiester and exocyclic amine moieties of the first oligonucleotide allows for optimal in situ synthesis of the second oligonucleotides that includes the spatial barcode. Suitable protecting groups for phosphodiester and exocyclic amine moieties are described herein and are well-known in the art and include the protecting groups employed in standard oligonucleotide synthesis using phosphoramidite chemistry.

The present disclosure describes a variety of embodiments for preparing a substrate having attached thereto a first oligonucleotide, wherein the first oligonucleotide includes protected phosphodiester and exocyclic amine moieties (see e.g., embodiments of FIGS. 32A-C to 36A-C).

In at least one exemplary embodiment, depicted in FIGS. 32A-C, the method further includes preparing the first oligonucleotide ex situ (e.g., on a separate substrate or feature using solid-phase automated synthesis), cleaving it from the separate substrate or feature with the protecting groups intact (see FIG. 32A), and subsequently attaching the ex situ synthesized oligonucleotide with protecting groups it to the substrate (see FIG. 32B). A free hydroxyl at the unattached end is available for subsequent spatially-directed in situ synthesis of a second oligonucleotide, e.g., a second oligonucleotide including a spatial barcode (see FIG. 32C).

Figure 33A:
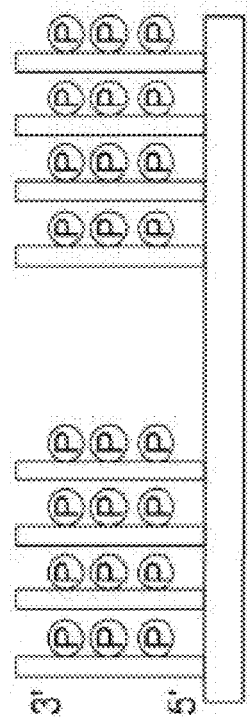
FIGS. 33A-B depict an illustrative embodiment of the methods for preparing a spatial array of the present disclosure.
Figure 33B:
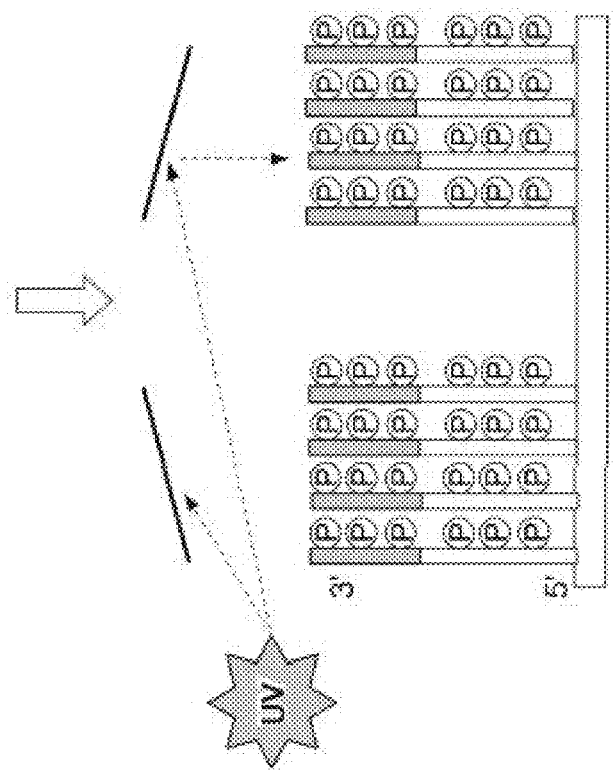

In at least another exemplary embodiment, depicted in FIGS. 33A-C, the method further includes preparing the first oligonucleotide in situ directly on the substrate using base-by-base phosphoramidite synthesis chemistry with phosphodiester and exocyclic amine protecting groups. Such a method can be use standard solid-phase oligonucleotide synthesis chemistry to provide a substrate with first oligonucleotide attached thereto by the 3'-end and having protecting groups. In at least one embodiment, as depicted in FIG. 33A, oligonucleotide synthesis chemistry in a 5'-to-3' direction can be carried out to provide the protected first oligonucleotides attached to the substrate through the 5'-end. In both cases, the free hydroxyl at the unattached end is available for subsequent spatially-directed in situ synthesis of a second oligonucleotide, e.g., a second oligonucleotide including a spatial barcode (see FIG. 32C).

In some embodiments, as depicted in FIG. 31B, a plurality of second oligonucleotides of about 8-mer to about 30-mer are prepared by spatially-directed in situ synthesis extending from the free end of the first oligonucleotide. As shown in FIG. 31B, the spatially-directed in situ synthesis can be a light-directed spatial synthesis which is carried out in the 5'-to-3' direction. This in situ synthesis method results in a plurality of second oligonucleotide each attached through its 5'-end to a 3'-end of a first oligonucleotide. FIG. 31B is a schematic representation of only two distinct regions each having four individual oligonucleotide molecules. Each region can have a different second oligonucleotide sequence, and all of the second oligonucleotide molecules in a region can have the same sequence, although as discussed further below, less than 100% yield in the in situ synthesis process results in less than perfect purity (or homogeneity) of oligonucleotide sequence (e.g., a second oligonucleotide) in a region.

In at least one embodiment of the present disclosure, spatially-directed synthesis of a plurality of oligonucleotides on a substrate in spatially distinct regions is carried out using light-directed synthesis or by mechanically-directed synthesis methods. A spatially-directed in situ synthesis method inherently correlates each sequence synthesized with the location of synthesis. In the schematic illustration of FIG. 31B, a light-directed spatial synthesis is used to synthesize a second oligonucleotide in a base-by-base step-wise fashion in each region. The region where each nucleotide base is added can be controlled by the precise location (and duration) of spatially-directed illumination of the substrate. The direction and duration of illumination can be precisely controlled, for example with maskless array synthesis (MAS) technology using computer-controlled digital micromirror devices (DMD), to provide distinct regions of 1 μm$^2$ or even smaller. It is only at these precisely illuminated regions on the substrate where deprotection of a photo-labile protecting group occurs, thereby allowing coupling of a nucleoside phosphoramidite that provides the next base in the oligonucleotide sequence. In some embodiments, the synthesis of the first oligonucleotide is not light-directed synthesis.

In some embodiments, light-directed spatial in situ synthesis provides optimal control in the synthesis of high-fidelity second oligonucleotide spatial barcode sequences at precise region locations on a substrate. Light-directed spatial synthesis of oligonucleotides refers to synthetic methods using photolabile nucleoside protecting groups and spatially-directed illumination to effect selective deprotection and base-by-base synthesis at specific locations on a substrate. Light-directed spatial synthesis of oligonucleotides uses an iterative cycle of phosphoramidite-based coupling chemistry with photo-labile protecting groups rather than dimethoxytrityl (DMT) protecting groups. The synthesis cycle, thus, is very similar to that used in standard solid-phase phosphoramidite synthesis of oligonucleotides with the following general steps: (1) photo-deprotection; (2) activation and coupling; (3) capping; and (4) drying. The drying step (4) can involve blowing helium to dry the substrate surface after coupling and acetonitrile wash, but before the next photodeprotection step. Techniques, protocols, reagents, materials, and other instrumentation useful for light-directed spatial synthesis of high-density oligonucleotide microarrays are described herein, are well-known in the art, and are commercially available. For example, U.S. Pat. Nos. 7,844,940, 8,030,477, PCT Publ. No. WO 99/63385A1, US Pat. Publ. No. 20150246336A1, Agbavwe et al., Efficiency, error and yield in light-directed maskless synthesis of DNA microarrays, *Journal of Nanobiotechnology* 9.1 (2011): 57; and Sack et al., Express photolithographic DNA microarray synthesis with optimized chemistry and high-efficiency photolabile groups, *Journal of Nanobiotechnology* 14.1 (2016): 14, describe materials and methods that can be used in the light-directed spatial synthesis methods of the present disclosure. The aforementioned patents and publications are each incorporated herein by reference in their entireties.

In some embodiments, the photo-deprotection step involves spatially-directed illumination of the substrate and is the step that ultimately defines the size and location of a region. Efficiency and accuracy of the photo-deprotection step in defining the regions on the substrate where specific oligonucleotides are synthesized depends largely on the illumination techniques and the photo-labile groups used. Photo-labile groups and illumination techniques useful for light-directed spatial synthesis methods are described herein, are well-known, and are commercially available (e.g., from Sigma-Aldrich, St. Louis, Mo., USA). For example, photo-labile protecting groups that can be used to prepare spatial array compositions of the present disclosure are described in US Pat. Publ. No. 20150246336A1; Agbavwe et al., Efficiency, error and yield in light-directed maskless synthesis of DNA microarrays *Journal of Nanobiotechnology* 9.1 (2011): 57; Kretschy et al., Next-Generation o-Nitrobenzyl Photolabile Groups for Light-Directed Chemistry and Microarray Synthesis, *Angewandte Chemie International Edition* 54.29 (2015): 8555-8559; Sack et al., Express photolithographic DNA microarray synthesis with optimized chemistry and high-efficiency photolabile groups, *Journal of Nanobiotechnology* 14.1 (2016): 14; Lietard et al., High-Density RNA Microarrays Synthesized In Situ by Photolithography, *Angew. Chem. Int. Ed.* 57 (2016): 15257-15261; and Holz et al., High-Efficiency Reverse (5'→3') Synthesis of Complex DNA Microarrays, *Scientific reports* 8.1 (2018): 15099, each of which are incorporated herein by reference in their entireties.

In at least one embodiment, the photo-labile protecting groups useful in the light-direct spatial synthesis methods of the present disclosure include NPPOC, Bz-NPPOC, and SPh-NPPOC which are shown in Table 2.

TABLE 2

Exemplary Photo-labile Protecting Groups

| Name | Structure (e.g., protecting 3'-OH of nucleoside) |
|---|---|
| NPPOC | 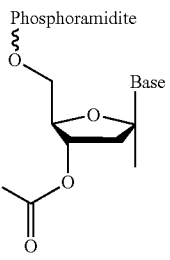 |
| Bz-NPPOC | 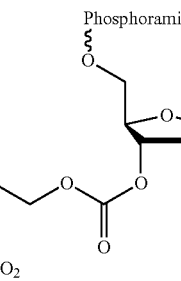 |
| SPh-NPPOC | 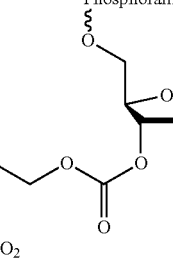 |

The schematic illustration of FIG. 31B depicts light-directed spatial synthesis of second oligonucleotide in the 5'-to-3' direction. The resulting plurality of the second oligonucleotide are thus attached through their 5'-ends to the free 3'-ends of the first oligonucleotide on the substrate. Accordingly, in at least one embodiment the light-directed spatial synthesis of the second oligonucleotides is carried out in the 5'-to-3' direction. Techniques, reagents, and photo-labile protecting groups useful for synthesis in the 5'-to-3' direction include those described in e.g., Holz et al., High-Efficiency Reverse (5'→3') Synthesis of Complex DNA Microarrays, *Scientific reports* 8.1 (2018): 15099, which is incorporated herein by reference. In at least one embodiment, light-directed spatial synthesis of a plurality of second oligonucleotides can be carried out using one or more of the photo-labile protecting groups of Table 1 to protect the 3'-OH. In at least one embodiment, the photo-labile protecting group used in light-directed spatial synthesis of the second oligonucleotide is Bz-NPPOC.

In at least one embodiment, the spatially-directed in situ synthesis can be carried out using mechanically-directed spatial synthesis. Mechanically-directed spatial synthesis of oligonucleotides refers to methods that use computer-controlled liquid dispensing and/or placement technology to mechanically direct nucleoside phosphoramidite reagents at distinct locations on a substrate, and thereby synthesizing an oligonucleotide (e.g., a second oligonucleotide) using standard solid-phase phosphoramidite chemistry at a distinct region on a substrate. A range of technologies for mechanical spatially-directed in situ synthesis of oligonucleotides are described herein and are well-known in the art.

The schematic illustration of FIG. 31B depicts only two regions, however it is contemplated that a spatial array composition made by the methods of the present disclosure can include millions of different regions on a substrate, each including a different second oligonucleotide spatial barcode. In at least one embodiment, the number of second oligonucleotides including different sequences is at least about 100,000, at least about 250,000, at least about 500,000, at least about 750,000, at least about 1,000,000, at least about 1,500,000, at least about 3,000,000, at least about 5,000,000, at least about 10,000,000, at least about 100,000,000, at least about 500,000,000, or at least about 1,000,000,000. In some embodiments, the number of second oligonucleotide including different sequences is about 100,000 to about 1,000,000,000, about 750,000 to about 1,500,000, about 1,000,000 to about 1,000,000,000, about 1,000,000 to about 10,000,000, or about 1,500,000 to about 5,000,000.

In order for a spatial array to accommodate these large numbers of different oligonucleotides on a substrate, it also is contemplated that the areas of the regions can be sufficiently small. Accordingly, in at least one embodiment of the method of the present disclosure the regions of the substrate have an area of less than about 2500 $\mu m^2$, less than about 1600 $\mu m^2$, less than about 400 $\mu m^2$, less than about 100 $\mu m^2$, less than about 50 $\mu m^2$, less than about 25 $\mu m^2$, less than about 15 $\mu m^2$, less than about 10 $\mu m^2$, less than about 5 $\mu m^2$, less than about 2 $\mu m^2$, less than about 1 $\mu m^2$, or smaller.

In at least one embodiment, methods of the present disclosure contemplate the spatially-directed in situ synthesis of second oligonucleotides including millions of different spatial barcodes each in a different region. In order to accommodate millions of distinct regions each with a distinct spatial barcode, the present disclosure contemplates that the second oligonucleotides have a length range of about 8 nucleotides to about 30 nucleotides. A length range of about 8 nucleotides to about 30 nucleotides allows for the plurality of second oligonucleotide to have extremely large number of distinct oligonucleotides that are indexed for their location on the substrate. For example, in the case of an 8 nucleotides sequence, there are $4^8$ or 65,536 different possible barcode sequences that can be used to identify distinct locations on a substrate. In the case of a 12 nucleotides sequence, there are $4^{12}$ or 16,777,216 different possible spatial barcodes that can be used to identify distinct locations on a substrate. Accordingly, in at least one embodiment of the method of the present disclosure the second oligonucleotide have a length selected from 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

In order to provide for optimal functionality of a spatial array, the correlation of the spatial barcodes with the locations should be high. Accordingly, the spatially-directed in situ synthesis of the spatial barcode should result in high fidelity or purity of spatial barcode in each of the regions. It is an advantage of the spatially-directed synthesis methods of the present disclosure that the second oligonucleotide are prepared on a substrate with high fidelity. Generally, the fidelity (or sequence purity) of oligonucleotide sequences prepared by step-wise solid-phase synthesis decreases as the length of the oligonucleotide being synthesized increases. For example, assuming a spatially-directed in situ synthesis having a coupling efficiency of 99.5%, the fidelity of 12 nucleotide barcode sequences in a region is ~95%. In some embodiments (e.g., as in FIGS. 32A-C), the use of spatially-directed in situ synthesis to prepare only the 8 to 30 nucleotide second oligonucleotides results in spatial barcodes of high-fidelity. Accordingly, in at least one embodiment of the methods of the present disclosure the resulting second oligonucleotide synthesized in each of the different regions of the substrate has a purity of at least 75%, at least 80%, at least 85%, at least 87%, at least 88%, at least 89%, at least 90%, at least 91%, at least 92%, at least 93%, at least 94%, at least 95%, at least 96%, at least 97%, at least 98%, at least 99%, or more.

In at least one embodiment, the second oligonucleotide is unique for each region of the substrate. Additionally or alternatively, in some embodiments, the second oligonucleotide spatial barcode includes a sequence that uniquely identifies it from the plurality of other spatial barcode sequences on the spatial array but does not interfere with the capture sequences (e.g., capture domains) of the oligonucleotides (e.g., capture probes) that target binding to nucleic acids in a sample. Unique spatial barcodes can be generated using random sequence generation, along with stringent filtering of sequences by mapping to the genomes of all common reference species using desired Tm intervals, and GC content, to minimize interference with capture sequence (e.g., capture domain) binding to analytes, and to optimize the difference from the other spatial barcodes. Thus, in at least one embodiment, the spatial barcodes of the spatial array are selected such that desired analytes of the biological sample applied to the array do not hybridize specifically to the spatial barcode of the second oligonucleotide. For example, in some embodiments, the spatial barcode of the spatial array have less than 80% sequence complementarity to the targeted nucleic acid sequences (e.g., analytes) in the sample applied to the spatial array. In some embodiments, spatial barcode has less than 70% sequence id complementarity entity, less than 60% sequence complementarity, less than 50% sequence complementarity, or less than 40% sequence complementarity to the nucleic acids in the biological sample targeted for capture by the plurality of oligonucleotide sequences.

In some embodiments, as depicted in FIG. 31C, a plurality of third oligonucleotides are attached to the unattached end of the second oligonucleotide. In at least one embodiment, the third oligonucleotide is in the same orientation as the second oligonucleotide. Thus, if the second oligonucleotide is attached to the first oligonucleotide through its 5'-end (in a 5'-to-3' orientation relative to the substrate) then the third oligonucleotide is attached through its 5'-end to the 3'-end of the second oligonucleotide. As exemplified in FIG. 31C, in at least one embodiment, the third oligonucleotides are attached through their 5'-ends to the 3'-ends of the plurality of second oligonucleotides. In some embodiments, the third oligonucleotide has a length of about 5 to about 40 nucleotides and includes a capture sequence (e.g., capture domain) capable of hybridizing to an analyte (e.g., nucleic acid) in a biological sample. As described further herein, in some embodiments, the third oligonucleotide includes a free 3'-OH and is capable of hybridizing to a complementary nucleic acid (e.g., an analyte) in a biological sample and then undergoing biosynthetic (e.g., polymerase catalyzed) extension from it 3'-OH.

In at least one embodiment, the plurality of third oligonucleotides have a length of at least about 5 nucleotides, at least about 10 nucleotides, at least about 15 nucleotides, at least about 20 nucleotides, at least about 27 nucleotides, at least about 30 nucleotides, at least about 33 nucleotides, or at least about 35 nucleotides. In some embodiments, the plurality of third oligonucleotide have a length of about 5 nucleotides to about 40 nucleotides, about 10 nucleotides to about 40 nucleotides, about 20 nucleotides to about 40 nucleotides, about 25 nucleotides to about 35 nucleotides, or about 27 nucleotides to about 33 nucleotides.

In at least one embodiment of the methods of the present disclosure, the third oligonucleotides are prepared off the substrate and attached as a whole segment by chemical coupling or ligation to the plurality of second oligonucleotides. In at least one embodiment, the plurality of third oligonucleotides are attached by ligation. In some embodiments, protected moieties of the first and second oligonucleotides are deprotected prior to ligating the plurality of third oligonucleotides.

In at least one embodiment where the method of the present disclosure further includes attaching a plurality of third oligonucleotides, the first oligonucleotide is attached to the substrate through its 5'-end, the plurality of second oligonucleotides are prepared by spatially-directed in situ synthesis on the 3'-end of the first oligonucleotide, and the plurality of third oligonucleotides are attached through their 5'-end to the 3'-end of the plurality of second oligonucleotides.

Alternatively, in at least one embodiment where the method of the present disclosure further includes attaching a plurality of third oligonucleotides, the first oligonucleotide can be attached to the substrate through its 3'-end, the plurality of second oligonucleotides are prepared by spatially-directed in situ synthesis on the 5'-end of the first oligonucleotide, and the plurality of third oligonucleotides are attached through their 3'-end to the 5'-end of the plurality of second oligonucleotides.

In at least one embodiment, the third oligonucleotide includes a capture sequence (e.g., a capture domain) capable of hybridizing to a nucleic acid sequence (e.g., an analyte) in a biological sample. In at least one embodiment, the capture sequence is located at the free 3'-end of the third oligonucleotide which is oriented with its 5'-end attached to the second oligonucleotide. In this orientation the free 3'-end can be extended (e.g., by template dependent polymerization). It is contemplated that in at least one embodiment, the capture sequence (e.g., capture domain) of the third oligonucleotide includes a sequence capable of hybridizing to a specific type of target nucleic acid that is present in a biological sample. For example, the capture sequence of the third oligonucleotide can be designed to selectively capture mRNA by hybridization to the poly-A tail. Accordingly, in at least one embodiment, the capture sequence of the third oligonucleotide includes a poly-T oligonucleotide. In some embodiments, the capture sequence can include nucleotides which are functionally analogous to poly-T and capable of binding (e.g., hybridizing) selectively to poly-A, such as a poly-U oligonucleotide. In at least one embodiment, the capture sequence of the third oligonucleotide includes a poly-T or poly-U sequence of at least about 5 nucleotides to about 40 nucleotides in length. In some embodiments, the capture sequence (e.g., capture domain) includes a poly-T or poly-U sequence of at least 5 nucleotides, 10 nucleotides, at least 15 nucleotides, at least 20 nucleotides, at least 25 nucleotides, at least 30 nucleotides, at least 35 nucleotides, or at least 40 nucleotides in length.

In some embodiments, it is contemplated that the capture sequence can be designed to selectively bind to a desired sub-type or subset of nucleic acid targets suspected of being present in a biological sample. For example, a particular type of RNA, such as mRNA, microRNA or rRNA, or a particular mRNA species that corresponds to a particular group of genes (e.g., gene specific capture domain). Thus, the capture sequence of the third oligonucleotide may include a sequence that specifically binds to a particular target gene or set of genes, and can be based on a particular sequence motif sequence or conserved sequence according to methods well known in the art.

In some embodiments, the third oligonucleotides of the plurality of the third oligonucleotides can include a random sequence. As is well-known in the art, such random sequences (e.g. random hexamers or nonamers) are effective for the capture nucleic acid targets (e.g., analytes) by selective binding. Accordingly, it is contemplated that the capture sequence (e.g., capture domain) of the third oligonucleotides of the plurality of third oligonucleotides can include a random sequence, where the random sequences are at least 6-mers, at least 8-mers, at least 10-mers, at least 12-mers, at least 14-mers, at least 16-mers, or longer. In some embodiments, the plurality of third oligonucleotides can include random sequences together with a poly-T or poly-U capture sequence. Accordingly, where a third oligonucleotide includes a poly-T or poly-U capture sequence, it can also include a random sequence. In some embodiments, where the third oligonucleotide is in a 5'-to-3' orientation, the random sequences are located at the 5'-end of the third oligonucleotide adjacent to the 3-end of the second oligonucleotide including the spatial barcode.

In at least one embodiment, the first, second, and third oligonucleotides are linked via phosphodiester bonds. Additionally, in some embodiments, it is contemplated that the oligonucleotides can be attached via non-natural oligonucleotide linkages, such as methylphosphonate or phosphorothioate bonds, or via other non-natural biocompatible linkages such as click-chemistry linkages. The bonds linking the oligonucleotides can be formed by synthetic phosphoramidite coupling chemistry, by a synthetic click-chemistry described herein, by a ligation reaction, by enzymatic biosynthesis of nucleic acid polymers (e.g., using a polymerase or transcriptase), or a combination of bond forming reactions. For example, in at least one embodiment, the second oligonucleotide is attached to the first oligonucleotide by standard phosphoramidite chemistry forming a phosphodiester linkage, and the third oligonucleotide is attached to the unattached end of the second oligonucleotide via a ligation reaction.

The plurality of first oligonucleotides on a spatial array can be attached (e.g., covalently bound or immobilized) to the substrate via either the 3'-end or 5'-end of the oligonucleotide. The attachment of an oligonucleotide to a substrate of a spatial array through a covalent bond can be either direct (e.g., substrate to 3'-end of oligonucleotide) or indirect (e.g., substrate to linker molecule to 3'-end of oligonucleotide). Typically, for commercially available DNA microarrays, the oligonucleotides are attached via a 3' linkage, thereby leaving a free 5'-end. The free 5'-end can be used for further synthesis on the oligonucleotide strand. However, oligonucleotides attached to the substrate via the 5'-end, provide an advantage in having their 3'-ends available for further biosynthetic extension (e.g., using polymerase or transcriptase) as described elsewhere herein.

In at least one embodiment, the first oligonucleotide is attached to the substrate through its 5'-end, the second oligonucleotide is attached to the 3'-end of the first oligonucleotide through its 5'-end, and the third oligonucleotide is attached to the 3'-end of the second oligonucleotide through its 5'-end.

In at least one embodiment, the first oligonucleotide is attached to the substrate through its 3'-end; the second oligonucleotide that is attached to the 5'-end of the first oligonucleotide through its 3'-end, and the third oligonucleotide is attached to the 5'-end of the second oligonucleotide through its 3'-end.

In at least one embodiment of the composition of the present disclosure the length of the oligonucleotide (e.g., a first oligonucleotide, a second oligonucleotide, and/or a third oligonucleotide) in each region is at least 10 nucleotides, at least 20 nucleotides, at least 30 nucleotides, at least 40 nucleotides, at least 50 nucleotides, or at least 60 nucleotides. In some embodiments the length of the oligonucleotide in each region is from 5 nucleotides to 100 nucleotides, from 10 nucleotides to 100 nucleotides, from 20 nucleotides to 100 nucleotides, from 40 nucleotides to 100 nucleotides, from 50 nucleotides to 90 nucleotides, or from 60 nucleotides to 80 nucleotides.

As described elsewhere herein, in some embodiments of the spatial arrays of the present disclosure, the first oligonucleotide of the spatial array includes a 2-mer to 40-mer having the common sequence attached across all, or a substantial contiguous portion, of the surface of the substrate. Thus, the step of attaching the common first oligonucleotide to the substrate does not need to be spatially directed. Accordingly, a variety of different embodiments can be used to attach prepare a substrate having a common first oligonucleotide of 2 to 40 nucleotides in length attached thereto. In some embodiments, the first oligonucleotide of the spatial array can include various domains described herein. For example, the first oligonucleotide can include a cleavage domain, a functional domain (e.g., sequencing handle), a unique molecular identifier, or combinations thereof.

As illustrated by FIGS. 32A-C, in at least one embodiment, a first oligonucleotide can be prepared ex situ by standard automated solid-phase oligonucleotide synthesis in a 3'-to-5' direction using phosphoramidite chemistry. However, as described elsewhere herein, protection of the phosphodiester and exocyclic amine moieties of the first oligonucleotide facilitates the spatially-directed in situ synthesis of the second oligonucleotide on the unattached end of the first oligonucleotide. Thus, as shown in FIG. 32A, in at least one embodiment, the first oligonucleotide is synthesized ex situ using standard techniques, however, the synthesized oligonucleotide is cleaved from the substrate without deprotecting the phosphodiester and exocyclic amine moieties that are protected during synthesis. The protected common oligonucleotide used for the first oligonucleotide is attached to the substrate with the protecting groups intact as shown in FIG. 32B.

The standard oligonucleotide synthesis method using phosphoramidite chemistry was developed in the 1980s and later enhanced with solid-phase supports and automation. It the method used by commercial synthesis of DNA and RNA oligonucleotides. Generally, solid-phase oligonucleotide synthesis proceeds in the 3'→5' direction rather than 5'→3' direction of natural biosynthesis. The solid-phase phosphoramidite synthesis cycle generally includes four steps: (1) detritylation; (2) coupling; (3) oxidation; and (4) capping. Briefly, the four steps in the synthesis cycle are as follows. In step (1), "detritylation," a 5'-DMT protecting group is removed from the first, solid-support-linked nucleoside. In step (2), "coupling," the de-protected 5'-OH of the first, solid-support-linked nucleoside attacks the phosphorus of the incoming second nucleoside to form a phosphite triester. In step (3), "oxidation," the relatively unstable phosphite triester is converted to a stable phosphate triester. In step (4), prior to moving to step (1) of the next cycle, "capping," is carried out wherein unreacted 5'-OH groups are acetylated, thereby preventing elongation of sequences with deletion mutations.

In at least one embodiment of the ex situ synthesis method, the final monomer unit added to the 5'-end during ex situ synthesis of the first oligonucleotide can include a non-natural nucleoside that facilitates attachment or immobilization of the first oligonucleotide to the substrate or linkers attached to the substrate via its 5'-end. Alternatively, in some embodiments of the ex situ synthesis method, the first monomer unit added to the 3'-end during ex situ synthesis of the first oligonucleotide can include a non-natural nucleoside that upon cleavage from the synthesis substrate or feature can facilitate attachment or immobilization of the first oligonucleotide to the substrate or linkers attached to the substrate via the 3'-end.

In at least one embodiment, the first oligonucleotide attached to the substrate is prepared by in situ synthesis on the substrate. Generally, because the sequence of the first oligonucleotide is the same across all regions of the substrate, it is not necessary to use spatially-directed in situ synthesis in such an embodiment. For example, in situ synthesis of the first oligonucleotide can be carried out on the substrate using standard solid-phase phosphoramidite chemistry and reagents. As noted above, maintaining protection of the phosphodiester and exocyclic amine moieties of the first oligonucleotide facilitates the spatially-directed in situ synthesis of the second oligonucleotide on the unattached end of the first oligonucleotide. Accordingly, in at least one embodiment, it is contemplated that the in situ synthesis first oligonucleotide on the substrate is carried out without the final step of deprotecting the phosphodiester and exocyclic amine moieties before the second oligonucleotide is synthesized.

FIGS. 33A-B illustrate an exemplary embodiment of a method for in situ synthesis of a common first oligonucleotide directly on the substrate. The synthesis can be carried out using step-wise solid-phase phosphoramidite chemistry but without final cleavage or deprotection steps. As shown in FIG. 33A, in this embodiment, the synthesis would result in a first oligonucleotide attached across the surface of the substrate with protected phosphodiester and exocyclic amine moieties. Following this in situ synthesis of the first oligonucleotide with protective groups intact, light-directed spatial synthesis of the second oligonucleotide to the 3'-ends of the first oligonucleotides can be carried out as shown in FIG. 33B.

In at least one embodiment, the first oligonucleotide attached to the substrate is prepared by spatially-directed in situ synthesis on the substrate. The spatially-directed oligonucleotide synthesis method used can include light-directed spatial synthesis and/or mechanically-directed spatial synthesis described elsewhere herein. In this embodiment, the spatially-directed synthesis can be used in essentially the same way as the in situ standard oligonucleotide synthesis for the preparation of the first oligonucleotide having a single sequence across all regions of the substrate. It is contemplated, however, that in some embodiments spatially-directed synthesis can be used to prepare a substrate having the first oligonucleotide attached in selected regions of the substrate. For example, in some embodiments, a spatial array could be prepared having more than one first oligonucleotide sequence in different locations of the substrate.

Accordingly, as shown in FIGS. 34A-B that in at least one embodiment the common first oligonucleotide can be in situ synthesized directly on the substrate however using light-directed synthesis with photolabile groups, rather than standard protective groups, such as dimethoxytrityl groups. In some embodiments, the synthesized first oligonucleotides would be prepared using light-directed deprotection but would not be cleaved from the substrate or deprotected as shown in FIG. 34A. Following this light-directed in situ synthesis of the first oligonucleotide with protective groups intact, light-directed spatial synthesis of the second oligonucleotide to the 3'-ends of the first oligonucleotides can be carried out as shown in FIG. 34B.

Generally, during standard automated oligonucleotide synthesis, following cleavage of the oligonucleotide from the synthesis substrate or feature, the protecting groups on the phosphates and bases are removed (or deprotected) by treatment in concentrated aqueous ammonia with heat. Accordingly, it is also contemplated in at least one embodiment that a first oligonucleotide is synthesized ex situ using standard automated synthesis, including cleavage and deprotection of the phosphodiesters and/or exocyclic amine moieties. As illustrated by the schematic of FIG. 35A, the cleaved and deprotected first oligonucleotides synthesized ex situ can be attached to the substrate surface through a linkage to the 5'-end as described elsewhere herein. Then, as depicted by FIG. 35B, the phosphodiester and/or exocyclic amine moieties can be protected in situ on the substrate. Following this in situ protection step, light-directed spatial synthesis of the second oligonucleotide to the 3'-ends of the first oligonucleotides can be carried out as shown in FIG. 35C.

In an embodiment illustrated by the schematic of FIG. 36A, ex situ synthesized first oligonucleotides can be cleaved from their synthesis substrate or feature, deprotected, and then attached to a substrate surface through a linkage to the 5'-end as described elsewhere herein. Then, as depicted by FIG. 36B, a complementary oligonucleotide can be hybridized to the common first oligonucleotides located across the substrate. The formation of a double-stranded structure by hybridization can effectively protect the phosphodiester and/or exocyclic amine moieties of the first oligonucleotide on the substrate. Following this in situ protection-by-hybridization step, light-directed spatial synthesis of the second oligonucleotide to the 3'-ends of the first oligonucleotides can be carried out as shown in FIG. 36C.

In at least one embodiment, the spatial array compositions prepared using the methods of the present disclosure can be useful for spatial transcriptomics applications as described in e.g., U.S. Patent App. No. US2014/0066318A1, incorporated by reference herein in its entirety. Briefly, in spatial transcriptomics a complex multi-cellular sample, such as a biological sample (e.g., tissue section), is immobilized on a spatial array of oligonucleotides. Typically, the oligonucleotide sequences are attached to the array substrate through their 5'-end and include an mRNA capture sequence at their 3'-end. Each of the oligonucleotides also includes 5'-adjacent to the capture sequence, a random primer sequence of at least 16-mer that allows for amplification of any captured sequences. The detection process results in amplification of the captured mRNA sequence as well as the spatial barcode. Sequencing of the amplicons thereby indicates not only the identity of the transcribed gene but also the location in the multi-cellular sample where the gene was transcribed.

Furthermore, in order to survey the genes undergoing transcription in a complex multi-cellular biological sample, the spatial array can include an extremely high density of different oligonucleotides specifically located on the substrate. For example, it is contemplated that spatial arrays useful in various applications, such as spatial transcriptomics, can include 1.5 million, 10 million, 100 million, and even up to 1.0 billion different oligonucleotides, each of which has a different spatial barcode sequence and is located in a different region on a substrate, wherein the regions are less than 5 µm², even as small as 1.0 µm².

As noted elsewhere herein, oligonucleotides of a spatial array can include a different spatial barcode that correlates with its location. In some embodiments, it is contemplated that additional oligonucleotides can be present on the same substrate as the spatial array that include a sequence identical to a barcode sequence of the spatial array. Such additional oligonucleotides can arise due to errors in synthesis or can be prepared intentionally on the substrate (e.g., for calibration or quality control purposes). Generally, these sequences located in a different location on the same substrate are not considered part of the spatial array and are kept to a level and/or location that avoids interference with the intended function of the spatial array.

In some embodiments, methods provided herein can be used to generate an array that allows resolution equal to or less than 10 µm, allowing single-cell resolution. In some embodiments, a spatial array is generated by providing a plurality of sets of primers on a substrate. In some embodiments, a set of the sets of primers includes a first primer and a second primer present at a 1:1 ratio. In some embodiments, the second primer has a sequence that is complementary to the first primer or to a template oligonucleotide.

In some embodiments, methods of preparing a spatial array provided herein include providing a substrate, immobilizing a plurality of sets of primers on the substrate, providing a template oligonucleotide having a reverse complement of a spatial barcode domain, a reverse complement of a capture domain, a first hybridization domain capable of hybridizing to the first primer, and a second hybridization domain, wherein a reverse complement of the second hybridization domain is capable of hybridizing to the second primer; hybridizing the template oligonucleotide to the first primer; extending the first primer using the template oligonucleotide as a template to generate a capture probe comprising the first primer, the spatial barcode, and the capture domain, which capture probe is immobilized on the substrate; and releasing the template oligonucleotide from the spatial array.

In some embodiments, the spatial array comprises a plurality of sets of primers affixed to the substrate. In some embodiments, a first primer and a second primer that are at a 1:1 ratio or about at a 1:1 ratio (e.g., at or about a 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9, or 1:2 ratio) and that are less than 10 µm apart on the substrate. In some embodiments, the first primer and the second primer are about 0.1 µm, 0.2 µm, 0.3 µm, 0.4 µm, 0.5 µm, 0.6 µm, 0.7 µm, 0.8 µm, 0.9 µm, 1.0 µm, 2.0 µm, 3.0 µm, 4.0 µm, 5.0 µm, 6.0 µm, 7.0 µm, 8.0 µm, 9.0 µm, 10.0 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, or 100 µm apart on the substrate.

In some embodiments, the first primer and the second primer are about 0.1 µm to about 100 µm apart on the substrate. In some embodiments, the first primer and the second primer are about 0.5 µm to about 50 µm apart on the substrate. In some embodiments, the first primer and the second primer are about 0.7 µm to about 25 µm apart on the substrate. In some embodiments, the first primer and the second primer are about 1.0 µm to about 20 µm apart on the substrate. In some embodiments, the first primer and the second primer are about 1.0 µm to about 15 µm apart on the substrate. In some embodiments, the first primer and the second primer are about 1.0 µm to about 10 µm apart on the substrate. In some embodiments, the first primer and the second primer are about 1.0 µm to about 5 µm apart on the substrate. In some embodiments, the first primer and the second primer are about 1.0 µm to about 2 µm apart on the substrate.

In some embodiments, the first primer is affixed to the substrate at the 5' end of the first primer. In some embodiments, the second primer is affixed to the substrate at the 5' end of the second primer.

In some aspects, the first primer is single stranded DNA. In some aspects, the first primer is RNA. In some aspects, the second primer is single stranded DNA. In some aspects, the second primer is RNA.

In some embodiments, the first primer on the substrate comprises a sequence that is complementary to the template oligonucleotide and allows the template oligonucleotide to bind to the first primer. In some embodiments, the first primer can also comprise a poly (A) or poly (T) domain that is complementary to a poly(T) or poly(A) domain of the second primer. In some embodiments, the first primer can also comprise a cleavage domain. In some embodiments, the second primer can also comprise a cleavage domain.

In some embodiments, the first primer and the second primer are used to amplify a template oligonucleotide to create a cluster of one or more capture probes. In some aspects, the template oligonucleotide includes a reverse complement of a unique molecular identifier (UMI).

In some embodiments, the template oligonucleotide is attached to a bead (e.g., any of the variety of beads described herein, e.g., a gel bead). In some embodiments, the template oligonucleotide is attached to the bead at the 3' end. In some embodiments, the template oligonucleotide is attached to the bead at the 5' end. In some embodiments, template oligonucleotides that have a bead at the 3' end also have 5' modification, which allows the template oligonucleotide to attach to a support (e.g., any of the variety of functionalized groups for attaching nucleic acids to substrates, e.g., slides, described herein or otherwise known in the art). In some embodiments, template oligonucleotides that have a bead at the 5' end also have 3' modification, which allows the template oligonucleotide to attach to a support (e.g., any of the variety of functionalized groups for attaching nucleic acids to substrates, e.g., slides, described herein or otherwise known in the art). In some aspects, the template oligonucleotide comprises a cleavage sequence that allows the template oligonucleotide to detach from the bead (e.g., after the oligonucleotide has been attached to the support).

In another embodiment, the primer on the support has a non-barcoded universal primer that hybridizes to the template oligonucleotide on beads. In some embodiments, after one round of synthesis, the template oligonucleotide (e.g., a barcode on the template oligonucleotide) is incorporated.

In some aspects, the bead is a gel bead. In some aspects, the bead is less than 10 µm in diameter. In some aspects, the bead is less than 5 µm in diameter. In some aspects, the bead is 2 µm in diameter. In some aspects, the bead is less than 2 µm in diameter. In some aspects, the bead is 1 µm in diameter. In some aspects, the bead is less than 1 µm in diameter.

In some aspects, after the template oligonucleotide binds to a primer, the bead is removed. In some aspects, the bead is removed prior to amplification of the template oligo. In some aspects, the bead is removed after amplification of the template oligo. In some embodiments, the bead is removed by a washing step. Removal of beads can be performed using techniques known in the art.

In some aspects, after binding of the template oligonucleotide to the first primer, the sequence of the first primer is extended. In some aspects, one or more beads (e.g., all of the beads or substantially all of the beads) that are attached to the template oligonucleotide(s) is removed after extension of the first primer. In some aspects, the one or more beads (e.g., all of the beads or substantially all of the beads) that are attached to the oligonucleotide(s) is removed before extension of the primer.

In some aspects, the one or more beads is non-spherical. In some aspects, the non-spherical bead or one or more non-spherical beads is primer loaded. In some aspects, the non-spherical bead or one or more non-spherical beads is hexagonal. In some aspects, hexagonal beads can form in a honeycomb pattern when placed on a support. In some aspects, the non-spherical bead or one or more non-spherical beads is cuboidal. In some aspects, one or more hexagonal or cuboidal beads allows for more compact packing of beads on a substrate than would occur with spherical beads. In some embodiments, after initial binding of the template oligonucleotide and a first primer, a capture probe is generated. In some aspects, the capture probe is generated using cluster expansion.

In some aspects, the capture probe is generated using bridge amplification. The term "bridge amplification" refers to a method of amplifying nucleic acid in which primers (e.g., a first primer and a second primer) that are extended in the reaction are tethered to a substrate by their 5' ends. In some embodiments, the process is repeated to provide amplified, immobilized nucleic acid molecules.

In some embodiments, bridge amplification comprises a first step comprising hybridization of the target nucleic acid to the first primer attached to the support. A first amplification product, which is complementary to the target nucleic acid, is then formed by extension of the first primer sequence. On subjecting the support to denaturation conditions the target nucleic acid is released and can then participate in further hybridization reactions with other first primer sequences which may be attached to the support. The first amplification product which is attached to the support, may then hybridize with the second primer attached to the support, forming a "bridge." In some embodiments, a second amplification product comprising a nucleic acid sequence complementary to the first amplification product can be formed by extension of the second primer sequence and is also attached to the support. Thus, the target nucleic acid and the first and second amplification products are capable of participating in a plurality of hybridization and extension processes, limited only by the initial presence of the target nucleic acid and the number of first primer and second primer sequences initially present and the result is a number of copies of the target sequence attached to the surface. Bridge amplification is further disclosed U.S. Appls. Nos. US-2008-0160580 and US-2008-0286795, each of which is incorporated by reference in its entirety. In some aspects, the capture probe includes a UMI (e.g., any of the variety of UMIs described herein). In some aspects, the capture probe includes the sequence of the first primer, a spatial barcode (e.g., any of the variety of spatial barcodes described herein), and/or a capture domain (e.g., any of the variety of capture domains described herein). In some aspects, the capture probe is immobilized on the substrate. In some aspects, the capture domain comprises a sequence complementary to an analyte of interest. In some aspects, the capture domain comprises a sequence designed to capture messenger RNA. In some aspects, the capture domain comprises a poly(T) domain. In some aspects, the capture domain comprises a target-specific sequence (e.g., a sequence complementary to the sequence of a target of interest, e.g., a target nucleic acid molecule, e.g., a specific messenger RNA or DNA). In some aspects, the capture domain comprises a random sequence (e.g. a hexamer).

In some embodiments, after a copy of the capture probe is generated, the copy of the template oligonucleotide is released by cleaving the cleavage domain after the copy of the capture probe is generated.

In some embodiments, after cluster amplification, all or a portion of the sequence (e.g., identity) of the generated capture probe is determined. In some aspects, the all or a portion of the sequence (e.g., identity) of the generated capture probe is determined after the template oligonucleotide is released. In some aspects, the all or a portion of the sequence (e.g., identity) of the generated capture probe is determined in situ. In some aspects, the all or a portion of the sequence (e.g., identity) of the generated capture probe is determined by in situ sequencing. As non-limiting examples, in situ sequencing can be performed via sequencing-by-synthesis (SBS), sequential fluorescence hybridization, sequencing by ligation, nucleic acid hybridization, or high-throughput digital sequencing techniques.

In some embodiments, after the probe is clonally expanded, spatial analysis of a biological analyte in a biological sample can be performed. For example, spatial analysis can include determining a location of an analyte in a biological sample. In some aspects, methods of performing spatial analysis of a biological analyte in a biological sample include preparing the spatial array (e.g., via any method discussed herein). In some aspects, the methods further include decoding the one or more capture probes by determining the identity of the spatial barcode of the one or more capture probes, thereby associating the spatial barcode of the one or more capture probe with a location on the spatial array; contacting the biological sample to the spatial array under conditions wherein the biological analyte binds a capture probe present in a cluster; extending the capture probe via a polymerization reaction using the biological analyte as a template to generate an extended capture probe that include the sequence of the capture probe and the reverse complement of the sequence of the biological analyte; determining the sequence of the extended capture probe; and associating the spatial barcode of the capture probe with the captured biological analyte, thereby determining spatial location of the analyte in the biological sample.

Generating Capture Probes

Capture probes described herein can contain various functional sequences and a capture domain. In some embodiments, the capture domain captures analytes in an unbiased manner. For example, if the capture domain is a poly(T) sequence, the capture domain can interact (e.g., hybridize) to the poly(A) tail of any given mRNA present in the biological sample, regardless of the identity of that mRNA. In some embodiments, the capture domain can capture analytes in an unbiased manner with via a capture domain having a random or degenerate sequence. As non-limiting examples, a capture domain can include a random hexamer or octamer sequence for unbiased capture. In some embodiments, the capture domain captures analytes in a biased manner. For example, the capture domain can be gene specific, such that a specific analyte (e.g., a specific nucleic acid, e.g., a specific mRNA or DNA sequence) or set of analytes (e.g., set of nucleic acids, e.g., a set of mRNAs or a set of DNAs, e.g., a set of mRNAs or a set of DNAs sharing a common or similar sequence) can be captured for spatial analysis in the biological sample. In some embodiments, the capture domain can capture rRNA analytes. For example, the capture domain can contain a degenerate sequence capable of interacting (e.g., hybridizing) with 16s rRNA. In some embodiments, the capture domain can interact with analytes containing V(D)J sequences. In some embodiments, the capture domain can interact with a capture agent barcode domain associated with an analyte capture agent (e.g., an analyte capture sequence). Capture domains for both unbiased analyte capture and biased capture can be generated from an existing array with a ligation strategy.

Figures 40, 41:
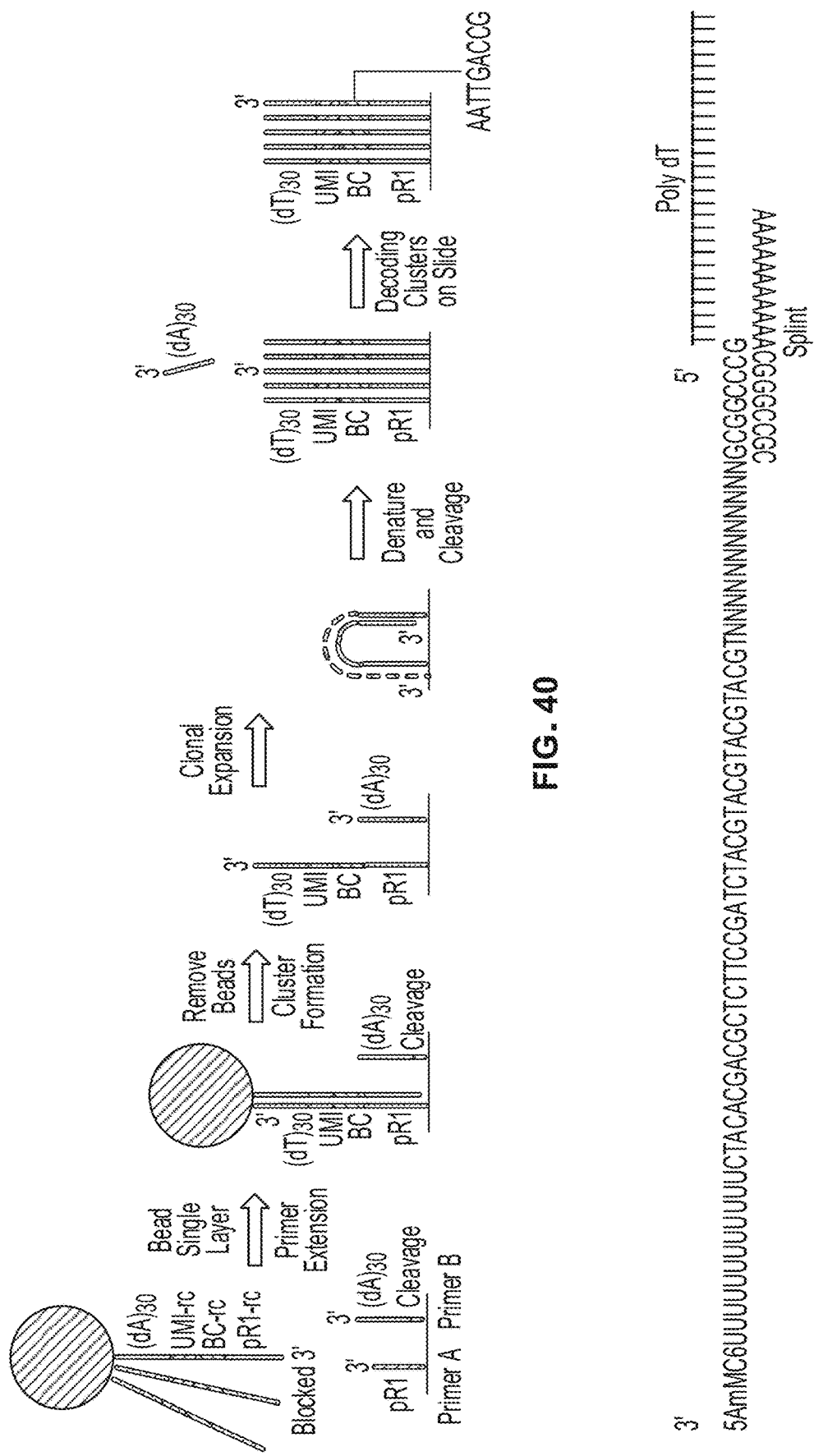
FIG. 40 is a workflow schematic showing oligonucleotide construction.
FIG. 41 shows a method for generating a capture probe.
Figure 42:
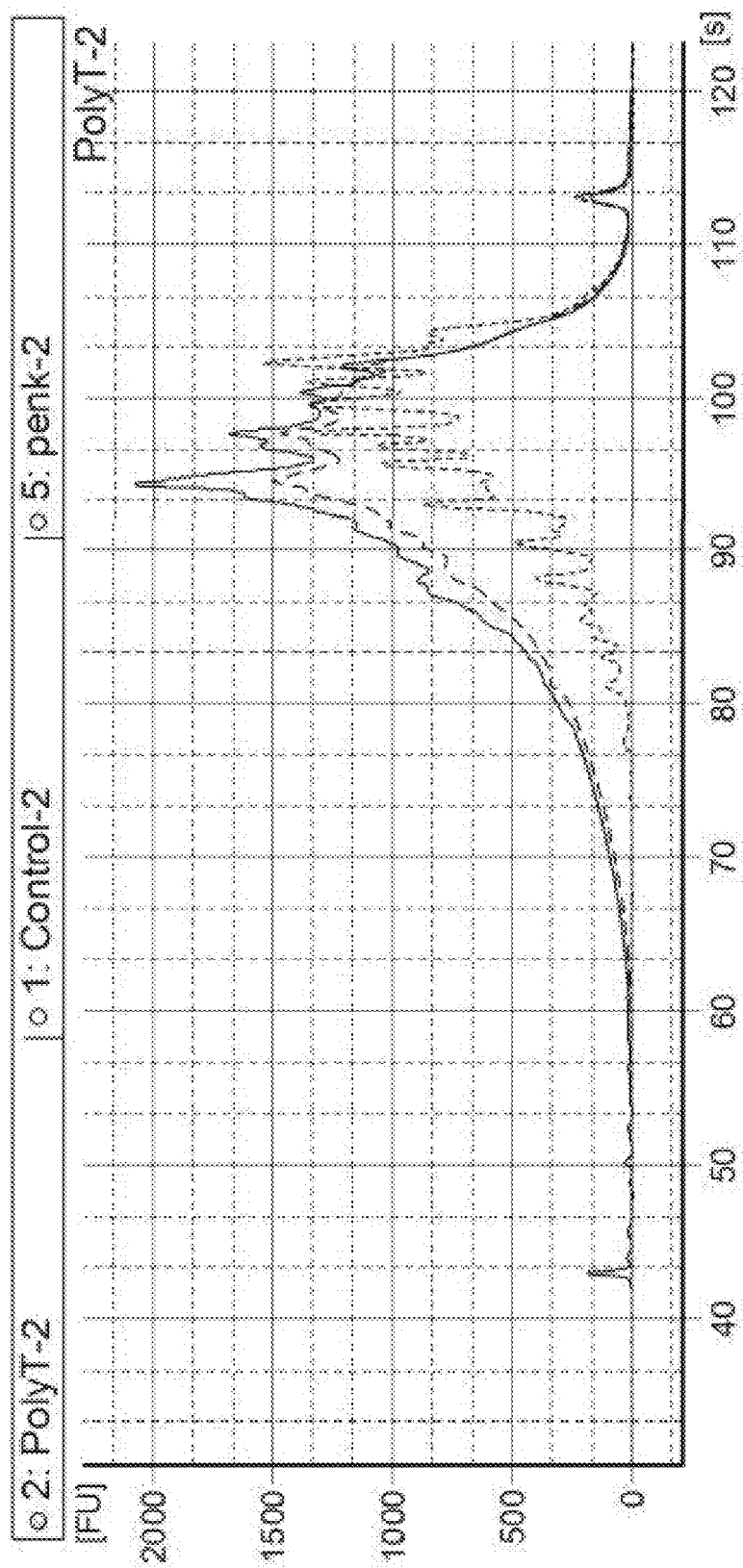
FIG. 42 is a graph showing detection of cDNA with ligated and unligated polyT and gene specific, e.g., Penk gene, capture domains.

Capture probes can be generated from existing arrays with a ligation strategy. In some embodiments, an array containing a plurality of oligonucleotides (e.g., in situ synthesized oligonucleotides) can be modified to generate a variety of capture probes. The oligonucleotides can include various domains such as, spatial barcodes, UMIs, functional domains (e.g., sequencing handle), cleavage domains, and/or ligation handles. As used herein, the term "ligation handle" refers to a portion of an oligonucleotide that is complementary to a portion of a different oligonucleotide. In some embodiments, the different oligonucleotide is a splint oligonucleotide having a sequence complementary to a donor oligonucleotide, and the donor oligonucleotide is ligated to the ligation handle. In some embodiments, the donor oligonucleotide includes a capture domain, such that upon ligation to oligonucleotide having a ligation handle, a capture probe is generated. For example, FIG. 41 shows an acceptor oligonucleotide on a immobilized substrate (e.g., an array), that contains from 5' to 3' an amino modifier C6, followed by 12 uracils that can function as a cleavage domain, a sequencing handle (e.g., R1), a 16 base pair spatial barcode, a 12 base pair UMI, and a ligation handle. In some embodiments, a splint oligonucleotide with a sequence complementary to the ligation handle of the acceptor oligonucleotide and an additional sequence complementary to an oligonucleotide (e.g., a donor oligonucleotide) containing a capture domain (e.g., a capture domain of interest) facilitates the ligation of the oligonucleotide and the oligonucleotide containing the capture domain. In some embodiments, the additional sequence complementary to the capture domain is a poly(A) sequence. In some embodiments, the additional sequence complementary to the capture domain is a sequence specific to a nucleic acid (e.g., an mRNA or DNA sequence). In some embodiments, the additional sequence complementary to the capture domain is a sequence specific to a subset of nucleic acids (e.g., a subset of mRNA or DNA sequences sharing a common or similar sequence). In embodiments where the splint oligonucleotide sequence complementary to the capture domain is a poly(A) sequence, the splint oligonucleotide can facilitate the ligation of a poly(T) capture domain to the oligonucleotide. In embodiments where the splint oligonucleotide sequence complementary to the capture domain is a sequence specific to a nucleic acid, the splint oligonucleotide can facilitate the ligation of that capture domain to the oligonucleotide. In some embodiments, the gene specific capture domain is for Penk mRNA. In embodiments where the splint oligonucleotide sequence complementary to the capture domain is a sequence specific to a subset of nucleic acids, the splint oligonucleotide can facilitate the ligation of that capture domain to the oligonucleotide.

Figure 44:
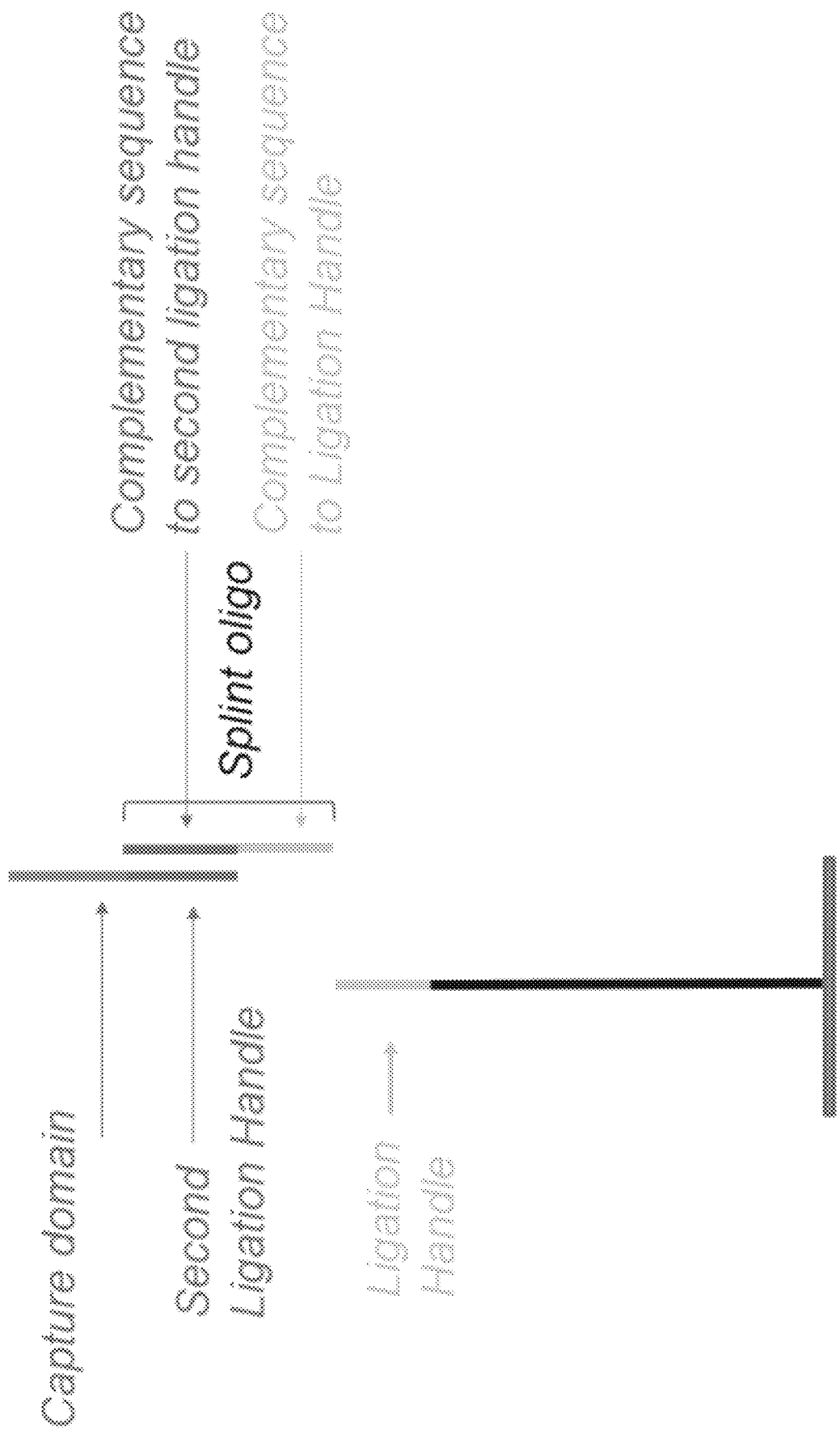
FIG. 44 shows an exemplary ligation-based method for generating a capture probe using two ligation handles.

Capture probes can be generated from existing arrays with a ligation strategy. In some embodiments, an array containing a plurality of oligonucleotides (e.g., in situ synthesized oligonucleotides) can be modified to generate a variety of capture probes. The oligonucleotides can include various domains such as, spatial barcodes, UMIs, functional domains (e.g., sequencing handle), cleavage domains, and/or ligation handles. For example, FIG. 44 shows an exemplary strategy where an acceptor oligonucleotide having a ligation handle is immobilized on a substrate (e.g., an array). In some embodiments, the acceptor oligonucleotide shown in FIG. 44 contains from 5' to 3' one or more of (e.g., each of) an amino modifier C6, 5 thymines, a sequencing handle (e.g., R1), a 16 base pair barcode, a 12 base pair, UMI, and a 7 base pair ligation handle (SEQ ID NO: 8). FIG. 44 shows the ligation handle at the 3' end of the acceptor oligonucleotide (e.g., acceptor oligonucleotide 2). In some embodiments, the ligation handle can be complementary to a sequence in the splint oligonucleotide. In some embodiments, the splint oligonucleotide can have a sequence complementary to a second ligation handle that is present in an oligonucleotide that also includes the capture domain. In some embodiments, the capture domain can be any of the capture domains described herein.

In some embodiments, the splint oligonucleotide includes a sequence that is complementary to an oligonucleotide (e.g., an acceptor oligonucleotide), or a portion thereof, and a sequence that is complementary to an oligonucleotide (e.g., a donor oligonucleotide) containing a capture domain, or a portion thereof (e.g., complementary to the capture domain itself or to a second ligation handle). In some embodiments, the splint oligonucleotide includes a sequence that is perfectly complementary (e.g., is 100% complementary) to an oligonucleotide (e.g., an acceptor oligonucleotide), or a portion thereof, and/or a sequence that is perfectly complementary to an oligonucleotide containing a capture domain, or a portion thereof (e.g., perfectly complementary to the capture domain itself or to a second ligation handle). In some embodiments, the splint oligonucleotide includes a sequence that is not perfectly complementary (e.g., is not 100% complementary) to an oligonucleotide (e.g., an acceptor oligonucleotide), or a portion thereof, and/or a sequence that is not perfectly complementary to an oligonucleotide containing a capture domain, or a portion thereof (e.g., not perfectly complementary to the capture domain itself or to a second ligation handle). In some embodiments, the splint oligonucleotide includes a sequence that is at least 70%, 75%, 80%, 85%, 90%, 95%, 96%, 97%, 98%, or 99% complementary to an oligonucleotide (e.g., an acceptor oligonucleotide), or a portion thereof, and/or a sequence that is complementary to an oligonucleotide containing a capture domain, or a portion thereof (e.g., at least 70%, 75%, 80%, 85%, 90%, 95%, 96%, 97%, 98%, or 99% complementary to the capture domain itself or to a second ligation handle). In some embodiments, the splint oligonucleotide includes a sequence that is perfectly complementary (e.g., is 100% complementary) to an oligonucleotide (e.g., an acceptor oligonucleotide), or a portion thereof, but is not perfectly complementary to a sequence that is complementary to an oligonucleotide containing a capture domain, or a portion thereof (e.g., not perfectly complementary to the capture domain itself or to a second ligation handle). In some embodiments, the splint oligonucleotide includes a sequence that is not perfectly complementary (e.g., is not 100% complementary) to an oligonucleotide (e.g., an acceptor oligonucleotide), or a portion thereof, but is perfectly complementary to a sequence that is complementary to an oligonucleotide containing a capture domain, or a portion thereof (e.g., perfectly complementary to the capture domain itself or to a second ligation handle). So long as the splint oligonucleotide is capable of hybridizing to an oligonucleotide (e.g., an acceptor oligonucleotide), or a portion thereof, and to a sequence that is complementary to an oligonucleotide containing a capture domain, or a portion thereof (e.g., to the capture domain itself or to a second ligation handle), the splint oligonucleotide need not have a sequence that is perfectly complementary to either the oligonucleotide (e.g., the acceptor oligonucleotide) or to the an oligonucleotide containing a capture domain.

The splint oligonucleotide can be about 20 to about 80 nucleotides long. In some embodiments, the splint oligonucleotide can be about 30 to about 70 nucleotides long. In some embodiments, the splint oligonucleotide can be about 40 to about 60 nucleotides long. In some embodiments, the splint oligonucleotide can be about 45 to about 55 nucleotides long.

In some embodiments, the spatial array is generated after ligating capture domains (e.g., poly(T) or gene specific capture domains) to the oligonucleotides (e.g., generating capture probes). The spatial array can be used with any of the spatial analysis methods described herein. For example, a biological sample can be provided to the generated spatial array generated. In some embodiments, the biological sample is permeabilized. In some embodiments, the biological sample is permeabilized under conditions sufficient to allow one or more analytes present in the biological sample to interact with the capture probes of the spatial array. After capture of analytes in the biological sample the analytes can be analyzed (e.g., reverse transcribed, amplified, sequenced) by any of the variety of methods described herein.

EXEMPLARY EMBODIMENTS

This disclosure relates to methods for building an array. In one aspect, provided herein are methods of generating an array for spatial analysis that includes: (a) providing an array that includes a plurality of in situ synthesized oligonucleotides, wherein each of the in situ synthesized oligonucleotides comprise a spatial barcode, and wherein the 3' end of each of the in situ synthesized oligonucleotides are attached to a solid support; (b) providing a plurality of primers complementary to a portion of one or more in situ synthesized oligonucleotides; (c) extending the primers using the one or more in situ synthesized oligonucleotides as a template, thereby generating a first oligonucleotide; (d) extending the first oligonucleotide to produce a 3' end overhang; (e) ligating a splint oligonucleotide to the 5' end of the one or more in situ synthesized oligonucleotides; and (f) ligating a second oligonucleotide to the 3' end of the first oligonucleotide, where the second oligonucleotide includes a sequence that is complementary to a portion of the splint oligonucleotide and a capture domain, thereby generating a plurality of capture probes to be used in an array for spatial analysis. In some embodiments, the splint oligonucleotide includes a sequence that is complementary to the 3' end overhang of the first oligonucleotide. In some embodiments, the plurality of in situ synthesized oligonucleotides include a first constant sequence. In some embodiments, the plurality of in situ synthesized oligonucleotides further comprise a second constant sequence. In some embodiments, the plurality of in situ synthesized oligonucleotides have a length of between 1 and 30 nucleotides. In some embodiments, the second oligonucleotide further includes a constant sequence, and where the constant sequence is complementary to a portion of the splint oligonucleotide. In some embodiments, the second oligonucleotide further includes a degenerate sequence. In some embodiments, the capture domain includes a poly-T sequence. In some embodiments, the 3' end overhang of step (d) is produced by an enzyme. In some embodiments, the enzyme is a template-independent polymerase. In some embodiments, the template-independent polymerase is at least one of terminal deoxynucleotidyl transferase (TdT) and poly A polymerase.

In one aspect, provided herein are methods for spatial analysis of a biological sample that includes: (a) providing an array produced by the method of claim 1; (b) contacting a biological sample with the array; (c) permeabilizing the biological sample under conditions sufficient to allow a plurality of biological analytes in the biological sample to interact with a plurality of capture probes on the array to generate a plurality of spatially barcoded biological analytes; and analyzing the plurality of spatially barcoded biological analytes, thereby determining the spatial location of the plurality of biological analytes.

Capture Probes

In some embodiments, the capture probe is a product of two or more oligonucleotide sequences. In some embodiments, two or more oligonucleotide sequences are ligated together. In some embodiments, the capture probe includes a splint oligonucleotide. In some embodiments, the capture probe includes one or more constant sequences. In some embodiments, the capture probe is generated by having an enzyme add polynucleotides at the end of an oligonucleotide sequence. In some embodiments, the capture probe includes a degenerate sequence. In some embodiments, the degenerate sequence functions as a unique molecular identifier.

In Situ Synthesized Oligonucleotides

In some embodiments, the capture probe includes an in situ synthesized oligonucleotide. In some embodiments, the in situ synthesized oligonucleotide includes one or more constant sequences. In some embodiments, a constant sequence may be a cleavable sequence. In some embodiments, the in situ synthesized oligonucleotide includes a barcode sequence. In some embodiments, the in situ synthesized oligonucleotide includes a variable barcode sequence. In some embodiments, the in situ synthesized oligo have a length of between 1 and 50 nucleotides (e.g. between 1 and 40, between 1 and 30, between 1 and 20, or between 1 and 10 nucleotides). In some embodiments, the in situ synthesized oligonucleotide is attached to an array. In some embodiments, the in situ synthesized oligonucleotide is attached to a feature. In some embodiments, the attachment is direct attachment. In some embodiments, the attachment is an indirect attachment.

Splint Oligonucleotides

The term "splint oligonucleotide", as used herein, refers to an oligonucleotide that, when hybridized to other polynucleotides, acts as a "splint" to position the polynucleotides next to one another so that they can be ligated together. In some embodiments, the splint oligonucleotide is DNA. In some embodiments, the splint oligonucleotide is RNA. In some embodiments, the splint oligonucleotide comprises a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In some embodiments, the splint oligonucleotide is approximately 40 nucleotides in length. In some embodiments, the splint oligonucleotide is between 10 and 50 oligonucleotides in length. In some embodiments, the splint oligonucleotide is between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length. In some embodiments, an RNA ligase is used to ligate two nucleotide sequences together. In some embodiments, a DNA ligase is used to ligate two oligonucleotide sequences together. In some embodiments, the DNA ligase is a T4 DNA ligase.

Degenerate Sequence

In some embodiments of any of the methods described herein, the capture probes may include a degenerate sequence. In some embodiments, a degenerate sequence is a sequence in which some positions of a nucleotide sequence contain a number of possible bases. In some embodiments of any of the methods described herein, a degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 0, 10, 15, 20, 25, or more degenerate positions within the nucleotide sequence. In some embodiments of any of the methods described herein, the degenerate sequence is used as a unique molecular identifier.

This disclosure relates to methods for preparing high-density spatially barcoded arrays and methods for spatial analysis (e.g., analysis of the spatial location(s) of one or more species of analytes in a biological sample) of analytes in a biological sample using a high-density spatially barcoded arrays.

In one aspect, provided herein are methods for preparing a high-density spatially barcoded array, comprising: (a) contacting an array comprising one or more pluralities of capture probes with a hydrogel including one or more pluralities of oligonucleotides; (b) attaching members of the one or more pluralities of capture probes to members of the one or more pluralities of oligonucleotides to form one or more pluralities of coupled capture probes; (c) reducing the size of the hydrogel including the one or more pluralities of coupled capture probes by removing water, forming a shrunken hydrogel including the one or more pluralities of coupled capture probes; thus generating a high-density spatially barcoded array.

In some embodiments, the one or more pluralities of capture probes are immobilized. In some embodiments, the one or more pluralities of immobilized capture probes are partitioned. In some embodiments, the one or more pluralities of immobilized capture probes are partitioned into a plurality of capture probe partitions. In some embodiments, a partitioned plurality of immobilized capture probes is different from another partitioned plurality of immobilized capture probes.

In some embodiments, one or more first pluralities of capture probes comprise a barcode sequence. In some embodiments, one or more pluralities of capture probes comprise a barcode sequence different from the barcode sequence of one or more other pluralities of capture probes. In some embodiments, one or more capture probe partitions comprise a plurality of immobilized capture probes including a barcode sequence different from the barcode sequence of the plurality of immobilized capture probes of one or more other capture probe partitions.

In some embodiments, the one or more pluralities of oligonucleotides are partitioned. In some embodiments, the one or more pluralities of oligonucleotides are partitioned into a plurality of oligonucleotide partitions. In some embodiments, one or more oligonucleotide partitions comprise a plurality of oligonucleotides different from one or more other oligonucleotide partitions. In some embodiments, one or more pluralities of oligonucleotides comprise a barcode sequence. In some embodiments, one or more pluralities of oligonucleotides comprise a barcode sequence different from the barcode sequence of one or more pluralities of oligonucleotides. In some embodiments, the barcode sequence of one or more pluralities of capture probes is different from the barcode sequence of one or more pluralities of oligonucleotides. In some embodiments, one or more oligonucleotide partitions comprise a plurality of oligonucleotides including a barcode sequence different from the barcode sequence of the plurality of oligonucleotides of one or more oligonucleotide partitions.

In some embodiments, the reduction in the size of the hydrogel is isometric.

In some embodiments, the removal of water comprises a dehydrating solvent. In some embodiments, the solvent comprises at least one of an alcohol, a ketone, an aldehyde, acetonitrile, or a combination thereof. In some embodiments, the solvent comprises at least one of glycerol, ethanol, acetonitrile, acetone, 2-propanol, and a combination thereof.

In some embodiments, the removal of water comprises a salt. In some embodiments, the salt comprises an inorganic salt.

In some embodiments, the removal of water comprises an acid.

In some embodiments, the removal of water comprises a dehydrating process.

In some embodiments, the shrunken hydrogel is about 2 to about 10 fold smaller in a linear dimension than the pre-shrunk hydrogel. In some embodiments, the shrunken hydrogel is at least 2-fold smaller in a linear dimension than the pre-shrunk hydrogel. In some embodiments, the shrunken hydrogel is at least 4-fold smaller in a linear dimension than the pre-shrunk hydrogel. In some embodiments, the shrunken hydrogel is at least 8-fold smaller in a linear dimension than the pre-shrunk hydrogel.

In some embodiments, the attaching comprises polymerase chain reaction.

In some embodiments, the hydrogel comprises a DNA polymerase, a plurality of primers, and a plurality of nucleotides.

In some embodiments, members of the plurality of capture probes are cross-linked to the hydrogel.

In some embodiments, members of the one or more pluralities of coupled capture probes are amplified.

In some embodiments, the coupled capture probe is amplified prior to the reduction of the size of the hydrogel.

In some embodiments, the hydrogel is prepared from hydrogel subunits including at least one of: acrylamide, bis-acrylamide, a poly(ethylene glycol), a polyaliphatic polyurethane, a polyether polyurethane, a polyester polyurethane, a polyethylene copolymer, a polyamide, a polyvinyl alcohol, polypropylene glycol, polytetramethylene oxide, polyvinyl pyrrolidone, polyacrylamide, poly(hydroxyethyl acrylate), poly(hydroxyethyl methacrylate), collagen, hyaluronic acid, chitosan, dextran, agarose, gelatin, alginate, a protein polymer, methylcellulose, and a combination thereof.

In some embodiments, one or more capture probes comprise a spatial barcode. In some embodiments, one or more capture probes comprise a unique molecular identifier. In some embodiments, one or more pluralities of capture probes comprise a spatial barcode, and a capture domain.

Also provided herein are methods for spatially profiling a plurality of analytes in a biological sample, including: (a) providing a high-density spatially barcoded array as described herein; (b) contacting the biological sample with the high-density spatially barcoded array under conditions such that one or more analytes present in the biological sample are captured by one or more features of the array; and (c) determining the spatial profile of the captured analytes.

In some embodiments, the biological sample is a tissue sample. In some embodiments, the tissue sample is a fresh-frozen tissue sample. In some embodiments, the tissue sample comprises a tumor cell. In some embodiments, the tissue sample comprises a tissue section.

In some embodiments, the analytes in the biological sample are migrated to the bead array. In some embodiments, the migrating comprises passive migration. In some embodiments, the migrating comprises active migration.

In some embodiments, the one or more analytes comprises at least one of RNA, DNA, protein, lipid, peptide, metabolite, small molecule, and a cell labeling agent.

Methods for Preparing High-Density Spatially Barcoded Arrays

Provided herein are methods for preparing a high-density spatially barcoded array, e.g., a high-diversity and high-density spatially barcoded array. For example, methods for preparing a high-density spatially barcoded array can include attaching capture probes to oligonucleotides in a hydrogel to form coupled capture probes and reducing the size of the hydrogel including the coupled capture probes. In some embodiments, a method for preparing a high-density spatially barcoded array, can include contacting an array including one or more pluralities of capture probes with a hydrogel including one or more pluralities of oligonucleotides; attaching members of the one or more pluralities of capture probes to members of the one or more pluralities of oligonucleotides to form one or more pluralities of coupled capture probes; reducing the size of the hydrogel including the one or more pluralities of coupled capture probes by removing water, forming a shrunken hydrogel including the one or more pluralities of coupled capture probes; thus generating a high-density spatially barcoded array.

In some embodiments, a capture probe is any capture probe as described herein. In some embodiments, the one or more pluralities of capture probes are immobilized.

The term "partition," as used herein, may be a verb or a noun. When used as a verb (e.g., "to partition," or "partitioning"), the term generally refers to the fractionation (subdivision) of a species or sample (e.g., a polynucleotide) such that one fraction (or subdivision) is sequestered from another. Each sequestered section is referred to using the noun "partition." In some embodiments, a partition maintains separation of its own contents from the contents of other partitions. A partition may be any suitable area in which one fraction of a sample is separated or sequestered from another. In some embodiments, a hydrogel can comprise one or more partitions of a species or sample (e.g., a polynucleotide), wherein the hydrogel matrix maintains the separation of the contents of one partition from the contents of other partitions. In some embodiments, a partition has defined dimensions.

In some embodiments, the one or more pluralities of immobilized capture probes are partitioned. In some embodiments, the one or more pluralities of immobilized capture probes are partitioned into a plurality of capture probe partitions. In some embodiments, a partitioned plurality of immobilized capture probes is different from another partitioned plurality of immobilized capture probes.

In some embodiments, one or more first pluralities of capture probes comprise a barcode sequence. In some embodiments, one or more pluralities of capture probes comprise a barcode sequence different from the barcode sequence of one or more other pluralities of capture probes. In some embodiments, one or more capture probe partitions comprise a plurality of immobilized capture probes including a barcode sequence different from the barcode sequence of the plurality of immobilized capture probes of one or more other capture probe partitions.

In some embodiments, the one or more pluralities of oligonucleotides are partitioned. In some embodiments, the one or more pluralities of oligonucleotides are partitioned into a plurality of oligonucleotide partitions. In some embodiments, one or more oligonucleotide partitions comprise a plurality of oligonucleotides different from one or more other oligonucleotide partitions. In some embodiments, one or more pluralities of oligonucleotides comprise a barcode sequence. In some embodiments, one or more pluralities of oligonucleotides comprise a barcode sequence different from the barcode sequence of one or more pluralities of oligonucleotides. In some embodiments, the barcode sequence of one or more pluralities of capture probes is different from the barcode sequence of one or more pluralities of oligonucleotides. In some embodiments, one or more oligonucleotide partitions comprise a plurality of oligonucleotides including a barcode sequence different from the barcode sequence of the plurality of oligonucleotides of one or more oligonucleotide partitions.

In some embodiments, each capture probe comprises a spatial barcode. In some embodiments, each capture probe from the plurality of capture probes comprises a unique molecular identifier. In some embodiments, each capture probe comprises a cleavage domain, a spatial barcode, a unique molecular identifier, and a capture domain.

A "coupled capture probe" as used herein refers to a capture probe that is attached to an oligonucleotide (e.g., an oligonucleotide in a hydrogel). For example, one or more domains of a capture probe can be attached to one or more domains of an oligonucleotide (e.g., an oligonucleotide in a hydrogel). "Attaching" can refer to any method that binds a capture probe to an oligonucleotide (e.g., an oligonucleotide in a hydrogel). For example, an oligonucleotide can be ligated to an end of a capture probe. As another example, PCR can be used to attach one or more domains of a capture probe to one or more domains of an oligonucleotide (e.g., an oligonucleotide in a hydrogel).

In some embodiments, members of the one or more pluralities of capture probes comprise a nucleic acid, e.g., an oligonucleotide. In some embodiments, attaching members of the one or more pluralities of capture probes to members of the one or more pluralities of oligonucleotides to form one or more pluralities of coupled capture probes comprises polymerase chain reaction (PCR). In some embodiments, the hydrogel includes PCR reagents such as a DNA polymerase, a plurality of primers, and a plurality of nucleotides. In some embodiments, members of the plurality of features are amplified (see, e.g., Mitra and Church, Nucleic Acids Res. 1999 Dec. 15; 27(24):e34, which is incorporated by reference herein in its entirety).

In some embodiments, chemical ligation can be used to ligate two or more oligonucleotides (e.g., a capture probe and an oligonucleotide from a hydrogel as described herein). In some embodiments, chemical ligation involves the use of condensing reagents. In some embodiments, condensing reagents are utilized to activate a phosphate group. In some embodiments, condensing reagents may be one or more of 1-25 ethyl-3-(3-dimethylaminopropyl) carbodiimide (EDCI), cyanogen bromide, imidazole derivatives, and 1-hydroxybenzotriazole (HOAt). In some embodiments, functional group pairs selected from one or more of a nucleophilic group and an electrophilic group, or an alkyne and an azide group are used for chemical ligation. In some embodiments, chemical ligation of two or more oligonucleotides requires a template strand that is complementary to the oligonucleotides to be ligated. In some embodiments, the chemical ligation process is similar to oligonucleotide synthesis.

In some embodiments, not all of the domains of a capture probe are attached to an oligonucleotide to form a coupled capture probe. For example, a coupled capture probe may comprise 1, 2, 3, 4, or 5 domains of the original capture probe. In some embodiments, all the domains of the capture probe are attached to the oligonucleotide. For example, the coupled capture probe comprises all the domains of the original capture probe.

In some embodiments, members of the one or more pluralities of capture probes are cross-linked to a hydrogel.

As used herein "shrinking" or "reducing the size of" a hydrogel refers to any process causing the hydrogel to physically contract and/or the size of the hydrogel to decrease in volume. For example, the scaffold of the gel may shrink or "implode" upon solvent removal (see, e.g., Long and Williams. Science. 2018; 362(6420):1244-1245, and Oran et al. Science. 2018; 362(6420):1281-1285; each of which is incorporated herein by reference in its entirety). As another example, the process to shrink or reduce the size of a hydrogel may be one that removes water (i.e., a dehydrating process) from the hydrogel. There are many methods known to one of skill in the art for shrinking or reducing the size of a hydrogel. Non-limiting examples of a method to shrink or reduce the size of a hydrogel include exposing the hydrogel to one or more of: a dehydrating solvent, a salt, heat, a vacuum, lyophilization, desiccation, filtration, and air-drying.

In some embodiments, the removal of water comprises a dehydrating solvent. Non-limiting examples of a dehydrating solvent include a ketone (such as methyl ethyl ketone (MEK)), isopropanol (IPA), acetone, 1-butanol, methanol (MeOH), dimethyl sulfoxide (DMSO), glycerol, propylene glycol, ethylene glycol, ethanol, (k) 1,4-dioxane, propylene carbonate, furfuryl alcohol, N,N-dimethylformamide (DMF), acetonitrile, and an aldehyde (such as formaldehyde or glutaraldehyde). In some embodiments, the solvent comprises at least one of an alcohol, a ketone, an aldehyde, acetonitrile, and a combination thereof. In some embodiments, the solvent comprises a solvent selected from the group consisting of: glycerol, ethanol, acetonitrile, acetone, 2-propanol, and a combination thereof.

In some embodiments, the removal of water comprises a salt. In some embodiments, the salt comprises an inorganic salt. Non-limiting examples of salts that may be used to shrink a hydrogel include inorganic salts such as aluminum, ammonium, barium, beryllium, calcium, cesium, lithium, magnesium, potassium, rubidium, sodium, and strontium salts. Further non-limiting examples of inorganic salts include sodium chloride, potassium chloride, lithium chloride, cesium chloride, sodium fluoride, sodium bromide, sodium iodide, sodium nitrite, potassium sulfate, potassium nitrate, potassium carbonate, potassium bicarbonate, sodium sulfate, sodium nitrate, sodium carbonate, sodium bicarbonate, calcium sulfate, copper oxychloride, calcium chloride, calcium carbonate, calcium bicarbonate, magnesium sulfate, magnesium nitrate, magnesium chloride, magnesium carbonate, magnesium bicarbonate, ammonium sulfate, ammonium chloride, ammonium nitrate, ammonium carbonate, ammonium bicarbonate, trisodium phosphate, tripotassium phosphate, calcium phosphate, copper(II) sulfate, sodium sulfide, potassium sulfide, calcium sulfide, potassium permanganate, iron(II) chloride, iron(III) chloride, iron (2+) sulfate, iron(III) sulfate, iron(II) nitrate, iron(III) nitrate, manganese(II) chloride, manganese(III) chloride, manganese(II) sulfate, manganese(II) nitrate, zinc chloride, zinc nitrate, zinc sulfate, ammonium orthomolybdate, monopotassium phosphate, nickel(II) sulfate, nickel(II) nitrate, sodium metavanadate, sodium paravanadate, potassium dichromate, ammonium dichromate, antipyonin, ammonium nitrite, potassium fluoride, sodium fluoride, ammonium fluoride, calcium fluoride, chrome alum, potassium alum, potassium iodide, sodium hypochlorite, tin(II) sulfate, tin(II) nitrate, gold selenite, dicesium chromate, potassium perchlorate, calcium perchlorate, aluminium sulphate, lead(II) bisulfate, barium phosphate, barium hydrogen orthophosphate, barium dihydrogen phosphate, silver dichromate, potassium bromate, sodium bromate, sodium iodate, sodium silicate, diammonium phosphate, ammonium phosphate, ammonium dihydrogen phosphate, chromium orthophosphate, copper(II) chloride, copper(I) chloride, sodium tetrametaphosphate, potassium heptafluoroniobate, zinc phosphate, sodium sulfite, copper(I) nitrate, copper(II) nitrate, potassium silicate, copper(II) carbonate basic, copper(II) carbonate salts of acrylic acid and sulfopropyl acrylate.

In some embodiments, the removal of water comprises an acid. In some embodiments, the hydrogel is exposed to a different pH environment. For example, the hydrogel can be exposed to an acidic pH or a basic pH. In some embodiments, the hydrogel is exposed to a pH of less than about 6.5, e.g., a pH of about 6, about 5.5, about 5, about 4.5, about 4, about 3.5, about 3, about 2.5, about 2, about 1.5, or about 1. In some embodiments, the hydrogel is exposed to a pH of greater than about 7.5, e.g., a pH of about 8, about 8.5, about 9, about 9.5, about 10, about 10.5, about 11, about 11.5, 10 about 12, about 12.5, about 13, about 13.5, or about 14.

In some embodiments, the removal of water comprises a dehydrating process such as heat, a vacuum, lyophilization, desiccation, filtration, and air-drying. In some embodiments, the hydrogel is exposed to an increased temperature, e.g., a higher temperature than about room temperature. For example, a temperature of about 37° C., 38 15° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. 60° C., 61° C., 62° C., 63° C., 64° C., 65° C., 66° C., 67° C., 68° C., 69° C., or 70° C., or higher. As another example, the hydrogel is exposed to an increase in temperature from about 37° C., 38° C., 39° C., 40° C., 41° C., 42° C., 43° C., 44° C., 45° C., 46° C., 47° C., 48° C., or 49° C. to about 50° C., 51 20° C., 52° C., 53° C., 54° C., 55° C., 56° C., 57° C., 58° C., 59° C. 60° C., 61° C., 62° C., 63° C., 64° C., 65° C., 66° C., 67° C., 68° C., 69° C., or 70° C., or higher).

In some embodiments, more than one method to shrink or reduce the size of a hydrogel can be used. For example, a hydrogel can be exposed to an acid and subsequently dehydrated by another method such as heat, a vacuum, lyophilization, desiccation, filtration, or a combination thereof.

In some embodiments, the hydrogel can further comprise a cross-linking agent. The cross linking agent may help stabilize the hydrogel and/or modulate the extent the hydrogel shrinks. Non-limiting examples of a cross-linking agent include disuccinimidyl suberate (DSS), dimethylsuberimidate (DMS), formalin, dimethyladipimidate (DMA), dithiobis(-succinimidyl propionate) (DSP), disuccinimidyl tartrate (DST), and ethylene glycol bis(succinimidyl succinate) (EGS). In some embodiments, the shrunken hydrogel is at least about 2-fold smaller in a linear dimension (e.g., along one axis) than the pre-shrunk hydrogel. For example, at least about 2.5, about 3, about 4, about 5, about 6, about 7, about 8, about 9, about 10, or more fold smaller in a linear dimension than the pre-shrunk hydrogel. In some embodiments, a shrunken hydrogel is about 2 to about 10 fold smaller in a linear dimension than the pre-shrunk hydrogel. For example, about 2 to about 3, about 2 to about 4, about 2 to about 5, about 2 to about 6, about 2 to about 7, about 2 to about 8, about 2 to about 9, about 9 to about 10, about 8 to about 10, about 7 to about 10, about 6 to about 10, about 5 to about 10, about 4 to about 10, or about 3 to about 10. In some embodiments, a shrunken hydrogel is about 2 to about 4, about 3 to about 5, about 4 to about 6, about 5 to about 7, about 6 to about 8 fold smaller in a linear dimension than the pre-shrunk hydrogel. In some embodiments, a shrunken hydrogel is about 2, about 3, about 4, about 5, about 6, about 7, about 8, about 9, or about 10 fold smaller in a linear dimension than the pre-shrunk hydrogel.

In some embodiments, the size of the hydrogel is reduced along more than one axes, e.g., along 2 or 3 axes. In some embodiments, each axis intersects each other axis at 90 degrees. In some embodiments, the size of the hydrogel along the first axis is about 20 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the size of the hydrogel along the second axis is about 2 to about 10 or more fold smaller than the pre-shrunk hydrogel, e.g., about 2, about 3, about 4, about 5, about 6, about 7, about 8, about 9, about 10 or more fold smaller than the pre-shrunk hydrogel. In some embodiments, the size of the hydrogel along the third axis is about 2 to about 10 or more fold smaller than the preshrunk hydrogel, e.g., about 2, about 3, about 4, about 5, about 6, about 7, about 8, about 9, about 10 or more fold smaller than the pre-shrunk hydrogel. In some embodiments, the reduction in the size of the hydrogel is isometric.

In some embodiments, a hydrogel is prepared from hydrogel subunits including at least one of: acrylamide, bis-acrylamide, a poly(ethylene glycol), a polyaliphatic polyurethane, a polyether polyurethane, a polyester polyurethane, a polyethylene copolymer, a polyamide, a polyvinyl alcohol, polypropylene glycol, polytetramethylene oxide, polyvinyl pyrrolidone, polyacrylamide, poly(hydroxyethyl acrylate), poly(hydroxyethyl methacrylate), collagen, hyaluronic acid, chitosan, dextran, agarose, gelatin, alginate, a protein polymer, methylcellulose, and a combination thereof.

In some embodiments, the size of a hydrogel including coupled capture probes is reduced, thus increasing the density of the coupled capture probe. In some embodiments, the volume of a partition of members of the plurality of capture probes in a hydrogel is reduced when the size of the hydrogel is reduced.

Methods for Spatial Analysis of Analytes Using a Barcoded Biological Sample

In some embodiments, a high-density spatially barcoded array (e.g., a high density spatially barcoded array as described herein) can be used for spatial analysis of analytes in the biological sample. For example, methods for spatially profiling a plurality of analytes in a biological sample can include providing a high-density spatially barcoded array as described herein; contacting the biological sample with the high-density spatially barcoded array under conditions such that one or more analytes present in the biological sample are captured by one or more capture probes of the array; and determining the spatial profile of the captured analytes.

This disclosure relates to methods for building an array. In some embodiments, methods of generating an array comprise: (a) providing an array including a plurality of features immobilized on a solid substrate, wherein each feature comprises a plurality of in situ synthesized oligonucleotides, and wherein each in situ synthesized oligonucleotide comprises a first barcode; (b) selecting one or more in situ synthesized oligonucleotides from the plurality of in situ synthesized oligonucleotides; (c) delivering an oligonucleotide to the one or more selected in situ synthesized oligonucleotides, wherein the oligonucleotide comprises a second barcode and a capture domain; and (d) attaching the oligonucleotide to the one or more selected in situ synthesized oligonucleotides, thereby generating one or more capture probes including the first barcode and the second barcode, thereby generating an array.

In some embodiments, each feature of the plurality of features is associated with one of a number of different first barcodes. In some embodiments, each oligonucleotide is associated with one of a number of different second barcodes.

In some embodiments, step (d) comprises ligating the oligonucleotide to the one or more selected in situ synthesized oligonucleotides. In some embodiments, the method comprises ligating the oligonucleotide to the one or more selected in situ synthesized oligonucleotides using a ligase. In some embodiments, the oligonucleotide is attached to the one or more selected in situ synthesized oligonucleotides by a chemical coupling reaction. In some embodiments, each of the in situ synthesized oligonucleotide comprises a 3' end that is masked by a protective group. In some embodiments, the method comprises removing the protective group from the one or more selected in situ synthesized oligonucleotides prior to delivering an oligonucleotide to the one or more selected in situ synthesized oligonucleotides. In some embodiments, the protective group is a photocleavable protective group. In some embodiments, the protective group is removed by exposing the one or more selected in situ synthesized oligonucleotides to light. In some embodiments, the protective group coupled to the one or more selected in situ synthesized oligonucleotides is removed by applying a photomask.

In some embodiments, the selected in situ synthesized oligonucleotides are separated from the remaining in situ synthesized oligonucleotides by one or more physical barriers, wherein the one or more physical barriers form one or more chambers, and wherein the oligonucleotide is delivered to the one or more chambers including the one or more selected in situ synthesized oligonucleotides. In some embodiments, the one or more physical barriers include a hydrophobic surface. In some embodiments, the one or more physical barriers include one or more chamber walls having a tapered end. In some embodiments, the oligonucleotide comprises a unique molecular identifier. In some embodiments, the oligonucleotide comprises a 3' end that is masked. In some embodiments, a free 3'-OH group on the capture probes is created.

In some embodiments, methods of generating an array comprise: (a) providing an array including two or more partitions, wherein each partition comprises a plurality of features immobilized on a substrate, wherein each feature comprises a plurality of in situ synthesized oligonucleotides, and wherein each in situ synthesized oligonucleotide comprises a first barcode; (b) delivering an oligonucleotide to a first partition, wherein the oligonucleotide comprises a second barcode and a capture domain; and (c) attaching the oligonucleotide to one or more in situ synthesized oligonucleotides in the first partition, thereby generating one or more capture probes including the first barcode and the second barcode in the first partition, thereby generating an array.

In some embodiments, methods provided herein further comprise: (d) delivering a second oligonucleotide to a second partition, wherein the second oligonucleotide includes a third barcode; and (e) attaching the second oligonucleotide to one or more in situ synthesized oligonucleotides in the second partition, thereby generating capture probes including the first barcode and the third barcode in the second partition.

In some embodiments, the two or more partitions are separated by one or more physical barriers. In some embodiments, the one or more physical barriers are printed on the solid substrate. In some embodiments, the one or more physical barriers form one or more chambers comprising one or more chamber walls. In some embodiments, the one or more chamber walls comprise a hydrophobic surface. In some embodiments, the one or more chamber walls comprise a tapered end in contact with the solid substrate. In some embodiments, the second nucleotide is delivered using a microfluidic device.

Chemical Ligation of Oligonucleotides

In some embodiments, chemical ligation can be used to ligate two or more oligonucleotides. In some embodiments, chemical ligation involves the use of condensing reagents. In some embodiments, condensing reagents are utilized to activate a phosphate group. In some embodiments, condensing reagents may be one or more of 1-ethyl-3-(3-dimethylaminopropyl) carbodiimide (EDCI), cyanogen bromide, imidazole derivatives, and 1-hydroxybenzotriazole (HOAt). In some embodiments, functional group pairs selected from one or more of a nucleophilic group and an electrophilic group, or an alkyne and an azide group are used for chemical ligation. In some embodiments, chemical ligation of two or more oligonucleotides requires a template strand that is complementary to the oligonucleotides to be ligated. In some embodiments, the chemical ligation process is similar to oligonucleotide synthesis.

Photocleavable Protective Group

In some embodiments, a photocleavable protective group (e.g. any photocleavable, photoremovable, photoreleasable, photoactivatable, or photosensitive protective group described herein or known in the art) may be coupled to one or both ends of an in situ synthesized oligonucleotide, a tagging probe (e.g. any of the tagging probes described herein), or a capture probe (e.g. any of the capture probe described herein). In some embodiments, a photocleavable protective group is a chemical modification to a molecule that can be removed with light. In some embodiments, the photocleavable protective group (PPG) is at least one of a nitrobenzyl-based PPG, a carbonyl-based PPG, or a benzyl-based PPG. In some embodiments, the photocleavable protective group is removed from one or more tagging probes by exposing the one or more tagging probes to a light.

The present disclosure provides sample preparation techniques that allow the enrichment of target analytes from a library, based on a barcode corresponding to a set spatial region of interest. Procedures for barcoding and isolating analytes from single cells are herein discussed. Enrichment of select target spatial barcodes corresponding to analytes of interest is more efficient, as not all analytes from a library are subject to downstream processes. Thus enrichment of analytes based on spatial barcodes may allow downstream processes such as sequencing to be more efficient or provide higher quality data from the desired analytes.

In some embodiments provided is a method for enriching a population of capture probes comprising: (a) providing a plurality of capture probes wherein:
(i) members of the plurality of capture probes comprise a plurality of different spatial barcodes, and (ii) each member of the population of capture probes to be enriched comprises a target spatial barcode; and (b) enriching the population of capture probes comprising the target spatial barcode.

In some embodiments provided is a method for spatial analysis of a tissue comprising: (a) providing a solid substrate comprising a plurality of capture probes, wherein a subset of capture probes is attached at a predetermined position on the solid substrate, and wherein each capture probe of the subset comprises an identical spatial barcode; (b) contacting a tissue sample with the solid substrate such that the subset of capture probes interacts with a plurality of analytes from the tissue sample to generate a plurality of spatially barcoded analyte molecules, wherein a member of the plurality of spatially barcoded analyte molecules comprises the identical spatial barcode or a complement thereof, (c) identifying a spatial region of interest within the tissue sample, wherein the spatial region of interest comprises the plurality of spatially barcoded analyte molecules; and (d) enriching the plurality of spatially barcoded analyte molecules for spatial analysis of the tissue sample.

In some embodiments, the solid substrate further comprises an additional subset of capture probes attached at a predetermined position on the solid substrate, wherein a member of the additional subset of capture probes comprises a second identical spatial barcode that is different from the spatial barcode.

In some embodiments, the solid substrate further comprises an additional subset of capture probes attached at a predetermined position on the solid substrate, wherein a member of the additional subset of capture probes comprises a third identical spatial barcode that is different from the previously used spatial barcodes.

In some embodiments, the capture probe comprises an analyte capture domain.

In some embodiments, the analyte comprises at least one of RNA, DNA, and a cell labeling agent.

In some embodiments, the cell labelling agent comprises an antigen binding molecule.

In some embodiments, the cell labelling agent comprises a region configured to couple to the capture domain of the capture probe.

In some embodiments, the spatial region of interest is identified by performing shallow sequencing of at least a subset of the plurality of spatially barcoded analyte molecules, and identifying a target spatial barcode.

In some embodiments, the spatial region of interest is identified by at least one of immunostaining, immunohistochemistry, microscopy, visual inspection, and combinations thereof.

In some embodiments, the method further comprises performing a nucleic acid extension reaction using (i) the plurality of spatially barcoded analyte molecules and (ii) a primer comprising a sequence specific for the identical spatial barcode or a complement thereof to generate an enriched plurality of spatially barcoded analyte molecules comprising the spatial barcode or a complement thereof.

In some embodiments, the analyte is amplified by performing a polymerase chain reaction (PCR).

In some embodiments, the method further comprises enriching a population of capture probes present in a sub-spatial region of interest: (a) wherein the sub-spatial region of interest is located within the spatial region of interest, wherein the sub-spatial region of interest comprises a sub-plurality of capture probes, and wherein: (i) members of the sub-plurality of capture probes comprise identical sub-spatial barcodes, (ii) members of the sub-plurality of capture probes to be enriched comprise a second target spatial barcode sequence; and (iii) the second target spatial barcode sequence is associated with the sub-spatial region of interest; and (b) enriching the population of capture probes comprising the second target spatial barcode sequence.

In some embodiments, the method further comprises enriching a population of capture probes present in a sub-sub-spatial region of interest: (a) wherein the sub-sub-spatial region of interest is located within the sub-spatial region of interest, wherein the sub-sub-spatial region of interest comprises a third plurality of capture probes, and wherein: (i) members of the third plurality of capture probes comprise a third plurality of spatially barcoded sequences, (ii) members of the third plurality of capture probes to be enriched comprise a third target spatial barcode sequence; and (iii) the third target spatial barcode sequence is associated with the sub-sub-spatial region of interest; and (b) enriching the population of capture probes comprising the third target spatial barcode sequence.

In some embodiments, the subset of spatial barcodes comprise one unique barcode.

In some embodiments, a spatial barcode sequence of the subset of spatial barcodes identifies an analyte derived from a single cell.

In some embodiments, the plurality of spatially barcoded analyte molecules corresponds to one or more mRNAs in the tissue sample.

In some embodiments, the plurality of spatially barcoded analyte molecules corresponds to one or more proteins in the tissue sample.

In some embodiments, the plurality of spatially barcoded analyte molecules corresponds to one or more antibodies in the tissue sample.

In some embodiments, the plurality of spatially barcoded analyte molecules corresponds to one or more T-cell receptors in the tissue sample.

In some embodiments, the plurality of spatially barcoded analyte molecules corresponds to one or more regions of genomic DNA in the tissue sample.

In some embodiments, the plurality of spatially barcoded analyte molecules corresponds to one or more regions of chromatin in the tissue sample.

In some embodiments, the plurality of spatially barcoded analyte molecules corresponds to a clustered regularly interspaced short palindromic repeat (CRISPR) ribonucleic acid (crRNA) or a single guide ribonucleic acid (sgRNA) in the tissue sample. In some embodiments, the plurality of spatially barcoded analyte molecules corresponds to a microbiome or a portion thereof.

Shallow Sequencing

As used herein, the coverage or depth of sequencing is the number of unique reads that include a given nucleotide in a reconstructed sequence. As used herein, shallow sequencing is a small or low number of unique reads of an identified analyte. In some embodiments, shallow sequencing is performed to identify a spatial region of interest. In some embodiments, shallow sequencing is performed on an entire tissue sample. In some embodiments, shallow sequencing is performed on an identified region of a tissue sample. In some embodiments, shallow sequencing is performed after identifying and/or selecting a region of a tissue sample by some other method.

Spatial Analyte Capture

As used herein, spatial analyte capture may utilize nucleic acid probes comprising spatial barcode sequences, which are immobilized on a solid substrate to generate an array. The spatial barcode sequences correspond to the location of the capture probes on the array. In some embodiments, biological samples, such as tissue sections, are placed onto the array and the DNA is processed, e.g. fragmented and provided with a binding domain that hybridizes to the probes on the array. In some embodiments, DNA polymerase extension or ligation reaction is performed in the tissue section on the array. In some embodiments, the probes to which the processed DNA in the tissue section binds, are extended using the bound DNA as a template to obtain complementary strands of DNA, which is therefore immobilized on the surface of the array. In some embodiments, probes to which the processed DNA in the tissue section binds, template the ligation of the bound DNA to a second strand of the probe or the strand of the DNA hybridized to the probe may template the ligation of the other strand of DNA to the probe, which is therefore immobilized on the surface of the array. In some embodiments, the spatial barcode sequences in the probes, the extended probes carry information about the position of the "captured" DNA in the biological specimen, e.g. tissue section. In some embodiments, the extended probes may be released from the surface of the array and analyzed, e.g. sequenced, which results in a genomic DNA "library" with exact positional information. In some embodiments, the sequence data can then be matched to a position in the biological specimen, e.g. tissue section. For instance, the tissue section may be visualized or imaged, e.g. stained and photographed, before or after the DNA synthesis or ligation step to facilitate the correlation of the positional tag in the DNA molecule with a position within the tissue section and the sequence data may be overlaid on an image of the tissue section, e.g. using a computer, to display the distribution pattern of any gene of interest across the tissue section. The visualization step is not essential as the tagged DNA molecule may be correlated with a position in the tissue sample using other means, e.g. the unique profile of the molecules captured with the same positional tag, i.e. at the same on the array, may enable the molecule to be correlated to a position within the tissue sample based on the characteristics of cells or areas of cells within the tissue sample. Other analytes may be captured by this method, including but not limited to RNA, specific sub-types of RNA, proteins, antibodies, genomic DNA, T-cell receptors, small molecules, or other material.

Target Barcode Sequence

In some embodiments, a target barcode sequence is a barcode sequence corresponding to a spatial region of interest. In some embodiments, a target barcode sequence is or includes a spatial barcode. In some embodiments, a target barcode sequence is identified by identifying a spatial region of interest and identifying the barcode associated with the spatial region of interest on the array. In some embodiments, a target barcode sequence is identified by performing shallow sequencing, and selecting a barcode based on the captured analytes. In some embodiments, a target barcode sequence is identified by a co-localization of a target barcode sequence with one or more additional barcode sequences. In some embodiments, a target barcode sequence is identified manually. In some embodiments, a target barcode sequence is identified using a computer. In some embodiments, a target barcode sequence is identified algorithmically. In some embodiments, the target barcode sequence corresponds to a plurality of spatial barcode sequences that identify a region, a sub-region, a sub-sub-region, or further spatial demarcation. In some embodiments, a target barcode sequence is a unique molecular identifier, which identifies one capture probe. In some embodiments, a target barcode sequence is used to identify and characterize captured analytes at single-cell resolution. In some embodiments, the identifying can comprise sequencing a plurality of capture probes to generate a plurality of sequencing reads, and analyzing the plurality of sequencing reads to identify the at least one target barcode sequence. In some embodiments, each of the plurality of capture probes can further comprise one or more functional sequences selected from the group consisting of a sequencing primer sequence and a sequence configured to attach to a flow cell of a sequencer. In some embodiments, the plurality of capture probes can comprise, from 5' to 3', a first functional domain (e.g., adapter sequence), a sequence derived from a template nucleic acid, and a second adapter sequence. The first adapter sequence may comprise a first sequence configured to attach to a flow cell of a sequencer, a first sequencing primer sequence, and a spatial barcode sequence. The second adapter sequence may comprise a second sequencing primer sequence and a second sequence configured to attach to a flow cell of a sequencer. The second adapter sequence can further comprise an index sequence.

Enriching Barcoded Nucleic Acids

In an aspect, the present disclosure provides methods of enriching a sample for target barcoded nucleic acids. The methods may comprise providing a plurality of capture probes comprising a plurality of different spatial barcode sequences, identifying at least one target barcode sequence from the plurality of different barcode sequences, and enriching the analyte detected (e.g., specifically bound to the capture probe) by the capture probes comprising the at least one target barcode sequence. Enriching may be performed by purifying capture probes comprising the at least one target barcode from a plurality of capture probes. Enriching may be performed by amplifying (i.e. increasing the numbers of) capture probes comprising the at least one target barcode from a plurality of capture probes. The amplification may include isothermal amplification. Enriching may be performed by both purifying and amplifying the capture probe comprising the at least one target barcode from a plurality of capture probes.

Spatial barcodes can be included in capture probes. For example, the capture probes can be co-partitioned into a partition with spatial barcodes to facilitate the barcoding reaction for spatial analysis. The spatial barcodes may be attached to a bead (e.g., in the context of a capture probe). The bead may be a gel bead. In some embodiments, the spatial barcodes are releasably attached to the bead or gel bead as described elsewhere herein (e.g. via a cleavage domain). The plurality of capture probes may be barcoded as described elsewhere herein.

In some embodiments, methods provided herein may comprise enriching nucleic acids comprising the at least one target barcode sequence. The enriching may comprise performing a nucleic acid extension reaction using a capture probe comprising the at least one target barcode sequence and a primer comprising a sequence specific for the at least one target barcode sequence to generate an enriched plurality of capture probes comprising the at least one target barcode sequence. The nucleic acid extension reaction may be a polymerase chain reaction (PCR). The nucleic acid extension reaction may comprise a polymerase. The nucleic acid extension reaction may result in amplification of the nucleic acid.

In some embodiments, methods provided herein may further comprise performing an additional PCR on the enriched plurality of capture probes comprising the at least one target barcode sequence. The additional PCR may comprise use of an additional primer comprising a sequence specific for the enriched plurality of capture probes comprising the at least one target barcode sequence. In some embodiments, the additional primer may comprise a sequence specific for the spatial barcode sequence of the enriched plurality of capture probes comprising the at least one target barcode sequence. In some embodiments, the additional primer may comprise a sequence substantially specific for the spatial barcode sequence of the enriched plurality of capture probes comprising the at least one target barcode sequence. For example, the additional primer may comprises a sequence having at least 50%, 55%, 60%, 65%, 70%, 75%, 80%, 85%, 90%, 91%, 92%, 93%, 94%, 95%, 96%, 97%, 98%, 99%, 99.5%, 99.9% or more sequence complementarity or sequence identity to the spatial barcode sequence of the enriched plurality of capture probes comprising the at least one target barcode sequence. In some embodiments, the additional primer may comprise a sequence specific for a 5' region of a spatial barcode sequence of the enriched plurality of capture probes comprising the at least one target barcode sequence. In some cases, the additional primer can comprise a sequence that has no (or low) sequence complementarity or identity to the spatial barcode sequence of the enriched plurality of capture probes comprising the at least one target barcode sequence.

In some embodiments, the additional primer may comprise one or more functional sequences that facilitate sequencing of the enriched plurality of capture probes. The one or more functional sequences may comprise a sequencing primer sequence. The one or more functional sequences may comprise a sequence configured to attach to a flow cell of a sequencer.

In some embodiments, methods provided herein may further comprise, subsequent to the nucleic acid extension reaction, performing a size selection process to remove unincorporated primers. The size selection process may comprise using a gel or gel-like polymer. The size selection process may use gel electrophoresis. In some cases, the size selection process may comprise using a solid support. The solid support may be an array.

In some embodiments, the enriched plurality of nucleic acids may comprise an affinity group. The affinity group may be incorporated to the enriched plurality of the nucleic acid via a polymerase extension reaction with a primer comprising the affinity group. The affinity group may be incorporated via enzymatic reaction with a nucleotide and the affinity group. The affinity group may be attached covalently or non-covalently. The method may further comprise coupling the enriched plurality of capture probes comprising the affinity group to a solid support specific for the affinity group. The solid support may be an array. The solid support may be a polymer matrix. The solid support may be a glass slide. The solid support may be a resin. In some embodiments, the solid support may comprise an antibody or antibody fragment. In some embodiments, the solid support comprises avidin or streptavidin and the affinity group comprises (or is) biotin. In some embodiments, the solid support comprises maltose and the affinity group comprises (or is) maltose binding protein. In some embodiments, the solid support comprises maltose-binding protein and the affinity group comprises (or is) maltose.

In some embodiments, prior to the nucleic acid extension reaction, a first capture probe complementary to a first portion of the at least one target barcode sequence and a second capture probe complementary to a second portion of the at least one target barcode sequence may be hybridized. The first capture probe can be ligated to the second capture probe to generate the primer comprising the sequence specific for the at least one target barcode sequence. The ligating may comprise using a DNA ligase.

In some embodiments, the enriching can result in at least 10-fold enrichment of capture probes comprising the at least one target barcode sequence. In some embodiments, the enriching can result in at least 20-fold enrichment of capture probes comprising the at least one target barcode sequence. The enrichment of nucleic acids may be observed by an increase in the percent of nucleic acids comprising the at least one target barcode sequence in the enriched plurality of capture probes compared to the percent amount of nucleic acids comprising the at least one target barcode sequence in the plurality of capture probes. The enriching may result in at least 50-fold enrichment of capture probes comprising the at least one target barcode sequence. The enriching may result in at least 100-fold enrichment of capture probes comprising the at least one target barcode sequence. The enriching may result in at least 200-fold enrichment of capture probes comprising the at least one target barcode sequence. The enriching may results in at least 500-fold enrichment of capture probes comprising the at least one target barcode sequence. The enriching may result in at least 1000-fold enrichment of capture probes comprising the at least one target barcode sequence.

Primers are used for multiple reactions described elsewhere herein. The primers may comprise a specific length of nucleotides. For example, the primers may be at least about 5, 6, 7, 8, 9, 10, 12, 14, 16, 18, 20, 22, 24, 25, 26, 28, 30, 40, 50 or more nucleotides long. Alternatively or in addition, the primers may be no more than 50, 40, 30, 28, 26, 25, 24, 22, 20, 18, 16, 14, 12, 10, 9, 8, 7, 6, 5, or fewer nucleotides long.

The primers may have a specific melting temperature. The melting temperature of the primer may be at least about 35 degrees Celsius (° C.), 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. 60° C., 61° C., 62° C., 63° C., 64° C., 65° C., or higher. The melting temperature of the primer may be no more than about 35° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. 60° C., 61° C., 62° C., 63° C., 64° C., 65° C., or lower.

In some cases, primers are ligated together to form a longer primer. The longer primer may be subsequently used for any PCR reactions, as described elsewhere herein. Ligating together shorter primers into a longer primer may increase the stringency of binding such that the targeted barcode is enriched. For example, the shorter primers may be able to distinguish mismatches better and thus bind only to sequences with perfect or near perfect complementarity. The longer primer may be more able to accommodate mismatches in sequences and bind to sequences that are not the targeted barcode. In some cases, more than 2 primers are ligated together to form a longer primer. For example, at least about 3, 4, 5, 6, 7, 8, 9, 10, or more primers may be ligated together to form a longer primer.

In some embodiments, the primer comprises an affinity group and the enriched plurality of capture probes comprises the affinity group. The affinity group may comprise biotin. The affinity group may comprise streptavidin or avidin. The affinity group may comprise dioxigenin. The affinity group may comprise a protein or polypeptide. The affinity group may comprise an antibody or antibody fragment. The affinity group may comprise a receptor or receptor ligand. The affinity group may comprise a sugar, a monosaccharide, a disaccharide, or a polysaccharide. The affinity group may comprise maltose.

Methods of the present disclosure may be used for various applications, such as, processing a single analyte (e.g., RNA, DNA, or protein) or multiple analytes (e.g., DNA and RNA, DNA and protein, RNA and protein, or RNA, DNA, and protein) from a single cell. For example, multiple analytes from the biological particle can be processed. The multiple analytes may be from the single cell. This may enable, for example, simultaneous proteomic, transcriptomic and genomic analysis of the cell.

Hierarchal Barcode Enrichment

In an aspect, the present disclosure provides methods of spatially designing or designating barcodes, such that the position of the barcodes are specifically identified. In some embodiments, a particular individual spot or bead may contain more than one spatial barcode, wherein each spatial barcode corresponds to a particular defined region on the spotted array. For example, multiple spatial barcode sequences associated with one particular spot on an array can provide a stronger address or attribution to a given location by providing duplicate or independent confirmation of the location. In some cases, the multiple spatial barcodes represent increasing specificity of the location of the particular array point. In a non-limiting example, a particular array point may be coded with two different spatial barcodes, wherein each spatial barcode identifies a particular defined region within the array, and an array point possessing both spatial barcodes identifies the sub-region where two defined regions overlap, e.g., such as the overlapping portion of a Venn diagram. In another non-limiting example, a particular array point may be coded with three or more different spatial barcodes, wherein the first spatial barcode identifies a first region within the array, the second spatial barcode identifies a second region, wherein the second region is a subregion entirely within the first region (a sub-spatial region), and the third spatial barcode identifies a third region, wherein the third region is a subregion entirely within the first and second subregions (a sub-spatial region), and so on. In some embodiments, each capture probe has a unique spatial barcode, or unique molecular identifier (UMI). In some embodiments, each capture probe has a UMI, as well as one or more target barcodes corresponding to one or more regions or sub-spatial regions.

In some embodiments, an array has multiple regions (also sometimes referred to as "spots" or "locations") and subregions. In some embodiments, an array has 10 regions or more. In some embodiments, an array has 20, 30, 40, 50, 60, 70, 80, 90, 100 regions, or more. In some embodiments, an array has 100, 200, 300, 400, 500, 600, 700, 800, 900, 1000 regions or more. In some embodiments, an array has 1000, 2000, 3000, 4000, 5000, 6000, 7000, 8000, 9000, 1000 regions or more. In some embodiments, the regions are identical in size. In some embodiments, the regions are not identical in size. The regions may take any shape, including but not limited to square, rectangle, circle, oval, pentagon, hexagon, octagon arc, arches, lens, crescent, and any combinations thereof. In some embodiments, a region of an array has multiple subregions. In some embodiments, a region of an array has 10, 20, 30, 40, 50, 60, 70, 80, 90, 100, 200, 300, 400, 500, 600, 700, 800, 900, 1000 subregions or more. In some embodiments, the subregions are identical in size to other subregions. In some embodiments, the subregions are not identical in size to other subregions. In some embodiments, the subregions are completely surrounded by a larger region. In some embodiments, subregions are partially surrounded by a larger region. In some embodiments, an array has multiple sub-subregions. In some embodiments, an array has 10, 20, 30, 40, 50, 60, 70, 80, 90, 100, 200, 300, 400, 500, 600, 700, 800, 900, 1000 sub-subregions or more. In some embodiments, the sub-subregions are identical in size to other sub-subregions. In some embodiments, the sub-subregions are not identical in size to other sub-subregions. In some embodiments, sub-subregions are completely surrounded by a larger region. In some embodiments, the larger region is a subregion. In some embodiments, the larger region is a region. In some embodiments, sub-subregions are partially surrounded by a larger subregion. In some embodiments, sub-subregions are partially surrounded by a larger region. In some embodiments, individual spots or beads comprise a region. In some embodiments, individual spots or beads comprise a subregion. In some embodiments, individual spots or beads comprise a sub-subregion. In some embodiments, individual spots or beads comprise a region corresponding to single cell resolution of the sample.

In some embodiments, the present disclosure provides methods of enriching a sample comprising more than one target barcoded nucleic acid. The methods may comprise providing a plurality of capture probes comprising a plurality of different spatial barcode sequences, identifying more than one target barcode sequence from the plurality of different spatial barcode sequences, and enriching capture probes comprising the more than one target barcode sequence. Enriching may be performed by purifying capture probes comprising the more than one target barcode from a plurality of capture probes. Enriching may be performed by amplifying (i.e. increasing the numbers of) capture probes comprising the more than one target barcode from a plurality of capture probes. Enriching may be performed by both purifying and amplifying the capture probe comprising the more than one target barcode from a plurality of capture probes. Enriching may be performed using target barcodes associated with smaller regions. Enriching may be performed using target barcodes of increasing specificity to a particular spot or location. For example, enriching may be performed by amplifying and/or purifying a first plurality of capture probes comprising a target barcode that is associated with a first region. The enriching may further comprise amplifying and/or purifying a second plurality of capture probes comprising a target barcode that is associated with a second region that is partially or completely within the first region. The enriching may further comprise amplifying and/or purifying a second plurality of capture probes comprising a target barcode that is associated with a second region that is partially within the first region. The enriching may further comprise amplifying and/or purifying a second plurality of capture probes comprising a target barcode that is associated with a second region that is completely within the first region. The enriching may further comprise amplifying and/or purifying a third plurality of capture probes comprising a target barcode that is associated with a third region that is partially or completely within the first and second regions. The enriching may further comprise amplifying and/or purifying a third plurality of capture probes comprising a target barcode that is associated with a third region that is partially within the first and second regions. The enriching may further comprise amplifying and/or purifying a third plurality of capture probes comprising a target barcode that is associated with a third region that is completely within the first and second regions. The enriching may further comprise amplifying and/or purifying a fourth plurality of capture probes comprising additional target barcodes that are associated with four or more regions that are partially or completely within the first, second, and third regions. The enriching may further comprise amplifying and/or purifying a fifth plurality of capture probes comprising additional target barcodes that are associated with five or more regions that are partially or completely within the first, second, third, and fourth regions. The enriching may further comprise amplifying and/or purifying additional pluralities of capture probes comprising additional target barcodes that are associated with 6, 7, 8, 9, 10, or more regions that are partially or completely within the previously identified regions and/or sub-spatial regions.

In some embodiments, the method may comprise enriching nucleic acids comprising more than one target barcode sequence. The enriching may comprise performing a nucleic acid extension reaction using a capture probe comprising more than one target barcode sequence and a primer comprising a sequence specific for more than one target barcode sequence to generate an enriched plurality of capture probes comprising more than one target barcode sequence. The nucleic acid extension reaction may be a polymerase chain reaction (PCR). The nucleic acid extension reaction may comprise a polymerase. The nucleic acid extension reaction may result in amplification of the nucleic acid.

In some embodiments, the method may further comprise performing additional rounds of PCR on the enriched plurality of capture probes corresponding to the number of spatial barcode sequences of a given location. The additional rounds of PCR may comprise use of additional primers comprising a sequence specific for the additional target barcode sequences (e.g., target barcode sequences associated with a subregion or sub-subregion of interest). In some embodiments, the additional primers may comprise a sequence specific for the spatial barcode sequence of the enriched plurality of capture probes comprising more than one target barcode sequence. In some embodiments, the additional primers may comprise a sequence substantially specific for an additional target barcode sequence of the enriched plurality of capture probes comprising more than one target barcode sequence. For example, the additional primer may comprises a sequence having at least 50%, 55%, 60%, 65%, 70%, 75%, 80%, 85%, 90%, 91%, 92%, 93%, 94%, 95%, 96%, 97%, 98%, 99%, 99.5%, 99.9% or more sequence complementarity or sequence identity to a target barcode sequence of the enriched plurality of capture probes comprising the more than one target barcode sequence. In some embodiments, the additional primers may comprise a sequence specific for a 5' region of a spatial barcode sequence of the enriched plurality of capture probes comprising more than one target barcode sequence. In some cases, the additional primer can comprise a sequence that has no (or low) sequence complementarity or identity to one or more spatial barcode sequences of the enriched plurality of capture probes comprising more than one target barcode sequence.

In some embodiments, each spatial barcode sequence of the plurality of different spatial barcode sequences can identify a capture probe as derived from a single cell. Alternatively or in addition, each spatial barcode sequence of the plurality of different spatial barcode sequences may identify a capture probe as derived from a single partition.
Identifying a Spatial Region of Interest In some embodiments, identifying a spatial region of interest includes any technique for observing and/or locating an area within a tissue. In some embodiments, identifying a spatial region of interest includes immunostaining techniques, including but not limited to, immunohistochemistry techniques. In some embodiments, identifying a spatial region of interest includes microscopy techniques, including but not limited to, optical microscopy, fluorescence microscopy, and confocal microscopy. In some embodiments, identifying a spatial region of interest includes visual inspection. In some embodiments, identifying a spatial region of interest includes shallow sequencing a spatial region. In some embodiments, identifying a spatial region of interest includes shallow sequencing the entire tissue sample.

In at least one embodiment, the present disclosure provides a method for preparing a composition comprising: providing a substrate comprising a first oligonucleotide attached to the substrate through its 3'-end or its 5'-end; and preparing by spatially-directed in situ synthesis on the unattached end of the first segment a plurality of second oligonucleotide segments of 8-mer to 30-mer each having a different sequence and located in a different region of the substrate.

In at least one embodiment, the method further comprises: attaching a plurality of third oligonucleotide segments to the unattached ends of the plurality of second oligonucleotide segments.

In at least one embodiment of the method of the present disclosure the spatially-directed in situ synthesis is light-directed spatial synthesis.

In at least one embodiment of the method of the present disclosure the spatially-directed in situ synthesis is mechanically-directed spatial synthesis.

In at least one embodiment of the method of the present disclosure, the first oligonucleotide segment is attached to the substrate through its 5'-end and the plurality of second oligonucleotide segments are prepared (e.g., generated) by spatially-directed in situ synthesis on the 3'-end of the first segment.

In at least one embodiment of the method of the present disclosure, the first oligonucleotide segment is attached to the substrate through its 3'-end and the plurality of second oligonucleotide segments are prepared (e.g., generated) by spatially-directed in situ synthesis on the 5'-end of the first segment.

In at least one embodiment, the present disclosure provides a method for preparing a composition comprising: providing a substrate comprising a first oligonucleotide segment attached through its 5'-end to the substrate, wherein the first oligonucleotide segment phosphodiester and exocyclic amine moieties are protected; preparing by in situ synthesis a plurality of second oligonucleotide segments of 8-mer to 20-mer attached through their 5'-ends to a 3'-end of a first oligonucleotide segment, wherein each of the plurality of second segments comprises a different sequence that identifies the region of the substrate where it is located; and ligating a plurality of third oligonucleotide segments through their 5'-ends to the 3'-ends of the plurality of second segments.

In at least one embodiment of the method of the present disclosure the regions of the substrate have an area of less than about 2500 $\mu m^2$, less than about 1600 $\mu m^2$, less than about 400 $\mu m^2$, less than about 100 $\mu m^2$, less than about 50 $\mu m^2$, less than about 25 $\mu m^2$, less than about 15 $\mu m^2$, less than about 10 $\mu m^2$, less than about 5 $\mu m^2$, less than about 2 $\mu m^2$, less than about 1 $\mu m^2$, or smaller.

In at least one embodiment of the method of the present disclosure the number of second oligonucleotide segment comprising different sequences is at least about 100,000, at least about 250,000, at least about 500,000, at least about 750,000, at least about 1,000,000, at least about 1,500,000, at least about 3,000,000, at least about 5,000,000, at least about 10,000,000, at least about 100,000,000, at least about 500,000,000, or at least about 1,000,000,000. In some embodiments, the number of second oligonucleotide segment comprising different sequences is about 100,000 to about 1,000,000,000, about 750,000 to about 1,500,000, about 1,000,000 to about 1,000,000,000, about 1,000,000 to about 10,000,000, or about 1,500,000 to about 5,000,000.

In at least one embodiment of the method of the present disclosure the second oligonucleotide segments have a length selected from 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, 26-mer, 27-mer, 28-mer, 29-mer, or 30-mer.

In at least one embodiment of the method of the present disclosure the second oligonucleotide segment in each of the different regions of the substrate has a purity of at least 75%, at least 80%, at least 85%, at least 87%, at least 88%, at least 89%, at least 90%, at least 91%, at least 92%, at least 93%, at least 94%, at least 95%, at least 96%, at least 97%, at least 98%, at least 99%, or more.

In at least one embodiment of the method of the present disclosure the first oligonucleotide segment further comprises protected phosphodiester and exocyclic amine moieties.

In at least one embodiment of the method of the present disclosure the substrate further comprises a complementary oligonucleotide hybridized to the first oligonucleotide segment.

In at least one embodiment of the method of the present disclosure the first oligonucleotide segment has a length of at least about 2-mer, at least about 5-mer, at least about 8-mer, at least about 10-mer, or at least about 15-mer at least about 18-mer, at least about 20-mer, at least about 22-mer, or at least about 25-mer, at least about 27-mer, at least about 30-mer, at least about 33-mer, or at least about 35-mer. In some embodiments the first oligonucleotide segment has a length of about 2-mer to about 45-mer, about 5-mer to about 40-mer, about 15-mer to about 40-mer about 25-mer to about 40-mer, about 25-mer to about 35-mer, or about 27-mer to about 33-mer.

In at least one embodiment of the method of the present disclosure the method further comprises preparing the first oligonucleotide segment off the substrate and subsequently attaching it to the substrate. In some embodiments the phosphodiester and exocyclic amine moieties of the first oligonucleotide segment are protected prior to attaching it to the substrate. In some embodiments the phosphodiester and exocyclic amine moieties of the first oligonucleotide segment are protected after attaching it to the substrate.

In at least one embodiment of the method of the present disclosure the method further comprises preparing the first oligonucleotide segment by synthesis on the substrate. In some embodiments the synthesis of the first oligonucleotide segment on the substrate is by light-directed spatial synthesis. In some embodiments the synthesis of the first oligonucleotide segment on the substrate is not spatially-directed.

In at least one embodiment of the method of the present disclosure the first oligonucleotide segment sequence comprises a cleavage site. In some embodiments, the cleavage site comprises a poly-U sequence.

In at least one embodiment of the method of the present disclosure the first oligonucleotide segment is attached to the substrate through a linker. In some embodiments, the linker comprises a chemical group selected from: silane, amine, peptide, polyethylene glycol, biotin, desthiobiotin, streptavidin, thiol, acrydite, azide, digoxigenin, hexynyl, or a combination thereof. In some embodiments, the linker is a branched linker or a dendrimeric linker.

In at least one embodiment of the method of the present disclosure that further comprises attaching a plurality of third oligonucleotide segments, the first oligonucleotide segment is attached to the substrate through its 5'-end, the plurality of second oligonucleotide segments are prepared by spatially-directed in situ synthesis on the 3'-end of the first segment, and the plurality of third oligonucleotide segments are attached through their 5'-end to the 3'-end of the plurality of second segments.

In at least one embodiment of the method of the present disclosure that further comprises attaching a plurality of third oligonucleotide segments, the plurality of third oligonucleotide segments are attached by ligation. In some embodiments, protected moieties of the first and second oligonucleotide segments are deprotected prior to ligating the plurality of third oligonucleotide segments.

In at least one embodiment of the method of the present disclosure that further comprises attaching a plurality of third oligonucleotide segments, the plurality of third oligonucleotide segments have a length of at least about 5-mer, at least about 7-mer, at least about 9-mer, at least about 13-mer, at least about 20-mer, at least about 25-mer, at least about 27-mer, at least about 30-mer, at least about 33-mer, or at least about 35-mer. In some embodiments, the plurality of third oligonucleotide segments have a length of about 5-mer to about 40-mer, 5-mer to about 20-mer, 5-mer to about 10-mer, about 10-mer to about 35-mer, about 15-mer to about 30-mer, about 25-mer to about 35-mer, or about 27-mer to about 33-mer.

In at least one embodiment of the method of the present disclosure that further comprises attaching a plurality of third oligonucleotide segments, each of the plurality of third oligonucleotide segments comprise a different 5-mer to 20-mer random sequence at the 5'-end.

In at least one embodiment of the method of the present disclosure that further comprises attaching a plurality of third oligonucleotide segments, each of the plurality of third oligonucleotide segments comprises an identical capture sequence of at least 6-mer at the 3'-end. In some embodiments, the capture sequence comprises a poly-T or a poly-U sequence.

In at least one embodiment the present disclosure also provides a composition comprising a plurality of oligonucleotides attached to a plurality of regions on a substrate, wherein each oligonucleotide comprises: a first oligonucleotide segment of 2-mer to 50-mer attached to the substrate through its 5'-end; and a second oligonucleotide segment of 8-mer to 30-mer that is attached to the 3'-end of the first segment through its 5'-end, wherein the second segment comprises a sequence that identifies the region where it is located.

In at least one embodiment of the composition each oligonucleotide further comprises: a third oligonucleotide segment of 11-mer to 50-mer that is attached to the 3'-end of the second segment through its 5'-end, wherein the third segment comprises a 5-mer to 20-mer random sequence at its 5'-end and a 6-mer to 38-mer capture sequence of at its 3'-end.

In at least one embodiment of the composition of the present disclosure the regions of the substrate have an area of less than about 2500 µm2, less than about 1600 µm2, less than about 400 µm2, less than about 100 µm2, less than about 50 µm2, less than about 25 µm2, less than about 15 µm2, less than about 10 µm2, less than about 5 µm2, less than about 2 µm2, less than about 1 µm2, or smaller.

In at least one embodiment of the composition of the present disclosure the number of second oligonucleotide segment comprising different sequences is at least about 100,000, at least about 250,000, at least about 500,000, at least about 750,000, at least about 1,000,000, at least about 1,500,000, at least about 3,000,000, at least about 5,000,000, at least about 10,000,000, at least about 100,000,000, at least about 500,000,000, or at least about 1,000,000,000. In some embodiments, the number of second oligonucleotide segment comprising different sequences is about 100,000 to about 1,000,000,000, about 750,000 to about 1,500,000, about 1,000,000 to about 1,000,000,000, about 1,000,000 to about 10,000,000, or about 1,500,000 to about 5,000,000.

In at least one embodiment of the composition of the present disclosure the second oligonucleotide segments have a length selected from 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, 26-mer, 27-mer, 28-mer, 29-mer, or 30-mer.

In at least one embodiment of the composition of the present disclosure the second oligonucleotide segment in each of the different regions of the substrate has a purity of at least 95%, at least 96%, at least 97%, at least 98%, at least 99%, or more.

In at least one embodiment of the composition of the present disclosure the first and second oligonucleotide segments further comprise protected phosphodiester and exocyclic amine moieties.

In at least one embodiment of the composition of the present disclosure the length of the oligonucleotide in each region is at least 10-mer, at least 20-mer, at least 30-mer, at least 40-mer, at least 50-mer, or at least 60-mer. In some embodiments the length of the oligonucleotide in each region is from 40-mer to 100-mer, from 50-mer to 90-mer, from 60-mer to 80-mer or 10-mer to 40-mer.

Generating Spatial Arrays

In at least one embodiment of the compositions and methods of the present disclosure, the plurality of oligonucleotides is attached to a substrate by any suitable means that immobilizes the oligonucleotide by either its 3' or 5' end in a region of the substrate and allows the unattached end to be available for further synthesis. Further synthesis can include in situ base-by-base step-wise synthesis (e.g., phosphoramidite chemistry) or biosynthesis via enzyme reactions (e.g., DNA polymerization or reverse transcription). Additionally, the means of attachment should also be suitable to allow at least a portion of the oligonucleotide to be capable of hybridization.

In at least one embodiment of the compositions and methods of the present disclosure, the plurality of oligonucleotides is attached to a substrate by a covalent linkage. Accordingly, in at least one embodiment, the plurality of oligonucleotides are attached to the substrate by a chemical reaction that forms one or more covalent bonds between a functional group on the substrate (or a linker group attached to the substrate) and a functional group on the 3'- or 5'-end of the oligonucleotide (or a linker group attached to the 3' or 5'-end of the oligonucleotide). Such functional groups can include a naturally occurring nucleotide functional group, e.g. a terminal hydroxyl group, or a non-natural functional group introduced during oligonucleotide synthesis, such as a 5'-amine group. Reagents and techniques for chemically modifying substrate materials and/or nucleotides with functional groups that are useful in the methods of the present disclosure are well known in the art. For example, functional groups that may be introduced on a substrate material that allow for attachment of an oligonucleotide (e.g., 5'-amine modified oligonucleotide) to a substrate include linkers with available carboxy, aldehyde or epoxy groups. Other functionalized linker compounds are known to the person skilled in the art.

The oligonucleotides of the plurality of oligonucleotides to be attached to a substrate in preparing a spatial array of the present disclosure can be understood as having at least three segments: a first oligonucleotide segment of 2-mer to 40-mer that is attached to the substrate through either its 3'-end or its 5'-end; a second oligonucleotide segment that is attached to the unattached end of the first segment, and comprises a barcode sequence of about 8-mer to 30-mer in length that indicates the region on the substrate where the second segment is located; and a plurality of third oligonucleotide segments of 5-mer to 50-mer attached to the second segment, wherein the third segment comprises a capture sequence at its 3'-end.

FIGS. 31A-C depict at least one embodiment of a method for preparing an exemplary spatial array composition of the present disclosure. First, as shown in FIG. 31A, a substrate is provided that comprises a first oligonucleotide segment attached through its 5'-end to the substrate. In at least one embodiment, the first oligonucleotide segment comprises a sequence that is identical across all of the plurality of the different oligonucleotides attached to the substrate. In some embodiments, the first oligonucleotide segment can be understood as a common oligonucleotide "lawn" across the surface of the substrate that does not differ in sequence in the various regions of the substrate. The free, unattached end of the first oligonucleotide segment, thus, effectively acts as the starting point on the spatial array for the spatially-directed in situ synthesis of the second oligonucleotide segment that comprises the barcode sequence.

In at least one embodiment, the length of the first oligonucleotide segment is the same across the surface of the substrate. While typically not critical to the function of the spatial array, in at least one embodiment, the length of the first oligonucleotide sequence should be at least about 2-mer. Furthermore, in some embodiments the length of the first oligonucleotide segment is at least 5-mer, at least about 10-mer, at least about 15-mer, at least about 20-mer, at least about 25-mer, at least about 27-mer, at least about 30-mer, at least about 33-mer, or at least about 35-mer. Similarly, in some embodiments the first oligonucleotide segment has a length of about 2-mer to about 40-mer, about 5-mer to about 40-mer, about 10-mer to about 30-mer, about 25-mer to about 35-mer, about 20-mer to about 40-mer, about 25-mer to about 40-mer, about 25-mer to about 35-mer, or about 27-mer to about 33-mer.

As further depicted in FIG. 31A, in at least one embodiment, the first oligonucleotide segment comprises phosphodiester and exocyclic amine moieties that are protected. Protection of the phosphodiester and exocyclic amine moieties of the first oligonucleotide segment allows for optimal in situ synthesis of the second oligonucleotide segments that comprise the barcode sequence. Suitable protecting groups for phosphodiester and exocyclic amine moieties are well-known in the art and include the protecting groups employed in standard oligonucleotide synthesis using phosphoramidite chemistry.

The present disclosure describes a variety of embodiments for preparing a substrate having attached thereto a first oligonucleotide segment, wherein the first oligonucleotide segment comprises protected phosphodiester and exocyclic amine moieties (see e.g., embodiments of FIGS. 32A-C to 36A-C).

In at least one exemplary embodiment, depicted in FIGS. 32A-C, the method further comprises preparing the first oligonucleotide segment ex situ (e.g., on a separate solid support using solid phase automated synthesis), cleaving it from the separate solid support with the protecting groups intact (see FIG. 32A), and subsequently attaching the ex situ synthesize oligonucleotide with protecting groups it to the substrate (see FIG. 32B). A free hydroxyl at the unattached end is available for subsequent spatially-directed in situ synthesis of a second oligonucleotide segment comprising a barcode sequence (see FIG. 32C).

In at least another exemplary embodiment, depicted in FIGS. 33A-B, the method further comprises preparing the first oligonucleotide segment in situ directly the solid support using base-by-base phosphoramidite synthesis chemistry with phosphodiester and exocyclic amine protecting groups. Such a method can be use standard solid-phase oligonucleotide synthesis chemistry to provide a substrate with first oligonucleotide segments attached thereto by the 3'-end and having protecting groups. In at least one embodiment, as depicted in FIG. 33A, oligonucleotide synthesis chemistry in a 5'-to-3' direction can be carried out to provide the protected first oligonucleotide segments attached to the substrate through the 5'-end. In both cases, the free hydroxyl at the unattached end is available for subsequent spatially-directed in situ synthesis of a second oligonucleotide segment comprising a barcode sequence (see FIG. 33C).

Second, as depicted in FIG. 31B, a plurality of second oligonucleotide segments of 8-mer to 30-mer are prepared by spatially-directed in situ synthesis extending from the free end of the first oligonucleotide segment. As shown in FIG. 31B, the spatially-directed in situ synthesis is a light-directed spatial synthesis which is carried out in the 5'-to-3' direction. This in situ synthesis method results in a plurality of second oligonucleotide segments each attached through its 5'-end to a 3'-end of a first oligonucleotide segment. FIG. 31B is a schematic representation of only two distinct regions each having four individual oligonucleotide molecules. Each region has a different second oligonucleotide segment sequence, and all of the second oligonucleotide segment molecules in a region ideally should have the same sequence, although as discussed further below, less than 100% yield in the in situ synthesis process results in less than perfect purity (or homogeneity) of oligonucleotide sequence in a region.

In at least one embodiment of the present disclosure, spatially-directed synthesis of a plurality of oligonucleotides on a substrate in spatially distinct regions is carried out using light-directed synthesis or by mechanically-directed synthesis methods. A spatially-directed in situ synthesis method inherently correlates each sequence synthesized with the location of synthesis. In the schematic illustration of FIG. 31B, a light-directed spatial synthesis is used to synthesize a second oligonucleotide segment in a base-by-base stepwise fashion in each region. The region where each nucleotide base is added is controlled by the precise location (and duration) of spatially-directed illumination of the substrate. The direction and duration of illumination can be precisely controlled, for example with maskless array synthesis (MAS) technology using computer-controlled digital micromirror devices (DMD), to provide distinct regions of 1 $\mu m^2$, or even smaller. It is only at these precisely illuminated regions on the substrate where deprotection of a photo-labile protecting group occurs, thereby allowing coupling of a nucleoside phosphoramidite that provides the next base in the oligonucleotide sequence.

Light-directed spatial in situ synthesis provides optimal control in the synthesis of high-fidelity second oligonucleotide segment barcode sequences at precise region locations on a substrate. Light-directed spatial synthesis of oligonucleotides refers to synthetic methods using photolabile nucleoside protecting groups and spatially-directed illumination to effect selective deprotection and base-by-base synthesis at specific locations on a substrate. Light-directed spatial synthesis of oligonucleotides uses an iterative cycle of phosphoramidite-based coupling chemistry with photolabile protecting groups rather than dimethoxytrityl (DMT) protecting groups. The synthesis cycle, thus, is very similar to that used in standard solid-phase phosphoramidite synthesis of oligonucleotides with the following general steps: (1) photo-deprotection; (2) activation and coupling; (3) capping; and (4) drying. The drying step (4) can involve blowing helium to dry the substrate surface after coupling and acetonitrile wash but before the next photodeprotection step. Techniques, protocols, reagents, materials, and other instrumentation useful for light-directed spatial synthesis of high-density oligonucleotide microarrays are well-known in the art and commercially available. For example, U.S. Pat. Nos. 7,844,940, 8,030,477, PCT Publ. No. WO 99/63385A1, US Pat. Publ. No. 20150246336A1, Agbavwe et al. "Efficiency, error and yield in light-directed maskless synthesis of DNA microarrays." *Journal of nanobiotechnology* 9.1 (2011): 57; and Sack et al. "Express photolithographic DNA microarray synthesis with optimized chemistry and high-efficiency photolabile groups." *Journal of nanobiotechnology* 14.1 (2016): 14, describe materials and methods that can be used in the light-directed spatial synthesis methods of the present disclosure.

The photo-deprotection step involves spatially-directed illumination of the substrate and is the step that ultimately defines the size and location of a region. Efficiency and accuracy of the photo-deprotection step in defining the regions on the substrate where specific oligonucleotides are synthesized depends largely on the illumination techniques and the photo-labile groups used. Photo-labile groups and illumination techniques useful for light-directed spatial synthesis methods are well-known and commercially available (e.g., from Sigma-Aldrich, St. Louis, Mo., USA). For example, photo-labile protecting groups that can be used to prepare spatial array compositions of the present disclosure are described in US Pat. Publ. No. 20150246336A1; Agbavwe et al. "Efficiency, error and yield in light-directed maskless synthesis of DNA microarrays." *Journal of nanobiotechnoloVy* 9.1 (2011): 57; Kretschy et al. "Next-Generation o-Nitrobenzyl Photolabile Groups for Light-Directed Chemistry and Microarray Synthesis." *Angewandte Chemie International Edition* 54.29 (2015): 8555-8559; Sack et al. "Express photolithographic DNA microarray synthesis with optimized chemistry and high-efficiency photolabile groups." *Journal of nanobiotechnology* 14.1 (2016): 14; Lietard et al., "High-Density RNA Microarrays Synthesized In Situ by Photolithography." *Angew. Chem. Int. Ed.* 57 (2016): 15257-15261; and Holz et al., "High-Efficiency Reverse (5'→3') Synthesis of Complex DNA Microarrays." *Scientific reports* 8.1 (2018): 15099.

In at least one embodiment, the photo-labile protecting groups useful in the light-direct spatial synthesis methods of the present disclosure include NPPOC, Bz-NPPOC, and SPh-NPPOC which are shown in Table 1.

TABLE 1

Exemplary Photo-labile Protecting Groups

| Name | Structure (e.g., protecting 3'-OH of nucleoside) |
| --- | --- |
| NPPOC | 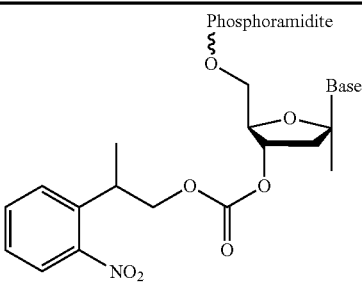 |
| Bz-NPPOC | 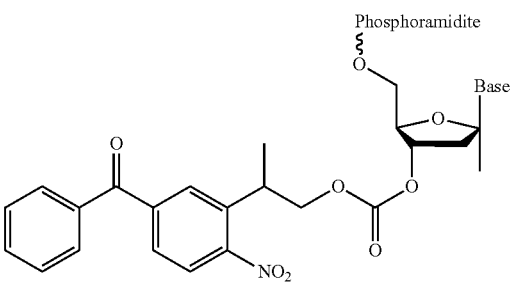 |
| SPh-NPPOC | 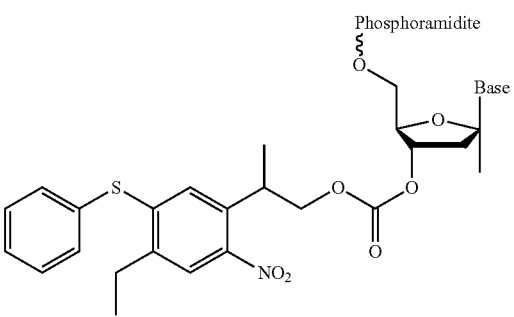 |

The schematic illustration of FIG. 31B depicts light-directed spatial synthesis of second oligonucleotide segments in the 5'-to-3' direction. The resulting plurality of the second oligonucleotide segments are thus attached through their 5'-ends to the free 3'-ends of the first oligonucleotide segment on the substrate. Accordingly, in at least one embodiment the light-directed spatial synthesis of the second oligonucleotides is carried out in the 5'-to-3' direction. Techniques, reagents, and photo-labile protecting groups useful for synthesis in the 5'-to-3' direction include those described in e.g., Holz et al., "High-Efficiency Reverse (5'-3') Synthesis of Complex DNA Microarrays." *Scientific reports* 8.1 (2018): 15099. In at least one embodiment, light-directed spatial synthesis of a plurality of second oligonucleotide segments can be carried out using one or more of the photo-labile protecting groups of Table 1 to protect the 3'-OH. In at least one embodiment, the photo-labile protecting group used in light-directed spatial synthesis of the second oligonucleotide segment is Bz-NPPOC.

In at least one embodiment, the spatially-directed in situ synthesis can be carried out using mechanically-directed spatial synthesis. Mechanically-directed spatial synthesis of oligonucleotides refers to methods that use computer-controlled liquid dispensing and/or placement technology to mechanically direct nucleoside phosphoramidite reagents at distinct locations on a substrate, and thereby synthesizing an oligonucleotide using standard solid-phase phosphoramidite chemistry at a distinct region on a substrate. A range of technologies for mechanical spatially-directed in situ synthesis of oligonucleotides are well-known in the art.

The schematic illustration of FIG. 31B depicts only two regions, however it is contemplated that a spatial array composition made by the methods of the present disclosure can include millions of different regions on a substrate, each comprising a different second oligonucleotide segment barcode sequence. In at least one embodiment, the number of second oligonucleotide segments comprising different sequences is at least about 100,000, at least about 250,000, at least about 500,000, at least about 750,000, at least about 1,000,000, at least about 1,500,000, at least about 3,000,000, at least about 5,000,000, at least about 10,000,000, at least about 100,000,000, at least about 500,000,000, or at least about 1,000,000,000. In some embodiments, the number of second oligonucleotide segment comprising different sequences is about 100,000 to about 1,000,000,000, about 750,000 to about 1,500,000, about 1,000,000 to about 1,000,000,000, about 1,000,000 to about 10,000,000, or about 1,500,000 to about 5,000,000.

In order for a spatial array to accommodate these large numbers of different oligonucleotides on a substrate, it also is contemplated that the areas of the regions need to be small. Accordingly, in at least one embodiment of the method of the present disclosure the regions of the substrate have an area of less than about 2500 µm², less than about 1600 µm², less than about 400 µm², less than about 100 µm², less than about 50 µm², less than about 25 µm², less than about 15 µm², less than about 10 µm², less than about 5 µm², less than about 2 µm², less than about 1 µm², or smaller.

In at least one embodiment, the methods of the present disclosure contemplate the spatially-directed in situ synthesis of second oligonucleotide segments comprising millions of different barcode sequences each in a different region. In order to accommodate millions of distinct regions each with a distinct barcode sequence, the present disclosure contemplates that the second oligonucleotide segments have a length range of 8-mer to 30-mer. A length range of 8-mer to 30-mer allows for the plurality of oligonucleotides to have extremely large number of distinct oligonucleotides that are indexed for their location on the substrate. For example, in the case of an 8-mer sequence, there are 48 or 65,536 different possible barcode sequences that can be used to identify distinct locations on a substrate. In the case of a 12-mer sequence, there are 412 or 16,777,216 different possible barcode sequences that can be used to identify distinct locations on a substrate. Accordingly, in at least one embodiment of the method of the present disclosure the second oligonucleotide segments have a length selected from 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, 26-mer, 27-mer, 28-mer, 29-mer, or 30-mer.

In order to provide for optimal functionality of a spatial array, the correlation of the barcode sequences with the locations should be high. Accordingly, the spatially-directed in situ synthesis of the barcode sequence should result in high fidelity or purity of barcode sequences in each of the regions. It is an advantage of the spatially-directed synthesis methods of the present disclosure that the second oligonucleotide segments are prepared on a substrate with high fidelity. Generally, the fidelity (or sequence purity) of oligonucleotide sequences prepared by step-wise solid-phase synthesis decreases as the length of the oligonucleotide being synthesized increases. For example, assuming a spatially-directed in situ synthesis having a coupling efficiency of 99.5%, the fidelity of 12-mer barcode sequences in a region is ~95%. In some embodiments (e.g., as in FIGS. 32A-C), the use of spatially-directed in situ synthesis to prepare only the 8-mer to 30-mer second oligonucleotide segments results in barcode sequences of high-fidelity. Accordingly, in at least one embodiment of the methods of the present disclosure the resulting second oligonucleotide segment synthesized in each of the different regions of the substrate has a purity of at least 75%, at least 80%, at least 85%, at least 87%, at least 88%, at least 89%, at least 90%, at least 91%, at least 92%, at least 93%, at least 94%, at least 95%, at least 96%, at least 97%, at least 98%, at least 99%, or more.

In at least one embodiment, the second oligonucleotide segment is unique for each region of the substrate. Additionally, in some embodiments, the second oligonucleotide segment barcode sequence comprises a sequence that uniquely identifies it from the plurality of other barcode sequences on the spatial array but does not interfere with the capture sequences of the oligonucleotides that target binding to nucleic acids in a sample. Unique barcode sequences may be generated using random sequence generation, along with stringent filtering of sequences by mapping to the genomes of all common reference species using desired Tm intervals, and GC content, to minimize interference with capture sequence binding to their targets, and to optimize the difference from the other barcode sequences. Thus, in at least one embodiment, the barcode sequences of the spatial array are selected such that desired target nucleic acids of the sample applied to the array do not hybridize specifically to the barcode sequence of the second oligonucleotide segment. For example, in some embodiments, the barcode sequences of the spatial array have less than 80% sequence identity to the targeted nucleic acid sequences in the sample applied to the spatial array. In some embodiments, barcode sequence has less than 70% sequence identity, less than 60% sequence identity, less than 50% sequence identity, or less than 40% sequence identity to the nucleic acids in the sample targeted for capture by the plurality oligonucleotide sequences.

Third, as depicted in FIG. 31C, a plurality of third oligonucleotide segments are attached to the unattached end of the second segment. In at least one embodiment, the third oligonucleotide segment is in the same orientation as the second segment. Thus, if the second segment is attached to the first segment through its 5'-end (in a 5'-to-3' orientation relative to the substrate) then the third oligonucleotide segment is attached through its 5'-end to the 3'-end of the second segment. As exemplified in FIG. 31C, in at least one embodiment, the third oligonucleotide segments are attached through their 5'-ends to the 3'-ends of the plurality of second segments. In some embodiments, the third oligonucleotide segment has a length of about 5-mer to about 40-mer and comprises a capture sequence capable of hybridizing to a nucleic acid in a sample. As described further herein, in some embodiments, the third oligonucleotide segment comprises a free 3'-OH and is capable of hybridizing to a complementary nucleic acid in a sample and then undergoing biosynthetic (e.g., polymerase catalyzed) extension from it 3'-OH.

In at least one embodiment, the plurality of third oligonucleotide segments have a length of at least about 5-mer, at least about 10-mer, at least about 15-mer, at least about 20-mer, at least about 27-mer, at least about 30-mer, at least about 33-mer, or at least about 35-mer. In some embodiments, the plurality of third oligonucleotide segments have a length of about 5-mer to about 40-mer, about 10-mer to about 40-mer, about 20-mer to about 40-mer, about 25-mer to about 35-mer, or about 27-mer to about 33-mer.

The 5-mer to 40-mer length of a third oligonucleotide segment makes its attachment by in situ synthesis on the ends of the second oligonucleotide segments problematic. The accumulating errors during in situ synthesis would compromise the ability of any capture sequences to function effectively on the spatial array. Accordingly, in at least one embodiment of the methods of the present disclosure, the third oligonucleotide segments are prepared off the substrate and attached as a whole segment by chemical coupling or ligation to the plurality of second oligonucleotide segments. In at least one embodiment, the plurality of third oligonucleotide segments are attached by ligation. In some embodiments, protected moieties of the first and second oligonucleotide segments are deprotected prior to ligating the plurality of third oligonucleotide segments.

In at least one embodiment where the method of the present disclosure further comprises attaching a plurality of third oligonucleotide segments, the first oligonucleotide segment is attached to the substrate through its 5'-end, the plurality of second oligonucleotide segments are prepared by spatially-directed in situ synthesis on the 3'-end of the first segment, and the plurality of third oligonucleotide segments are attached through their 5'-end to the 3'-end of the plurality of second segments.

Alternatively, in at least one embodiment where the method of the present disclosure further comprises attaching a plurality of third oligonucleotide segments, the first oligonucleotide segment is attached to the substrate through its 3'-end, the plurality of second oligonucleotide segments are prepared by spatially-directed in situ synthesis on the 5'-end of the first segment, and the plurality of third oligonucleotide segments are attached through their 3'-end to the 5'-end of the plurality of second segments.

In at least one embodiment, the third oligonucleotide segment comprises a capture sequence capable of hybridizing to a nucleic acid sequence in a sample. In at least one embodiment, the capture sequence is located at the free 3'-end of the third oligonucleotide segment which is oriented with its 5'-end attached to the second oligonucleotide segment. In this orientation the free 3'-end can be extended (e.g. by template dependent polymerization). It is contemplated that in at least one embodiment, the capture sequence of the third segment comprises a sequence capable of hybridizing to a specific type of target nucleic acid that is present in a sample. For example, the capture sequence of the third segment can be designed to selectively capture mRNA by hybridization to the poly-A tail. Accordingly, in at least one embodiment, the capture sequence of the third oligonucleotide segment comprises a poly-T oligonucleotide. Alternatively, in some embodiments, the capture sequence may comprise nucleotides which are functionally analogous to poly-T and capable of binding selectively to poly-A, such as a poly-U oligonucleotide. In at least one embodiment, the capture sequence of the third oligonucleotide comprises is a poly-T or poly-U sequence of at least 5-mer to 40-mer in length. In some embodiments, the capture sequence comprises a poly-T or poly-U sequence of at least 5-mer, 10-mer, at least 15-mer, at least 20-mer, at least 25-mer, at least 30-mer, at least 35-mer, or at least 40-mer in length.

In some embodiments, it is contemplated that the capture sequence can be designed to selectively bind to a desired sub-type or subset of nucleic acid targets suspected of being present in a sample. For example, a particular type of RNA, such as mRNA, microRNA or rRNA, or a particular mRNA species that corresponds to a particular group of genes. Thus, capture sequence of the third oligonucleotide segment may include a sequence that specifically binds to a particular target gene or set of genes, and can be based on a particular sequence motif sequence or conserved sequence according to methods well known in the art.

In some embodiments, the third segments of the plurality of the oligonucleotide can also comprise a random sequence. As is well-known in the art, such random sequences (e.g. random hexamers or nonamers) are effective for the capture nucleic acid targets by selective binding. Accordingly, it is contemplated that the capture sequence of the third segments of the plurality of oligonucleotides can comprise a random sequence, where the random sequences are at least 6-mers, at least 8-mers, at least 10-mers, at least 12-mers, at least 14-mers, at least 16-mers, or longer. In some embodiments, the plurality of third oligonucleotide segments can include random sequences together with a poly-T or poly-U capture sequence. Accordingly, where a third oligonucleotide comprises a poly-T or poly-U capture sequence, it may also comprise a random sequence. In some embodiments, where the third segment is in a 5'-to-3' orientation, the random sequences are located at the 5'-end of the third segment adjacent to the 3-end of the second segment comprising the barcode sequence.

In at least one embodiment, the first, second, and third oligonucleotide segments are linked via phosphodiester bonds. Additionally, in some embodiments, it is contemplated that the oligonucleotide segments can be attached via non-natural oligonucleotide linkages, such as methylphosphonate or phosphorothioate bonds, or via other non-natural biocompatible linkages such as click-chemistry linkages. The bonds linking the segments can be formed by synthetic phosphoramidite coupling chemistry, by a synthetic click-chemistry, by a ligation reaction, by enzymatic biosynthesis of nucleic acid polymers (e.g., using a polymerase or transcriptase), or a combination of bond forming reactions. For example, in at least one embodiment, the second oligonucleotide segment is attached to the first oligonucleotide segment by standard phosphoramidite chemistry forming a phosphodiester linkage, and the third oligonucleotide segment is attached to the unattached end of the second segment via a ligation reaction.

The plurality of oligonucleotides on a spatial array can be attached (e.g., covalently bound or immobilized) to the substrate via either the 3'-end or 5'-end of the oligonucleotide. The attachment of an oligonucleotide to a substrate of a spatial array through a covalent bound can be either direct (e.g., substrate to 3'-end of oligonucleotide) or indirect (e.g., substrate to linker molecule to 3'-end of oligonucleotide). Typically, for commercially available DNA microarrays, the oligonucleotides are attached via a 3' linkage, thereby leaving a free 5'-end. The free 5'-end can be used for further synthesis on the oligonucleotide strand. However, oligonucleotides attached to the substrate via the 5'-end, provide an advantage in having their 3'-ends available for further biosynthetic extension (e.g., using polymerase or transcriptase) as described elsewhere herein.

In at least one embodiment, the first oligonucleotide segment is attached to the substrate through its 5'-end, the second oligonucleotide segment is attached to the 3'-end of the first segment through its 5'-end, and the third segment is attached to the 3'-end of the second segment through its 5'-end.

In at least one embodiment, the first oligonucleotide segment is attached to the substrate through its 3'-end; the second oligonucleotide segment that is attached to the 5'-end of the first segment through its 3'-end, and the third segment is attached to the 5'-end of the second segment through its 3'-end.

In at least one embodiment of the composition of the present disclosure the length of the oligonucleotide in each region is at least 10-mer, at least 20-mer, at least 30-mer, at least 40-mer, at least 50-mer, or at least 60-mer. In some embodiments the length of the oligonucleotide in each region is from 5-mer to 100-mer, from 10-mer to 100-mer, from 20-mer to 100-mer, from 40-mer to 100-mer, from 50-mer to 90-mer, or from 60-mer to 80-mer.

As described elsewhere herein, some embodiments of the spatial arrays of the present disclosure, the first oligonucleotide segment of the spatial array comprises a 2-mer to 40-mer having the common sequence attached across all, or a substantial contiguous portion, of the surface of the substrate. Thus, the step of attaching the common first oligonucleotide segment to the substrate does not need to be spatially directed. Accordingly, a variety of different embodiments can be used to attach prepare a substrate having a common first oligonucleotide segment of 2-mer to 40-mer attached thereto.

As illustrated by FIGS. 32A-C, in at least one embodiment, a first oligonucleotide segment is prepared ex situ by standard automated solid-phase oligonucleotide synthesis in a 3'-to-5' direction using phosphoramidite chemistry. However, as described elsewhere herein, protection of the phosphodiester and exocyclic amine moieties of the first oligonucleotide segment facilitates the spatially-directed in situ synthesis of the second oligonucleotide segment on the unattached end of the first oligonucleotide segment. Thus, as shown in FIG. 32A, in at least one embodiment, the first oligonucleotide segment is synthesized ex situ using standard techniques, however, the synthesized oligonucleotide is cleaved from the solid-support without deprotecting the phosphodiester and exocyclic amine moieties that are protected during synthesis. The protected common oligonucleotide used for the first segment is attached to the substrate with the protecting groups intact as show in FIG. 32B.

The standard oligonucleotide synthesis method using phosphoramidite chemistry was developed in the 1980s and later enhanced with solid-phase supports and automation. It the method used by commercial synthesis of DNA and RNA oligonucleotides. Generally, solid-phase oligonucleotide synthesis proceeds in the 3'→5' direction rather than 5'→3' direction of natural biosynthesis. The solid-phase phosphoramidite synthesis cycle generally comprises four steps: (1) detritylation; (2) coupling; (3) oxidation; and (4) capping. Briefly, the four steps in the synthesis cycle are as follows. In step (1), "detritylation," a 5'-DMT protecting group is removed from the first, solid-support-linked nucleoside. In step (2), "coupling," the de-protected 5'-OH of the first, solid-support-linked nucleoside attacks the phosphorus of the incoming second nucleoside to form a phosphite triester. In step (3), "oxidation," the relatively unstable phosphite triester is converted to a stable phosphate triester. In step (4), prior to moving to step (1) of the next cycle, "capping," is carried out wherein unreacted 5'-OH groups are acetylated, thereby preventing elongation of sequences with deletion mutations.

In at least one embodiment of the ex situ synthesis method, the final monomer unit added to the 5'-end during ex situ synthesis of the first oligonucleotide segment can comprise a non-natural nucleoside that facilitates attachment or immobilization of the first oligonucleotide segment to the substrate or linkers attached to the substrate via its 5'-end. Alternatively, in some embodiments of the ex situ synthesis method, the first monomer unit added to the 3'-end during ex situ synthesis of the first oligonucleotide segment can comprise a non-natural nucleoside that upon cleavage from the synthesis solid support can facilitate attachment or immobilization of the first oligonucleotide segment to the substrate or linkers attached to the substrate via the 3'-end.

In at least one embodiment, the first oligonucleotide segment attached to the substrate is prepared by in situ synthesis on the substrate. Generally, because the sequence of the first oligonucleotide segment is the same across all regions of the substrate, it is not necessary to use spatially-directed in situ synthesis in such an embodiment. For example, in situ synthesis of the first oligonucleotide can be carried out on the substrate using standard solid-phase phosphoramidite chemistry and reagents. As noted above, maintaining protection of the phosphodiester and exocyclic amine moieties of the first oligonucleotide segment facilitates the spatially-directed in situ synthesis of the second oligonucleotide segment on the unattached end of the first oligonucleotide segment. Accordingly, in at least one embodiment, it is contemplated that the in situ synthesis first oligonucleotide segment on the substrate is carried out without the final step of deprotecting the phosphodiester and exocyclic amine moieties before the second segment is synthesized.

FIG. 33A-B illustrate at least one embodiment of a method for in situ synthesis of a common first oligonucleotide segment directly on the substrate. The synthesis is carried out using step-wise solid-phase phosphoramidite chemistry but without final cleavage or deprotection steps. As shown in FIG. 33A, in this embodiment, the synthesis would result in a first oligonucleotide segment attached across the surface of the substrate with protected phosphodiester and exocyclic amine moieties. Following this in situ synthesis of the first oligonucleotide segment with protective groups intact, light-directed spatial synthesis of the second oligonucleotide segment to the 3'-ends of the first segments can be carried out as shown in FIG. 33B.

In at least one embodiment, the first oligonucleotide segment attached to the substrate is prepared by spatially-directed in situ synthesis on the substrate. The spatially-directed oligonucleotide synthesis method used can include light-directed spatial synthesis and mechanically-directed spatial synthesis described elsewhere herein. In this embodiment, the spatially-directed synthesis can be used in essentially the same way as the in situ standard oligonucleotide synthesis for the preparation of the first oligonucleotide segment having a single sequence across all regions of the substrate. It is contemplated, however, that in some embodiments spatially-directed synthesis can be used to prepare a substrate having the first oligonucleotide attached in selected regions of the substrate. For example, in some embodiments, a spatial array could be prepared having more than one first oligonucleotide segment sequence in different locations of the substrate.

Accordingly, as shown in FIGS. 34A-B that in at least one embodiment the common first oligonucleotide segment can be in situ synthesized directly on the substrate however using light-directed synthesis with photolabile groups, rather than standard protective groups, such as dimethoxytrityl groups. The synthesized first oligonucleotide segments would be prepared using light-directed deprotection but would not be cleaved from the substrate or deprotected as shown in FIG. 34A. Following this light-directed in situ synthesis of the first oligonucleotide segment with protective groups intact, light-directed spatial synthesis of the second oligonucleotide segment to the 3'-ends of the first segments can be carried out as shown in FIG. 34B.

Generally, during standard automated oligonucleotide synthesis, following cleavage of the oligonucleotide from the synthesis solid support, the protecting groups on the phosphates and bases are removed (or deprotected) by treatment in concentrated aqueous ammonia with heat. Accordingly, it is also contemplated in at least one embodiment that a first oligonucleotide is synthesized ex situ using standard automated synthesis, including cleavage and deprotection of the phosphodiesters and/or exocyclic amine moieties. As illustrated by the schematic of FIG. 35A, the cleaved and deprotected first oligonucleotide segments synthesized ex situ can be attached to the substrate surface through a linkage to the 5'-end as described elsewhere herein. Then, as depicted by FIG. 35B, the phosphodiester and/or exocyclic amine moieties can be protected in situ on the substrate. Following this in situ protection step, light-directed spatial synthesis of the second oligonucleotide segment to the 3'-ends of the first segments can be carried out as shown in FIG. 35C.

In another embodiment illustrated by the schematic of FIG. 36A, ex situ synthesized first oligonucleotide segments can be cleaved from their synthesis support, deprotected, and then attached to a substrate surface through a linkage to the 5'-end as described elsewhere herein. Then, as depicted by FIG. 36B, a complementary oligonucleotide can be hybridized to the common first oligonucleotide segments located across the substrate. The formation of a double-stranded structure by hybridization can effectively protect the phosphodiester and/or exocyclic amine moieties of the first oligonucleotide segment on the substrate. Following this in situ protection-by-hybridization step, light-directed spatial synthesis of the second oligonucleotide segment to the 3'-ends of the first segments can be carried out as shown in FIG. 36C.

In at least one embodiment, the spatial array compositions prepared using the methods of the present disclosure can be useful for spatial transcriptomics applications as described in e.g., US2014/0066318A1. Briefly, in spatial transcriptomics a complex multi-cellular sample, such as a tissue sample, is immobilized on a spatial array of oligonucleotides. Typically, the oligonucleotide sequences are attached to the array substrate through their 5'-end and include an mRNA capture sequence at their 3'-end. Each of the oligonucleotides also includes 5'-adjacent to the capture sequence, a random primer sequence of at least 16-mer that allows for amplification of any captured sequences. The detection process results in amplification of the captured mRNA sequence as well as the barcode sequence. Sequencing of the amplicons thereby indicates not only the identity of the transcribed gene but also the location in the multi-cellular sample where the gene was transcribed.

Furthermore, in order to survey the genes undergoing transcription in a complex multi-cellular sample, the spatial array should include an extremely high density of different oligonucleotides specifically located on the substrate. For example, it is contemplated that spatial arrays useful in various applications, such as spatial transcriptomics, can include 1.5 million, 10 million, 100 million, and even up to 1.0 billion different oligonucleotides, each of which has a different barcode sequence and is located in a different region on a substrate, wherein the regions are less than 5 $\mu m^2$, even as small as 1.0 $\mu m^2$.

As noted elsewhere herein, each oligonucleotide of a spatial array should comprise a different barcode sequence that correlates with its location. In some embodiments, it is contemplated that additional oligonucleotides may be present on the same substrate as the spatial array, that comprise a sequence identical to a barcode sequence of the spatial array. Such additional oligonucleotides may arise due to errors in synthesis or can be prepared intentionally on the substrate (e.g., for calibration or QC purposes). Generally, these sequences located in a different location on the same substrate are not considered part of the spatial array and are kept to a level and/or location that avoids interference with the intended function of the spatial array.

As illustrated by the particular exemplary application of spatial transcriptomics, the ability to accurately correlate the barcode sequence of each oligonucleotide on a spatial array with a location (or region) on the substrate is critical to the utility of the spatial array. Accordingly, the preparation of spatial arrays requires methods for immobilizing up to a billion different oligonucleotides, each with a specific barcode sequence, in a specific identifiable region on a substrate.

Disclosed herein is a method of preparing a spatial array comprising (a) providing a solid support; (b) immobilizing a plurality of sets of primers on the solid support, wherein a first set of the plurality of sets of primers comprises a first primer and a second primer, wherein the first primer and the second primer are at a 1:1 ratio; and wherein the first primer and the second primer are less than 10 µm apart; (c) providing a template oligonucleotide comprising a reverse complement of a spatial barcode domain, a reverse complement of a capture domain, a first hybridization domain capable of hybridizing to the first primer, and a second hybridization domain, wherein a reverse complement of the second hybridization domain is capable of hybridizing to the second primer; (d) hybridizing the template oligonucleotide to the first primer; (e) extending the first primer using the template oligonucleotide as a template to generate a capture probe comprising the first primer, the spatial barcode, and the capture domain, which capture probe is immobilized on the solid support; and (f) releasing the template oligonucleotide from the spatial array. In some aspects, the method further comprises amplifying the capture probe to create a cluster of one or more capture probes. In some aspects, amplifying comprises: (a) hybridizing the capture probe to the second primer; (b) extending the second primer using the capture probe as a template to generate a copy of the template oligonucleotide that is immobilized on the solid support; (c) hybridizing the copy of the template oligonucleotide to a first primer of a second set of the plurality of primers; and (d) extending the first primer of the second set of the plurality of primers using the copy of template oligonucleotide as a template to generate a copy of the capture probe that is immobilized on the solid support, wherein the cluster of capture probes comprises the capture probe and the copy of the capture probe.

In some aspects, the template oligonucleotide comprises a reverse complement of a unique molecular identifier (UMI), and wherein the generated capture probe comprises the UMI.

In some aspects, the first primer is affixed to the solid support at a 5' end of the first primer.

In some aspects, the first primer comprises a sequence that is complementary to the template oligonucleotide.

In some aspects, the first primer comprises poly (A) domain.

In some aspects, the first primer comprises cleavage domain. In some aspects, the second primer is affixed to the solid support at a 5' end of the second primer. In some aspects, the second primer comprises a cleavage domain. In some aspects, the copy of the template oligonucleotide is released by cleaving the cleavage domain after the copy of the capture probe is generated.

In some aspects, the template oligonucleotide is attached to a bead. In some aspects, the bead is a gel bead. In some aspects, the bead is 2 microns or less in diameter. In some aspects, the bead is 1 micron or less in diameter. In some aspects, the bead is removed prior to the step of extending the first primer. In some aspects, the bead is removed after the step of extending the first primer.

In some aspects, the identity of the generated capture probe is determined. In some aspects, the identity of the generated capture probe is determined after the template oligonucleotide is released. In some aspects, the identity of the generated capture probe is determined in situ. In some aspects, the identity of the generated capture probe is determined by in situ sequencing. In some aspects, in situ sequencing is performed via sequencing-by-synthesis (SBS), sequential fluorescence hybridization, sequencing by ligation, nucleic acid hybridization, or high-throughput digital sequencing techniques.

In some aspects, the capture domain comprises a sequence complementary to an analyte of interest. In some aspects, the capture domain comprises a poly(T) domain.

In some aspects, the solid support comprises a glass slide. In some aspects, the glass slide is a treated glass slide.

Also disclosed herein is a method for spatial analysis of a biological analyte in a biological sample comprising: (a) preparing a spatial array by a method as provided herein; (b) decoding the one or more capture probes by determining the identity of the spatial barcode of the one or more capture probes, thereby associating the spatial barcode of the one or more capture probe with a location on the spatial array; (c) contacting the biological sample to the spatial array under conditions wherein the biological analyte binds the cluster; (d) extending the one or more capture probes via a polymerization reaction using the biological analyte as a template to generate an extended one or more capture probes comprising the one or more capture probes and the reverse complement of the biological analyte; (e) determining the sequence of the extended one or more capture probes, and associating the spatial barcode of the one or more capture probes with the captured biological analyte; thereby determining spatial location of the biological analyte.

Also disclosed herein is a spatial array produced by any one of the methods as provided herein.

Further, disclosed herein is a spatial array comprising (a) a solid support; and (b) a plurality of sets of primers immobilized on the solid support, wherein a first set of the plurality of sets of primers comprises a first primer and a second primer, wherein the first primer and the second primer are at a 1:1 ratio; wherein the first primer and the second primer in each set are less than 10 μm apart; and wherein the first primer comprises a sequence that is complementary to a capture probe. In some aspects, the spatial array further comprises a template oligonucleotide comprising a reverse complement of a unique molecular identifier (UMI), and wherein the capture probe comprises the UMI.

In some aspects, the first primer is affixed to the solid support at a 5' end of the first primer. In some aspects, the first primer comprises a sequence that is complementary to the template oligonucleotide. In some aspects, the first primer comprises poly (A) domain.

In some aspects, the first primer comprises cleavage domain. In some aspects, the second primer is affixed to the solid support at a 5' end of the second primer. In some aspects, the second primer comprises a cleavage domain.

In some aspects, the template oligonucleotide is attached to a bead. In some aspects, the bead is a gel bead. In some aspects, the bead is 2 microns or less in diameter. In some aspects, the bead is 1 micron or less in diameter.

In some aspects, the solid support comprises a glass slide. In some aspects, the glass slide is a treated glass slide.

Provided herein are methods of preparing a spatial array. A "spatial array" as disclosed herein is an array that allows resolution equal to or less than 10 μm, allowing single-cell resolution. A spatial array comprises plurality of sets of primers on the solid support. The sets of primers comprises a sets of a first primer and a second primer at a 1:1 ratio. The second primer has a sequence that is complementary to the first primer or to a template oligonucleotide.

The methods of preparing a spatial array include providing a solid support, immobilizing a plurality of sets of primers on the solid support, providing a template oligonucleotide having a reverse complement of a spatial barcode domain, a reverse complement of a capture domain, a first hybridization domain capable of hybridizing to the first primer, and a second hybridization domain, wherein a reverse complement of the second hybridization domain is capable of hybridizing to the second primer; hybridizing the template oligonucleotide to the first primer; extending the first primer using the template oligonucleotide as a template to generate a capture probe comprising the first primer, the spatial barcode, and the capture domain, which capture probe is immobilized on the solid support; and releasing the template oligonucleotide from the spatial array.

The spatial array comprises a plurality of sets of primers affixed to the solid support. The plurality of sets of primers includes a first primer and a second primer that are at a 1:1 ratio and that are less than 10 μm apart. The first primer is affixed to the solid support at the 5' end of the first primer. The second primer is affixed to the solid support at the 5' end of the second primer.

The first primer and/or the second primer can be a nucleotide. In some aspects, the first primer is single stranded DNA. In some aspects, the first primer is RNA. In some aspects, the second primer is single stranded DNA. In some aspects, the second primer is RNA.

The first primer on the solid support comprises a sequence that is complementary to the template oligonucleotide and allows the template oligonucleotide to bind to the first primer. The first primer can also comprise a poly (A) or poly (T) domain that is complementary to a poly(T) or poly(A) domain of the second primer. The first primer can also comprise a cleavage domain. The second primer can also comprise a cleavage domain.

The first primer and the second primer are used to amplify a template oligonucleotide to create a cluster of one or more capture probes. In some aspects, the template oligonucleotide includes a reverse complement of a unique molecular identifier (UMI). Further, the template oligonucleotide is attached to a bead. In some aspects, the bead is a gel bead. In some aspects, the bead is less than 10 μm in diameter. In some aspects, the bead is less than 5 μm in diameter. In some aspects, the bead is 2 μm in diameter. In some aspects, the bead is less than 2 μm in diameter. In some aspects, the bead is 1 μm in diameter. In some aspects, the bead is less than 1 μm in diameter.

In some aspects, after binding of the template oligonucleotide to the first primer, the sequence of the primer is extended. In some aspects, the layer of beads that is attached to the oligos is removed after extension of the primer. In some aspects, the layer of beads that is attached to the oligos is removed before extension of the primer.

After initial binding of the template oligonucleotide and the primers, a capture probe is generated. In some aspects, the capture probe is generated using cluster expansion.

In some aspects, the capture probe comprises a UMI. In some aspects, the capture probe includes sequences for first primer, the spatial barcode, and the capture domain. In some aspects, the capture probe is immobilized on the solid support. In some aspects, the capture domain comprises a sequence complementary to an analyte of interest. In some aspects, the capture domain comprises a poly(T) domain.

After a copy of the capture probe is generated, the copy of the template oligonucleotide is released by cleaving the cleavage domain after the copy of the capture probe is generated.

After cluster amplification, the identity of the generated capture probe is determined. In some aspects, the identity of the generated capture probe is determined after the template oligonucleotide is released. In some aspects, the identity of the generated capture probe is determined in situ. In some aspects, the identity of the generated capture probe is determined by in situ sequencing. In situ sequencing is performed via sequencing-by-synthesis (SBS), sequential fluorescence hybridization, sequencing by ligation, nucleic acid hybridization, or high-throughput digital sequencing techniques.

After the probe is clonally expanded, spatial analysis of a biological analyte in a biological sample can be performed. In some aspects, method of performing spatial analysis of a biological analyte in a biological sample include preparing the spatial array as discussed above. In some aspects, the methods further include decoding the one or more capture probes by determining the identity of the spatial barcode of the one or more capture probes, thereby associating the spatial barcode of the one or more capture probe with a location on the spatial array; contacting the biological sample to the spatial array under conditions wherein the biological analyte binds the cluster; extending the one or more capture probes via a polymerization reaction using the biological analyte as a template to generate an extended one or more capture probes comprising the one or more capture probes and the reverse complement of the biological analyte; and determining the sequence of the extended one or more capture probes, and associating the spatial barcode of the one or more capture probes with the captured biological analyte thereby determining spatial location of the biological analyte.

Example 1—Method for Building an Array for Spatial Synthesis

Figure 24:
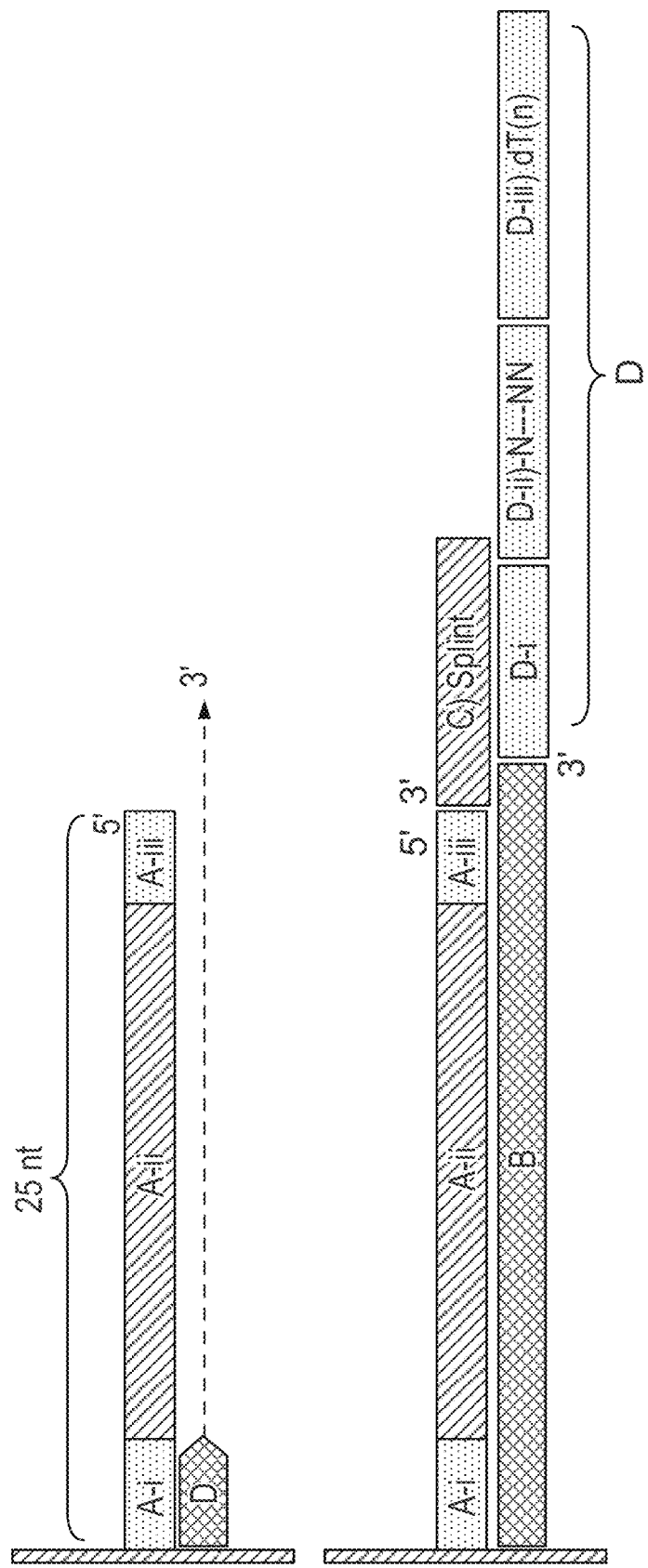
FIG. 24 is a schematic diagram showing a method for generating capture probes of an array for spatial analysis of analytes in biological sample.

In a non-limiting example, capture probes can be generated using a plurality of oligonucleotides for spatially barcoding analytes on an array (FIG. 24). The oligonucleotides "A" include a constant sequence (A-i), and a spatial barcode sequence (A-ii), and optionally a second constant sequence (A-iii). A primer complementary to a portion of the oligonucleotide is hybridized with and extended using the oligonucleotide as a template to generate a first oligonucleotide. The first oligonucleotide is further extended to create a 3' end overhang, where an enzyme (e.g., template independent polymerase) is used to introduce additional polynucleotides at the end of the first oligonucleotide. A splint oligonucleotide "C" can be provided that hybridizes the 3' end (e.g., overhang) of the first oligonucleotide. A second oligonucleotide is ligated to the 3' end of the first oligonucleotide to generate a capture probe.

As shown in FIG. 24 the second oligonucleotide "D" contains several domains. D-i contains a sequence complementary to a portion of the splint oligonucleotide, D-ii is a degenerate sequence that can serve as a unique molecular identifier, and D-iii is a capture domain that can be used to capture an analyte in a biological sample. D-iii optionally contains a poly-T sequence. Furthermore, D-iii can also be used to ligate to the analyte in a biological sample. The capture probes can be used to spatially locate analytes according to the methods described herein.

Example 2—Method for Spatial Analysis of a Biological Sample

Figure 25:
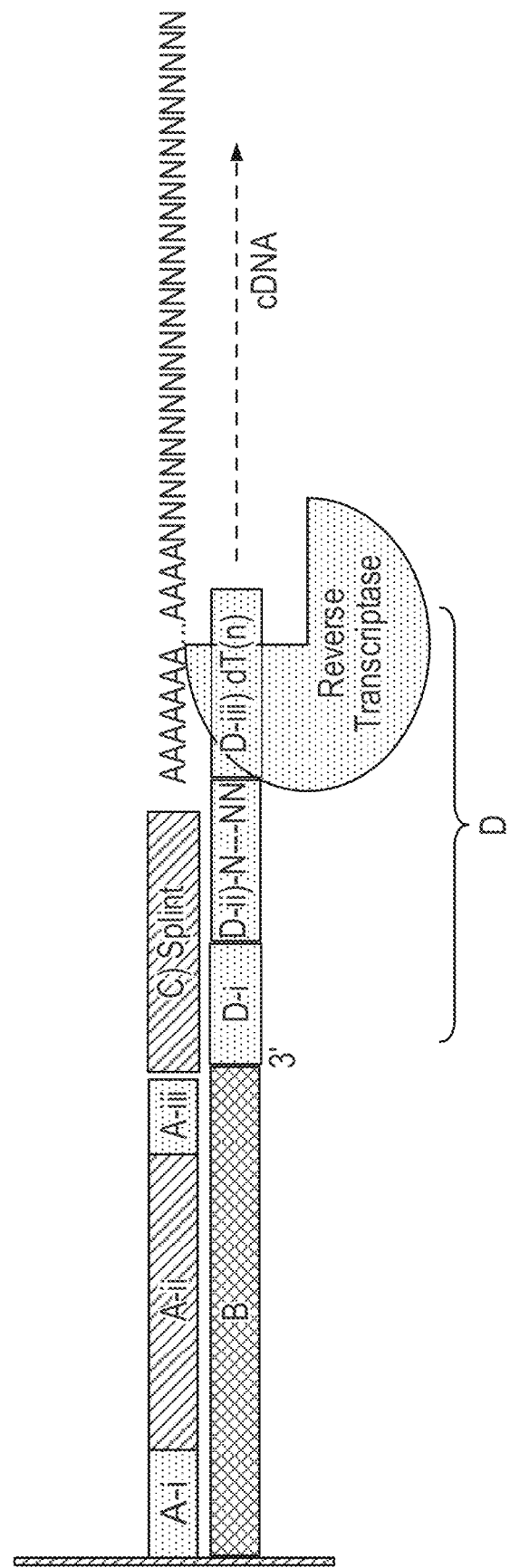
FIG. 25 is a schematic diagram showing a method of capturing an analyte with a capture domain and performing reverse transcription to obtain a complementary cDNA sequence.

In a non-limiting example, the array generated as described in Example 1 is used for spatial analysis of a biological sample. The capture domain (D-iii) is used to hybridize with the poly-A tail of an mRNA molecule SEQ ID NO: 8 (FIG. 25). Reverse transcription is carried out using a reverse transcriptase enzyme to generate cDNA complementary to the captured mRNA. The sequence and location of the captured mRNA are determined by sequencing the capture probe that contains the spatial barcode as well as the complementary cDNA.

Example 3—Methods for Preparing High-Density Spatially Barcoded Arrays

Figure 26:
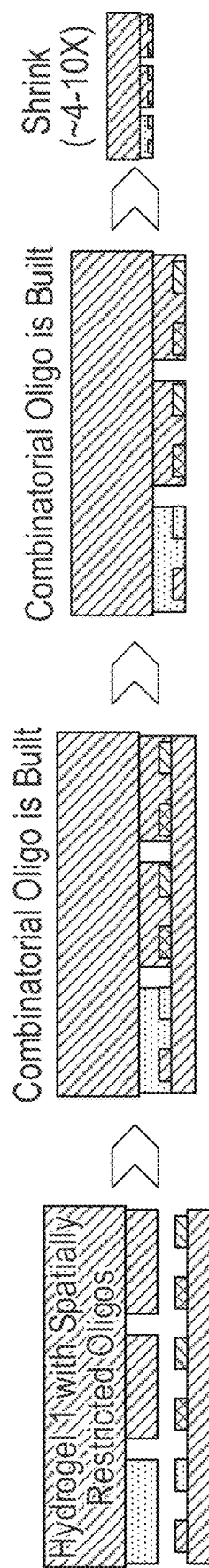
FIG. 26 shows a schematic depicting steps involved in generating a high-density spatially barcoded array with increased resolution.

An array including one or more pluralities of first oligonucleotides is contacted with a hydrogel including one or more pluralities of second oligonucleotides. A first oligonucleotide can have a capture domain, a second oligonucleotide can have a capture domain, or both first and second oligonucleotides can have a capture domain. Members of the one or more pluralities of the first oligonucleotides are attached to members of the one or more pluralities of second oligonucleotides to form one or more pluralities of coupled capture probes (e.g., a combinatorial oligo array is built). The size of the hydrogel containing the one or more pluralities of coupled capture probes is then reduced by removing water, which forms a shrunken hydrogel array containing the one or more pluralities of coupled capture probes (FIG. 26). The shrunken hydrogel array can be contacted with a biological sample under conditions sufficient to allow analytes present in the biological sample to interact with the coupled capture probes of the shrunken hydrogel array.

Figure 27:
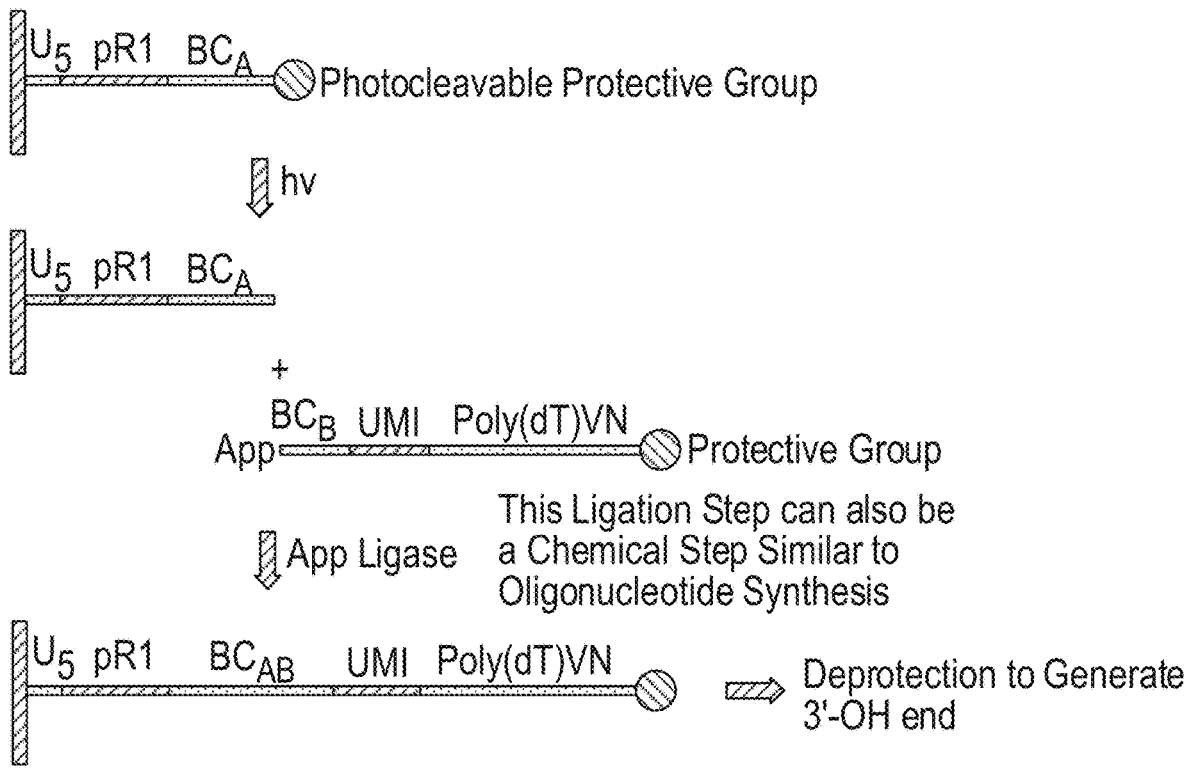
FIG. 27 is a schematic diagram showing an exemplary two-step barcode construction process to build an array.
Figure 28:
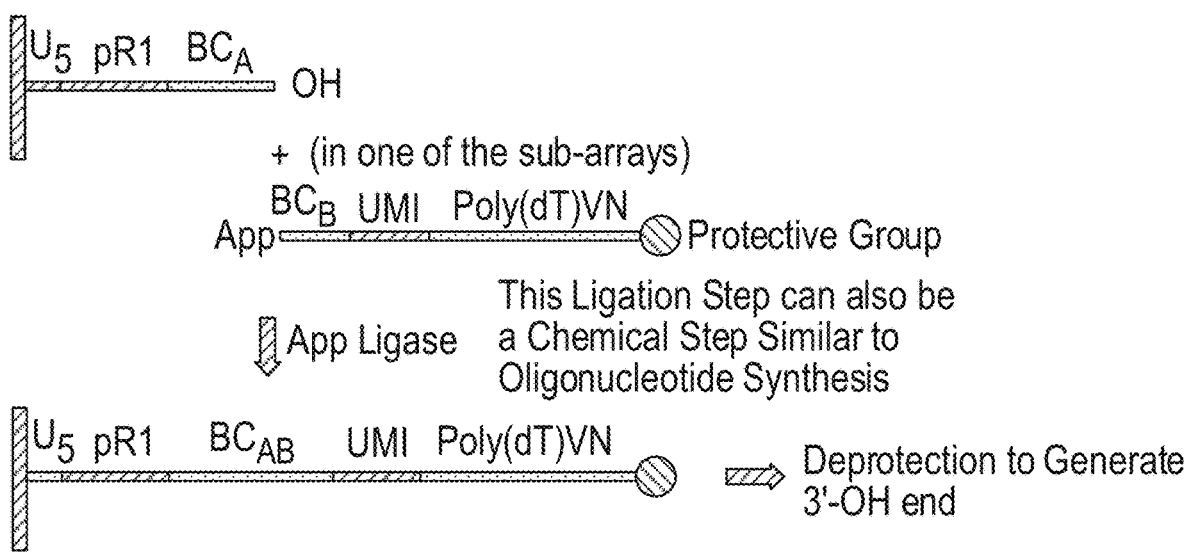
FIG. 28 is a schematic diagram showing an exemplary two-step barcode construction process to build an array.

Example 4—Method for Building an Array Using a Two-Step Barcode Construction Process and a Protective Group In a non-limiting example, a two-step spatial barcode construction process is used to build an array with high complexity. An array that includes a plurality of features immobilized on a substrate is provided, where each feature includes a plurality of first oligonucleotides, and each first oligonucleotide includes a first spatial barcode (FIG. 27). The first spatial barcode is associated with a particular feature, such that different features of the array are associated with different spatial barcodes. The plurality of first oligonucleotides are attached to a plurality of features or the substrate (e.g., direct attachment) at one end, and include a photocleavable protective group at the other end. A subset of the first oligonucleotides are exposed to a light source and the protective group on the selected first oligonucleotides are removed, leaving the first oligonucleotides 3' end available for attaching a second oligonucleotide. Next, a second oligonucleotide is ligated to the first oligonucleotide that have had the protective groups removed, where the second oligonucleotide includes a second spatial barcode, a unique molecular identifier sequence, and a capture domain (e.g., a poly-T sequence). In some cases, the second oligonucleotide also contains a protective group at the 3' end. The first oligonucleotide and the second oligonucleotide can be ligated using a ligase (e.g., App ligase). Alternatively, the first oligonucleotide and the second oligonucleotide are ligated through a chemical step (e.g., similar to oligonucleotide synthesis). Capture probes are thereby generated that contain the first spatial barcode and the second spatial barcode. Optionally, the protective group at the 3' end of the capture probes may be removed to generate a free 3'-OH end.

Example 5—Method for Building an Array by Building Separate Sub-Arrays

In a non-limiting example, a two-step spatial barcode construction process is used to build an array with high complexity. An array that includes a plurality of sub-arrays is provided, with each sub-array comprising a plurality of features immobilized on a substrate, where each feature includes a plurality of first oligonucleotides, and each first oligonucleotide includes a first spatial barcode (BCA). The sub-array can include features wherein each feature is associated with a first spatial barcode unique to the feature of origin on the sub-array. Therefore, any one particular feature of the sub-array associated with a first spatial barcode, can be represented multiple times if the sub-array or subtemplate is printed at multiple locations (see FIGS. 29 and 30). A plurality of second oligonucleotides are delivered to a first sub-array, where each second oligonucleotide includes a second spatial barcode (BCB), a unique molecular identifier sequence, and a capture domain (e.g. a poly-T sequence). In some cases, the second oligonucleotides also contain a protective group at the 3' end. The second oligonucleotides are ligated to the first oligonucleotides on the first subarray using a ligase, thereby generating capture probes that include the first spatial barcode and the second spatial barcode. Alternatively, the first oligonucleotides and the second oligonucleotides are ligated through a chemical step (e.g. similar to oligonucleotide synthesis). Optionally, the protective group at the 3' end of the capture probes may be removed to generate a 3'-OH end.

Next, a second plurality of third oligonucleotides may be delivered to a second subarray, where each third oligonucleotide includes a third spatial barcode, a unique molecular identifier sequence, and a second capture domain (e.g., a poly-T sequence). In some cases, the third oligonucleotides also contain a protective group at the 3' end. The third oligonucleotides are ligated to a fourth oligonucleotide containing the first spatial barcode on the first sub-array using a ligase, thereby generating capture probes that include the first spatial barcode, the third spatial barcode, and the second capture domain. Optionally, the protective group at the 3' end of the capture probes can be removed to generate a 3'-OH end.

Example 6—Method for Preparing a Slide that Contains a High Density Array

In a non-limiting example, the method of building a high density array as described in Examples 4 and 5 involves building the array on a substrate (e.g., a slide). A slide is provided that includes a plurality of identical sub-arrays, where each sub-array contains a plurality of first oligonucleotides immobilized on the slide, and each first oligonucleotide includes a first spatial barcode (BCA). In some cases, there are no gaps between the sub-arrays.

Figure 29:
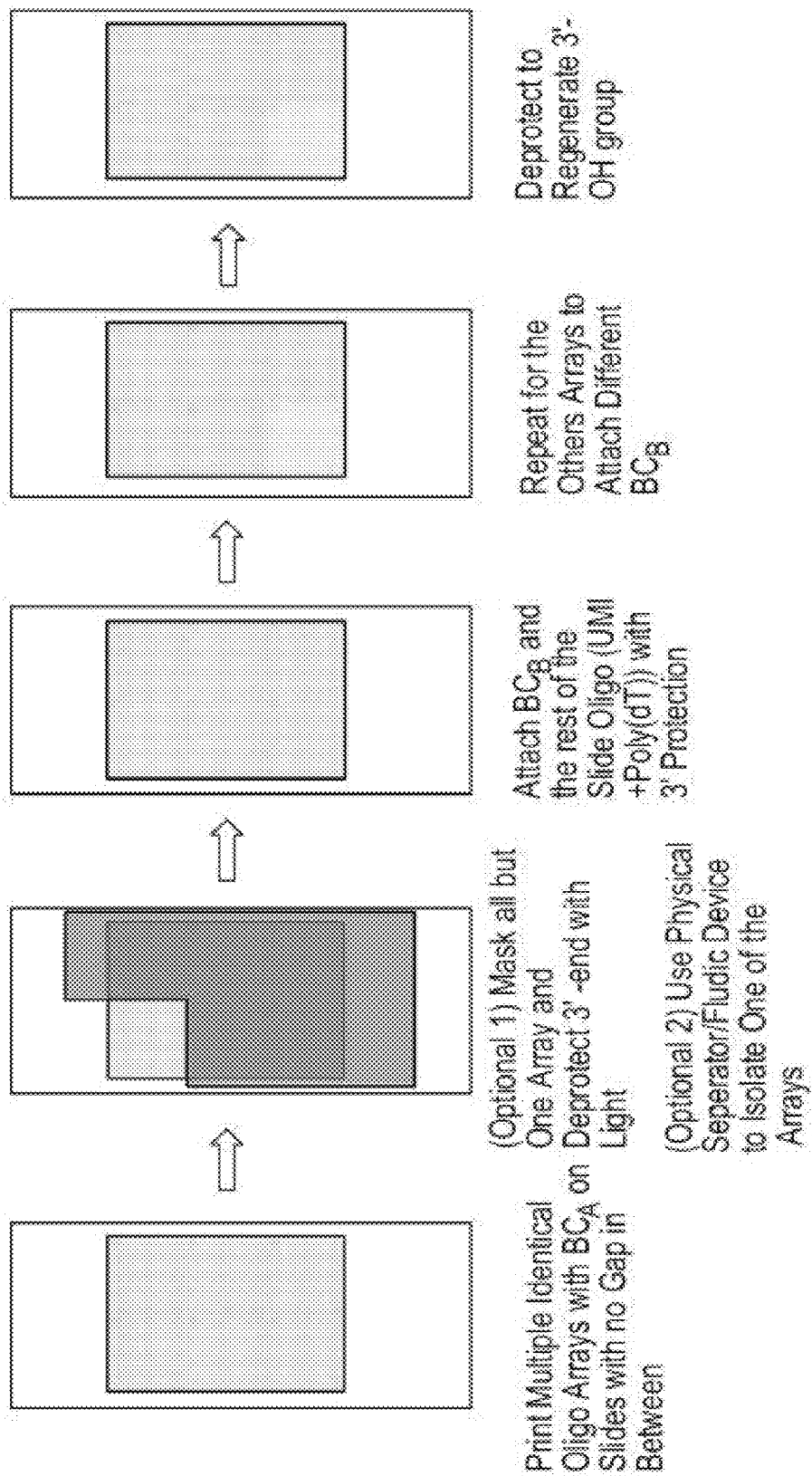
FIG. 29 is a schematic diagram showing an exemplary spatial array preparation process.

In one example, the plurality of first oligonucleotides are attached to the plurality of features or the substrate (e.g., direct attachment) at one end, and include a photocleavable protective group at the other end. A first sub-array is exposed to light while the remaining sub-arrays are masked from the light. The protective group on the first oligonucleotides on the first sub-array are thereby removed, leaving the first oligonucleotides available for attaching additional polynucleotides. Second oligonucleotides that contain a second spatial barcode (BCB) are attached to first oligonucleotides on the first sub-array that have had the protective group removed to generate capture probes that include both the first spatial barcode and second spatial barcode. The second oligonucleotides further include a unique molecular identifier and a capture domain (e.g. a poly-T sequence), and optionally a protective group attached to the 3' end. Next, a second sub-array is exposed to light while the remaining sub-arrays are masked from the light, and the above steps are repeated with third oligonucleotides that contain a third barcode (FIG. 29). Upon iteratively generating capture probes in all sub-arrays on the slide, the 3' protective group on the capture probes are removed.

In one example, one or more physical barriers are used to isolate a first subarray and second oligonucleotides that contain a second spatial barcode are delivered to the isolated first sub-array using a microfluidic device to generate capture probes that include both the first spatial barcode and the second spatial barcode. A second sub-array is then isolated and third oligonucleotides that contain a third spatial barcode are delivered to the second sub-array to generate capture probes that include both the first spatial barcode and the third spatial barcode. Upon iteratively generating capture probes in all sub-arrays, the protective group at the 3' end of the capture probes may be removed to generate a 3'-OH end.

Figure 30:
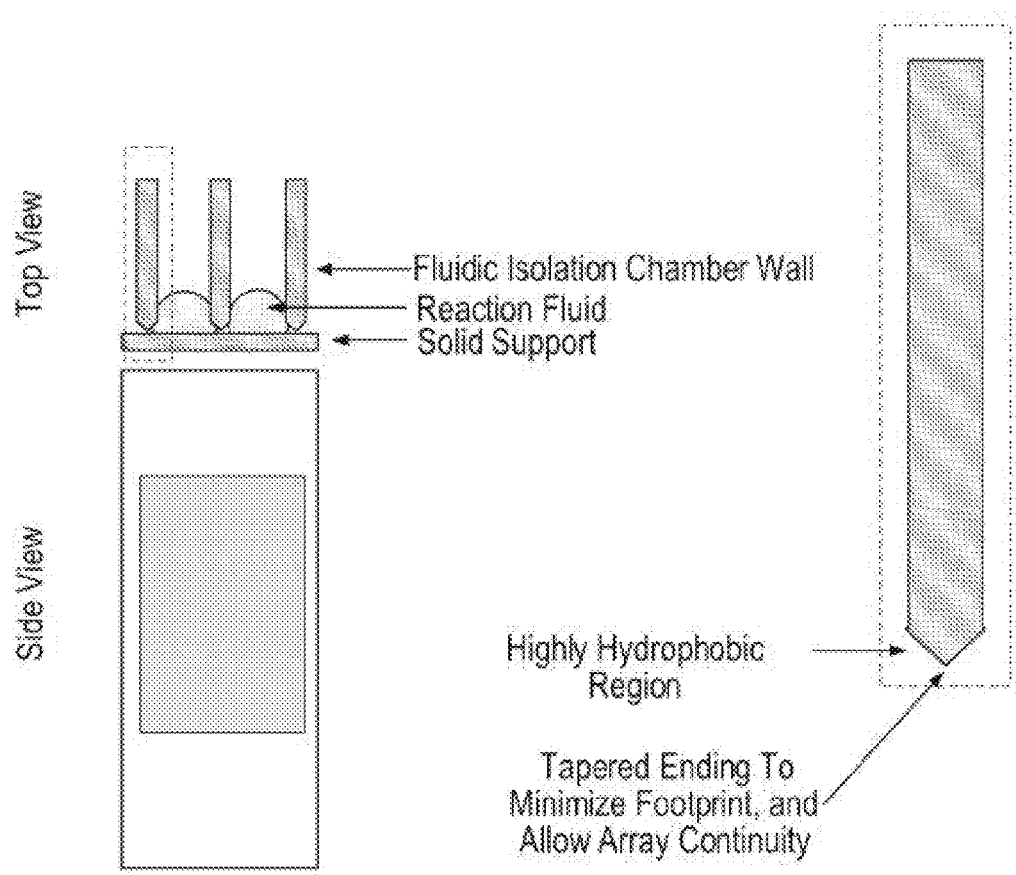
FIG. 30 is a schematic diagram showing an exemplary design for a fluidic isolation chamber.

Fluidic isolation chambers can be used to isolate sub-arrays on a slide, such that oligonucleotides containing different barcodes can be applied to different sub-arrays, as shown in FIG. 30. The fluidic isolation chambers contain chamber walls that may further include a tapered end that is highly hydrophobic and is designed to minimize footprint and allow for array continuity.

Example 7—Enrichment of a Spatial Barcode

Figure 38:
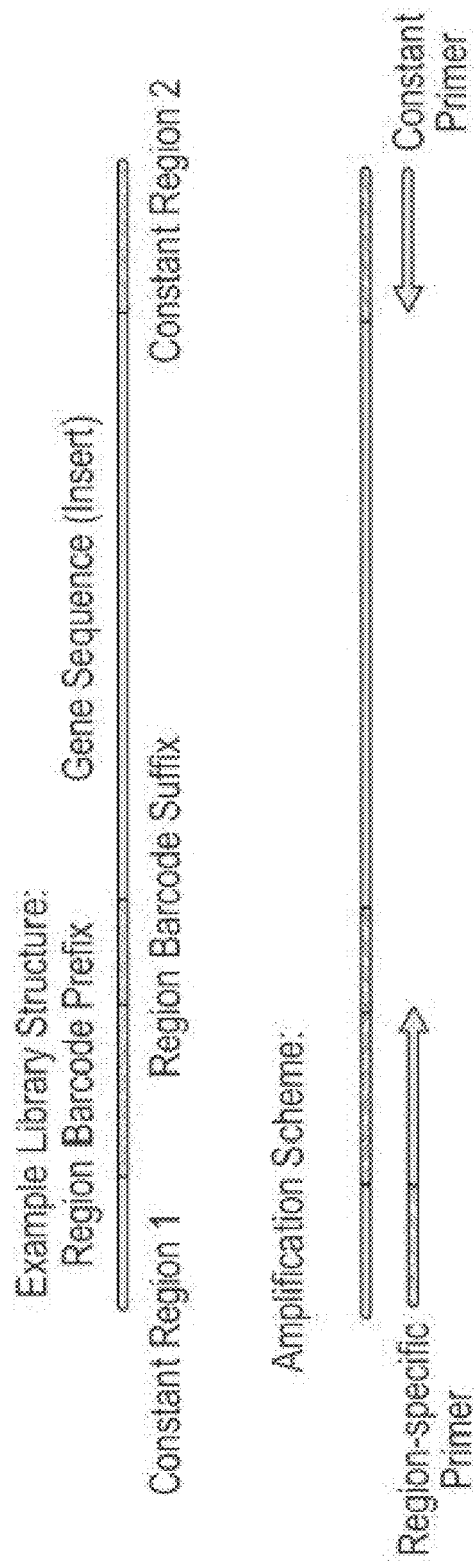
FIG. 38 shows an example of a library structure and amplification scheme including a two level spatial barcode, wherein the spatial barcode includes a region spatial barcode prefix and a specific spatial barcode suffix.
Figure 39:
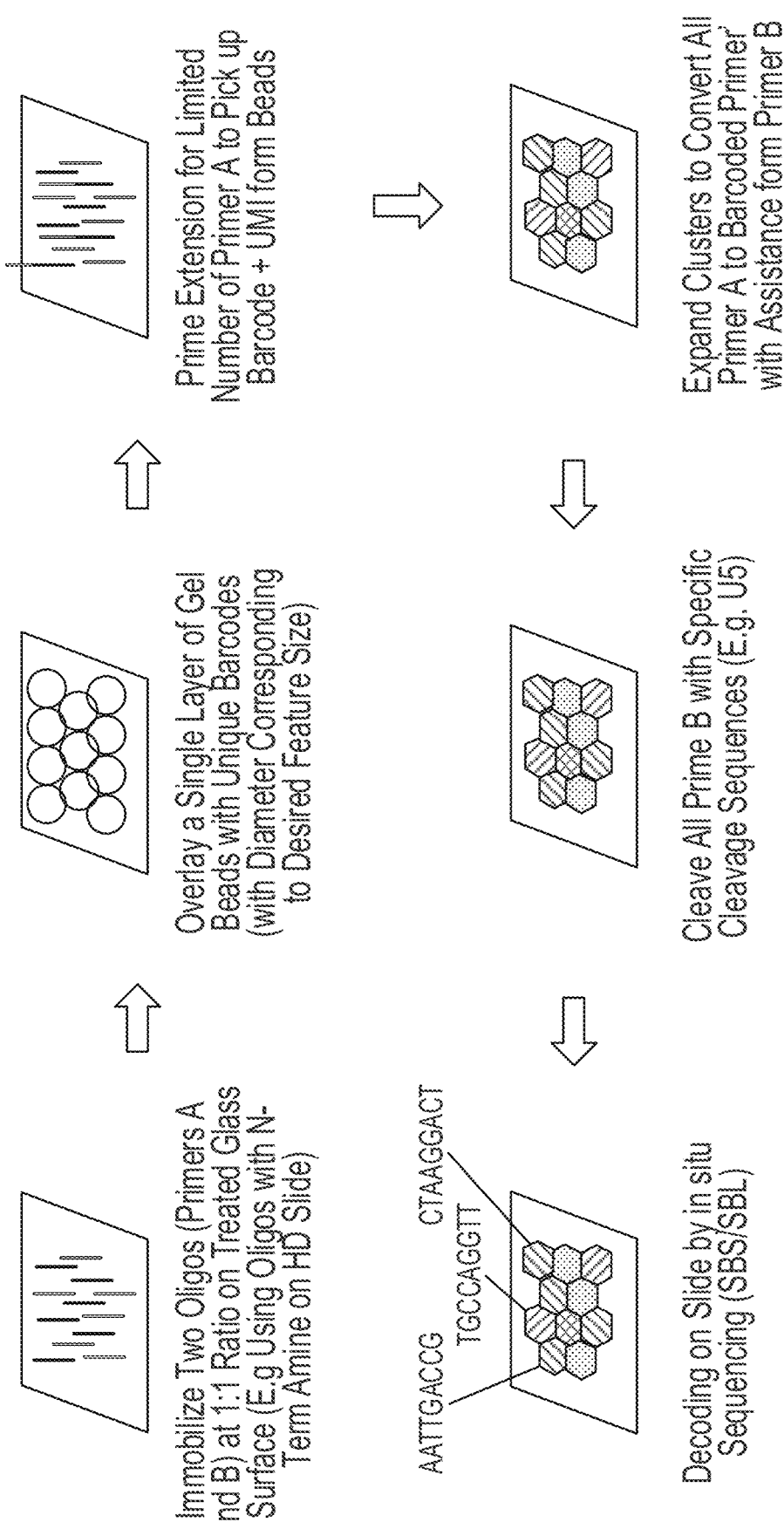
FIG. 39 is a workflow schematic showing exemplary, non-limiting, non-exhaustive steps for preparing a spatial array and decoding the clusters on the slide.

A sequencing library structure is shown in FIG. 38. A capture probe including an analyte, at least one spatial barcode, a region upstream of the at least one spatial barcode, and a region downstream of the analyte is enriched by the following method. A PCR reaction is initialized using a primer with complementarity to the spatial barcode and another primer with complementarity to a region (e.g., constant region 2) downstream of the analyte. The region may be a sequencing index or handle which has a known and/or ubiquitous sequence such that the primer does not enrich certain sequences over other sequences. A second round of PCR is then run by introducing another primer with complementarity to the region upstream of the spatial barcode (e.g., constant region 1). This region may be a sequencing index or handle which has a known and/or ubiquitous sequence such that this primer does not enrich certain sequences over other sequences (FIG. 38). This exemplary method allows for the enrichment of the desired spatial barcode and analyte sequence while retaining DNA regions upstream and downstream of the spatial barcode that may be useful for any downstream DNA processing.

Example 8—Hierarchical Enrichment

Figure 37:
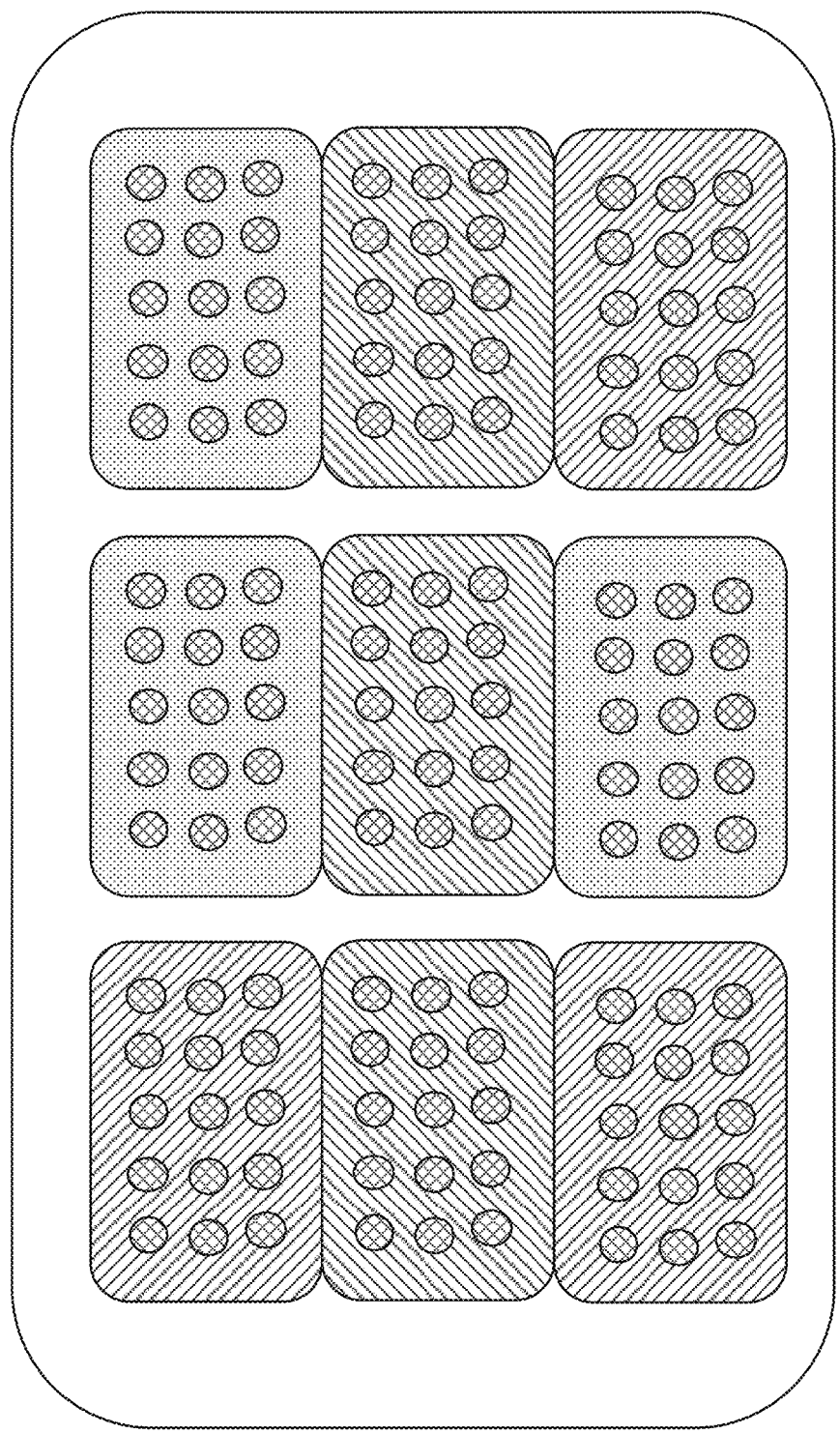
FIG. 37 shows an example of a spatially hierarchical spatial array, in which one region is divided into nine subregions, which is further divided into fifteen sub-sub regions. Each spatial barcode of the 135 sub-sub regions includes a region spatial barcode, a sub region spatial barcode, and a sub-sub region spatial barcode.

Spatial enrichment can be performed on different pluralities of spatial barcodes, wherein the different spatial barcodes correspond to regions, sub regions, and sub-sub regions. FIG. 37 shows an example wherein one region includes nine sub-regions, in which each sub-region further includes fifteen sub-sub regions. In this example, each of the 135 sub-sub regions possesses a spatial barcode (e.g., sub-sub spatial barcode) unique to that sub-sub region, specifically including the spatial barcode of one of the nine subregions (sub spatial barcode), and the spatial barcode of the region (first common sub spatial barcode).

An enrichment protocol can be performed using primers directed to at least one, or more than one, spatial barcode (e.g., region spatial barcode, sub spatial barcode, sub-sub spatial barcode). For example, a library can be created from the analytes captured by the array. The library can contain constant regions and spatial barcode regions. Primers can be employed to hybridize to the regional spatial barcode and amplify members of the library that contain the region specific spatial barcode. Primers can be employed to hybridize to regional and sub-regional spatial barcodes and amplify members of the library that contain region specific and subregion specific spatial barcodes. Enriching multiple levels (e.g., region, subregion, sub-sub region) of spatial barcodes can provide sequencing regions of interest at a lower cost.

Example 9—Spatial Enrichment

Capture probes with individual spatial barcodes will be linked to beads and the beads are attached to create a high density bead array. The capture probes containing the spatial barcodes will be printed in 16 identical arrays on a slide, wherein each array contains a plurality of target barcode sequences in a pre-defined pattern. Fresh, non-fixed mouse brain tissue will be trimmed and frozen in −40° C. cold isopentane and subsequently will be mounted for sectioning with a cryostat at 10 μm. A slice of tissue will be applied onto each capture probe array.

The SuperScript™ III One-step RT-PCR System with Platinum® Taq DNA Polymerase from Invitrogen can be used when performing the cDNA synthesis. For each reaction 25 μl 2× reaction mix (SuperScript™ III One-step RT-PCR System with Platinum (® Taq DNA Polymerase, Invitrogen), 22.5 μl H2O and 0.5 μl 100×BSA can be mixed and heated to 50° C. SuperScript III/Platinum Taq enzyme mix can be added to the reaction mix, 2 μl per reaction, and 50 μl of the 10 reaction mix can be added to each well on the chip. The chip can be incubated at 50° C. for 30 min.

Prior to tissue application, fluorescent marker probes will be hybridized to spot or beads comprising marker oligonucleotides printed on the capture probe array. The fluorescent marker probes can aid in the orientation of the resulting image after tissue visualization, making it possible to combine the image with the resulting expression profiles for individual capture probe spatial barcode sequences obtained after sequencing. To hybridize fluorescent probes, a hybridization solution containing 4×SSC and 0.1% SDS, 2 μM detection probe (P) will be incubated for 4 min at 50° C. Meanwhile, the high density bead array can be attached to a ChipClip. The array can be subsequently incubated at 50° C. for 30 min at 300 rpm shake with 50 μL of hybridization solution per well.

Capture probes can be released using an enzyme mixture in TdT buffer or with heated TdT buffer. For example, 38 μl of cleavage mixture can be placed in a clean 0.2 ml PCR tube. The mixture can contain: 1× TdT buffer (20 mM Tris-acetate (pH 7.9), 50 mM Potassium Acetate and 10 mM Magnesium Acetate), 0.1 μg/μl BSA; 0.1 U/μl USER Enzyme; released cDNA; and released surface probes. To the PCR tube, 0.5 μl RNase H (5 U/μl, final concentration of 0.06 U/μl), 1 μl TdT (20 U/μl, final concentration of 0.5 U/μl), and 0.5 μl dATPs (100 mM, final concentration of 1.25 mM), can be added. For dA tailing, the tube can be incubated in a thermocycler at 37° C. for 15 min followed by an inactivation of TdT at 70° C. for 10 min. After dA tailing, a PCR master mix can be prepared. The mix can contain: 1× Faststart HiFi PCR Buffer (pH 8.3) with 1.8 mM MgCl2; 0.2 mM of each dNTP; 0.2 sM of each primer, A (complementary to the amplification domain of the capture probe) and B_(dT)24 (complementary to the poly-A tail to be added to the 3' end of the first cDNA strand); and 0.1 U/μl Faststart HiFi DNA polymerase. 23 μl of PCR Master mix can be placed into nine clean 0.2 ml PCR tubes. 2 μl of dA tailing mixture can be added to eight of the tubes, while 2 μl water (RNase/DNase free) can be added to the last tube (negative control). PCR amplification can be carried out with the following program: Hot start at 95° C. for 2 minutes, second strand synthesis at 50° C. for 2 minutes and 72° C. for 3 5 minutes, amplification with 30 PCR cycles at 95° C. for 30 seconds, 65° C. for 1 minutes, 72° C. for 3 minutes, and a final extension at 72° C. for 10 minutes.

A dsDNA library for Illumina® sequencing using sample indexing can be carried out according to manufacturer's instructions. Sequencing can be carried out on a HiSeq2000 platform. The sequencing data can be converted from FASTQ format to FASTA format using the FastX toolkit FASTQ-to-FASTA converter. The sequencing reads can be aligned to the capture probe positional domain (tag) sequences using Blastn and the reads with hits better than 1e-6 to one of tag sequences were sorted out to individual files for each tag sequence respectively. The file of tag sequence reads can then be aligned using Blastn to the mouse transcriptome, and hits collected.

The expression profiles for individual capture probe spatial barcode sequences can be combined with the spatial information obtained from the tissue sections through staining. The transcriptomic data from the cellular compartments of the tissue section can be analyzed in a directly comparative fashion, with the availability to distinguish distinct expression features for different cellular subtypes in a given structural context.

Example 10—Generating Gene Specific Capture Probes

Capture probes containing various functional sequences and gene specific or general (e.g., poly(T)) capture domains were generated with a ligation strategy. FIG. 41 shows an immobilized oligonucleotide, acceptor oligonucleotide, on a substrate, from 3' to 5' containing an amino modifier C6 at its 3' end, followed by 12 uracils that can function as a cleavage domain, a sequencing handle (e.g., R1), a 16 base pair spatial barcode, a 12 base pair UMI, and a ligation handle (SEQ ID NO: 9). A splint oligonucleotide (SEQ ID NO: 10) with a sequence complementary to the ligation handle and an additional sequence (e.g., poly(A) or gene specific sequence) facilitates the ligation of oligonucleotide and the capture domain (SEQ ID NO: 11). Ligation of both poly(T) (e.g., mRNA) and a specific mRNA (e.g., Penk) capture domains to the immobilized oligonucleotide was completed using a mixture containing 30 µM Poly dT or capture sequence (e.g., Penk), 30 µM splint oligonucleotide, and 100 units of ligase. The mixture was placed on top of the slide for 60 minutes then removed before washing and adding tissue. All tissues were permeabilized without pre-permeabilization for a duration of 3, 6, or 9 minutes (FIG. 43). The data show Poly dT was successfully ligated to the immobilized oligonucleotide and capable of capturing mRNA in a biased manner. Additionally, a capture domain for the Penk mRNA was successfully ligated and capable of capturing Penk mRNA. As shown in the table below, ligating a Poly dT capture domain did not affect sequencing efficiency. The reads mapped to the transcriptome for gene specific data are relatively high for a single gene capture (e.g., Penk), but the ligation strategy and subsequent gene specific mRNA capture is possible.

ligation probe are mixed and warmed up to 98° C. for 2 minutes, and then cooled down to 4° C. at a rate of 0.1° C./second.

Next, 100 µl probe and ligase mix are added to each well, and incubated at 22° C. for 60 minutes. After 60 minutes, 100 µl of volume is removed and discard. 100 µl of 2×SSC buffer that has been heated to 50° C. is added to each well and incubated for 2 minutes. After 2 minutes, 100 rd of the 2×SSC buffer is removed from the well and discard. This process is repeated 2 times for a total of 3 washes in 2×SSC buffer at 50° C.

After the 3 washes in 2×SSC buffer, 100 µl of room temperature 0.2×SSC buffer is added to each well and incubated for 1 minute. 100 µl of 0.2×SSC buffer is then removed, followed by addition of 100 µl of 0.1×SSC buffer.

The slide can be stored at 4° C. until ready for fluorescent probe hybridization and imaging.

Ligation Reaction Reagent Mix:

|  | Stock Concentration | Desired Concentration | Volume (µl) |
| --- | --- | --- | --- |
| Desired final volume |  |  | 100 |
| H₂O |  |  | 55 |
| ATP | 100 | 2.5 | 2.5 |
| 5X Ligation Buffer | 5X | 1X | 20 |
| Ligase | 1000 | 100 | 10 |
| PolyT + splint oligonucleotide | 250 | 30 | 12 |

| Name | Reads Mapped Confidently to transcriptome | Reads Mapped Confidently to Genome | Fraction reads with primer or homopolymer sequence | Fraction reads with any polyA sequence | Fraction ribosomal protein UMI counts | Fraction mitochondrial UMI counts |
| --- | --- | --- | --- | --- | --- | --- |
| Ligated PolyT (N = 6) | 81.42% | 90.94% | 13.58% | 4.30% | 9.84% | 25.80% |
| No Ligate Average (N = 6) | 83.12% | 92.67% | 13.37% | 2.52% | 10.18% | 26.15% |
| Penk Average (N = 6) | 13.33% | 53.07% | 10.78% | 0.28% | 1.18% | 2.78% |

Example 11—Ligation of Capture Domains to Immobilized Oligonucleotides

The following ligation protocol and reagents provide for the ligation of capture domains to existing arrays. A portion of a splint oligonucleotide is complementary to the ligation handle of an acceptor oligonucleotide, acceptor oligonucleotide 2, on the surface of the array. Another portion of the splint oligonucleotide is complementary to a second ligation handle sequence present in an oligonucleotide that also includes the capture domain. The splint oligonucleotide facilitates the ligation of the capture domain (e.g., via hybridization to the second ligation handle) to the immobilized oligonucleotide (e.g., ligation handle of the immobilized oligonucleotide).

Ligation Protocol:

Equal amounts of a splint oligonucleotide and a capture domain are incubated at room temperature overnight. Alternatively, equal amounts of a splint oligonucleotide and a Reagents in the Ligation Reaction Reagent Mix Table:

| Item | 10x Part Number | Origin | Composition |
| --- | --- | --- | --- |
| 5X Ligation Buffer | 210007 | 10x Manufactured (bulk formulation) | 35% Glycerol, 250 mM Tris-HCl pH 7.5, 50 mM MgCl₂ |
| Bulk, ATP 100 mM | 210010 | 10x Manufactured (bulk formulation) | 100 mM (powder disodium salt dissolved in Nuclease-Free Water). pH adjusted to 6.8-7.2 using 10M NaOH |
| DTT-Free T4 Ligase | 310280 | Enzymatics (Qiagen) | Buffer: 10 mM Tris-HCl, 50 mM KCl, 0.1 mM EDTA, 50% glycerol, pH 7.5 |

SEQUENCE LISTING

Synthetic PURAMATRIX polypeptide sequence
SEQ ID NO: 1 RADARADARADARADA

Synthetic EAK16 polypeptide sequence
SEQ ID NO: 2 AEAEAKAKAEAEAKAK

Synthetic KLD12 polypeptide sequence
SEQ ID NO: 3 KLDLKLDLKLDL 18s cDNA Probe 1 (P1)
SEQ ID NO: 4 GAGGAATTCCCAGTAAGT 18s cDNA Probe 2 (P2)
SEQ ID NO: 5 GAGATTGAGCAATAACAG 18s cDNA Probe 3 (P3)
SEQ ID NO: 6 GTAGTTCCGACCATAAAC 18s cDNA Probe 4 (P4)
SEQ ID NO: 7 GGTGACTCTAGATAACCT Analyte poly(A) tail from a biological sample
SEQ ID NO: 8 AAAAAAAAAAANNNNNNNNNNNNNNNNNNNNNN Acceptor Oligonucleotide
SEQ ID NO: 9
UUUUUUUUUUUUCTACACGACTCTTCCGATCTACGTACGTACGTACGTN
NNNNNNNNNNNGCGGCCCG Splint oligonucleotide
SEQ ID NO: 10 AAAAAAAAAACGGGCCGC Capture domain poly(T) sequence
SEQ ID NO: 11 TTTTTTTTTTTTTTTTTTTTTTTTT Acceptor Oligonucleotide 2
SEQ ID NO: 12
TTTTTCTACACGACGCTCTTCCGATCTACGTACGTACGTACGTNNNNNN
NNNNNNCGCTACG

What is claimed is:

1. A method for identifying a location of an analyte in a biological sample, the method comprising:
   (a) contacting the biological sample with a first substrate;
   (b) adding a hydrogel matrix to the biological sample on the first substrate, thereby isometrically expanding the biological sample;
   (c) hybridizing the analyte to a capture probe comprising a capture domain and a spatial barcode, wherein the capture probe is affixed to an array;
   (d) extending the capture probe using the analyte as a template; and
   (e) determining (i) the spatial barcode or a complement thereof, and (ii) all or a portion of the analyte from the biological sample or a complement thereof, and using the determined sequences of (i) and (ii) to identify the location of the analyte in the biological sample.

2. The method of claim 1, wherein the hydrogel matrix comprises a macromolecular polymer gel.

3. The method of claim 2, wherein the macromolecular polymer gel comprises a network of polymer chains that are crosslinked to each other.

4. The method of claim 1, wherein the hydrogel matrix comprises a polyelectrolyte gel.

5. The method of claim 1, wherein isometrically expanding the biological sample increases resolution of the biological sample as compared to a biological sample that has not been isometrically expanded.

6. The method of claim 1, wherein the capture probe is affixed to the array on the first substrate.

7. The method of claim 1, wherein the capture probe is affixed to the array on a second substrate.

8. The method of claim 7, further comprising aligning the first substrate with the second substrate comprising the array, such that at least a portion of the biological sample is aligned with at least a portion of the array.

9. The method of claim 1, further comprising imaging the biological sample.

10. The method of claim 1, further comprising staining the biological sample using immunofluorescence, immunohistochemistry, hematoxylin, or eosin.

11. The method of claim 1, further comprising permeabilizing the biological sample with a permeabilization agent to allow an analyte in the biological sample to interact with the capture domain.

12. The method of claim 11, wherein the permeabilization agent comprises proteinase K or pepsin.

13. The method of claim 1, further comprising extending the capture probe using the analyte as a template, thereby generating an extended capture probe.

14. The method of claim 13, further comprising amplifying all or a portion of the extended capture probe, or a complement thereof.

15. The method of claim 1, wherein the determining step comprises sequencing.

16. The method of claim 15, wherein the sequencing comprises high-throughput sequencing.

17. The method of claim 1, wherein the capture domain comprises a poly(T) sequence.

18. The method of claim 1, wherein the capture domain is a non-homopolymeric sequence.

19. The method of claim 1, wherein the capture probe further comprises one or more functional domains, a unique molecular identifier, a cleavage domain, and combinations thereof.

20. The method of claim 1, wherein the analyte comprises DNA or RNA.

21. The method of claim 20, wherein the RNA is mRNA.

22. The method of claim 1, wherein the biological sample comprises a fixed sample.

23. The method of claim 22, wherein the fixed sample is a formalin-fixed, paraffin embedded tissue sample.

24. The method of claim 1, wherein the biological sample comprises a fresh frozen sample.

25. The method of claim 1, wherein the biological sample comprises a tissue section.

26. The method of claim 1, further comprising identifying a location of a different type of analyte in the biological sample.

27. The method of claim 26, wherein the identifying the different type of analyte comprises:
   contacting the biological sample with a plurality of analyte capture agents, wherein an analyte capture agent of the plurality of analyte capture agents comprises an analyte binding moiety and a capture agent barcode domain, wherein the analyte binding moiety binds to the different type of analyte, and wherein the capture agent barcode domain comprises an analyte binding moiety barcode and an analyte capture sequence; and
   hybridizing the analyte capture sequence to the capture domain.

28. The method of claim 27, further comprising determining (I) all or part of the sequence of the capture agent barcode domain; and (II) the spatial barcode of the capture probe comprising the capture domain that is hybridized to the analyte capture sequence, or a complement thereof, and using the determined sequence of (I) and (II) to analyze the different type of analyte in the biological sample.

29. The method of claim 27, wherein the different type of analyte is a protein.

* * * * *

UNITED STATES PATENT AND TRADEMARK OFFICE
CERTIFICATE OF CORRECTION

PATENT NO. : 11,753,675 B2
APPLICATION NO. : 17/974226
DATED : September 12, 2023
INVENTOR(S) : Eswar Prasad Ramachandran Iyer It is certified that error appears in the above-identified patent and that said Letters Patent is hereby corrected as shown below:

On the Title Page

Item [56], Column 2, Line 2, Delete "1211-1219 ." and insert -- 1211-1219. --.

Signed and Sealed this
Twelfth Day of December, 2023

Katherine Kelly Vidal
*Director of the United States Patent and Trademark Office*